US006432993B1

(12) United States Patent
Fujita et al.

(10) Patent No.: US 6,432,993 B1
(45) Date of Patent: *Aug. 13, 2002

(54) SUBSTITUTED FUSED HETEROCYCLIC COMPOUND

(75) Inventors: Takashi Fujita, Kashiwa; Kunio Wada, Asaka; Toshihiko Fujiwara, Ebina, all of (JP)

(73) Assignee: Sankyo Company, Limited, Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/543,667

(22) Filed: Apr. 7, 2000

Related U.S. Application Data

(63) Continuation-in-part of application No. PCT/JP98/04548, filed on Oct. 8, 1998.

(30) Foreign Application Priority Data

Oct. 8, 1997 (JP) .............................. 9-276063

(51) Int. Cl.$^7$ .................... A61K 31/425; C07D 277/04; C07D 235/04
(52) U.S. Cl. ........................ 514/369; 514/394; 514/399; 548/183; 548/186; 548/189; 548/304.7
(58) Field of Search ................................ 514/369, 399, 514/394; 548/183, 189, 186, 304.7

(56) References Cited

U.S. PATENT DOCUMENTS

| 5,624,935 | A |   | 4/1997 | Fujita et al. | 514/303 |
| 5,739,345 | A |   | 4/1998 | Fujita et al. | 548/183 |
| 5,753,681 | A |   | 5/1998 | Fujiwara et al. | 514/337 |
| 5,798,375 | A | * | 8/1998 | Tsujita et al. | 514/369 |
| 5,834,501 | A |   | 11/1998 | Fujita et al. | 514/369 |
| 5,886,014 | A | * | 3/1999 | Fujita et al. | 514/369 |
| 5,962,470 | A |   | 10/1999 | Fujita et al. | 514/303 |
| 5,977,365 | A |   | 11/1999 | Fujita et al. | 546/118 |

FOREIGN PATENT DOCUMENTS

| EP | 0441605 A |   | 8/1991 |
| EP | 676398 A |   | 10/1995 |
| EP | 745600 |  * | 12/1996 |
| EP | 753298 A |   | 1/1997 |
| EP | 796618 A |   | 9/1997 |
| JP | 10-72371 |   | 3/1998 |
| WO | WO 92/02520 |   | 2/1992 |
| WO | WO 92/03425 |   | 3/1992 |
| WO | WO 92/07839 |   | 5/1992 |
| WO | WO 92/07850 |   | 5/1992 |

OTHER PUBLICATIONS

A.Y. Chang et al, "The Hypoglycemic Effect of Ciglitazone in Obese, Hyperglycemic Animal Models", *Prog. Clin. Biol. Res.*, pp. 177–192 (1988).

T. Sohda et al, "Studies on Antidiabetic Agents. II. Synthesis of 5–[4(1–Methylcyclohexylmethoxy)–benzyl]thiazolidine–2,4–dione (ADD–3878) and Its Derivatives", *Chem. Phar. Bull.*, vol. 30(10), pp. 3580–3600 (1982).

T. Fujiwara et al, "Characterization of New Oral Antidiabetic Agent CS–045", *Diabetes*, vol. 37(11), pp. 1549–1558 (Nov. 1988).

T. Sohda et al, "Studies on Antidiabetic Agents", *Arzneim.–Forsch./Drug Res.*, vol. 40(I), Nr. 1, pp. 37–42 (1990).

J.R. Colca et al, "Pioglitazone Hydrochloride Inhibits Cholesterol Absorption and Lowers Plasma Cholesterol Concentrations in Cholesterol–Fed Rats", *Diabetes*, vol. 40(12), pp. 1669–1674 (Dec. 1991).

A.K. Saha et al, "Lipid Abnormalities in Tissues of the KKA$^y$ Mouse: Effects of Pioglitazone on Malonyl–CoA and Diacylglycerol", *The American Physiological Society*, vol. 267, pp. E95–E101 (1994).

(List continued on next page.)

*Primary Examiner*—Mukund J. Shah
*Assistant Examiner*—Sudhaker B. Patel
(74) *Attorney, Agent, or Firm*—Frishauf, Holtz, Goodman & Chick, P.C.

(57) ABSTRACT

Substituted fused heterocyclic compounds of the formula (I) and pharmacologically acceptable salts thereof:

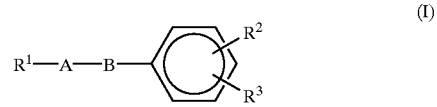

wherein $R^1$ is a group of the formula (II) or (III):

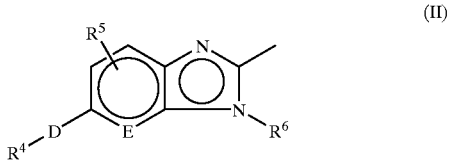

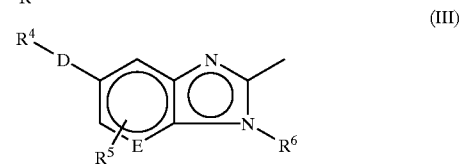

$R^4$ is a substituted phenyl or a pyridyl which may have a substituent. $R^5$ is hydrogen or the like. $R^6$ is hydrogen, a $C_{1-6}$ alkyl group or the like. D is oxygen or sulfur. E is a CH group or nitrogen. $R^2$ is hydrogen or the like. $R^3$ is a 2,4-dioxothiazolidin-5-ylmethyl group or the like. A is a $C_{1-6}$ alkylene group. B is oxygen or sulfur. These compounds and salts are useful as the active ingredient of pharmaceutical compositions which can be used to treat patients because these compounds and salts have excellent insulin-resistance improving action, lipid-peroxide-production inhibitory action, 5-lipoxygenase inhibitory action and the like.

68 Claims, No Drawings

OTHER PUBLICATIONS

N.D. Oakes et al, "A New Antidiabetic Agent, BRL 49653, Reduces Lipid Availability and Improves Insulin Action and Glucoregulation in the Rat", *Diabetes*, vol. 43(10), pp. 1203–1210 (Oct. 1994).

H. Ikeda et al, "Effects of Pioglitazone on Glucose and Lipid Metabolism in Normal and Insulin Resistant Animals", *Arzneim.–Forsch./Drug Res.*, vol. 40(I), Nr. 2, pp. 156–162 (1990).

L. Bowen et al, "The Effect of CP 68,722, a Thiozolidinedione Derivative, on Insulin Sensitivity in Lean and Obese Zuker Rats" *Metabolism*, vol. 40, No. 10, pp. 1025–1030 (Oct. 1991).

J.W. Kemnitz et al, "Pioglitazone Increases Insulin Sensitivity, Reduces Blood Glucose, Insulin, and Lipid Levels, and Lowers Blood Pressure in Obese, Insulin–Resistant Rhesus Monkeys", *Diabetes*, vol. 43(2), pp. 204–211 (Feb. 1994).

H. Keen, "Insulin Resistance and the Prevention of Diabetes Mellitus", *The New England Journal of Medicine*, vol. 331, No. 18, pp. 1226–1227 (Nov. 1994).

S. Yoshioka et al, "Antihypertensive Effects of CS–045 Treatment in Obese Zucker Rats", *Metabolism*, vol. 42, No. 1, pp. 75–80 (Jan. 1993).

R.K. Dubey et al, "Pioglitazone Attenuates Hypertension and Inhibits Growth of Renal Arteriolar Smooth Muscle in Rats", *The American Physiological Society*, vol. 265, pp. R726–R732 (1993).

F. Zhang et al, "Effects of Pioglitazone on Calcium Channels in Vascular Smooth Muscle", *Hypertension*, vol. 24(2), pp. 170–175 (1994).

J. Ohsumi et al, "Troglitazone Prevents the Inhibitory Effects of Inflammatory Cytokines on Insulin–Induced Adipocyte Differentiation in 3T3–L1 Cells", *Endocrinology*, vol. 135, No. 5, pp. 2279–2282 (1994).

D. Szalkowski et al, "Antidiabetic Thiazolidinediones Block the Inhibitory Effect of Tumor Necrosis Factor–$\alpha$ on Differentiation, Insulin–Stimulated Glucose Uptake, and Gene Expression in 3T3–L1 Cells", *Endocrinology*, vol. 136, No. 4, pp. 1474–1481 (1995).

\* cited by examiner

SUBSTITUTED FUSED HETEROCYCLIC COMPOUND

This application is a continuation-in-part application of International Application PCT/JP98/04548 filed Oct. 8, 1998.

The present invention relates to a substituted fused heterocyclic compound or a pharmacologically acceptable salt thereof having excellent insulin resistance improving action, anti-inflammatory action, immunomodulatory action, aldose reductase inhibitory action, 5-lipoxygenase inhibitory action, lipid peroxide production inhibitory action, peroxisome proliferator activated receptor (which will hereinafter be abbreviated as "PPAR") activating action, anti-osteoporosis action, leukotrienes antagonism, fat-cell formation promoting action, cancer-cell proliferation inhibitory action and calcium antagonism; a pharmaceutical composition comprising, as an effective ingredient, the above-described substituted fused heterocyclic compound or a pharmacologically acceptable salt thereof; use of the above-described substituted fused heterocyclic compound or a pharmacologically acceptable salt thereof for the preparation of a pharmaceutical composition; a method for the prevention or treatment of diabetes or like diseases, which comprises administering an effective amount of the above-described substituted fused heterocyclic compound or a pharmacologically acceptable salt thereof to a warm-blooded animal; or a pharmaceutical composition obtained by using, in combination, the above-described substituted fused heterocyclic compound or a pharmacologically acceptable salt thereof and at least one compound selected from α-glucosidase inhibitors, aldose reductase inhibitors, biguanide preparations, statin base compounds, squalene synthesis inhibitors, fibrate base compounds, LDL catabolism promoters and angiotensin-converting enzyme inhibitors.

BACKGROUND OF THE INVENTION

It is reported that thiazolidine compounds, oxazolidine compounds and the like are useful as preventive agents and/or remedies for various diseases such as diabetes and hyperlipidemia.

For example, a number of thiazolidine compounds having hypoglycemic action are disclosed in Chem. Pharm. Bull., 30, 3580–3600(1982), Prog. Clin. Biol. Res., 265, 177–192 (1988), Diabetes, 37(11), 1549–1558(1988), Arzneim.-Forsch., 40(1), 37–42(1990), EP0441605A and the like.

The action of thiazolidine compounds on hyperlipidemia is reported in Diabetes, 40(12), 1669–1674(1991), Am. J. Physiol., 267(1 Pt 1), E95–E101(1994), Diabetes, 43(10), 1203–1210(1994) and the like.

The action of thiazolidine compounds on glucose tolerance insufficiency and insulin resistance is disclosed in Arzneim.-Forsch., 40(2 Pt 1), 156–162(1990), Metabolism, 40(10), 1025–1230(1991), Diabetes, 43(2), 204–211(1994) and the like.

It is recently reported in N. Engl. J. Med., 331(18), 1226–1227(1994) that a normal person having insulin resistance has developed diabetes without glucose tolerance insufficiency and also that a medicament for improving insulin resistance is useful as a preventive agent the onset of diabetes in such a normal person.

The action of thiazolidine compounds on hypertension is reported in Metabolism, 42(1), 75–80(1993), Am. J. Physiol., 265(4 Pt 2), R726–R732(1933), Diabetes, 43(2), 204–211(1994) and the like.

The action of thiazolidine compounds on coronary artery diseases is reported in Am. J. Physiol., 265(4 Pt 2), R726–R732(1933), Hypertension, 24(2), 170–175(1994) and the like.

The action of thiazolidine compounds on arteriosclerosis is reported in Am. J. Physiol., 265(4 Pt 2), R726–R732 (1933) and the like.

The action of thiazolidine compounds on cachexia is reported in Endocrinology, 135(5), 2279–2282(1994), Endocrinology, 136(4), 1474–1481(1995) and the like.

Among thiazolidine compounds having hypoglycemic action, compounds containing a heterocyclic group are disclosed in WO92/07839A, WO92/07850A and EP00745600A.

In addition, oxazolidine-2,4-dione compounds having hypoglycemic action are disclosed in WO92/02520A and the like.

In WO92/03425A, it is disclosed that compounds containing a 3,5-dioxooxadiazolidin-2-ylmethylphenyl or a N-hydroxyureido group exhibit hypoglycemic action.

In EP00676398A, 5-{4-[5-(3,5-di-t-butyl-4-hydroxyphenylthio)-3-methyl-3H-imidazo[4,5-b]pyridin-2-ylmethoxy]benzyl}thiazolidine-2,4-dione is disclosed only as one of the exemplified compounds.

DISCLOSURE OF THE INVENTION

As a result of investigation for many years on the synthesis of a series of substituted fused heterocyclic compounds and their pharmacological activity, the present inventors have found that a substituted condensed heterocyclic compound having a novel structure has excellent insulin-resistance improving action, anti-inflammatory action, immunomodulatory action, aldose reductase inhibitory action, 5-lipoxygenase inhibitory action, lipid-peroxide-production inhibitory action, PPAR activating action, anti-osteoporosis action, leukotrienes antagonism, fat-cell-formation promoting action, cancer-cell proliferation inhibitory action and calcium antagonism; has reduced side effects; and moreover has high fat solubility.

Another object of the present invention is to provide a preventive agent and/or remedy, which comprises as an effective ingredient the above-described substituted fused heterocyclic compound or a pharmacologically acceptable salt thereof, for diseases alleviated by the above-described actions such as diabetes, hyperlipidemia, obesity, impaired glucose tolerance, hypertension, fatty liver, diabetic complications (e.g. retinopathy, nephropathy, neurosis, cataracts and coronary artery diseases and the like), arteriosclerosis, pregnancy diabetes, polycystic ovary syndrome, cardiovascular diseases (e.g. ischemic heart disease and the like), cell injury (e.g. brain injury induced by strokes and the like) induced by atherosclerosis or ischemic heart disease, gout, inflammatory diseases (e.g. arthrosteitis, pain, pyrexia, rheumatoid arthritis, inflammatory enteritis, acne, sunburn, psoriasis, eczema, allergosis, asthma, GI ulcer, cachexia, autoimmune diseases, pancreatitis and the like), cancer, osteoporosis and cataracts.

Another object of the present invention is to provide a pharmaceutical composition (particularly suited is a preventive agent and/or remedy for diabetes or diabetic complications) obtained by using, in combination, the above-described substituted fused heterocyclic compound or a pharmacologically acceptable salt thereof and at least one compound selected from α-glucosidase inhibitors, aldose reductase inhibitors, biguanide preparations, statin base compounds, squalene synthesis inhibitors, fibrate base compounds, LDL catabolism promoters and angiotensin-converting enzyme inhibitors.

The present invention thus provides (i) pharmaceutical compositions containing as an active ingredient, a substituted fused heterocyclic compound of the formula (I) or a pharmacologically acceptable salt or prodrug thereof and (ii) methods of treating by administering said active ingredient to a warm-blooded animal, particularly to a human.

In the present invention, a substituted fused heterocyclic compound is represented by the following formula (I):

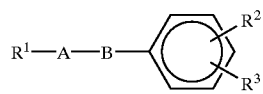
(I)

wherein:

$R^1$ represents a group of the following formula:

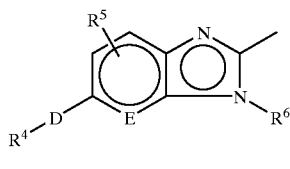
(II)

or a group of the following formula:

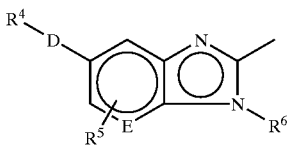
(III)

[in which:

$R^4$ represents a phenyl group which is substituted with 1 to 5 substituents selected from Substituents α or a pyridyl group which may be substituted with 1 to 4 substituents selected from Substituents α, $R^5$ represents a hydrogen atom or a substituent selected from Substituents α

$R^6$ represents a hydrogen atom, a $C_{1-6}$ alkyl group, a $C_{6-10}$ aryl group which may be substituted with 1 to 3 substituents selected from Substituents β or a $C_{7-16}$ aralkyl group which may be substituted with 1 to 3 substituents selected from Substituents β, D represents an oxygen or sulfur atom, and E represents a CH group or nitrogen atom], $R^2$ represents a hydrogen atom or a substituent selected from Substituents α, $R^3$ represents a group of the following formula:

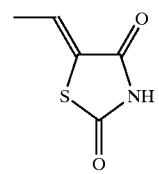
(IV-1)

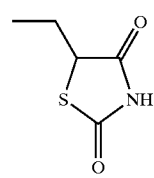
(IV-2)

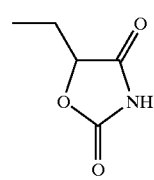
(IV-3)

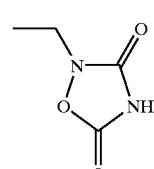
(IV-4)

or

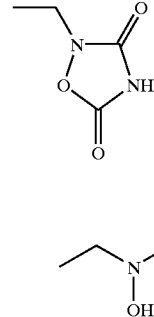
(IV-5)

A represents a $C_{1-6}$ alkylene group, and

B represents an oxygen or sulfur atom, with the proviso that 5-{4-[5-(3,5-di-t-butyl-4-hydroxyphenylthio)-3-methyl-3H-imidazo[4,5-b]pyridin-2-ylmethoxy]benzyl}thiazolidine-2,4-dione is excluded.

<Substituents α>

A halogen atom, a hydroxyl group, a $C_{1-6}$ alkyl group, a halogeno($C_{1-6}$ alkyl) group, a $C_{1-6}$ alkoxy group, a $C_{1-6}$ alkylthio group, an amino group which may be substituted with substituents selected from Substituents γ, $C_{3-10}$ cycloalkyl, $C_{6-10}$ aryl, $C_{7-16}$ aralkyl, $C_{6-10}$ aryloxy, $C_{7-16}$ aralkyloxy and $C_{6-10}$ arylthio groups which may each be substituted with 1 to 3 substituents selected from Substituents β, a $C_{1-7}$ aliphatic acyloxy group, a 4- to 7-membered saturated nitrogen-containing heterocyclic group, a 5- or 6-membered aromatic nitrogen-containing heterocyclic group, a nitro group, and a cyano group.

<Substituents β>

A halogen atom, a hydroxyl group, a $C_{1-6}$ alkyl group, a halogeno($C_{1-6}$ alkyl) group, a $C_{1-6}$ alkoxy group, an amino group which may be substituted with substituents selected from Substituents γ, a $C_{6-10}$ aryl group and a nitro group.

<Substituents γ>

A $C_{1-10}$ alkyl group, and $C_{6-10}$ aryl and $C_{7-16}$ aralkyl groups each of which may have a substituent and an acyl group which may have substituents (said acyl group is a $C_{1-7}$ aliphatic acyl group or a $C_{7-11}$ aromatic acyl, $C_{8-12}$ aromatic aliphatic acyl, $C_{4-11}$ cycloalkylcarbonyl or 5- or 6-membered aromatic nitrogen-containing heterocyclic carbonyl group each of which may have substituents).

In the above description, examples of the "halogen atom" in the definition of Substituents α and β include fluorine, chlorine, bromine and iodine atoms, of which fluorine and chlorine atoms are preferred.

In the above description, the "$C_{1-6}$ alkyl group" in the definition of $R^6$ and Substituents α, β and γ is a linear or branched $C_{1-6}$ alkyl group. Examples include methyl, ethyl, propyl, isopropyl, butyl, isobutyl, s-butyl, t-butyl, pentyl, isopentyl, 2-methylbutyl, neopentyl, 1-ethylpropyl, hexyl, 4-methylpentyl, 3-methypentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl groups. With reference to $R^6$, a $C_{1-4}$ alkyl group is preferred, of which a $C_{1-2}$ alkyl group is more preferred and a methyl group is particularly preferred. With reference to Substituents α, methyl and t-butyl groups are preferred, while with reference to Substituents β, methyl, ethyl and t-butyl groups are preferred.

In the above description, the "halogeno($C_{1-6}$ alkyl) group" in the definition of Substituents α or β is the above-exemplified $C_{1-6}$ alkyl group having one to three of the above-exemplified halogen atoms bound thereto. Examples include trifluoromethyl, trichloromethyl, tribromomethyl, difluoromethyl, dichloromethyl, dibromomethyl, fluoromethyl, 2,2,2-trichloroethyl, 2,2,2-trifluoroethyl, 2-bromoethyl, 2-chloroethyl, 2-fluoroethyl, 2-iodoethyl, 3-chloropropyl, 4-fluorobutyl, 6-iodohexyl and 2,2-dibromoethyl groups, of which a halogeno($C_{1-2}$ alkyl) group is preferred and a trifluoromethyl group is particularly preferred.

In the above description, the "$C_{1-6}$ alkoxy group" in the definition of Substituents α and β is the above-described $C_{1-6}$ alkyl group bound to an oxygen atom. Examples include methoxy, ethoxy, propoxy, isopropoxy, butoxy, isobutoxy, s-butoxy, t-butoxy, pentoxy, isopentoxy, 2-methylbutoxy, neopentoxy, 1-ethylpropoxy, hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy and 2-ethylbutoxy groups, of which a $C_{1-2}$ alkoxy group is preferred and a methoxy group is particularly preferred.

In the above description, the "$C_{1-6}$ alkylthio group" in the definition of Substituents α is the above-exemplified $C_{1-6}$ alkyl group bound to a sulfur atom. Examples include methylthio, ethylthio, propylthio, isopropylthio, butylthio, isobutylthio, s-butylthio, t-butylthio, pentylthio, isopentylthio, 2-methylbutylthio, neopentylthio, 1-ethylpropylthio, hexylthio, 4-methylpentylthio, 3-methylpentylthio, 2-methylpentylthio, 1-methylpentylthio, 3,3-dimethylbutylthio, 2,2-dimethylbutylthio, 1,1-dimethylbutylthio, 1,2-dimethylbutylthio, 1,3-dimethylbutylthio, 2,3-dimethylbutylthio and 2-ethylbutylthio groups, of which a $C_{1-2}$ alkylthio group is preferred and a methylthio group is particularly preferred.

In the above description, the "amino group which may be substituted with substituents selected from Substituents γ" in the definition of each of Substituents α and β means an amino group which may be substituted with 1 or 2 substituents which are the same or different and are selected from Substituents γ consisting of $C_{1-10}$ alkyl groups, $C_{6-10}$ aryl and $C_{7-16}$ aralkyl groups each of which may have substituents (said substituents means 1 to 3 groups selected from the group consisting of halogen atoms and hydroxyl, $C_{1-6}$ alkyl, halogeno($C_{1-6}$ alkyl), $C_{1-6}$ alkoxy and $C_{1-6}$ alkylthio groups) and acyl groups which may have substituents (each of which means a $C_{1-7}$ aliphatic acyl group or a $C_{7-11}$ aromatic acyl, $C_{8-12}$ aromatic-aliphatic acyl, $C_{4-11}$ cycloalkylcarbonyl or 5- or 6-membered aromatic nitrogen-containing heterocyclic carbonyl group which may be substituted with 1 to 3 substituents selected from the group consisting of halogen atoms and hydroxyl, $C_{1-6}$ alkyl, halogeno($C_{1-6}$ alkyl), $C_{1-6}$ alkoxy and $C_{1-6}$ alkylthio groups).

In the above description, the "$C_{1-10}$ alkyl group" in the definition of Substituents γ means a linear or branched alkyl group having 1 to 10 carbon atoms and examples include the above-exemplified $C_{1-6}$ alkyl, heptyl, 1-methylhexyl, 2-methylhexyl, 3-methylhexyl, 4-methylhexyl, 5-methylhexyl, 1-propylbutyl, 4,4-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl, 5,5-dimethylhexyl, nonyl, 3-methyloctyl, 4-methyloctyl, 5-methyloctyl, 6-methyloctyl, 1-propylhexyl, 2-ethylheptyl, 6,6-dimethylheptyl, decyl, 1-methylnonyl, 3-methylnonyl, 8-methylnonyl, 3-ethyloctyl, 3,7-dimethyloctyl and 7,7-dimethyloctyl groups, of which $C_{1-8}$ alkyl groups are preferred and methyl, butyl, isobutyl, pentyl, hexyl, heptyl and octyl groups are particularly preferred.

In the above description, the $C_{6-10}$ aryl part of the "$C_{6-10}$ aryl group which may have a substituent" in the definition of Substituents γ means a $C_{6-10}$ aromatic hydrocarbon group and examples include phenyl, indenyl and naphthyl groups, of which phenyl groups are preferred.

In the above description, the $C_{7-16}$ aralkyl part of the "$C_{7-16}$ aralkyl group which may have a substituent" in the definition of Substituents γ means the above-described $C_{6-10}$ aryl group bound to the above-described $C_{1-6}$ alkyl group and examples include benzyl, naphthylmethyl, indenylmethyl, diphenylmethyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphtylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 5-phenylpentyl, 5-naphthylpentyl, 6-phenylhexyl and 6-naphthylhexyl groups, of which benzyl groups are preferred.

In the above description, the "$C_{1-7}$ aliphatic acyl group" in the definition of Substituents γ means a hydrogen atom or a saturated or unsaturated $C_{1-6}$ chain hydrocarbon group bound to a carbonyl group and examples include formyl, acetyl, propionyl, butyryl, isobutyryl, valeryl, isovaleryl, pivaloyl, hexanoyl, acryloyl, methacryloyl and crotonoyl groups, of which acetyl, propionyl and pivaloyl groups are preferred and acetyl groups are particularly preferred.

In the above description, the $C_{7-11}$ aromatic acyl part of the "$C_{7-11}$ aromatic acyl group which may have substituents" in the definition of Substituents γ means a $C_{6-10}$ aryl group bound to a carbonyl group and examples include benzoyl, 1-indanecarbonyl, 2-indanecarbonyl and 1- or 2-naphthoyl groups, of which benzoyl and naphthoyl groups are preferred.

In the above description, the $C_{8-12}$ aromatic-aliphatic acyl part of the "$C_{8-12}$ aromatic-aliphatic acyl group which may have substituents" in the definition of Substituents γ means a phenyl group bound to a $C_{2-6}$ aliphatic acyl group and examples include phenylacetyl, 3-phenylpropionyl, 4-phenylbutyryl, 5-phenylpentanoyl and 6-phenylhexanoyl groups, of which the phenylacetyl group is preferred.

In the above description, the $C_{4-11}$ cycloalkylcarbonyl part of the "$C_{4-11}$ cycloalkylcarbonyl group which may have substituents" in the definition of Substituents γ means a $C_{3-10}$ cycloalkyl group (which means a 3- to 10-membered saturated cyclic hydrocarbon group which may be condensed and examples include cyclopropyl, cyclobutyl, cyclopentyl, cyclohexyl, cycloheptyl, norbornyl and adamantyl groups, of which $C_{3-6}$ cycloalkyl groups are preferred) bound to a carbonyl group and examples include cyclopropanoyl, cyclobutyryl, cyclopentanoyl, cyclohexanoyl, cycloheptylcarbonyl, norbornylcarbonyl and adamantylcarbonyl groups, of which $C_{4-7}$ cycloalkylcarbonyl groups are preferred and cyclopentanoyl and cyclohexanoyl groups are particularly preferred.

In the above description, the "5- or 6-membered aromatic nitrogen-containing heterocyclic carbonyl group part of the 5- or 6-membered aromatic nitrogen-containing heterocyclic carbonyl group which may have substituents" in the definition of Substituents γ means a 5- or 6-membered aromatic heterocycle which contains at least one nitrogen atom and at the same time, may contain further hetero atoms selected from the hetero atom group consisting of a nitrogen atom, an oxygen atom and a sulfur atom (examples of such heterocycles include pyrrolyl, imidazolyl, pyrazolyl, triazolyl, tetrazolyl, pyridyl, pyrazinyl, pyrimidinyl, pyridazinyl, thiazolyl, oxazolyl, oxadiazolyl and thiadiazolyl groups) bound to a carbonyl group and examples include pyrrolylcarbonyl, imidazolylcarbonyl, pyrazolylcarbonyl, triazolylcarbonyl, tetrazolylcarbonyl, nicotinoyl, isonicotinoyl, pyrazinylcarbonyl, pyrimidinylcarbonyl, pyridazinylcarbonyl, thiazolylcarbonyl, oxazolylcarbonyl, oxadiazolylcarbonyl and thiadiazolylcarbonyl groups, of which pyridylcarbonyl groups are preferred and nicotinoyl and isonicotinoyl groups are particularly preferred.

Examples of the "amino group which may be substituted with substituents selected from Substituents γ" in the definition of such Substituents α or β include amino, methylamino, ethylamino, propylamino, isopropylamino, butylamino, s-butylamino, t-butylamino, pentylamino, hexylamino, dimethylamino, diethylamino, N-ethyl-N-methylamino, dipropylamino, dibutylamino, dipentylamino, dihexylamino, phenylamino, 2-, 3- or 4-fluorophenylamino, 2-, 3- or 4-chlorophenylamino, 2-, 3- or 4-bromophenylamino, 2,3-difluorophenylamino, 2,4-difluorophenylamino, 2,4-dichlorophenylamino, 1- or 2-indenylamino, 1- or 2-naphthylamino, diphenylamino, benzylamino, 2-, 3- or 4-fluorobenzylamino, 2-, 3- or 4-chlorobenzylamino, 2-, 3- or 4-bromobenzylamino, 2,3-difluorobenzylamino, 2,4-difluorobenzylamino, 2,4-dichlorobenzylamino, 1- or 2-naphthylmethylamino, 1-indenylmethylamino, 1- or 2-phenethylamino, 1-, 2- or 3-phenylpropylamino, 4-phenylbutylamino, 1-phenylbutylamino, 5-phenylpentylamino, 6-phenylhexylamino, dibenzylamino, formylamino, acetylamino, propionylamino, buturylamino, isobutyrylamino, valerylamino, isovalerylamino, pivaloylamino, hexanoylamino, acryloylamino, methacryloylamino, crotonoylamino, benzoylamino, 1-indanecarbonylamino, 1- or 2-naphthoylamino, 2-, 3- or 4-fluorobenzoylamino, 2-, 3, or 4-chlorobenzoylamino, 2-, 3- or 4-bromobenzoylamino, 2,3-difluorobenzoylamino, 2,4-difluorobenzoylamino, 2,4-dichlorobenzoylamino, 2,6-diisopropylbenzoylamino, 4-trifluoromethylbenzoylamino, 4-hydroxy-3,5-dimethylbenzoylamino, 4-hydroxy-3,5-di-t-butylbenzoylamino, 1-indanecarbonylamino, 1- or 2-naphthoylamino, phenylacetylamino, 3-phenylpropionylamino, 4-phenylbutyrylamino, 5-phenylpentanoylamino, 6-phenylhexanoylamino, 2-, 3- or 4-fluorophenylacetylamino, 2-, 3- or 4-chlorophenylacetylamino, 2-, 3- or 4-bromophenylacetylamino, 2,3-difluorophenylacetylamino, 2,4-difluorophenylacetylamino, 2,4-dichlorophenylacetylamino, cyclopropionylamino, cyclobutyrylamino, cyclopentanoylamino, cyclohexanoylamino, pyrrolylcarbonylamino, imidazolylcarbonylamino, pyrazolylcarbonylamino, triazolylcarbonylamino, tetrazolylcarbonylamino, nicotinoylamino, isonicotinoylamino, pyrazinylcarbonylamino, pyrimidinylcarbonylamino, pyridazinylcarbonylamino, thiazolylcarbonylamino, oxazolylcarbonylamino, oxadiazolylcarbonylamino, thiadiazolylcarbonylamino, N,N-diacetylamino, N-formyl-N-hexylamino, N-acetyl-N-methylamino, N-acetyl-N-ethylamino, N-acetyl-N-propylamino, N-acetyl-N-butylamino, N-acetyl-N-pentylamino, N-acetyl-N-hexylamino, N-benzoyl-N-methylamino, N-benzoyl-N-ethylamino, N-benzoyl-N-propylamino, N-benzoyl-N-butylamino, N-benzoyl-N-pentylamino, N-benzoyl-N-hexylamino, N-benzoyl-N-phenylamino, N-benzyl-N-benzoylamino, N-4-trifluoromethylbenzyl-N-2,4-difluorobenzoylamino, N-2,4-difluorobenzyl-N-nicotinoylamino, N-3-chlorobenzoyl-N-methylamino, N-3-chlorobenzoyl-N-hexylamino, N-3-chlorobenzoyl-N-acetylamino, N-2,4-difluorobenzoyl-N-hexylamino, N-2,4-difluorobenzoyl-N-phenylamino, N-2,4-difluorobenzoyl-N-phenylamino, N-4-trifluoromethylbenzoyl-N-butylamino, N-3,5-di-t-butyl-4-hydroxybenzoyl-N-hexylamino, N-hexyl-N-1-naphthoylamino, N-hexyl-N-2-naphthoylamino, N-hexyl-N-phenylacetylamino, N-isobutyl-N-cycloheptanoylamino, N-butyl-N-nicotinoylamino, N-hexyl-N-nicotinoylamino and N-isonicotinoyl-N-hexylamino groups, of which amino groups, amino groups substituted with one or two substituents (said substituents may be the same or different and each independently represents a group selected from the class consisting of $C_{1-10}$ alkyl groups and $C_{6-10}$ aryl and $C_{7-16}$ aralkyl groups which may each have substituents) and acylamino groups which may be substituted with a substituent selected from Substituents γ (the acylamino group means an amino group substituted with the above-described acyl group) are preferred; amino groups, mono- or di-$C_{1-10}$ alkylamino groups and acylamino groups which may each be substituted with a $C_{1-10}$ alkyl group or a $C_{7-16}$ aralkyl group which may have a substituent are more preferred; amino, mono- or di-$C_{1-10}$ aralkylamino groups or $C_{7-11}$ aromatic acylamino, $C_{4-11}$ cycloalkylcarbonylamino and 5- or 6-membered aromatic nitrogen-containing heterocyclic carbonylamino groups which may each have a substituent are still more preferred; and amino, dimethylamino, hexylamino, acetylamino, benzoylamino, 3-chlorobenzoylamino, 2,4-difluorobenzoylamino, 4-hydroxy-3,5-di-t-butylbenzoylamino, naphthoylamino, cyclopentanoylamino, cyclohexanoylamino, nicotinoylamino, isonicotinoylamino, N-acetyl-N-hexylamino and adamantylcarbonylamino groups are particularly preferred.

The $C_{3-10}$ cycloalkyl part of the "$C_{3-10}$ cycloalkyl group which may be substituted with 1 to 3 substituents selected from Substituents β" has the same meaning as described above. Preferred examples include $C_{3-10}$ cycloalkyl groups which may each be substituted with one substituent selected from Substituents β, of which $C_{3-10}$ cycloalkyl groups which may each be substituted with one substituent selected from the group consisting of halogen atoms and $C_{1-6}$ alkyl and halogeno($C_{1-6}$ alkyl) groups; adamantyl groups which may be substituted with one fluorine atom, chlorine atom, hydroxyl group, methyl group, ethyl group, t-butyl group, trifluoromethyl group, methoxy group, amino group, methylamino group or dimethylamino group is more preferred; and an adamantyl group is particularly preferred.

In the above description, the $C_{6-10}$ aryl part of the "$C_{6-10}$ aryl group" of the "$C_{6-10}$ aryl group which may be substituted with 1 to 3 substituents selected from Substituents β" in the definitions of $R^6$ and Substituents α, and that of the "$C_{6-10}$ aryl group" or in the definition of Substituents β has the same meaning as described above. As $R^6$, preferred are phenyl groups which may be substituted with 1 to 3 substituents selected from the group consisting of halogen atoms and hydroxyl, $C_{1-6}$ alkyl and halogeno($C_{1-6}$ alkyl) groups and particularly preferred are phenyl groups which may each be substituted with one substituent selected from the group consisting of fluorine and chlorine atoms, and hydroxyl, methyl, ethyl and trifluoromethyl groups. With reference to Substituents α, preferred are $C_{6-10}$ aryl groups which may each be substituted with one substituent selected from Substituents β; more preferred are $C_{6-10}$ aryl groups which may each be substituted with one amino group which may be substituted with a halogen atom, a hydroxyl group, a $C_{1-6}$ alkyl group, a halogeno($C_{1-6}$ alkyl) group, a $C_{1-6}$ alkoxy group or a substituent selected from Substituents γ; still more preferred are phenyl groups which may be substituted with one fluorine atom, chlorine atom, hydroxyl group, methyl group, ethyl group, t-butyl group, trifluoromethyl group, methoxy group, amino group, methylamino group or dimethylamino group; and particularly preferred is a phenyl or 4-hydroxyphenyl group. With reference to Substituents β, preferred is a phenyl group.

In the above description, the $C_{7-16}$ aralkyl part of the "$C_{7-16}$ aralkyl group which may be substituted with 1 to 3 substituents selected from Substituents β" in the definition of $R^6$ or Substituents α has the same meaning as described above. With reference to $R^6$, preferred are benzyl groups which may be substituted with 1 to 3 substituents selected from the group consisting of halogen atoms and hydroxyl, $C_{1-6}$ alkyl and halogeno($C_{1-6}$ alkyl) groups and particularly preferred are benzyl groups which may be substituted with a substituent selected from the group consisting of fluorine and chlorine atoms and hydroxyl, methyl, ethyl and trifluoromethyl groups. In reference to Substituent α, preferred are $C_{7-16}$ aralkyl groups which may each be substituted with one substituent selected from Substituents β; more preferred are benzyl groups which may be substituted with an amino group which may be substituted with a substituent selected from a halogen atom, hydroxyl group, $C_{1-6}$ alkyl group, halogeno($C_{1-6}$ alkyl) group, $C_{1-6}$ alkoxy group and Substituents γ; still more preferred are benzyl groups which may be substituted with one fluorine atom, chlorine atom, hydroxyl group, methyl group, ethyl group, t-butyl group, trifluoromethyl group, methoxy group, amino group, methylamino group or dimethylamino group; and particularly preferred are benzyl groups.

In the above description, the $C_{6-10}$ aryloxy part of the "$C_{6-10}$ aryloxy group which may be substituted with 1 to 3 substituents selected from Substituents β" means the above-described $C_{6-10}$ aryl group bound to an oxygen atom and examples include phenoxy, 1-indenyloxy, 2-indenyloxy, 3-indenyloxy, 1-naphthyloxy and 2-naphthyloxy groups, of which phenoxy groups are preferred.

In the above description, the $C_{7-16}$ aralkyloxy part of the "$C_{7-16}$ aralkyloxy group which may be substituted with 1 to 3 substituents selected from Substituents β" in the definition of Substituents α means the above-described $C_{7-16}$ aralkyl group bound to an oxygen atom and examples include benzyloxy, naphthylmethoxy, indenylmethoxy, diphenylmethoxy, 1-phenethyloxy, 2-phenethyloxy, 1-naphthylethoxy, 2-naphthylethoxy, 1-phenylpropoxy, 2-phenylpropoxy, 3-phenylpropoxy, 1-naphthylpropoxy, 2-naphthylpropoxy, 3-naphthylpropoxy, 1-phenylbutoxy, 2-phenylbutoxy, 3-phenylbutoxy, 4-phenylbutoxy, 1-naphthylbutoxy, 2-naphthylbutoxy, 3-naphthylbutoxy, 4-naphthylbutoxy, 5-phenylpentyloxy, 5-naphthylpentyloxy, 6-phenylhexyloxy and 6-naphthylhexyloxy groups, of which benzyloxy groups are preferred.

In the above description, the $C_{6-10}$ arylthio part of the "$C_{6-10}$ arylthio group which may be substituted with 1 to 3 substituents selected from Substituents β" means the above-described $C_{6-10}$ aryl group bound to a sulfur atom and examples include phenylthio, 1-indenylthio, 2-indenylthio, 3-indenylthio, 1-naphthylthio and 2-naphthylthio groups, of which phenylthio groups are preferred.

In the above description, the "$C_{1-7}$ aliphatic acyloxy group" in the definition of Substituents α is the above-exemplified $C_{1-7}$ aliphatic acyl group bound to an oxygen atom. Examples include formyloxy, acetoxy, propionyloxy, butyryloxy, isobutyryloxy, valeryloxy, isovaleryloxy, pivaloyloxy, hexanoyloxy, acryloyloxy, methacryloyloxy and crotonoyloxy groups, of which acetoxy groups are preferred.

In the above description, the "4- to 7-membered saturated nitrogen-containing heterocyclic group" in the definition of Substituents α means a 4- to 7-membered saturated heterocyclic group which contains at least one nitrogen atom and at the same time may contain further hetero atoms selected from the hetero atom group consisting of nitrogen, oxygen and sulfur atoms. Examples include azetidinyl, pyrrolidinyl, imidazolidinyl, thiazolidinyl, pyrazolidinyl, piperidinyl, morpholinyl, thiomorpholinyl, piperazinyl and homopiperazinyl groups, of which pyrrolidinyl, piperidinyl and morpholinyl groups are preferred and pyrrolidin-1-yl, piperidin-1-yl and morpholin-4-yl groups are particularly preferred.

In the above description, the "5- or 6-membered aromatic nitrogen-containing heterocyclic group" in the definition of Substituents α has the same meaning as defined above and preferred are imidazolyl, tetrazolyl and pyridinyl groups, of which pyridin-2-yl and pyridin-3-yl groups are particularly preferred.

In the above description, the "phenyl group substituted with 1 to 5 substituents selected from Substituents α" in the definition of $R^4$ is a phenyl group substituted with 1 to 5 substituents selected from the group consisting of halogen atoms; hydroxyl groups; $C_{1-6}$ alkyl groups; halogeno($C_{1-6}$ alkyl) groups; $C_{1-6}$ alkoxy groups; $C_{1-6}$ alkylthio groups; amino groups which may be substituted with a substituent selected from Substituents γ; $C_{3-10}$ cycloalkyl, $C_{6-10}$ aryl, $C_{7-16}$ aralkyl, $C_{6-10}$ aryloxy, $C_{7-16}$ aralkyloxy and $C_{6-10}$ arylthio groups which may each be substituted with 1 to 3 substituents selected from Substituents β; $C_{1-7}$ aliphatic acyloxy groups; 4- to 7-membered saturated nitrogen-containing heterocyclic groups; 5- or 6-membered aromatic nitrogen-containing heterocyclic groups; nitro groups; and cyano groups. Examples include 2-, 3- or 4-fluorophenyl, 2-, 3- or 4-chlorophenyl, 2-, 3- or 4-bromophenyl, 2-, 3- or 4-iodophenyl, 2,4-difluorophenyl, 3,5-difluorophenyl, pentafluorophenyl, 3,5-dichlorophenyl, 2-, 3- or 4-hydroxyphenyl, 3,5-dihydroxyphenyl, 2-, 3- or 4-methylphenyl, 2-, 3- or 4-ethylphenyl, 2-, 3- or 4-propylphenyl, 2-, 3- or 4-isopropylphenyl, 2-, 3- or 4-butylphenyl, 2-, 3- or 4-s-butylphenyl, 2-, 3- or 4-t-butylphenyl, 2-, 3- or 4-trifluoromethylphenyl, 2-, 3- or 4-methoxyphenyl, 2-, 3- or 4-ethoxyphenyl, 2-, 3- or 4-propoxyphenyl, 2-, 3- or 4-isopropoxyphenyl, 2-, 3- or 4-butoxyphenyl, 2-, 3- or 4-s-butoxyphenyl, 2-, 3- or 4-t-butoxyphenyl, 2-, 3- or 4-methylthiophenyl, 2-, 3- or 4-ethylthiophenyl, 2-, 3- or 4-isopropylthiophenyl, 2-, 3- or 4-aminophenyl, 3,5-diaminophenyl, 2-, 3- or 4-methylaminophenyl, 2-, 3- or 4-dimethylaminophenyl, 2-, 3- or 4-(N-ethyl-N-methylamino)phenyl, 2-, 3- or 4-diethylaminophenyl, 2-, 3- or 4-(n-pentylamino)phenyl, 2-, 3- or 4-(n-hexylamino)phenyl, 2-, 3- or 4-phenylaminophenyl, 2-, 3- or 4-benzylaminophenyl, 2-, 3- or 4-formylaminophenyl, 2-, 3- or 4-acetylaminophenyl, 2-, 3- or 4-propionylaminophenyl, 2-, 3- or 4-benzoylaminophenyl, 2-, 3- or 4-(2-, 3- or 4-fluorobenzoylamino)phenyl, 2-, 3- or 4-(2-, 3- or 4-chlorobenzoylamino)phenyl, 2-, 3- or 4-(2,4-difluorobenzoylamino)phenyl, 2-, 3- or 4-(4-hydroxy-3,5-dimethylbenzoylamino)phenyl, 2-, 3- or 4-(4-hydroxy-3,5-di-t-butylbenzoylamino)phenyl, 2-, 3- or 4-(1- or 2-naphthoylamino)phenyl, 2-, 3- or 4-phenylacetylaminophenyl, 2-, 3- or 4-(2-, 3- or 4-fluorophenylacetylamino)phenyl, 2-, 3- or 4-(2-, 3- or 4-chlorophenylacetylamino)phenyl, 2-, 3- or 4-(3-phenylpropionylamino)phenyl, 2-, 3- or 4-cyclopentanoylaminophenyl, 2-, 3- or 4-cyclohexanoylaminophenyl, 2-, 3- or 4-nicotinoylaminophenyl, 2-, 3- or 4-isonicotinoylaminophenyl, 2-, 3- or 4-(N-acetyl-N-methylamino)phenyl, 2-, 3- or 4-(N-acetyl-N-pentylamino)phenyl, 2-, 3- or 4-(N-acetyl-N-hexylamino)phenyl, 2-, 3- or 4-(N-benzoyl-N-hexylamino)phenyl, 2-, 3- or 4-(N-3-chlorobenzoyl-N-methylamino)phenyl, 2-, 3- or 4-(N-3-chlorobenzoyl-N-hexylamino)phenyl, 2-, 3- or 4-(N-2,4-difluorobenzoyl-N-hexylamino)phenyl, 2-, 3- or 4-[N-(1- or 2-naphthoyl)-N-hexylamino]phenyl, 2-, 3- or 4-(N-hexyl-N-phenylacetylamino)phenyl, 2-, 3- or 4-(N-isobutyl-N-cycloheptanoyl)amino)phenyl, 2-, 3- or 4-(N-butyl-N-nicotinoylamino)-phenyl, 2-, 3- or 4-cyclopentylphenylyl, 2-, 3- or 4-cyclohexylphenylyl, 2-, 3- or 4-(1-adamantyl)phenyl, 2-, 3- or 4-biphenylyl, 2-, 3- or 4-(2'-, 3'- or 4'-hydroxy)-biphenylyl, 2-, 3- or 4-(4-hydroxy-3,5-dimethylphenyl)phenyl, 2-, 3- or 4-(4-hydroxy-3,5-diisopropylphenyl)phenyl, 2-, 3- or 4-(3,5-di-t-butyl-4-hydroxyphenyl)phenyl, 2-, 3- or 4-benzylphenyl, 2-, 3- or 4-(4-hydroxybenzyl)phenyl, 2-, 3- or 4-(4-hydroxy-3,5-dimethylbenzyl)phenyl, 2-, 3- or 4-(3,5-di-t-butyl-4-hydroxybenzyl)phenyl, 2-, 3- or 4-phenoxyphenyl, 2-, 3- or 4-(4-hydroxyphenoxy)phenyl, 2-, 3- or 4-(4-hydroxy-3,5-dimethylphenoxy)phenyl, 2-, 3- or 4-(3,5-di-t-butyl-4-hydroxyphenoxy)phenyl, 2-, 3- or 4-benzyloxyphenyl, 2-, 3- or 4-(4-hydroxybenzyloxy)phenyl, 2-, 3- or 4-(4-hydroxy-3,5-dimethylbenzyloxy)phenyl, 2-, 3- or 4-(3,5-di-t-butyl-4-hydroxybenzyloxy)phenyl, 2-, 3- or 4-phenylthiophenyl, 2-, 3- or 4-(4-hydroxyphenylthio)phenyl, 2-, 3- or 4-(3,5-dimethyl-4-hydroxyphenylthio)phenyl, 2-, 3- or 4-(3,5-di-t-butyl-4-hydroxyphenylthio)phenyl, 2-, 3- or 4-formyloxyphenyl, 2-, 3- or 4-acetoxyphenyl, 2-, 3- or 4-propionyloxyphenyl, 2-, 3- or 4-(1 -azetidinyl)phenyl 2-, 3- or 4-(1-, 2- or 3-pyrrolidinyl)phenyl, 2-, 3- or 4-(1-, 2-, 3- or 4-piperidinyl)phenyl, 2-, 3- or 4-(2-, 3- or 4-morpholinyl)phenyl, 2-, 3- or 4-(2-, 3- or 4-thiomorpholinyl)phenyl, 2-, 3- or 4-(1- or 2-piperazinyl)phenyl, 2-, 3- or 4-(1-, 2- or 4-imidazolyl)phenyl, 2-, 3- or 4-(teterazol-5-yl)phenyl, 2-, 3- or 4-(2-, 3- or 4-pyridyl)phenyl, 2-, 3- or 4-nitrophenyl, 2-, 3- or 4-cyanophenyl, 2- or 3-chloro-4-hydroxyphenyl, 4-chloro-3,5-dihydroxyphenyl, 3,5-dichloro-4-hydroxyphenyl, 2-fluoro-4-hydroxy-3,5-dimethylphenyl, 3-fluoro-5-hydroxy-2,6-dimethylphenyl, 4-fluoro-3-hydroxy-2,5-dimethylphenyl, 2-chloro-4-hydroxy-3,5-dimethylphenyl, 3-chloro-5-hydroxy-2,6-dimethylphenyl, 4-chloro-3-hydroxy-2,5-dimethylphenyl, 2- or 3-amino-4-chlorophenyl, 2,3-dichloro-4-aminophenyl, 2- or 3-chloro-4-methylaminophenyl, 2-hydroxy-3- or 4-methylphenyl, 2-hydroxy-3,4-dimethylphenyl, 3-hydroxy-4- or 5-methylphenyl, 3-hydroxy-2,4-dimethylphenyl, 4-hydroxy-2- or 3-methylphenyl, 2- or 3-ethyl-4-hydroxyphenyl, 4-hydroxy-2- or 3-propylphenyl, 4-hydroxy-2- or 3-isopropylphenyl, 2- or 3-t-butyl-4-hydroxyphenyl, 4-hydroxy-2,3-dimethylphenyl, 4-hydroxy-2,5-dimethylphenyl, 4-hydroxy-3,5-dimethylphenyl, 3,5-diethyl-4-hydroxyphenyl, 3-t-butyl-4-hydroxy-5-methylphenyl, 4-hydroxy-3,5-dipropylphenyl, 4-hydroxy-3,5-diisopropylphenyl, 2,5-di-t-butyl-4-hydroxyphenyl, 3,5-di-t-butyl-4-hydroxyphenyl, 4-hydroxy-2,3,5-trimethylphenyl, 4-hydroxy-2,3,6-trimethylphenyl, 4-hydroxy-2,3,5,6-tetramethylphenyl, 4-hydroxy-3,5-dimethoxyphenyl, 2- or 3-hydroxy-4-dimethylaminophenyl, 4-benzyl-(2- or 3-hydroxy)phenyl, 3-, 5- or 6-benzyl-2-hydroxyphenyl, 3-hydroxy-4-nitrophenyl, 3-amino-4-methylphenyl, 4-amino-2,3-dimethylphenyl, 4-amino-2,6-dimethylphenyl, 4-amino-3,5-dimethylphenyl, 4-amino-3,5-diethylphenyl, 4-amino-3,5-dipropylphenyl, 4-amino-3,5-diisopropylphenyl, 4-amino-3,5-di-t-butylphenyl, 4-methylamino-3,5-dimethylphenyl, 4-(N-ethyl-N-methylamino)-3,5-dimethylphenyl, 4-acetylamino-3,5-dimethylphenyl, 4-acetylamino-3,5-di-t-butylphenyl, 4-benzoylamino-3,5-dimethylphenyl, 4-acetoxy-3,5-dimethylphenyl, 4-acetoxy-2,3,5-trimethylphenyl and 3,5-dimethyl-4-nitrophenyl groups.

In the above description, the "pyridyl group which may be substituted with 1 to 4 substituents selected from Substituents α" in the definition of $R^4$ is a pyridyl group which may be substituted with 1 to 4 substituents selected from the group consisting of halogen atoms; hydroxyl groups; $C_{1-6}$ alkyl groups; halogeno($C_{1-6}$ alkyl) groups; $C_{1-6}$ alkoxy groups; $C_{1-6}$ alkylthio groups; amino groups which may each be substituted with substituents selected from Substituents γ; $C_{3-10}$ cycloalkyl, $C_{6-10}$ aryl, $C_{7-16}$ aralkyl, $C_{6-10}$ aryloxy, $C_{7-16}$ aralkyloxy and $C_{6-10}$ arylthio groups which may each be substituted with 1 to 3 substituents selected from Substituents β; $C_{1-7}$ aliphatic acyloxy groups; 4- to 7-membered saturated nitrogen-containing heterocyclic groups; 5- or 6-membered aromatic nitrogen-containing heterocyclic groups; nitro groups; and cyano groups. Examples include 2-, 3- or 4-pyridyl, 3-, 4-, 5- or 6-fluoro-2-pyridyl, 2-, 4-, 5- or 6-fluoro-3-pyridyl, 2- or 3-fluoro-4-pyridyl, 3-, 4-, 5- or 6-chloro-2-pyridyl, 2-, 4-, 5- or 6-chloro-3-pyridyl, 2- or 3-chloro-4-pyridyl, 3-, 4-, 5- or 6-bromo-2-pyridyl, 2-, 4-, 5- or 6-bromo-3-pyridyl, 2- or 3-bromo-4-pyridyl, 3-, 4-, 5- or 6-iodo-2-pyridyl, 2-, 4-, 5- or 6-iodo-3-pyridyl, 2- or 3-iodo-4-pyridyl, 3-, 4-, 5- or 6-hydroxy-2-pyridyl, 2-, 4-, 5- or 6-hydroxy-3-pyridyl, 2- or 3-hydroxy-4-pyridyl, 3-, 4-, 5- or 6-methyl-2-pyridyl, 2-, 4-, 5- or 6-methyl-3-pyridyl, 2- or 3-methyl-4-pyridyl, 3,5-dimethyl-4-pyridyl, 3-, 4-, 5- or 6-ethyl-2-pyridyl, 2-, 4-, 5- or 6-ethyl-3-pyridyl, 2- or 3-ethyl-4-pyridyl, 3,5-diethyl-4-pyridyl, 3-, 4-, 5- or 6-propyl-2-pyridyl, 2-, 4-, 5- or 6-propyl-3-pyridyl, 2- or 3-propyl-4-pyridyl, 3,5-dipropyl-4-pyridyl, 3-, 4-, 5- or 6-isopropyl-2-pyridyl, 2-, 4-, 5- or 6-isopropyl-3-pyridyl, 2- or 3-isopropyl-4-pyridyl, 3,5-diisopropyl-4-pyridyl, 3-, 4-, 5- or 6-t-butyl-2-pyridyl, 2-, 4-, 5- or 6-t-butyl-3-pyridyl, 2- or 3-t-butyl-4-pyridyl, 3,5-di-t-butyl-4-pyridyl, 3-, 4-, 5- or 6-trifluoromethyl-2-pyridyl, 2-, 4-, 5- or 6-trifluoromethyl-3-pyridyl, 2- or 3-trifluoromethyl-4-pyridyl, 3-, 4-, 5- or 6-methoxy-2-pyridyl, 2-, 4-, 5- or 6-methoxy-3-pyridyl, 2- or 3-methoxy- 4-pyridyl, 3-, 4-, 5- or 6-ethoxy-2-pyridyl, 2-, 4-, 5- or 6-ethoxy-3-pyridyl, 2- or 3-ethoxy-4-pyridyl, 3-, 4-, 5- or 6-propoxy-2-pyridyl, 2-, 4-, 5- or 6-propoxy-3-pyridyl, 2- or 3-propoxy-4-pyridyl, 3-, 4-, 5- or 6-isopropoxy-2-pyridyl, 2-, 4-, 5- or 6-isopropoxy-3-pyridyl, 2- or 3-isopropoxy-4-pyridyl, 3-, 4-, 5- or 6-t-butoxy-2-pyridyl, 2-, 4-, 5- or 6-t-butoxy-3-pyridyl, 2- or 3-t-butoxy-4-pyridyl, 4-methylthio-2-pyridyl, 6-isopropylthio-3-pyridyl, 6-t-butylthio-2-pyridyl, 3-, 4-, 5- or 6-amino-2-pyridyl, 2-, 4-, 5- or 6-amino-3-pyridyl, 2- or 3-amino-4-pyridyl, 3-, 4-, 5- or 6-methylamino-2-pyridyl, 2-, 4-, 5- or 6-methylamino-3-pyridyl, 2- or 3-methylamino-4-pyridyl, 5-phenylamino-2-pyridyl, 5-benzylamino-2-pyridyl, 5-acetylamino-2-pyridyl, 5-benzoylamino-2-pyridyl, 5-phenylacetylamino-2-pyridyl, 6-phenyl-2-pyridyl, 6-(4-hydroxyphenyl)-2-pyridyl, 6-(4-hydroxy-3,5-dimethylphenyl)-2-pyridyl, 6-(3,5-di-t-butyl-4-hydroxyphenyl)-2-pyridyl, 6-benzyl-2-pyridyl, 6-(4-hydroxybenzyl)-2-pyridyl, 6-(4-hydroxy-3,5-dimethylbenzyl)-2-pyridyl, 6-(3,5-di-t-butyl-4-hydroxybenzyl)-2-pyridyl, 6-phenoxy-2-pyridyl, 6-(4-hydroxyphenoxy)-2-pyridyl, 6-(4-hydroxy-3,5-dimethylphenoxy)-2-pyridyl, 6-(3,5-di-t-butyl-4-hydroxyphenoxy)-2-pyridyl, 6-benzyloxy-2-pyridyl, 6-(4-hydroxybenzyloxy)-2-pyridyl, 6-(4-hydroxy-3,5-dimethylbenzyloxy)-2-pyridyl, 6-(3,5-di-t-butyl-4-hydroxybenzyloxy)-2-pyridyl, 6-phenylthio-2-pyridyl, 6-(4-hydroxyphenylthio)-2-pyridyl, 6-(4-hydroxy-3,5-dimethylphenylthio)-2-pyridyl, 6-(3,5-di-t-butyl-4-hydroxyphenylthio)-2-pyridyl, 3-, 4-, 5- or 6-formyloxy-2-pyridyl, 2-, 4-, 5- or 6-formyloxy-3-pyridyl, 2- or 3-formyloxy-4-pyridyl, 3-, 4-, 5- or 6-acetoxy-2-pyridyl, 2-, 4-, 5- or 6-acetoxy-3-pyridyl, 2- or 3-acetoxy-4-pyridyl, 6-(1-pyrrolidinyl)-2-pyridyl, 6-(1-piperidinyl)-2-pyridyl, 6-(4-morpholinyl)-2-pyridyl, 3-, 4-, 5- or 6-nitro-2-pyridyl, 2-, 4-, 5- or 6-nitro-3-pyridyl, 2- or 3-nitro-4-pyridyl, 5-amino-6-fluoro-2-pyridyl, 5-amino-6-chloro-2-pyridyl, 6-chloro-3-nitro-2-pyridyl, 6-methoxy-5-methyl-3-pyridyl, 6-methyl-2-nitro-3-pyridyl, 6-chloro-3-nitro-2-pyridyl, 6-methoxy-3-nitro-2-pyridyl, 6-isopropoxy-3-nitro-2-pyridyl, 6-t-butoxy-3-nitro-2-pyridyl and 6-(4-hydroxy-3,5-dimethylphenoxy)-5-nitro-2-pyridyl groups.

As such a "pyridyl group which may be substituted with 1 to 4 substituents selected from Substituents α", preferred are pyridyl groups which may be substituted with the following substituents (said substituents are halogen atoms, hydroxyl groups, $C_{1-6}$ alkyl groups, halogeno($C_{1-6}$ alkyl) groups, $C_{1-6}$ alkoxy groups, $C_{1-6}$ alkylthio groups, amino groups which may be substituted with substituents selected from Substituents γ and nitro groups); more preferred are pyridyl groups which may be substituted with the following substituents (said substituents are fluorine atoms, chlorine atoms, hydroxyl groups, methyl groups, ethyl groups, t-butyl groups, trifluoromethyl groups, methoxy groups, amino groups, methylamino groups, dimethylamino groups and nitro groups); and particularly preferred are pyridyl groups.

In the above description, the "$C_{1-6}$ alkylene group" in the definition of A is a linear or branched $C_{1-6}$ alkylene group. Examples include methylene, methylmethylene, ethylene, propylene, trimethylene, methylethylene, ethylethylene, tetramethylene, 1-methyltrimethylene, 2-methyltrimethylene, 3-methyltrimethylene, 1,1-dimethylethylene, pentamethylene, 1-methyltetramethylene, 2-methyltetramnethylene, 3-methyltetramethylene, 4-methyltetramethylene, propylethylene, 1,1-dimethyltrimethylene, 2,2-dimethyltrimethylene, 3,3-dimethyltrimethylene, hexamethylene, 1-methylpentamethylene, 2-methylpentamethylene, 3-methylpentamethylene, 4-methylpentamethylene, 5-methylpentamethylene, 1,1-dimethyltetramethylene, 2,2-dimethyltetramethylene, 3,3-dimethyltetramethylene, 4,4-dimethyltetramethylene, butylethylene and isobutylethylene, of which $C_{1-4}$ alkylene groups are preferred, $C_{1-2}$ alkylene groups are more preferred and methylene groups are most preferred.

The compound (I) of the present invention can be converted into its salt by a conventional method. Examples of such salts include alkali metal salts such as sodium salts, potassium salts and lithium salts; alkaline earth metal salts such as calcium salts and magnesium salts; metal salts such as aluminum salts, iron salts, zinc salts, copper salts, nickel salts and cobalt salts; inorganic salts such as ammonium salts and organic amine salts such as t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-N-phenethylamine salts, piperazine salts, tetramethylammonium salts and tris(hydroxymethyl)aminemethane salts; hydrohalogenated salts such as hydrofluoric acid salts, hydrochlorides, hydrobromides and hydroiodides; inorganic acid salts such as nitrates, perchlorates, sulfates and phosphates; lower alkanesulfonate salts such as methanesulfonates, trifluoromethanesulfonates and ethanesulfonates; arylsulfonate salts such as benzensulfonates and p-toluenesulfonates; organic acid salts such as acetates, malates, fumarates, succinates, citrates, tartrates, oxalates and maleates; and amino acid salts such as ornithinates, glutamates and aspartates, of which hydrohalogenated salts and organic acid salts are preferred.

When the compound (I) of the present invention is left in air or is recrystallized, it can absorb water or has adsorbed water attached on the surface and sometimes becomes a hydrate. In addition, the compound (I) of the present invention can absorb other solvents and form their solvates. Such solvates (including hydrates) are embraced in the present invention and are included when reference is made to a substituted fused heterocyclic compound (I) or a pharmacologically acceptable salt thereof.

Furthermore, compounds which are converted under physiological conditions into the corresponding compound (I) or a pharmacologically acceptable salt thereof, that is, so-called prodrugs are also embraced in the present invention.

Incidentally, the compound (I) of the present invention has various isomers.

Described specifically, when $R^3$ represents a 2,4-dioxothiazolidin-5-ylmethyl group (IV-2) or 2,4-dioxooxazolidin-5-ylmethyl (IV-3), the thiazolidine or oxazolidine ring of it has an asymmetric carbon atom at the 5-position so that there exist stereoisomers in the R-form and S-form. Each of the stereoisomers and a mixture composed of the stereoisomers at any ratio are all embraced in the present invention. In the case of such a stereoisomer, the compound (I) can be synthesized from optically resolved raw materials or the synthesized compound (I) can be optically resolved, if necessary, by a conventional optical resolution method or separation method.

When in the compound (I) of the present invention, $R^3$ represents a 2,4-dioxothiazolin-5-ylmethyl group (IV-2), 2,4-dioxooxazolidin-5-ylmethyl group (IV-3) or 3,5-dioxooxadiazolidin-2-ylmethyl group (IV-4), it is presumed to exist as various tautomers and each of them or a mixture of them at any ratio are all embraced in the present invention. Such isomers are, for example, as illustrated below:

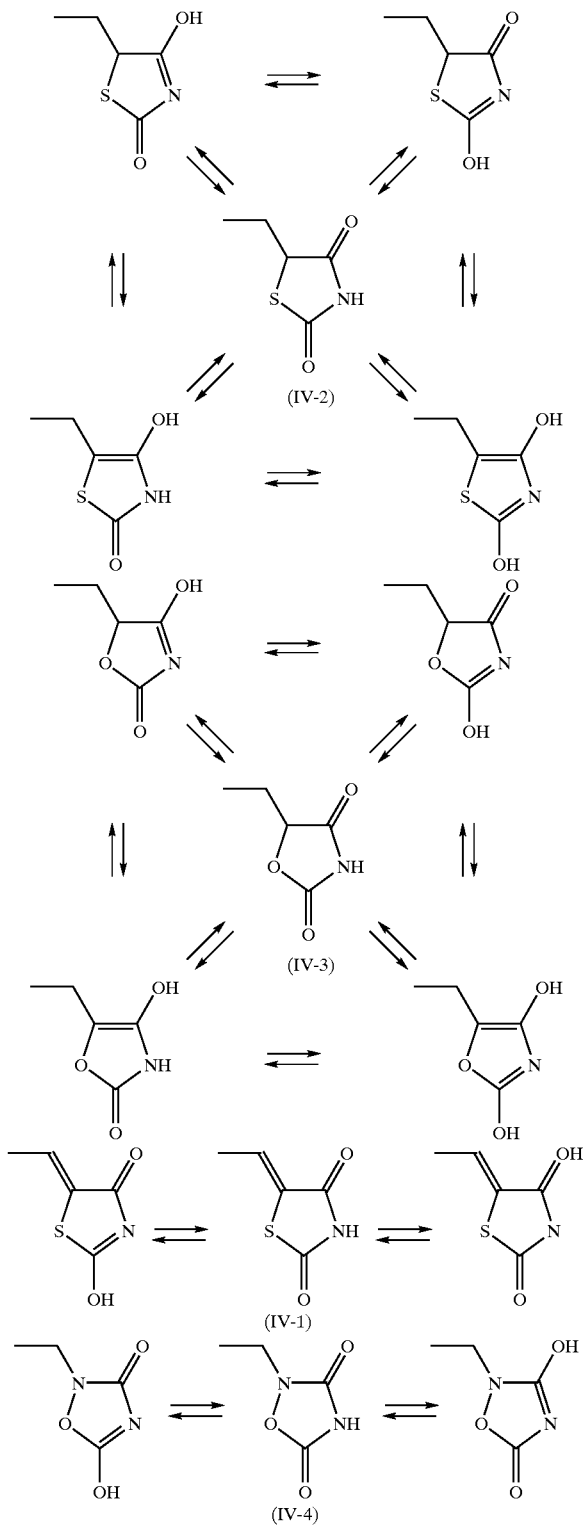

Examples of medicaments which may form a pharmaceutical composition, when used in combination with a compound (I) of the present invention or a pharmacologically acceptable salt thereof include α-glucosidase inhibitors, aldose reductase inhibitors, biguanide preparations, statin base compounds, squalene synthesis inhibitors, fibrate base compounds, LDL catabolism promoters and angiotensin-converting enzyme inhibitors.

In the above description, an α-glucosidase inhibitor is a medicament having action in inhibiting a digestive enzyme such as amylase, maltase, α-dextrinase or sucrase, thereby retarding the digestion of starch or sucrose. Examples of them include acarbose, N-(1,3-dihydroxy-2-propyl) variolamine (common name: voglibose) and miglitol.

In the above description, an aldose reductase inhibitor is a medicament which inhibits a rate-limiting enzyme of the first step of the polyol pathway, thereby inhibiting diabetic complications. Examples include tolrestat, epalrestat, 2,7-difluoro-spiro(9H-fluoren-9,4'-imidazolidine)-2',5'-dione (common name: imirestat), 3-[(4-bromo-2-fluorophenyl)methyl]-7-chloro-3,4-dihydro-2,4-dioxo-1(2H)-quinozolineacetic acid (common name: zenarestat), 6-fluoro-2,3-dihydro-2,5'-dioxo-spiro[4H-1-benzopyran-4,4'-imidazolidine]-2-carboxamide (SNK-860), zopolrestat, sorbinil and 1-[(3-bromo-2-benzofuranyl)sulfonyl]-2,4-imidazolidinedione (M-16209).

In the above description, a biguanide preparation is a medicament having effects in anaerobic glycolysis promotion, insulin action reinforcement at the periphery, intestinal glucose absorption inhibition, hepatic gluconeogenesis inhibition and fatty-acid oxidation inhibition and examples include phenformin, metformin and buformin.

In the above description, a statin base compound is a medicament which inhibits hydroxymethylglutaryl CoA (HMG-CoA) reductase, thereby lowering the blood cholesterol level and examples include pravastatin and the sodium salt thereof, simvastatin, lovastatin, atorvastatin and fluvastatin.

In the above description, a squalene synthesis inhibitor is a medicament for inhibiting squalene synthesis, thereby lowering the blood cholesterol level and examples include monopotassium (S)-α-[bis(2,2-dimethyl-1-oxopropoxy)methoxy]phosphinyl-3-phenoxybenzenebutanesulfonate (BMS-188494).

In the above description, a fibrate base compound is a medicament for inhibiting synthesis and secretion of triglycerides in the liver and activating lipoprotein lipase, thereby lowering the triglyceride level in the blood. Examples include bezafibrate, beclobrate, binifibrate, ciprofibrate, clinofibrate, clofibrate, clofibric acid, ethofibrate, fenofibrate, gemfibrozil, nicofibrate, pirifibrate, ronifibrate, simfibrate and theofibrate.

In the above description, a LDL catabolism promoter is a medicament for increasing LDL (low-density lipoprotein) receptors, thereby lowering the blood cholesterol level and examples include compounds described in Japanese Patent Application Kokai Hei 7-316144 or salts thereof, more specifically, N-[2-[4-bis(4-fluorophenyl)methyl-1-piperazinyl]ethyl]-7,7-diphenyl-2,4,6-heptatrienoic amide.

The above-described statin base compounds, squalene synthesis inhibitors, fibrate base compounds and LDL catabolism promoters can be replaced with another chemical effective for lowering the blood cholesterol or triglyceride level. Examples of such a medicament include nicotinic acid derivative preparations such as nicomol and niceritrol; antioxidants such as probucol; and ion exchange resin preparations such as cholestyramine.

In the above description, an angiotensin-converting enzyme inhibitor is a medicament for inhibiting angiotensin-converting enzyme, thereby lowering the blood pressure and at the same time, partially lowering the blood sugar level of a patient suffering from diabetes. Examples include captopril, enalapril, alacepril, delapril, ramipril, lisinopril, imidapril, benazepril, ceronaprilI cilazapril, enalaprilat, fosinopril, moveltipril, perindopril, quinapril, spirapril, temocapril and trandolapril.

In reference to the compound (I) of the present invention, preferred examples include:

(1) compounds wherein $R^1$ represents a group of the formula (II), (2) compounds wherein $R^2$ and $R^5$ are the same or different and represent a hydrogen atom, a halogen atom, a hydroxyl group, a $C_{1-6}$ alkyl group, a halogeno($C_{1-6}$ alkyl) group, a $C_{1-6}$ alkoxy group, a $C_{1-6}$ alkylthio group or an amino group which may be substituted with substituents selected from Substituents γ, (3) compounds wherein $R^2$ and $R^5$ are the same or different and each represents a hydrogen atom, a fluorine atom, a chlorine atom, a hydroxyl group, a methyl group, an ethyl group, a trifluoromethyl group, a methoxy group, a methylthio group or an amino group, (4) compounds wherein $R^2$ and $R^5$ each represent a hydrogen atom, (5) compounds wherein $R^3$ represents a group of any one of the formulas (IV-1) to (IV-3), (6) compounds wherein $R^3$ represents a group of the formula (IV-2) or (IV-3), (7) compounds wherein $R^3$ represents a group of the formula (IV-2), (8) compounds wherein $R^4$ represents a pyridyl group which may be substituted with one substituent described below (the substituent is a halogen atom, a hydroxyl group, a $C_{1-6}$ alkyl group, a halogeno($C_{1-6}$ alkyl) group, a $C_{1-6}$ alkoxy group, a $C_{1-6}$ alkylthio group, an amino group which may be substituted with substituents selected from Substituents γ, or a nitro group), (9) compounds wherein $R^4$ represents a pyridyl group which may be substituted with one substituent described below (the substituent is a fluorine atom, a chlorine atom, a hydroxyl group, a methyl group, an ethyl group, a t-butyl group, a trifluoromethyl group, a methoxy group, a methylthio group, an amino group, a methylamino group, a dimethylamino group or a nitro group),

(10) compounds having as $R^4$ a pyridyl group,

(11) compounds wherein $R^4$ is a phenyl group substituted with at least one substituent selected from the following substituents (the substituents consist of $C_{3-10}$ cycloalkyl, $C_{6-10}$ aryl and $C_{7-16}$ aralkyl groups each of which may be substituted with 1 to 3 substituents selected from Substituents β, 4- to 7-membered saturated nitrogen-containing heterocyclic groups and 5- or 6-membered aromatic nitrogen-containing heterocyclic groups),

(12) compounds wherein $R^4$ is a phenyl group substituted with one substituent described below (the substituent is a $C_{3-10}$ cycloalkyl, $C_{6-10}$ aryl or $C_{7-16}$ aralkyl group which may be substituted with one substituent selected from Substituents β, a 4- to 7-membered saturated nitrogen-containing heterocyclic group or a 5- or 6-membered aromatic nitrogen-containing heterocyclic group,

(13) compounds wherein $R^4$ is a phenyl group substituted with one substituent described below (the substituent is a $C_{3-10}$ cycloalkyl, $C_{6-10}$ aryl or $C_{7-16}$ aralkyl group which may be substituted with a halogen atom, hydroxyl group, $C_{1-6}$ alkyl group, halogeno($C_{1-6}$ alkyl) group, $C_{1-6}$ alkoxy group or amino group which may be substituted with substituents selected from Substituents γ, a 4- to 7-membered saturated nitrogen-containing heterocyclic group, or a 5- or 6-membered aromatic nitrogen-containing heterocyclic group),

(14) compounds wherein $R^4$ is a phenyl group substituted with one substituent described below (the substituent is a phenyl or benzyl group which may be substituted with a halogen atom, hydroxyl group, $C_{1-6}$ alkyl group, halogeno($C_{1-6}$ alkyl) group, $C_{1-6}$ alkoxy group or amino group which may be substituted with substituents selected from Substituents γ, an adamantyl group, a pyrrolidinyl group, a morpholinyl group, a piperidinyl group, an imidazolyl group, a tetrazolyl group or a pyridinyl group),

(15) compounds wherein $R^4$ is a phenyl group substituted with one substituent described below (the substituent is a phenyl or benzyl group which may be substituted with a fluorine atom, chlorine atom, hydroxyl group, methyl group, ethyl group, t-butyl group, trifluoromethyl group, methoxy group, amino group, methylamino group or dimethylamino group, an adamantyl group, a pyrrolidinyl group, a morpholinyl group, a piperidinyl group, an imidazolyl group, a tetrazolyl group or a pyridinyl group),

(16) compounds wherein $R^4$ is a 4-biphenylyl, 4-benzylphenyl, 4'-hydroxybiphenylyl, (pyrrolidin-1-yl)phenyl, (morpholin-4-yl)phenyl, (piperidin-1-yl) phenyl, (pyridin-2-yl)phenyl, (pyridin-3-yl)phenyl or 4-(1-adamantyl)phenyl group,

(17) compounds wherein $R^4$ is a phenyl group which is substituted with one acylamino group, wherein the amino moiety may be substituted with a further substituent selected from Substituents γ, and said phenyl group may be further substituted with 1 to 3 substituents selected from the following substituents (the substituents consist of halogen atoms and hydroxyl, $C_{1-6}$ alkyl, halogeno($C_{1-6}$ alkyl), $C_{1-6}$ alkoxy and $C_{1-6}$ alkylthio groups),

(18) compounds wherein $R^4$ is a phenyl group which is substituted with one acylamino group, wherein the amino moiety may be substituted with a substituent selected from Substituents γ, and said phenyl group may be further substituted with 1 to 3 substituents selected from the following substituents (the substituents consist of halogen atoms and $C_{1-6}$ alkyl groups),

(19) compounds wherein $R^4$ is a phenyl group which is substituted with one acylamino group, wherein the amino moiety may be further substituted with a $C_{1-10}$ alkyl group or a $C_{7-12}$ aralkyl group which may have substituents, and said phenyl group may be further substituted with 1 to 3 $C_{1-6}$ alkyl groups),

(20) compounds wherein $R^4$ is a phenyl group which is substituted with one substituent described below (the substituent is a $C_{7-11}$ aromatic acylamino, $C_{4-11}$ cycloalkylcarbonylamino or 5- or 6-membered aromatic nitrogen-containing heterocyclic carbonylamino group which may have substituents),

(21) compounds wherein $R^4$ is a phenyl group substituted with a benzoylamino, 3-chlorobenzoylamino, 2,4-difluorobenzoylamino, 4-hydroxy-3,5-di-t-butylbenzoylamino, naphthoylamino, cyclopentanoylamino, cyclohexanoylamino, nicotinoylamino, isonicotinoylamino, N-acetyl-N-hexylamino or adamantylcarbonylamino group,

(22) compounds wherein $R^4$ is a phenyl group which is substituted with one amino, amino substituted with 1 or 2 substituents (the substituents are the same or different and each is a group selected from $C_{1-10}$ alkyl, and $C_{6-10}$ aryl and $C_{7-16}$ aralkyl each of which may have substituents), nitro or cyano group, and said phenyl group may be further substituted with 1 to 3 substituents selected from the following substituents (the substituents consist of halogen atoms and hydroxyl, $C_{1-6}$ alkyl, halogeno($C_{1-6}$ alkyl), $C_{1-6}$ alkoxy and $C_{1-6}$ alkylthio groups),

(23) compounds wherein $R^4$ is a phenyl group which is substituted with one amino, mono- or di-($C_{1-10}$ alkyl) amino, or cyano group and at the same time, may be substituted with 1 or 2 $C_{1-6}$ alkyl groups,

(24) compounds wherein $R^4$ is a 4-aminophenyl, 4-amino-3,5-dimethylphenyl, 4-amino-3,5-di-t-butylphenyl, 3- or 4-dimethylaminophenyl or 4-cyanophenyl group,

(25) compounds wherein $R^4$ is a phenyl group which is substituted with one $C_{6-10}$ aryloxy, $C_{7-16}$ aralkyloxy or $C_{6-10}$ arylthio group which may be substituted with 1 to 3 substituents selected from Substituents β, and said phenyl group may be further substituted with 1 to 3 substituents selected from the following substituents (the substituents consist of halogen atoms and hydroxyl, $C_{1-6}$ alkyl, halogeno($C_{1-6}$ alkyl), $C_{1-6}$ alkoxy and $C_{1-6}$ alkylthio groups),

(26) compounds wherein $R^4$ is a phenyl group which is substituted with a $C_{6-10}$ aryloxy which may be substituted with 1 to 3 substituents selected from Substituents β, and said phenyl group may be further substituted with 1 to 2 $C_{1-6}$ alkyl groups,

(27) compounds wherein $R^4$ is a phenyl group substituted with a $C_{6-10}$ aryloxy group which may be substituted with one substituent selected from Substituents A,

(28) compounds wherein $R^4$ is a 4-phenoxyphenyl group,

(29) compounds wherein $R^4$ is a phenyl group substituted with 1 to 5 substituents selected from the following substituents (the substituents consist of halogen atoms and hydroxyl, $C_{1-6}$ alkyl, halogeno($C_{1-6}$ alkyl), $C_{1-6}$ alkoxy, $C_{1-6}$ alkylthio and $C_{1-7}$ aliphatic acyloxy groups),

(30) compounds wherein $R^4$ is a phenyl group which is substituted with one halogen atom, hydroxyl group, $C_{1-6}$ alkyl group, halogeno($C_{1-6}$ alkyl) group, $C_{1-6}$ alkoxy group, $C_{1-6}$ alkylthio group or $C_{1-7}$ aliphatic acyloxy group, and said phenyl group may be further substituted with 1 to 4 substituents selected from the following substituents (the substituents consist of halogen atoms and $C_{1-6}$ alkyl and halogeno($C_{1-6}$ alkyl) groups),

(31) compounds wherein $R^4$ is a phenyl group substituted with one $C_{1-6}$ alkyl group, halogeno($C_{1-6}$ alkyl) group, $C_{1-6}$ alkoxy group or $C_{1-6}$ alkylthio group or with 1 to 5 halogen atoms,

(32) compounds wherein $R^4$ is a phenyl group substituted with one halogeno($C_{1-2}$ alkyl), $C_{1-2}$ alkoxy or $C_{1-2}$ alkylthio group or with 1 to 5 fluorine atoms or chlorine atoms,

(33) compounds wherein $R^4$ is a 4-trifluoromethylphenyl, 4-methylthiophenyl, 4-methoxyphenyl or pentafluorophenyl group,

(34) compounds wherein $R^4$ is a phenyl group which is substituted with one hydroxyl or $C_{1-7}$ aliphatic acyloxy group, and said phenyl group may be further substituted with 1 to 3 substituents selected from the following substituents (the substituents consist of halogen atoms and $C_{1-6}$ alkyl groups),

(35) compounds wherein $R^4$ is a phenyl group which is substituted with one hydroxyl group, and said phenyl group may be further substituted with 1 to 3 substituents selected from the following substituents (the substituents consist of halogen atoms and $C_{1-6}$ alkyl groups),

(36) compounds wherein $R^4$ is a phenyl group which is substituted with one hydroxyl group, and said phenyl group may be further substituted with 1 to 3 substituents selected from the following substituents (the substituents consist of fluorine and chlorine atoms and methyl and t-butyl groups),

(37) compounds wherein $R^4$ is a 4-hydroxyphenyl, 4-hydroxy-3,5-dimethylphenyl, 4-hydroxy-3,5-di-t-butylphenyl, 4-hydroxy-2,3,5-trimethylphenyl or 2-chloro-4-hydroxy-3,5-dimethylphenyl group,

(38) compounds wherein $R^6$ is a hydrogen atom, a $C_{1-6}$ alkyl group, or a phenyl or benzyl group which may be substituted with 1 to 3 substituents selected from the following substituents (the substituents consist of halogen atoms and hydroxyl, $C_{1-6}$ alkyl and halogeno($C_{1-6}$ alkyl) groups),

(39) compounds wherein $R^6$ is a hydrogen atom, a $C_{1-4}$ alkyl group, or a phenyl or benzyl group which may be substituted with one substituent described below (the substituent is a fluorine atom, a chlorine atom, a hydroxyl group, a methyl group or an ethyl group),

(40) compounds wherein $R^6$ is a hydrogen atom or a $C_{1-4}$ alkyl group,

(41) compounds wherein $R^6$ is a $C_{1-2}$ alkyl group,

(42) compounds wherein $R^6$ is a methyl group,

(43) compounds wherein A is a $C_{1-4}$ alkylene group,

(44) compounds wherein A is a $C_{1-2}$ alkylene group,

(45) compounds wherein A is a methylene group,

(46) compounds wherein B is an oxygen atom,

(47) compounds wherein D is an oxygen atom,

(48) compounds wherein D is a sulfur atom,

(49) compounds wherein E is a CH group, and

(50) compounds wherein E is a nitrogen atom.

Any combinations of two to nine groups selected from (1), (2)–(4), (5)–(7), (8)–(37), (38)–(42), (43)–(45), (46), (47)–(48) and (49)–(50) are also preferred.

Some compounds of the present invention are shown in Tables 1–10. It should however be borne in mind that the present invention is not limited to them. Compounds in Tables 1 to 10 each have the structural formula of (I-1) to (I-10) and abbreviations in the tables are as follows:

Ac: acetyl group

Ada(1): 1-adamantyl group

Bu: butyl group sBu: s-butyl group tBu: t-butyl group

Bz: benzyl group

Et: ethyl group

Hx: hexyl group cHx: cyclohexyl group

Imid(1): 1-imidazolyl group

Me: methyl group

Mor(4): 4-morpholinyl group
Np(1): 1-naphthyl group
Np(2): 2-naphthyl group
Ph: phenyl group
Pip(1): 1-piperidyl group
Pipra(1): 1-piperazinyl group
Pn: pentyl group
cPn: cyclopentyl group Pr: propyl group
iPr: isopropyl group
Pyr(2): 2-pyridyl group
Pyr(3): 3-pyridyl group
Pyr(4): 4-pyridyl group
Pyrd(1): 1-pyrrolidinyl group
TioMor(4): 4-thiomorpholinyl group
Tz: tetrazol-5-yl group

TABLE 1

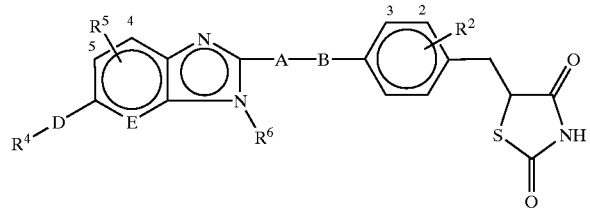

(I-1)

| Cpd. No. | $R^2$ | $R^4$ | $R^5$ | $R^6$ | —A— | B | D | E |
|---|---|---|---|---|---|---|---|---|
| 1-1 | H | 2-F—Ph | H | Me | —CH$_2$— | O | O | CH |
| 1-2 | H | 3-F—Ph | H | Me | —CH$_2$— | O | O | CH |
| 1-3 | H | 4-F—Ph | H | Me | —CH$_2$— | O | O | CH |
| 1-4 | H | 4-F—Ph | H | Me | —CH$_2$— | O | S | CH |
| 1-5 | H | 2-Cl—Ph | H | Me | —CH$_2$— | O | O | CH |
| 1-6 | H | 3-Cl—Ph | H | Me | —CH$_2$— | O | O | CH |
| 1-7 | H | 4-Cl—Ph | H | Me | —CH$_2$— | O | O | CH |
| 1-8 | H | 4-Cl—Ph | H | Me | —CH$_2$— | O | S | CH |
| 1-9 | H | 4-Br—Ph | H | Me | —CH$_2$— | O | O | CH |
| 1-10 | H | 2-OH—Ph | H | H | —CH$_2$— | O | O | CH |
| 1-11 | H | 2-OH—Ph | H | Me | —CH$_2$— | O | O | CH |
| 1-12 | H | 2-OH—Ph | H | Me | —CH$_2$— | O | O | N |
| 1-13 | H | 2-OH—Ph | H | Me | —CH$_2$— | O | S | CH |
| 1-14 | H | 2-OH—Ph | H | Me | —CH$_2$— | O | S | N |
| 1-15 | H | 2-OH—Ph | H | Me | —CH$_2$— | S | O | CH |
| 1-16 | H | 2-OH—Ph | H | Me | —(CH$_2$)$_2$— | O | O | CH |
| 1-17 | H | 2-OH—Ph | H | Me | —(CH$_2$)$_2$— | O | O | N |
| 1-18 | H | 2-OH—Ph | H | Me | —(CH$_2$)$_2$— | O | S | CH |
| 1-19 | H | 2-OH—Ph | H | Me | —CH(Me)— | O | O | CH |
| 1-20 | H | 2-OH—Ph | H | Me | —(CH$_2$)$_3$— | O | O | CH |
| 1-21 | H | 2-OH—Ph | H | Me | —(CH$_2$)$_3$— | O | S | CH |
| 1-22 | H | 2-OH—Ph | H | Me | —(CH$_2$)$_3$— | S | O | CH |
| 1-23 | H | 2-OH—Ph | H | Et | —CH$_2$— | O | O | CH |
| 1-24 | H | 2-OH—Ph | H | Et | —CH$_2$— | O | O | N |
| 1-25 | H | 2-OH—Ph | H | Et | —CH$_2$— | O | S | CH |
| 1-26 | H | 2-OH—Ph | H | Et | —(CH$_2$)$_2$— | O | O | CH |
| 1-27 | H | 2-OH—Ph | H | tBu | —CH$_2$— | O | O | CH |
| 1-28 | H | 2-OH—Ph | H | tBu | —CH$_2$— | O | S | CH |
| 1-29 | H | 2-OH—Ph | H | Ph | —CH$_2$— | O | O | CH |
| 1-30 | H | 2-OH—Ph | H | Bz | —CH$_2$— | O | O | CH |
| 1-31 | H | 2-OH—Ph | 5-Cl | Me | —CH$_2$— | O | O | CH |
| 1-32 | H | 2-OH—Ph | 5-Me | Me | —CH$_2$— | O | O | CH |
| 1-33 | H | 2-OH—Ph | 5-MeO | Me | —CH$_2$— | O | O | CH |
| 1-34 | 2-Cl | 2-OH—Ph | H | Me | —CH$_2$— | O | O | CH |
| 1-35 | 3-Cl | 2-OH—Ph | H | Me | —CH$_2$— | O | O | CH |
| 1-36 | 2-Me | 2-OH—Ph | H | Me | —CH$_2$— | O | O | CH |
| 1-37 | 3-Me | 2-OH—Ph | H | Me | —CH$_2$— | O | O | CH |
| 1-38 | 2-MeO | 2-OH—Ph | H | Me | —CH$_2$— | O | O | CH |
| 1-39 | 3-MeO | 2-OH—Ph | H | Me | —CH$_2$— | O | O | CH |
| 1-40 | H | 3-OH—Ph | H | H | —CH$_2$— | O | O | CH |
| 1-41 | H | 3-OH—Ph | H | Me | —CH$_2$— | O | O | CH |
| 1-42 | H | 3-OH—Ph | H | Me | —CH$_2$— | O | O | N |
| 1-43 | H | 3-OH—Ph | H | Me | —CH$_2$— | O | S | CH |
| 1-44 | H | 3-OH—Ph | H | Me | —CH$_2$— | O | S | N |
| 1-45 | H | 3-OH—Ph | H | Me | —CH$_2$— | S | O | CH |
| 1-46 | H | 3-OH—Ph | H | Me | —(CH$_2$)$_2$— | O | O | CH |
| 1-47 | H | 3-OH—Ph | H | Me | —(CH$_2$)$_2$— | O | O | N |
| 1-48 | H | 3-OH—Ph | H | Me | —(CH$_2$)$_2$— | O | S | CH |
| 1-49 | H | 3-OH—Ph | H | Me | —CH(Me)— | O | O | CH |
| 1-50 | H | 3-OH—Ph | H | Me | —(CH$_2$)$_3$— | O | O | CH |
| 1-51 | H | 3-OH—Ph | H | Et | —CH$_2$— | O | O | CH |

TABLE 1-continued

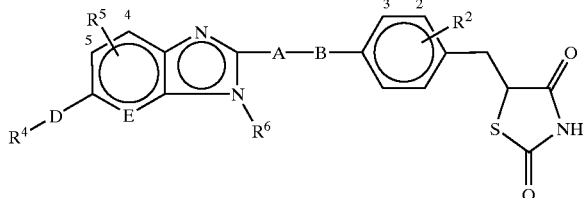

(I-1)

| Cpd. No. | $R^2$ | $R^4$ | $R^5$ | $R^6$ | —A— | B | D | E |
|---|---|---|---|---|---|---|---|---|
| 1-52 | H | 3-OH—Ph | H | Et | —CH$_2$— | O | O | N |
| 1-53 | H | 3-OH—Ph | H | Et | —CH$_2$— | O | S | CH |
| 1-54 | H | 3-OH—Ph | H | Et | —(CH$_2$)$_2$— | O | O | CH |
| 1-55 | H | 3-OH—Ph | H | tBu | —CH$_2$— | O | O | CH |
| 1-56 | H | 3-OH—Ph | H | tBu | —CH$_2$— | O | S | CH |
| 1-57 | H | 3-OH—Ph | H | Ph | —CH$_2$— | O | O | CH |
| 1-58 | H | 3-OH—Ph | H | Bz | —CH$_2$— | O | O | CH |
| 1-59 | H | 3-OH—Ph | 5-Cl | Me | —CH$_2$— | O | O | CH |
| 1-60 | H | 3-OH—Ph | 5-Me | Me | —CH$_2$— | O | O | CH |
| 1-61 | H | 3-OH—Ph | 5-MeO | Me | —CH$_2$— | O | O | CH |
| 1-62 | 2-Cl | 3-OH—Ph | H | Me | —CH$_2$— | O | O | CH |
| 1-63 | 3-Cl | 3-OH—Ph | H | Me | —CH$_2$— | O | O | CH |
| 1-64 | 2-Me | 3-OH—Ph | H | Me | —CH$_2$— | O | O | CH |
| 1-65 | 3-Me | 3-OH—Ph | H | Me | —CH$_2$— | O | O | CH |
| 1-66 | 2-MeO | 3-OH—Ph | H | Me | —CH$_2$— | O | O | CH |
| 1-67 | 3-MeO | 3-OH—Ph | H | Me | —CH$_2$— | O | O | CH |
| 1-68 | H | 4-OH—Ph | H | H | —CH$_2$— | O | O | CH |
| 1-69 | H | 4-OH—Ph | H | H | —CH$_2$— | O | S | CH |
| 1-70 | H | 4-OH—Ph | H | Me | —CH$_2$— | O | O | CH |
| 1-71 | H | 4-OH—Ph | H | Me | —CH$_2$— | O | O | N |
| 1-72 | H | 4-OH—Ph | H | Me | —CH$_2$— | O | S | CH |
| 1-73 | H | 4-OH—Ph | H | Me | —CH$_2$— | O | S | N |
| 1-74 | H | 4-OH—Ph | H | Me | —CH$_2$— | S | O | CH |
| 1-75 | H | 4-OH—Ph | H | Me | —CH$_2$— | S | O | N |
| 1-76 | H | 4-OH—Ph | H | Me | —CH$_2$— | S | S | CH |
| 1-77 | H | 4-OH—Ph | H | Me | —CH$_2$— | S | S | N |
| 1-78 | H | 4-OH—Ph | H | Me | —(CH$_2$)$_2$— | O | O | CH |
| 1-79 | H | 4-OH—Ph | H | Me | —(CH$_2$)$_2$— | O | O | N |
| 1-80 | H | 4-OH—Ph | H | Me | —(CH$_2$)$_2$— | O | S | CH |
| 1-81 | H | 4-OH—Ph | H | Me | —(CH$_2$)$_2$— | O | S | N |
| 1-82 | H | 4-OH—Ph | H | Me | —(CH$_2$)$_2$— | S | O | CH |
| 1-83 | H | 4-OH—Ph | H | Me | —CH(Me)— | O | O | CH |
| 1-84 | H | 4-OH—Ph | H | Me | —CH(Me)— | O | S | CH |
| 1-85 | H | 4-OH—Ph | H | Me | —(CH$_2$)$_3$— | O | O | CH |
| 1-86 | H | 4-OH—Ph | H | Me | —(CH$_2$)$_3$— | O | S | CH |
| 1-87 | H | 4-OH—Ph | H | Me | —(CH$_2$)$_4$— | O | O | CH |
| 1-88 | H | 4-OH—Ph | H | Et | —CH$_2$— | O | O | CH |
| 1-89 | H | 4-OH—Ph | H | Et | —CH$_2$— | O | O | N |
| 1-90 | H | 4-OH—Ph | H | Et | —CH$_2$— | O | S | CH |
| 1-91 | H | 4-OH—Ph | H | Et | —CH$_2$— | O | S | N |
| 1-92 | H | 4-OH—Ph | H | Et | —CH$_2$— | S | O | CH |
| 1-93 | H | 4-OH—Ph | H | Et | —(CH$_2$)$_2$— | O | O | CH |
| 1-94 | H | 4-OH—Ph | H | Et | —(CH$_2$)$_2$— | O | S | CH |
| 1-95 | H | 4-OH—Ph | H | Pr | —CH$_2$— | O | O | CH |
| 1-96 | H | 4-OH—Ph | H | iPr | —CH$_2$— | O | O | CH |
| 1-97 | H | 4-OH—Ph | H | Bu | —CH$_2$— | O | O | CH |
| 1-98 | H | 4-OH—Ph | H | sBu | —CH$_2$— | O | O | CH |
| 1-99 | H | 4-OH—Ph | H | sBu | —(CH$_2$)$_3$— | O | O | CH |
| 1-100 | H | 4-OH—Ph | H | tBu | —CH$_2$— | O | O | CH |
| 1-101 | H | 4-OH—Ph | H | tBu | —CH$_2$— | O | S | CH |
| 1-102 | H | 4-OH—Ph | H | Ph | —CH$_2$— | O | O | CH |
| 1-103 | H | 4-OH—Ph | H | Ph | —CH$_2$— | O | O | N |
| 1-104 | H | 4-OH—Ph | H | Ph | —CH$_2$— | O | S | CH |
| 1-105 | H | 4-OH—Ph | H | Ph | —(CH$_2$)$_2$— | O | O | CH |
| 1-106 | H | 4-OH—Ph | H | Bz | —CH$_2$— | O | O | CH |
| 1-107 | H | 4-OH—Ph | H | Bz | —CH$_2$— | O | O | N |
| 1-108 | H | 4-OH—Ph | H | Bz | —CH$_2$— | O | S | CH |
| 1-109 | H | 4-OH—Ph | H | Bz | —(CH$_2$)$_2$— | O | O | CH |
| 1-110 | H | 4-OH—Ph | 5-F | Me | —CH$_2$— | O | O | CH |
| 1-111 | H | 4-OH—Ph | 4-Cl | Me | —CH$_2$— | O | O | CH |
| 1-112 | H | 4-OH—Ph | 5-Cl | Me | —CH$_2$— | O | O | CH |
| 1-113 | H | 4-OH—Ph | 4-Me | Me | —CH$_2$— | O | O | CH |
| 1-114 | H | 4-OH—Ph | 5-Me | Me | —CH$_2$— | O | O | CH |
| 1-115 | H | 4-OH—Ph | 4-MeO | Me | —CH$_2$— | O | O | CH |

TABLE 1-continued

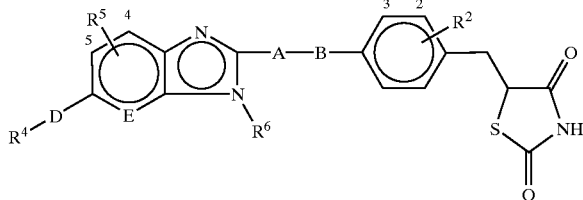

(I-1)

| Cpd. No. | R² | R⁴ | R⁵ | R⁶ | —A— | B | D | E |
|---|---|---|---|---|---|---|---|---|
| 1-116 | H | 4-OH—Ph | 5-MeO | Me | —CH₂— | O | O | CH |
| 1-117 | H | 4-OH—Ph | 5-MeO | Me | —CH₂— | O | S | CH |
| 1-118 | H | 4-OH—Ph | 5-MeS | Me | —CH₂— | O | O | CH |
| 1-119 | 3-F | 4-OH—Ph | H | Me | —CH₂— | O | O | CH |
| 1-120 | 2-Cl | 4-OH—Ph | H | Me | —CH₂— | O | O | CH |
| 1-121 | 3-Cl | 4-OH—Ph | H | Me | —CH₂— | O | O | CH |
| 1-122 | 2-Me | 4-OH—Ph | H | Me | —CH₂— | O | O | CH |
| 1-123 | 3-Me | 4-OH—Ph | H | Me | —CH₂— | O | O | CH |
| 1-124 | 3-CF₃ | 4-OH—Ph | H | Me | —CH₂— | O | O | CH |
| 1-125 | 2-MeO | 4-OH—Ph | H | Me | —CH₂— | O | O | CH |
| 1-126 | 3-MeO | 4-OH—Ph | H | Me | —CH₂— | O | O | CH |
| 1-127 | H | 2-Me—Ph | H | Me | —CH₂— | O | O | CH |
| 1-128 | H | 3-Me—Ph | H | Me | —CH₂— | O | O | CH |
| 1-129 | H | 4-Me—Ph | H | Me | —CH₂— | O | O | CH |
| 1-130 | H | 3-CF₃—Ph | H | Me | —CH₂— | O | O | CH |
| 1-131 | H | 4-CF₃—Ph | H | Me | —CH₂— | O | O | CH |
| 1-132 | H | 4-MeO—Ph | H | Me | —CH₂— | O | O | CH |
| 1-133 | H | 4-EtO—Ph | H | Me | —CH₂— | O | O | CH |
| 1-134 | H | 4-iPrO—Ph | H | Me | —CH₂— | O | O | CH |
| 1-135 | H | 4-iPrO—Ph | H | Me | —CH₂— | O | S | CH |
| 1-136 | H | 4-MeS—Ph | H | Me | —CH₂— | O | O | CH |
| 1-137 | H | 4-MeS—Ph | H | Me | —CH₂— | O | S | CH |
| 1-138 | H | 2-NH₂—Ph | H | Me | —CH₂— | O | O | CH |
| 1-139 | H | 2-NH₂—Ph | H | Me | —CH₂— | O | S | CH |
| 1-140 | H | 3-NH₂—Ph | H | Me | —CH₂— | O | O | CH |
| 1-141 | H | 3-NH₂—Ph | H | Me | —CH₂— | O | S | CH |
| 1-142 | H | 4-NH₂—Ph | H | Me | —CH₂— | O | O | CH |
| 1-143 | H | 4-NH₂—Ph | H | Me | —CH₂— | O | O | N |
| 1-144 | H | 4-NH₂—Ph | H | Me | —CH₂— | O | S | CH |
| 1-145 | H | 4-NH₂—Ph | H | Et | —CH₂— | O | O | CH |
| 1-146 | H | 4-NH₂—Ph | H | Et | —CH₂— | O | S | CH |
| 1-147 | H | 2-NHMe—Ph | H | Me | —CH₂— | O | O | CH |
| 1-148 | H | 3-NHMe—Ph | H | Me | —CH₂— | O | O | CH |
| 1-149 | H | 4-NHMe—Ph | H | Me | —CH₂— | O | O | CH |
| 1-150 | H | 4-NHMe—Ph | H | Me | —CH₂— | O | S | CH |
| 1-151 | H | 2-N(Me)₂—Ph | H | Me | —CH₂— | O | O | CH |
| 1-152 | H | 2-N(Me)₂—Ph | H | Me | —CH₂— | O | S | CH |
| 1-153 | H | 3-N(Me)₂—Ph | H | Me | —CH₂— | O | O | CH |
| 1-154 | H | 3-N(Me)₂—Ph | H | Me | —CH₂— | O | S | CH |
| 1-155 | H | 4-N(Me)₂—Ph | H | Me | —CH₂— | O | O | CH |
| 1-156 | H | 4-N(Me)₂—Ph | H | Me | —CH₂— | O | O | N |
| 1-157 | H | 4-N(Me)₂—Ph | H | Me | —CH₂— | O | S | CH |
| 1-158 | H | 4-N(Me)₂—Ph | H | Et | —CH₂— | O | O | CH |
| 1-159 | H | 4-N(Me)₂—Ph | H | Et | —CH₂— | O | S | CH |
| 1-160 | H | 4-NHEt—Ph | H | Me | —CH₂— | O | O | CH |
| 1-161 | H | 4-NMeEt—Ph | H | Me | —CH₂— | O | O | CH |
| 1-162 | H | 4-NHPh—Ph | H | Me | —CH₂— | O | O | CH |
| 1-163 | H | 4-NHBz—Ph | H | Me | —CH₂— | O | O | CH |
| 1-164 | H | 4-NHAc—Ph | H | Me | —CH₂— | O | O | CH |
| 1-165 | H | 4-NHAc—Ph | H | Me | —CH₂— | O | S | CH |
| 1-166 | H | 4-N(Me)Ac—Ph | H | Me | —CH₂— | O | O | CH |
| 1-167 | H | 4-N(Me)Ac—Ph | H | Me | —CH₂— | O | S | CH |
| 1-168 | H | 3-Ph—Ph | H | Me | —CH₂— | O | O | CH |
| 1-169 | H | 4-Ph—Ph | H | Me | —CH₂— | O | O | CH |
| 1-170 | H | 4-Ph—Ph | H | Me | —CH₂— | O | S | CH |
| 1-171 | H | 4-(4-OH—Ph)Ph | H | Me | —CH₂— | O | O | CH |
| 1-172 | H | 4-(4-OH—Ph)Ph | H | Me | —CH₂— | O | S | CH |
| 1-173 | H | 4-(4-OH-3, 5-diMe—Ph)Ph | H | Me | —CH₂— | O | O | CH |
| 1-174 | H | 4-(4-OH-3, 5-diMe—Ph)Ph | H | Me | —CH₂— | O | O | N |
| 1-175 | H | 4-(4-OH-3, 5-diMe—Ph)Ph | H | Me | —CH₂— | O | S | CH |

TABLE 1-continued

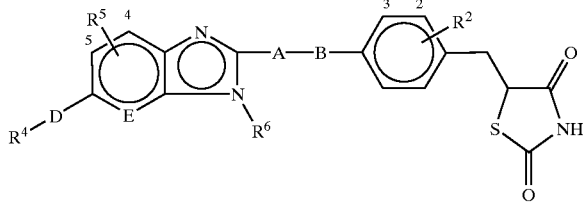

(I-1)

| Cpd. No. | R² | R⁴ | R⁵ | R⁶ | —A— | B | D | E |
|---|---|---|---|---|---|---|---|---|
| 1-176 | H | 4-(4-OH-3,5-diMe—Ph)Ph | H | Et | —CH₂— | O | O | CH |
| 1-177 | H | 4-(4-OH-3,5-diMe—Ph)Ph | H | Et | —CH₂— | O | S | CH |
| 1-178 | H | 4-(4-OH-3,5-ditBu—Ph)Ph | H | Me | —CH₂— | O | O | CH |
| 1-179 | H | 4-(4-OH-3,5-ditBu—Ph)Ph | H | Me | —CH₂— | O | O | N |
| 1-180 | H | 4-(4-OH-3,5-ditBu—Ph)Ph | H | Me | —CH₂— | O | S | CH |
| 1-181 | H | 4-(4-OH-3,5-ditBu—Ph)Ph | H | Et | —CH₂— | O | O | CH |
| 1-182 | H | 4-(4-OH-3,5-ditBu—Ph)Ph | H | Et | —CH₂— | O | S | CH |
| 1-183 | H | 3-Bz—Ph | H | Me | —CH₂— | O | O | CH |
| 1-184 | H | 4-Bz—Ph | H | Me | —CH₂— | O | O | CH |
| 1-185 | H | 4-Bz—Ph | H | Me | —CH₂— | O | S | CH |
| 1-186 | H | 4-(4-OH—Bz)Ph | H | Me | —CH₂— | O | O | CH |
| 1-187 | H | 4-(4-OH—Bz)Ph | H | Me | —CH₂— | O | S | CH |
| 1-188 | H | 4-(4-OH-3,5-diMe—Bz)Ph | H | Me | —CH₂— | O | O | CH |
| 1-189 | H | 4-(4-OH-3,5-diMe—Bz)Ph | H | Me | —CH₂— | O | S | CH |
| 1-190 | H | 4-(4-OH-3,5-ditBu—Bz)Ph | H | Me | —CH₂— | O | O | CH |
| 1-191 | H | 4-(4-OH-3,5-ditBu—Bz)Ph | H | Me | —CH₂— | O | S | CH |
| 1-192 | H | 3-PhO—Ph | H | Me | —CH₂— | O | O | CH |
| 1-193 | H | 4-PhO—Ph | H | Me | —CH₂— | O | O | CH |
| 1-194 | H | 4-PhO—Ph | H | Me | —CH₂— | O | S | CH |
| 1-195 | H | 3-PhS—Ph | H | Me | —CH₂— | O | O | CH |
| 1-196 | H | 4-PhS—Ph | H | Me | —CH₂— | O | O | CH |
| 1-197 | H | 4-PhS—Ph | H | Me | —CH₂— | O | S | CH |
| 1-198 | H | 4-AcO—Ph | H | Me | —CH₂— | O | O | CH |
| 1-199 | H | 2-Pyrd(1)-Ph | H | Me | —CH₂— | O | O | CH |
| 1-200 | H | 2-Pyrd(1)-Ph | H | Me | —CH₂— | O | O | N |
| 1-201 | H | 2-Pyrd(1)-Ph | H | Me | —CH₂— | O | S | CH |
| 1-202 | H | 2-Pyrd(1)-Ph | H | Me | —(CH₂)₂— | O | O | CH |
| 1-203 | H | 2-Pyrd(1)-Ph | H | Et | —CH₂— | O | O | CH |
| 1-204 | H | 2-Pyrd(1)-Ph | H | Et | —CH₂— | O | S | CH |
| 1-205 | H | 2-Pyrd(1)-Ph | H | tBu | —CH₂— | O | O | CH |
| 1-206 | H | 3-Pyrd(1)-Ph | H | Me | —CH₂— | O | O | CH |
| 1-207 | H | 3-Pyrd(1)-Ph | H | Me | —CH₂— | O | O | N |
| 1-208 | H | 3-Pyrd(1)-Ph | H | Me | —CH₂— | O | S | CH |
| 1-209 | H | 3-Pyrd(1)-Ph | H | Me | —(CH₂)₂— | O | O | CH |
| 1-210 | H | 3-Pyrd(1)-Ph | H | Et | —CH₂— | O | O | CH |
| 1-211 | H | 3-Pyrd(1)-Ph | H | Et | —CH₂— | O | S | CH |
| 1-212 | H | 3-Pyrd(1)-Ph | H | tBu | —CH₂— | O | O | CH |
| 1-213 | H | 4-Pyrd(1)-Ph | H | H | —CH₂— | O | O | CH |
| 1-214 | H | 4-Pyrd(1)-Ph | H | Me | —CH₂— | O | O | CH |
| 1-215 | H | 4-Pyrd(1)-Ph | H | Me | —CH₂— | O | O | N |
| 1-216 | H | 4-Pyrd(1)-Ph | H | Me | —CH₂— | O | S | CH |
| 1-217 | H | 4-Pyrd(1)-Ph | H | Me | —CH₂— | O | S | N |
| 1-218 | H | 4-Pyrd(1)-Ph | H | Me | —CH₂— | S | O | CH |
| 1-219 | H | 4-Pyrd(1)-Ph | H | Me | —(CH₂)₂— | O | O | CH |
| 1-220 | H | 4-Pyrd(1)-Ph | H | Me | —(CH₂)₂— | O | O | N |
| 1-221 | H | 4-Pyrd(1)-Ph | H | Me | —(CH₂)₂— | O | S | CH |
| 1-222 | H | 4-Pyrd(1)-Ph | H | Me | —CH(Me)— | O | O | CH |
| 1-223 | H | 4-Pyrd(1)-Ph | H | Me | —(CH₂)₃— | O | O | CH |
| 1-224 | H | 4-Pyrd(1)-Ph | H | Et | —CH₂— | O | O | CH |
| 1-225 | H | 4-Pyrd(1)-Ph | H | Et | —CH₂— | O | O | N |
| 1-226 | H | 4-Pyrd(1)-Ph | H | Et | —CH₂— | O | S | CH |
| 1-227 | H | 4-Pyrd(1)-Ph | H | Et | —(CH₂)₂— | O | O | CH |
| 1-228 | H | 4-Pyrd(1)-Ph | H | tBu | —CH₂— | O | O | CH |

TABLE 1-continued

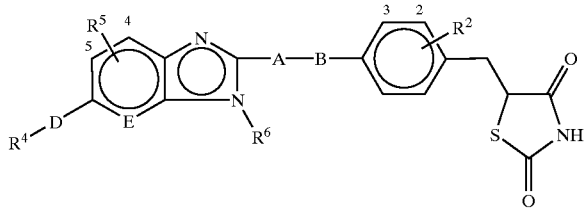

(I-1)

| Cpd. No. | R² | R⁴ | R⁵ | R⁶ | —A— | B | D | E |
|---|---|---|---|---|---|---|---|---|
| 1-229 | H | 4-Pyrd(1)-Ph | H | tBu | —CH₂— | O | S | CH |
| 1-230 | H | 4-Pyrd(1)-Ph | H | Ph | —CH₂— | O | O | CH |
| 1-231 | H | 4-Pyrd(1)-Ph | H | Bz | —CH₂— | O | O | CH |
| 1-232 | H | 4-Pyrd(1)-Ph | 5-Cl | Me | —CH₂— | O | O | CH |
| 1-233 | H | 4-Pyrd(1)-Ph | 5-Me | Me | —CH₂— | O | O | CH |
| 1-234 | H | 4-Pyrd(1)-Ph | 5-MeO | Me | —CH₂— | O | O | CH |
| 1-235 | 2-Cl | 4-Pyrd(1)-Ph | H | Me | —CH₂— | O | O | CH |
| 1-236 | 3-Cl | 4-Pyrd(1)-Ph | H | Me | —CH₂— | O | O | CH |
| 1-237 | 2-Me | 4-Pyrd(1)-Ph | H | Me | —CH₂— | O | O | CH |
| 1-238 | 3-Me | 4-Pyrd(1)-Ph | H | Me | —CH₂— | O | O | CH |
| 1-239 | 2-MeO | 4-Pyrd(1)-Ph | H | Me | —CH₂— | O | O | CH |
| 1-240 | 3-MeO | 4-Pyrd(1)-Ph | H | Me | —CH₂— | O | O | CH |
| 1-241 | H | 2-Pip(1)-Ph | H | Me | —CH₂— | O | O | CH |
| 1-242 | H | 2-Pip(1)-Ph | H | Me | —CH₂— | O | O | N |
| 1-243 | H | 2-Pip(1)-Ph | H | Me | —CH₂— | O | S | CH |
| 1-244 | H | 2-Pip(1)-Ph | H | Me | —(CH₂)₂— | O | O | CH |
| 1-245 | H | 2-Pip(1)-Ph | H | Et | —CH₂— | O | O | CH |
| 1-246 | H | 2-Pip(1)-Ph | H | Et | —CH₂— | O | S | CH |
| 1-247 | H | 2-Pip(1)-Ph | H | tBu | —CH₂— | O | O | CH |
| 1-248 | H | 3-Pip(1)-Ph | H | Me | —CH₂— | O | O | CH |
| 1-249 | H | 3-Pip(1)-Ph | H | Me | —CH₂— | O | O | N |
| 1-250 | H | 3-Pip(1)-Ph | H | Me | —CH₂— | O | S | CH |
| 1-251 | H | 3-Pip(1)-Ph | H | Me | —(CH₂)₂— | O | O | CH |
| 1-252 | H | 3-Pip(1)-Ph | H | Et | —CH₂— | O | O | CH |
| 1-253 | H | 3-Pip(1)-Ph | H | Et | —CH₂— | O | S | CH |
| 1-254 | H | 3-Pip(1)-Ph | H | Et | —(CH₂)₃— | S | O | CH |
| 1-255 | H | 3-Pip(1)-Ph | H | tBu | —CH₂— | O | O | CH |
| 1-256 | H | 4-Pip(1)-Ph | H | H | —CH₂— | O | O | CH |
| 1-257 | H | 4-Pip(1)-Ph | H | Me | —CH₂— | O | O | CH |
| 1-258 | H | 4-Pip(1)-Ph | H | Me | —CH₂— | O | O | N |
| 1-259 | H | 4-Pip(1)-Ph | H | Me | —CH₂— | O | S | CH |
| 1-260 | H | 4-Pip(1)-Ph | H | Me | —CH₂— | O | S | N |
| 1-261 | H | 4-Pip(1)-Ph | H | Me | —CH₂— | S | O | CH |
| 1-262 | H | 4-Pip(1)-Ph | H | Me | —(CH₂)₂— | O | O | CH |
| 1-263 | H | 4-Pip(1)-Ph | H | Me | —(CH₂)₂— | O | O | N |
| 1-264 | H | 4-Pip(1)-Ph | H | Me | —(CH₂)₂— | O | S | CH |
| 1-265 | H | 4-Pip(1)-Ph | H | Me | —CH(Me)— | O | O | CH |
| 1-266 | H | 4-Pip(1)-Ph | H | Me | —(CH₂)₃— | O | O | CH |
| 1-267 | H | 4-Pip(1)-Ph | H | Et | —CH₂— | O | O | CH |
| 1-268 | H | 4-Pip(1)-Ph | H | Et | —CH₂— | O | O | N |
| 1-269 | H | 4-Pip(1)-Ph | H | Et | —CH₂— | O | S | CH |
| 1-270 | H | 4-Pip(1)-Ph | H | Et | —(CH₂)₂— | O | O | CH |
| 1-271 | H | 4-Pip(1)-Ph | H | tBu | —CH₂— | O | O | CH |
| 1-272 | H | 4-Pip(1)-Ph | H | tBu | —CH₂— | O | S | CH |
| 1-273 | H | 4-Pip(1)-Ph | H | Ph | —CH₂— | O | O | CH |
| 1-274 | H | 4-Pip(1)-Ph | H | Bz | —CH₂— | O | O | CH |
| 1-275 | H | 4-Pip(1)-Ph | 4-Cl | Me | —CH₂— | O | O | CH |
| 1-276 | H | 4-Pip(1)-Ph | 5-Me | Me | —CH₂— | O | O | CH |
| 1-277 | H | 4-Pip(1)-Ph | 5-MeO | Me | —CH₂— | O | O | CH |
| 1-278 | 2-Cl | 4-Pip(1)-Ph | H | Me | —CH₂— | O | O | CH |
| 1-279 | 3-Cl | 4-Pip(1)-Ph | H | Me | —CH₂— | O | O | CH |
| 1-280 | 2-Me | 4-Pip(1)-Ph | H | Me | —CH₂— | O | O | CH |
| 1-281 | 3-Me | 4-Pip(1)-Ph | H | Me | —CH₂— | O | O | CH |
| 1-282 | 2-MeO | 4-Pip(1)-Ph | H | Me | —CH₂— | O | O | CH |
| 1-283 | 3-MeO | 4-Pip(1)-Ph | H | Me | —CH₂— | O | O | CH |
| 1-284 | H | 2-Mor(4)-Ph | H | Me | —CH₂— | O | O | CH |
| 1-285 | H | 2-Mor(4)-Ph | H | Me | —CH₂— | O | O | N |
| 1-286 | H | 2-Mor(4)-Ph | H | Me | —CH₂— | O | S | CH |
| 1-287 | H | 2-Mor(4)-Ph | H | Me | —(CH₂)₂— | O | O | CH |
| 1-288 | H | 2-Mor(4)-Ph | H | Me | —(CH₂)₃— | O | O | CH |
| 1-289 | H | 2-Mor(4)-Ph | H | Et | —CH₂— | O | O | CH |
| 1-290 | H | 2-Mor(4)-Ph | H | Et | —CH₂— | O | S | CH |
| 1-291 | H | 2-Mor(4)-Ph | H | tBu | —CH₂— | O | O | CH |
| 1-292 | H | 3-Mor(4)-Ph | H | Me | —CH₂— | O | O | CH |

TABLE 1-continued

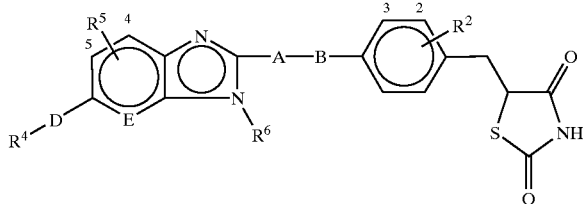

(I-1)

| Cpd. No. | $R^2$ | $R^4$ | $R^5$ | $R^6$ | —A— | B | D | E |
|---|---|---|---|---|---|---|---|---|
| 1-293 | H | 3-Mor(4)-Ph | H | Me | —CH$_2$— | O | O | N |
| 1-294 | H | 3-Mor(4)-Ph | H | Me | —CH$_2$— | O | S | CH |
| 1-295 | H | 3-Mor(4)-Ph | H | Me | —(CH$_2$)$_2$— | O | O | CH |
| 1-296 | H | 3-Mor(4)-Ph | H | Me | —(CH$_2$)$_3$— | O | O | CH |
| 1-297 | H | 3-Mor(4)-Ph | H | Et | —CH$_2$— | O | O | CH |
| 1-298 | H | 3-Mor(4)-Ph | H | Et | —CH$_2$— | O | S | CH |
| 1-299 | H | 3-Mor(4)-Ph | H | tBu | —CH$_2$— | O | O | CH |
| 1-300 | 3-MeO | 3-Mor(4)-Ph | 4-Me | Pr | —(CH$_2$)$_3$— | S | S | CH |
| 1-301 | H | 4-Mor(4)-Ph | H | H | —CH$_2$— | O | O | CH |
| 1-302 | H | 4-Mor(4)-Ph | H | Me | —CH$_2$— | O | O | CH |
| 1-303 | H | 4-Mor(4)-Ph | H | Me | —CH$_2$— | O | O | N |
| 1-304 | H | 4-Mor(4)-Ph | H | Me | —CH$_2$— | O | S | CH |
| 1-305 | H | 4-Mor(4)-Ph | H | Me | —CH$_2$— | O | S | N |
| 1-306 | H | 4-Mor(4)-Ph | H | Me | —CH$_2$— | S | O | CH |
| 1-307 | H | 4-Mor(4)-Ph | H | Me | —(CH$_2$)$_2$— | O | O | CH |
| 1-308 | H | 4-Mor(4)-Ph | H | Me | —(CH$_2$)$_2$— | O | O | N |
| 1-309 | H | 4-Mor(4)-Ph | H | Me | —(CH$_2$)$_2$— | O | S | CH |
| 1-310 | H | 4-Mor(4)-Ph | H | Me | —CH(Me)— | O | O | CH |
| 1-311 | H | 4-Mor(4)-Ph | H | Me | —(CH$_2$)$_3$— | O | O | CH |
| 1-312 | H | 4-Mor(4)-Ph | H | Et | —CH$_2$— | O | O | CH |
| 1-313 | H | 4-Mor(4)-Ph | H | Et | —CH$_2$— | O | O | N |
| 1-314 | H | 4-Mor(4)-Ph | H | Et | —CH$_2$— | O | S | CH |
| 1-315 | H | 4-Mor(4)-Ph | H | Et | —(CH$_2$)$_2$— | O | O | CH |
| 1-316 | H | 4-Mor(4)-Ph | H | tBu | —CH$_2$— | O | O | CH |
| 1-317 | H | 4-Mor(4)-Ph | H | tBu | —CH$_2$— | O | S | CH |
| 1-318 | H | 4-Mor(4)-Ph | H | Ph | —CH$_2$— | O | O | CH |
| 1-319 | H | 4-Mor(4)-Ph | H | Bz | —CH$_2$— | O | O | CH |
| 1-320 | H | 4-Mor(4)-Ph | 5-Cl | Me | —CH$_2$— | O | O | CH |
| 1-321 | H | 4-Mor(4)-Ph | 5-Me | Me | —CH$_2$— | O | O | CH |
| 1-322 | H | 4-Mor(4)-Ph | 5-MeO | Me | —CH$_2$— | O | O | CH |
| 1-323 | 2-Cl | 4-Mor(4)-Ph | H | Me | —CH$_2$— | O | O | CH |
| 1-324 | 3-Cl | 4-Mor(4)-Ph | H | Me | —CH$_2$— | O | O | CH |
| 1-325 | 2-Me | 4-Mor(4)-Ph | H | Me | —CH$_2$— | O | O | CH |
| 1-326 | 3-Me | 4-Mor(4)-Ph | H | Me | —CH$_2$— | O | O | CH |
| 1-327 | 2-MeO | 4-Mor(4)-Ph | H | Me | —CH$_2$— | O | O | CH |
| 1-328 | 3-MeO | 4-Mor(4)-Ph | H | Me | —CH$_2$— | O | O | CH |
| 1-329 | H | 2-TioMor(4)-Ph | H | Me | —CH$_2$— | O | O | CH |
| 1-330 | H | 2-TioMor(4)-Ph | H | Me | —CH$_2$— | O | S | CH |
| 1-331 | H | 3-TioMor(4)-Ph | H | Me | —CH$_2$— | O | O | CH |
| 1-332 | H | 3-TioMor(4)-Ph | H | Me | —CH$_2$— | O | S | CH |
| 1-333 | H | 4-TioMor(4)-Ph | H | Me | —CH$_2$— | O | O | CH |
| 1-334 | H | 4-TioMor(4)-Ph | H | Me | —CH$_2$— | O | O | N |
| 1-335 | H | 4-TioMor(4)-Ph | H | Me | —CH$_2$— | O | S | CH |
| 1-336 | H | 4-TioMor(4)-Ph | H | Et | —CH$_2$— | O | O | CH |
| 1-337 | H | 4-TioMor(4)-Ph | H | Et | —CH$_2$— | O | S | CH |
| 1-338 | H | 2-Pipra(1)-Ph | H | Me | —CH$_2$— | O | O | CH |
| 1-339 | H | 2-Pipra(1)-Ph | H | Me | —CH$_2$— | O | S | CH |
| 1-340 | H | 3-Pipra(1)-Ph | H | Me | —CH$_2$— | O | O | CH |
| 1-341 | H | 3-Pipra(1)-Ph | H | Me | —CH$_2$— | O | S | CH |
| 1-342 | H | 4-Pipra(1)-Ph | H | Me | —CH$_2$— | O | O | CH |
| 1-343 | H | 4-Pipra(1)-Ph | H | Me | —CH$_2$— | O | O | N |
| 1-344 | H | 4-Pipra(1)-Ph | H | Me | —CH$_2$— | O | S | CH |
| 1-345 | H | 4-Pipra(1)-Ph | H | Me | —(CH$_2$)$_2$— | O | O | CH |
| 1-346 | H | 4-Pipra(1)-Ph | H | Me | —(CH$_2$)$_3$— | O | O | CH |
| 1-347 | H | 4-Pipra(1)-Ph | H | Et | —CH$_2$— | O | O | CH |
| 1-348 | H | 4-Pipra(1)-Ph | H | Et | —CH$_2$— | O | S | CH |
| 1-349 | H | 4-Pipra(1)-Ph | H | tBu | —CH$_2$— | O | O | CH |
| 1-350 | H | 2-NO$_2$—Ph | H | Me | —CH$_2$— | O | O | CH |
| 1-351 | H | 3-NO$_2$—Ph | H | Me | —CH$_2$— | O | O | CH |
| 1-352 | H | 4-NO$_2$—Ph | H | Me | —CH$_2$— | O | O | CH |
| 1-353 | H | 4-NO$_2$—Ph | H | Me | —CH$_2$— | O | S | CH |
| 1-354 | H | 3-F-4-OH—Ph | H | Me | —CH$_2$— | O | O | CH |
| 1-355 | H | 2-Cl-4-OH—Ph | H | Me | —CH$_2$— | O | O | CH |
| 1-356 | H | 2-Cl-4-OH—Ph | H | Me | —CH$_2$— | O | S | CH |

TABLE 1-continued (I-1)

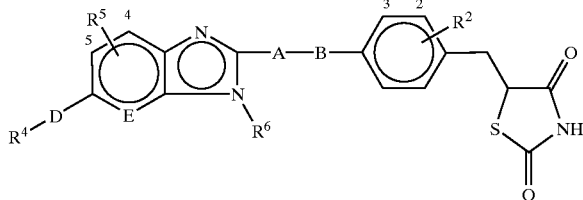

| Cpd. No. | R² | R⁴ | R⁵ | R⁶ | —A— | B | D | E |
|---|---|---|---|---|---|---|---|---|
| 1-357 | H | 3-Cl-4-OH—Ph | H | Me | —CH₂— | O | O | CH |
| 1-358 | H | 3-Cl-4-OH—Ph | H | Me | —CH₂— | O | O | N |
| 1-359 | H | 3-Cl-4-OH—Ph | H | Me | —CH₂— | O | S | CH |
| 1-360 | H | 3-Cl-4-OH—Ph | H | Et | —CH₂— | O | O | CH |
| 1-361 | H | 3-Cl-4-OH—Ph | H | Et | —CH₂— | O | S | CH |
| 1-362 | H | 2-F-4-OH-3,5-diMe—Ph | H | Me | —CH₂— | O | O | CH |
| 1-363 | H | 2-F-4-OH-3,5-diMe—Ph | H | Me | —CH₂— | O | S | CH |
| 1-364 | H | 4-F-3-OH-2,5-diEt—Ph | H | Me | —CH₂— | O | O | CH |
| 1-365 | H | 4-F-3-OH-2,5-diEt—Ph | H | Me | —CH₂— | O | S | CH |
| 1-366 | H | 2-Cl-4-OH-3,5-diMe—Ph | H | H | —CH₂— | O | O | CH |
| 1-367 | H | 2-Cl-4-OH-3,5-diMe—Ph | H | H | —CH₂— | O | S | CH |
| 1-368 | H | 2-Cl-4-OH-3,5-diMe—Ph | H | Me | —CH₂— | O | O | CH |
| 1-369 | H | 2-Cl-4-OH-3,5-diMe—Ph | H | Me | —CH₂— | O | O | N |
| 1-370 | H | 2-Cl-4-OH-3,5-diMe—Ph | H | Me | —CH₂— | O | S | CH |
| 1-371 | H | 2-Cl-4-OH-3,5-diMe—Ph | H | Me | —CH₂— | O | S | N |
| 1-372 | H | 2-Cl-4-OH-3,5-diMe—Ph | H | Me | —CH₂— | S | O | CH |
| 1-373 | H | 2-Cl-4-OH-3,5-diMe—Ph | H | Me | —CH₂— | S | O | N |
| 1-374 | H | 2-Cl-4-OH-3,5-diMe—Ph | H | Me | —CH₂— | S | S | CH |
| 1-375 | H | 2-Cl-4-OH-3,5-diMe—Ph | H | Me | —CH₂— | S | S | N |
| 1-376 | H | 2-Cl-4-OH-3,5-diMe—Ph | H | Me | —(CH₂)₂— | O | O | CH |
| 1-377 | H | 2-Cl-4-OH-3,5-diMe—Ph | H | Me | —(CH₂)₂— | O | O | N |
| 1-378 | H | 2-Cl-4-OH-3,5-diMe—Ph | H | Me | —(CH₂)₂— | O | S | CH |
| 1-379 | H | 2-Cl-4-OH-3,5-diMe—Ph | H | Me | —(CH₂)₂— | O | S | N |
| 1-380 | H | 2-Cl-4-OH-3,5-diMe—Ph | H | Me | —(CH₂)₂— | S | O | CH |
| 1-381 | H | 2-Cl-4-OH-3,5-diMe—Ph | H | Me | —CH(Me)— | O | O | CH |
| 1-382 | H | 2-Cl-4-OH-3,5-diMe—Ph | H | Me | —CH(Me)— | O | S | CH |
| 1-383 | H | 2-Cl-4-OH-3,5-diMe—Ph | H | Me | —(CH₂)₃— | O | O | CH |
| 1-384 | H | 2-Cl-4-OH-3,5-diMe—Ph | H | Me | —(CH₂)₃— | O | S | CH |
| 1-385 | H | 2-Cl-4-OH-3,5-diMe—Ph | H | Me | —(CH₂)₄— | O | O | CH |
| 1-386 | H | 2-Cl-4-OH-3,5-diMe—Ph | H | Et | —CH₂— | O | O | CH |
| 1-387 | H | 2-Cl-4-OH-3,5-diMe—Ph | H | Et | —CH₂— | O | O | N |
| 1-388 | H | 2-Cl-4-OH-3,5-diMe—Ph | H | Et | —CH₂— | O | S | CH |
| 1-389 | H | 2-Cl-4-OH-3,5-diMe—Ph | H | Et | —CH₂— | O | S | N |
| 1-390 | H | 2-Cl-4-OH-3,5-diMe—Ph | H | Et | —CH₂— | S | O | CH |

TABLE 1-continued (I-1)

| Cpd. No. | $R^2$ | $R^4$ | $R^5$ | $R^6$ | —A— | B | D | E |
|---|---|---|---|---|---|---|---|---|
| 1-391 | H | 2-Cl-4-OH-3,5-diMe—Ph | H | Et | —(CH$_2$)$_2$— | O | O | CH |
| 1-392 | H | 2-Cl-4-OH-3,5-diMe—Ph | H | Et | —(CH$_2$)$_2$— | O | S | CH |
| 1-393 | H | 2-Cl-4-OH-3,5-diMe—Ph | H | Pr | —CH$_2$— | O | O | CH |
| 1-394 | H | 2-Cl-4-OH-3,5-diMe—Ph | H | iPr | —CH$_2$— | O | O | CH |
| 1-395 | H | 2-Cl-4-OH-3,5-diMe—Ph | H | Bu | —CH$_2$— | O | O | CH |
| 1-396 | H | 2-Cl-4-OH-3,5-diMe—Ph | H | sBu | —CH$_2$— | O | O | CH |
| 1-397 | H | 2-Cl-4-OH-3,5-diMe—Ph | H | sBu | —(CH$_2$)$_3$— | O | O | CH |
| 1-398 | H | 2-Cl-4-OH-3,5-diMe—Ph | H | tBu | —CH$_2$— | O | O | CH |
| 1-399 | H | 2-Cl-4-OH-3,5-diMe—Ph | H | tBu | —CH$_2$— | O | S | CH |
| 1-400 | H | 2-Cl-4-OH-3,5-diMe—Ph | H | Ph | —CH$_2$— | O | O | CH |
| 1-401 | H | 2-Cl-4-OH-3,5-diMe—Ph | H | Ph | —CH$_2$— | O | O | N |
| 1-402 | H | 2-Cl-4-OH-3,5-diMe—Ph | H | Ph | —CH$_2$— | O | S | CH |
| 1-403 | H | 2-Cl-4-OH-3,5-diMe—Ph | H | Ph | —(CH$_2$)$_2$— | O | O | CH |
| 1-404 | H | 2-Cl-4-OH-3,5-diMe—Ph | H | Bz | —CH$_2$— | O | O | CH |
| 1-405 | H | 2-Cl-4-OH-3,5-diMe—Ph | H | Bz | —CH$_2$— | O | O | N |
| 1-406 | H | 2-Cl-4-OH-3,5-diMe—Ph | H | Bz | —CH$_2$— | O | S | CH |
| 1-407 | H | 2-Cl-4-OH-3,5-diMe—Ph | H | Bz | —(CH$_2$)$_2$— | O | O | CH |
| 1-408 | H | 2-Cl-4-OH-3,5-diMe—Ph | 5-F | Me | —CH$_2$— | O | O | CH |
| 1-409 | H | 2-Cl-4-OH-3,5-diMe—Ph | 4-Cl | Me | —CH$_2$— | O | O | CH |
| 1-410 | H | 2-Cl-4-OH-3,5-diMe—Ph | 5-Cl | M | —CH$_2$— | O | O | CH |
| 1-411 | H | 2-Cl-4-OH-3,5-diMe—Ph | 4-Me | Me | —CH$_2$— | O | O | CH |
| 1-412 | H | 2-Cl-4-OH-3,5-diMe—Ph | 5-Me | Me | —CH$_2$— | O | O | CH |
| 1-413 | H | 2-Cl-4-OH-3,5-diMe—Ph | 4-MeO | Me | —CH$_2$— | O | O | CH |
| 1-414 | H | 2-Cl-4-OH-3,5-diMe—Ph | 5-MeO | Me | —CH$_2$— | O | O | CH |
| 1-415 | H | 2-Cl-4-OH-3,5-diMe—Ph | 5-MeS | Me | —CH$_2$— | O | O | CH |
| 1-416 | 3-F | 2-Cl-4-OH-3,5-diMe—Ph | H | Me | —CH$_2$— | O | O | CH |
| 1-417 | 2-Cl | 2-Cl-4-OH-3,5-diMe—Ph | H | Me | —CH$_2$— | O | O | CH |
| 1-418 | 3-Cl | 2-Cl-4-OH-3,5-diMe—Ph | H | Me | —CH$_2$— | O | O | CH |
| 1-419 | 2-Me | 2-Cl-4-OH-3,5-diMe—Ph | H | Me | —CH$_2$— | O | O | CH |
| 1-420 | 3-Me | 2-Cl-4-OH-3,5-diMe—Ph | H | Me | —CH$_2$— | O | O | CH |
| 1-421 | 3-CF$_3$ | 2-Cl-4-OH-3,5-diMe—Ph | H | Me | —CH$_2$— | O | O | CH |
| 1-422 | 2-MeO | 2-Cl-4-OH-3,5-diMe—Ph | H | Me | —CH$_2$— | O | O | CH |

TABLE 1-continued

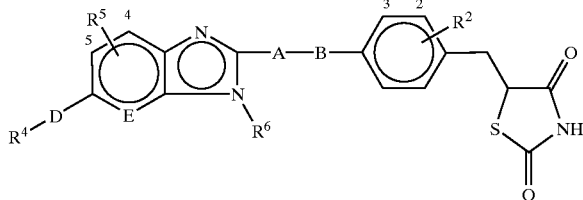

(I-1)

| Cpd. No. | R² | R⁴ | R⁵ | R⁶ | —A— | B | D | E |
|---|---|---|---|---|---|---|---|---|
| 1-423 | 3-MeO | 2-Cl-4-OH-3,5-diMe—Ph | H | Me | —CH$_2$— | O | O | CH |
| 1-424 | H | 2-Cl-4-OH-3,5-diMe—Ph | H | Me | —CH$_2$— | O | O | CH |
| 1-425 | H | 2-Cl-4-OH-3,5-diEt—Ph | H | Me | —CH$_2$— | O | S | CH |
| 1-426 | H | 2-Cl-4-OH-3,5-ditBu—Ph | H | Me | —CH$_2$— | O | O | CH |
| 1-427 | H | 2-Cl-4-OH-3,5-ditBu—Ph | H | Me | —CH$_2$— | O | S | CH |
| 1-428 | H | 3-Cl-5-OH-2,6-diMe—Ph | H | Me | —CH$_2$— | O | O | CH |
| 1-429 | H | 3-Cl-5-OH-2,6-diMe—Ph | H | Me | —CH$_2$— | O | O | N |
| 1-430 | H | 3-Cl-5-OH-2,6-diMe—Ph | H | Me | —CH$_2$— | O | S | CH |
| 1-431 | H | 3-Cl-5-OH-2,6-diMe—Ph | H | Et | —CH$_2$— | O | O | CH |
| 1-432 | H | 3-Cl-5-OH-2,6-diMe—Ph | H | Et | —CH$_2$— | O | S | CH |
| 1-433 | H | 4-Cl-3-OH-2,5-diMe—Ph | H | Me | —CH$_2$— | O | O | CH |
| 1-434 | H | 4-Cl-3-OH-2,5-diMe—Ph | H | Me | —CH$_2$— | O | O | N |
| 1-435 | H | 4-Cl-3-OH-2,5-diMe—Ph | H | Me | —CH$_2$— | O | S | CH |
| 1-436 | H | 4-Cl-3-OH-2,5-diMe—Ph | H | Et | —CH$_2$— | O | O | CH |
| 1-437 | H | 4-Cl-3-OH-2,5-diMe—Ph | H | Et | —CH$_2$— | O | S | CH |
| 1-438 | H | 3-Cl-4-NH$_2$—Ph | H | Me | —CH$_2$— | O | O | CH |
| 1-439 | H | 3-Cl-4-NH$_2$—Ph | H | Me | —CH$_2$— | O | S | CH |
| 1-440 | H | 3,5-diCl-4-NH$_2$—Ph | H | Me | —CH$_2$— | O | O | CH |
| 1-441 | H | 3,5-diCl-4-NH$_2$—Ph | H | Me | —CH$_2$— | O | O | N |
| 1-442 | H | 3,5-diCl-4-NH$_2$—Ph | H | Me | —CH$_2$— | O | S | CH |
| 1-443 | H | 3,5-diCl-4-NH$_2$—Ph | H | Et | —CH$_2$— | O | O | CH |
| 1-444 | H | 3,5-diCl-4-NH$_2$—Ph | H | Et | —CH$_2$— | O | S | CH |
| 1-445 | H | 3,5-diF-4-NH$_2$—Ph | H | Me | —CH$_2$— | O | O | CH |
| 1-446 | H | 3,5-diF-4-NH$_2$—Ph | H | Me | —CH$_2$— | O | S | CH |
| 1-447 | H | 4-NHMe-3-Cl—Ph | H | Me | —CH$_2$— | O | O | CH |
| 1-448 | H | 4-NHMe-3-Cl—Ph | H | Me | —CH$_2$— | O | S | CH |
| 1-449 | H | 3-Cl-4-Pyrd(1)-Ph | H | Me | —CH$_2$— | O | O | CH |
| 1-450 | H | 3-Cl-4-Pyrd(1)-Ph | H | Me | —CH$_2$— | O | S | CH |
| 1-451 | H | 3-OH-4-Pyrd(1)-Ph | H | Me | —CH$_2$— | O | O | CH |
| 1-452 | H | 3-OH-4-Pyrd(1)-Ph | H | Me | —CH$_2$— | O | S | CH |
| 1-453 | H | 3-Cl-6-Me-4-Pyrd(1)-Ph | H | Me | —CH$_2$— | O | O | CH |
| 1-454 | H | 3-Cl-6-Me-4-Pyrd(1)-Ph | H | Me | —CH$_2$— | O | S | CH |
| 1-455 | H | 2-Me-4-Pip(1)-Ph | H | Me | —CH$_2$— | O | O | CH |
| 1-456 | H | 2-Me-4-Pip(1)-Ph | H | Me | —CH$_2$— | O | S | CH |

TABLE 1-continued

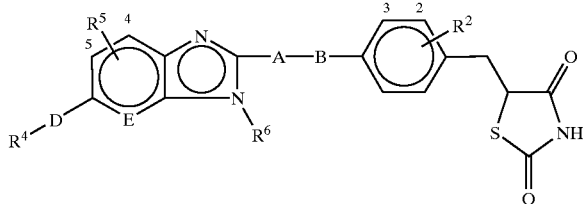

(I-1)

| Cpd. No. | $R^2$ | $R^4$ | $R^5$ | $R^6$ | —A— | B | D | E |
|---|---|---|---|---|---|---|---|---|
| 1-457 | H | 2-Me-4-Mor(4)-Ph | H | Me | —CH$_2$— | O | O | CH |
| 1-458 | H | 2-Me-4-Mor(4)-Ph | H | Me | —CH$_2$— | O | S | CH |
| 1-459 | H | 2-OH-3-Me—Ph | H | Me | —CH$_2$— | O | O | CH |
| 1-460 | H | 2-OH-3-Me—Ph | H | Me | —CH$_2$— | O | S | CH |
| 1-461 | H | 2-OH-4-Me—Ph | H | Me | —CH$_2$— | O | O | CH |
| 1-462 | H | 2-OH-4-Me—Ph | H | Me | —CH$_2$— | O | S | CH |
| 1-463 | H | 2-OH-3,4-diMe—Ph | H | Me | —CH$_2$— | O | O | CH |
| 1-464 | H | 2-OH-3,4-diMe—Ph | H | Me | —CH$_2$— | O | O | N |
| 1-465 | H | 2-OH-3,4-diMe—Ph | H | Me | —CH$_2$— | O | S | CH |
| 1-466 | H | 2-OH-3,4-diMe—Ph | H | Et | —CH$_2$— | O | O | CH |
| 1-467 | H | 2-OH-3,4-diMe—Ph | H | Et | —CH$_2$— | O | S | CH |
| 1-468 | H | 3-OH-2-Me—Ph | H | Me | —CH$_2$— | O | O | CH |
| 1-469 | H | 3-OH-2-Me—Ph | H | Me | —CH$_2$— | O | S | CH |
| 1-470 | H | 3-OH-4-Me—Ph | H | Me | —CH$_2$— | O | O | CH |
| 1-471 | H | 3-OH-4-Me—Ph | H | Me | —CH$_2$— | O | S | CH |
| 1-472 | H | 3-OH-5-Me—Ph | H | Me | —CH$_2$— | O | O | CH |
| 1-473 | H | 3-OH-5-Me—Ph | H | Me | —CH$_2$— | O | S | CH |
| 1-474 | H | 3-OH-6-Me—Ph | H | Me | —CH$_2$— | O | O | CH |
| 1-475 | H | 3-OH-6-Me—Ph | H | Me | —CH$_2$— | O | S | CH |
| 1-476 | H | 3-OH-2,4-diMe—Ph | H | Me | —CH$_2$— | O | O | CH |
| 1-477 | H | 3-OH-2,4-diMe—Ph | H | Me | —CH$_2$— | O | O | N |
| 1-478 | H | 3-OH-2,4-diMe—Ph | H | Me | —CH$_2$— | O | S | CH |
| 1-479 | H | 3-OH-2,4-diMe—Ph | H | Et | —CH$_2$— | O | O | CH |
| 1-480 | H | 3-OH-2,4-diMe—Ph | H | Et | —CH$_2$— | O | S | CH |
| 1-481 | H | 4-OH-2-Me—Ph | H | Me | —CH$_2$— | O | O | CH |
| 1-482 | H | 4-OH-2-Me—Ph | H | Me | —CH$_2$— | O | O | N |
| 1-483 | H | 4-OH-2-Me—Ph | H | Me | —CH$_2$— | O | S | CH |
| 1-484 | H | 4-OH-2-Me—Ph | H | Et | —CH$_2$— | O | O | CH |
| 1-485 | H | 4-OH-2-Me—Ph | H | Et | —CH$_2$— | O | S | CH |
| 1-486 | H | 4-OH-3-Me—Ph | H | Me | —CH$_2$— | O | O | CH |
| 1-487 | H | 4-OH-3-Me—Ph | H | Me | —CH$_2$— | O | O | N |
| 1-488 | H | 4-OH-3-Me—Ph | H | Me | —CH$_2$— | O | S | CH |
| 1-489 | H | 4-OH-3-Me—Ph | H | Me | —(CH$_2$)$_2$— | O | O | CH |
| 1-490 | H | 4-OH-3-Me—Ph | H | Et | —CH$_2$— | O | O | CH |
| 1-491 | H | 4-OH-3-Me—Ph | H | Et | —CH$_2$— | O | S | CH |
| 1-492 | H | 4-OH-3-Me—Ph | H | tBu | —CH$_2$— | O | O | CH |
| 1-493 | H | 4-OH-3-Me—Ph | 5-Cl | Me | —CH$_2$— | O | O | CH |
| 1-494 | H | 4-OH-2-Et—Ph | H | Me | —CH$_2$— | O | O | CH |
| 1-495 | H | 4-OH-2-Et—Ph | H | Me | —CH$_2$— | O | S | CH |
| 1-496 | H | 4-OH-3-Et—Ph | H | Me | —CH$_2$— | O | O | CH |
| 1-497 | H | 4-OH-3-Et—Ph | H | Me | —CH$_2$— | O | S | CH |
| 1-498 | H | 4-OH-3-Pr—Ph | H | Me | —CH$_2$— | O | O | CH |
| 1-499 | H | 4-OH-2-tBu—Ph | H | Me | —CH$_2$— | O | O | CH |
| 1-500 | H | 4-OH-2-tBu—Ph | H | Me | —CH$_2$— | O | S | CH |
| 1-501 | H | 4-OH-3-tBu—Ph | H | Me | —CH$_2$— | O | O | CH |
| 1-502 | H | 4-OH-3-tBu—Ph | H | Me | —CH$_2$— | O | O | N |
| 1-503 | H | 4-OH-3-tBu—Ph | H | Me | —CH$_2$— | O | S | CH |
| 1-504 | H | 4-OH-3-tBu—Ph | H | Et | —CH$_2$— | O | O | CH |
| 1-505 | H | 4-OH-3-tBu—Ph | H | Et | —CH$_2$— | O | S | CH |
| 1-506 | H | 4-OH-2,3-diMe—Ph | H | Me | —CH$_2$— | O | O | CH |

TABLE 1-continued (I-1)

| Cpd. No. | R² | R⁴ | R⁵ | R⁶ | —A— | B | D | E |
|---|---|---|---|---|---|---|---|---|
| 1-507 | H | 4-OH-2,3-diMe—Ph | H | Me | —CH₂— | O | O | N |
| 1-508 | H | 4-OH-2,3-diMe—Ph | H | Me | —CH₂— | O | S | CH |
| 1-509 | H | 4-OH-2,3-diMe—Ph | H | Me | —(CH₂)₃— | S | O | CH |
| 1-510 | H | 4-OH-2,3-diMe—Ph | H | Et | —CH₂— | O | O | CH |
| 1-511 | H | 4-OH-2,3-diMe—Ph | H | Et | —CH₂— | O | S | CH |
| 1-512 | H | 4-OH-2,3-diMe—Ph | H | tBu | —CH₂— | O | O | CH |
| 1-513 | H | 4-OH-2,5-diMe—Ph | H | Me | —CH₂— | O | O | CH |
| 1-514 | H | 4-OH-2,5-diMe—Ph | H | Me | —CH₂— | O | O | N |
| 1-515 | H | 4-OH-2,5-diMe—Ph | H | Me | —CH₂— | O | S | CH |
| 1-516 | H | 4-OH-2,5-diMe—Ph | H | Et | —CH₂— | O | O | CH |
| 1-517 | H | 4-OH-2,5-diMe—Ph | H | Et | —CH₂— | O | S | CH |
| 1-518 | H | 4-OH-3,5-diMe—Ph | H | H | —CH₂— | O | O | CH |
| 1-519 | H | 4-OH-3,5-diMe—Ph | H | H | —CH₂— | O | S | CH |
| 1-520 | H | 4-OH-3,5-diMe—Ph | H | Me | —CH₂— | O | O | CH |
| 1-521 | H | 4-OH-3,5-diMe—Ph | H | Me | —CH₂— | O | O | N |
| 1-522 | H | 4-OH-3,5-diMe—Ph | H | Me | —CH₂— | O | S | CH |
| 1-523 | H | 4-OH-3,5-diMe—Ph | H | Me | —CH₂— | O | S | N |
| 1-524 | H | 4-OH-3,5-diMe—Ph | H | Me | —CH₂— | S | O | CH |
| 1-525 | H | 4-OH-3,5-diMe—Ph | H | Me | —CH₂— | S | O | N |
| 1-526 | H | 4-OH-3,5-diMe—Ph | H | Me | —CH₂— | S | S | CH |
| 1-527 | H | 4-OH-3,5-diMe—Ph | H | Me | —CH₂— | S | S | N |
| 1-528 | H | 4-OH-3,5-diMe—Ph | H | Me | —(CH₂)₂— | O | O | CH |
| 1-529 | H | 4-OH-3,5-diMe—Ph | H | Me | —(CH₂)₂— | O | O | N |
| 1-530 | H | 4-OH-3,5-diMe—Ph | H | Me | —(CH₂)₂— | O | S | CH |
| 1-531 | H | 4-OH-3,5-diMe—Ph | H | Me | —(CH₂)₂— | O | S | N |
| 1-532 | H | 4-OH-3,5-diMe—Ph | H | Me | —(CH₂)₂— | S | O | CH |
| 1-533 | H | 4-OH-3,5-diMe—Ph | H | Me | —CH(Me)— | O | O | CH |
| 1-534 | H | 4-OH-3,5-diMe—Ph | H | Me | —CH(Me)— | O | S | CH |
| 1-535 | H | 4-OH-3,5-diMe—Ph | H | Me | —(CH₂)₃— | O | O | CH |
| 1-536 | H | 4-OH-3,5-diMe—Ph | H | Me | —(CH₂)₃— | O | S | CH |
| 1-537 | H | 4-OH-3,5-diMe—Ph | H | Me | —(CH₂)₄— | O | O | CH |
| 1-538 | H | 4-OH-3,5-diMe—Ph | H | Et | —CH₂— | O | O | CH |

TABLE 1-continued (I-1)

| Cpd. No. | R² | R⁴ | R⁵ | R⁶ | —A— | B | D | E |
|---|---|---|---|---|---|---|---|---|
| 1-539 | H | 4-OH-3,5-diMe—Ph | H | Et | —CH₂— | O | O | N |
| 1-540 | H | 4-OH-3,5-diMe—Ph | H | Et | —CH₂— | O | S | CH |
| 1-541 | H | 4-OH-3,5-diMe—Ph | H | Et | —CH₂— | O | S | N |
| 1-542 | H | 4-OH-3,5-diMe—Ph | H | Et | —CH₂— | S | O | CH |
| 1-543 | H | 4-OH-3,5-diMe—Ph | H | Et | —(CH₂)₂— | O | O | CH |
| 1-544 | H | 4-OH-3,5-diMe—Ph | H | Et | —(CH₂)₂— | O | S | CH |
| 1-545 | H | 4-OH-3,5-diMe—Ph | H | Pr | —CH₂— | O | O | CH |
| 1-546 | H | 4-OH-3,5-diMe—Ph | H | iPr | —CH₂— | O | O | CH |
| 1-547 | H | 4-OH-3,5-diMe—Ph | H | Bu | —CH₂— | O | O | CH |
| 1-543 | H | 4-OR-3,5-diMe—Ph | H | sBu | —CH₂— | O | O | CH |
| 1-549 | H | 4-OH-3,5-diMe—Ph | H | sBu | —(CH₂)₃— | O | O | CH |
| 1-550 | H | 4-OH-3,5-diMe—Ph | H | tBu | —CH₂— | O | O | CH |
| 1-551 | H | 4-OH-3,5-diMe—Ph | H | tBu | —CH₂— | O | S | CH |
| 1-552 | H | 4-OH-3,5-diMe—Ph | H | Ph | —CH₂— | O | O | CH |
| 1-553 | H | 4-OH-3,5-diMe—Ph | H | Ph | —CH₂— | O | O | N |
| 1-554 | H | 4-OH-3,5-diMe—Ph | H | Ph | —CH₂— | O | S | CH |
| 1-555 | H | 4-OH-3,5-diMe—Ph | H | Ph | —(CH₂)₂— | O | O | CH |
| 1-556 | H | 4-OH-3,5-diMe—Ph | H | Bz | —CH₂— | O | O | CH |
| 1-557 | H | 4-OH-3,5-diMe—Ph | H | Bz | —CH₂— | O | O | N |
| 1-558 | H | 4-OH-3,5-diMe—Ph | H | Bz | —CH₂— | O | S | CH |
| 1-559 | H | 4-OH-3,5-diMe—Ph | H | Bz | —(CH₂)₂— | O | O | CH |
| 1-560 | H | 4-OH-3,5-diMe—Ph | 5-F | Me | —CH₂— | O | O | CH |
| 1-561 | H | 4-OH-3,5-diMe—Ph | 4-Cl | Me | —CH₂— | O | O | CH |
| 1-562 | H | 4-OH-3,5-diMe—Ph | 5-Cl | Me | —CH₂— | O | O | CH |
| 1-563 | H | 4-OH-3,5-diMe—Ph | 4-Me | Me | —CH₂— | O | O | CH |
| 1-564 | H | 4-OH-3,5-diMe—Ph | 5-Me | Me | —CH₂— | O | O | CH |
| 1-565 | H | 4-OH-3,5-diMe—Ph | 4-MeO | Me | —CH₂— | O | O | CH |
| 1-566 | H | 4-OH-3,5-diMe—Ph | 5-MeO | Me | —CH₂— | O | O | CH |
| 1-567 | H | 4-OH-3,5-diMe—Ph | 5-MeS | Me | —CH₂— | O | O | CH |
| 1-568 | 3-F | 4-OH-3,5-diMe—Ph | H | Me | —CH₂— | O | O | CH |
| 1-569 | 2-Cl | 4-OH-3,5-diMe—Ph | H | Me | —CH₂— | O | O | CH |
| 1-570 | 3-Cl | 4-OH-3,5-diMe—Ph | H | Me | —CH₂— | O | O | CH |

TABLE 1-continued (I-1)

| Cpd. No. | R² | R⁴ | R⁵ | R⁶ | —A— | B | D | E |
|---|---|---|---|---|---|---|---|---|
| 1-571 | 2-Me | 4-OH-3,5-diMe—Ph | H | Me | —CH₂— | O | O | CH |
| 1-572 | 3-Me | 4-OH-3,5-diMe—Ph | H | Me | —CH₂— | O | O | CH |
| 1-573 | 3-CF₃ | 4-OH-3,5-diMe—Ph | H | Me | —CH₂— | O | O | CH |
| 1-574 | 2-MeO | 4-OH-3,5-diMe—Ph | H | Me | —CH₂— | O | O | CH |
| 1-575 | 2-MeO | 4-OH-3,5-diMe—Ph | H | Me | —CH₂— | O | S | CH |
| 1-576 | 3-MeO | 4-OH-3,5-diMe—Ph | H | Me | —CH₂— | O | O | CH |
| 1-577 | H | 3,5-diEt-4-OH—Ph | H | Me | —CH₂— | O | O | CH |
| 1-578 | H | 3,5-diEt-4-OH—Ph | H | Me | —CH₂— | O | O | N |
| 1-579 | H | 3,5-diEt-4-OH—Ph | H | Me | —CH₂— | O | S | CH |
| 1-580 | H | 3,5-diEt-4-OH—Ph | H | Et | —CH₂— | O | O | CH |
| 1-581 | H | 3,5-diEt-4-OH—Ph | H | Et | —CH₂— | O | S | CH |
| 1-582 | H | 3-tBu-4-OH-5-Me—Ph | H | Me | —CH₂— | O | O | CH |
| 1-583 | H | 3-tBu-4-OH-5-Me—Ph | H | Me | —CH₂— | O | O | N |
| 1-584 | H | 3-tBu-4-OH-5-Me—Ph | H | Me | —CH₂— | O | S | CH |
| 1-585 | H | 3-Bu-4-OH-5-Me—Ph | H | Et | —CH₂— | O | O | CH |
| 1-586 | H | 3-tBu-4-OH-5-Me—Ph | H | Et | —CH₂— | O | S | CH |
| 1-587 | H | 4-OH-3,5-diPr—Ph | H | Me | —CH₂— | O | O | CH |
| 1-588 | H | 4-OH-3,5-diPr—Ph | H | Me | —CH₂— | O | S | CH |
| 1-589 | H | 4-OH-3,5-diPr—Ph | H | Me | —CH₂— | O | O | CH |
| 1-590 | H | 4-OH-3,5-diPr—Ph | H | Me | —CH₂— | O | S | CH |
| 1-591 | H | 3,5-ditBu-4-OH—Ph | H | H | —CH₂— | O | O | CH |
| 1-592 | H | 3,5-ditBu-4-OH—Ph | H | H | —CH₂— | O | S | CH |
| 1-593 | H | 3,5-ditBu-4-OH—Ph | H | Me | —CH₂— | O | O | CH |
| 1-594 | H | 3,5-ditBu-4-OH—Ph | H | Me | —CH₂— | O | O | N |
| 1-595 | H | 3,5-ditBu-4-OH—Ph | H | Me | —CH₂— | O | S | CH |
| 1-596 | H | 3,5-ditBu-4-OH—Ph | H | Me | —CH₂— | O | S | N |
| 1-597 | H | 3,5-ditBu-4-OH—Ph | H | Me | —CH₂— | S | O | CH |
| 1-598 | H | 3,5-ditBu-4-OH—Ph | H | Me | —CH₂— | S | O | N |
| 1-599 | H | 3,5-ditBu-4-OH—Ph | H | Me | —CH₂— | S | S | CH |
| 1-600 | H | 3,5-ditBu-4-OH—Ph | H | Me | —CH₂— | S | S | N |
| 1-601 | H | 3,5-ditBu-4-OH—Ph | H | Me | —(CH₂)₂— | O | O | CH |
| 1-602 | H | 3,5-ditBu-4-OH—Ph | H | Me | —(CH₂)₂— | O | O | N |

TABLE 1-continued (I-1)

| Cpd. No. | R² | R⁴ | R⁵ | R⁶ | —A— | B | D | E |
|---|---|---|---|---|---|---|---|---|
| 1-603 | H | 3,5-ditBu-4-OH—Ph | H | Me | —(CH₂)₂— | O | S | CH |
| 1-604 | H | 3,5-ditBu-4-OH—Ph | H | Me | —(CH₂)₂— | O | S | N |
| 1-605 | H | 3,5-ditBu-4-OH—Ph | H | Me | —(CH₂)₂— | S | O | CH |
| 1-606 | H | 3,5-ditBu-4-OH—Ph | H | Me | —CH(Me)— | O | O | CH |
| 1-607 | H | 3,5-ditBu-4-OH—Ph | H | Me | —CH(Me)— | O | S | CH |
| 1-608 | H | 3,5-ditBu-4-OH—Ph | H | Me | —(CH₂)₃— | O | O | CH |
| 1-609 | H | 3,5-ditBu-4-OH—Ph | H | Me | —(CH₂)₃— | O | S | CH |
| 1-610 | H | 3,5-ditBu-4-OH—Ph | H | Me | —(CH₂)₄— | O | O | CH |
| 1-611 | H | 3,5-ditBu-4-OH—Ph | H | Et | —CH₂— | O | O | CH |
| 1-612 | H | 3,5-ditBu-4-OH—Ph | H | Et | —CH₂— | O | O | N |
| 1-613 | H | 3,5-ditBu-4-OH—Ph | H | Et | —CH₂— | O | S | CH |
| 1-614 | H | 3,5-ditBu-4-OH—Ph | H | Et | —CH₂— | O | S | N |
| 1-615 | H | 3,5-ditBu-4-OH—Ph | H | Et | —CH₂— | S | O | CH |
| 1-616 | H | 3,5-ditBu-4-OH—Ph | H | Et | —(CH₂)₂— | O | O | CH |
| 1-617 | H | 3,5-ditBu-4-OH—Ph | H | Et | —(CH₂)₂— | O | S | CH |
| 1-618 | H | 3,5-ditBu-4-OH—Ph | H | Pr | —CH₂— | O | O | CH |
| 1-619 | H | 3,5-ditBu-4-OH—Ph | H | iPr | —CH₂— | O | O | CH |
| 1-620 | H | 3,5-ditBu-4-OH—Ph | H | Bu | —CH₂— | O | O | CH |
| 1-621 | H | 3,5-ditBu-4-OH—Ph | H | sBu | —CH₂— | O | O | CH |
| 1-622 | H | 3,5-ditBu-4-OH—Ph | H | sBu | —(CH₂)₃— | O | O | CH |
| 1-623 | H | 3,5-ditBu-4-OH—Ph | H | tBu | —CH₂— | O | O | CH |
| 1-624 | H | 3,5-ditBu-4-OH—Ph | H | tBu | —CH₂— | O | S | CH |
| 1-625 | H | 3,5-ditBu-4-OH—Ph | H | Ph | —CH₂— | O | O | CH |
| 1-626 | H | 3,5-ditBu-4-OH—Ph | H | Ph | —CH₂— | O | O | N |
| 1-627 | H | 3,5-ditBu-4-OH—Ph | H | Ph | —CH₂— | O | S | CH |
| 1-628 | H | 3,5-ditBu-4-OH—Ph | H | Ph | —(CH₂)₂— | O | O | CH |
| 1-629 | H | 3,5-ditBu-4-OH—Ph | H | Bz | —CH₂— | O | O | CH |
| 1-630 | H | 3,5-ditBu-4-OH—Ph | H | Bz | —CH₂— | O | O | N |
| 1-631 | H | 3,5-ditBu-4-OH—Ph | H | Bz | —CH₂— | O | S | CH |
| 1-632 | H | 3,5-ditBu-4-OH—Ph | H | Bz | —(CH₂)₂— | O | O | CH |
| 1-633 | H | 3,5-ditBu-4-OH—Ph | 5-F | Me | —CH₂— | O | O | CH |
| 1-634 | H | 3,5-ditBu-4-OH—Ph | 5-Cl | Me | —CH₂— | O | S | CH |

TABLE 1-continued (I-1)

| Cpd. No. | R² | R⁴ | R⁵ | R⁶ | —A— | B | D | E |
|---|---|---|---|---|---|---|---|---|
| 1-635 | H | 3,5-ditBu-4-OH—Ph | 5-Cl | Me | —CH₂— | O | O | CH |
| 1-636 | H | 3,5-ditBu-4-OH—Ph | 4-Me | Me | —CH₂— | O | O | CH |
| 1-637 | H | 3,5-ditBu-4-OH—Ph | 5-Me | Me | —CH₂— | O | O | CH |
| 1-638 | H | 3,5-ditBu-4-OH—Ph | 4-MeO | Me | —CH₂— | O | O | CH |
| 1-639 | H | 3,5-ditBu-4-OH—Ph | 5-MeO | Me | —CH₂— | O | O | CH |
| 1-640 | 3-F | 3,5-ditBu-4-OH—Ph | H | Me | —CH₂— | O | O | CH |
| 1-641 | 2-Cl | 3,5-ditBu-4-OH—Ph | H | Me | —CH₂— | O | O | CH |
| 1-642 | 3-Cl | 3,5-ditBu-4-OH—Ph | H | Me | —CH₂— | O | O | CH |
| 1-643 | 2-Me | 3,5-ditBu-4-OH—Ph | H | Me | —CH₂— | O | O | CH |
| 1-644 | 3-Me | 3,5-ditBu-4-OH—Ph | H | Me | —CH₂— | O | O | CH |
| 1-645 | 3-CF₃ | 3,5-ditBu-4-OH—Ph | H | Me | —CH₂— | O | O | CH |
| 1-646 | 2-MeO | 3,5-ditBu-4-OH—Ph | H | Me | —CH₂— | O | O | CH |
| 1-647 | 3-MeO | 3,5-ditBu-4-OH—Ph | H | Me | —CH₂— | O | O | CH |
| 1-648 | H | 4-OH-2,3,5-triMe—Ph | H | H | —CH₂— | O | O | CH |
| 1-649 | H | 4-OH-2,3,5-triMe—Ph | H | H | —CH₂— | O | S | CH |
| 1-650 | H | 4-OH-2,3,5-triMe—Ph | H | Me | —CH₂— | O | O | CH |
| 1-651 | H | 4-OH-2,3,5-triMe—Ph | H | Me | —CH₂— | O | O | N |
| 1-652 | H | 4-OH-2,3,5-triMe—Ph | H | Me | —CH₂— | O | S | CH |
| 1-653 | H | 4-OH-2,3,5-triMe—Ph | H | Me | —CH₂— | O | S | N |
| 1-654 | H | 4-OH-2,3,5-triMe—Ph | H | Me | —CH₂— | S | O | CH |
| 1-655 | H | 4-OH-2,3,5-triMe—Ph | H | Me | —CH₂— | S | O | N |
| 1-656 | H | 4-OH-2,3,5-triMe—Ph | H | Me | —CH₂— | S | S | CH |
| 1-657 | H | 4-OH-2,3,5-triMe—Ph | H | Me | —CH₂— | S | S | N |
| 1-658 | H | 4-OH-2,3,5-triMe—Ph | H | Me | —(CH₂)₂— | O | O | CH |
| 1-659 | H | 4-OH-2,3,5-triMe—Ph | H | Me | —(CH₂)₂— | O | O | N |
| 1-660 | H | 4-OH-2,3,5-triMe—Ph | H | Me | —(CH₂)₂— | O | S | CH |
| 1-661 | H | 4-OH-2,3,5-triMe—Ph | H | Me | —(CH₂)₂— | O | S | N |
| 1-662 | H | 4-OH-2,3,5-triMe—Ph | H | Me | —(CH₂)₂— | S | O | CH |
| 1-663 | H | 4-OH-2,3,5-triMe—Ph | H | Me | —CH(Me)— | O | O | CH |
| 1-664 | H | 4-OH-2,3,5-triMe—Ph | H | Me | —CH(Me)— | O | S | CH |
| 1-665 | H | 4-OH-2,3,5-triMe—Ph | H | Me | —(CH₂)₃— | O | O | CH |
| 1-666 | H | 4-OH-2,3,5-triMe—Ph | H | Me | —(CH₂)₃— | O | S | CH |

TABLE 1-continued (I-1)

| Cpd. No. | R² | R⁴ | R⁵ | R⁶ | —A— | B | D | E |
|---|---|---|---|---|---|---|---|---|
| 1-667 | H | 4-OH-2,3,5-triMe—Ph | H | Me | —(CH₂)₄— | O | O | CH |
| 1-668 | H | 4-OH-2,3,5-triMe—Ph | H | Et | —CH₂— | O | O | CH |
| 1-669 | H | 4-OH-2,3,5-triMe—Ph | H | Et | —CH₂— | O | O | N |
| 1-670 | H | 4-OH-2,3,5-triMe—Ph | H | Et | —CH₂— | O | S | CH |
| 1-671 | H | 4-OH-2,3,5-triMe—Ph | H | Et | —CH₂— | O | S | N |
| 1-672 | H | 4-OH-2,3,5-triMe—Ph | H | Et | —CH₂— | S | O | CH |
| 1-673 | H | 4-OH-2,3,5-triMe-Ph | H | Et | —(CH₂)₂— | O | O | CH |
| 1-674 | H | 4-OH-2,3,5-triMe—Ph | H | Et | —(CH₂)₂— | O | S | CH |
| 1-675 | H | 4-OH-2,3,5-triMe—Ph | H | Pr | —CH₂— | O | O | CH |
| 1-676 | H | 4-OH-2,3,5-triMe—Ph | H | iPr | —CH₂— | O | O | CH |
| 1-677 | H | 4-OH-2,3,5-triMe—Ph | H | Bu | —CH₂— | O | O | CH |
| 1-678 | H | 4-OH-2,3,5-triMe—Ph | H | sBu | —CH₂— | O | O | CH |
| 1-679 | H | 4-OH-2,3,5-triMe—Ph | H | sBu | —(CH₂)₃— | O | O | CH |
| 1-680 | H | 4-OH-2,3,5-triMe—Ph | H | tBu | —CH₂— | O | O | CH |
| 1-681 | H | 4-OH-2,3,5-triMe—Ph | H | tBu | —CH₂— | O | S | CH |
| 1-682 | H | 4-OH-2,3,5-triMe—Ph | H | Ph | —CH₂— | O | O | CH |
| 1-683 | H | 4-OH-2,3,5-triMe—Ph | H | Ph | —CH₂— | O | O | N |
| 1-684 | H | 4-OH-2,3,5-triMe—Ph | H | Ph | —CH₂— | O | S | CH |
| 1-685 | H | 4-OH-2,3,5-triMe—Ph | H | Ph | —(CH₂)₂— | O | O | CH |
| 1-686 | H | 4-OH-2,3,5-triMe—Ph | H | Bz | —CH₂— | O | O | CH |
| 1-687 | H | 4-OH-2,3,5-triMe—Ph | H | Bz | —CH₂— | O | O | N |
| 1-688 | H | 4-OH-2,3,5-triMe-Ph | H | Bz | —CH₂— | O | S | CH |
| 1-689 | H | 4-OH-2,3,5-triMe—Ph | H | Bz | —(CH₂)₂— | O | O | CH |
| 1-690 | H | 4-OH-2,3,5-triMe—Ph | 5-F | Me | —CH₂— | O | O | CH |
| 1-691 | H | 4-OH-2,3,5-triMe—Ph | 4-Cl | Me | —CH₂— | O | O | CH |
| 1-692 | H | 4-OH-2,3,5-triMe—Ph | 5-Cl | Me | —CH₂— | O | O | CH |
| 1-693 | H | 4-OH-2,3,5-triMe—Ph | 4-Me | Me | —CH₂— | O | O | CH |
| 1-694 | H | 4-OH-2,3,5-triMe—Ph | 5-Me | Me | —CH₂— | O | O | CH |
| 1-695 | H | 4-OH-2,3,5-triMe—Ph | 4-MeO | Me | —CH₂— | O | O | CH |
| 1-696 | H | 4-OH-2,3,5-triMe—Ph | 5-MeO | Me | —CH₂— | O | O | CH |
| 1-697 | H | 4-OH-2,3,5-triMe—Ph | 5-MeS | Me | —CH₂— | O | O | CH |
| 1-698 | 3-F | 4-OH-2,3,5-triMe—Ph | H | Me | —CH₂— | O | O | CH |

TABLE 1-continued

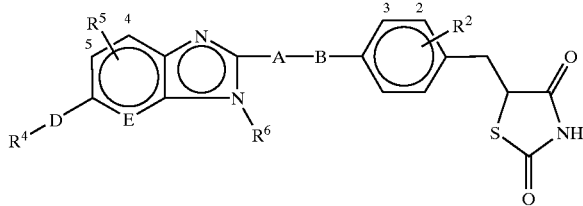

(I-1)

| Cpd. No. | $R^2$ | $R^4$ | $R^5$ | $R^6$ | —A— | B | D | E |
|---|---|---|---|---|---|---|---|---|
| 1-699 | 2-Cl | 4-OH-2,3,5-triMe—Ph | H | Me | —CH$_2$— | O | O | CH |
| 1-700 | 3-Cl | 4-OH-2,3,5-triMe—Ph | H | Me | —CH$_2$— | O | O | CH |
| 1-701 | 2-Me | 4-OH-2,3,5-triMe—Ph | H | Me | —CH$_2$— | O | O | CH |
| 1-702 | 3-Me | 4-OH-2,3,5-triMe—Ph | H | Me | —CH$_2$— | O | O | CH |
| 1-703 | 3-CF$_3$ | 4-OH-2,3,5-triMe—Ph | H | Me | —CH$_2$— | O | O | CH |
| 1-704 | 2-MeO | 4-OH-2,3,5-triMe—Ph | H | Me | —CH$_2$— | O | O | CH |
| 1-705 | 3-MeO | 4-OH-2,3,5-triMe—Ph | H | Me | —CH$_2$— | O | O | CH |
| 1-706 | H | 4-OH-2,3,6-triMe—Ph | H | Me | —CH$_2$— | O | O | CH |
| 1-707 | H | 4-OH-2,3,6-triMe—Ph | H | Me | —CH$_2$— | O | O | N |
| 1-708 | H | 4-OH-2,3,6-triMe—Ph | H | Me | —CH$_2$— | O | S | CH |
| 1-709 | H | 4-OH-2,3,6-triMe—Ph | H | Et | —CH$_2$— | O | O | CH |
| 1-710 | H | 4-OH-2,3,6-triMe—Ph | H | Et | —CH$_2$— | O | S | CH |
| 1-711 | H | 4-OH-2,3,5,6-tetraMe—Ph | H | Me | —CH$_2$— | O | O | CH |
| 1-712 | H | 4-OH-2,3,5,6-tetraMe—Ph | H | Me | —CH$_2$— | O | O | N |
| 1-713 | H | 4-OH-2,3,5,6-tetraMe—Ph | H | Me | —CH$_2$— | O | S | CH |
| 1-714 | H | 4-OH-2,3,5,6-tetraMe—Ph | H | Et | —CH$_2$— | O | O | CH |
| 1-715 | H | 4-OH-2,3,5,6-tetraMe—Ph | H | Et | —CH$_2$— | O | S | CH |
| 1-716 | H | 4-OH-3,5-diCF$_3$—Ph | H | Me | —CH$_2$— | O | O | CH |
| 1-717 | H | 4-OH-3,5-diCF$_3$—Ph | H | Me | —CH$_2$— | O | S | CH |
| 1-718 | H | 4-OH-3,5-diMeO—Ph | H | Me | —CH$_2$— | O | O | CH |
| 1-719 | H | 4-OH-3,5-diMeO—Ph | H | Me | —CH$_2$— | O | S | CH |
| 1-720 | H | 4-OH-3,5-diBuO—Ph | H | Me | —CH$_2$— | O | O | CH |
| 1-721 | H | 4-OH-3,5-diBuO—Ph | H | Me | —CH$_2$— | O | S | CH |
| 1-722 | H | 3-NH$_2$-4-Me—Ph | H | Me | —CH$_2$— | O | O | CH |
| 1-723 | H | 3-NH$_2$-4-Me—Ph | H | Me | —CH$_2$— | O | O | N |
| 1-724 | H | 3-NH$_2$-4-Me—Ph | H | Me | —CH$_2$— | O | S | CH |
| 1-725 | H | 3-NH$_2$-4-Me—Ph | H | Et | —CH$_2$— | O | O | CH |
| 1-726 | H | 3-NH$_2$-4-Me—Ph | H | Et | —CH$_2$— | O | S | CH |
| 1-727 | H | 4-NH$_2$-2,3-diMe—Ph | H | Me | —CH$_2$— | O | O | CH |
| 1-728 | H | 4-NH$_2$-2,3-diMe—Ph | H | Me | —CH$_2$— | O | O | N |
| 1-729 | H | 4-NH$_2$-2,3-diMe—Ph | H | Me | —CH$_2$— | O | S | CH |
| 1-730 | H | 4-NH$_2$-2,3-diMe—Ph | H | Et | —CH$_2$— | O | O | CH |
| 1-731 | H | 4-NH$_2$-2,3-diMe—Ph | H | Et | —CH$_2$— | O | S | CH |
| 1-732 | H | 4-NH$_2$-2,6-diMe—Ph | H | Me | —CH$_2$— | O | O | CH |

TABLE 1-continued (I-1)

| Cpd. No. | R² | R⁴ | R⁵ | R⁶ | —A— | B | D | E |
|---|---|---|---|---|---|---|---|---|
| 1-733 | H | 4-NH₂-2,6-diMe—Ph | H | Me | —CH₂— | O | O | N |
| 1-734 | H | 4-NH₂-2,6-diMe—Ph | H | Me | —CH₂— | O | S | CH |
| 1-735 | H | 4-NH₂-2,6-diMe—Ph | H | Et | —CH₂— | O | O | CH |
| 1-736 | H | 4-NH₂-2,6-diMe—Ph | H | Et | —CH₂— | O | S | CH |
| 1-737 | H | 4-NH₂-3,5-diMe—Ph | H | H | —CH₂— | O | O | CH |
| 1-738 | H | 4-NH₂-3,5-diMe—Ph | H | H | —CH₂— | O | S | CH |
| 1-739 | H | 4-NH₂-3,5-diMe—Ph | H | Me | —CH₂— | O | O | CH |
| 1-740 | H | 4-NH₂-3,5-diMe—Ph | H | Me | —CH₂— | O | O | N |
| 1-741 | H | 4-NH₂-3,5-diMe—Ph | H | Me | —CH₂— | O | S | CH |
| 1-742 | H | 4-NH₂-3,5-diMe—Ph | H | Me | —CH₂— | O | S | N |
| 1-743 | H | 4-NH₂-3,5-diMe—Ph | H | Me | —CH₂— | S | O | CH |
| 1-744 | H | 4-NH₂-3,5-diMe—Ph | H | Me | —CH₂— | S | O | N |
| 1-745 | H | 4-NH₂-3,5-diMe—Ph | H | Me | —CH₂— | S | S | CH |
| 1-746 | H | 4-NH₂-3,5-diMe—Ph | H | Me | —CH₂— | S | S | N |
| 1-747 | H | 4-NH₂-3,5-diMe—Ph | H | Me | —(CH₂)₂— | O | O | CH |
| 1-748 | H | 4-NH₂-3,5-diMe—Ph | H | Me | —(CH₂)₂— | O | O | N |
| 1-749 | H | 4-NH₂-3,5-diMe—Ph | H | Me | —(CH₂)₂— | O | S | CH |
| 1-750 | H | 4-NH₂-3,5-diMe—Ph | H | Me | —(CH₂)₂— | O | S | N |
| 1-751 | H | 4-NH₂-3,5-diMe—Ph | H | Me | —(CH₂)₂— | S | O | CH |
| 1-752 | H | 4-NH₂-3,5-diMe—Ph | H | Me | —CH(Me)— | O | O | CH |
| 1-753 | H | 4-NH₂-3,5-diMe—Ph | H | Me | —CH(Me)— | O | S | CH |
| 1-754 | H | 4-NH₂-3,5-diMe—Ph | H | Me | —(CH₂)₃— | O | O | CH |
| 1-755 | H | 4-NH₂-3,5-diMe—Ph | H | Me | —(CH₂)₃— | O | S | CH |
| 1-756 | H | 4-NH₂-3,5-diMe—Ph | H | Me | —(CH₂)₄— | O | O | CH |
| 1-757 | H | 4-NH₂-3,5-diMe—Ph | H | Et | —CH₂— | O | O | CH |
| 1-758 | H | 4-NH₂-3,5-diMe—Ph | H | Et | —CH₂— | O | O | N |
| 1-759 | H | 4-NH₂-3,5-diMe—Ph | H | Et | —CH₂— | O | S | CH |
| 1-760 | H | 4-NH₂-3,5-diMe—Ph | H | Et | —CH₂— | O | S | N |
| 1-761 | H | 4-NH₂-3,5-diMe—Ph | H | Et | —CH₂— | S | O | CH |
| 1-762 | H | 4-NH₂-3,5-diMe—Ph | H | Et | —(CH₂)₂— | O | O | CH |
| 1-763 | H | 4-NH₂-3,5-diMe—Ph | H | Et | —(CH₂)₂— | O | S | CH |
| 1-764 | H | 4-NH₂-3,5-diMe—Ph | H | Pr | —CH₂— | O | O | CH |

TABLE 1-continued (I-1)

| Cpd. No. | R² | R⁴ | R⁵ | R⁶ | —A— | B | D | E |
|---|---|---|---|---|---|---|---|---|
| 1-765 | H | 4-NH₂-3,5-diMe—Ph | H | iPr | —CH₂— | O | O | CH |
| 1-766 | H | 4-NH₂-3,5-diMe—Ph | H | Bu | —CH₂— | O | O | CH |
| 1-767 | H | 4-NH₂-3,5-diMe—Ph | H | sBu | —CH₂— | O | O | CH |
| 1-768 | H | 4-NH₂-3,5-diMe—Ph | H | sBu | —(CH₂)₃— | O | O | CH |
| 1-769 | H | 4-NH₂-3,5-diMe—Ph | H | tBu | —CH₂— | O | O | CH |
| 1-770 | H | 4-NH₂-3,5-diMe—Ph | H | tBu | —CH₂— | O | S | CH |
| 1-771 | H | 4-NH₂-3,5-diMe—Ph | H | Ph | —CH₂— | O | O | CN |
| 1-772 | H | 4-NH₂-3,5-diMe—Ph | H | Ph | —CH₂— | O | O | N |
| 1-773 | H | 4-NH₂-3,5-diMe—Ph | H | Ph | —CH₂— | O | S | CH |
| 1-774 | H | 4-NH₂-3,5-diMe—Ph | H | Ph | —)CH₂)₂— | O | O | CH |
| 1-775 | H | 4-NH₂-3,5-diMe—Ph | H | Bz | —CH₂— | O | O | CH |
| 1-776 | H | 4-NH₂-3,5-diMe—Ph | H | Bz | —CH₂— | O | O | N |
| 1-777 | H | 4-NH₂-3,5-diMe—Ph | H | Bz | —CH₂— | O | S | CH |
| 1-778 | H | 4-NH₂-3,5-diMe—Ph | H | Bz | —(CH₂)₂— | O | O | CH |
| 1-779 | H | 4-NH₂-3,5-diMe—Ph | 5-F | Me | —CH₂— | O | O | CH |
| 1-780 | H | 4-NH₂-3,5-diMe—Ph | 4-Cl | Me | —CH₂— | O | O | CH |
| 1-781 | H | 4-NH₂-3,5-diMe—Ph | 5-Cl | Me | —CH₂— | O | O | CN |
| 1-782 | H | 4-NH₂-3,5-diMe—Ph | 4-Me | Me | —CH₂— | O | O | CH |
| 1-783 | H | 4-NH₂-3,5-diMe—Ph | 5-Me | Me | —CH₂— | O | O | CH |
| 1-784 | H | 4-NH₂-3,5-diMe—Ph | 4-MeO | Me | —CH₂— | O | O | CH |
| 1-785 | H | 4-NH₂-3,5-diMe—Ph | 5-MeO | Me | —CH₂— | O | O | CH |
| 1-786 | 3-F | 4-NH₂-3,5-diMe—Ph | H | Me | —CH₂— | O | O | CH |
| 1-787 | 2-Cl | 4-NH₂-3,5-diMe—Ph | H | Me | —CH₂— | O | O | CH |
| 1-788 | 3-Cl | 4-NH₂-3,5-diMe—Ph | H | Me | —CH₂— | O | O | CH |
| 1-789 | 2-Me | 4-NH₂-3,5-diMe—Ph | H | Me | —CH₂— | O | O | CH |
| 1-790 | 3-Me | 4-NH₂-3,5-diMe—Ph | H | Me | —CH₂— | O | O | CH |
| 1-791 | 3-CF₃ | 4-NH₂-3,5-diMe—Ph | H | Me | —CH₂— | O | O | CH |
| 1-792 | 2-MeO | 4-NH₂-3,5-diMe—Ph | H | Me | —CH₂— | O | O | CH |
| 1-793 | 3-MeO | 4-NH₂-3,5-diMe—Ph | H | Me | —CH₂— | O | O | CH |
| 1-794 | H | 4-NH₂-3,5-diEt—Ph | H | Me | —CH₂— | O | O | CH |
| 1-795 | H | 4-NH₂-3,5-diEt—Ph | H | Me | —CH₂— | O | O | N |
| 1-796 | H | 4-NH₂-3,5-diEt—Ph | H | Me | —CH₂— | O | O | CH |

TABLE 1-continued (I-1)

| Cpd. No. | R² | R⁴ | R⁵ | R⁶ | —A— | B | D | E |
|---|---|---|---|---|---|---|---|---|
| 1-797 | H | 4-NH₂-3,5-diEt—Ph | H | Et | —CH₂— | O | O | CH |
| 1-798 | H | 4-NH₂-3,5-diEt—Ph | H | Et | —CH₂— | O | O | CH |
| 1-799 | H | 4-NH₂-3,5-ditBu—Ph | H | Me | —CH₂— | O | O | CH |
| 1-800 | H | 4-NH₂-3,5-ditBu—Ph | H | Me | —CH₂— | O | S | CH |
| 1-801 | H | 4-NHMe-3,5-diMe—Ph | H | Me | —CH₂— | O | O | CH |
| 1-802 | H | 4-NHMe-3,5-diMe—Ph | H | Me | —CH₂— | O | O | N |
| 1-803 | H | 4-NHMe-3,5-diMe—Ph | H | Me | —CH₂— | O | S | CH |
| 1-804 | H | 4-NHMe-3,5-diMe—Ph | H | Et | —CH₂— | O | O | CH |
| 1-805 | H | 4-NHMe-3,5-diMe—Ph | H | Et | —CH₂— | O | S | CH |
| 1-806 | H | 4-NHEt-3,5-diMe—Ph | H | Me | —CH₂— | O | O | CH |
| 1-807 | H | 4-NHEt-3,5-diMe—Ph | H | Me | —CH₂— | O | S | CH |
| 1-808 | H | 4-NHAc-3,5-diMe—Ph | H | Me | —CH₂— | O | O | CH |
| 1-809 | H | 4-NHAc-3,5-diMe—Ph | H | Me | —CH₂— | O | S | CH |
| 1-810 | H | 4-NO₂-2,6-diMe—Ph | H | Me | —CH₂— | O | O | CH |
| 1-811 | H | 4-NO₂-2,6-diMe—Ph | H | Me | —CH₂— | O | S | CH |
| 1-812 | H | 4-NO₂-3,5-diMe—Ph | H | Me | —CH₂— | O | O | CH |
| 1-813 | H | 4-NO₂-3,5-diMe—Ph | H | Me | —CH₂— | O | O | N |
| 1-814 | H | 4-NO₂-3,5-diMe—Ph | H | Me | —CH₂— | O | S | CH |
| 1-815 | H | 4-NO₂-3,5-diMe—Ph | H | Et | —CH₂— | O | O | CH |
| 1-816 | H | 4-NO₂-3,5-diMe—Ph | H | Et | —CH₂— | O | S | CH |
| 1-817 | H | 4-NO₂-3,5-diBu—Ph | H | Me | —CH₂— | O | O | CH |
| 1-818 | H | 4-NO₂-3,5-diBu—Ph | H | Me | —CH₂— | O | S | CH |
| 1-819 | H | Pyr(2) | H | H | —CH₂— | O | O | CH |
| 1-820 | H | Pyr(2) | H | H | —CH₂— | O | S | CH |
| 1-821 | H | Pyr(2) | H | Me | —CH₂— | O | O | CH |
| 1-822 | H | Pyr(2) | H | Me | —CH₂— | O | O | N |
| 1-823 | H | Pyr(2) | H | Me | —CH₂— | O | S | CH |
| 1-824 | H | Pyr(2) | H | Me | —CH₂— | O | S | N |
| 1-825 | H | Pyr(2) | H | Me | —CH₂— | S | O | CH |
| 1-826 | H | Pyr(2) | H | Me | —CH₂— | S | O | N |
| 1-827 | H | Pyr(2) | H | Me | —CH₂— | S | S | CH |
| 1-828 | H | Pyr(2) | H | Me | —CH₂— | S | S | N |
| 1-829 | H | Pyr(2) | H | Me | —(CH₂)₂— | O | O | CH |
| 1-830 | H | Pyr(2) | H | Me | —(CH₂)₂— | O | O | N |
| 1-831 | H | Pyr(2) | H | Me | —(CH₂)₂— | O | S | CH |
| 1-832 | H | Pyr(2) | H | Me | —(CH₂)₂— | O | S | N |
| 1-833 | H | Pyr(2) | H | Me | —(CH₂)₂— | S | O | CH |
| 1-834 | H | Pyr(2) | H | Me | —CH(Me)— | O | O | CH |
| 1-835 | H | Pyr(2) | H | Me | —CH(Me)— | O | S | CH |
| 1-836 | H | Pyr(2) | H | Me | —(CH₂)₃— | O | O | CH |
| 1-837 | H | Pyr(2) | H | Me | —(CH₂)₃— | O | S | CH |
| 1-838 | H | Pyr(2) | H | Me | —(CH₂)₄— | O | O | CH |

TABLE 1-continued

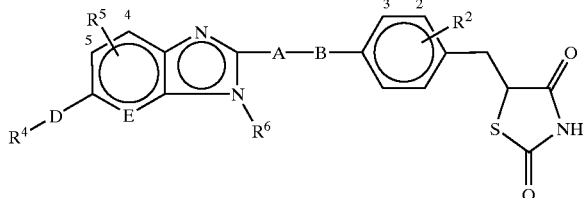

(I-1)

| Cpd. No. | $R^2$ | $R^4$ | $R^5$ | $R^6$ | —A— | B | D | E |
|---|---|---|---|---|---|---|---|---|
| 1-839 | H | Pyr(2) | H | Et | —CH$_2$— | O | O | CH |
| 1-840 | H | Pyr(2) | H | Et | —CH$_2$— | O | O | N |
| 1-841 | H | Pyr(2) | H | Et | —CH$_2$— | O | S | CH |
| 1-842 | H | Pyr(2) | H | Et | —CH$_2$— | O | S | N |
| 1-843 | H | Pyr(2) | H | Et | —CH$_2$— | S | O | CH |
| 1-844 | H | Pyr(2) | H | Et | —(CH$_2$)$_2$— | O | O | CH |
| 1-845 | H | Pyr(2) | H | Et | —(CH$_2$)$_2$— | O | S | CH |
| 1-846 | H | Pyr(2) | H | Pr | —CH$_2$— | O | O | CH |
| 1-847 | H | Pyr(2) | H | iPr | —CH$_2$— | O | O | CH |
| 1-848 | H | Pyr(2) | H | Bu | —CH$_2$— | O | O | CH |
| 1-849 | H | Pyr(2) | H | sBu | —CH$_2$— | O | O | CH |
| 1-850 | H | Pyr(2) | H | sBu | —(CH$_2$)$_3$— | O | O | CH |
| 1-851 | H | Pyr(2) | H | tBu | —CH$_2$— | O | O | CH |
| 1-852 | H | Pyr(2) | H | tBu | —CH$_2$— | O | S | CH |
| 1-853 | H | Pyr(2) | H | Ph | —CH$_2$— | O | O | CH |
| 1-854 | H | Pyr(2) | H | Ph | —CH$_2$— | O | O | N |
| 1-855 | H | Pyr(2) | H | Ph | —CH$_2$— | O | S | CH |
| 1-856 | H | Pyr(2) | H | Ph | —(CH$_2$)$_2$— | O | O | CH |
| 1-857 | H | Pyr(2) | H | Bz | —CH$_2$— | O | O | CH |
| 1-858 | H | Pyr(2) | H | Bz | —CH$_2$— | O | O | N |
| 1-859 | H | Pyr(2) | H | Bz | —CH$_2$— | O | S | CH |
| 1-860 | H | Pyr(2) | H | Bz | —(CH$_2$)$_2$— | O | O | CH |
| 1-861 | H | Pyr(2) | 5-F | Me | —CH$_2$— | O | O | CH |
| 1-862 | H | Pyr(2) | 4-Cl | Me | —CH$_2$— | O | O | CH |
| 1-863 | H | Pyr(2) | 5-Cl | Me | —CH$_2$— | O | O | CH |
| 1-864 | H | Pyr(2) | 4-Me | Me | —CH$_2$— | O | O | CH |
| 1-865 | H | Pyr(2) | 5-Me | Me | —CH$_2$— | O | O | CH |
| 1-866 | H | Pyr(2) | 4-MeO | Me | —CH$_2$— | O | O | CH |
| 1-867 | H | Pyr(2) | 5-MeO | Me | —CH$_2$— | O | O | CH |
| 1-868 | H | Pyr(2) | 5-MeS | Me | —CH$_2$— | O | O | CH |
| 1-869 | 3-F | Pyr(2) | H | Me | —CH$_2$— | O | O | CH |
| 1-870 | 2-Cl | Pyr(2) | H | Me | —CH$_2$— | O | O | CH |
| 1-871 | 3-Cl | Pyr(2) | H | Me | —CH$_2$— | O | O | CH |
| 1-872 | 2-Me | Pyr(2) | H | Me | —CH$_2$— | O | O | CH |
| 1-873 | 3-Me | Pyr(2) | H | Me | —CH$_2$— | O | O | CH |
| 1-874 | 3-CF$_3$ | Pyr(2) | H | Me | —CH$_2$— | O | O | CH |
| 1-875 | 2-MeO | Pyr(2) | H | Me | —CH$_2$— | O | O | CH |
| 1-876 | 3-MeO | Pyr(2) | H | Me | —CH$_2$— | O | O | CH |
| 1-877 | H | 5-F—Pyr(2) | H | Me | —CH$_2$— | O | O | CH |
| 1-878 | H | 5-F—Pyr(2) | H | Me | —CH$_2$— | O | S | CH |
| 1-879 | H | 6-F—Pyr(2) | H | Me | —CH$_2$— | O | O | CH |
| 1-880 | H | 6-F—Pyr(2) | H | Me | —CH$_2$— | O | S | CH |
| 1-881 | H | 5-Cl—Pyr(2) | H | Me | —CH$_2$— | O | O | CH |
| 1-882 | H | 5-Cl—Pyr(2) | H | Me | —CH$_2$— | O | O | N |
| 1-883 | H | 5-Cl—Pyr(2) | H | Me | —CH$_2$— | O | S | CH |
| 1-884 | H | 5-Cl—Pyr(2) | H | Et | —CH$_2$— | O | O | CH |
| 1-885 | H | 5-Cl—Pyr(2) | H | Et | —CH$_2$— | O | S | CH |
| 1-886 | H | 6-Cl—Pyr(2) | H | Me | —CH$_2$— | O | O | CH |
| 1-887 | H | 6-Cl—Pyr(2) | H | Me | —CH$_2$— | O | O | N |
| 1-888 | H | 6-Cl—Pyr(2) | H | Me | —CH$_2$— | O | S | CH |
| 1-889 | H | 6-Cl—Pyr(2) | H | Et | —CH$_2$— | O | O | CH |
| 1-890 | H | 6-Cl—Pyr(2) | H | Et | —CH$_2$— | O | S | CH |
| 1-891 | H | 6-Me—Pyr(2) | H | Me | —CH$_2$— | O | O | CH |
| 1-892 | H | 6-Me—Pyr(2) | H | Me | —CH$_2$— | O | S | CH |
| 1-893 | H | 6-Et—Pyr(2) | H | Me | —CH$_2$— | O | O | CH |
| 1-894 | H | 6-CF$_3$—Pyr(2) | H | Me | —CH$_2$— | O | O | CH |
| 1-895 | H | 6-MeO—Pyr(2) | H | Me | —CH$_2$— | O | O | CH |
| 1-896 | H | 6-MeO—Pyr(2) | H | Me | —CH$_2$— | O | O | CH |
| 1-897 | H | 6-MeO—Pyr(2) | H | Me | —CH$_2$— | O | S | CH |
| 1-898 | H | 6-MeO—Pyr(2) | H | Et | —CH$_2$— | O | O | CH |
| 1-899 | H | 6-MeO—Pyr(2) | H | Et | —CH$_2$— | O | S | CH |
| 1-900 | H | 6-EtO—Pyr(2) | H | Me | —CH$_2$— | O | O | CH |
| 1-901 | H | 6-EtO—Pyr(2) | H | Me | —CH$_2$— | O | S | CH |
| 1-902 | H | 6-iPrO—Pyr(2) | H | Me | —CH$_2$— | O | O | CH |

TABLE 1-continued

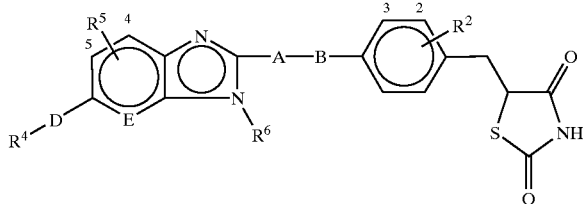

(I-1)

| Cpd. No. | R² | R⁴ | R⁵ | R⁶ | —A— | B | D | E |
|---|---|---|---|---|---|---|---|---|
| 1-903 | H | 6-MeS—Pyr(2) | H | Me | —CH₂— | O | O | CH |
| 1-904 | H | 3-NH₂—Pyr(2) | H | Me | —CH₂— | O | O | CH |
| 1-905 | H | 3-NH₂—Pyr(2) | H | Me | —CH₂— | O | O | N |
| 1-906 | H | 3-NH₂—Pyr(2) | H | Me | —CH₂— | O | S | CH |
| 1-907 | H | 3-NH₂—Pyr(2) | H | Et | —CH₂— | O | O | CH |
| 1-908 | H | 3-NH₂—Pyr(2) | H | Et | —CH₂— | O | S | CH |
| 1-909 | H | 5-NH₂—Pyr(2) | H | Me | —CH₂— | O | O | CH |
| 1-910 | H | 5-NH₂—Pyr(2) | H | Me | —CH₂— | O | O | N |
| 1-911 | H | 5-NH₂—Pyr(2) | H | Me | —CH₂— | O | S | CH |
| 1-912 | H | 5-NH₂—Pyr(2) | H | Et | —CH₂— | O | O | CH |
| 1-913 | H | 5-NH₂—Pyr(2) | H | Et | —CH₂— | O | S | CH |
| 1-914 | H | 3-NHMe—Pyr(2) | H | Me | —CH₂— | O | O | CH |
| 1-915 | H | 3-NHMe—Pyr(2) | H | Me | —CH₂— | O | S | CH |
| 1-916 | H | 5-NHMe—Pyr(2) | H | Me | —CH₂— | O | O | CH |
| 1-917 | H | 5-NHMe—Pyr(2) | H | Me | —CH₂— | O | S | CH |
| 1-918 | H | 3-N(Me)₂—Pyr(2) | H | Me | —CH₂— | O | O | CH |
| 1-919 | H | 5-N(Me)₂—Pyr(2) | H | Me | —CH₂— | O | O | CH |
| 1-920 | H | 3-NO₂—Pyr(2) | H | Me | —CH₂— | O | O | CH |
| 1-921 | H | 3-NO₂—Pyr(2) | H | Me | —CH₂— | O | O | N |
| 1-922 | H | 3-NO₂—Pyr(2) | H | Me | —CH₂— | O | S | CH |
| 1-923 | H | 3-NO₂—Pyr(2) | H | Et | —CH₂— | O | O | CH |
| 1-924 | H | 3-NO₂—Pyr(2) | H | Et | —CH₂— | O | S | CH |
| 1-925 | H | 5-NO₂—Pyr(2) | H | Me | —CH₂— | O | O | CH |
| 1-926 | H | 5-NO₂—Pyr(2) | H | Me | —CH₂— | O | O | N |
| 1-927 | H | 5-NO₂—Pyr(2) | H | Me | —CH₂— | O | S | CH |
| 1-928 | H | 5-NO₂—Pyr(2) | H | Et | —CH₂— | O | O | CH |
| 1-929 | H | 5-NO₂—Pyr(2) | H | Et | —CH₂— | O | S | CH |
| 1-930 | H | 5-NH₂-6-Cl—Pyr(2) | H | Me | —CH₂— | O | O | CH |
| 1-931 | H | 5-NH₂-6-Cl—Pyr(2) | H | Me | —CH₂— | O | O | N |
| 1-932 | H | 5-NH₂-6-Cl—Pyr(2) | H | Me | —CH₂— | O | S | CH |
| 1-933 | H | 5-NH₂-6-Cl—Pyr(2) | H | Et | —CH₂— | O | O | CH |
| 1-934 | H | 5-NH₂-6-Cl—Pyr(2) | H | Et | —CH₂— | O | S | CH |
| 1-935 | 3-MeO | 5-NH₂-6-Cl—Pyr(2) | 5-MeO | Et | —(CH₂)₄— | S | S | CH |
| 1-936 | H | Pyr(3) | H | H | —CH₂— | O | O | CH |
| 1-937 | H | Pyr(3) | H | H | —CH₂— | O | S | CH |
| 1-938 | H | Pyr(3) | H | Me | —CH₂— | O | O | CH |
| 1-939 | H | Pyr(3) | H | Me | —CH₂— | O | O | N |
| 1-940 | H | Pyr(3) | H | Me | —CH₂— | O | S | CH |
| 1-941 | H | Pyr(3) | H | Me | —CH₂— | O | S | N |
| 1-942 | H | Pyr(3) | H | Me | —CH₂— | S | O | CH |
| 1-943 | H | Pyr(3) | H | Me | —CH₂— | S | O | N |
| 1-944 | H | Pyr(3) | H | Me | —CH₂— | S | S | CH |
| 1-945 | H | Pyr(3) | H | Me | —CH₂— | S | S | N |
| 1-946 | H | Pyr(3) | H | Me | —(CH₂)₂— | O | O | CH |
| 1-947 | H | Pyr(3) | H | Me | —(CH₂)₂— | O | O | N |
| 1-948 | H | Pyr(3) | H | Me | —(CH₂)₂— | O | S | CH |
| 1-949 | H | Pyr(3) | H | Me | —(CH₂)₂— | O | S | N |
| 1-950 | H | Pyr(3) | H | Me | —(CH₂)₂— | S | O | CH |
| 1-951 | H | Pyr(3) | H | Me | —CH(Me)— | O | O | CH |
| 1-952 | H | Pyr(3) | H | Me | —CH(Me)— | O | S | CH |
| 1-953 | H | Pyr(3) | H | Me | —(CH₂)₃— | O | O | CH |
| 1-954 | H | Pyr(3) | H | Me | —(CH₂)₃— | O | S | CH |
| 1-955 | H | Pyr(3) | H | Me | —(CH₂)₄— | O | O | CH |
| 1-956 | H | Pyr(3) | H | Et | —CH₂— | O | O | CH |
| 1-957 | H | Pyr(3) | H | Et | —CH₂— | O | O | N |
| 1-958 | H | Pyr(3) | H | Et | —CH₂— | O | S | CH |
| 1-959 | H | Pyr(3) | H | Et | —CH₂— | O | S | N |
| 1-960 | H | Pyr(3) | H | Et | —CH₂— | S | O | CH |

TABLE 1-continued

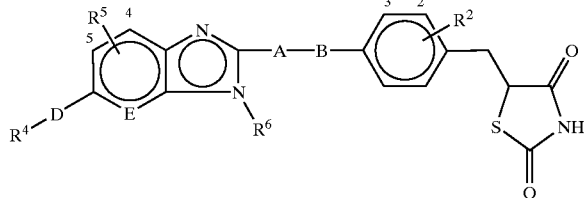

(I-1)

| Cpd. No. | R² | R⁴ | R⁵ | R⁶ | —A— | B | D | E |
|---|---|---|---|---|---|---|---|---|
| 1-961 | H | Pyr(3) | H | Et | —(CH₂)₂— | O | O | CH |
| 1-962 | H | Pyr(3) | H | Et | —(CH₂)₂— | O | S | CH |
| 1-963 | H | Pyr(3) | H | Pr | —CH₂— | O | O | CH |
| 1-964 | H | Pyr(3) | H | iPr | —CH₂— | O | O | CH |
| 1-965 | H | Pyr(3) | H | Bu | —CH₂— | O | O | CH |
| 1-966 | H | Pyr(3) | H | sBu | —CH₂— | O | O | CH |
| 1-967 | H | Pyr(3) | H | sBu | —(CH₂)₃— | O | O | CH |
| 1-968 | H | Pyr(3) | H | tBu | —CH₂— | O | O | CH |
| 1-969 | H | Pyr(3) | H | tBu | —CH₂— | O | S | CH |
| 1-970 | H | Pyr(3) | H | Pn | —(CH₂)₃— | O | O | CH |
| 1-971 | H | Pyr(3) | H | Ph | —CH₂— | O | O | CH |
| 1-972 | H | Pyr(3) | H | Ph | —CH₂— | O | O | N |
| 1-973 | H | Pyr(3) | H | Ph | —CH₂— | O | S | CH |
| 1-974 | H | Pyr(3) | H | Ph | —(CH₂)₂— | O | O | CH |
| 1-975 | H | Pyr(3) | H | Bz | —CH₂— | O | O | CH |
| 1-976 | H | Pyr(3) | H | Bz | —CH₂— | O | O | N |
| 1-977 | H | Pyr(3) | H | Bz | —CH₂— | O | S | CH |
| 1-978 | H | Pyr(3) | H | Bz | —(CH₂)₂— | O | O | CH |
| 1-979 | H | Pyr(3) | 5-F | Me | —CH₂— | O | O | CH |
| 1-980 | H | Pyr(3) | 4-Cl | Me | —CH₂— | O | O | CH |
| 1-981 | H | Pyr(3) | 5-Cl | Me | —CH₂— | O | O | CH |
| 1-982 | H | Pyr(3) | 4-Me | Me | —CH₂— | O | O | CH |
| 1-983 | H | Pyr(3) | 5-Me | Me | —CH₂— | O | O | CH |
| 1-984 | H | Pyr(3) | 4-MeO | Me | —CH₂— | O | O | CH |
| 1-985 | H | Pyr(3) | 5-MeO | Me | —CH₂— | O | O | CH |
| 1-986 | H | Pyr(3) | 5-MeS | Me | —CH₂— | O | O | CH |
| 1-987 | 3-F | Pyr(3) | H | Me | —CH₂— | O | O | CH |
| 1-988 | 2-Cl | Pyr(3) | H | Me | —CH₂— | O | O | CH |
| 1-989 | 3-Cl | Pyr(3) | H | Me | —CH₂— | O | O | CH |
| 1-990 | 2-Me | Pyr(3) | H | Me | —CH₂— | O | O | CH |
| 1-991 | 3-Me | Pyr(3) | H | Me | —CH₂— | O | O | CH |
| 1-992 | 3-CF₃ | Pyr(3) | H | Me | —CH₂— | O | O | CH |
| 1-993 | 2-MeO | Pyr(3) | H | Me | —CH₂— | O | O | CH |
| 1-994 | 3-MeO | Pyr(3) | H | Me | —CH₂— | O | O | CH |
| 1-995 | H | 6-Cl—Pyr(3) | H | Me | —CH₂— | O | O | CH |
| 1-996 | H | 6-Cl—Pyr(3) | H | Me | —CH₂— | O | S | CH |
| 1-997 | H | 6-Me—Pyr(3) | H | Me | —CH₂— | O | O | CH |
| 1-998 | H | 6-Me—Pyr(3) | H | Me | —CH₂— | O | S | CH |
| 1-999 | H | 5-MeO—Pyr(3) | H | Me | —CH₂— | O | O | CH |
| 1-1000 | H | 5-MeO—Pyr(3) | H | Me | —CH₂— | O | O | N |
| 1-1001 | H | 5-MeO—Pyr(3) | H | Me | —CH₂— | O | S | CH |
| 1-1002 | H | 5-MeO—Pyr(3) | H | Et | —CH₂— | O | O | CH |
| 1-1003 | H | 5-MeO—Pyr(3) | H | Et | —CH₂— | O | S | CH |
| 1-1004 | H | 6-MeO—Pyr(3) | H | Me | —CH₂— | O | O | CH |
| 1-1005 | H | 6-MeO—Pyr(3) | H | Me | —CH₂— | O | O | N |
| 1-1006 | H | 6-MeO—Pyr(3) | H | Me | —CH₂— | O | S | CH |
| 1-1007 | H | 6-MeO—Pyr(3) | H | Me | —(CH₂)₂— | O | O | CH |
| 1-1008 | H | 6-MeO—Pyr(3) | H | Me | —(CH₂)₃— | O | O | CH |
| 1-1009 | H | 6-MeO—Pyr(3) | H | Et | —CH₂— | O | O | CH |
| 1-1010 | H | 6-MeO—Pyr(3) | H | Et | —CH₂— | O | S | CH |
| 1-1011 | H | 6-MeO—Pyr(3) | H | tBu | —CH₂— | O | O | CH |
| 1-1012 | H | 6-EtO—Pyr(3) | H | Me | —CH₂— | O | O | CH |
| 1-1013 | H | 6-EtO—Pyr(3) | H | Me | —CH₂— | O | S | CH |
| 1-1014 | H | 6-iPrO—Pyr(3) | H | Me | —CH₂— | O | O | CH |
| 1-1015 | H | 6-iPrO—Pyr(3) | H | Me | —CH₂— | O | O | N |
| 1-1016 | H | 6-iPrO—Pyr(3) | H | Me | —CH₂— | O | S | CH |
| 1-1017 | H | 6-iPrO—Pyr(3) | H | Et | —CH₂— | O | O | CH |
| 1-1018 | H | 6-iPrO—Pyr(3) | H | Et | —CH₂— | O | S | CH |
| 1-1019 | H | 6-MeO-5-Me—Pyr(3) | H | Me | —CH₂— | O | O | CH |
| 1-1020 | H | 6-MeO-5-Me—Pyr(3) | H | Me | —CH₂— | O | O | N |
| 1-1021 | H | 6-MeO-5-Me—Pyr(3) | H | Me | —CH₂— | O | S | CH |

TABLE 1-continued

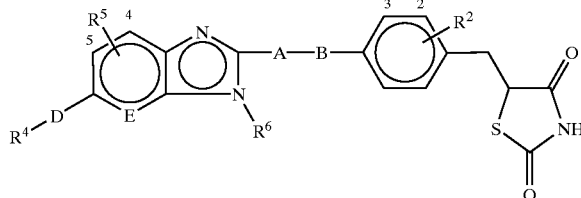

(I-1)

| Cpd. No. | R² | R⁴ | R⁵ | R⁶ | —A— | B | D | E |
|---|---|---|---|---|---|---|---|---|
| 1-1022 | H | 6-MeO-5-Me—Pyr(3) | H | Et | —CH₂— | O | O | CH |
| 1-1023 | H | 6-MeO-5-Me—Pyr(3) | H | Et | —CH₂— | O | S | CH |
| 1-1024 | H | 2-NO₂-6-Me—Pyr(3) | H | Me | —CH₂— | O | O | CH |
| 1-1025 | H | 2-NO₂-6-Me—Pyr(3) | H | Me | —CH₂— | O | O | N |
| 1-1026 | H | 2-NO₂-6-Me—Pyr(3) | H | Me | —CH₂— | O | S | CH |
| 1-1027 | H | 2-NO₂-6-Me—Pyr(3) | H | Et | —CH₂— | O | O | CH |
| 1-1028 | H | 2-NO₂-6-Me—Pyr(3) | H | Et | —CH₂— | O | S | CH |
| 1-1029 | H | Pyr(4) | H | H | —CH₂— | O | O | CH |
| 1-1030 | H | Pyr(4) | H | H | —CH₂— | O | S | CH |
| 1-1031 | H | Pyr(4) | H | Me | —CH₂— | O | O | CH |
| 1-1032 | H | Pyr(4) | H | Me | —CH₂— | O | O | N |
| 1-1033 | H | Pyr(4) | H | Me | —CH₂— | O | S | CH |
| 1-1034 | H | Pyr(4) | H | Me | —CH₂— | O | S | N |
| 1-1035 | H | Pyr(4) | H | Me | —CH₂— | S | O | CH |
| 1-1036 | H | Pyr(4) | H | Me | —CH₂— | S | O | N |
| 1-1037 | H | Pyr(4) | H | Me | —CH₂— | S | S | CH |
| 1-1038 | H | Pyr(4) | H | Me | —CH₂— | S | S | N |
| 1-1039 | H | Pyr(4) | H | Me | —(CH₂)₂— | O | O | CH |
| 1-1040 | H | Pyr(4) | H | Me | —(CH₂)₂— | O | O | N |
| 1-1041 | H | Pyr(4) | H | Me | —(CH₂)₂— | O | S | CH |
| 1-1042 | H | Pyr(4) | H | Me | —(CH₂)₂— | O | S | N |
| 1-1043 | H | Pyr(4) | H | Me | —(CH₂)₂— | S | O | CH |
| 1-1044 | H | Pyr(4) | H | Me | —CH(Me)— | O | O | CH |
| 1-1045 | H | Pyr(4) | H | Me | —CH(Me)— | O | S | CH |
| 1-1046 | H | Pyr(4) | H | Me | —(CH₂)₃— | O | O | CH |
| 1-1047 | H | Pyr(4) | H | Me | —(CH₂)₃— | O | S | CH |
| 1-1048 | H | Pyr(4) | H | Me | —(CH₂)₄— | O | O | CH |
| 1-1049 | H | Pyr(4) | H | Et | —CH₂— | O | O | CH |
| 1-1050 | H | Pyr(4) | H | Et | —CH₂— | O | O | N |
| 1-1051 | H | Pyr(4) | H | Et | —CH₂— | O | S | CH |
| 1-1052 | H | Pyr(4) | H | Et | —CH₂— | O | S | N |
| 1-1053 | H | Pyr(4) | H | Et | —CH₂— | S | O | CH |
| 1-1054 | H | Pyr(4) | H | Et | —(CH₂)₂— | O | O | CH |
| 1-1055 | H | Pyr(4) | H | Et | —(CH₂)₂— | O | S | CH |
| 1-1056 | H | Pyr(4) | H | Pr | —CH₂— | O | O | CH |
| 1-1057 | H | Pyr(4) | H | iPr | —CH₂— | O | O | CH |
| 1-1058 | H | Pyr(4) | H | Bu | —CH₂— | O | O | CH |
| 1-1059 | H | Pyr(4) | H | sBu | —CH₂— | O | O | CH |
| 1-1060 | H | Pyr(4) | H | sBu | —(CH₂)₃— | O | O | CH |
| 1-1061 | H | Pyr(4) | H | tBu | —CH₂— | O | O | CH |
| 1-1062 | H | Pyr(4) | H | tBu | —CH₂— | O | S | CH |
| 1-1063 | H | Pyr(4) | H | Ph | —CH₂— | O | O | CH |
| 1-1064 | H | Pyr(4) | H | Ph | —CH₂— | O | O | N |
| 1-1065 | H | Pyr(4) | H | Ph | —CH₂— | O | S | CH |
| 1-1066 | H | Pyr(4) | H | Ph | —(CH₂)₂— | O | O | CH |
| 1-1067 | H | Pyr(4) | H | Bz | —CH₂— | O | O | CH |
| 1-1068 | H | Pyr(4) | H | Bz | —CH₂— | O | O | N |
| 1-1069 | H | Pyr(4) | H | Bz | —CH₂— | O | S | CH |
| 1-1070 | H | Pyr(4) | H | Bz | —(CH₂)₂— | O | O | CH |
| 1-1071 | H | Pyr(4) | 5-F | Me | —CH₂— | O | O | CH |
| 1-1072 | H | Pyr(4) | 4-Cl | Me | —CH₂— | O | O | CH |
| 1-1073 | H | Pyr(4) | 5-Cl | Me | —CH₂— | O | O | CH |
| 1-1074 | H | Pyr(4) | 4-Me | Me | —CH₂— | O | O | CH |
| 1-1075 | H | Pyr(4) | 5-Me | Me | —CH₂— | O | O | CH |
| 1-1076 | H | Pyr(4) | 4-MeO | Me | —CH₂— | O | O | CH |
| 1-1077 | H | Pyr(4) | 5-MeO | Me | —CH₂— | O | O | CH |
| 1-1078 | H | Pyr(4) | 5-MeS | Me | —CH₂— | O | O | CH |

TABLE 1-continued

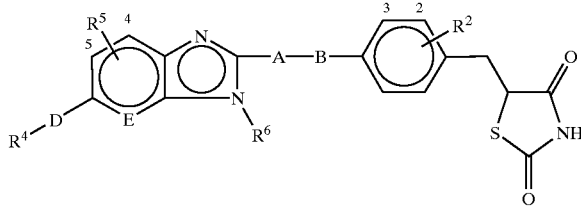

(I-1)

| Cpd. No. | $R^2$ | $R^4$ | $R^5$ | $R^6$ | —A— | B | D | E |
|---|---|---|---|---|---|---|---|---|
| 1-1079 | 3-F | Pyr(4) | H | Me | —CH$_2$— | O | O | CH |
| 1-1080 | 2-Cl | Pyr(4) | H | Me | —CH$_2$— | O | O | CH |
| 1-1081 | 3-Cl | Pyr(4) | H | Me | —CH$_2$— | O | O | CH |
| 1-1082 | 2-Me | Pyr(4) | H | Me | —CH$_2$— | O | O | CH |
| 1-1083 | 3-Me | Pyr(4) | H | Me | —CH$_2$— | O | O | CH |
| 1-1084 | 3-CF$_3$ | Pyr(4) | H | Me | —CH$_2$— | O | O | CH |
| 1-1085 | 2-MeO | Pyr(4) | H | Me | —CH$_2$— | O | O | CH |
| 1-1086 | 3-MeO | Pyr(4) | H | Me | —CH$_2$— | O | O | CH |
| 1-1087 | H | 2-F—Pyr(4) | H | Me | —CH$_2$— | O | O | CH |
| 1-1088 | H | 2-F—Pyr(4) | H | Me | —CH$_2$— | O | S | CH |
| 1-1089 | H | 2-Cl—Pyr(4) | H | Me | —CH$_2$— | O | O | CH |
| 1-1090 | H | 2-Cl—Pyr(4) | H | Me | —CH$_2$— | O | S | CH |
| 1-1091 | H | 2-Me—Pyr(4) | H | Me | —CH$_2$— | O | O | CH |
| 1-1092 | H | 2-Me—Pyr(4) | H | Me | —CH$_2$— | O | O | N |
| 1-1093 | H | 2-Me—Pyr(4) | H | Me | —CH$_2$— | O | S | CH |
| 1-1094 | H | 2-Me—Pyr(4) | H | Et | —CH$_2$— | O | O | CH |
| 1-1095 | H | 2-Me—Pyr(4) | H | Et | —CH$_2$— | O | S | CH |
| 1-1096 | H | 2-Et—Pyr(4) | H | Me | —CH$_2$— | O | O | CH |
| 1-1097 | H | 2-Et—Pyr(4) | H | Me | —CH$_2$— | O | S | CH |
| 1-1098 | H | 2,6-diMe—Pyr(4) | H | Me | —CH$_2$— | O | O | CH |
| 1-1099 | H | 2,6-diMe—Pyr(4) | H | Me | —CH$_2$— | O | O | N |
| 1-1100 | H | 2,6-diMe—Pyr(4) | H | Me | —CH$_2$— | O | S | CH |
| 1-1101 | H | 2,6-diMe—Pyr(4) | H | Me | —(CH$_2$)$_2$— | O | O | CH |
| 1-1102 | H | 2,6-diMe—Pyr(4) | H | Et | —CH$_2$— | O | O | CH |
| 1-1103 | H | 2,6-diMe—Pyr(4) | H | Et | —CH$_2$— | O | S | CH |
| 1-1104 | H | 2,6-diMe—Pyr(4) | H | tBu | —CH$_2$— | O | O | CH |
| 1-1105 | H | 3,6-diMe—Pyr(4) | H | Me | —CH$_2$— | O | O | CH |
| 1-1106 | H | 3,6-diMe—Pyr(4) | H | Me | —CH$_2$— | O | O | N |
| 1-1107 | H | 3,6-diMe—Pyr(4) | H | Me | —CH$_2$— | O | S | CH |
| 1-1108 | H | 3,6-diMe—Pyr(4) | H | Et | —CH$_2$— | O | O | CH |
| 1-1109 | H | 3,6-diMe—Pyr(4) | H | Et | —CH$_2$— | O | S | CH |
| 1-1110 | H | 2-MeO—Pyr(4) | H | Me | —CH$_2$— | O | O | CH |
| 1-1111 | H | 2-MeO—Pyr(4) | H | Me | —CH$_2$— | O | O | N |
| 1-1112 | H | 2-MeO—Pyr(4) | H | Me | —CH$_2$— | O | S | CH |
| 1-1113 | H | 2-MeO—Pyr(4) | H | Et | —CH$_2$— | O | O | CH |
| 1-1114 | H | 2-MeO—Pyr(4) | H | Et | —CH$_2$— | O | S | CH |
| 1-1115 | H | 2-EtO—Pyr(4) | H | Me | —CH$_2$— | O | O | CH |
| 1-1116 | H | 2-Imid(1)-Ph | H | Me | —CH$_2$— | O | O | N |
| 1-1117 | H | 2-Imid(1)-Ph | H | Me | —CH$_2$— | O | O | CH |
| 1-1118 | H | 2-Imid(1)-Ph | H | Me | —CH$_2$— | O | S | CH |
| 1-1119 | H | 2-Imid(1)-Ph | H | Me | —CH$_2$— | O | S | N |
| 1-1120 | H | 3-Imid(1)-Ph | H | Me | —CH$_2$— | O | O | N |
| 1-1121 | H | 3-Imid(1)-Ph | H | Me | —CH$_2$— | O | O | CH |
| 1-1122 | H | 3-Imid(1)-Ph | H | Me | —CH$_2$— | O | S | CH |
| 1-1123 | H | 3-Imid(1)-Ph | H | Me | —CH$_2$— | O | S | N |
| 1-1124 | H | 4-Imid(1)-Ph | H | H | —CH$_2$— | O | O | CH |
| 1-1125 | H | 4-Imid(1)-Ph | H | H | —CH$_2$— | O | S | CH |
| 1-1126 | H | 4-Imid(1)-Ph | H | Me | —CH$_2$— | O | O | CH |
| 1-1127 | H | 4-Imid(1)-Ph | H | Me | —CH$_2$— | O | O | N |
| 1-1128 | H | 4-Imid(1)-Ph | H | Me | —CH$_2$— | O | S | CH |
| 1-1129 | H | 4-Imid(1)-Ph | H | Me | —CH$_2$— | O | S | N |
| 1-1130 | H | 4-Imid(1)-Ph | H | Me | —CH$_2$— | S | O | CH |
| 1-1131 | H | 4-Imid(1)-Ph | H | Me | —CH$_2$— | S | O | N |
| 1-1132 | H | 4-Imid(1)-Ph | H | Me | —CH$_2$— | S | S | CH |
| 1-1133 | H | 4-Imid(1)-Ph | H | Me | —CH$_2$— | S | S | N |
| 1-1134 | H | 4-Imid(1)-Ph | H | Me | —(CH$_2$)$_2$— | O | O | CH |
| 1-1135 | H | 4-Imid(1)-Ph | H | Me | —(CH$_2$)$_2$— | O | O | N |
| 1-1136 | H | 4-Imid(1)-Ph | H | Me | —(CH$_2$)$_2$— | O | S | CH |
| 1-1137 | H | 4-Imid(1)-Ph | H | Me | —(CH$_2$)$_2$— | O | S | N |
| 1-1138 | H | 4-Imid(1)-Ph | H | Et | —CH$_2$— | O | O | CH |
| 1-1139 | H | 4-Imid(1)-Ph | H | Et | —CH$_2$— | O | O | N |
| 1-1140 | H | 4-Imid(1)-Ph | H | Et | —CH$_2$— | O | S | CH |
| 1-1141 | H | 4-Imid(1)-Ph | H | Et | —CH$_2$— | O | S | N |
| 1-1142 | H | 4-Imid(1)-Ph | H | Ph | —CH$_2$— | O | O | CH |

TABLE 1-continued

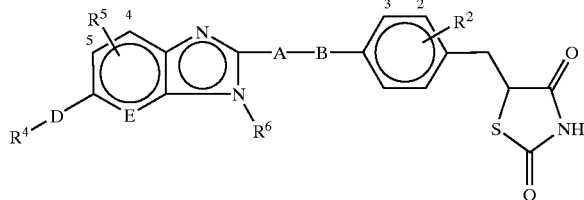
(I-1)

| Cpd. No. | $R^2$ | $R^4$ | $R^5$ | $R^6$ | —A— | B | D | E |
|---|---|---|---|---|---|---|---|---|
| 1-1143 | H | 4-Imid(1)-Ph | H | Bz | —CH$_2$— | O | O | CH |
| 1-1144 | H | 2-Tz—Ph | H | Me | —CH$_2$— | O | O | N |
| 1-1145 | H | 2-Tz—Ph | H | Me | —CH$_2$— | O | O | CH |
| 1-1146 | H | 2-Tz—Ph | H | Me | —CH$_2$— | O | S | CH |
| 1-1147 | H | 2-Tz—Ph | H | Me | —CH$_2$— | O | S | N |
| 1-1148 | H | 3-Tz—Ph | H | Me | —CH$_2$— | O | O | N |
| 1-1149 | H | 3-Tz—Ph | H | Me | —CH$_2$— | O | O | CH |
| 1-1150 | H | 3-Tz—Ph | H | Me | —CH$_2$— | O | S | CH |
| 1-1151 | H | 3-Tz—Ph | H | Me | —CH$_2$— | O | S | N |
| 1-1152 | H | 4-Tz—Ph | H | H | —CH$_2$— | O | O | CH |
| 1-1153 | H | 4-Tz—Ph | H | H | —CH$_2$— | O | S | CH |
| 1-1154 | H | 4-Tz—Ph | H | Me | —CH$_2$— | O | O | CH |
| 1-1155 | H | 4-Tz—Ph | H | Me | —CH$_2$— | O | O | N |
| 1-1156 | H | 4-Tz—Ph | H | Me | —CH$_2$— | O | S | CH |
| 1-1157 | H | 4-Tz—Ph | H | Me | —CH$_2$— | O | S | N |
| 1-1158 | H | 4-Tz—Ph | H | Me | —CH$_2$— | S | O | CH |
| 1-1159 | H | 4-Tz—Ph | H | Me | —CH$_2$— | S | O | N |
| 1-1160 | H | 4-Tz—Ph | H | Me | —CH$_2$— | S | S | CH |
| 1-1161 | H | 4-Tz—Ph | H | Me | —CH$_2$— | S | S | N |
| 1-1162 | H | 4-Tz—Ph | H | Me | —(CH$_2$)$_2$— | O | O | CH |
| 1-1163 | H | 4-Tz—Ph | H | Me | —(CH$_2$)$_2$— | O | O | N |
| 1-1164 | H | 4-Tz—Ph | H | Me | —(CH$_2$)$_2$— | O | S | CH |
| 1-1165 | H | 4-Tz—Ph | H | Me | —(CH$_2$)$_2$— | O | S | N |
| 1-1166 | H | 4-Tz—Ph | H | Et | —CH$_2$— | O | O | CH |
| 1-1167 | H | 4-Tz—Ph | H | Et | —CH$_2$— | O | O | N |
| 1-1168 | H | 4-Tz—Ph | H | Et | —CH$_2$— | O | S | CH |
| 1-1169 | H | 4-Tz—Ph | H | Et | —CH$_2$— | O | S | N |
| 1-1170 | H | 4-Tz—Ph | H | Ph | —CH$_2$— | O | O | CH |
| 1-1171 | H | 4-Tz—Ph | H | Bz | —CH$_2$— | O | O | CH |
| 1-1172 | H | 2-Ada(1)-Ph | H | Me | —CH$_2$— | O | O | N |
| 1-1173 | H | 2-Ada(1)-Ph | H | Me | —CH$_2$— | O | O | CH |
| 1-1174 | H | 2-Ada(1)-Ph | H | Me | —CH$_2$— | O | S | CH |
| 1-1175 | H | 2-Ada(1)-Ph | H | Me | —CH$_2$— | O | S | N |
| 1-1176 | H | 3-Ada(1)-Ph | H | Me | —CH$_2$— | O | O | CH |
| 1-1177 | H | 3-Ada(1)-Ph | H | Me | —CH$_2$— | O | O | N |
| 1-1178 | H | 3-Ada(1)-Ph | H | Me | —CH$_2$— | O | S | CH |
| 1-1179 | H | 3-Ada(1)-Ph | H | Me | —CH$_2$— | O | S | N |
| 1-1180 | H | 4-Ada(1)-Ph | H | H | —CH$_2$— | O | O | CH |
| 1-1181 | H | 4-Ada(1)-Ph | H | H | —CH$_2$— | O | S | CH |
| 1-1182 | H | 4-Ada(1)-Ph | H | Me | —CH$_2$— | O | O | CH |
| 1-1183 | H | 4-Ada(1)-Ph | H | Me | —CH$_2$— | O | O | N |
| 1-1184 | H | 4-Ada(1)-Ph | H | Me | —CH$_2$— | O | S | CH |
| 1-1185 | H | 4-Ada(1)-Ph | H | Me | —CH$_2$— | O | S | N |
| 1-1186 | H | 4-Ada(1)-Ph | H | Me | —CH$_2$— | S | O | CH |
| 1-1187 | H | 4-Ada(1)-Ph | H | Me | —CH$_2$— | S | O | N |
| 1-1188 | H | 4-Ada(1)-Ph | H | Me | —CH$_2$— | S | S | CH |
| 1-1189 | H | 4-Ada(1)-Ph | H | Me | —CH$_2$— | S | S | N |
| 1-1190 | H | 4-Ada(1)-Ph | H | Me | —(CH$_2$)$_2$— | O | O | CH |
| 1-1191 | H | 4-Ada(1)-Ph | H | Me | —(CH$_2$)$_2$— | O | O | N |
| 1-1192 | H | 4-Ada(1)-Ph | H | Me | —(CH$_2$)$_2$— | O | S | CH |
| 1-1193 | H | 4-Ada(1)-Ph | H | Me | —(CH$_2$)$_2$— | O | S | N |
| 1-1194 | H | 4-Ada(1)-Ph | H | Et | —CH$_2$— | O | O | CH |
| 1-1195 | H | 4-Ada(1)-Ph | H | Et | —CH$_2$— | O | O | N |
| 1-1196 | H | 4-Ada(1)-Ph | H | Et | —CH$_2$— | O | S | CH |
| 1-1197 | H | 4-Ada(1)-Ph | H | Et | —CH$_2$— | O | S | N |
| 1-1198 | H | 4-Ada(1)-Ph | H | Ph | —CH$_2$— | O | O | CH |
| 1-1199 | H | 4-Ada(1)-Ph | H | Bz | —CH$_2$— | O | O | CH |
| 1-1200 | H | 2-CN—Ph | H | Me | —CH$_2$— | O | O | N |
| 1-1201 | H | 2-CN—Ph | H | Me | —CH$_2$— | O | O | CH |
| 1-1202 | H | 2-CN—Ph | H | Me | —CH$_2$— | O | S | CH |
| 1-1203 | H | 2-CN—Ph | H | Me | —CH$_2$— | O | S | N |
| 1-1204 | H | 3-CN—Ph | H | Me | —CH$_2$— | O | O | CH |
| 1-1205 | H | 3-CN—Ph | H | Me | —CH$_2$— | O | O | N |
| 1-1206 | H | 3-CN—Ph | H | Me | —CH$_2$— | O | S | CH |

TABLE 1-continued (I-1)

| Cpd. No. | R² | R⁴ | R⁵ | R⁶ | —A— | B | D | E |
|---|---|---|---|---|---|---|---|---|
| 1-1207 | H | 3-CN—Ph | H | Me | —CH₂— | O | S | N |
| 1-1208 | H | 4-CN—Ph | H | H | —CH₂— | O | O | CH |
| 1-1209 | H | 4-CN—Ph | H | H | —CH₂— | O | S | CH |
| 1-1210 | H | 4-CN—Ph | H | Me | —CH₂— | O | O | CH |
| 1-1211 | H | 4-CN—Ph | H | Me | —CH₂— | O | O | N |
| 1-1212 | H | 4-CN—Ph | H | Me | —CH₂— | O | S | CH |
| 1-1213 | H | 4-CN—Ph | H | Me | —CH₂— | O | S | N |
| 1-1214 | H | 4-CN—Ph | H | Me | —CH₂— | S | O | CH |
| 1-1215 | H | 4-CN—Ph | H | Me | —CH₂— | S | O | N |
| 1-1216 | H | 4-CN—Ph | H | Me | —CH₂— | S | S | CH |
| 1-1217 | H | 4-CN—Ph | H | Me | —CH₂— | S | S | N |
| 1-1218 | H | 4-CN—Ph | H | Me | —(CH₂)₂— | O | O | CH |
| 1-1219 | H | 4-CN—Ph | H | Me | —(CH₂)₂— | O | O | N |
| 1-1220 | H | 4-CN—Ph | H | Me | —(CH₂)₂— | O | S | CH |
| 1-1221 | H | 4-CN—Ph | H | Me | —(CH₂)₂— | O | S | N |
| 1-1222 | H | 4-CN—Ph | H | Et | —CH₂— | O | O | CH |
| 1-1223 | H | 4-CN—Ph | H | Et | —CH₂— | O | O | N |
| 1-1224 | H | 4-CN—Ph | H | Et | —CH₂— | O | S | CH |
| 1-1225 | H | 4-CN—Ph | H | Et | —CH₂— | O | S | N |
| 1-1226 | H | 4-CN—Ph | H | Ph | —CH₂— | O | O | CH |
| 1-1227 | H | 4-CN—Ph | H | Bz | —CH₂— | O | O | CH |
| 1-1228 | H | 4-Bz-2-OH—Ph | H | Me | —CH₂— | O | O | CH |
| 1-1229 | H | 4-Bz-2-OH—Ph | H | Me | —CH₂— | O | O | N |
| 1-1230 | H | 4-Bz-3-OH—Ph | H | Me | —CH₂— | O | O | CH |
| 1-1231 | H | 4-Bz-3-OH—Ph | H | Me | —CH₂— | O | O | N |
| 1-1232 | H | 4-Bz-3-OH—Ph | H | Me | —CH₂— | O | S | CH |
| 1-1233 | H | 4-Bz-3-OH—Ph | H | Me | —CH₂— | O | S | N |
| 1-1234 | H | 4-OH-2,5-ditBu—Ph | H | Me | —CH₂— | O | O | CH |
| 1-1235 | H | pentaF—Ph | H | Me | —CH₂— | O | O | CH |
| 1-1236 | H | pentaF—Ph | H | Me | —CH₂— | O | O | CH |
| 1-1237 | H | pentaF—Ph | H | Me | —CH₂— | O | S | CH |
| 1-1238 | H | pentaF—Ph | H | Me | —CH₂— | O | S | N |
| 1-1239 | H | 4-NHPn—Ph | H | Me | —CH₂— | O | O | CH |
| 1-1240 | H | 2-NHHx—Ph | H | Me | —CH₂— | O | O | CH |
| 1-1241 | H | 3-NHHx—Ph | H | Me | —CH₂— | O | O | CH |
| 1-1242 | H | 4-NHHx—Ph | H | Me | —CH₂— | O | O | CH |
| 1-1243 | H | 4-NHHx—Ph | H | Me | —CH₂— | O | O | N |
| 1-1244 | H | 4-NHHx—Ph | H | Me | —CH₂— | O | S | CH |
| 1-1245 | H | 4-NHHx—Ph | H | Me | —CH₂— | O | S | N |
| 1-1246 | H | 2-NHCOPh—Ph | H | Me | —CH₂— | O | O | CH |
| 1-1247 | H | 3-NHCOPh—Ph | H | Me | —CH₂— | O | O | CH |
| 1-1248 | H | 4-NHCOPh—Ph | H | Me | —CH₂— | O | O | CH |
| 1-1249 | H | 4-NHCOPh—Ph | H | Me | —CH₂— | O | O | N |
| 1-1250 | H | 4-NHCOPh—Ph | H | Me | —CH₂— | O | S | CH |
| 1-1251 | H | 4-NHCOPh—Ph | H | Me | —CH₂— | O | S | N |
| 1-1252 | H | 4-NHCO(3-F—Ph)—Ph | H | Me | —CH₂— | O | O | CH |
| 1-1253 | H | 4-NHCO(2-Cl—Ph)—Ph | H | Me | —CH₂— | O | O | CH |
| 1-1254 | H | 2-NHCO(3-Cl—Ph)—Ph | H | Me | —CH₂— | O | O | CH |
| 1-1255 | H | 3-NHCO(3-Cl—Ph)—Ph | H | Me | —CH₂— | O | O | CH |
| 1-1256 | H | 4-NHCO(3-Cl—Ph)—Ph | H | Me | —CH₂— | O | O | CH |
| 1-1257 | H | 4-NHCO(3-Cl—Ph)—Ph | H | Me | —CH₂— | O | O | N |

TABLE 1-continued

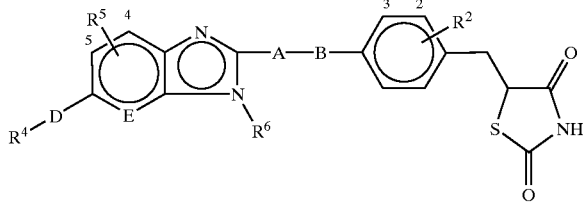

(I-1)

| Cpd. No. | $R^2$ | $R^4$ | $R^5$ | $R^6$ | —A— | B | D | E |
|---|---|---|---|---|---|---|---|---|
| 1-1258 | H | 4-NHCO(3-Cl—Ph)—Ph | H | Me | —CH$_2$— | O | S | CH |
| 1-1259 | H | 4-NHCO(3-Cl—Ph)—Ph | H | Me | —CH$_2$— | O | S | N |
| 1-1260 | H | 4-NHCO(4-Cl—Ph)—Ph | H | Me | —CH$_2$— | O | O | CH |
| 1-1261 | H | 2-NHCO(2,4-diF—Ph)—Ph | H | Me | —CH$_2$— | O | O | CH |
| 1-1262 | H | 3-NHCO(2,4-diF—Ph)—Ph | H | Me | —CH$_2$— | O | O | CH |
| 1-1263 | H | 4-NHCO(2,4-diF—Ph)—Ph | H | Me | —CH$_2$— | O | O | CH |
| 1-1264 | H | 4-NHCO(2,4-diF—Ph)—Ph | H | Me | —CH$_2$— | O | O | N |
| 1-1265 | H | 4-NHCO(2,4-diF—Ph)—Ph | H | Me | —CH$_2$— | O | S | CH |
| 1-1266 | H | 4-NHCO(2,4-diF—Ph)—Ph | H | Me | —CH$_2$— | O | S | N |
| 1-1267 | H | 2-NHCO(4-OH-3,5-ditBu—Ph)—Ph | H | Me | —CH$_2$— | O | O | CH |
| 1-1268 | H | 3-NHCO(4-OH-3,5-ditBu—Ph)—Ph | H | Me | —CH$_2$— | O | O | CH |
| 1-1269 | H | 4-NHCO(4-OH-3,5-ditBu—Ph)—Ph | H | Me | —CH$_2$— | O | O | CH |
| 1-1270 | H | 4-NHCO(4-OH-3,5-ditBu—Ph)—Ph | H | Me | —CH$_2$— | O | O | N |
| 1-1271 | H | 4-NHCO(4-OH-3,5-ditBu—Ph)—Ph | H | Me | —CH$_2$— | O | S | CH |
| 1-1272 | H | 4-NHCO(4-OH-3,5-ditBu—Ph)—Ph | H | Me | —CH$_2$— | O | S | N |
| 1-1273 | H | 4-NHCONp(1)-Ph | H | Me | —CH$_2$— | O | O | CH |
| 1-1274 | H | 4-NHCONp(1)-Ph | H | Me | —CH$_2$— | O | O | N |
| 1-1275 | H | 4-NHCONp(1)-Ph | H | Me | —CH$_2$— | O | S | CH |
| 1-1276 | H | 4-NHCONp(1)-Ph | H | Me | —CH$_2$— | O | S | N |
| 1-1277 | H | 4-NHCONp(2)-Ph | H | Me | —CH$_2$— | O | O | CH |
| 1-1278 | H | 4-NHCONp(2)-Ph | H | Me | —CH$_2$— | O | O | N |
| 1-1279 | H | 4-NHCONp(2)-Ph | H | Me | —CH$_2$— | O | S | CH |
| 1-1280 | H | 4-NHCONp(2)-Ph | H | Me | —CH$_2$— | O | S | N |
| 1-1281 | H | 4-NHCOBz—Ph | H | Me | —CH$_2$— | O | O | CH |
| 1-1282 | H | 4-NHCO(2-Cl—Bz)—Ph | H | Me | —CH$_2$— | O | O | CH |
| 1-1283 | H | 2-NHCO(3-Cl—Bz)—Ph | H | Me | —CH$_2$— | O | O | CH |
| 1-1284 | H | 3-NHCO(3-Cl—Bz)—Ph | H | Me | —CH$_2$— | O | O | CH |
| 1-1285 | H | 4-NHCO(3-Cl—Bz)—Ph | H | Me | —CH$_2$— | O | O | CH |
| 1-1286 | H | 4-NHCO(3-Cl—Bz)—Ph | H | Me | —CH$_2$— | O | O | N |
| 1-1287 | H | 4-NHCO(3-Cl—Bz)—Ph | H | Me | —CH$_2$— | O | S | CH |
| 1-1288 | H | 4-NHCO(3-Cl—Bz)—Ph | H | Me | —CH$_2$— | O | S | N |
| 1-1289 | H | 4-NHCO(4-Cl—Bz)—Ph | H | Me | —CH$_2$— | O | O | CH |
| 1-1290 | H | 2-NHCOcPn—Ph | H | Me | —CH$_2$— | O | O | CH |
| 1-1291 | H | 3-NHCOcPn—Ph | H | Me | —CH$_2$— | O | O | CH |
| 1-1292 | H | 4-NHCOcPn—Ph | H | Me | —CH$_2$— | O | O | CH |
| 1-1293 | H | 4-NHCOcPn—Ph | H | Me | —CH$_2$— | O | O | N |
| 1-1294 | H | 4-NHCOcPn—Ph | H | Me | —CH$_2$— | O | S | CH |
| 1-1295 | H | 4-NHCOcPn—Ph | H | Me | —CH$_2$— | O | S | N |
| 1-1296 | H | 2-NHCOcHx—Ph | H | Me | —CH$_2$— | O | O | CH |
| 1-1297 | H | 3-NHCOcHx—Ph | H | Me | —CH$_2$— | O | O | CH |
| 1-1298 | H | 4-NHCOcHx—Ph | H | Me | —CH$_2$— | O | O | CH |

TABLE 1-continued

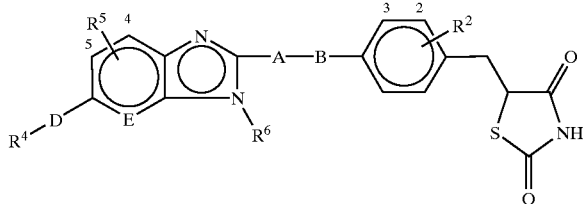
(I-1)

| Cpd. No. | R² | R⁴ | R⁵ | R⁶ | —A— | B | D | E |
|---|---|---|---|---|---|---|---|---|
| 1-1299 | H | 4-NHCOcHx—Ph | H | Me | —CH₂— | O | O | N |
| 1-1300 | H | 4-NHCOcHx—Ph | H | Me | —CH₂— | O | S | CH |
| 1-1301 | H | 4-NHCOcHx—Ph | H | Me | —CH₂— | O | S | N |
| 1-1302 | H | 4-NHCOPyr(2)-Ph | H | Me | —CH₂— | O | O | CH |
| 1-1303 | H | 2-NHCOPyr(3)-Ph | H | Me | —CH₂— | O | O | CH |
| 1-1304 | H | 3-NHCOPyr(3)-Ph | H | Me | —CH₂— | O | O | CH |
| 1-1305 | H | 4-NHCOPyr(3)-Ph | H | Me | —CH₂— | O | O | CH |
| 1-1306 | H | 4-NHCOPyr(3)-Ph | H | Me | —CH₂— | O | O | N |
| 1-1307 | H | 4-NHCOPyr(3)-Ph | H | Me | —CH₂— | O | S | CH |
| 1-1308 | H | 4-NHCOPyr(3)-Ph | H | Me | —CH₂— | O | S | N |
| 1-1309 | H | 2-NHCOPyr(4)-Ph | H | Me | —CH₂— | O | O | CH |
| 1-1310 | H | 3-NHCOPyr(4)-Ph | H | Me | —CH₂— | O | O | CH |
| 1-1311 | H | 4-NHCOPyr(4)-Ph | H | Me | —CH₂— | O | O | CH |
| 1-1312 | H | 4-NHCOPyr(4)-Ph | H | Me | —CH₂— | O | O | N |
| 1-1313 | H | 4-NHCOPyr(4)-Ph | H | Me | —CH₂— | O | S | CH |
| 1-1314 | H | 4-NHCOPyr(4)-Ph | H | Me | —CH₂— | O | S | N |
| 1-1315 | H | 4-N(Ac)Pn—Ph | H | Me | —CH₂— | O | O | CH |
| 1-1316 | H | 2-N(Ac)Hx—Ph | H | Me | —CH₂— | O | O | CH |
| 1-1317 | H | 3-N(Ac)Hx—Ph | H | Me | —CH₂— | O | O | CH |
| 1-1318 | H | 4-N(Ac)Hx—Ph | H | Me | —CH₂— | O | O | CH |
| 1-1319 | H | 4-N(Ac)Hx—Ph | H | Me | —CH₂— | O | O | N |
| 1-1320 | H | 4-N(Ac)Hx—Ph | H | Me | —CH₂— | O | S | CH |
| 1-1321 | H | 4-N(Ac)Hx—Ph | H | Me | —CH₂— | O | S | N |
| 1-1322 | H | 4-N(COPh)Hx—Ph | H | Me | —CH₂— | O | O | CH |
| 1-1323 | H | 4-N[CO(3-Cl—Ph)]Hx—Ph | H | Me | —CH₂— | O | O | CH |
| 1-1324 | H | 4-N[CO(2,4-diF—Ph)]Hx—Ph | H | Me | —CH₂— | O | O | CH |
| 1-1325 | H | 4-N[CONO(1)]Hx—Ph | H | Me | —CH₂— | O | O | CH |
| 1-1326 | H | 4-N(COBz)Hx—Ph | H | Me | —CH₂— | O | O | CH |
| 1-1327 | H | 2-Ph—Ph Hx—Ph | H | Me | —CH₂— | O | O | CH |

TABLE 2

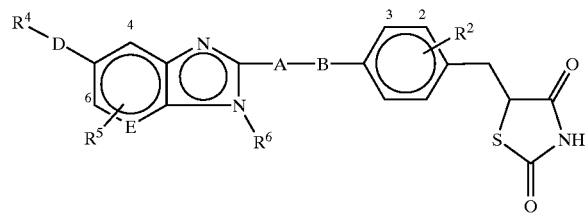
(I-2)

| Cpd. No. | R² | R⁴ | R⁵ | R⁶ | -A- | B | D | E |
|---|---|---|---|---|---|---|---|---|
| 2-1 | H | 4-F-Ph | H | Me | —CH₂— | O | O | CH |
| 2-2 | H | 4-Cl-Ph | H | Me | —CH₂— | O | O | CH |
| 2-3 | H | 2-OH-Ph | H | Me | —CH₂— | O | O | CH |
| 2-4 | H | 2-OH-Ph | H | Me | —CH₂— | O | S | CH |
| 2-5 | H | 2-OH-Ph | H | Me | —CH₂— | S | O | CH |
| 2-6 | H | 2-OH-Ph | H | Me | —(CH₂)₂— | O | O | CH |
| 2-7 | H | 2-OH-Ph | H | Et | —CH₂— | O | O | CH |
| 2-8 | H | 2-OH-Ph | H | Et | —CH₂— | O | S | CH |
| 2-9 | H | 2-OH-Ph | H | tBu | —CH₂— | O | O | CH |
| 2-10 | H | 3-OH-Ph | H | Me | —CH₂— | O | O | CH |

TABLE 2-continued (I-2)

| Cpd. No. | R² | R⁴ | R⁵ | R⁶ | -A- | B | D | E |
|---|---|---|---|---|---|---|---|---|
| 2-11 | H | 3-OH-Ph | H | Me | —CH₂— | O | S | CH |
| 2-12 | H | 3-OH-Ph | H | Me | —CH₂— | S | O | CH |
| 2-13 | H | 3-OH-Ph | H | Me | —(CH₂)₂— | O | O | CH |
| 2-14 | H | 3-OH-Ph | H | Me | —(CH₂)₂— | O | S | CH |
| 2-15 | H | 3-OH-Ph | H | Et | —CH₂— | O | O | CH |
| 2-16 | H | 3-OH-Ph | H | Et | —CH₂— | O | S | CH |
| 2-17 | H | 3-OH-Ph | H | tBu | —CH₂— | O | O | CH |
| 2-18 | H | 4-OH-Ph | H | H | —CH₂— | O | O | CH |
| 2-19 | H | 4-OH-Ph | H | Me | —CH₂— | O | O | CH |
| 2-20 | H | 4-OH-Ph | H | Me | —CH₂— | O | O | N |
| 2-21 | H | 4-OH-Ph | H | Me | —CH₂— | O | S | CH |
| 2-22 | H | 4-OH-Ph | H | Me | —CH₂— | O | S | N |
| 2-23 | H | 4-OH-Ph | H | Me | —CH₂— | S | O | CH |
| 2-24 | H | 4-OH-Ph | H | Me | —CH₂— | S | O | N |
| 2-25 | H | 4-OH-Ph | H | Me | —CH₂— | S | S | CH |
| 2-26 | H | 4-OH-Ph | H | Me | —CH₂— | S | S | N |
| 2-27 | H | 4-OH-Ph | H | Me | —(CH₂)₂— | O | O | CH |
| 2-28 | H | 4-OH-Ph | H | Me | —(CH₂)₂— | O | O | N |
| 2-29 | H | 4-OH-Ph | H | Me | —(CH₂)₂— | O | S | CH |
| 2-30 | H | 4-OH-Ph | H | Me | —CH(Me)— | O | O | CH |
| 2-31 | H | 4-OH-Ph | H | Me | —(CH₂)₃— | O | O | CH |
| 2-32 | H | 4-OH-Ph | H | Et | —CH₂— | O | O | CH |
| 2-33 | H | 4-OH-Ph | H | Et | —CH₂— | O | O | N |
| 2-34 | H | 4-OH-Ph | H | Et | —CH₂— | O | S | CH |
| 2-35 | H | 4-OH-Ph | H | Et | —(CH₂)₂— | O | O | CH |
| 2-36 | H | 4-OH-Ph | H | tBu | —CH₂— | O | O | CH |
| 2-37 | H | 4-OH-Ph | H | tBu | —CH₂— | O | S | CH |
| 2-38 | H | 4-OH-Ph | H | Ph | —CH₂— | O | O | CH |
| 2-39 | H | 4-OH-Ph | H | Bz | —CH₂— | O | O | CH |
| 2-40 | H | 4-OH-Ph | 6-Cl | Me | —CH₂— | O | O | CH |
| 2-41 | H | 4-OH-Ph | 6-Me | Me | —CH₂— | O | O | CH |
| 2-42 | H | 4-OH-Ph | 6-MeO | Me | —CH₂— | O | O | CH |
| 2-43 | 2-Cl | 4-OH-Ph | H | Me | —CH₂— | O | O | CH |
| 2-44 | 3-Cl | 4-OH-Ph | H | Me | —CH₂— | O | O | CH |
| 2-45 | 2-Me | 4-OH-Ph | H | Me | —CH₂— | O | O | CH |
| 2-46 | 3-Me | 4-OH-Ph | H | Me | —CH₂— | O | O | CH |
| 2-47 | 2-MeO | 4-OH-Ph | H | Me | —CH₂— | O | O | CH |
| 2-48 | 3-MeO | 4-OH-Ph | H | Me | —CH₂— | O | O | CH |
| 2-49 | H | 3-CF₃-Ph | H | Me | —CH₂— | O | O | CH |
| 2-50 | H | 4-iPrO-Ph | H | Me | —CH₂— | O | O | CH |
| 2-51 | H | 4-MeS-Ph | H | Me | —CH₂— | O | O | CH |
| 2-52 | H | 2-NH₂-Ph | H | Me | —CH₂— | O | O | CH |
| 2-53 | H | 3-NH₂-Ph | H | Me | —CH₂— | O | O | CH |
| 2-54 | H | 4-NH₂-Ph | H | Me | —CH₂— | O | O | CH |
| 2-55 | H | 4-NH₂-Ph | H | Me | —CH₂— | O | S | CH |
| 2-56 | H | 4-NHMe-Ph | H | Me | —CH₂— | O | O | CH |
| 2-57 | H | 2-N(Me)₂-Ph | H | Me | —CH₂— | O | O | CH |
| 2-58 | H | 3-N(Me)₂-Ph | H | Me | —CH₂— | O | O | CH |
| 2-59 | H | 4-N(Me)₂-Ph | H | Me | —CH₂— | O | O | CH |
| 2-60 | H | 4-N(Me)₂-Ph | H | Me | —CH₂— | O | S | CH |
| 2-61 | H | 4-N(Me)₂-Ph | H | Et | —CH₂— | O | O | CH |
| 2-62 | H | 4-NHAc-Ph | H | Me | —CH₂— | O | O | CH |
| 2-63 | H | 4-N(Me)Ac-Ph | H | Me | —CH₂— | O | O | CH |
| 2-64 | H | 4-Ph-Ph | H | Me | —CH₂— | O | O | CH |
| 2-65 | H | 4-(4-OH-Ph)Ph | H | Me | —CH₂— | O | O | CH |
| 2-66 | H | 4-(4-OH-3,5-diMe-Ph)Ph | H | Me | —CH₂— | O | O | CH |
| 2-67 | H | 4-(4-OH-3,5-diMe-Ph)Ph | H | Me | —CH₂— | O | S | CH |
| 2-68 | H | 4-(4-OH-3,5-ditBu-Ph)Ph | H | Me | —CH₂— | O | O | CH |
| 2-69 | H | 4-(4-OH-3,5-ditBu-Ph)Ph | H | Me | —CH₂— | O | S | CH |
| 2-70 | H | 4-Bz-Ph | H | Me | —CH₂— | O | O | CH |
| 2-71 | H | 4-(4-OH-Bz)Ph | H | Me | —CH₂— | O | O | CH |

TABLE 2-continued (I-2)

| Cpd. No. | R² | R⁴ | R⁵ | R⁶ | -A- | B | D | E |
|---|---|---|---|---|---|---|---|---|
| 2-72 | H | 4-(4-OH-3,5-diMe-Bz)Ph | H | Me | —CH₂— | O | O | CH |
| 2-73 | H | 4-(4-OH-3,5-ditBu-Bz)Ph | H | Me | —CH₂— | O | O | CH |
| 2-74 | H | 4-PhO-Ph | H | Me | —CH₂— | O | O | CH |
| 2-75 | H | 4-PhS-Ph | H | Me | —CH₂— | O | O | CH |
| 2-76 | H | 2-Pyrd(1)-Ph | H | Me | —CH₂— | O | O | CH |
| 2-77 | H | 2-Pyrd(1)-Ph | H | Me | —CH₂— | O | O | N |
| 2-78 | H | 2-Pyrd(1)-Ph | H | Me | —CH₂— | O | S | CH |
| 2-79 | H | 2-Pyrd(1)-Ph | H | Et | —CH₂— | O | O | CH |
| 2-80 | H | 2-Pyrd(1)-Ph | H | Et | —CH₂— | O | S | CH |
| 2-81 | H | 3-Pyrd(1)-Ph | H | Me | —CH₂— | O | O | CH |
| 2-82 | H | 3-Pyrd(1)-Ph | H | Me | —CH₂— | O | O | N |
| 2-83 | H | 3-Pyrd(1)-Ph | H | Me | —CH₂— | O | S | CH |
| 2-84 | H | 3-Pyrd(1)-Ph | H | Me | —(CH₂)₂— | O | O | CH |
| 2-85 | H | 3-Pyrd(1)-Ph | H | Et | —CH₂— | O | O | CH |
| 2-86 | H | 4-Pyrd(1)-Ph | H | Me | —CH₂— | O | O | CH |
| 2-87 | H | 4-Pyrd(1)-Ph | H | Me | —CH₂— | O | O | N |
| 2-88 | H | 4-Pyrd(1)-Ph | H | Me | —CH₂— | O | S | CH |
| 2-89 | H | 4-Pyrd(1)-Ph | H | Me | —(CH₂)₂— | O | O | CH |
| 2-90 | H | 4-Pyrd(1)-Ph | H | Me | —(CH₂)₃— | O | O | CH |
| 2-91 | H | 4-Pyrd(1)-Ph | H | Et | —CH₂— | O | O | CH |
| 2-92 | H | 4-Pyrd(1)-Ph | H | Et | —CH₂— | O | S | CH |
| 2-93 | H | 4-Pyrd(1)-Ph | H | tBu | —CH₂— | O | O | CH |
| 2-94 | H | 2-Pip(1)-Ph | H | Me | —CH₂— | O | O | CH |
| 2-95 | H | 2-Pip(1)-Ph | H | Me | —CH₂— | O | O | N |
| 2-96 | H | 2-Pip(1)-Ph | H | Me | —CH₂— | O | S | CH |
| 2-97 | H | 2-Pip(1)-Ph | H | Et | —CH₂— | O | O | CH |
| 2-98 | H | 2-Pip(1)-Ph | H | Et | —CH₂— | O | S | CH |
| 2-99 | H | 3-Pip(1)-Ph | H | Me | —CH₂— | O | O | CH |
| 2-100 | H | 3-Pip(1)-Ph | H | Me | —CH₂— | O | O | N |
| 2-101 | H | 3-Pip(1)-Ph | H | Me | —CH₂— | O | S | CH |
| 2-102 | H | 3-Pip(1)-Ph | H | Et | —CH₂— | O | O | CH |
| 2-103 | H | 3-Pip(1)-Ph | H | Et | —CH₂— | O | S | CH |
| 2-104 | H | 3-Pip(1)-Ph | H | Et | —(CH₂)₃— | S | O | CH |
| 2-105 | H | 4-Pip(1)-Ph | H | Me | —CH₂— | O | O | CH |
| 2-106 | H | 4-Pip(1)-Ph | H | Me | —CH₂— | O | O | N |
| 2-107 | H | 4-Pip(1)-Ph | H | Me | —CH₂— | O | S | CH |
| 2-108 | H | 4-Pip(1)-Ph | H | Me | —(CH₂)₂— | O | O | CH |
| 2-109 | H | 4-Pip(1)-Ph | H | Me | —(CH₂)₃— | O | O | CH |
| 2-110 | H | 4-Pip(1)-Ph | H | Et | —CH₂— | O | O | CH |
| 2-111 | H | 4-Pip(1)-Ph | H | Et | —CH₂— | O | S | CH |
| 2-112 | H | 4-Pip(1)-Ph | H | tBu | —CH₂— | O | O | CH |
| 2-113 | H | 4-Pip(1)-Ph | 4-Cl | Me | —CH₂— | O | O | CH |
| 2-114 | 2-MeO | 4-Pip(1)-Ph | H | Me | —CH₂— | O | O | CH |
| 2-115 | H | 2-Mor(4)-Ph | H | Me | —CH₂— | O | O | CH |
| 2-116 | H | 2-Mor(4)-Ph | H | Me | —CH₂— | O | O | N |
| 2-117 | H | 2-Mor(4)-Ph | H | Me | —CH₂— | O | S | CH |
| 2-118 | H | 2-Mor(4)-Ph | H | Me | —(CH₂)₃— | O | O | CH |
| 2-119 | H | 2-Mor(4)-Ph | H | Et | —CH₂— | O | O | CH |
| 2-120 | H | 2-Mor(4)-Ph | H | Et | —CH₂— | O | S | CH |
| 2-121 | H | 3-Mor(4)-Ph | H | Me | —CH₂— | O | O | CH |
| 2-122 | H | 3-Mor(4)-Ph | H | Me | —CH₂— | O | O | N |
| 2-123 | H | 3-Mor(4)-Ph | H | Me | —CH₂— | O | S | CH |
| 2-124 | H | 3-Mor(4)-Ph | H | Me | —(CH₂)₃— | O | O | CH |
| 2-125 | H | 3-Mor(4)-Ph | H | Et | —CH₂— | O | O | CH |
| 2-126 | H | 3-Mor(4)-Ph | H | Et | —CH₂— | O | S | CH |
| 2-127 | H | 4-Mor(4)-Ph | H | Me | —CH₂— | O | O | CH |
| 2-128 | H | 4-Mor(4)-Ph | H | Me | —CH₂— | O | O | N |
| 2-129 | H | 4-Mor(4)-Ph | H | Me | —CH₂— | O | S | CH |
| 2-130 | H | 4-Mor(4)-Ph | H | Me | —(CH₂)₂— | O | O | CH |
| 2-131 | H | 4-Mor(4)-Ph | H | Et | —CH₂— | O | O | CH |
| 2-132 | H | 4-Mor(4)-Ph | H | Et | —CH₂— | O | S | CH |
| 2-133 | H | 4-Mor(4)-Ph | H | tBu | —CH₂— | O | O | CH |
| 2-134 | H | 2-TioMor(4)-Ph | H | Me | —CH₂— | O | O | CH |

TABLE 2-continued (I-2)

[Structure: benzimidazole-type ring system with R⁴-D, positions 4, 6, R⁵-E, N, R⁶, connected via A-B to phenyl with R², position 2, 3, linked to thiazolidinedione (S, NH, two C=O)]

| Cpd. No. | R² | R⁴ | R⁵ | R⁶ | -A- | B | D | E |
|---|---|---|---|---|---|---|---|---|
| 2-135 | H | 3-TioMor(4)-Ph | H | Me | —CH₂— | O | O | CH |
| 2-136 | H | 4-TioMor(4)-Ph | H | Me | —CH₂— | O | O | CH |
| 2-137 | H | 4-TioMor(4)-Ph | H | Me | —CH₂— | O | S | CH |
| 2-138 | H | 2-Pipra(1)-Ph | H | Me | —CH₂— | O | O | CH |
| 2-139 | H | 3-Pipra(1)-Ph | H | Me | —CH₂— | O | O | CH |
| 2-140 | H | 4-Pipra(1)-Ph | H | Me | —CH₂— | O | O | CH |
| 2-141 | H | 4-Pipra(1)-Ph | H | Me | —CH₂— | O | O | N |
| 2-142 | H | 4-Pipra(1)-Ph | H | Me | —CH₂— | O | S | CH |
| 2-143 | H | 4-Pipra(1)-Ph | H | Me | —(CH₂)₃— | O | O | CH |
| 2-144 | H | 4-Pipra(1)-Ph | H | Et | —CH₂— | O | O | CH |
| 2-145 | H | 4-Pipra(1)-Ph | H | Et | —CH₂— | O | S | CH |
| 2-146 | H | 4-NO₂-Ph | H | Me | —CH₂— | O | O | CH |
| 2-147 | H | 2-Cl-4-OH-Ph | H | Me | —CH₂— | O | O | CH |
| 2-148 | H | 3-Cl-4-OH-Ph | H | Me | —CH₂— | O | O | CH |
| 2-149 | H | 3-Cl-4-OH-Ph | H | Me | —CH₂— | O | S | CH |
| 2-150 | H | 2-F-4-OH-3,5-diMe-Ph | H | Me | —CH₂— | O | O | CH |
| 2-151 | H | 4-F-3-OH-2,5-diEt-Ph | H | Me | —CH₂— | O | O | CH |
| 2-152 | H | 2-Cl-4-OH-3,5-diMe-Ph | H | H | —CH₂— | O | O | CH |
| 2-153 | H | 2-Cl-4-OH-3,5-diMe-Ph | H | Me | —CH₂— | O | O | CH |
| 2-154 | H | 2-Cl-4-OH-3,5-diMe-Ph | H | Me | —CH₂— | O | O | N |
| 2-155 | H | 2-Cl-4-OH-3,5-diMe-Ph | H | Me | —CH₂— | O | S | CH |
| 2-156 | H | 2-Cl-4-OH-3,5-diMe-Ph | H | Me | —CH₂— | O | S | N |
| 2-157 | H | 2-Cl-4-OH-3,5-diMe-Ph | H | Me | —CH₂— | S | O | CH |
| 2-158 | H | 2-Cl-4-OH-3,5-diMe-Ph | H | Me | —CH₂— | S | S | CH |
| 2-159 | H | 2-Cl-4-OH-3,5-diMe-Ph | H | Me | —(CH₂)₂— | O | O | CH |
| 2-160 | H | 2-Cl-4-OH-3,5-diMe-Ph | H | Me | —(CH₂)₂— | O | O | N |
| 2-161 | H | 2-Cl-4-OH-3,5-diMe-Ph | H | Me | —(CH₂)₂— | O | S | CH |
| 2-162 | H | 2-Cl-4-OH-3,5-diMe-Ph | H | Me | —CH(Me)— | O | O | CH |
| 2-163 | H | 2-Cl-4-OH-3,5-diMe-Ph | H | Me | —(CH₂)₃— | O | O | CH |
| 2-164 | H | 2-Cl-4-OH-3,5-diMe-Ph | H | Me | —(CH₂)₄— | O | O | CH |
| 2-165 | H | 2-Cl-4-OH-3,5-diMe-Ph | H | Et | —CH₂— | O | O | CH |
| 2-166 | H | 2-Cl-4-OH-3,5-diMe-Ph | H | Et | —CH₂— | O | O | N |
| 2-167 | H | 2-Cl-4-OH-3,5-diMe-Ph | H | Et | —CH₂— | O | S | CH |
| 2-168 | H | 2-Cl-4-OH-3,5-diMe-Ph | H | Et | —(CH₂)₂— | O | O | CH |
| 2-169 | H | 2-Cl-4-OH-3,5-diMe-Ph | H | tBu | —CH₂— | O | O | CH |
| 2-170 | H | 2-Cl-4-OH-3,5-diMe-Ph | H | tBu | —CH₂— | O | S | CH |
| 2-171 | H | 2-Cl-4-OH-3,5-diMe-Ph | H | Ph | —CH₂— | O | O | CH |
| 2-172 | H | 2-Cl-4-OH-3,5-diMe-Ph | H | Bz | —CH₂— | O | O | CH |
| 2-173 | H | 2-Cl-4-OH-3,5-diMe-Ph | 6-Cl | Me | —CH₂— | O | O | CH |
| 2-174 | H | 2-Cl-4-OH-3,5-diMe-Ph | 6-Me | Me | —CH₂— | O | O | CH |

TABLE 2-continued (I-2)

| Cpd. No. | R² | R⁴ | R⁵ | R⁶ | -A- | B | D | E |
|---|---|---|---|---|---|---|---|---|
| 2-175 | H | 2-Cl-4-OH-3,5-diMe-Ph | 6-MeO | Me | —CH₂— | O | O | CH |
| 2-176 | 2-Cl | 2-Cl-4-OH-3,5-diMe-Ph | H | Me | —CH₂— | O | O | CH |
| 2-177 | 3-Cl | 2-Cl-4-OH-3,5-diMe-Ph | H | Me | —CH₂— | O | O | CH |
| 2-178 | 2-Me | 2-Cl-4-OH-3,5-diMe-Ph | H | Me | —CH₂— | O | O | CH |
| 2-179 | 3-Me | 2-Cl-4-OH-3,5-diMe-Ph | H | Me | —CH₂— | O | O | CH |
| 2-180 | 2-MeO | 2-Cl-4-OH-3,5-diMe-Ph | H | Me | —CH₂— | O | O | CH |
| 2-181 | H | 2-Cl-4-OH-3,5-diEt-Ph | H | Me | —CH₂— | O | O | CH |
| 2-182 | H | 2-Cl-4-OH-3,5-ditBu-Ph | H | Me | —CH₂— | O | O | CH |
| 2-183 | H | 3-Cl-5-OH-2,6-diMe-Ph | H | Me | —CH₂— | O | O | CH |
| 2-184 | H | 3-Cl-5-OH-2,6-diMe-Ph | H | Me | —CH₂— | O | S | CH |
| 2-185 | H | 4-Cl-3-OH-2,5-diMe-Ph | H | Me | —CH₂— | O | O | CH |
| 2-186 | H | 4-Cl-3-OH-2,5-diMe-Ph | H | Me | —CH₂— | O | S | CH |
| 2-187 | H | 3-Cl-4-NH₂-Ph | H | Me | —CH₂— | O | O | CH |
| 2-188 | H | 3,5-diCl-4-NH₂-Ph | H | Me | —CH₂— | O | O | CH |
| 2-189 | H | 3,5-diCl-4-NH₂-Ph | H | Me | —CH₂— | O | S | CH |
| 2-190 | H | 3,5-diF-4-NH₂-Ph | H | Me | —CH₂— | O | O | CH |
| 2-191 | H | 4-NHMe-3-Cl-Ph | H | Me | —CH₂— | O | O | CH |
| 2-192 | H | 3-Cl-4-Pyrd(1)-Ph | H | Me | —CH₂— | O | O | CH |
| 2-193 | H | 3-OH-4-Pyrd(1)-Ph | H | Me | —CH₂— | O | O | CH |
| 2-194 | H | 3-Cl-6-Me-4 Pyrd(1)-Ph | H | Me | —CH₂— | O | O | CH |
| 2-195 | H | 2-Me-4-Pip(1)-Ph | H | Me | —CH₂— | O | O | CH |
| 2-196 | H | 2-Me-4-Mor(4)-Ph | H | Me | —CH₂— | O | O | CH |
| 2-197 | H | 2-OH-3-Me-Ph | H | Me | —CH₂— | O | O | CH |
| 2-198 | H | 2-OH-4-Me-Ph | H | Me | —CH₂— | O | O | CH |
| 2-199 | H | 2-OH-3,4-diMe-Ph | H | Me | —CH₂— | O | O | CH |
| 2-200 | H | 2-OH-3,4-diMe-Ph | H | Me | —CH₂— | O | S | CH |
| 2-201 | H | 3-OH-2-Me-Ph | H | Me | —CH₂— | O | O | CH |
| 2-202 | H | 3-OH-4-Me-Ph | H | Me | —CH₂— | O | O | CH |
| 2-203 | H | 3-OH-5-Me-Ph | H | Me | —CH₂— | O | O | CH |
| 2-204 | H | 3-OH-6-Me-Ph | H | Me | —CH₂— | O | O | CH |
| 2-205 | H | 3-OH-2,4-diMe-Ph | H | Me | —CH₂— | O | O | CH |
| 2-206 | H | 3-OH-2,4-diMe-Ph | H | Me | —CH₂— | O | S | CH |
| 2-207 | H | 4-OH-2-Me-Ph | H | Me | —CH₂— | O | O | CH |
| 2-208 | H | 4-OH-2-Me-Ph | H | Me | —CH₂— | O | S | CH |
| 2-209 | H | 4-OH-3-Me-Ph | H | Me | —CH₂— | O | O | CH |
| 2-210 | H | 4-OH-3-Me-Ph | H | Me | —CH₂— | O | O | N |
| 2-211 | H | 4-OH-3-Me-Ph | H | Me | —CH₂— | O | S | CH |
| 2-212 | H | 4-OH-3-Me-Ph | H | Et | —CH₂— | O | O | CH |
| 2-213 | H | 4-OH-3-Me-Ph | H | Et | —CH₂— | O | S | CH |
| 2-214 | H | 4-OH-3-Me-Ph | 6-Cl | Me | —CH₂— | O | O | CH |
| 2-215 | H | 4-OH-2-Et-Ph | H | Me | —CH₂— | O | O | CH |

TABLE 2-continued (I-2)

| Cpd. No. | R² | R⁴ | R⁵ | R⁶ | -A- | B | D | E |
|---|---|---|---|---|---|---|---|---|
| 2-216 | H | 4-OH-3-Et-Ph | H | Me | —CH₂— | O | O | CH |
| 2-217 | H | 4-OH-2-tBu-Ph | H | Me | —CH₂— | O | O | CH |
| 2-218 | H | 4-OH-3-tBu-Ph | H | Me | —CH₂— | O | O | CH |
| 2-219 | H | 4-OH-3-tBu-Ph | H | Me | —CH₂— | O | S | CH |
| 2-220 | H | 4-OH-2,3-diMe-Ph | H | Me | —CH₂— | O | O | CH |
| 2-221 | H | 4-OH-2,3-diMe-Ph | H | Me | —CH₂— | O | O | N |
| 2-222 | H | 4-OH-2,3-diMe-Ph | H | Me | —CH₂— | O | S | CH |
| 2-223 | H | 4-OH-2,3-diMe-Ph | H | Me | —(CH₂)₃— | S | O | CH |
| 2-224 | H | 4-OH-2,3-diMe-Ph | H | Et | —CH₂— | O | O | CH |
| 2-225 | H | 4-OH-2,3-diMe-Ph | H | Et | —CH₂— | O | S | CH |
| 2-226 | H | 4-OH-2,5-diMe-Ph | H | Me | —CH₂— | O | O | CH |
| 2-227 | H | 4-OH-2,5-diMe-Ph | H | Me | —CH₂— | O | S | CH |
| 2-228 | H | 4-OH-3,5-diMe-Ph | H | H | —CH₂— | O | O | CH |
| 2-229 | H | 4-OH-3,5-diMe-Ph | H | Me | —CH₂— | O | O | CH |
| 2-230 | H | 4-OH-3,5-diMe-Ph | H | Me | —CH₂— | O | O | N |
| 2-231 | H | 4-OH-3,5-diMe-Ph | H | Me | —CH₂— | O | S | CH |
| 2-232 | H | 4-OH-3,5-diMe-Ph | H | Me | —CH₂— | O | S | N |
| 2-233 | H | 4-OH-3,5-diMe-Ph | H | Me | —CH₂— | S | O | CH |
| 2-234 | H | 4-OH-3,5-diMe-Ph | H | Me | —(CH₂)₂— | O | O | CH |
| 2-235 | H | 4-OH-3,5-diMe-Ph | H | Me | —(CH₂)₂— | O | O | N |
| 2-236 | H | 4-OH-3,5-diMe-Ph | H | Me | —(CH₂)₂— | O | S | CH |
| 2-237 | H | 4-OH-3,5-diMe-Ph | H | Me | —CH(Me)— | O | O | CH |
| 2-238 | H | 4-OH-3,5-diMe-Ph | H | Me | —(CH₂)₃— | O | O | CH |
| 2-239 | H | 4-OH-3,5-diMe-Ph | H | Et | —CH₂— | O | O | CH |
| 2-240 | H | 4-OH-3,5-diMe-Ph | H | Et | —CH₂— | O | O | N |
| 2-241 | H | 4-OH-3,5-diMe-Ph | H | Et | —CH₂— | O | S | CH |
| 2-242 | H | 4-OH-3,5-diMe-Ph | H | Et | —(CH₂)₂— | O | O | CH |
| 2-243 | H | 4-OH-3,5-diMe-Ph | H | sBu | —CH₂— | O | O | CH |
| 2-244 | H | 4-OH-3,5-diMe-Ph | H | tBu | —CH₂— | O | O | CH |
| 2-245 | H | 4-OH-3,5-diMe-Ph | H | tBu | —CH₂— | O | S | CH |
| 2-246 | H | 4-OH-3,5-diMe-Ph | H | Ph | —CH₂— | O | O | CH |
| 2-247 | H | 4-OH-3,5-diMe-Ph | H | Bz | —CH₂— | O | O | CH |
| 2-248 | H | 4-OH-3,5-diMe-Ph | 6-Cl | Me | —CH₂— | O | O | CH |
| 2-249 | H | 4-OH-3,5-diMe-Ph | 6-Me | Me | —CH₂— | O | O | CH |

TABLE 2-continued

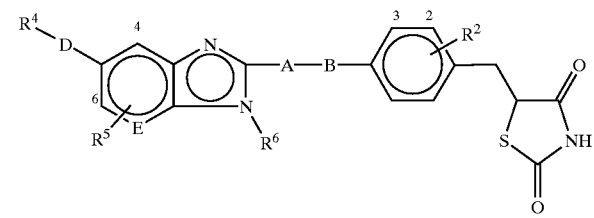

(I-2)

| Cpd. No. | R² | R⁴ | R⁵ | R⁶ | -A- | B | D | E |
|---|---|---|---|---|---|---|---|---|
| 2-250 | H | 4-OH-3,5-diMe-Ph | 6-MeO | Me | —CH₂— | O | O | CH |
| 2-251 | 2-Cl | 4-OH-3,5-diMe-Ph | H | Me | —CH₂— | O | O | CH |
| 2-252 | 3-Cl | 4-OH-3,5-diMe-Ph | H | Me | —CH₂— | O | O | CH |
| 2-253 | 2-Me | 4-OH-3,5-diMe-Ph | H | Me | —CH₂— | O | O | CH |
| 2-254 | 3-Me | 4-OH-3,5-diMe-Ph | H | Me | —CH₂— | O | O | CH |
| 2-255 | 2-MeO | 4-OH-3,5-diMe-Ph | H | Me | —CH₂— | O | O | CH |
| 2-256 | 3-MeO | 4-OH-3,5-diMe-Ph | H | Me | —CH₂— | O | O | CH |
| 2-257 | H | 3,5-diEt-4-OH-Ph | H | Me | —CH₂— | O | O | CH |
| 2-258 | H | 3,5-diEt-4-OH-Ph | H | Me | —CH₂— | O | S | CH |
| 2-259 | H | 3-tBu-4-OH-5-Me-Ph | H | Me | —CH₂— | O | O | CH |
| 2-260 | H | 3-tBu-4-OH-5-Me-Ph | H | Me | —CH₂— | O | S | CH |
| 2-261 | H | 4-OH-3,5-diPr-Ph | H | Me | —CH₂— | O | O | CH |
| 2-262 | H | 4-OH-3,5-diiPr-Ph | H | Me | —CH₂— | O | O | CH |
| 2-263 | H | 3,5-ditBu-4-OH-Ph | H | H | —CH₂— | O | O | CH |
| 2-264 | H | 3,5-ditBu-4-OH-Ph | H | Me | —CH₂— | O | O | CH |
| 2-265 | H | 3,5-ditBu-4-OH-Ph | H | Me | —CH₂— | O | O | N |
| 2-266 | H | 3,5-ditBu-4-OH-Ph | H | Me | —CH₂— | O | S | CH |
| 2-267 | H | 3,5-ditBu-4-OH-Ph | H | Me | —CH₂— | O | S | N |
| 2-268 | H | 3,5-ditBu-4-OH-Ph | H | Me | —CH₂— | S | O | CH |
| 2-269 | H | 3,5-ditBu-4-OH-Ph | H | Me | —CH₂— | S | S | CH |
| 2-270 | H | 3,5-ditBu-4-OH-Ph | H | Me | —(CH₂)₂— | O | O | CH |
| 2-271 | H | 3,5-ditBu-4-OH-Ph | H | Me | —(CH₂)₂— | O | O | N |
| 2-272 | H | 3,5-ditBu-4-OH-Ph | H | Me | —(CH₂)₂— | O | S | CH |
| 2-273 | H | 3,5-ditBu-4-OH-Ph | H | Me | —CH(Me)— | O | O | CH |
| 2-274 | H | 3,5-ditBu-4-OH-Ph | H | Me | —(CH₂)₃— | O | O | CH |
| 2-275 | H | 3,5-ditBu-4-OH-Ph | H | Me | —(CH₂)₃— | O | S | CH |
| 2-276 | H | 3,5-ditBu-4-OH-Ph | H | Et | —CH₂— | O | O | CH |
| 2-277 | H | 3,5-ditBu-4-OH-Ph | H | Et | —CH₂— | O | O | N |
| 2-278 | H | 3,5-ditBu-4-OH-Ph | H | Et | —CH₂— | O | S | CH |
| 2-279 | H | 3,5-ditBu-4-OH-Ph | H | Et | —(CH₂)₂— | O | O | CH |
| 2-280 | H | 3,5-ditBu-4-OH-Ph | H | tBu | —CH₂— | O | O | CH |
| 2-281 | H | 3,5-ditBu-4-OH-Ph | H | tBu | —CH₂— | O | S | CH |

TABLE 2-continued (I-2)

| Cpd. No. | R² | R⁴ | R⁵ | R⁶ | -A- | B | D | E |
|---|---|---|---|---|---|---|---|---|
| 2-282 | H | 3,5-ditBu-4-OH-Ph | H | Ph | —CH₂— | O | O | CH |
| 2-283 | H | 3,5-ditBu-4-OH-Ph | H | Bz | —CH₂— | O | O | CH |
| 2-284 | H | 3,5-ditBu-4-OH-Ph | 6-Cl | Me | —CH₂— | O | S | CH |
| 2-285 | H | 3,5-ditBu-4-OH-Ph | 6-Cl | Me | —CH₂— | O | O | CH |
| 2-286 | H | 3,5-ditBu-4-OH-Ph | 6-Me | Me | —CH₂— | O | O | CH |
| 2-287 | H | 3,5-ditBu-4-OH-Ph | 6-MeO | Me | —CH₂— | O | O | CH |
| 2-288 | 2-Cl | 3,5-ditBu-4-OH-Ph | H | Me | —CH₂— | O | O | CH |
| 2-289 | 3-Cl | 3,5-ditBu-4-OH-Ph | H | Me | —CH₂— | O | O | CH |
| 2-290 | 2-Me | 3,5-ditBu-4-OH-Ph | H | Me | —CH₂— | O | O | CH |
| 2-291 | 3-Me | 3,5-ditBu-4-OH-Ph | H | Me | —CH₂— | O | O | CH |
| 2-292 | 2-MeO | 3,5-ditBu-4-OH-Ph | H | Me | —CH₂— | O | O | CH |
| 2-293 | 3-MeO | 3,5-ditBu-4-OH-Ph | H | Me | —CH₂— | O | O | CH |
| 2-294 | H | 4-OH-2,3,5-triMe-Ph | H | H | —CH₂— | O | O | CH |
| 2-295 | H | 4-OH-2,3,5-triMe-Ph | H | H | —CH₂— | O | S | CH |
| 2-296 | H | 4-OH-2,3,5-triMe-Ph | H | Me | —CH₂— | O | O | CH |
| 2-297 | H | 4-OH-2,3,5-triMe-Ph | H | Me | —CH₂— | O | O | N |
| 2-298 | H | 4-OH-2,3,5-triMe-Ph | H | Me | —CH₂— | O | S | CH |
| 2-299 | H | 4-OH-2,3,5-triMe-Ph | H | Me | —CH₂— | O | S | N |
| 2-300 | H | 4-OH-2,3,5-triMe-Ph | H | Me | —CH₂— | S | O | CH |
| 2-301 | H | 4-OH-2,3,5-triMe-Ph | H | Me | —(CH₂)₂— | O | O | CH |
| 2-302 | H | 4-OH-2,3,5-triMe-Ph | H | Me | —(CH₂)₂— | O | O | N |
| 2-303 | H | 4-OH-2,3,5-triMe-Ph | H | Me | —(CH₂)₂— | O | S | CH |
| 2-304 | H | 4-OH-2,3,5-triMe-Ph | H | Me | —CH(Me)— | O | O | CH |
| 2-305 | H | 4-OH-2,3,5-triMe-Ph | H | Me | —(CH₂)₃— | O | O | CH |
| 2-306 | H | 4-OH-2,3,5-triMe-Ph | H | Et | —CH₂— | O | O | CH |
| 2-307 | H | 4-OH-2,3,5-triMe-Ph | H | Et | —CH₂— | O | O | N |
| 2-308 | H | 4-OH-2,3,5-triMe-Ph | H | Et | —CH₂— | O | S | CH |
| 2-309 | H | 4-OH-2,3,5-triMe-Ph | H | Et | —CH₂— | O | S | N |
| 2-310 | H | 4-OH-2,3,5-triMe-Ph | H | Et | —(CH₂)₂— | O | O | CH |
| 2-311 | H | 4-OH-2,3,5-triMe-Ph | H | iPr | —CH₂— | O | O | CH |
| 2-312 | H | 4-OH-2,3,5-triMe-Ph | H | tBu | —CH₂— | O | O | CH |
| 2-313 | H | 4-OH-2,3,5-triMe-Ph | H | tBu | —CH₂— | O | S | CH |

TABLE 2-continued (I-2)

| Cpd. No. | R² | R⁴ | R⁵ | R⁶ | -A- | B | D | E |
|---|---|---|---|---|---|---|---|---|
| 2-314 | H | 4-OH-2,3,5-triMe-Ph | H | Ph | —CH₂— | O | O | CH |
| 2-315 | H | 4-OH-2,3,5-triMe-Ph | H | Bz | —CH₂— | O | O | CH |
| 2-316 | H | 4-OH-2,3,5-triMe-Ph | 6-Cl | Me | —CH₂— | O | O | CH |
| 2-317 | H | 4-OH-2,3,5-triMe-Ph | 6-Me | Me | —CH₂— | O | O | CH |
| 2-318 | H | 4-OH-2,3,5-triMe-Ph | 6-MeO | Me | —CH₂— | O | O | CH |
| 2-319 | 2-Cl | 4-OH-2,3,5-triMe-Ph | H | Me | —CH₂— | O | O | CH |
| 2-320 | 3-Cl | 4-OH-2,3,5-triMe-Ph | H | Me | —CH₂— | O | O | CH |
| 2-321 | 2-Me | 4-OH-2,3,5-triMe-Ph | H | Me | —CH₂— | O | O | CH |
| 2-322 | 3-Me | 4-OH-2,3,5-triMe-Ph | H | Me | —CH₂— | O | O | CH |
| 2-323 | 2-MeO | 4-OH-2,3,5-triMe-Ph | H | Me | —CH₂— | O | O | CH |
| 2-324 | 2-MeO | 4-OH-2,3,5-triMe-Ph | H | Me | —CH₂— | O | O | CH |
| 2-325 | H | 4-OH-2,3,6-triMe-Ph | H | Me | —CH₂— | O | O | CH |
| 2-326 | H | 4-OH-2,3,6-triMe-Ph | H | Me | —CH₂— | O | S | CH |
| 2-327 | H | 4-OH-2,3,5,6-tetraMe-Ph | H | Me | —CH₂— | O | O | CH |
| 2-328 | H | 4-OH-2,3,5,6-tetraMe-Ph | H | Me | —CH₂— | O | S | CH |
| 2-329 | H | 4-OH-3,5-diCF₃-Ph | H | Me | —CH₂— | O | O | CH |
| 2-330 | H | 4-OH-3,5-diMeO-Ph | H | Me | —CH₂— | O | O | CH |
| 2-331 | H | 4-OH-3,5-ditBuO-Ph | H | Me | —CH₂— | O | O | CH |
| 2-332 | H | 3-NH₂-4-Me-Ph | H | Me | —CH₂— | O | O | CH |
| 2-333 | H | 3-NH₂-4-Me-Ph | H | Me | —CH₂— | O | S | CH |
| 2-334 | H | 4-NH₂-2,3-diMe-Ph | H | Me | —CH₂— | O | O | CH |
| 2-335 | H | 4-NH₂-2,3-diMe-Ph | H | Me | —CH₂— | O | S | CH |
| 2-336 | H | 4-NH₂-2,6-diMe-Ph | H | Me | —CH₂— | O | O | CH |
| 2-337 | H | 4-NH₂-2,6-diMe-Ph | H | Me | —CH₂— | O | S | CH |
| 2-338 | H | 4-NH₂-3,5-diMe-Ph | H | H | —CH₂— | O | O | CH |
| 2-339 | H | 4-NH₂-3,5-diMe-Ph | H | Me | —CH₂— | O | O | CH |
| 2-340 | H | 4-NH₂-3,5-diMe-Ph | H | Me | —CH₂— | O | O | N |
| 2-341 | H | 4-NH₂-3,5-diMe-Ph | H | Me | —CH₂— | O | S | CH |
| 2-342 | H | 4-NH₂-3,5-diMe-Ph | H | Me | —CH₂— | O | S | N |
| 2-343 | H | 4-NH₂-3,5-diMe-Ph | H | Me | —CH₂— | S | O | CH |
| 2-344 | H | 4-NH₂-3,5-diMe-Ph | H | Me | —(CH₂)₂— | O | O | CH |
| 2-345 | H | 4-NH₂-3,5-diMe-Ph | H | Me | —(CH₂)₂— | O | O | N |
| 2-346 | H | 4-NH₂-3,5-diMe-Ph | H | Me | —(CH₂)₂— | O | S | CH |

TABLE 2-continued (I-2)

| Cpd. No. | R² | R⁴ | R⁵ | R⁶ | -A- | B | D | E |
|---|---|---|---|---|---|---|---|---|
| 2-347 | H | 4-NH₂-3,5-diMe-Ph | H | Me | —CH(Me)— | O | O | CH |
| 2-348 | H | 4-NH₂-3,5-diMe-Ph | H | Me | —(CH₂)₃— | O | O | CH |
| 2-349 | H | 4-NH₂-3,5-diMe-Ph | H | Et | —CH₂— | O | O | CH |
| 2-350 | H | 4-NH₂-3,5-diMe-Ph | H | Et | —CH₂— | O | O | N |
| 2-351 | H | 4-NH₂-3,5-diMe-Ph | H | Et | —CH₂— | O | S | CH |
| 2-352 | H | 4-NH₂-3,5-diMe-Ph | H | Et | —(CH₂)₂— | O | O | CH |
| 2-353 | H | 4-NH₂-3,5-diMe-Ph | H | tBu | —CH₂— | O | O | CH |
| 2-354 | H | 4-NH₂-3,5-diMe-Ph | H | tBu | —CH₂— | O | S | CH |
| 2-355 | H | 4-NH₂-3,5-diMe-Ph | H | Ph | —CH₂— | O | O | CH |
| 2-356 | H | 4-NH₂-3,5-diMe-Ph | H | Bz | —CH₂— | O | O | CH |
| 2-357 | H | 4-NH₂-3,5-diMe-Ph | 6-Cl | Me | —CH₂— | O | O | CH |
| 2-358 | H | 4-NH₂-3,5-diMe-Ph | 6-Me | Me | —CH₂— | O | O | CH |
| 2-359 | H | 4-NH₂-3,5-diMe-Ph | 6-MeO | Me | —CH₂— | O | O | CH |
| 2-360 | 2-Cl | 4-NH₂-3,5-diMe-Ph | H | Me | —CH₂— | O | O | CH |
| 2-361 | 3-Cl | 4-NH₂-3,5-diMe-Ph | H | Me | —CH₂— | O | O | CH |
| 2-362 | 2-Me | 4-NH₂-3,5-diMe-Ph | H | Me | —CH₂— | O | O | CH |
| 2-363 | 3-Me | 4-NH₂-3,5-diMe-Ph | H | Me | —CH₂— | O | O | CH |
| 2-364 | 2-MeO | 4-NH₂-3,5-diMe-Ph | H | Me | —CH₂— | O | O | CH |
| 2-365 | 3-MeO | 4-NH₂-3,5-diMe-Ph | H | Me | —CH₂— | O | O | CH |
| 2-366 | H | 4-NH₂-3,5-diEt-Ph | H | Me | —CH₂— | O | O | CH |
| 2-367 | H | 4-NH₂-3,5-diEt-Ph | H | Me | —CH₂— | O | S | CH |
| 2-368 | H | 4-NH₂-3,5-ditBu-Ph | H | Me | —CH₂— | O | O | CH |
| 2-369 | H | 4-NHMe-3,5-diMe-Ph | H | Me | —CH₂— | O | O | CH |
| 2-370 | H | 4-NHMe-3,5-diMe-Ph | H | Me | —CH₂— | O | S | CH |
| 2-371 | H | 4-NHEt-3,5-diMe-Ph | H | Me | —CH₂— | O | O | CH |
| 2-372 | H | 4-NHAc-3,5-diMe-Ph | H | Me | —CH₂— | O | O | CH |
| 2-373 | H | 4-NO₂-2,6-diMe-Ph | H | Me | —CH₂— | O | O | CH |
| 2-374 | H | 4-NO₂-3,5-diMe-Ph | H | Me | —CH₂— | O | O | CH |
| 2-375 | H | 4-NO₂-3,5-diMe-Ph | H | Me | —CH₂— | O | S | CH |
| 2-376 | H | 4-NO₂-3,5-ditBu-Ph | H | Me | —CH₂— | O | O | CH |
| 2-377 | H | Pyr(2) | H | H | —CH₂— | O | O | CH |
| 2-378 | H | Pyr(2) | H | Me | —CH₂— | O | O | CH |
| 2-379 | H | Pyr(2) | H | Me | —CH₂— | O | O | N |
| 2-380 | H | Pyr(2) | H | Me | —CH₂— | O | S | CH |
| 2-381 | H | Pyr(2) | H | Me | —CH₂— | O | S | N |

TABLE 2-continued (I-2)

| Cpd. No. | R² | R⁴ | R⁵ | R⁶ | -A- | B | D | E |
|---|---|---|---|---|---|---|---|---|
| 2-382 | H | Pyr(2) | H | Me | —CH₂— | S | O | CH |
| 2-383 | H | Pyr(2) | H | Me | —(CH₂)₂— | O | O | CH |
| 2-384 | H | Pyr(2) | H | Me | —(CH₂)₂— | O | O | N |
| 2-385 | H | Pyr(2) | H | Me | —(CH₂)₂— | O | S | CH |
| 2-386 | H | Pyr(2) | H | Me | —CH(Me)— | O | O | CH |
| 2-387 | H | Pyr(2) | H | Me | —(CH₂)₃— | O | O | CH |
| 2-388 | H | Pyr(2) | H | Et | —CH₂— | O | O | CH |
| 2-389 | H | Pyr(2) | H | Et | —CH₂— | O | O | N |
| 2-390 | H | Pyr(2) | H | Et | —CH₂— | O | S | CH |
| 2-391 | H | Pyr(2) | H | Et | —(CH₂)₂— | O | O | CH |
| 2-392 | H | Pyr(2) | H | tBu | —CH₂— | O | O | CH |
| 2-393 | H | Pyr(2) | H | tBu | —CH₂— | O | S | CH |
| 2-394 | H | Pyr(2) | H | Ph | —CH₂— | O | O | CH |
| 2-395 | H | Pyr(2) | H | Bz | —CH₂— | O | O | CH |
| 2-396 | H | Pyr(2) | 4-Cl | Me | —CH₂— | O | O | CH |
| 2-397 | H | Pyr(2) | 6-Cl | Me | —CH₂— | O | O | CH |
| 2-398 | H | Pyr(2) | 6-Me | Me | —CH₂— | O | O | CH |
| 2-399 | H | Pyr(2) | 6-MeO | Me | —CH₂— | O | O | CH |
| 2-400 | 2-Cl | Pyr(2) | H | Me | —CH₂— | O | O | CH |
| 2-401 | 3-Cl | Pyr(2) | H | Me | —CH₂— | O | O | CH |
| 2-402 | 2-Me | Pyr(2) | H | Me | —CH₂— | O | O | CH |
| 2-403 | 3-Me | Pyr(2) | H | Me | —CH₂— | O | O | CH |
| 2-404 | 2-MeO | Pyr(2) | H | Me | —CH₂— | O | O | CH |
| 2-405 | 3-MeO | Pyr(2) | H | Me | —CH₂— | O | O | CH |
| 2-406 | H | 5-F-Pyr(2) | H | Me | —CH₂— | O | O | CH |
| 2-407 | H | 6-F-Pyr(2) | H | Me | —CH₂— | O | O | CH |
| 2-408 | H | 5-Cl-Pyr(2) | H | Me | —CH₂— | O | O | CH |
| 2-409 | H | 5-Cl-Pyr(2) | H | Me | —CH₂— | O | S | CH |
| 2-410 | H | 6-Cl-Pyr(2) | H | Me | —CH₂— | O | O | CH |
| 2-411 | H | 6-Cl-Pyr(2) | H | Me | —CH₂— | O | S | CH |
| 2-412 | H | 6-Me-Pyr(2) | H | Me | —CH₂— | O | O | CH |
| 2-413 | H | 6-MeO-Pyr(2) | H | Me | —CH₂— | O | O | CH |
| 2-414 | H | 6-MeO-Pyr(2) | H | Me | —CH₂— | O | S | CH |
| 2-415 | H | 6-EtO-Pyr(2) | H | Me | —CH₂— | O | O | CH |
| 2-416 | H | 3-NH₂-Pyr(2) | H | Me | —CH₂— | O | O | CH |
| 2-417 | H | 3-NH₂-Pyr(2) | H | Me | —CH₂— | O | S | CH |
| 2-418 | H | 5-NH₂-Pyr(2) | H | Me | —CH₂— | O | O | CH |
| 2-419 | H | 5-NH₂-Pyr(2) | H | Me | —CH₂— | O | S | CH |
| 2-420 | H | 3-NHMe-Pyr(2) | H | Me | —CH₂— | O | O | CH |
| 2-421 | H | 5-NHMe-Pyr(2) | H | Me | —CH₂— | O | O | CH |
| 2-422 | H | 3-NO₂-Pyr(2) | H | Me | —CH₂— | O | O | CH |
| 2-423 | H | 3-NO₂-Pyr(2) | H | Me | —CH₂— | O | S | CH |
| 2-424 | H | 5-NO₂-Pyr(2) | H | Me | —CH₂— | O | O | CH |
| 2-425 | H | 5-NO₂-Pyr(2) | H | Me | —CH₂— | O | S | CH |
| 2-426 | H | 5-NH₂-6-Cl-Pyr(2) | H | Me | —CH₂— | O | O | CH |
| 2-427 | H | 5-NH₂-6-Cl-Pyr(2) | H | Me | —CH₂— | O | S | CH |
| 2-428 | 3-MeO | 5-NH₂-6-Cl-Pyr(2) | 6-MeO | Et | —(CH₂)₄— | S | S | CH |
| 2-429 | H | Pyr(3) | H | H | —CH₂— | O | O | CH |
| 2-430 | H | Pyr(3) | H | Me | —CH₂— | O | O | CH |
| 2-431 | H | Pyr(3) | H | Me | —CH₂— | O | O | N |
| 2-432 | H | Pyr(3) | H | Me | —CH₂— | O | S | CH |
| 2-433 | H | Pyr(3) | H | Me | —CH₂— | O | S | N |
| 2-434 | H | Pyr(3) | H | Me | —CH₂— | S | O | CH |
| 2-435 | H | Pyr(3) | H | Me | —(CH₂)₂— | O | O | CH |
| 2-436 | H | Pyr(3) | H | Me | —(CH₂)₂— | O | O | N |
| 2-437 | H | Pyr(3) | H | Me | —(CH₂)₂— | O | S | CH |
| 2-438 | H | Pyr(3) | H | Me | —CH(Me)— | O | O | CH |
| 2-439 | H | Pyr(3) | H | Me | —(CH₂)₃— | O | O | CH |
| 2-440 | H | Pyr(3) | H | Et | —CH₂— | O | O | CH |
| 2-441 | H | Pyr(3) | H | Et | —CH₂— | O | O | N |
| 2-442 | H | Pyr(3) | H | Et | —CH₂— | O | S | CH |
| 2-443 | H | Pyr(3) | H | Et | —CH₂— | O | S | N |

TABLE 2-continued (I-2)

| Cpd. No. | $R^2$ | $R^4$ | $R^5$ | $R^6$ | -A- | B | D | E |
|---|---|---|---|---|---|---|---|---|
| 2-444 | H | Pyr(3) | H | Et | —(CH$_2$)$_2$— | O | O | CH |
| 2-445 | H | Pyr(3) | H | tBu | —CH$_2$— | O | O | CH |
| 2-446 | H | Pyr(3) | H | tBu | —CH$_2$— | O | S | CH |
| 2-447 | H | Pyr(3) | H | Ph | —(CH$_2$)$_3$— | O | O | CH |
| 2-448 | H | Pyr(3) | H | Ph | —CH$_2$— | O | O | CH |
| 2-449 | H | Pyr(3) | H | Ph | —CH$_2$— | O | O | N |
| 2-450 | H | Pyr(3) | H | Ph | —CH$_2$— | O | S | CH |
| 2-451 | H | Pyr(3) | H | Bz | —CH$_2$— | O | O | CH |
| 2-452 | H | Pyr(3) | 6-Cl | Me | —CH$_2$— | O | O | CH |
| 2-453 | H | Pyr(3) | 6-Me | Me | —CH$_2$— | O | O | CH |
| 2-454 | H | Pyr(3) | 6-MeO | Me | —CH$_2$— | O | O | CH |
| 2-455 | 2-Cl | Pyr(3) | H | Me | —CH$_2$— | O | O | CH |
| 2-456 | 3-Cl | Pyr(3) | H | Me | —CH$_2$— | O | O | CH |
| 2-457 | 2-Me | Pyr(3) | H | Me | —CH$_2$— | O | O | CH |
| 2-458 | 3-Me | Pyr(3) | H | Me | —CH$_2$— | O | O | CH |
| 2-459 | 2-MeO | Pyr(3) | H | Me | —CH$_2$— | O | O | CH |
| 2-460 | 3-MeO | Pyr(3) | H | Me | —CH$_2$— | O | O | CH |
| 2-461 | H | 6-Cl-Pyr(3) | H | Me | —CH$_2$— | O | O | CH |
| 2-462 | H | 6-Me-Pyr(3) | H | Me | —CH$_2$— | O | O | CH |
| 2-463 | H | 5-MeO-Pyr(3) | H | Me | —CH$_2$— | O | O | CH |
| 2-464 | H | 5-MeO-Pyr(3) | H | Me | —CH$_2$— | O | S | CH |
| 2-465 | H | 6-MeO-Pyr(3) | H | Me | —CH$_2$— | O | O | CH |
| 2-466 | H | 6-MeO-Pyr(3) | H | Me | —CH$_2$— | O | O | N |
| 2-467 | H | 6-MeO-Pyr(3) | H | Me | —CH$_2$— | O | S | CH |
| 2-468 | H | 6-MeO-Pyr(3) | H | Me | —(CH$_2$)$_3$— | O | O | CH |
| 2-469 | H | 6-MeO-Pyr(3) | H | Et | —CH$_2$— | O | O | CH |
| 2-470 | H | 6-MeO-Pyr(3) | H | Et | —CH$_2$— | O | S | CH |
| 2-471 | H | 6-EtO-Pyr(3) | H | Me | —CH$_2$— | O | O | CH |
| 2-472 | H | 6-iPrO-Pyr(3) | H | Me | —CH$_2$— | O | O | CH |
| 2-473 | H | 6-iPrO-Pyr(3) | H | Me | —CH$_2$— | O | S | CH |
| 2-474 | H | 6-MeO-5-Me-Pyr(3) | H | Me | —CH$_2$— | O | O | CH |
| 2-475 | H | 6-MeO-5-Me-Pyr(3) | H | Me | —CH$_2$— | O | S | CH |
| 2-476 | H | 2-NO$_2$-6-Me-Pyr(3) | H | Me | —CH$_2$— | O | O | CH |
| 2-477 | H | 2-NO$_2$-6-Me-Pyr(3) | H | Me | —CH$_2$— | O | S | CH |
| 2-478 | H | Pyr(4) | H | H | —CH$_2$— | O | O | CH |
| 2-479 | H | Pyr(4) | H | Me | —CH$_2$— | O | O | CH |
| 2-480 | H | Pyr(4) | H | Me | —CH$_2$— | O | O | N |
| 2-481 | H | Pyr(4) | H | Me | —CH$_2$— | O | S | CH |
| 2-482 | H | Pyr(4) | H | Me | —CH$_2$— | O | S | N |
| 2-483 | H | Pyr(4) | H | Me | —CH$_2$— | S | O | CH |
| 2-484 | H | Pyr(4) | H | Me | —CH$_2$— | S | S | CH |
| 2-485 | H | Pyr(4) | H | Me | —(CH$_2$)$_2$— | O | O | CH |
| 2-486 | H | Pyr(4) | H | Me | —(CH$_2$)$_2$— | O | O | N |
| 2-487 | H | Pyr(4) | H | Me | —(CH$_2$)$_2$— | O | S | CH |
| 2-488 | H | Pyr(4) | H | Me | —CH(Me)— | O | O | CH |
| 2-489 | H | Pyr(4) | H | Me | —(CH$_2$)$_3$— | O | O | CH |
| 2-490 | H | Pyr(4) | H | Et | —CH$_2$— | O | O | CH |
| 2-491 | H | Pyr(4) | H | Et | —CH$_2$— | O | O | N |
| 2-492 | H | Pyr(4) | H | Et | —CH$_2$— | O | S | CH |
| 2-493 | H | Pyr(4) | H | Et | —(CH$_2$)$_2$— | O | O | CH |
| 2-494 | H | Pyr(4) | H | tBu | —CH$_2$— | O | O | CH |
| 2-495 | H | Pyr(4) | H | tBu | —CH$_2$— | O | S | CH |
| 2-496 | H | Pyr(4) | H | Ph | —CH$_2$— | O | O | CH |
| 2-497 | H | Pyr(4) | H | Bz | —CH$_2$— | O | O | CH |
| 2-498 | H | Pyr(4) | H | Bz | —CH$_2$— | O | S | CH |
| 2-499 | H | Pyr(4) | 6-Cl | Me | —CH$_2$— | O | O | CH |
| 2-500 | H | Pyr(4) | 6-Me | Me | —CH$_2$— | O | O | CH |
| 2-501 | H | Pyr(4) | 6-MeO | Me | —CH$_2$— | O | O | CH |
| 2-502 | 2-Cl | Pyr(4) | H | Me | —CH$_2$— | O | O | CH |
| 2-503 | 3-Cl | Pyr(4) | H | Me | —CH$_2$— | O | O | CH |
| 2-504 | 2-Me | Pyr(4) | H | Me | —CH$_2$— | O | O | CH |

TABLE 2-continued (I-2)

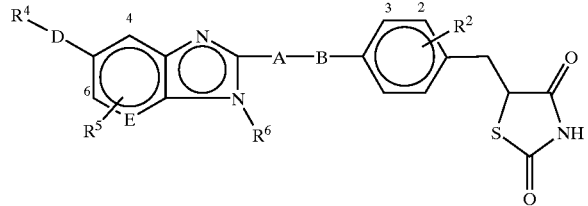

| Cpd. No. | R² | R⁴ | R⁵ | R⁶ | -A- | B | D | E |
|---|---|---|---|---|---|---|---|---|
| 2-505 | 3-Me | Pyr(4) | H | Me | —CH₂— | O | O | CH |
| 2-506 | 2-MeO | Pyr(4) | H | Me | —CH₂— | O | O | CH |
| 2-507 | 3-MeO | Pyr(4) | H | Me | —CH₂— | O | O | CH |
| 2-508 | H | 2-F-Pyr(4) | H | Me | —CH₂— | O | O | CH |
| 2-509 | H | 2-Cl-Pyr(4) | H | Me | —CH₂— | O | O | CH |
| 2-510 | H | 2-Me-Pyr(4) | H | Me | —CH₂— | O | O | CH |
| 2-511 | H | 2-Me-Pyr(4) | H | Me | —CH₂— | O | S | CH |
| 2-512 | H | 2-Et-Pyr(4) | H | Me | —CH₂— | O | O | CH |
| 2-513 | H | 2,6-diMe-Pyr(4) | H | Me | —CH₂— | O | O | CH |
| 2-514 | H | 2,6-diMe-Pyr(4) | H | Me | —CH₂— | O | O | N |
| 2-515 | H | 2,6-diMe-Pyr(4) | H | Me | —CH₂— | O | S | CH |
| 2-516 | H | 2,6-diMe-Pyr(4) | H | Et | —CH₂— | O | O | CH |
| 2-517 | H | 2,6-diMe-Pyr(4) | H | Et | —CH₂— | O | S | CH |
| 2-518 | H | 3,6-diMe-Pyr(4) | H | Me | —CH₂— | O | O | CH |
| 2-519 | H | 3,6-diMe-Pyr(4) | H | Me | —CH₂— | O | S | CH |
| 2-520 | H | 2-MeO-Pyr(4) | H | Me | —CH₂— | O | O | CH |
| 2-521 | H | 2-MeO-Pyr(4) | H | Me | —CH₂— | O | S | CH |
| 2-522 | H | 4-Imid(1)-Ph | H | Me | —CH₂— | O | O | CH |
| 2-523 | H | 4-Imid(1)-Ph | H | Me | —CH₂— | O | O | N |
| 2-524 | H | 4-Imid(1)-Ph | H | Me | —CH₂— | O | S | CH |
| 2-525 | H | 4-Imid(1)-Ph | H | Me | —CH₂— | O | S | N |
| 2-526 | H | 4-Tz-Ph | H | Me | —CH₂— | O | O | CH |
| 2-527 | H | 4-Tz-Ph | H | Me | —CH₂— | O | O | N |
| 2-528 | H | 4-Tz-Ph | H | Me | —CH₂— | O | S | CH |
| 2-529 | H | 4-Tz-Ph | H | Me | —CH₂— | O | S | N |
| 2-530 | H | 4-Ada(1)-Ph | H | Me | —CH₂— | O | O | CH |
| 2-531 | H | 4-Ada(1)-Ph | H | Me | —CH₂— | O | O | N |
| 2-532 | H | 4-Ada(1)-Ph | H | Me | —CH₂— | O | S | CH |
| 2-533 | H | 4-Ada(1)-Ph | H | Me | —CH₂— | O | S | N |
| 2-534 | H | 4-CN-Ph | H | Me | —CH₂— | O | O | CH |
| 2-535 | H | 4-CN-Ph | H | Me | —CH₂— | O | O | N |
| 2-536 | H | 4-CN-Ph | H | Me | —CH₂— | O | S | CH |
| 2-537 | H | 4-CN-Ph | H | Me | —CH₂— | O | S | N |
| 2-538 | H | 4-Bz-3-OH-Ph | H | Me | —CH₂— | O | O | CH |
| 2-539 | H | 4-Bz-3-OH-Ph | H | Me | —CH₂— | O | O | N |
| 2-540 | H | 4-OH-2,5-ditBu-Ph | H | Me | —CH₂— | O | O | CH |
| 2-541 | H | pentaF-Ph | H | Me | —CH₂— | O | O | CH |
| 2-542 | H | 4-NHCOPh-Ph | H | Me | —CH₂— | O | O | CH |
| 2-543 | H | 4-NHCO(3-Cl-Ph)-Ph | H | Me | —CH₂— | O | O | CH |
| 2-544 | H | 4-NHCO(2,4-diF-Ph)-Ph | H | Me | —CH₂— | O | O | CH |
| 2-545 | H | 4-NHCO(4-OH-3,5-ditBu-Ph)-Ph | H | Me | —CH₂— | O | O | CH |
| 2-546 | H | 4-NHCONp(1)-Ph | H | Me | —CH₂— | O | O | CH |
| 2-547 | H | 4-NHCO(3-Cl-Bz)-Ph | H | Me | —CH₂— | O | O | CH |
| 2-548 | H | 4-NHCOcPn-Ph | H | Me | —CH₂— | O | O | CH |
| 2-549 | H | 4-NHCOcHx-Ph | H | Me | —CH₂— | O | O | CH |
| 2-550 | H | 4-NHCOPyr(3)-Ph | H | Me | —CH₂— | O | O | CH |
| 2-551 | H | 4-NHCOPyr(4)-Ph | H | Me | —CH₂— | O | O | CH |
| 2-552 | H | 4-NHHx-Ph | H | Me | —CH₂— | O | O | CH |
| 2-553 | H | 4-NH(Ac)Hx-Ph | H | Me | —CH₂— | O | O | CH |

TABLE 3

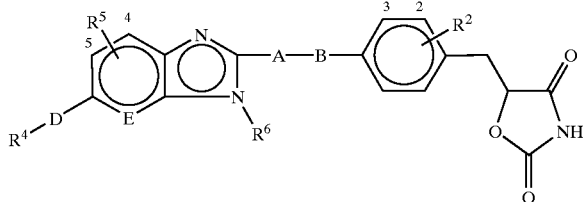

(I-3)

| Cpd. No. | R² | R⁴ | R⁵ | R⁶ | —A— | B | D | E |
|---|---|---|---|---|---|---|---|---|
| 3-1 | H | 4-F—Ph | H | Me | —CH₂— | O | O | CH |
| 3-2 | H | 4-Cl—Ph | H | Me | —CH₂— | O | O | CH |
| 3-3 | H | 2-OH—Ph | H | Me | —CH₂— | O | O | CH |
| 3-4 | H | 2-OH—Ph | H | Me | —CH₂— | O | S | CH |
| 3-5 | H | 2-OH—Ph | H | Me | —CH₂— | S | O | CH |
| 3-6 | H | 2-OH—Ph | H | Me | —(CH₂)₂— | O | O | CH |
| 3-7 | H | 2-OH—Ph | H | Et | —CH₂— | O | O | CH |
| 3-8 | H | 2-OH—Ph | H | Et | —CH₂— | O | S | CH |
| 3-9 | H | 2-OH—Ph | H | tBu | —CH₂— | O | O | CH |
| 3-10 | H | 3-OH—Ph | H | Me | —CH₂— | O | O | CH |
| 3-11 | H | 3-OH—Ph | H | Me | —CH₂— | O | S | CH |
| 3-12 | H | 3-OH—Ph | H | Me | —CH₂— | S | O | CH |
| 3-13 | H | 3-OH—Ph | H | Me | —(CH₂)₂— | O | O | CH |
| 3-14 | H | 3-OH—Ph | H | Me | —(CH₂)₂— | O | S | CH |
| 3-15 | H | 3-OH—Ph | H | Et | —CH₂— | O | O | CH |
| 3-16 | H | 3-OH—Ph | H | Et | —CH₂— | O | S | CH |
| 3-17 | H | 3-OH—Ph | H | tBu | —CH₂— | O | O | CH |
| 3-18 | H | 4-OH—Ph | H | H | —CH₂— | O | O | CH |
| 3-19 | H | 4-OH—Ph | H | Me | —CH₂— | O | O | CH |
| 3-20 | H | 4-OH—Ph | H | Me | —CH₂— | O | O | N |
| 3-21 | H | 4-OH—Ph | H | Me | —CH₂— | O | S | CH |
| 3-22 | H | 4-OH—Ph | H | Me | —CH₂— | O | S | N |
| 3-23 | H | 4-OH—Ph | H | Me | —CH₂— | S | O | CH |
| 3-24 | H | 4-OH—Ph | H | Me | —CH₂— | S | O | N |
| 3-25 | H | 4-OH—Ph | H | Me | —CH₂— | S | S | CH |
| 3-26 | H | 4-OH—Ph | H | Me | —CH₂— | S | S | N |
| 3-27 | H | 4-OH—Ph | H | Me | —(CH₂)₂— | O | O | CH |
| 3-28 | H | 4-OH—Ph | H | Me | —(CH₂)₂— | O | O | N |
| 3-29 | H | 4-OH—Ph | H | Me | —(CH₂)₂— | O | S | CH |
| 3-30 | H | 4-OH—Ph | H | Me | —CH(Me)— | O | O | CH |
| 3-31 | H | 4-OH—Ph | H | Me | —(CH₂)₃— | O | O | CH |
| 3-32 | H | 4-OH—Ph | H | Et | —CH₂— | O | O | CH |
| 3-33 | H | 4-OH—Ph | H | Et | —CH₂— | O | O | N |
| 3-34 | H | 4-OH—Ph | H | Et | —CH₂— | O | S | CH |
| 3-35 | H | 4-OH—Ph | H | Et | —(CH₂)₂— | O | O | CH |
| 3-36 | H | 4-OH—Ph | H | tBu | —CH₂— | O | O | CH |
| 3-37 | H | 4-OH—Ph | H | tBu | —CH₂— | O | S | CH |
| 3-38 | H | 4-OH—Ph | H | Ph | —CH₂— | O | O | CH |
| 3-39 | H | 4-OH—Ph | H | Bz | —CH₂— | O | O | CH |
| 3-40 | H | 4-OH—Ph | 5-Cl | Me | —CH₂— | O | O | CH |
| 3-41 | H | 4-OH—Ph | 5-Me | Me | —CH₂— | O | O | CH |
| 3-42 | H | 4-OH—Ph | 5-MeO | Me | —CH₂— | O | O | CH |
| 3-43 | 2-Cl | 4-OH—Ph | H | Me | —CH₂— | O | O | CH |
| 3-44 | 3-Cl | 4-OH—Ph | H | Me | —CH₂— | O | O | CH |
| 3-45 | 2-Me | 4-OH—Ph | H | Me | —CH₂— | O | O | CH |
| 3-46 | 3-Me | 4-OH—Ph | H | Me | —CH₂— | O | O | CH |
| 3-47 | 2-MeO | 4-OH—Ph | H | Me | —CH₂— | O | O | CH |
| 3-48 | 3-MeO | 4-OH—Ph | H | Me | —CH₂— | O | O | CH |
| 3-49 | H | 3-CF₃—Ph | H | Me | —CH₂— | O | O | CH |
| 3-50 | H | 4-iPrO—Ph | H | Me | —CH₂— | O | O | CH |
| 3-51 | H | 4-MeS—Ph | H | Me | —CH₂— | O | O | CH |
| 3-52 | H | 2-NH₂—Ph | H | Me | —CH₂— | O | O | CH |
| 3-53 | H | 3-NH₂—Ph | H | Me | —CH₂— | O | O | CH |
| 3-54 | H | 4-NH₂—Ph | H | Me | —CH₂— | O | O | CH |
| 3-55 | H | 4-NH₂—Ph | H | Me | —CH₂— | O | S | CH |
| 3-56 | H | 4-NHMe—Ph | H | Me | —CH₂— | O | O | CH |
| 3-57 | H | 2-N(Me)₂—Ph | H | Me | —CH₂— | O | O | CH |
| 3-58 | H | 3-N(Me)₂—Ph | H | Me | —CH₂— | O | O | CH |
| 3-59 | H | 4-N(Me)₂—Ph | H | Me | —CH₂— | O | O | CH |
| 3-60 | H | 4-N(Me)₂—Ph | H | Me | —CH₂— | O | S | CH |
| 3-61 | H | 4-N(Me)₂—Ph | H | Et | —CH₂— | O | O | CH |
| 3-62 | H | 4-NHAc—Ph | H | Me | —CH₂— | O | O | CH |
| 3-63 | H | 4-N(Me)Ac—Ph | H | Me | —CH₂— | O | O | CH |
| 3-64 | H | 4-Ph—Ph | H | Me | —CH₂— | O | O | CH |
| 3-65 | H | 4-(4-OH—Ph)Ph | H | Me | —CH₂— | O | O | CH |

TABLE 3-continued

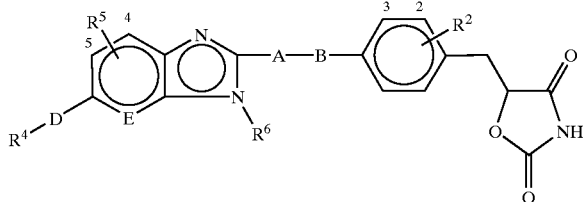

(I-3)

| Cpd. No. | $R^2$ | $R^4$ | $R^5$ | $R^6$ | —A— | B | D | E |
|---|---|---|---|---|---|---|---|---|
| 3-66 | H | 4-(4-OH-3,5-diMe—Ph)Ph | H | Me | —CH$_2$— | O | O | CH |
| 3-67 | H | 4-(4-OH-3,5-diMe—Ph)Ph | H | Me | —CH$_2$— | O | S | CH |
| 3-68 | H | 4-(4-OH-3,5-ditBu—Ph)Ph | H | Me | —CH$_2$— | O | O | CH |
| 3-69 | H | 4-(4-OH-3,5-ditBu—Ph)Ph | H | Me | —CH$_2$— | O | S | CH |
| 3-70 | H | 4-Bz—Ph | H | Me | —CH$_2$— | O | O | CH |
| 3-71 | H | 4-(4-OH—Bz)Ph | H | Me | —CH$_2$— | O | O | CH |
| 3-72 | H | 4-(4-OH-3,5-diMe—Bz)Ph | H | Me | —CH$_2$— | O | O | CH |
| 3-73 | H | 4-(4-OH-3,5-ditBu—Bz)Ph | H | Me | —CH$_2$— | O | O | CH |
| 3-74 | H | 4-PhO—Ph | H | Me | —CH$_2$— | O | O | CH |
| 3-75 | H | 4-PhS—Ph | H | Me | —CH$_2$— | O | O | CH |
| 3-76 | H | 2-Pyrd(1)-Ph | H | Me | —CH$_2$— | O | O | CH |
| 3-77 | H | 2-Pyrd(1)-Ph | H | Me | —CH$_2$— | O | O | N |
| 3-78 | H | 2-Pyrd(1)-Ph | H | Me | —CH$_2$— | O | S | CH |
| 3-79 | H | 2-Pyrd(1)-Ph | H | Et | —CH$_2$— | O | O | CH |
| 3-80 | H | 2-Pyrd(1)-Ph | H | Et | —CH$_2$— | O | S | CH |
| 3-81 | H | 3-Pyrd(1)-Ph | H | Me | —CH$_2$— | O | O | CH |
| 3-82 | H | 3-Pyrd(1)-Ph | H | Me | —CH$_2$— | O | O | N |
| 3-83 | H | 3-Pyrd(1)-Ph | H | Me | —CH$_2$— | O | S | CH |
| 3-84 | H | 3-Pyrd(1)-Ph | H | Me | —(CH$_2$)$_2$— | O | O | CH |
| 3-85 | H | 3-Pyrd(1)-Ph | H | Et | —CH$_2$— | O | O | CH |
| 3-86 | H | 4-Pyrd(1)-Ph | H | Me | —CH$_2$— | O | O | CH |
| 3-87 | H | 4-Pyrd(1)-Ph | H | Me | —CH$_2$— | O | O | N |
| 3-88 | H | 4-Pyrd(1)-Ph | H | Me | —CH$_2$— | O | S | CH |
| 3-89 | H | 4-Pyrd(1)-Ph | H | Me | —(CH$_2$)$_2$— | O | O | CH |
| 3-90 | H | 4-Pyrd(1)-Ph | H | Me | —(CH$_2$)$_3$— | O | O | CH |
| 3-91 | H | 4-Pyrd(1)-Ph | H | Et | —CH$_2$— | O | O | CH |
| 3-92 | H | 4-Pyrd(1)-Ph | H | Et | —CH$_2$— | O | S | CH |
| 3-93 | H | 4-Pyrd(1)-Ph | H | tBu | —CH$_2$— | O | O | CH |
| 3-94 | H | 2-Pip(1)-Ph | H | Me | —CH$_2$— | O | O | CH |
| 3-95 | H | 2-Pip(1)-Ph | H | Me | —CH$_2$— | O | O | N |
| 3-96 | H | 2-Pip(1)-Ph | H | Me | —CH$_2$— | O | S | CH |
| 3-97 | H | 2-Pip(1)-Ph | H | Et | —CH$_2$— | O | O | CH |
| 3-98 | H | 2-Pip(1)-Ph | H | Et | —CH$_2$— | O | S | CH |
| 3-99 | H | 3-Pip(1)-Ph | H | Me | —CH$_2$— | O | O | CH |
| 3-100 | H | 3-Pip(1)-Ph | H | Me | —CH$_2$— | O | O | N |
| 3-101 | H | 3-Pip(1)-Ph | H | Me | —CH$_2$— | O | S | CH |
| 3-102 | H | 3-Pip(1)-Ph | H | Et | —CH$_2$— | O | O | CH |
| 3-103 | H | 3-Pip(1)-Ph | H | Et | —CH$_2$— | O | S | CH |
| 3-104 | H | 3-Pip(1)-Ph | H | Et | —(CH$_2$)$_3$— | S | O | CH |
| 3-105 | H | 4-Pip(1)-Ph | H | Me | —CH$_2$— | O | O | CH |
| 3-106 | H | 4-Pip(1)-Ph | H | Me | —CH$_2$— | O | O | N |
| 3-107 | H | 4-Pip(1)-Ph | H | Me | —CH$_2$— | O | S | CH |
| 3-108 | H | 4-Pip(1)-Ph | H | Me | —(CH$_2$)$_2$— | O | O | CH |
| 3-109 | H | 4-Pip(1)-Ph | H | Me | —(CH$_2$)$_3$— | O | O | CH |
| 3-110 | H | 4-Pip(1)-Ph | H | Et | —CH$_2$— | O | O | CH |
| 3-111 | H | 4-Pip(1)-Ph | H | Et | —CH$_2$— | O | S | CH |
| 3-112 | H | 4-Pip(1)-Ph | H | tBu | —CH$_2$— | O | O | CH |
| 3-113 | H | 4-Pip(1)-Ph | 4-Cl | Me | —CH$_2$— | O | O | CH |
| 3-114 | 2-MeO | 4-Pip(1)-Ph | H | Me | —CH$_2$— | O | O | CH |
| 3-115 | H | 2-Mor(4)-Ph | H | Me | —CH$_2$— | O | O | CH |
| 3-116 | H | 2-Mor(4)-Ph | H | Me | —CH$_2$— | O | O | N |
| 3-117 | H | 2-Mor(4)-Ph | H | Me | —CH$_2$— | O | S | CH |
| 3-118 | H | 2-Mor(4)-Ph | H | Me | —(CH$_2$)$_3$— | O | O | CH |
| 3-119 | H | 2-Mor(4)-Ph | H | Et | —CH$_2$— | O | O | CH |
| 3-120 | H | 2-Mor(4)-Ph | H | Et | —CH$_2$— | O | S | CH |
| 3-121 | H | 3-Mor(4)-Ph | H | Me | —CH$_2$— | O | O | CH |
| 3-122 | H | 3-Mor(4)-Ph | H | Me | —CH$_2$— | O | O | N |
| 3-123 | H | 3-Mor(4)-Ph | H | Me | —CH$_2$— | O | S | CH |
| 3-124 | H | 3-Mor(4)-Ph | H | Me | —(CH$_2$)$_3$— | O | O | CH |

TABLE 3-continued

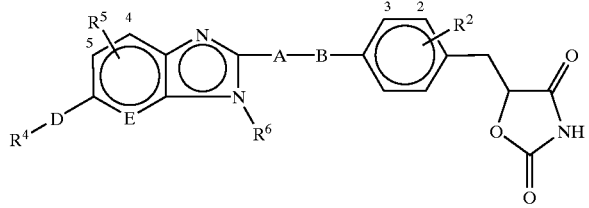
(I-3)

| Cpd. No. | R² | R⁴ | R⁵ | R⁶ | —A— | B | D | E |
|---|---|---|---|---|---|---|---|---|
| 3-125 | H | 3-Mor(4)-Ph | H | Et | —CH₂— | O | O | CH |
| 3-126 | H | 3-Mor(4)-Ph | H | Et | —CH₂— | O | S | CH |
| 3-127 | H | 4-Mor(4)-Ph | H | Me | —CH₂— | O | O | CH |
| 3-128 | H | 4-Mor(4)-Ph | H | Me | —CH₂— | O | O | N |
| 3-129 | H | 4-Mor(4)-Ph | H | Me | —CH₂— | O | S | CH |
| 3-130 | H | 4-Mor(4)-Ph | H | Me | —(CH₂)₂— | O | O | CH |
| 3-131 | H | 4-Mor(4)-Ph | H | Et | —CH₂— | O | O | CH |
| 3-132 | H | 4-Mor(4)-Ph | H | Et | —CH₂— | O | S | CH |
| 3-133 | H | 4-Mor(4)-Ph | H | tBu | —CH₂— | O | O | CH |
| 3-134 | H | 2-TioMor(4)-Ph | H | Me | —CH₂— | O | O | CH |
| 3-135 | H | 3-TioMor(4)-Ph | H | Me | —CH₂— | O | O | CH |
| 3-136 | H | 4-TioMor(4)-Ph | H | Me | —CH₂— | O | O | CH |
| 3-137 | H | 4-TioMor(4)-Ph | H | Me | —CH₂— | O | S | CH |
| 3-138 | H | 2-Pipra(1)-Ph | H | Me | —CH₂— | O | O | CH |
| 3-139 | H | 3-Pipra(1)-Ph | H | Me | —CH₂— | O | O | CH |
| 3-140 | H | 4-Pipra(1)-Ph | H | Me | —CH₂— | O | O | CH |
| 3-141 | H | 4-Pipra(1)-Ph | H | Me | —CH₂— | O | O | N |
| 3-142 | H | 4-Pipra(1)-Ph | H | Me | —CH₂— | O | S | CH |
| 3-143 | H | 4-Pipra(1)-Ph | H | Me | —(CH₂)₃— | O | O | CH |
| 3-144 | H | 4-Pipra(1)-Ph | H | Et | —CH₂— | O | O | CH |
| 3-145 | H | 4-Pipra(1)-Ph | H | Et | —CH₂— | O | S | CH |
| 3-146 | H | 4-NO₂—Ph | H | Me | —CH₂— | O | O | CH |
| 3-147 | H | 2-Cl-4-OH—Ph | H | Me | —CH₂— | O | O | CH |
| 3-148 | H | 3-Cl-4-OH—Ph | H | Me | —CH₂— | O | O | CH |
| 3-149 | H | 3-Cl-4-OH—Ph | H | Me | —CH₂— | O | S | CH |
| 3-150 | H | 2-F-4-OH-3,5-diMe—Ph | H | Me | —CH₂— | O | O | CH |
| 3-151 | H | 4-F-3-OH-2,5-diEt—Ph | H | Me | —CH₂— | O | O | CH |
| 3-152 | H | 2-Cl-4-OH-3,5-diMe—Ph | H | H | —CH₂— | O | O | CH |
| 3-153 | H | 2-Cl-4-OH-3,5-diMe—Ph | H | Me | —CH₂— | O | O | CH |
| 3-154 | H | 2-Cl-4-OH-3,5-diMe—Ph | H | Me | —CH₂— | O | O | N |
| 3-155 | H | 2-Cl-4-OH-3,5-diMe—Ph | H | Me | —CH₂— | O | S | CH |
| 3-156 | H | 2-Cl-4-OH-3,5-diMe—Ph | H | Me | —CH₂— | O | S | N |
| 3-157 | H | 2-Cl-4-OH-3,5-diMe—Ph | H | Me | —CH₂— | S | O | CH |
| 3-158 | H | 2-Cl-4-OH-3,5-diMe—Ph | H | Me | —CH₂— | S | S | CH |
| 3-159 | H | 2-Cl-4-OH-3,5-diMe—Ph | H | Me | —(CH₂)₂— | O | O | CH |
| 3-160 | H | 2-Cl-4-OH-3,5-diMe—Ph | H | Me | —(CH₂)₂— | O | O | N |
| 3-161 | H | 2-Cl-4-OH-3,5-diMe—Ph | H | Me | —(CH₂)₂— | O | S | CH |
| 3-162 | H | 2-Cl-4-OH-3,5-diMe—Ph | H | Me | —CH(Me)— | O | O | CH |
| 3-163 | H | 2-Cl-4-OH-3,5-diMe—Ph | H | Me | —(CH₂)₃— | O | O | CH |
| 3-164 | H | 2-Cl-4-OH-3,5-diMe—Ph | H | Me | —(CH₂)₄— | O | O | CH |
| 3-165 | H | 2-Cl-4-OH-3,5-diMe—Ph | H | Et | —CH₂— | O | O | CH |
| 3-166 | H | 2-Cl-4-OH-3,5-diMe—Ph | H | Et | —CH₂— | O | O | N |
| 3-167 | H | 2-Cl-4-OH-3,5-diMe—Ph | H | Et | —CH₂— | O | S | CH |
| 3-168 | H | 2-Cl-4-OH-3,5-diMe—Ph | H | Et | —(CH₂)₂— | O | O | CH |
| 3-169 | H | 2-Cl-4-OH-3,5-diMe—Ph | H | tBu | —CH₂— | O | O | CH |

TABLE 3-continued

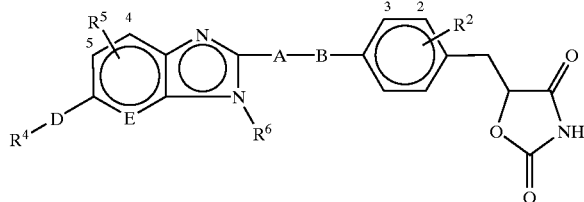

(I-3)

| Cpd. No. | $R^2$ | $R^4$ | $R^5$ | $R^6$ | —A— | B | D | E |
|---|---|---|---|---|---|---|---|---|
| 3-170 | H | 2-Cl-4-OH-3,5-diMe—Ph | H | tBu | —CH$_2$— | O | S | CH |
| 3-171 | H | 2-Cl-4-OH-3,5-diMe—Ph | H | Ph | —CH$_2$— | O | O | CH |
| 3-172 | H | 2-Cl-4-OH-3,5-diMe—Ph | H | Bz | —CH$_2$— | O | O | CH |
| 3-173 | H | 2-Cl-4-OH-3,5-diMe—Ph | 5-Cl | Me | —CH$_2$— | O | O | CH |
| 3-174 | H | 2-Cl-4-OH-3,5-diMe—Ph | 5-Me | Me | —CH$_2$— | O | O | CH |
| 3-175 | H | 2-Cl-4-OH-3,5-diMe—Ph | 5-MeO | Me | —CH$_2$— | O | O | CH |
| 3-176 | 2-Cl | 2-Cl-4-OH-3,5-diMe—Ph | H | Me | —CH$_2$— | O | O | CH |
| 3-177 | 3-Cl | 2-Cl-4-OH-3,5-diMe—Ph | H | Me | —CH$_2$— | O | O | CH |
| 3-178 | 2-Me | 2-Cl-4-OH-3,5-diMe—Ph | H | Me | —CH$_2$— | O | O | CH |
| 3-179 | 3-Me | 2-Cl-4-OH-3,5-diMe—Ph | H | Me | —CH$_2$— | O | O | CH |
| 3-180 | 2-MeO | 2-Cl-4-OH-3,5-diMe—Ph | H | Me | —CH$_2$— | O | O | CH |
| 3-181 | H | 2-Cl-4-OH-3,5-diMe—Ph | H | Me | —CH$_2$— | O | O | CH |
| 3-182 | H | 2-Cl-4-OH-3,5-ditBu—Ph | H | Me | —CH$_2$— | O | O | CH |
| 3-183 | H | 3-Cl-5-OH-2,6-diMe—Ph | H | Me | —CH$_2$— | O | O | CH |
| 3-184 | H | 3-Cl-5-OH-2,6-diMe—Ph | H | Me | —CH$_2$— | O | S | CH |
| 3-185 | H | 4-Cl-3-OH-2,5-diMe—Ph | H | Me | —CH$_2$— | O | O | CH |
| 3-186 | H | 4-Cl-3-OH-2,5-diMe—Ph | H | Me | —CH$_2$— | O | S | CH |
| 3-187 | H | 3-Cl-4-NH$_2$—Ph | H | Me | —CH$_2$— | O | O | CH |
| 3-188 | H | 3,5-diCl-4-NH$_2$—Ph | H | Me | —CH$_2$— | O | O | CH |
| 3-189 | H | 3,5-diCl-4-NH$_2$—Ph | H | Me | —CH$_2$— | O | S | CH |
| 3-190 | H | 3,5-diF-4-NH$_2$—Ph | H | Me | —CH$_2$— | O | O | CH |
| 3-191 | H | 4-NHMe-3-Cl—Ph | H | Me | —CH$_2$— | O | O | CH |
| 3-192 | H | 3-Cl-4-Pyrd(1)-Ph | H | Me | —CH$_2$— | O | O | CH |
| 3-193 | H | 3-OH-4-Pyrd(1)-Ph | H | Me | —CH$_2$— | O | O | CH |
| 3-194 | H | 3-Cl-6-Me-4-Pyrd(1)-Ph | H | Me | —CH$_2$— | O | O | CH |
| 3-195 | H | 2-Me-4-Pip(1)-Ph | H | Me | —CH$_2$— | O | O | CH |
| 3-196 | H | 2-Me-4-Mor(4)-Ph | H | Me | —CH$_2$— | O | O | CH |
| 3-197 | H | 2-OH-3-Me—Ph | H | Me | —CH$_2$— | O | O | CH |
| 3-198 | H | 2-OH-4-Me—Ph | H | Me | —CH$_2$— | O | O | CH |
| 3-199 | H | 2-OH-3,4-diMe—Ph | H | Me | —CH$_2$— | O | O | CH |
| 3-200 | H | 2-OH-3,4-diMe—Ph | H | Me | —CH$_2$— | O | S | CH |
| 3-201 | H | 3-OH-2-Me—Ph | H | Me | —CH$_2$— | O | O | CH |
| 3-202 | H | 3-OH-4-Me—Ph | H | Me | —CH$_2$— | O | O | CH |
| 3-203 | H | 3-OH-5-Me—Ph | H | Me | —CH$_2$— | O | O | CH |
| 3-204 | H | 3-OH-6-Me—Ph | H | Me | —CH$_2$— | O | O | CH |
| 3-205 | H | 3-OH-2,4-diMe—Ph | H | Me | —CH$_2$— | O | O | CH |

TABLE 3-continued

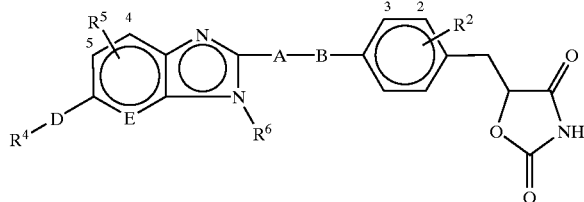

(I-3)

| Cpd. No. | $R^2$ | $R^4$ | $R^5$ | $R^6$ | —A— | B | D | E |
|---|---|---|---|---|---|---|---|---|
| 3-206 | H | 3-OH-2,4-diMe—Ph | H | Me | —CH$_2$— | O | S | CH |
| 3-207 | H | 4-OH-2-Me—Ph | H | Me | —CH$_2$— | O | O | CH |
| 3-208 | H | 4-OH-2-Me—Ph | H | Me | —CH$_2$— | O | S | CH |
| 3-209 | H | 4-OH-3-Me—Ph | H | Me | —CH$_2$— | O | O | CH |
| 3-210 | H | 4-OH-3-Me—Ph | H | Me | —CH$_2$— | O | O | N |
| 3-211 | H | 4-OH-3-Me—Ph | H | Me | —CH$_2$— | O | S | CH |
| 3-212 | H | 4-OH-3-Me—Ph | H | Et | —CH$_2$— | O | O | CH |
| 3-213 | H | 4-OH-3-Me—Ph | H | Et | —CH$_2$— | O | S | CH |
| 3-214 | H | 4-OH-3-Me—Ph | 5-Cl | Me | —CH$_2$— | O | O | CH |
| 3-215 | H | 4-OH-2-Et—Ph | H | Me | —CH$_2$— | O | O | CH |
| 3-216 | H | 4-OH-3-Et—Ph | H | Me | —CH$_2$— | O | O | CH |
| 3-217 | H | 4-OH-2-tBu—Ph | H | Me | —CH$_2$— | O | O | CH |
| 3-218 | H | 4-OH-3-tBu—Ph | H | Me | —CH$_2$— | O | O | CH |
| 3-219 | H | 4-OH-3-tBu—Ph | H | Me | —CH$_2$— | O | S | CH |
| 3-220 | H | 4-OH-2,3-diMe—Ph | H | Me | —CH$_2$— | O | O | CH |
| 3-221 | H | 4-OH-2,3-diMe—Ph | H | Me | —CH$_2$— | O | O | N |
| 3-222 | H | 4-OH-2,3-diMe—Ph | H | Me | —CH$_2$— | O | S | CH |
| 3-223 | H | 4-OH-2,3-diMe—Ph | H | Me | —(CH$_2$)$_3$— | S | O | CH |
| 3-224 | H | 4-OH-2,3-diMe—Ph | H | Et | —CH$_2$— | O | O | CH |
| 3-225 | H | 4-OH-2,3-diMe—Ph | H | Et | —CH$_2$— | O | S | CH |
| 3-226 | H | 4-OH-2,5-diMe—Ph | H | Me | —CH$_2$— | O | O | CH |
| 3-227 | H | 4-OH-2,5-diMe—Ph | H | Me | —CH$_2$— | O | S | CH |
| 3-228 | H | 4-OH-3,5-diMe—Ph | H | H | —CH$_2$— | O | O | CH |
| 3-229 | H | 4-OH-3,5-diMe—Ph | H | Me | —CH$_2$— | O | O | CH |
| 3-230 | H | 4-OH-3,5-diMe—Ph | H | Me | —CH$_2$— | O | O | N |
| 3-231 | H | 4-OH-3,5-diMe—Ph | H | Me | —CH$_2$— | O | S | CH |
| 3-232 | H | 4-OH-3,5-diMe—Ph | H | Me | —CH$_2$— | O | S | N |
| 3-233 | H | 4-OH-3,5-diMe—Ph | H | Me | —CH$_2$— | S | O | CH |
| 3-234 | H | 4-OH-3,5-diMe—Ph | H | Me | —(CH$_2$)$_2$— | O | O | CH |
| 3-235 | H | 4-OH-3,5-diMe—Ph | H | Me | —(CH$_2$)$_2$— | O | O | N |
| 3-236 | H | 4-OH-3,5-diMe—Ph | H | Me | —(CH$_2$)$_2$— | O | S | CH |
| 3-237 | H | 4-OH-3,5-diMe—Ph | H | Me | —CH(Me)— | O | O | CH |
| 3-238 | H | 4-OH-3,5-diMe—Ph | H | Me | —(CH$_2$)$_3$— | O | O | CH |
| 3-239 | H | 4-OH-3,5-diMe—Ph | H | Et | —CH$_2$— | O | O | CH |
| 3-240 | H | 4-OH-3,5-diMe—Ph | H | Et | —CH$_2$— | O | O | N |
| 3-241 | H | 4-OH-3,5-diMe—Ph | H | Et | —CH$_2$— | O | S | CH |
| 3-242 | H | 4-OH-3,5-diMe—Ph | H | Et | —(CH$_2$)$_2$— | O | O | CH |
| 3-243 | H | 4-OH-3,5-diMe—Ph | H | sBu | —CH$_2$— | O | O | CH |
| 3-244 | H | 4-OH-3,5-diMe—Ph | H | tBu | —CH$_2$— | O | O | CH |

TABLE 3-continued

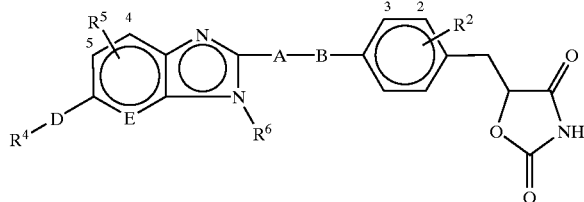

(I-3)

| Cpd. No. | $R^2$ | $R^4$ | $R^5$ | $R^6$ | —A— | B | D | E |
|---|---|---|---|---|---|---|---|---|
| 3-245 | H | 4-OH-3,5-diMe—Ph | H | tBu | —CH$_2$— | O | S | CH |
| 3-246 | H | 4-OH-3,5-diMe—Ph | H | Ph | —CH$_2$— | O | O | CH |
| 3-247 | H | 4-OH-3,5-diMe—Ph | H | Bz | —CH$_2$— | O | O | CH |
| 3-248 | H | 4-OH-3,5-diMe—Ph | 5-Cl | Me | —CH$_2$— | O | O | CH |
| 3-249 | H | 4-OH-3,5-diMe—Ph | 5-Me | Me | —CH$_2$— | O | O | CH |
| 3-250 | H | 4-OH-3,5-diMe—Ph | 5-MeO | Me | —CH$_2$— | O | O | CH |
| 3-251 | 2-Cl | 4-OH-3,5-diMe—Ph | H | Me | —CH$_2$— | O | O | CH |
| 3-252 | 3-Cl | 4-OH-3,5-diMe—Ph | H | Me | —CH$_2$— | O | O | CH |
| 3-253 | 2-Me | 4-OH-3,5-diMe—Ph | H | Me | —CH$_2$— | O | O | CH |
| 3-254 | 3-Me | 4-OH-3,5-diMe—Ph | H | Me | —CH$_2$— | O | O | CH |
| 3-255 | 2-MeO | 4-OH-3,5-diMe—Ph | H | Me | —CH$_2$— | O | O | CH |
| 3-256 | 3-MeO | 4-OH-3,5-diMe—Ph | H | Me | —CH$_2$— | O | O | CH |
| 3-257 | H | 3,5-diEt-4-OH—Ph | H | Me | —CH$_2$— | O | O | CH |
| 3-258 | H | 3,5-diEt-4-OH—Ph | H | Me | —CH$_2$— | O | S | CH |
| 3-259 | H | 3-tBu-4-OH-5-Me—Ph | H | Me | —CH$_2$— | O | O | CH |
| 3-260 | H | 3-tBu-4-OH-5-Me—Ph | H | Me | —CH$_2$— | O | S | CH |
| 3-261 | H | 4-OH-3,5-diPr—Ph | H | Me | —CH$_2$— | O | O | CH |
| 3-262 | H | 4-OH-3,5-diiPr—Ph | H | Me | —CH$_2$— | O | O | CH |
| 3-263 | H | 3,5-ditBu-4-OH—Ph | H | H | —CH$_2$— | O | O | CH |
| 3-264 | H | 3,5-ditBu-4-OH—Ph | H | Me | —CH$_2$— | O | O | CH |
| 3-265 | H | 3,5-ditBu-4-OH—Ph | H | Me | —CH$_2$— | O | O | N |
| 3-266 | H | 3,5-ditBu-4-OH—Ph | H | Me | —CH$_2$— | O | S | CH |
| 3-267 | H | 3,5-ditBu-4-OH—Ph | H | Me | —CH$_2$— | O | S | N |
| 3-268 | H | 3,5-ditBu-4-OH—Ph | H | Me | —CH$_2$— | S | O | CH |
| 3-269 | H | 3,5-ditBu-4-OH—Ph | H | Me | —CH$_2$— | S | S | CH |
| 3-270 | H | 3,5-ditBu-4-OH—Ph | H | Me | —(CH$_2$)$_2$— | O | O | CH |
| 3-271 | H | 3,5-ditBu-4-OH—Ph | H | Me | —(CH$_2$)$_2$— | O | O | N |
| 3-272 | H | 3,5-ditBu-4-OH—Ph | H | Me | —(CH$_2$)$_2$— | O | S | CH |
| 3-273 | H | 3,5-ditBu-4-OH—Ph | H | Me | —CH(Me)— | O | O | CH |
| 3-274 | H | 3,5-ditBu-4-OH—Ph | H | Me | —(CH$_2$)$_3$— | O | O | CH |
| 3-275 | H | 3,5-ditBu-4-OH—Ph | H | Me | —(CH$_2$)$_3$— | O | S | CH |
| 3-276 | H | 3,5-ditBu-4-OH—Ph | H | Et | —CH$_2$— | O | O | CH |

TABLE 3-continued

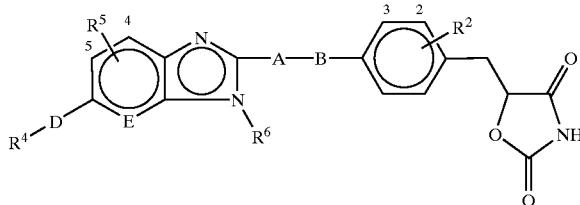

(I-3)

| Cpd. No. | R² | R⁴ | R⁵ | R⁶ | —A— | B | D | E |
|---|---|---|---|---|---|---|---|---|
| 3-277 | H | 3,5-ditBu-4-OH—Ph | H | Et | —CH₂— | O | O | N |
| 3-278 | H | 3,5-ditBu-4-OH—Ph | H | Et | —CH₂— | O | S | CH |
| 3-279 | H | 3,5-ditBu-4-OH—Ph | H | Et | —(CH₂)₂— | O | O | CH |
| 3-280 | H | 3,5-ditBu-4-OH—Ph | H | tBu | —CH₂— | O | O | CH |
| 3-281 | H | 3,5-ditBu-4-OH—Ph | H | tBu | —CH₂— | O | S | CH |
| 3-282 | H | 3,5-ditBu-4-OH—Ph | H | Ph | —CH₂— | O | O | CH |
| 3-283 | H | 3,5-ditBu-4-OH—Ph | H | Bz | —CH₂— | O | O | CH |
| 3-284 | H | 3,5-ditBu-4-OH—Ph | 5-Cl | Me | —CH₂— | O | S | CH |
| 3-285 | H | 3,5-ditBu-4-OH—Ph | 5-Cl | Me | —CH₂— | O | O | CH |
| 3-286 | H | 3,5-ditBu-4-OH—Ph | 5-Me | Me | —CH₂— | O | O | CH |
| 3-287 | H | 3,5-ditBu-4-OH—Ph | 5-MeO | Me | —CH₂— | O | O | CH |
| 3-288 | 2-Cl | 3,5-ditBu-4-OH—Ph | H | Me | —CH₂— | O | O | CH |
| 3-289 | 3-Cl | 3,5-ditBu-4-OH—Ph | H | Me | —CH₂— | O | O | CH |
| 3-290 | 2-Me | 3,5-ditBu-4-OH—Ph | H | Me | —CH₂— | O | O | CH |
| 3-291 | 3-Me | 3,5-ditBu-4-OH—Ph | H | Me | —CH₂— | O | O | CH |
| 3-292 | 2-MeO | 3,5-ditBu-4-OH—Ph | H | Me | —CH₂— | O | O | CH |
| 3-293 | 3-MeO | 3,5-ditBu-4-OH—Ph | H | Me | —CH₂— | O | O | CH |
| 3-294 | H | 4-OH-2,3,5-triMe—Ph | H | H | —CH₂— | O | O | CH |
| 3-295 | H | 4-OH-2,3,5-triMe—Ph | H | H | —CH₂— | O | S | CH |
| 3-296 | H | 4-OH-2,3,5-triMe—Ph | H | Me | —CH₂— | O | O | CH |
| 3-297 | H | 4-OH-2,3,5-triMe—Ph | H | Me | —CH₂— | O | O | N |
| 3-298 | H | 4-OH-2,3,5-triMe—Ph | H | Me | —CH₂— | O | S | CH |
| 3-299 | H | 4-OH-2,3,5-triMe—Ph | H | Me | —CH₂— | O | S | N |
| 3-300 | H | 4-OH-2,3,5-triMe—Ph | H | Me | —CH₂— | S | O | CH |
| 3-301 | H | 4-OH-2,3,5-triMe—Ph | H | Me | —(CH₂)₂— | O | O | CH |
| 3-302 | H | 4-OH-2,3,5-triMe—Ph | H | Me | —(CH₂)₂— | O | O | N |
| 3-303 | H | 4-OH-2,3,5-triMe—Ph | H | Me | —(CH₂)₂— | O | S | CH |
| 3-304 | H | 4-OH-2,3,5-triMe—Ph | H | Me | —CH(Me)— | O | O | CH |
| 3-305 | H | 4-OH-2,3,5-triMe—Ph | H | Me | —(CH₂)₃— | O | O | CH |
| 3-306 | H | 4-OH-2,3,5-triMe—Ph | H | Et | —CH₂— | O | O | CH |
| 3-307 | H | 4-OH-2,3,5-triMe—Ph | H | Et | —CH₂— | O | O | N |
| 3-308 | H | 4-OH-2,3,5-triMe—Ph | H | Et | —CH₂— | O | S | CH |

TABLE 3-continued

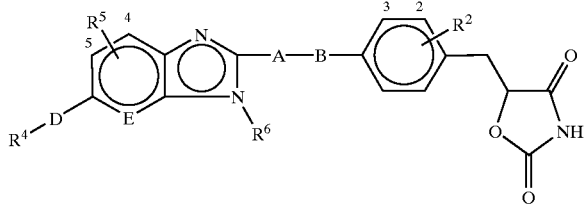

(I-3)

| Cpd. No. | R² | R⁴ | R⁵ | R⁶ | —A— | B | D | E |
|---|---|---|---|---|---|---|---|---|
| 3-309 | H | 4-OH-2,3,5-triMe—Ph | H | Et | —CH₂— | O | S | N |
| 3-310 | H | 4-OH-2,3,5-triMe—Ph | H | Et | —(CH₂)₂— | O | O | CH |
| 3-311 | H | 4-OH-2,3,5-triMe—Ph | H | iPr | —CH₂— | O | O | CH |
| 3-312 | H | 4-OH-2,3,5-triMe—Ph | H | tBu | —CH₂— | O | O | CH |
| 3-313 | H | 4-OH-2,3,5-triMe—Ph | H | tBu | —CH₂— | O | S | CH |
| 3-314 | H | 4-OH-2,3,5-triMe—Ph | H | Ph | —CH₂— | O | O | CH |
| 3-315 | H | 4-OH-2,3,5-triMe—Ph | H | Bz | —CH₂— | O | O | CH |
| 3-316 | H | 4-OH-2,3,5-triMe—Ph | 5-Cl | Me | —CH₂— | O | O | CH |
| 3-317 | H | 4-OH-2,3,5-triMe—Ph | 5-Me | Me | —CH₂— | O | O | CH |
| 3-318 | H | 4-OH-2,3,5-triMe—Ph | 5-MeO | Me | —CH₂— | O | O | CH |
| 3-319 | 2-Cl | 4-OH-2,3,5-triMe—Ph | H | Me | —CH₂— | O | O | CH |
| 3-320 | 3-Cl | 4-OH-2,3,5-triMe—Ph | H | Me | —CH₂— | O | O | CH |
| 3-321 | 2-Me | 4-OH-2,3,5-triMe—Ph | H | Me | —CH₂— | O | O | CH |
| 3-322 | 3-Me | 4-OH-2,3,5-triMe—Ph | H | Me | —CH₂— | O | O | CH |
| 3-323 | 2-MeO | 4-OH-2,3,5-triMe—Ph | H | Me | —CH₂— | O | O | CH |
| 3-324 | 2-MeO | 4-OH-2,3,5-triMe—Ph | H | Me | —CH₂— | O | O | CH |
| 3-325 | H | 4-OH-2,3,6-triMe—Ph | H | Me | —CH₂— | O | O | CH |
| 3-326 | H | 4-OH-2,3,6-triMe—Ph | H | Me | —CH₂— | O | S | CH |
| 3-327 | H | 4-OH-2,3,5,6-tetraMe—Ph | H | Me | —CH₂— | O | O | CH |
| 3-328 | H | 4-OH-2,3,5,6-tetraMe—Ph | H | Me | —CH₂— | O | S | CH |
| 3-329 | H | 4-OH-3,5-diCF₃—Ph | H | Me | —CH₂— | O | O | CH |
| 3-330 | H | 4-OH-3,5-diMeO—Ph | H | Me | —CH₂— | O | O | CH |
| 3-331 | H | 4-OH-3,5-ditBuO—Ph | H | Me | —CH₂— | O | O | CH |
| 3-332 | H | 3-NH₂-4-Me—Ph | H | Me | —CH₂— | O | O | CH |
| 3-333 | H | 3-NH₂-4-Me—Ph | H | Me | —CH₂— | O | S | CH |
| 3-334 | H | 4-NH₂-2,3-diMe—Ph | H | Me | —CH₂— | O | O | CH |
| 3-335 | H | 4-NH₂-2,3-diMe—Ph | H | Me | —CH₂— | O | S | CH |
| 3-336 | H | 4-NH₂-2,6-diMe—Ph | H | Me | —CH₂— | O | O | CH |
| 3-337 | H | 4-NH₂-2,6-diMe—Ph | H | Me | —CH₂— | O | S | CH |
| 3-338 | H | 4-NH₂-3,5-diMe—Ph | H | H | —CH₂— | O | O | CH |
| 3-339 | H | 4-NH₂-3,5-diMe—Ph | H | Me | —CH₂— | O | O | CH |
| 3-340 | H | 4-NH₂-3,5-diMe—Ph | H | Me | —CH₂— | O | O | N |
| 3-341 | H | 4-NH₂-3,5-diMe—Ph | H | Me | —CH₂— | O | S | CH |

TABLE 3-continued

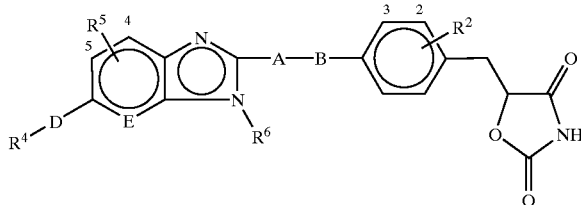

(I-3)

| Cpd. No. | R² | R⁴ | R⁵ | R⁶ | —A— | B | D | E |
|---|---|---|---|---|---|---|---|---|
| 3-342 | H | 4-NH₂-3,5-diMe—Ph | H | Me | —CH₂— | O | S | N |
| 3-343 | H | 4-NH₂-3,5-diMe—Ph | H | Me | —CH₂— | S | O | CH |
| 3-344 | H | 4-NH₂-3,5-diMe—Ph | H | Me | —(CH₂)₂— | O | O | CH |
| 3-345 | H | 4-NH₂-3,5-diMe—Ph | H | Me | —(CH₂)₂— | O | O | N |
| 3-346 | H | 4-NH₂-3,5-diMe—Ph | H | Me | —(CH₂)₂— | O | S | CH |
| 3-347 | H | 4-NH₂-3,5-diMe—Ph | H | Me | —CH(Me)— | O | O | CH |
| 3-348 | H | 4-NH₂-3,5-diMe—Ph | H | Me | —(CH₂)₃— | O | O | CH |
| 3-349 | H | 4-NH₂-3,5-diMe—Ph | H | Et | —CH₂— | O | O | CH |
| 3-350 | H | 4-NH₂-3,5-diMe—Ph | H | Et | —CH₂— | O | O | N |
| 3-351 | H | 4-NH₂-3,5-diMe—Ph | H | Et | —CH₂— | O | S | CH |
| 3-352 | H | 4-NH₂-3,5-diMe—Ph | H | Et | —(CH₂)₂— | O | O | CH |
| 3-353 | H | 4-NH₂-3,5-diMe—Ph | H | tBu | —CH₂— | O | O | CH |
| 3-354 | H | 4-NH₂-3,5-diMe—Ph | H | tBu | —CH₂— | O | S | CH |
| 3-355 | H | 4-NH₂-3,5-diMe—Ph | H | Ph | —CH₂— | O | O | CH |
| 3-356 | H | 4-NH₂-3,5-diMe—Ph | H | Bz | —CH₂— | O | O | CH |
| 3-357 | H | 4-NH₂-3,5-diMe—Ph | 5-Cl | Me | —CH₂— | O | O | CH |
| 3-358 | H | 4-NH₂-3,5-diMe—Ph | 5-Me | Me | —CH₂— | O | O | CH |
| 3-359 | H | 4-NH₂-3,5-diMe—Ph | 5-MeO | Me | —CH₂— | O | O | CH |
| 3-360 | 2-Cl | 4-NH₂-3,5-diMe—Ph | H | Me | —CH₂— | O | O | CH |
| 3-361 | 3-Cl | 4-NH₂-3,5-diMe—Ph | H | Me | —CH₂— | O | O | CH |
| 3-362 | 2-Me | 4-NH₂-3,5-diMe—Ph | H | Me | —CH₂— | O | O | CH |
| 3-363 | 3-Me | 4-NH₂-3,5-diMe—Ph | H | Me | —CH₂— | O | O | CH |
| 3-364 | 2-MeO | 4-NH₂-3,5-diMe—Ph | H | Me | —CH₂— | O | O | CH |
| 3-365 | 3-MeO | 4-NH₂-3,5-diMe—Ph | H | Me | —CH₂— | O | O | CH |
| 3-366 | H | 4-NH₂-3,5-diEt—Ph | H | Me | —CH₂— | O | O | CH |
| 3-367 | H | 4-NH₂-3,5-diEt—Ph | H | Me | —CH₂— | O | S | CH |
| 3-368 | H | 4-NH₂-3,5-ditBu—Ph | H | Me | —CH₂— | O | O | CH |
| 3-369 | H | 4-NHMe-3,5-diMe—Ph | H | Me | —CH₂— | O | O | CH |
| 3-370 | H | 4-NHMe-3,5-diMe—Ph | H | Me | —CH₂— | O | S | CH |
| 3-371 | H | 4-NHEt-3,5-diMe—Ph | H | Me | —CH₂— | O | O | CH |
| 3-372 | H | 4-NHAc-3,5-diMe—Ph | H | Me | —CH₂— | O | O | CH |
| 3-373 | H | 4-NO₂-2,6-diMe—Ph | H | Me | —CH₂— | O | O | CH |

TABLE 3-continued

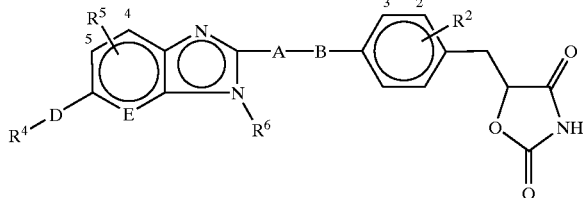

(I-3)

| Cpd. No. | $R^2$ | $R^4$ | $R^5$ | $R^6$ | —A— | B | D | E |
|---|---|---|---|---|---|---|---|---|
| 3-374 | H | 4-NO$_2$-3,5-diMe—Ph | H | Me | —CH$_2$— | O | O | CH |
| 3-375 | H | 4-NO$_2$-3,5-diMe—Ph | H | Me | —CH$_2$— | O | S | CH |
| 3-376 | H | 4-NO$_2$-3,5-ditBu—Ph | H | Me | —CH$_2$— | O | O | CH |
| 3-377 | H | Pyr(2) | H | H | —CH$_2$— | O | O | CH |
| 3-378 | H | Pyr(2) | H | Me | —CH$_2$— | O | O | CH |
| 3-379 | H | Pyr(2) | H | Me | —CH$_2$— | O | O | N |
| 3-380 | H | Pyr(2) | H | Me | —CH$_2$— | O | S | CH |
| 3-381 | H | Pyr(2) | H | Me | —CH$_2$— | O | S | N |
| 3-382 | H | Pyr(2) | H | Me | —CH$_2$— | S | O | CH |
| 3-383 | H | Pyr(2) | H | Me | —(CH$_2$)$_2$— | O | O | CH |
| 3-384 | H | Pyr(2) | H | Me | —(CH$_2$)$_2$— | O | O | N |
| 3-385 | H | Pyr(2) | H | Me | —(CH$_2$)$_2$— | O | S | CH |
| 3-386 | H | Pyr(2) | H | Me | —CH(Me)— | O | O | CH |
| 3-387 | H | Pyr(2) | H | Me | —(CH$_2$)$_3$— | O | O | CH |
| 3-388 | H | Pyr(2) | H | Et | —CH$_2$— | O | O | CH |
| 3-389 | H | Pyr(2) | H | Et | —CH$_2$— | O | O | N |
| 3-390 | H | Pyr(2) | H | Et | —CH$_2$— | O | S | CH |
| 3-391 | H | Pyr(2) | H | Et | —(CH$_2$)$_2$— | O | O | CH |
| 3-392 | H | Pyr(2) | H | tBu | —CH$_2$— | O | O | CH |
| 3-393 | H | Pyr(2) | H | tBu | —CH$_2$— | O | S | CH |
| 3-394 | H | Pyr(2) | H | Ph | —CH$_2$— | O | O | CH |
| 3-395 | H | Pyr(2) | H | Bz | —CH$_2$— | O | O | CH |
| 3-396 | H | Pyr(2) | 4-Cl | Me | —CH$_2$— | O | O | CH |
| 3-397 | H | Pyr(2) | 5-Cl | Me | —CH$_2$— | O | O | CH |
| 3-398 | H | Pyr(2) | 5-Me | Me | —CH$_2$— | O | O | CH |
| 3-399 | H | Pyr(2) | 5-MeO | Me | —CH$_2$— | O | O | CH |
| 3-400 | 2-Cl | Pyr(2) | H | Me | —CH$_2$— | O | O | CH |
| 3-401 | 3-Cl | Pyr(2) | H | Me | —CH$_2$— | O | O | CH |
| 3-402 | 2-Me | Pyr(2) | H | Me | —CH$_2$— | O | O | CH |
| 3-403 | 3-Me | Pyr(2) | H | Me | —CH$_2$— | O | O | CH |
| 3-404 | 2-MeO | Pyr(2) | H | Me | —CH$_2$— | O | O | CH |
| 3-405 | 3-MeO | Pyr(2) | H | Me | —CH$_2$— | O | O | CH |
| 3-406 | H | 5-F—Pyr(2) | H | Me | —CH$_2$— | O | O | CH |
| 3-407 | H | 6-F—Pyr(2) | H | Me | —CH$_2$— | O | O | CH |
| 3-408 | H | 5-Cl—Pyr(2) | H | Me | —CH$_2$— | O | O | CH |
| 3-409 | H | 5-Cl—Pyr(2) | H | Me | —CH$_2$— | O | S | CH |
| 3-410 | H | 6-Cl—Pyr(2) | H | Me | —CH$_2$— | O | O | CH |
| 3-411 | H | 6-Cl—Pyr(2) | H | Me | —CH$_2$— | O | S | CH |
| 3-412 | H | 6-Me—Pyr(2) | H | Me | —CH$_2$— | O | O | CH |
| 3-413 | H | 6-MeO—Pyr(2) | H | Me | —CH$_2$— | O | O | CH |
| 3-414 | H | 6-MeO—Pyr(2) | H | Me | —CH$_2$— | O | S | CH |
| 3-415 | H | 6-EtO—Pyr(2) | H | Me | —CH$_2$— | O | O | CH |
| 3-416 | H | 3-NH$_2$—Pyr(2) | H | Me | —CH$_2$— | O | O | CH |
| 3-417 | H | 3-NH$_2$—Pyr(2) | H | Me | —CH$_2$— | O | S | CH |
| 3-418 | H | 5-NH$_2$—Pyr(2) | H | Me | —CH$_2$— | O | O | CH |
| 3-419 | H | 5-NH$_2$—Pyr(2) | H | Me | —CH$_2$— | O | S | CH |
| 3-420 | H | 3-NHMe—Pyr(2) | H | Me | —CH$_2$— | O | O | CH |
| 3-421 | H | 5-NHMe—Pyr(2) | H | Me | —CH$_2$— | O | O | CH |
| 3-422 | H | 3-NO$_2$—Pyr(2) | H | Me | —CH$_2$— | O | O | CH |
| 3-423 | H | 3-NO$_2$—Pyr(2) | H | Me | —CH$_2$— | O | S | CH |
| 3-424 | H | 5-NO$_2$—Pyr(2) | H | Me | —CH$_2$— | O | O | CH |
| 3-425 | H | 5-NO$_2$—Pyr(2) | H | Me | —CH$_2$— | O | S | CH |
| 3-426 | H | 5-NH$_2$-6-Cl—Pyr(2) | H | Me | —CH$_2$— | O | O | CH |
| 3-427 | H | 5-NH$_2$-6-Cl—Pyr(2) | H | Me | —CH$_2$— | O | S | CH |
| 3-428 | 3-MeO | 5-NH$_2$-6-Cl—Pyr(2) | 5-MeO | Et | —(CH$_2$)$_4$— | S | S | CH |
| 3-429 | H | Pyr(3) | H | H | —CH$_2$— | O | O | CH |
| 3-430 | H | Pyr(3) | H | Me | —CH$_2$— | O | O | CH |
| 3-431 | H | Pyr(3) | H | Me | —CH$_2$— | O | O | N |
| 3-432 | H | Pyr(3) | H | Me | —CH$_2$— | O | S | CH |

TABLE 3-continued

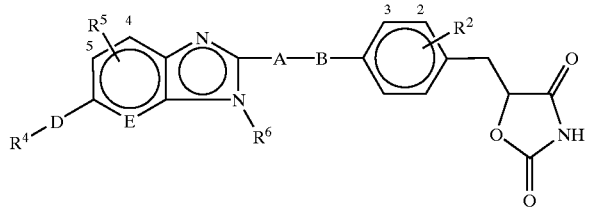

(I-3)

| Cpd. No. | $R^2$ | $R^4$ | $R^5$ | $R^6$ | —A— | B | D | E |
|---|---|---|---|---|---|---|---|---|
| 3-433 | H | Pyr(3) | H | Me | —CH$_2$— | O | S | N |
| 3-434 | H | Pyr(3) | H | Me | —CH$_2$— | S | O | CH |
| 3-435 | H | Pyr(3) | H | Me | —(CH$_2$)$_2$— | O | O | CH |
| 3-436 | H | Pyr(3) | H | Me | —(CH$_2$)$_2$— | O | O | N |
| 3-437 | H | Pyr(3) | H | Me | —(CH$_2$)$_2$— | O | S | CH |
| 3-438 | H | Pyr(3) | H | Me | —CH(Me)— | O | O | CH |
| 3-439 | H | Pyr(3) | H | Me | —(CH$_2$)$_3$— | O | O | CH |
| 3-440 | H | Pyr(3) | H | Et | —CH$_2$— | O | O | CH |
| 3-441 | H | Pyr(3) | H | Et | —CH$_2$— | O | O | N |
| 3-442 | H | Pyr(3) | H | Et | —CH$_2$— | O | S | CH |
| 3-443 | H | Pyr(3) | H | Et | —CH$_2$— | O | S | N |
| 3-444 | H | Pyr(3) | H | Et | —(CH$_2$)$_2$— | O | O | CH |
| 3-445 | H | Pyr(3) | H | tBu | —CH$_2$— | O | O | CH |
| 3-446 | H | Pyr(3) | H | tBu | —CH$_2$— | O | S | CH |
| 3-447 | H | Pyr(3) | H | Pn | —(CH$_2$)$_3$— | O | O | CH |
| 3-448 | H | Pyr(3) | H | Ph | —CH$_2$— | O | O | CH |
| 3-449 | H | Pyr(3) | H | Ph | —CH$_2$— | O | O | N |
| 3-450 | H | Pyr(3) | H | Ph | —CH$_2$— | O | S | CH |
| 3-451 | H | Pyr(3) | H | Bz | —CH$_2$— | O | O | CH |
| 3-452 | H | Pyr(3) | 5-Cl | Me | —CH$_2$— | O | O | CH |
| 3-453 | H | Pyr(3) | 5-Me | Me | —CH$_2$— | O | O | CH |
| 3-454 | H | Pyr(3) | 5-MeO | Me | —CH$_2$— | O | O | CH |
| 3-455 | 2-Cl | Pyr(3) | H | Me | —CH$_2$— | O | O | CH |
| 3-456 | 3-Cl | Pyr(3) | H | Me | —CH$_2$— | O | O | CH |
| 3-457 | 2-Me | Pyr(3) | H | Me | —CH$_2$— | O | O | CH |
| 3-458 | 3-Me | Pyr(3) | H | Me | —CH$_2$— | O | O | CH |
| 3-459 | 2-MeO | Pyr(3) | H | Me | —CH$_2$— | O | O | CH |
| 3-460 | 3-MeO | Pyr(3) | H | Me | —CH$_2$— | O | O | CH |
| 3-461 | H | 6-Cl—Pyr(3) | H | Me | —CH$_2$— | O | O | CH |
| 3-462 | H | 6-Me—Pyr(3) | H | Me | —CH$_2$— | O | O | CH |
| 3-463 | H | 5-MeO—Pyr(3) | H | Me | —CH$_2$— | O | O | CH |
| 3-464 | H | 5-MeO—Pyr(3) | H | Me | —CH$_2$— | O | S | CH |
| 3-465 | H | 6-MeO—Pyr(3) | H | Me | —CH$_2$— | O | O | CH |
| 3-466 | H | 6-MeO—Pyr(3) | H | Me | —CH$_2$— | O | O | N |
| 3-467 | H | 6-MeO—Pyr(3) | H | Me | —CH$_2$— | O | S | CH |
| 3-468 | H | 6-MeO—Pyr(3) | H | Me | —(CH$_2$)$_3$— | O | O | CH |
| 3-469 | H | 6-MeO—Pyr(3) | H | Et | —CH$_2$— | O | O | CH |
| 3-470 | H | 6-MeO—Pyr(3) | H | Et | —CH$_2$— | O | S | CH |
| 3-471 | H | 6-EtO—Pyr(3) | H | Me | —CH$_2$— | O | O | CH |
| 3-472 | H | 6-iPrO—Pyr(3) | H | Me | —CH$_2$— | O | O | CH |
| 3-473 | H | 6-iPrO—Pyr(3) | H | Me | —CH$_2$— | O | S | CH |
| 3-474 | H | 6-MeO-5-Me—Pyr(3) | H | Me | —CH$_2$— | O | O | CH |
| 3-475 | H | 6-MeO-5-Me—Pyr(3) | H | Me | —CH$_2$— | O | S | CH |
| 3-476 | H | 2-NO$_2$-6-Me—Pyr(3) | H | Me | —CH$_2$— | O | O | CH |
| 3-477 | H | 2-NO$_2$-6-Me—Pyr(3) | H | Me | —CH$_2$— | O | S | CH |
| 3-478 | H | Pyr(4) | H | H | —CH$_2$— | O | O | CH |
| 3-479 | H | Pyr(4) | H | Me | —CH$_2$— | O | O | CH |
| 3-480 | H | Pyr(4) | H | Me | —CH$_2$— | O | O | N |
| 3-481 | H | Pyr(4) | H | Me | —CH$_2$— | O | S | CH |
| 3-482 | H | Pyr(4) | H | Me | —CH$_2$— | O | S | N |
| 3-483 | H | Pyr(4) | H | Me | —CH$_2$— | S | O | CH |
| 3-484 | H | Pyr(4) | H | Me | —CH$_2$— | S | S | CH |
| 3-485 | H | Pyr(4) | H | Me | —(CH$_2$)$_2$— | O | O | CH |
| 3-486 | H | Pyr(4) | H | Me | —(CH$_2$)$_2$— | O | O | N |
| 3-487 | H | Pyr(4) | H | Me | —(CH$_2$)$_2$— | O | S | CH |
| 3-488 | H | Pyr(4) | H | Me | —CH(Me)— | O | O | CH |
| 3-489 | H | Pyr(4) | H | Me | —(CH$_2$)$_3$— | O | O | CH |
| 3-490 | H | Pyr(4) | H | Et | —CH$_2$— | O | O | CH |
| 3-491 | H | Pyr(4) | H | Et | —CH$_2$— | O | O | N |
| 3-492 | H | Pyr(4) | H | Et | —CH$_2$— | O | S | CH |
| 3-493 | H | Pyr(4) | H | Et | —(CH$_2$)$_2$— | O | O | CH |

TABLE 3-continued

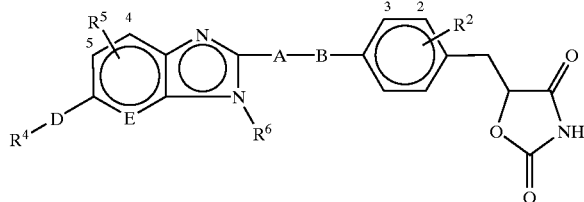

(I-3)

| Cpd. No. | $R^2$ | $R^4$ | $R^5$ | $R^6$ | —A— | B | D | E |
|---|---|---|---|---|---|---|---|---|
| 3-494 | H | Pyr(4) | H | tBu | —CH$_2$— | O | O | CH |
| 3-495 | H | Pyr(4) | H | tBu | —CH$_2$— | O | S | CH |
| 3-496 | H | Pyr(4) | H | Ph | —CH$_2$— | O | O | CH |
| 3-497 | H | Pyr(4) | H | Bz | —CH$_2$— | O | O | CH |
| 3-498 | H | Pyr(4) | H | Bz | —CH$_2$— | O | S | CH |
| 3-499 | H | Pyr(4) | 5-Cl | Me | —CH$_2$— | O | O | CH |
| 3-500 | H | Pyr(4) | 5-Me | Me | —CH$_2$— | O | O | CH |
| 3-501 | H | Pyr(4) | 5-MeO | Me | —CH$_2$— | O | O | CH |
| 3-502 | 2-Cl | Pyr(4) | H | Me | —CH$_2$— | O | O | CH |
| 3-503 | 3-Cl | Pyr(4) | H | Me | —CH$_2$— | O | O | CH |
| 3-504 | 2-Me | Pyr(4) | H | Me | —CH$_2$— | O | O | CH |
| 3-505 | 3-Me | Pyr(4) | H | Me | —CH$_2$— | O | O | CH |
| 3-506 | 2-MeO | Pyr(4) | H | Me | —CH$_2$— | O | O | CH |
| 3-507 | 3-MeO | Pyr(4) | H | Me | —CH$_2$— | O | O | CH |
| 3-508 | H | 2-F—Pyr(4) | H | Me | —CH$_2$— | O | O | CH |
| 3-509 | H | 2-Cl—Pyr(4) | H | Me | —CH$_2$— | O | O | CH |
| 3-510 | H | 2-Me—Pyr(4) | H | Me | —CH$_2$— | O | O | CH |
| 3-511 | H | 2-Me—Pyr(4) | H | Me | —CH$_2$— | O | S | CH |
| 3-512 | H | 2-Et—Pyr(4) | H | Me | —CH$_2$— | O | O | CH |
| 3-513 | H | 2,6-diMe—Pyr(4) | H | Me | —CH$_2$— | O | O | CH |
| 3-514 | H | 2,6-diMe—Pyr(4) | H | Me | —CH$_2$— | O | O | N |
| 3-515 | H | 2,6-diMe—Pyr(4) | H | Me | —CH$_2$— | O | S | CH |
| 3-516 | H | 2,6-diMe—Pyr(4) | H | Et | —CH$_2$— | O | O | CH |
| 3-517 | H | 2,6-diMe—Pyr(4) | H | Et | —CH$_2$— | O | S | CH |
| 3-518 | H | 3,6-diMe—Pyr(4) | H | Me | —CH$_2$— | O | O | CH |
| 3-519 | H | 3,6-diMe—Pyr(4) | H | Me | —CH$_2$— | O | S | CH |
| 3-520 | H | 2-MeO—Pyr(4) | H | Me | —CH$_2$— | O | O | CH |
| 3-521 | H | 2-MeO—Pyr(4) | H | Me | —CH$_2$— | O | S | CH |
| 3-522 | H | 4-Imid(1)-Ph | H | Me | —CH$_2$— | O | O | CH |
| 3-523 | H | 4-Imid(1)-Ph | H | Me | —CH$_2$— | O | O | N |
| 3-524 | H | 4-Imid(1)-Ph | H | Me | —CH$_2$— | O | S | CH |
| 3-525 | H | 4-Imid(1)-Ph | H | Me | —CH$_2$— | O | S | N |
| 3-526 | H | 4-Tz—Ph | H | Me | —CH$_2$— | O | O | CH |
| 3-527 | H | 4-Tz—Ph | H | Me | —CH$_2$— | O | O | N |
| 3-528 | H | 4-Tz—Ph | H | Me | —CH$_2$— | O | S | CH |
| 3-529 | H | 4-Tz—Ph | H | Me | —CH$_2$— | O | S | N |
| 3-530 | H | 4-Ada(1)-Ph | H | Me | —CH$_2$— | O | O | CH |
| 3-531 | H | 4-Ada(1)-Ph | H | Me | —CH$_2$— | O | O | N |
| 3-532 | H | 4-Ada(1)-Ph | H | Me | —CH$_2$— | O | S | CH |
| 3-533 | H | 4-Ada(1)-Ph | H | Me | —CH$_2$— | O | S | N |
| 3-534 | H | 4-CN—Ph | H | Me | —CH$_2$— | O | O | CH |
| 3-535 | H | 4-CN—Ph | H | Me | —CH$_2$— | O | O | N |
| 3-536 | H | 4-CN—Ph | H | Me | —CH$_2$— | O | S | CH |
| 3-537 | H | 4-CN—Ph | H | Me | —CH$_2$— | O | S | N |
| 3-538 | H | 4-Bz-3-OH—Ph | H | Me | —CH$_2$— | O | O | CH |
| 3-539 | H | 4-Bz-3-OH—Ph | H | Me | —CH$_2$— | O | O | N |
| 3-540 | H | 4-OH-2,5-ditBu—Ph | H | Me | —CH$_2$— | O | O | CH |
| 3-541 | H | pentaF—Ph | H | Me | —CH$_2$— | O | O | CH |
| 3-542 | H | 4-NHCOPh—Ph | H | Me | —CH$_2$— | O | O | CH |
| 3-543 | H | 4-NHCO(3-Cl—Ph)—Ph | H | Me | —CH$_2$— | O | O | CH |
| 3-544 | H | 4-NHCO(2,4-diF—Ph)—Ph | H | Me | —CH$_2$— | O | O | CH |
| 3-545 | H | 4-NHCO(4-OH-3,5-ditBu—Ph)—Ph | H | Me | —CH$_2$— | O | O | CH |
| 3-546 | H | 4-NHCONp(1)-Ph | H | Me | —CH$_2$— | O | O | CH |
| 3-547 | H | 4-NHCO(3-Cl—Bz)—Ph | H | Me | —CH$_2$— | O | O | CH |
| 3-548 | H | 4-NHCOcPn—Ph | H | Me | —CH$_2$— | O | O | CH |
| 3-549 | H | 4-NHCOcHx—Ph | H | Me | —CH$_2$— | O | O | CH |
| 3-550 | H | 4-NHCOPyr(3)-Ph | H | Me | —CH$_2$— | O | O | CH |
| 3-551 | H | 4-NHCOPyr(4)-Ph | H | Me | —CH$_2$— | O | O | CH |

TABLE 3-continued

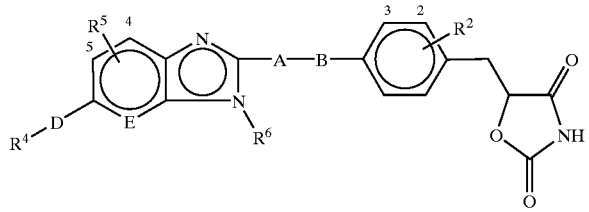

(I-3)

| Cpd. No. | R² | R⁴ | R⁵ | R⁶ | —A— | B | D | E |
|---|---|---|---|---|---|---|---|---|
| 3-552 | H | 4-NHHx—Ph | H | Me | —CH₂— | O | O | CH |
| 3-553 | H | 4-NH(Ac)Hx—Ph | H | Me | —CH₂— | O | O | CH |

TABLE 4

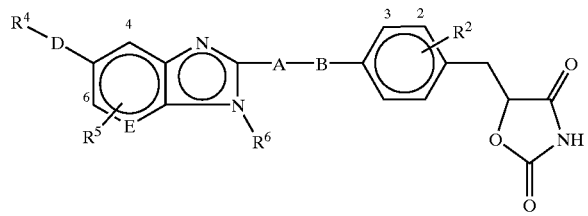

(I-4)

| Cpd. No. | R² | R⁴ | R⁵ | R⁶ | —A— | B | D | E |
|---|---|---|---|---|---|---|---|---|
| 4-1 | H | 4-F—Ph | H | Me | —CH₂— | O | O | CH |
| 4-2 | H | 4-Cl—Ph | H | Me | —CH₂— | O | O | CH |
| 4-3 | H | 2-OH—Ph | H | Me | —CH₂— | O | O | CH |
| 4-4 | H | 2-OH—Ph | H | Me | —CH₂— | O | S | CH |
| 4-5 | H | 2-OH—Ph | H | Et | —CH₂— | O | O | CH |
| 4-6 | H | 2-OH—Ph | H | Et | —CH₂— | O | S | CH |
| 4-7 | H | 3-OH—Ph | H | Me | —CH₂— | O | O | CH |
| 4-8 | H | 3-OH—Ph | H | Me | —CH₂— | O | S | CH |
| 4-9 | H | 3-OH—Ph | H | Et | —CH₂— | O | O | CH |
| 4-10 | H | 3-OH—Ph | H | Et | —CH₂— | O | S | CH |
| 4-11 | H | 4-OH—Ph | H | Me | —CH₂— | O | O | CH |
| 4-12 | H | 4-OH—Ph | H | Me | —CH₂— | O | O | N |
| 4-13 | H | 4-OH—Ph | H | Me | —CH₂— | O | S | CH |
| 4-14 | H | 4-OH—Ph | H | Me | —(CH₂)₂— | O | O | CH |
| 4-15 | H | 4-OH—Ph | H | Et | —CH₂— | O | O | CH |
| 4-16 | H | 4-OH—Ph | H | Et | —CH₂— | O | S | CH |
| 4-17 | H | 4-OH—Ph | H | tBu | —CH₂— | O | O | CH |
| 4-18 | H | 3-CF₃—Ph | H | Me | —CH₂— | O | O | CH |
| 4-19 | H | 4-iPrO—Ph | H | Me | —CH₂— | O | O | CH |
| 4-20 | H | 4-MeS—Ph | H | Me | —CH₂— | O | O | CH |
| 4-21 | H | 2-NH₂—Ph | H | Me | —CH₂— | O | O | CH |
| 4-22 | H | 3-NH₂—Ph | H | Me | —CH₂— | O | O | CH |
| 4-23 | H | 4-NH₂—Ph | H | Me | —CH₂— | O | O | CH |
| 4-24 | H | 4-NHMe—Ph | H | Me | —CH₂— | O | O | CH |
| 4-25 | H | 4-N(Me)₂—Ph | H | Me | —CH₂— | O | O | CH |
| 4-26 | H | 4-N(Me)₂—Ph | H | Et | —CH₂— | O | O | CH |
| 4-27 | H | 4-Ph—Ph | H | Me | —CH₂— | O | O | CH |
| 4-28 | H | 4-(4-OH-3,5-diMe—Ph)Ph | H | Me | —CH₂— | O | O | CH |
| 4-29 | H | 4-(4-OH-3,5-ditBu—Ph)Ph | H | Me | —CH₂— | O | O | CH |
| 4-30 | H | 4-(4-OH—Bz)Ph | H | Me | —CH₂— | O | O | CH |
| 4-31 | H | 4-PhS—Ph | H | Me | —CH₂— | O | O | CH |
| 4-32 | H | 2-Pyrd(1)-Ph | H | Me | —CH₂— | O | O | CH |
| 4-33 | H | 2-Pyrd(1)-Ph | H | Me | —CH₂— | O | S | CH |
| 4-34 | H | 3-Pyrd(1)-Ph | H | Me | —CH₂— | O | O | CH |
| 4-35 | H | 3-Pyrd(1)-Ph | H | Me | —CH₂— | O | S | CH |
| 4-36 | H | 3-Pyrd(1)-Ph | H | Me | —(CH₂)₂— | O | O | CH |
| 4-37 | H | 3-Pyrd(1)-Ph | H | Et | —CH₂— | O | O | CH |
| 4-38 | H | 4-Pyrd(1)-Ph | H | Me | —CH₂— | O | O | CH |
| 4-39 | H | 4-Pyrd(1)-Ph | H | Me | —CH₂— | O | O | N |
| 4-40 | H | 4-Pyrd(1)-Ph | H | Me | —CH₂— | O | S | CH |
| 4-41 | H | 4-Pyrd(1)-Ph | H | Me | —(CH₂)₃— | O | O | CH |

TABLE 4-continued

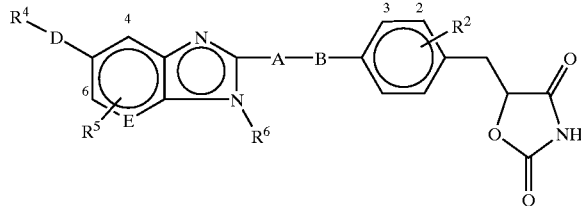

(I-4)

| Cpd. No. | R² | R⁴ | R⁵ | R⁶ | —A— | B | D | E |
|---|---|---|---|---|---|---|---|---|
| 4-42 | H | 4-Pyrd(1)-Ph | H | Et | —CH₂— | O | O | CH |
| 4-43 | H | 4-Pyrd(1)-Ph | H | Et | —CH₂— | O | S | CH |
| 4-44 | H | 2-Pip(1)-Ph | H | Me | —CH₂— | O | O | CH |
| 4-45 | H | 2-Pip(1)-Ph | H | Me | —CH₂— | O | S | CH |
| 4-46 | H | 3-Pip(1)-Ph | H | Me | —CH₂— | O | O | CH |
| 4-47 | H | 3-Pip(1)-Ph | H | Me | —CH₂— | O | S | CH |
| 4-48 | H | 3-Pip(1)-Ph | H | Et | —(CH₂)₃— | S | O | CH |
| 4-49 | H | 4-Pip(1)-Ph | H | Me | —CH₂— | O | O | CH |
| 4-50 | H | 4-Pip(1)-Ph | H | Me | —CH₂— | O | O | N |
| 4-51 | H | 4-Pip(1)-Ph | H | Me | —CH₂— | O | S | CH |
| 4-52 | H | 4-Pip(1)-Ph | H | Me | —(CH₂)₂— | O | O | CH |
| 4-53 | H | 4-Pip(1)-Ph | H | Me | —(CH₂)₃— | O | O | CH |
| 4-54 | H | 4-Pip(1)-Ph | H | Et | —CH₂— | O | O | CH |
| 4-55 | H | 4-Pip(1)-Ph | H | Et | —CH₂— | O | S | CH |
| 4-56 | H | 4-Pip(1)-Ph | H | tBu | —CH₂— | O | O | CH |
| 4-57 | H | 4-Pip(1)-Ph | 4-Cl | Me | —CH₂— | O | O | CH |
| 4-58 | 2-MeO | 4-Pip(1)-Ph | H | Me | —CH₂— | O | O | CH |
| 4-59 | H | 2-Mor(4)-Ph | H | Me | —CH₂— | O | O | CH |
| 4-60 | H | 2-Mor(4)-Ph | H | Me | —CH₂— | O | S | CH |
| 4-61 | H | 2-Mor(4)-Ph | H | Me | —(CH₂)₃— | O | O | CH |
| 4-62 | H | 3-Mor(4)-Ph | H | Me | —CH₂— | O | O | CH |
| 4-63 | H | 3-Mor(4)-Ph | H | Me | —CH₂— | O | S | CH |
| 4-64 | H | 3-Mor(4)-Ph | H | Me | —(CH₂)₃— | O | O | CH |
| 4-65 | H | 3-Mor(4)-Ph | H | Et | —CH₂— | O | O | CH |
| 4-66 | H | 4-Mor(4)-Ph | H | Me | —CH₂— | O | O | CH |
| 4-67 | H | 4-Mor(4)-Ph | H | Me | —CH₂— | O | O | N |
| 4-68 | H | 4-Mor(4)-Ph | H | Me | —CH₂— | O | S | CH |
| 4-69 | H | 4-Mor(4)-Ph | H | Et | —CH₂— | O | O | CH |
| 4-70 | H | 4-Mor(4)-Ph | H | Et | —CH₂— | O | S | CH |
| 4-71 | H | 4-TioMor(4)-Ph | H | Me | —CH₂— | O | O | CH |
| 4-72 | H | 4-Pipra(1)-Ph | H | Me | —CH₂— | O | O | CH |
| 4-73 | H | 4-Pipra(1)-Ph | H | Me | —CH₂— | O | S | CH |
| 4-74 | H | 4-Pipra(1)-Ph | H | Me | —(CH₂)₃— | O | O | CH |
| 4-75 | H | 4-Pipra(1)-Ph | H | Et | —CH₂— | O | O | CH |
| 4-76 | H | 4-NO₂—Ph | H | Me | —CH₂— | O | O | CH |
| 4-77 | H | 3-Cl-4-OH—Ph | H | Me | —CH₂— | O | O | CH |
| 4-78 | H | 2-Cl-4-OH-3,5-diMe—Ph | H | Me | —CH₂— | O | O | CH |
| 4-79 | H | 2-Cl-4-OH-3,5-diMe—Ph | H | Me | —CH₂— | O | O | N |
| 4-80 | H | 2-Cl-4-OH-3,5-diMe—Ph | H | Me | —CH₂— | O | S | CH |
| 4-81 | H | 2-Cl-4-OH-3,5-diMe—Ph | H | Me | —(CH₂)₂— | O | O | CH |
| 4-82 | H | 2-Cl-4-OH-3,5-diMe—Ph | H | Me | —(CH₂)₄— | O | O | CH |
| 4-83 | H | 2-Cl-4-OH-3,5-diMe—Ph | H | Et | —CH₂— | O | O | CH |
| 4-84 | H | 2-Cl-4-OH-3,5-diMe—Ph | H | Et | —CH₂— | O | S | CH |
| 4-85 | H | 2-Cl-4-OH-3,5-diMe—Ph | H | tBu | —CH₂— | O | O | CH |
| 4-86 | H | 2-Cl-4-OH-3,5-diMe—Ph | 6-MeO | Me | —CH₂— | O | O | CH |
| 4-87 | 3-Cl | 2-Cl-4-OH-3,5-diMe—Ph | H | Me | —CH₂— | O | O | CH |
| 4-88 | 2-MeO | 2-Cl-4-OH-3,5-diMe—Ph | H | Me | —CH₂— | O | O | CH |
| 4-89 | H | 3-Cl-5-OH-2,6-diMe—Ph | H | Me | —CH₂— | O | O | CH |
| 4-90 | H | 4-Cl-3-OH-2,5-diMe—Ph | H | Me | —CH₂— | O | O | CH |
| 4-91 | H | 3-Cl-4-NH₂—Ph | H | Me | —CH₂— | O | O | CH |

TABLE 4-continued

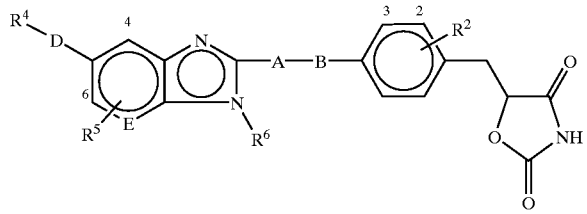

(I-4)

| Cpd. No. | R² | R⁴ | R⁵ | R⁶ | —A— | B | D | E |
|---|---|---|---|---|---|---|---|---|
| 4-92 | H | 3,5-diCl-4-NH₂—Ph | H | Me | —CH₂— | O | O | CH |
| 4-93 | H | 4-NHMe-3-Cl—Ph | H | Me | —CH₂— | O | O | CH |
| 4-94 | H | 3-Cl-4-Pyrd(1)-Ph | H | Me | —CH₂— | O | O | CH |
| 4-95 | H | 3-OH-4-Pyrd(1)-Ph | H | Me | —CH₂— | O | O | CH |
| 4-96 | H | 3-Cl-6-Me-4-Pyrd(1)-Ph | H | Me | —CH₂— | O | O | CH |
| 4-97 | H | 2-Me-4-Mor(4)-Ph | H | Me | —CH₂— | O | O | CH |
| 4-98 | H | 2-OH-3-Me—Ph | H | Me | —CH₂— | O | O | CH |
| 4-99 | H | 2-OH-4-Me—Ph | H | Me | —CH₂— | O | O | CH |
| 4-100 | H | 2-OH-3,4-diMe—Ph | H | Me | —CH₂— | O | O | CH |
| 4-101 | H | 3-OH-2-Me—Ph | H | Me | —CH₂— | O | O | CH |
| 4-102 | H | 3-OH-4-Me—Ph | H | Me | —CH₂— | O | O | CH |
| 4-103 | H | 3-OH-5-Me—Ph | H | Me | —CH₂— | O | O | CH |
| 4-104 | H | 3-OH-6-Me—Ph | H | Me | —CH₂— | O | O | CH |
| 4-105 | H | 3-OH-2,4-diMe—Ph | H | Me | —CH₂— | O | O | CH |
| 4-106 | H | 4-OH-2-Me—Ph | H | Me | —CH₂— | O | O | CH |
| 4-107 | H | 4-OH-3-Me—Ph | H | Me | —CH₂— | O | O | CH |
| 4-108 | H | 4-OH-3-Me—Ph | H | Me | —CH₂— | O | S | CH |
| 4-109 | H | 4-OH-3-Me—Ph | H | Et | —CH₂— | O | O | CH |
| 4-110 | H | 4-OH-3-Me—Ph | 6-Cl | Me | —CH₂— | O | O | CH |
| 4-111 | H | 4-OH-2-tBu—Ph | H | Me | —CH₂— | O | O | CH |
| 4-112 | H | 4-OH-3-tBu—Ph | H | Me | —CH₂— | O | O | CH |
| 4-113 | H | 4-OH-2,3-diMe—Ph | H | Me | —CH₂— | O | O | CH |
| 4-114 | H | 4-OH-2,3-diMe—Ph | H | Me | —CH₂— | O | S | CH |
| 4-115 | H | 4-OH-2,3-diMe—Ph | H | Me | —(CH₂)₃— | S | O | CH |
| 4-116 | H | 4-OH-2,3-diMe—Ph | H | Et | —CH₂— | O | O | CH |
| 4-117 | H | 4-OH-2,5-diMe—Ph | H | Me | —CH₂— | O | O | CH |
| 4-118 | H | 4-OH-3,5-diMe—Ph | H | Me | —CH₂— | O | O | CH |
| 4-119 | H | 4-OH-3,5-diMe—Ph | H | Me | —CH₂— | O | O | N |
| 4-120 | H | 4-OH-3,5-diMe—Ph | H | Me | —CH₂— | O | S | CH |
| 4-121 | H | 4-OH-3,5-diMe—Ph | H | Me | —CH₂— | S | O | CH |
| 4-122 | H | 4-OH-3,5-diMe—Ph | H | Me | —(CH₂)₂— | O | O | CH |
| 4-123 | H | 4-OH-3,5-diMe—Ph | H | Et | —CH₂— | O | O | CH |
| 4-124 | H | 4-OH-3,5-diMe—Ph | H | Et | —CH₂— | O | S | CH |
| 4-125 | H | 4-OH-3,5-diMe—Ph | H | sBu | —CH₂— | O | O | CH |
| 4-126 | H | 4-OH-3,5-diMe—Ph | H | tBu | —CH₂— | O | O | CH |
| 4-127 | H | 4-OH-3,5-diMe—Ph | H | Ph | —CH₂— | O | O | CH |
| 4-128 | H | 3,5-diEt-4-OH—Ph | H | Me | —CH₂— | O | O | CH |
| 4-129 | H | 3-tBu-4-OH-5-Me—Ph | H | Me | —CH₂— | O | O | CH |
| 4-130 | H | 3-tBu-4-OH-5-Me—Ph | H | Me | —CH₂— | O | S | CH |

TABLE 4-continued

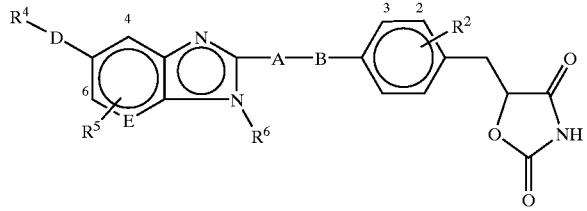

(I-4)

| Cpd. No. | R² | R⁴ | R⁵ | R⁶ | —A— | B | D | E |
|---|---|---|---|---|---|---|---|---|
| 4-131 | H | 4-OH-3,5-diPr—Ph | H | Me | —CH₂— | O | O | CH |
| 4-132 | H | 4-OH-3,5-diiPr—Ph | H | Me | —CH₂— | O | O | CH |
| 4-133 | H | 3,5-ditBu-4-OH—Ph | H | Me | —CH₂— | O | O | CH |
| 4-134 | H | 3,5-ditBu-4-OH—Ph | H | Me | —CH₂— | O | O | N |
| 4-135 | H | 3,5-ditBu-4-OH—Ph | H | Me | —CH₂— | O | S | CH |
| 4-136 | H | 3,5-ditBu-4-OH—Ph | H | Me | —CH₂— | S | S | CH |
| 4-137 | H | 3,5-ditBu-4-OH—Ph | H | Me | —(CH₂)₂— | O | O | CH |
| 4-138 | H | 3,5-ditBu-4-OH—Ph | H | Me | —(CH₂)₂— | O | S | CH |
| 4-139 | H | 3,5-ditBu-4-OH—Ph | H | Me | —(CH₂)₃— | O | S | CH |
| 4-140 | H | 3,5-ditBu-4-OH—Ph | H | Et | —CH₂— | O | O | CH |
| 4-141 | H | 3,5-ditBu-4-OH—Ph | H | Et | —CH₂— | O | S | CH |
| 4-142 | H | 3,5-ditBu-4-OH—Ph | H | tBu | —CH₂— | O | O | CH |
| 4-143 | H | 3,5-ditBu-4-OH—Ph | 6-Cl | Me | —CH₂— | O | S | CH |
| 4-144 | H | 4-OH-2,3,5-triMe—Ph | H | H | —CH₂— | O | S | CH |
| 4-145 | H | 4-OH-2,3,5-triMe—Ph | H | Me | —CH₂— | O | O | CH |
| 4-146 | H | 4-OH-2,3,5-triMe—Ph | H | Me | —CH₂— | O | O | N |
| 4-147 | H | 4-OH-2,3,5-triMe—Ph | H | Me | —CH₂— | O | S | CH |
| 4-148 | H | 4-OH-2,3,5-triMe—Ph | H | Me | —(CH₂)₂— | O | O | CH |
| 4-149 | H | 4-OH-2,3,5-triMe—Ph | H | Me | —(CH₂)₃— | O | O | CH |
| 4-150 | H | 4-OH-2,3,5-triMe—Ph | H | Et | —CH₂— | O | O | CH |
| 4-151 | H | 4-OH-2,3,5-triMe—Ph | H | Et | —CH₂— | O | S | CH |
| 4-152 | H | 4-OH-2,3,5-triMe—Ph | H | iPr | —CH₂— | O | O | CH |
| 4-153 | H | 4-OH-2,3,5-triMe—Ph | H | tBu | —CH₂— | O | O | CH |
| 4-154 | H | 4-OH-2,3,5-triMe—Ph | H | Ph | —CH₂— | O | O | CH |
| 4-155 | H | 4-OH-2,3,5-triMe—Ph | H | Bz | —CH₂— | O | O | CH |
| 4-156 | H | 4-OH-2,3,5-triMe—Ph | 6-Cl | Me | —CH₂— | O | O | CH |
| 4-157 | 2-Cl | 4-OH-2,3,5-triMe—Ph | H | Me | —CH₂— | O | O | CH |
| 4-158 | 2-MeO | 4-OH-2,3,5-triMe—Ph | H | Me | —CH₂— | O | O | CH |
| 4-159 | H | 4-OH-2,3,6-triMe—Ph | H | Me | —CH₂— | O | O | CH |
| 4-160 | H | 4-OH-2,3,5,6-tetraMe—Ph | H | Me | —CH₂— | O | O | CH |
| 4-161 | H | 4-OH-3,5-diMeO—Ph | H | Me | —CH₂— | O | O | CH |
| 4-162 | H | 3-NH₂-4-Me—Ph | H | Me | —CH₂— | O | O | CH |

TABLE 4-continued

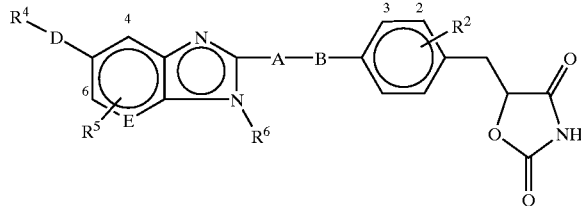

(I-4)

| Cpd. No. | R² | R⁴ | R⁵ | R⁶ | —A— | B | D | E |
|---|---|---|---|---|---|---|---|---|
| 4-163 | H | 4-NH₂-2,3-diMe—Ph | H | Me | —CH₂— | O | O | CH |
| 4-164 | H | 4-NH₂-2,6-diMe—Ph | H | Me | —CH₂— | O | O | CH |
| 4-165 | H | 4-NH₂-3,5-diMe—Ph | H | H | —CH₂— | O | O | CH |
| 4-166 | H | 4-NH₂-3,5-diMe—Ph | H | Me | —CH₂— | O | O | CH |
| 4-167 | H | 4-NH₂-3,5-diMe—Ph | H | Me | —CH₂— | O | O | N |
| 4-168 | H | 4-NH₂-3,5-diMe—Ph | H | Me | —CH₂— | O | S | CH |
| 4-169 | H | 4-NH₂-3,5-diMe—Ph | H | Me | —(CH₂)₂— | O | O | CH |
| 4-170 | H | 4-NH₂-3,5-diMe—Ph | H | Et | —CH₂— | O | O | CH |
| 4-171 | H | 4-NH₂-3,5-diMe—Ph | H | Et | —CH₂— | O | S | CH |
| 4-172 | H | 4-NH₂-3,5-diMe—Ph | H | tBu | —CH₂— | O | O | CH |
| 4-173 | H | 4-NH₂-3,5-Me—Ph | H | Ph | —CH₂— | O | O | CH |
| 4-174 | H | 4-NH₂-3,5-diMe—Ph | H | Bz | —CH₂— | O | O | CH |
| 4-175 | H | 4-NH₂-3,5-diMe—Ph | H | Me | —CH₂— | O | O | CH |
| 4-176 | H | 4-NHMe-3,5-diMe—Ph | H | Me | —CH₂— | O | O | CH |
| 4-177 | H | 4-NHAc-3,5-diMe—Ph | H | Me | —CH₂— | O | O | CH |
| 4-178 | H | 4-NO₂-3,5-diMe—Ph | H | Me | —CH₂— | O | O | CH |
| 4-179 | H | 4-NO₂-3,5-diMe—Ph | H | Me | —CH₂— | O | S | CH |
| 4-180 | H | Pyr(2) | H | Me | —CH₂— | O | O | CH |
| 4-181 | H | Pyr(2) | H | Me | —CH₂— | O | O | N |
| 4-182 | H | Pyr(2) | H | Me | —CH₂— | O | S | CH |
| 4-183 | H | Pyr(2) | H | Me | —(CH₂)₂— | O | O | CH |
| 4-184 | H | Pyr(2) | H | Me | —(CH₂)₃— | O | O | CH |
| 4-185 | H | Pyr(2) | H | Et | —CH₂— | O | O | CH |
| 4-186 | H | Pyr(2) | H | Et | —CH₂— | O | S | CH |
| 4-187 | H | Pyr(2) | H | tBu | —CH₂— | O | O | CH |
| 4-188 | H | Pyr(2) | H | Ph | —CH₂— | O | O | CH |
| 4-189 | H | Pyr(2) | 6-Cl | Me | —CH₂— | O | O | CH |
| 4-190 | H | 5-Cl—Pyr(2) | H | Me | —CH₂— | O | O | CH |
| 4-191 | H | 6-Cl—Pyr(2) | H | Me | —CH₂— | O | O | CH |
| 4-192 | H | 6-Me—Pyr(2) | H | Me | —CH₂— | O | O | CH |
| 4-193 | H | 6-MeO—Pyr(2) | H | Me | —CH₂— | O | O | CH |
| 4-194 | H | 3-NH₂—Pyr(2) | H | Me | —CH₂— | O | O | CH |
| 4-195 | H | 5-NH₂—Pyr(2) | H | Me | —CH₂— | O | O | CH |
| 4-196 | H | 3-NO₂—Pyr(2) | H | Me | —CH₂— | O | O | CH |
| 4-197 | H | 5-NO₂—Pyr(2) | H | Me | —CH₂— | O | O | CH |
| 4-198 | H | 5-NH₂-6-Cl—Pyr(2) | H | Me | —CH₂— | O | O | CH |
| 4-199 | 3-MeO | 5-NH₂-6-Cl—Pyr(2) | 6-MeO | Et | —(CH₂)₄— | S | S | CH |
| 4-200 | H | Pyr(3) | H | Me | —CH₂— | O | O | CH |
| 4-201 | H | Pyr(3) | H | Me | —CH₂— | O | O | N |
| 4-202 | H | Pyr(3) | H | Me | —CH₂— | O | S | CH |
| 4-203 | H | Pyr(3) | H | Me | —(CH₂)₂— | O | O | CH |
| 4-204 | H | Pyr(3) | H | Me | —(CH₂)₃— | O | O | CH |
| 4-205 | H | Pyr(3) | H | Et | —CH₂— | O | O | CH |
| 4-206 | H | Pyr(3) | H | Et | —CH₂— | O | S | CH |
| 4-207 | H | Pyr(3) | H | tBu | —CH₂— | O | O | CH |

TABLE 4-continued

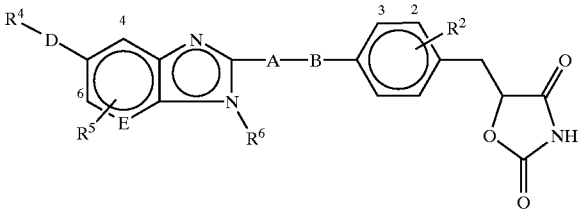

(I-4)

| Cpd. No. | R² | R⁴ | R⁵ | R⁶ | —A— | B | D | E |
|---|---|---|---|---|---|---|---|---|
| 4-208 | H | Pyr(3) | H | Pn | —(CH₂)₃— | O | O | CH |
| 4-209 | H | Pyr(3) | H | Ph | —CH₂— | O | O | CH |
| 4-210 | H | Pyr(3) | H | Ph | —CH₂— | O | S | CH |
| 4-211 | H | Pyr(3) | H | Bz | —CH₂— | O | O | CH |
| 4-212 | 2-Cl | Pyr(3) | H | Me | —CH₂— | O | O | CH |
| 4-213 | H | 5-MeO—Pyr(3) | H | Me | —CH₂— | O | O | CH |
| 4-214 | H | 6-MeO—Pyr(3) | H | Me | —CH₂— | O | O | CH |
| 4-215 | H | 6-MeO—Pyr(3) | H | Me | —CH₂— | O | S | CH |
| 4-216 | H | 6-MeO—Pyr(3) | H | Me | —(CH₂)₃— | O | O | CH |
| 4-217 | H | 6-iPrO—Pyr(3) | H | Me | —CH₂— | O | O | CH |
| 4-218 | H | 6-MeO-5-Me—Pyr(3) | H | Me | —CH₂— | O | O | CH |
| 4-219 | H | 2-NO₂-6-Me—Pyr(3) | H | Me | —CH₂— | O | O | CH |
| 4-220 | H | Pyr(4) | H | Me | —CH₂— | O | O | CH |
| 4-221 | H | Pyr(4) | H | Me | —CH₂— | O | O | N |
| 4-222 | H | Pyr(4) | H | Me | —CH₂— | O | S | CH |
| 4-223 | H | Pyr(4) | H | Me | —CH₂— | S | S | CH |
| 4-224 | H | Pyr(4) | H | Me | —(CH₂)₂— | O | O | CH |
| 4-225 | H | Pyr(4) | H | Et | —CH₂— | O | O | CH |
| 4-226 | H | Pyr(4) | H | Et | —CH₂— | O | S | CH |
| 4-227 | H | Pyr(4) | H | tBu | —CH₂— | O | O | CH |
| 4-228 | H | Pyr(4) | H | Ph | —CH₂— | O | O | CH |
| 4-229 | H | Pyr(4) | H | Bz | —CH₂— | O | S | CH |
| 4-230 | 3-Cl | Pyr(4) | H | Me | —CH₂— | O | O | CH |
| 4-231 | H | 2-Me—Pyr(4) | H | Me | —CH₂— | O | O | CH |
| 4-232 | H | 2,6-diMe—Pyr(4) | H | Me | —CH₂— | O | O | CH |
| 4-233 | H | 2,6-diMe—Pyr(4) | H | Me | —CH₂— | O | S | CH |
| 4-234 | H | 3,6-diMe—Pyr(4) | H | Me | —CH₂— | O | O | CH |
| 4-235 | H | 2-MeO—Pyr(4) | H | Me | —CH₂— | O | O | CH |
| 4-236 | H | 4-Imid(1)-Ph | H | Me | —CH₂— | O | O | CH |
| 4-237 | H | 4-Tz—Ph | H | Me | —CH₂— | O | O | CH |
| 4-238 | H | 4-Ada(1)-Ph | H | Me | —CH₂— | O | O | CH |
| 4-239 | H | 4-CN—Ph | H | Me | —CH₂— | O | O | CH |
| 4-240 | H | 4-Bz-3-OH—Ph | H | Me | —CH₂— | O | O | CH |
| 4-241 | H | pentaF—Ph | H | Me | —CH₂— | O | O | CH |
| 4-242 | H | 4-NHCOPh—Ph | H | Me | —CH₂— | O | O | CH |
| 4-243 | H | 4-NHCO(3-Cl—Ph)—Ph | H | Me | —CH₂— | O | O | CH |
| 4-244 | H | 4-NHCO(2,4-diF—Ph)—Ph | H | Me | —CH₂— | O | O | CH |
| 4-245 | H | 4-NHCO(4-OH-3,5-di-tBu—Ph)—Ph | H | Me | —CH₂— | O | O | CH |
| 4-246 | H | 4-NHCONp(1)-Ph | H | Me | —CH₂— | O | O | CH |
| 4-247 | H | 4-NHCO(3-Cl—Bz)—Ph | H | Me | —CH₂— | O | O | CH |
| 4-248 | H | 4-NHCOcPn—Ph | H | Me | —CH₂— | O | O | CH |
| 4-249 | H | 4-NHCOcHx—Ph | H | Me | —CH₂— | O | O | CH |
| 4-250 | H | 4-NHCOPyr(3)-Ph | H | Me | —CH₂— | O | O | CH |
| 4-251 | H | 4-NHCOPyr(4)-Ph | H | Me | —CH₂— | O | O | CH |
| 4-252 | H | 4-NHHx—Ph | H | Me | —CH₂— | O | O | CH |
| 4-253 | H | 4-NH(Ac)Hx—Ph | H | Me | —CH₂— | O | O | CH |

TABLE 5

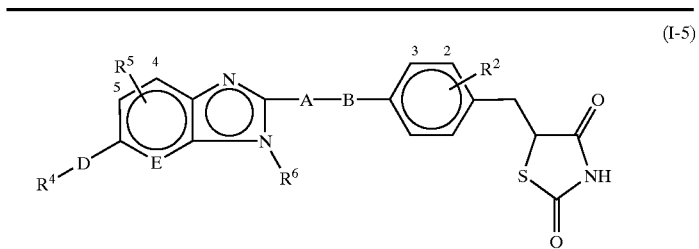

(I-5)

| Cpd. No. | R² | R⁴ | R⁵ | R⁶ | -A- | B | D | E |
|---|---|---|---|---|---|---|---|---|
| 5-1 | H | 4-F—Ph | H | Me | —CH₂— | O | O | CH |
| 5-2 | H | 4-Cl—Ph | H | Me | —CH₂— | O | O | CH |
| 5-3 | H | 2-OH—Ph | H | Me | —CH₂— | O | O | CH |
| 5-4 | H | 2-OH—Ph | H | Me | —CH₂— | O | S | CH |
| 5-5 | H | 2-OH—Ph | H | Et | —CH₂— | O | O | CH |
| 5-6 | H | 2-OH—Ph | H | Et | —CH₂— | O | S | CH |
| 5-7 | H | 3-OH—Ph | H | Me | —CH₂— | O | O | CH |
| 5-8 | H | 3-OH—Ph | H | Me | —CH₂— | O | S | CH |
| 5-9 | H | 3-OH—Ph | H | Et | —CH₂— | O | O | CH |
| 5-10 | H | 3-OH—Ph | H | Et | —CH₂— | O | S | CH |
| 5-11 | H | 4-OH—Ph | H | Me | —CH₂— | O | O | CH |
| 5-12 | H | 4-OH—Ph | H | Me | —CH₂— | O | O | N |
| 5-13 | H | 4-OH—Ph | H | Me | —CH₂— | O | S | CH |
| 5-14 | H | 4-OH—Ph | H | Me | —(CH₂)₂— | O | O | CH |
| 5-15 | H | 4-OH—Ph | H | Et | —CH₂— | O | O | CH |
| 5-16 | H | 4-OH—Ph | H | Et | —CH₂— | O | S | CH |
| 5-17 | H | 4-OH—Ph | H | tBu | —CH₂— | O | O | CH |
| 5-18 | H | 3-CF₃—Ph | H | Me | —CH₂— | O | O | CH |
| 5-19 | H | 4-iPrO—Ph | H | Me | —CH₂— | O | O | CH |
| 5-20 | H | 4-MeS—Ph | H | Me | —CH₂— | O | O | CH |
| 5-21 | H | 2-NH₂-Ph | H | Me | —CH₂— | O | O | CH |
| 5-22 | H | 3-NH₂-Ph | H | Me | —CH₂— | O | O | CH |
| 5-23 | H | 4-NH₂-Ph | H | Me | —CH₂— | O | O | CH |
| 5-24 | H | 4-NHMe-Ph | H | Me | —CH₂— | O | O | CH |
| 5-25 | H | 4-N(Me)₂-Ph | H | Me | —CH₂— | O | O | CH |
| 5-26 | H | 4-N(Me)₂-Ph | H | Et | —CH₂— | O | O | CH |
| 5-27 | H | 4-Ph—Ph | H | Me | —CH₂— | O | O | CH |
| 5-28 | H | 4-(4-OH-3,5-diMe-Ph)Ph | H | Me | —CH₂— | O | O | CH |
| 5-29 | H | 4-(4-OH-3,5-ditBu-Ph)Ph | H | Me | —CH₂— | O | O | CH |
| 5-30 | H | 4-(4-OH-Bz)Ph | H | Me | —CH₂— | O | O | CH |
| 5-31 | H | 4-PhS—Ph | H | Me | —CH₂— | O | O | CH |
| 5-32 | H | 2-Pyrd(1)-Ph | H | Me | —CH₂— | O | O | CH |
| 5-33 | H | 2-Pyrd(1)-Ph | H | Me | —CH₂— | O | S | CH |
| 5-34 | H | 3-Pyrd(1)-Ph | H | Me | —CH₂— | O | O | CH |
| 5-35 | H | 3-Pyrd(1)-Ph | H | Me | —CH₂— | O | S | CH |
| 5-36 | H | 3-Pyrd(1)-Ph | H | Me | —(CH₂)₂— | O | O | CH |
| 5-37 | H | 3-Pyrd(1)-Ph | H | Et | —CH₂— | O | O | CH |
| 5-38 | H | 4-Pyrd(1)-Ph | H | Me | —CH₂— | O | O | CH |
| 5-39 | H | 4-Pyrd(1)-Ph | H | Me | —CH₂— | O | O | N |
| 5-40 | H | 4-Pyrd(1)-Ph | H | Me | —CH₂— | O | S | CH |
| 5-41 | H | 4-Pyrd(1)-Ph | H | Me | —(CH₂)₃— | O | O | CH |
| 5-42 | H | 4-Pyrd(1)-Ph | H | Et | —CH₂— | O | O | CH |
| 5-43 | H | 4-Pyrd(1)-Ph | H | Et | —CH₂— | O | S | CH |
| 5-44 | H | 2-Pip(1)-Ph | H | Me | —CH₂— | O | O | CH |
| 5-45 | H | 2-Pip(1)-Ph | H | Me | —CH₂— | O | S | CH |
| 5-46 | H | 3-Pip(1)-Ph | H | Me | —CH₂— | O | O | CH |
| 5-47 | H | 3-Pip(1)-Ph | H | Me | —CH₂— | O | S | CH |
| 5-48 | H | 3-Pip(1)-Ph | H | Et | —(CH₂)₃— | S | O | CH |
| 5-49 | H | 4-Pip(1)-Ph | H | Me | —CH₂— | O | O | CH |
| 5-50 | H | 4-Pip(1)-Ph | H | Me | —CH₂— | O | O | N |
| 5-51 | H | 4-Pip(1)-Ph | H | Me | —CH₂— | O | S | CH |
| 5-52 | H | 4-Pip(1)-Ph | H | Me | —(CH₂)₂— | O | O | CH |
| 5-53 | H | 4-Pip(1)-Ph | H | Me | —(CH₂)₃— | O | O | CH |
| 5-54 | H | 4-Pip(1)-Ph | H | Et | —CH₂— | O | O | CH |
| 5-55 | H | 4-Pip(1)-Ph | H | Et | —CH₂— | O | S | CH |
| 5-56 | H | 4-Pip(1)-Ph | H | tBu | —CH₂— | O | O | CH |
| 5-57 | H | 4-Pip(1)-Ph | 4-Cl | Me | —CH₂— | O | O | CH |
| 5-58 | 2-MeO | 4-Pip(1)-Ph | H | Me | —CH₂— | O | O | CH |
| 5-59 | H | 2-Mor(4)-Ph | H | Me | —CH₂— | O | O | CH |
| 5-60 | H | 2-Mor(4)-Ph | H | Me | —CH₂— | O | S | CH |
| 5-61 | H | 2-Mor(4)-Ph | H | Me | —(CH₂)₃— | O | O | CH |
| 5-62 | H | 3-Mor(4)-Ph | H | Me | —CH₂— | O | O | CH |
| 5-63 | H | 3-Mor(4)-Ph | H | Me | —CH₂— | O | S | CH |

TABLE 5-continued

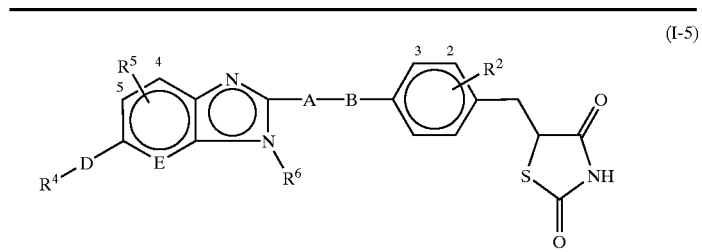

(I-5)

| Cpd. No. | R² | R⁴ | R⁵ | R⁶ | -A- | B | D | E |
|---|---|---|---|---|---|---|---|---|
| 5-64 | H | 3-Mor(4)-Ph | H | Me | —(CH₂)₃— | O | O | CH |
| 5-65 | H | 3-Mor(4)-Ph | H | Et | —CH₂— | O | O | CH |
| 5-66 | H | 4-Mor(4)-Ph | H | Me | —CH₂— | O | O | CH |
| 5-67 | H | 4-Mor(4)-Ph | H | Me | —CH₂— | O | O | N |
| 5-68 | H | 4-Mor(4)-Ph | H | Me | —CH₂— | O | S | CH |
| 5-69 | H | 4-Mor(4)-Ph | H | Et | —CH₂— | O | O | CH |
| 5-70 | H | 4-Mor(4)-Ph | H | Et | —CH₂— | O | S | CH |
| 5-71 | H | 4-TioMor(4)-Ph | H | Me | —CH₂— | O | O | CH |
| 5-72 | H | 4-Pipra(1)-Ph | H | Me | —CH₂— | O | O | CH |
| 5-73 | H | 4-Pipra(1)-Ph | H | Me | —CH₂— | O | S | CH |
| 5-74 | H | 4-Pipra(1)-Ph | H | Me | —(CH₂)₃— | O | O | CH |
| 5-75 | H | 4-Pipra(1)-Ph | H | Et | —CH₂— | O | O | CH |
| 5-76 | H | 4-NO₂—Ph | H | Me | —CH₂— | O | O | CH |
| 5-77 | H | 3-Cl-4-OH—Ph | H | Me | —CH₂— | O | O | CH |
| 5-78 | H | 2-Cl-4-OH-3,5-diMe-Ph | H | Me | —CH₂— | O | O | CH |
| 5-79 | H | 2-Cl-4-OH-3,5,-diMe-Ph | H | Me | —CH₂— | O | O | N |
| 5-80 | H | 2-Cl-4-OH-3,5-diMe-Ph | H | Me | —CH₂— | O | S | CH |
| 5-81 | H | 2-Cl-4-OH-3,5-diMe-Ph | H | Me | —(CH₂)₂— | O | O | CH |
| 5-82 | H | 2-Cl-4-OH-3,5-diMe-Ph | H | Me | —(CH₂)₄— | O | O | CH |
| 5-83 | H | 2-Cl-4-OH-3,5-diMe-Ph | H | Et | —CH₂— | O | O | CH |
| 5-84 | H | 2-Cl-4-OH-3,5-diMe-Ph | H | Et | —CH₂— | O | S | CH |
| 5-85 | H | 2-Cl-4-OH-3,5-diMe-Ph | H | tBu | —CH₂— | O | O | CH |
| 5-86 | H | 2-Cl-4-OH-3,5-diMe-Ph | 5-MeO | Me | —CH₂— | O | O | CH |
| 5-87 | 3-Cl | 2-Cl-4-OH-3,5-diMe-Ph | H | Me | —CH₂— | O | O | CH |
| 5-88 | 2-MeO | 2-Cl-4-OH-3,5-diMe-Ph | H | Me | —CH₂— | O | O | CH |
| 5-89 | H | 3-Cl-5-OH-2,6-diMe-Ph | H | Me | —CH₂— | O | O | CH |
| 5-90 | H | 4-Cl-3-OH-2,5-diMe-Ph | H | Me | —CH₂— | O | O | CH |
| 5-91 | H | 3-Cl-4-NH₂—Ph | H | Me | —CH₂— | O | O | CH |
| 5-92 | H | 3,5-diCl-4-NH₂—Ph | H | Me | —CH₂— | O | O | CH |
| 5-93 | H | 4-NHMe-3-Cl-Ph | H | Me | —CH₂— | O | O | CH |
| 5-94 | H | 3-Cl-4-Pyrd(1)-Ph | H | Me | —CH₂— | O | O | CH |
| 5-95 | H | 3-OH-4-Pyrd(1)-Ph | H | Me | —CH₂— | O | O | CH |
| 5-96 | H | 3-Cl-6-Me-4-Pyrd(1)-Ph | H | Me | —CH₂— | O | O | CH |
| 5-97 | H | 2-Me-4-Mor(4)-Ph | H | Me | —CH₂— | O | O | CH |
| 5-98 | H | 2-OH-3-Me-Ph | H | Me | —CH₂— | O | O | CH |
| 5-99 | H | 2-OH-4-Me-Ph | H | Me | —CH₂— | O | O | CH |
| 5-100 | H | 2-OH-3,4-diMe-Ph | H | Me | —CH₂— | O | O | CH |
| 5-101 | H | 3-OH-2-Me-Ph | H | Me | —CH₂— | O | O | CH |
| 5-102 | H | 3-OH-4-Me-Ph | H | Me | —CH₂— | O | O | CH |
| 5-103 | H | 3-OH-5-Me-Ph | H | Me | —CH₂— | O | O | CH |
| 5-104 | H | 3-OH-6-Me-Ph | H | Me | —CH₂— | O | O | CH |
| 5-105 | H | 3-OH-2,4-diMe-Ph | H | Me | —CH₂— | O | O | CH |
| 5-106 | H | 4-OH-2-Me-Ph | H | Me | —CH₂— | O | O | CH |
| 5-107 | H | 4-OH-3-Me-Ph | H | Me | —CH₂— | O | O | CH |
| 5-108 | H | 4-OH-3-Me-Ph | H | Me | —CH₂— | O | S | CH |

TABLE 5-continued

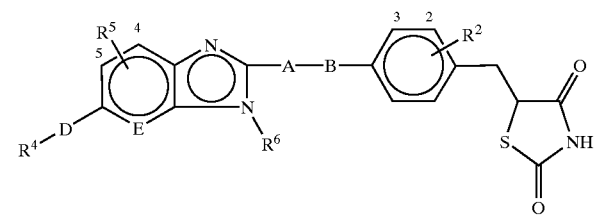

(I-5)

| Cpd. No. | R² | R⁴ | R⁵ | R⁶ | -A- | B | D | E |
|---|---|---|---|---|---|---|---|---|
| 5-109 | H | 4-OH-3-Me-Ph | H | Et | —CH₂— | O | O | CH |
| 5-110 | H | 4-OH-3-Me-Ph | 5-Cl | Me | —CH₂— | O | O | CH |
| 5-111 | H | 4-OH-2-tBu-Ph | H | Me | —CH₂— | O | O | CH |
| 5-112 | H | 4-OH-3-tBu-Ph | H | Me | —CH₂— | O | O | CH |
| 5-113 | H | 4-OH-2,3-diMe-Ph | H | Me | —CH₂— | O | O | CH |
| 5-114 | H | 4-OH-2,3-diMe-Ph | H | Me | —CH₂— | O | S | CH |
| 5-115 | H | 4-OH-2,3-diMe-Ph | H | Me | —(CH₂)₃— | S | O | CH |
| 5-116 | H | 4-OH-2,3-diMe-Ph | H | Et | —CH₂— | O | O | CH |
| 5-117 | H | 4-OH-2,5-diMe-Ph | H | Me | —CH₂— | O | O | CH |
| 5-118 | H | 4-OH-3,5-diMe-Ph | H | Me | —CH₂— | O | O | CH |
| 5-119 | H | 4-OH-3,5-diMe-Ph | H | Me | —CH₂— | O | O | N |
| 5-120 | H | 4-OH-3,5-diMe-Ph | H | Me | —CH₂— | O | S | CH |
| 5-121 | H | 4-OH-3,5-diMe-Ph | H | Me | —CH₂— | S | O | CH |
| 5-122 | H | 4-OH-3,5-diMe-Ph | H | Me | —(CH₂)₂— | O | O | CH |
| 5-123 | H | 4-OH-3,5-diMe-Ph | H | Et | —CH₂— | O | O | CH |
| 5-124 | H | 4-OH-3,5-diMe-Ph | H | Et | —CH₂— | O | S | CH |
| 5-125 | H | 4-OH-3,5-diMe-Ph | H | sBu | —CH₂— | O | O | CH |
| 5-126 | H | 4-OH-3,5-diMe-Ph | H | tBu | —CH₂— | O | O | CH |
| 5-127 | H | 4-OH-3,5-diMe-Ph | H | Ph | —CH₂— | O | O | CH |
| 5-128 | H | 3,5-diEt-4-OH—Ph | H | Me | —CH₂— | O | O | CH |
| 5-129 | H | 3-tBu-4-OH-5-Me-Ph | H | Me | —CH₂— | O | O | CH |
| 5-130 | H | 3-tBu-4-OH-5-Me-Ph | H | Me | —CH₂— | O | S | CH |
| 5-131 | H | 4-OH-3,5-diPr—Ph | H | Me | —CH₂— | O | O | CH |
| 5-132 | H | 4-OH-3,5-diiPr—Ph | H | Me | —CH₂— | O | O | CH |
| 5-133 | H | 3,5-ditBu-4-OH—Ph | H | Me | —CH₂— | O | O | CH |
| 5-134 | H | 3,5-ditBu-4-OH—Ph | H | Me | —CH₂— | O | O | N |
| 5-135 | H | 3,5-ditBu-4-OH—Ph | H | Me | —CH₂— | O | S | CH |
| 5-136 | H | 3,5-ditBu-4-OH—Ph | H | Me | —CH₂— | S | S | CH |
| 5-137 | H | 3,5-ditBu-4-OH—Ph | H | Me | —(CH₂)₂— | O | O | CH |
| 5-138 | H | 3,5-ditBu-4-OH—Ph | H | Me | —(CH₂)₂— | O | S | CH |
| 5-139 | H | 3,5-ditBu-4-OH—Ph | H | Me | —(CH₂)₃— | O | S | CH |
| 5-140 | H | 3,5-ditBu-4-OH—Ph | H | Et | —CH₂— | O | O | CH |
| 5-141 | H | 3,5-ditBu-4-OH—Ph | H | Et | —CH₂— | O | S | CH |
| 5-142 | H | 3,5-ditBu-4-OH—Ph | H | tBu | —CH₂— | O | O | CH |

TABLE 5-continued (I-5)

| Cpd. No. | R² | R⁴ | R⁵ | R⁶ | -A- | B | D | E |
|---|---|---|---|---|---|---|---|---|
| 5-143 | H | 3,5-ditBu-4-OH—Ph | 5-Cl | Me | —CH₂— | O | S | CH |
| 5-144 | H | 4-OH-2,3,5-triMe-Ph | H | H | —CH₂— | O | S | CH |
| 5-145 | H | 4-OH-2,3,5-triMe-Ph | H | Me | —CH₂— | O | O | CH |
| 5-146 | H | 4-OH-2,3,5-triMe-Ph | H | Me | —CH₂— | O | O | N |
| 5-147 | H | 4-OH-2,3,5-triMe-Ph | H | Me | —CH₂— | O | S | CH |
| 5-148 | H | 4-OH-2,3,5-triMe-Ph | H | Me | —(CH₂)₂— | O | O | CH |
| 5-149 | H | 4-OH-2,3,5-triMe-Ph | H | Me | —(CH₂)3— | O | O | CH |
| 5-150 | H | 4-OH-2,3,5-triMe-Ph | H | Et | —CH₂— | O | O | CH |
| 5-151 | H | 4-OH-2,3,5-triMe-Ph | H | Et | —CH₂— | O | S | CH |
| 5-152 | H | 4-OH-2,3,5-triMe-Ph | H | iPr | —CH₂— | O | O | CH |
| 5-153 | H | 4-OH-2,3,5-triMe-Ph | H | tBu | —CH₂— | O | O | CH |
| 5-154 | H | 4-OH-2,3,5-triMe-Ph | H | Ph | —CH₂— | O | O | CH |
| 5-155 | H | 4-OH-2,3,5-triMe-Ph | H | Bz | —CH₂— | O | O | CH |
| 5-156 | H | 4-OH-2,3,5-triMe-Ph | 5-Cl | Me | —CH₂— | O | O | CH |
| 5-157 | 2-Cl | 4-OH-2,3,5-triMe-Ph | H | Me | —CH₂— | O | O | CH |
| 5-158 | 2-MeO | 4-OH-2,3,5-triMe-Ph | H | Me | —CH₂— | O | O | CH |
| 5-159 | H | 4-OH-2,3,6-triMe-Ph | H | Me | —CH₂— | O | O | CH |
| 5-160 | H | 4-OH-2,3,5,6-tetraMe-Ph | H | Me | —CH₂— | O | O | CH |
| 5-161 | H | 4-OH-3,5-diMeO—Ph | H | Me | —CH₂— | O | O | CH |
| 5-162 | H | 3-NH₂-4-Me-Ph | H | Me | —CH₂— | O | O | CH |
| 5-163 | H | 4-NH₂-2,3-diMe-Ph | H | Me | —CH₂— | O | O | CH |
| 5-164 | H | 4-NH₂-2,6-diMe-Ph | H | Me | —CH₂— | O | O | CH |
| 5-165 | H | 4-NH₂-3,5-diMe-Ph | H | H | —CH₂— | O | O | CH |
| 5-166 | H | 4-NH₂-3,5-diMe-Ph | H | Me | —CH₂— | O | O | CH |
| 5-167 | H | 4-NH₂-3,5-diMe-Ph | H | Me | —CH₂— | O | O | N |
| 5-168 | H | 4-NH₂-3,5-diMe-Ph | H | Me | —CH₂— | O | S | CH |
| 5-169 | H | 4-NH₂-3,5-diMe-Ph | H | Me | —(CH₂)₂— | O | O | CH |
| 5-170 | H | 4-NH₂-3,5-diMe-Ph | H | Et | —CH₂— | O | O | CH |
| 5-171 | H | 4-NH₂-3,5 diMe-Ph | H | Et | —CH₂— | O | S | CH |
| 5-172 | H | 4-NH₂-3,5-diMe-Ph | H | tBu | —CH₂— | O | O | CH |
| 5-173 | H | 4-NH₂-3,5-diMe-Ph | H | Ph | —CH₂— | O | O | CH |
| 5-174 | H | 4-NH₂-3,5-diMe-Ph | H | Bz | —CH₂— | O | O | CH |
| 5-175 | H | 4-NH₂-3,5-diEt-Ph | H | Me | —CH₂— | O | O | CH |

TABLE 5-continued

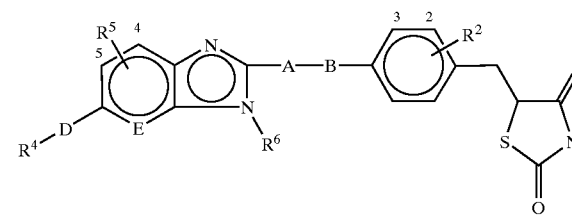

(I-5)

| Cpd. No. | R² | R⁴ | R⁵ | R⁶ | -A- | B | D | E |
|---|---|---|---|---|---|---|---|---|
| 5-176 | H | 4-NHMe-3,5-diMe-Ph | H | Me | —CH₂— | O | O | CH |
| 5-177 | H | 4-NHAc-3,5-diMe-Ph | H | Me | —CH₂— | O | O | CH |
| 5-178 | H | 4-NO₂-3,5-diMe-Ph | H | Me | —CH₂— | O | O | CH |
| 5-179 | H | 4-NO₂-3,5-diMe-Ph | H | Me | —CH₂— | O | S | CH |
| 5-180 | H | Pyr(2) | H | Me | —CH₂— | O | O | CH |
| 5-181 | H | Pyr(2) | H | Me | —CH₂— | O | O | N |
| 5-182 | H | Pyr(2) | H | Me | —CH₂— | O | S | CH |
| 5-183 | H | Pyr(2) | H | Me | —(CH₂)₂— | O | O | CH |
| 5-184 | H | Pyr(2) | H | Me | —(CH₂)₃— | O | O | CH |
| 5-185 | H | Pyr(2) | H | Et | —CH₂— | O | O | CH |
| 5-186 | H | Pyr(2) | H | Et | —CH₂— | O | S | CH |
| 5-187 | H | Pyr(2) | H | tBu | —CH₂— | O | O | CH |
| 5-188 | H | Pyr(2) | H | Ph | —CH₂— | O | O | CH |
| 5-189 | H | Pyr(2) | 5-Cl | Me | —CH₂— | O | O | CH |
| 5-190 | H | 5-Cl-Pyr(2) | H | Me | —CH₂— | O | O | CH |
| 5-191 | H | 6-Cl-Pyr(2) | H | Me | —CH₂— | O | O | CH |
| 5-192 | H | 6-Me-Pyr(2) | H | Me | —CH₂— | O | O | CH |
| 5-193 | H | 6-MeO-Pyr(2) | H | Me | —CH₂— | O | O | CH |
| 5-194 | H | 3-NH₂-Pyr(2) | H | Me | —CH₂— | O | O | CH |
| 5-195 | H | 5-NH₂-Pyr(2) | H | Me | —CH₂— | O | O | CH |
| 5-196 | H | 3-NO₂-Pyr(2) | H | Me | —CH₂— | O | O | CH |
| 5-197 | H | 5-NO₂-Pyr(2) | H | Me | —CH₂— | O | O | CH |
| 5-198 | H | 5-NH₂-6-Cl-Pyr(2) | H | Me | —CH₂— | O | O | CH |
| 5-199 | 3-MeO | 5-NH₂-6-Cl-Pyr(2) | 5-MeO | Et | —(CH₂)₄— | S | S | CH |
| 5-200 | H | Pyr(3) | H | Me | —CH₂— | O | O | CH |
| 5-201 | H | Pyr(3) | H | Me | —CH₂— | O | O | N |
| 5-202 | H | Pyr(3) | H | Me | —CH₂— | O | S | CH |
| 5-203 | H | Pyr(3) | H | Me | —(CH₂)₂— | O | O | CH |
| 5-204 | H | Pyr(3) | H | Me | —(CH₂)₃— | O | O | CH |
| 5-205 | H | Pyr(3) | H | Et | —CH₂— | O | O | CH |
| 5-206 | H | Pyr(3) | H | Et | —CH₂— | O | S | CH |
| 5-207 | H | Pyr(3) | H | tBu | —CH₂— | O | O | CH |
| 5-208 | H | Pyr(3) | H | Pn | —(CH₂)₃— | O | O | CH |
| 5-209 | H | Pyr(3) | H | Ph | —CH₂— | O | O | CH |
| 5-210 | H | Pyr(3) | H | Ph | —CH₂— | O | S | CH |
| 5-211 | H | Pyr(3) | H | Bz | —CH₂— | O | O | CH |
| 5-212 | 2-Cl | Pyr(3) | H | Me | —CH₂— | O | O | CH |
| 5-213 | H | 5-MeO-Pyr(3) | H | Me | —CH₂— | O | O | CH |
| 5-214 | H | 6-MeO-Pyr(3) | H | Me | —CH₂— | O | O | CH |
| 5-215 | H | 6-MeO-Pyr(3) | H | Me | —CH₂— | O | S | CH |
| 5-216 | H | 6-MeO-Pyr(3) | H | Me | —(CH₂)₃— | O | O | CH |
| 5-217 | H | 6-iPrO-Pyr(3) | H | Me | —CH₂— | O | O | CH |
| 5-218 | H | 6-MeO-5-Me-Pyr(3) | H | Me | —CH₂— | O | O | CH |
| 5-219 | H | 2-NO₂-6-Me-Pyr(3) | H | Me | —CH₂— | O | O | CH |
| 5-220 | H | Pyr(4) | H | Me | —CH₂— | O | O | CH |
| 5-221 | H | Pyr(4) | H | Me | —CH₂— | O | O | N |
| 5-222 | H | Pyr(4) | H | Me | —CH₂— | O | S | CH |
| 5-223 | H | Pyr(4) | H | Me | —CH₂— | S | S | CH |
| 5-224 | H | Pyr(4) | H | Me | —(CH₂)₂— | O | O | CH |
| 5-225 | H | Pyr(4) | H | Et | —CH₂— | O | O | CH |
| 5-226 | H | Pyr(4) | H | Et | —CH₂— | O | S | CH |
| 5-227 | H | Pyr(4) | H | tBu | —CH₂— | O | O | CH |
| 5-228 | H | Pyr(4) | H | Ph | —CH₂— | O | O | CH |
| 5-229 | H | Pyr(4) | H | Bz | —CH₂— | O | S | CH |
| 5-230 | 3-Cl | Pyr(4) | H | Me | —CH₂— | O | O | CH |
| 5-231 | H | 2-Me-Pyr(4) | H | Me | —CH₂— | O | O | CH |
| 5-232 | H | 2,6-diMe-Pyr(4) | H | Me | —CH₂— | O | O | CH |

TABLE 5-continued (I-5)

| Cpd. No. | R² | R⁴ | R⁵ | R⁶ | -A- | B | D | E |
|---|---|---|---|---|---|---|---|---|
| 5-233 | H | 2,6-diMe-Pyr(4) | H | Me | —CH₂— | O | S | CH |
| 5-234 | H | 3,6-diMe-Pyr(4) | H | Me | —CH₂— | O | O | CH |
| 5-235 | H | 2-MeO-Pyr(4) | H | Me | —CH₂— | O | O | CH |
| 5-236 | H | 4-Imid(1)-Ph | H | Me | —CH₂— | O | O | CH |
| 5-237 | H | 4-Tz-Ph | H | Me | —CH₂— | O | O | CH |
| 5-238 | H | 4-Ada(1)-Ph | H | Me | —CH₂— | O | O | CH |
| 5-239 | H | 4-CN-Ph | H | Me | —CH₂— | O | O | CH |
| 5-240 | H | 4-Bz-3-OH—Ph | H | Me | —CH₂— | O | O | CH |
| 5-241 | H | pentaF—Ph | H | Me | —CH₂— | O | O | CH |
| 5-242 | H | 4-NHCOPh—Ph | H | Me | —CH₂— | O | O | CH |
| 5-243 | H | 4-NHCO(3-Cl-Ph)—Ph | H | Me | —CH₂— | O | O | CH |
| 5-244 | H | 4-NHCO(2,4-diF-Ph)—Ph | H | Me | —CH₂— | O | O | CH |
| 5-245 | H | 4-NHCO(4-OH-3,5-ditBu-Ph)—Ph | H | Me | —CH₂— | O | O | CH |
| 5-246 | H | 4-NHCONp(1)-Ph | H | Me | —CH₂— | O | O | CH |
| 5-247 | H | 4-NHCO(3-Cl-Bz)—Ph | H | Me | —CH₂— | O | O | CH |
| 5-248 | H | 4-NHCOcPn-Ph | H | Me | —CH₂— | O | O | CH |
| 5-249 | H | 4-NHCOcHx-Ph | H | Me | —CH₂— | O | O | CH |
| 5-250 | H | 4-NHCOPyr(3)-Ph | H | Me | —CH₂— | O | O | CH |
| 5-251 | H | 4-NHCOPyr(4)-Ph | H | Me | —CH₂— | O | O | CH |
| 5-252 | H | 4-NHHx-Ph | H | Me | —CH₂— | O | O | CH |
| 5-253 | H | 4-NH(Ac)Hx-Ph | H | Me | —CH₂— | O | O | CH |

TABLE 6

(I-6)

| Cpd. No. | R² | R⁴ | R⁵ | R⁶ | —A— | B | D | E |
|---|---|---|---|---|---|---|---|---|
| 6-1 | H | 4-F—Ph | H | Me | —CH₂— | O | O | CH |
| 6-2 | H | 4-Cl—Ph | H | Me | —CH₂— | O | O | CH |
| 6-3 | H | 2-OH—Ph | H | Me | —CH₂— | O | O | CH |
| 6-4 | H | 2-OH—Ph | H | Me | —CH₂— | O | S | CH |
| 6-5 | H | 3-OH—Ph | H | Me | —CH₂— | O | O | CH |
| 6-6 | H | 3-OH—Ph | H | Me | —CH₂— | O | S | CH |
| 6-7 | H | 4-OH—Ph | H | Me | —CH₂— | O | O | CH |
| 6-8 | H | 4-OH—Ph | H | Me | —CH₂— | O | O | N |
| 6-9 | H | 4-OH—Ph | H | Me | —CH₂— | O | S | CH |
| 6-10 | H | 4-OH—Ph | H | Et | —CH₂— | O | O | CH |
| 6-11 | H | 4-OH—Ph | H | Et | —CH₂— | O | S | CH |
| 6-12 | H | 3-CF₃—Ph | H | Me | —CH₂— | O | O | CH |
| 6-13 | H | 4-iPrO—Ph | H | Me | —CH₂— | O | O | CH |
| 6-14 | H | 4-MeS—Ph | H | Me | —CH₂— | O | O | CH |
| 6-15 | H | 2-NH₂—Ph | H | Me | —CH₂— | O | O | CH |
| 6-16 | H | 3-NH₂—Ph | H | Me | —CH₂— | O | O | CH |
| 6-17 | H | 4-NH₂—Ph | H | Me | —CH₂— | O | O | CH |

TABLE 6-continued (I-6)

| Cpd. No. | R² | R⁴ | R⁵ | R⁶ | —A— | B | D | E |
|---|---|---|---|---|---|---|---|---|
| 6-18 | H | 4-NHMe—Ph | H | Me | —CH₂— | O | O | CH |
| 6-19 | H | 4-N(Me)₂—Ph | H | Me | —CH₂— | O | O | CH |
| 6-20 | H | 4-N(Me)₂—Ph | H | Et | —CH₂— | O | O | CH |
| 6-21 | H | 4-Ph—Ph | H | Me | —CH₂— | O | O | CH |
| 6-22 | H | 4-(4-OH-3,5-diMe—Ph)Ph | H | Me | —CH₂— | O | O | CH |
| 6-23 | H | 4-(4-OH-3,5-ditBu—Ph)Ph | H | Me | —CH₂— | O | O | CH |
| 6-24 | H | 4-(4-OH-Bz)Ph | H | Me | —CH₂— | O | O | CH |
| 6-25 | H | 4-PhS—Ph | H | Me | —CH₂— | O | O | CH |
| 6-26 | H | 2-Pyrd(1)-Ph | H | Me | —CH₂— | O | O | CH |
| 6-27 | H | 3-Pyrd(1)-Ph | H | Me | —CH₂— | O | O | CH |
| 6-28 | H | 3-Pyrd(1)-Ph | H | Me | —CH₂— | O | S | CH |
| 6-29 | H | 3-Pyrd(1)-Ph | H | Me | —(CH₂)₂— | O | O | CH |
| 6-30 | H | 3-Pyrd(1)-Ph | H | Et | —CH₂— | O | O | CH |
| 6-31 | H | 4-Pyrd(1)-Ph | H | Me | —CH₂— | O | O | CH |
| 6-32 | H | 4-Pyrd(1)-Ph | H | Me | —CH₂— | O | S | CH |
| 6-33 | H | 4-Pyrd(1)-Ph | H | Me | —(CH₂)₃— | O | O | CH |
| 6-34 | H | 2-Pip(1)-Ph | H | Me | —CH₂— | O | O | CH |
| 6-35 | H | 3-Pip(1)-Ph | H | Me | —CH₂— | O | O | CH |
| 6-36 | H | 3-Pip(1)-Ph | H | Me | —CH₂— | O | S | CH |
| 6-37 | H | 3-Pip(1)-Ph | H | Et | —(CH₂)₃— | S | O | CH |
| 6-38 | H | 4-Pip(1)-Ph | H | Me | —CH₂— | O | O | CH |
| 6-39 | H | 4-Pip(1)-Ph | H | Me | —CH₂— | O | S | CH |
| 6-40 | H | 4-Pip(1)-Ph | H | Me | —(CH₂)₂— | O | O | CH |
| 6-41 | H | 4-Pip(1)-Ph | H | Me | —(CH₂)₃— | O | O | CH |
| 6-42 | H | 4-Pip(1)-Ph | H | tBu | —CH₂— | O | O | CH |
| 6-43 | H | 4-Pip(1)-Ph | 4-Cl | Me | —CH₂— | O | O | CH |
| 6-44 | 2-MeO | 4-Pip(1)-Ph | H | Me | —CH₂— | O | O | CH |
| 6-45 | H | 2-Mor(4)-Ph | H | Me | —CH₂— | O | O | CH |
| 6-46 | H | 2-Mor(4)-Ph | H | Me | —(CH₂)₃— | O | O | CH |
| 6-47 | H | 3-Mor(4)-Ph | H | Me | —CH₂— | O | O | CH |
| 6-48 | H | 3-Mor(4)-Ph | H | Me | —CH₂— | O | S | CH |
| 6-49 | H | 3-Mor(4)-Ph | H | Me | —(CH₂)₃— | O | O | CH |
| 6-50 | H | 3-Mor(4)-Ph | H | Et | —CH₂— | O | O | CH |
| 6-51 | H | 4-Mor(4)-Ph | H | Me | —CH₂— | O | O | CH |
| 6-52 | H | 4-Mor(4)-Ph | H | Me | —CH₂— | O | S | CH |
| 6-53 | H | 4-TioMor(4)-Ph | H | Me | —CH₂— | O | O | CH |
| 6-54 | H | 4-Pipra(1)-Ph | H | Me | —CH₂— | O | O | CH |
| 6-55 | H | 4-Pipra(1)-Ph | H | Me | —(CH₂)₃— | O | O | CH |
| 6-56 | H | 4-Pipra(1)-Ph | H | Et | —CH₂— | O | O | CH |
| 6-57 | H | 4-NO₂—Ph | H | Me | —CH₂— | O | O | CH |
| 6-58 | H | 2-Cl-4-OH-3,5-diMe—Ph | H | Me | —CH₂— | O | O | CH |
| 6-59 | H | 2-Cl-4-OH-3,5-diMe—Ph | H | Me | —CH₂— | O | O | N |
| 6-60 | H | 2-Cl-4-OH-3,5-diMe—Ph | H | Me | —CH₂— | O | S | CH |
| 6-61 | H | 2-Cl-4-OH-3,5-diMe—Ph | H | Me | —(CH₂)₄— | O | O | CH |
| 6-62 | H | 2-Cl-4-OH-3,5-diMe—Ph | H | Et | —CH₂— | O | O | CH |
| 6-63 | H | 2-Cl-4-OH-3,5-diMe—Ph | H | Et | —CH₂— | O | S | CH |
| 6-64 | H | 2-Cl-4-OH-3,5-diMe—Ph | 6-MeO | Me | —CH₂— | O | O | CH |
| 6-65 | 3-Cl | 2-Cl-4-OH-3,5-diMe—Ph | H | Me | —CH₂— | O | O | CH |
| 6-66 | 2-MeO | 2-Cl-4-OH-3,5-diMe—Ph | H | Me | —CH₂— | O | O | CH |
| 6-67 | H | 4-Cl-3-OH-2,5-diMe—Ph | H | Me | —CH₂— | O | O | CH |
| 6-68 | H | 3-Cl-4-NH₂—Ph | H | Me | —CH₂— | O | O | CH |

TABLE 6-continued (I-6)

| Cpd. No. | R² | R⁴ | R⁵ | R⁶ | —A— | B | D | E |
|---|---|---|---|---|---|---|---|---|
| 6-69 | H | 3,5-diCl-4-NH₂—Ph | H | Me | —CH₂— | O | O | CH |
| 6-70 | H | 4-NHMe-3-Cl—Ph | H | Me | —CH₂— | O | O | CH |
| 6-71 | H | 3-Cl-4-Pyrd(1)-Ph | H | Me | —CH₂— | O | O | CH |
| 6-72 | H | 3-OH-4-Pyrd(1)-Ph | H | Me | —CH₂— | O | O | CH |
| 6-73 | H | 3-Cl-6-Me-4-Pyrd(1)-Ph | H | Me | —CH₂— | O | O | CH |
| 6-74 | H | 2-Me-4-Mor(4)-Ph | H | Me | —CH₂— | O | O | CH |
| 6-75 | H | 2-OH-3-Me—Ph | H | Me | —CH₂— | O | O | CH |
| 6-76 | H | 2-OH-4-Me—Ph | H | Me | —CH₂— | O | O | CH |
| 6-77 | H | 2-OH-3,4-diMe—Ph | H | Me | —CH₂— | O | O | CH |
| 6-78 | H | 3-OH-2-Me—Ph | H | Me | —CH₂— | O | O | CH |
| 6-79 | H | 3-OH-4-Me—Ph | H | Me | —CH₂— | O | O | CH |
| 6-80 | H | 3-OH-5-Me—Ph | H | Me | —CH₂— | O | O | CH |
| 6-81 | H | 3-OH-6-Me—Ph | H | Me | —CH₂— | O | O | CH |
| 6-82 | H | 3-OH-2,4-diMe—Ph | H | Me | —CH₂— | O | O | CH |
| 6-83 | H | 4-OH-2-Me—Ph | H | Me | —CH₂— | O | O | CH |
| 6-84 | H | 4-OH-3-Me—Ph | H | Me | —CH₂— | O | O | CH |
| 6-85 | H | 4-OH-3-Me—Ph | H | Et | —CH₂— | O | O | CH |
| 6-86 | H | 4-OH-3-Me—Ph | 6-Cl | Me | —CH₂— | O | O | CH |
| 6-87 | H | 4-OH-2-tBu—Ph | H | Me | —CH₂— | O | O | CH |
| 6-88 | H | 4-OH-2,3-diMe—Ph | H | Me | —CH₂— | O | O | CH |
| 6-89 | H | 4-OH-2,3-diMe—Ph | H | Me | —CH₂— | O | S | CH |
| 6-90 | H | 4-OH-2,3-diMe—Ph | H | Me | —(CH₂)₃— | S | O | CH |
| 6-91 | H | 4-OH-2,3-diMe—Ph | H | Et | —CH₂— | O | O | CH |
| 6-92 | H | 4-OH-2,5-diMe—Ph | H | Me | —CH₂— | O | O | CH |
| 6-93 | H | 4-OH-3,5-diMe—Ph | H | Me | —CH₂— | O | O | CH |
| 6-94 | H | 4-OH-3,5-diMe—Ph | H | Me | —CH₂— | O | O | N |
| 6-95 | H | 4-OH-3,5-diMe—Ph | H | Me | —CH₂— | O | S | CH |
| 6-96 | H | 4-OH-3,5-diMe—Ph | H | Me | —CH₂— | S | O | CH |
| 6-97 | H | 4-OH-3,5-diMe—Ph | H | Me | —(CH₂)₂— | O | O | CH |
| 6-98 | H | 4-OH-3,5-diMe—Ph | H | Et | —CH₂— | O | O | CH |
| 6-99 | H | 4-OH-3,5-diMe—Ph | H | Et | —CH₂— | O | S | CH |
| 6-100 | H | 4-OH-3,5-diMe—Ph | H | sBu | —CH₂— | O | O | CH |
| 6-101 | H | 4-OH-3,5-diMe—Ph | H | Ph | —CH₂— | O | O | CH |
| 6-102 | H | 3,5-diEt-4-OH—Ph | H | Me | —CH₂— | O | O | CH |
| 6-103 | H | 3-tBu-4-OH-5-Me—Ph | H | Me | —CH₂— | O | O | CH |
| 6-104 | H | 3-tBu-4-OH-5-Me—Ph | H | Me | —CH₂— | O | S | CH |
| 6-105 | H | 4-OH-3,5-diPr—Ph | H | Me | —CH₂— | O | O | CH |
| 6-106 | H | 4-OH-3,5-diiPr—Ph | H | Me | —CH₂— | O | O | CH |

TABLE 6-continued

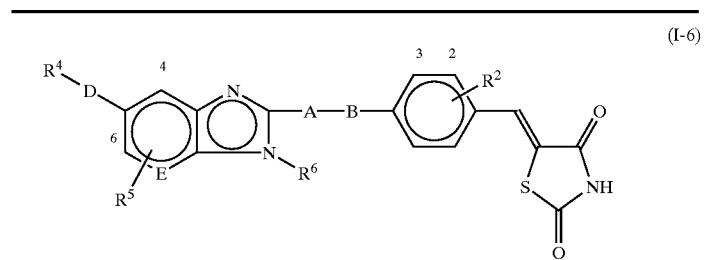

(I-6)

| Cpd. No. | R² | R⁴ | R⁵ | R⁶ | —A— | B | D | E |
|---|---|---|---|---|---|---|---|---|
| 6-107 | H | 3,5-ditBu-4-OH—Ph | H | Me | —CH₂— | O | O | CH |
| 6-108 | H | 3,5-ditBu-4-OH—Ph | H | Me | —CH₂— | O | O | N |
| 6-109 | H | 3,5-ditBu-4-OH—Ph | H | Me | —CH₂— | O | S | CH |
| 6-110 | H | 3,5-ditBu-4-OH—Ph | H | Me | —CH₂— | S | S | CH |
| 6-111 | H | 3,5-ditBu-4-OH—Ph | H | Me | —(CH₂)₂— | O | S | CH |
| 6-112 | H | 3,5-ditBu-4-OH—Ph | H | Me | —(CH₂)₃— | O | S | CH |
| 6-113 | H | 3,5-ditBu-4-OH—Ph | H | Et | —CH₂— | O | O | CH |
| 6-114 | H | 3,5-ditBu-4-OH—Ph | H | Et | —CH₂— | O | S | CH |
| 6-115 | H | 3,5-ditBu-4-OH—Ph | 6-Cl | Me | —CH₂— | O | S | CH |
| 6-116 | H | 4-OH-2,3,5-triMe—Ph | H | H | —CH₂— | O | S | CH |
| 6-117 | H | 4-OH-2,3,5-triMe—Ph | H | Me | —CH₂— | O | O | CH |
| 6-118 | H | 4-OH-2,3,5-triMe—Ph | H | Me | —CH₂— | O | O | N |
| 6-119 | H | 4-OH-2,3,5-triMe—Ph | H | Me | —CH₂— | O | S | CH |
| 6-120 | H | 4-OH-2,3,5-triMe—Ph | H | Me | —(CH₂)₂— | O | O | CH |
| 6-121 | H | 4-OH-2,3,5-triMe—Ph | H | Me | —(CH₂)₃— | O | O | CH |
| 6-122 | H | 4-OH-2,3,5-triMe—Ph | H | Et | —CH₂— | O | O | CH |
| 6-123 | H | 4-OH-2,3,5-triMe—Ph | H | Et | —CH₂— | O | S | CH |
| 6-124 | H | 4-OH-2,3,5-triMe—Ph | H | iPr | —CH₂— | O | O | CH |
| 6-125 | H | 4-OH-2,3,5-triMe—Ph | H | Ph | —CH₂— | O | O | CH |
| 6-126 | H | 4-OH-2,3,5-triMe—Ph | H | Bz | —CH₂— | O | O | CH |
| 6-127 | H | 4-OH-2,3,5-triMe—Ph | 6-Cl | Me | —CH₂— | O | O | CH |
| 6-128 | 2-Cl | 4-OH-2,3,5-triMe—Ph | H | Me | —CH₂— | O | O | CH |
| 6-129 | 2-MeO | 4-OH-2,3,5-triMe—Ph | H | Me | —CH₂— | O | O | CH |
| 6-130 | H | 4-OH-2,3,6-triMe—Ph | H | Me | —CH₂— | O | O | CH |
| 6-131 | H | 4-OH-2,3,5,6-tetraMe—Ph | H | Me | —CH₂— | O | O | CH |
| 6-132 | H | 4-OH-3,5-diMeO—Ph | H | Me | —CH₂— | O | O | CH |
| 6-133 | H | 3-NH₂-4-Me—Ph | H | Me | —CH₂— | O | O | CH |
| 6-134 | H | 4-NH₂-2,3-diMe—Ph | H | Me | —CH₂— | O | O | CH |
| 6-135 | H | 4-NH₂-2,6-diMe—Ph | H | Me | —CH₂— | O | O | CH |
| 6-136 | H | 4-NH₂-3,5-diMe—Ph | H | H | —CH₂— | O | O | CH |
| 6-137 | H | 4-NH₂-3,5-diMe—Ph | H | Me | —CH₂— | O | O | CH |
| 6-138 | H | 4-NH₂-3,5-diMe—Ph | H | Me | —CH₂— | O | O | N |

TABLE 6-continued

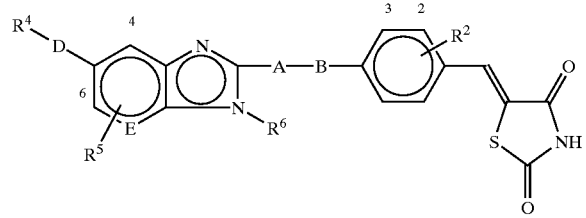

(I-6)

| Cpd. No. | R² | R⁴ | R⁵ | R⁶ | —A— | B | D | E |
|---|---|---|---|---|---|---|---|---|
| 6-139 | H | 4-NH₂-3,5-diMe—Ph | H | Me | —CH₂— | O | S | CH |
| 6-140 | H | 4-NH₂-3,5-diMe—Ph | H | Me | —(CH₂)₂— | O | O | CH |
| 6-141 | H | 4-NH₂-3,5-diMe—Ph | H | Et | —CH₂— | O | O | CH |
| 6-142 | H | 4-NH₂-3,5-diMe—Ph | H | Et | —CH₂— | O | S | CH |
| 6-143 | H | 4-NH₂-3,5-diMe—Ph | H | Ph | —CH₂— | O | O | CH |
| 6-144 | H | 4-NH₂-3,5-diMe—Ph | H | Bz | —CH₂— | O | O | CH |
| 6-145 | H | 4-NHMe-3,5-diMe—Ph | H | Me | —CH₂— | O | O | CH |
| 6-146 | H | 4-NHAc-3,5-diMe—Ph | H | Me | —CH₂— | O | O | CH |
| 6-147 | H | 4-NO₂-3,5-diMe—Ph | H | Me | —CH₂— | O | O | CH |
| 6-148 | H | 4-NO₂-3,5-diMe—Ph | H | Me | —CH₂— | O | S | CH |
| 6-149 | H | Pyr(2) | H | Me | —CH₂— | O | O | CH |
| 6-150 | H | Pyr(2) | H | Me | —CH₂— | O | O | N |
| 6-151 | H | Pyr(2) | H | Me | —CH₂— | O | S | CH |
| 6-152 | H | Pyr(2) | H | Me | —(CH₂)₂— | O | O | CH |
| 6-153 | H | Pyr(2) | H | Me | —(CH₂)₃— | O | O | CH |
| 6-154 | H | Pyr(2) | H | Et | —CH₂— | O | O | CH |
| 6-155 | H | Pyr(2) | H | Et | —CH₂— | O | S | CH |
| 6-156 | H | Pyr(2) | H | Ph | —CH₂— | O | O | CH |
| 6-157 | H | Pyr(2) | 6-Cl | Me | —CH₂— | O | O | CH |
| 6-158 | H | 5-Cl-Pyr(2) | H | Me | —CH₂— | O | O | CH |
| 6-159 | H | 6-Cl-Pyr(2) | H | Me | —CH₂— | O | O | CH |
| 6-160 | H | 6-MeO-Pyr(2) | H | Me | —CH₂— | O | O | CH |
| 6-161 | H | 3-NH₂-Pyr(2) | H | Me | —CH₂— | O | O | CH |
| 6-162 | H | 5-NH₂-Pyr(2) | H | Me | —CH₂— | O | O | CH |
| 6-163 | H | 3-NO₂-Pyr(2) | H | Me | —CH₂— | O | O | CH |
| 6-164 | H | 5-NO₂-Pyr(2) | H | Me | —CH₂— | O | O | CH |
| 6-165 | 3-MeO | 5-NH₂-6-Cl-Pyr(2) | 6-MeO | Et | —(CH₂)₄— | S | S | CH |
| 6-166 | H | Pyr(3) | H | Me | —CH₂— | O | O | CH |
| 6-167 | H | Pyr(3) | H | Me | —CH₂— | O | O | N |
| 6-168 | H | Pyr(3) | H | Me | —CH₂— | O | S | CH |
| 6-169 | H | Pyr(3) | H | Me | —(CH₂)₃— | O | O | CH |
| 6-170 | H | Pyr(3) | H | Et | —CH₂— | O | O | CH |
| 6-171 | H | Pyr(3) | H | Et | —CH₂— | O | S | CH |
| 6-172 | H | Pyr(3) | H | Pn | —(CH₂)₃— | O | O | CH |
| 6-173 | H | Pyr(3) | H | Ph | —CH₂— | O | O | CH |
| 6-174 | H | Pyr(3) | H | Ph | —CH₂— | O | S | CH |
| 6-175 | 2-Cl | Pyr(3) | H | Me | —CH₂— | O | O | CH |
| 6-176 | H | 6-MeO-Pyr(3) | H | Me | —CH₂— | O | O | CH |
| 6-177 | H | 6-MeO-Pyr(3) | H | Me | —CH₂— | O | S | CH |
| 6-178 | H | 6-MeO-Pyr(3) | H | Me | —(CH₂)₃— | O | O | CH |
| 6-179 | H | 6-iPrO-Pyr(3) | H | Me | —CH₂— | O | O | CH |
| 6-180 | H | 6-MeO-5-Me-Pyr(3) | H | Me | —CH₂— | O | O | CH |
| 6-181 | H | 2-NO₂-6-Me-Pyr(3) | H | Me | —CH₂— | O | O | CH |
| 6-182 | H | Pyr(4) | H | Me | —CH₂— | O | O | CH |
| 6-183 | H | Pyr(4) | H | Me | —CH₂— | O | O | N |
| 6-184 | H | Pyr(4) | H | Me | —CH₂— | O | S | CH |
| 6-185 | H | Pyr(4) | H | Me | —CH₂— | S | S | CH |
| 6-186 | H | Pyr(4) | H | Me | —(CH₂)₂— | O | O | CH |
| 6-187 | H | Pyr(4) | H | Et | —CH₂— | O | O | CH |
| 6-188 | H | Pyr(4) | H | Et | —CH₂— | O | S | CH |
| 6-189 | H | Pyr(4) | H | Ph | —CH₂— | O | O | CH |

TABLE 6-continued

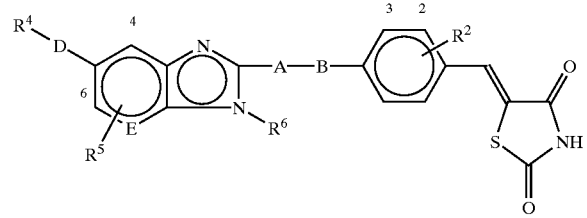

(I-6)

| Cpd. No. | $R^2$ | $R^4$ | $R^5$ | $R^6$ | —A— | B | D | E |
|---|---|---|---|---|---|---|---|---|
| 6-190 | H | Pyr(4) | H | Bz | —CH$_2$— | O | S | CH |
| 6-191 | 3-Cl | Pyr(4) | H | Me | —CH$_2$— | O | O | CH |
| 6-192 | H | 2-Me-Pyr(4) | H | Me | —CH$_2$— | O | O | CH |
| 6-193 | H | 2,6-diMe-Pyr(4) | H | Me | —CH$_2$— | O | O | CH |
| 6-194 | H | 2,6-diMe-Pyr(4) | H | Me | —CH$_2$— | O | S | CH |
| 6-195 | H | 3,6-diMe-Pyr(4) | H | Me | —CH$_2$— | O | O | CH |
| 6-196 | H | 2-MeO-Pyr(4) | H | Me | —CH$_2$— | O | O | CH |
| 6-197 | H | 4-Imid(1)-Ph | H | Me | —CH$_2$— | O | O | CH |
| 6-198 | H | 4-Tz—Ph | H | Me | —CH$_2$— | O | O | CH |
| 6-199 | H | 4-Ada(1)-Ph | H | Me | —CH$_2$— | O | O | CH |
| 6-200 | H | 4-CN—Ph | H | Me | —CH$_2$— | O | O | CH |
| 6-201 | H | 4-Bz-3-OH—Ph | H | Me | —CH$_2$— | O | O | CH |
| 6-202 | H | pentaF—Ph | H | Me | —CH$_2$— | O | O | CH |
| 6-203 | H | 4-NHCOPh—Ph | H | Me | —CH$_2$— | O | O | CH |
| 6-204 | H | 4-NHCO(3-Cl—Ph)—Ph | H | Me | —CH$_2$— | O | O | CH |
| 6-205 | H | 4-NHCO(2,4-diF—Ph)—Ph | H | Me | —CH$_2$— | O | O | CH |
| 6-206 | H | 4-NHCO(4-OH—3,5-ditBu—Ph)—Ph | H | Me | —CH$_2$— | O | O | CH |
| 6-207 | H | 4-NHCONp(1)-Ph | H | Me | —CH$_2$— | O | O | CH |
| 6-208 | H | 4-NHCO(3-Cl-Bz)—Ph | H | Me | —CH$_2$— | O | O | CH |
| 6-209 | H | 4-NHCOcPn—Ph | H | Me | —CH$_2$— | O | O | CH |
| 6-210 | H | 4-NHCOcHx—Ph | H | Me | —CH$_2$— | O | O | CH |
| 6-211 | H | 4-NHCOPyr(3)-Ph | H | Me | —CH$_2$— | O | O | CH |
| 6-212 | H | 4-NHCOPyr(4)-Ph | H | Me | —CH$_2$— | O | O | CH |
| 6-213 | H | 4-NHHx—Ph | H | Me | —CH$_2$— | O | O | CH |
| 6-214 | H | 4-NH(Ac)Hx—Ph | H | Me | —CH$_2$— | O | O | CH |

TABLE 7

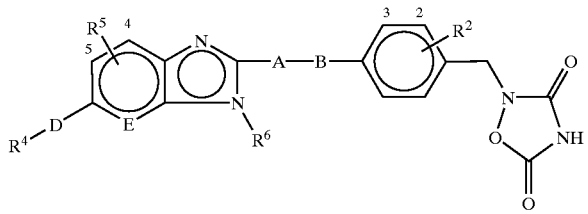

(I-7)

| Cpd. No. | $R^2$ | $R^4$ | $R^5$ | $R^6$ | —A— | B | D | E |
|---|---|---|---|---|---|---|---|---|
| 7-1 | H | 4-F—Ph | H | Me | —CH$_2$— | O | O | CH |
| 7-2 | H | 4-Cl—Ph | H | Me | —CH$_2$— | O | O | CH |
| 7-3 | H | 2-OH—Ph | H | Me | —CH$_2$— | O | O | CH |
| 7-4 | H | 2-OH—Ph | H | Me | —CH$_2$— | O | S | CH |
| 7-5 | H | 2-OH—Ph | H | Et | —CH$_2$— | O | O | CH |
| 7-6 | H | 2-OH—Ph | H | Et | —CH$_2$— | O | S | CH |
| 7-7 | H | 3-OH—Ph | H | Me | —CH$_2$— | O | O | CH |
| 7-8 | H | 3-OH—Ph | H | Me | —CH$_2$— | O | S | CH |
| 7-9 | H | 3-OH—Ph | H | Et | —CH$_2$— | O | O | CH |
| 7-10 | H | 3-OH—Ph | H | Et | —CH$_2$— | O | S | CH |
| 7-11 | H | 4-OH—Ph | H | Me | —CH$_2$— | O | O | CH |
| 7-12 | H | 4-OH—Ph | H | Me | —CH$_2$— | O | O | N |
| 7-13 | H | 4-OH—Ph | H | Me | —CH$_2$— | O | S | CH |
| 7-14 | H | 4-OH—Ph | H | Me | —(CH$_2$)$_2$— | O | O | CH |

TABLE 7-continued

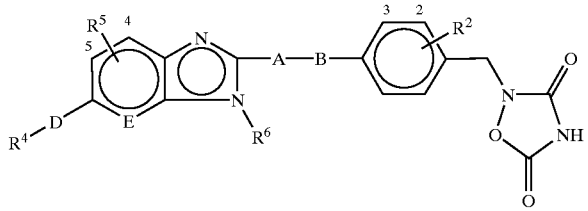

(I-7)

| Cpd. No. | R² | R⁴ | R⁵ | R⁶ | —A— | B | D | E |
|---|---|---|---|---|---|---|---|---|
| 7-15 | H | 4-OH—Ph | H | Et | —CH₂— | O | O | CH |
| 7-16 | H | 4-OH—Ph | H | Et | —CH₂— | O | S | CH |
| 7-17 | H | 4-OH—Ph | H | tBu | —CH₂— | O | O | CH |
| 7-18 | H | 3-CF₃—Ph | H | Me | —CH₂— | O | O | CH |
| 7-19 | H | 4-iPrO—Ph | H | Me | —CH₂— | O | O | CH |
| 7-20 | H | 4-MeS—Ph | H | Me | —CH₂— | O | O | CH |
| 7-21 | H | 2-NH₂—Ph | H | Me | —CH₂— | O | O | CH |
| 7-22 | H | 3-NH₂—Ph | H | Me | —CH₂— | O | O | CH |
| 7-23 | H | 4-NH₂—Ph | H | Me | —CH₂— | O | O | CH |
| 7-24 | H | 4-NHMe—Ph | H | Me | —CH₂— | O | O | CH |
| 7-25 | H | 4-N(Me)₂—Ph | H | Me | —CH₂— | O | O | CH |
| 7-26 | H | 4-N(Me)₂—Ph | H | Et | —CH₂— | O | O | CH |
| 7-27 | H | 4-Ph—Ph | H | Me | —CH₂— | O | O | CH |
| 7-28 | H | 4-(4-OH-3,5-diMe—Ph)Ph | H | Me | —CH₂— | O | O | CH |
| 7-29 | H | 4-(4-OH-3,5-ditBu—Ph)Ph | H | Me | —CH₂— | O | O | CH |
| 7-30 | H | 4-(4-OH—Bz)Ph | H | Me | —CH₂— | O | O | CH |
| 7-31 | H | 4-PhS—Ph | H | Me | —CH₂— | O | O | CH |
| 7-32 | H | 2-Pyrd(1)-Ph | H | Me | —CH₂— | O | O | CH |
| 7-33 | H | 2-Pyrd(1)-Ph | H | Me | —CH₂— | O | S | CH |
| 7-34 | H | 3-Pyrd(1)-Ph | H | Me | —CH₂— | O | O | CH |
| 7-35 | H | 3-Pyrd(1)-Ph | H | Me | —CH₂— | O | S | CH |
| 7-36 | H | 3-Pyrd(1)-Ph | H | Me | —(CH₂)₂— | O | O | CH |
| 7-37 | H | 3-Pyrd(1)-Ph | H | Et | —CH₂— | O | O | CH |
| 7-38 | H | 4-Pyrd(1)-Ph | H | Me | —CH₂— | O | O | CH |
| 7-39 | H | 4-Pyrd(1)-Ph | H | Me | —CH₂— | O | O | N |
| 7-40 | H | 4-Pyrd(1)-Ph | H | Me | —CH₂— | O | S | CH |
| 7-41 | H | 4-Pyrd(1)-Ph | H | Me | —(CH₂)₃— | O | O | CH |
| 7-42 | H | 4-Pyrd(1)-Ph | H | Et | —CH₂— | O | O | CH |
| 7-43 | H | 4-Pyrd(1)-Ph | H | Et | —CH₂— | O | S | CH |
| 7-44 | H | 2-Pip(1)-Ph | H | Me | —CH₂— | O | O | CH |
| 7-45 | H | 2-Pip(1)-Ph | H | Me | —CH₂— | O | S | CH |
| 7-46 | H | 3-Pip(1)-Ph | H | Me | —CH₂— | O | O | CH |
| 7-47 | H | 3-Pip(1)-Ph | H | Me | —CH₂— | O | S | CH |
| 7-48 | H | 3-Pip(1)-Ph | H | Et | —(CH₂)₃— | S | O | CH |
| 7-49 | H | 4-Pip(1)-Ph | H | Me | —CH₂— | O | O | CH |
| 7-50 | H | 4-Pip(1)-Ph | H | Me | —CH₂— | O | O | N |
| 7-51 | H | 4-Pip(1)-Ph | H | Me | —CH₂— | O | S | CH |
| 7-52 | H | 4-Pip(1)-Ph | H | Me | —(CH₂)₂— | O | O | CH |
| 7-53 | H | 4-Pip(1)-Ph | H | Me | —(CH₂)₃— | O | O | CH |
| 7-54 | H | 4-Pip(1)-Ph | H | Et | —CH₂— | O | O | CH |
| 7-55 | H | 4-Pip(1)-Ph | H | Et | —CH₂— | O | S | CH |
| 7-56 | H | 4-Pip(1)-Ph | H | tBu | —CH₂— | O | O | CH |
| 7-57 | H | 4-Pip(1)-Ph | 4-Cl | Me | —CH₂— | O | O | CH |
| 7-58 | 2-MeO | 4-Pip(1)-Ph | H | Me | —CH₂— | O | O | CH |
| 7-59 | H | 2-Mor(4)-Ph | H | Me | —CH₂— | O | O | CH |
| 7-60 | H | 2-Mor(4)-Ph | H | Me | —CH₂— | O | S | CH |
| 7-61 | H | 2-Mor(4)-Ph | H | Me | —(CH₂)₃— | O | O | CH |
| 7-62 | H | 3-Mor(4)-Ph | H | Me | —CH₂— | O | O | CH |
| 7-63 | H | 3-Mor(4)-Ph | H | Me | —CH₂— | O | S | CH |
| 7-64 | H | 3-Mor(4)-Ph | H | Me | —(CH₂)₃— | O | O | CH |
| 7-65 | H | 3-Mor(4)-Ph | H | Et | —CH₂— | O | O | CH |
| 7-66 | H | 4-Mor(4)-Ph | H | Me | —CH₂— | O | O | CH |
| 7-67 | H | 4-Mor(4)-Ph | H | Me | —CH₂— | O | O | N |
| 7-68 | H | 4-Mor(4)-Ph | H | Me | —CH₂— | O | S | CH |
| 7-69 | H | 4-Mor(4)-Ph | H | Et | —CH₂— | O | O | CH |
| 7-70 | H | 4-Mor(4)-Ph | H | Et | —CH₂— | O | S | CH |
| 7-71 | H | 4-TioMor(4)-Ph | H | Me | —CH₂— | O | O | CH |
| 7-72 | H | 4-Pipra(1)-Ph | H | Me | —CH₂— | O | O | CH |
| 7-73 | H | 4-Pipra(1)-Ph | H | Me | —CH₂— | O | S | CH |
| 7-74 | H | 4-Pipra(1)-Ph | H | Me | —(CH₂)₃— | O | O | CH |
| 7-75 | H | 4-Pipra(1)-Ph | H | Et | —CH₂— | O | O | CH |
| 7-76 | H | 4-NO₂—Ph | H | Me | —CH₂— | O | O | CH |
| 7-77 | H | 3-Cl-4-OH—Ph | H | Me | —CH₂— | O | O | CH |

TABLE 7-continued

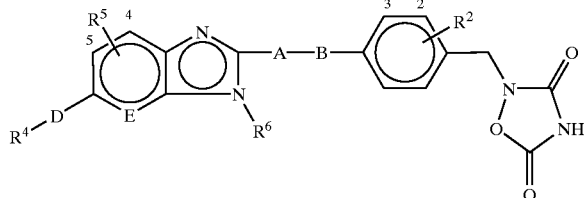

(I-7)

| Cpd. No. | R² | R⁴ | R⁵ | R⁶ | —A— | B | D | E |
|---|---|---|---|---|---|---|---|---|
| 7-78 | H | 2-Cl-4-OH-3,5-diMe—Ph | H | Me | —CH₂— | O | O | CH |
| 7-79 | H | 2-Cl-4-OH-3,5-diMe—Ph | H | Me | —CH₂— | O | O | N |
| 7-80 | H | 2-Cl-4-OH-3,5-diMe—Ph | H | Me | —CH₂— | O | S | CH |
| 7-81 | H | 2-Cl-4-OH-3,5-diMe—Ph | H | Me | —(CH₂)₂— | O | O | CH |
| 7-82 | H | 2-Cl-4-OH-3,5-diMe—Ph | H | Me | —(CH₂)₄— | O | O | CH |
| 7-83 | H | 2-Cl-4-OH-3,5-diMe—Ph | H | Et | —CH₂— | O | O | CH |
| 7-84 | H | 2-Cl-4-OH-3,5-diMe—Ph | H | Et | —CH₂— | O | S | CH |
| 7-85 | H | 2-Cl-4-OH-3,5-diMe—Ph | H | tBu | —CH₂— | O | O | CH |
| 7-86 | H | 2-Cl-4-OH-3,5-diMe—Ph | 5-MeO | Me | —CH₂— | O | O | CH |
| 7-87 | 3-Cl | 2-Cl-4-OH-3,5-diMe—Ph | H | Me | —CH₂— | O | O | CH |
| 7-88 | 2-MeO | 2-Cl-4-OH-3,5-diMe—Ph | H | Me | —CH₂— | O | O | CH |
| 7-89 | H | 3-Cl-5-OH-2,6-diMe—Ph | H | Me | —CH₂— | O | O | CH |
| 7-90 | H | 4-Cl-3-OH-2,5-diMe—Ph | H | Me | —CH₂— | O | O | CH |
| 7-91 | H | 3-Cl-4-NH₂—Ph | H | Me | —CH₂— | O | O | CH |
| 7-92 | H | 3,5-diCl-4-NH₂—Ph | H | Me | —CH₂— | O | O | CH |
| 7-93 | H | 4-NHMe-3-Cl—Ph | H | Me | —CH₂— | O | O | CH |
| 7-94 | H | 3-Cl-4-Pyrd(1)-Ph | H | Me | —CH₂— | O | O | CH |
| 7-95 | H | 3-OH-4-Pyrd(1)-Ph | H | Me | —CH₂— | O | O | CH |
| 7-96 | H | 3-Cl-6-Me-4-Pyrd(1)-Ph | H | Me | —CH₂— | O | O | CH |
| 7-97 | H | 2-Me-4-Mor(4)-Ph | H | Me | —CH₂— | O | O | CH |
| 7-98 | H | 2-OH-3-Me—Ph | H | Me | —CH₂— | O | O | CH |
| 7-99 | H | 2-OH-4-Me—Ph | H | Me | —CH₂— | O | O | CH |
| 7-100 | H | 2-OH-3,4-diMe—Ph | H | Me | —CH₂— | O | O | CH |
| 7-101 | H | 3-OH-2-Me—Ph | H | Me | —CH₂— | O | O | CH |
| 7-102 | H | 3-OH-4-Me—Ph | H | Me | —CH₂— | O | O | CH |
| 7-103 | H | 3-OH-5-Me—Ph | H | Me | —CH₂— | O | O | CH |
| 7-104 | H | 3-OH-6-Me—Ph | H | Me | —CH₂— | O | O | CH |
| 7-105 | H | 3-OH-2,4-diMe—Ph | H | Me | —CH₂— | O | O | CH |
| 7-106 | H | 4-OH-2-Me—Ph | H | Me | —CH₂— | O | O | CH |
| 7-107 | H | 4-OH-3-Me—Ph | H | Me | —CH₂— | O | O | CH |
| 7-108 | H | 4-OH-3-Me—Ph | H | Me | —CH₂— | O | S | CH |
| 7-109 | H | 4-OH-3-Me—Ph | H | Et | —CH₂— | O | O | CH |
| 7-110 | H | 4-OH-3-Me—Ph | 5-Cl | Me | —CH₂— | O | O | CH |
| 7-111 | H | 4-OH-2-tBu—Ph | H | Me | —CH₂— | O | O | CH |
| 7-112 | H | 4-OH-3-tBu—Ph | H | Me | —CH₂— | O | O | CH |
| 7-113 | H | 4-OH-2,3-diMe—Ph | H | Me | —CH₂— | O | O | CH |
| 7-114 | H | 4-OH-2,3-diMe—Ph | H | Me | —CH₂— | O | S | CH |
| 7-115 | H | 4-OH-2,3-diMe—Ph | H | Me | —(CH₂)₃— | S | O | CH |
| 7-116 | H | 4-OH-2,3-diMe—Ph | H | Et | —CH₂— | O | O | CH |
| 7-117 | H | 4-OH-2,5-diMe—Ph | H | Me | —CH₂— | O | O | CH |

TABLE 7-continued

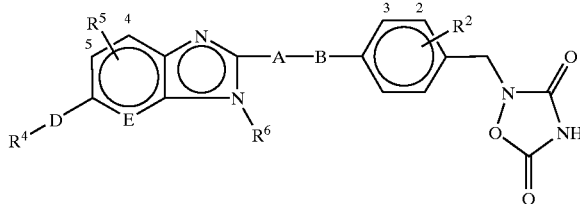

(I-7)

| Cpd. No. | R² | R⁴ | R⁵ | R⁶ | —A— | B | D | E |
|---|---|---|---|---|---|---|---|---|
| 7-118 | H | 4-OH-3,5-diMe—Ph | H | Me | —CH₂— | O | O | CH |
| 7-119 | H | 4-OH-3,5-diMe—Ph | H | Me | —CH₂— | O | O | N |
| 7-120 | H | 4-OH-3,5-diMe—Ph | H | Me | —CH₂— | O | S | CH |
| 7-121 | H | 4-OH-3,5-diMe—Ph | H | Me | —CH₂— | S | O | CH |
| 7-122 | H | 4-OH-3,5-diMe—Ph | H | Me | —(CH₂)₂— | O | O | CH |
| 7-123 | H | 4-OH-3,5-diMe—Ph | H | Et | —CH₂— | O | O | CH |
| 7-124 | H | 4-OH-3,5-diMe—Ph | H | Et | —CH₂— | O | S | CH |
| 7-125 | H | 4-OH-3,5-diMe—Ph | H | sBu | —CH₂— | O | O | CH |
| 7-126 | H | 4-OH-3,5-diMe—Ph | H | tBu | —CH₂— | O | O | CH |
| 7-127 | H | 4-OH-3,5-diMe—Ph | H | Ph | —CH₂— | O | O | CH |
| 7-128 | H | 3,5-diEt-4-OH—Ph | H | Me | —CH₂— | O | O | CH |
| 7-129 | H | 3-tBu-4-OH-5-Me—Ph | H | Me | —CH₂— | O | O | CH |
| 7-130 | H | 3-tBu-4-OH-5-Me—Ph | H | Me | —CH₂— | O | S | CH |
| 7-131 | H | 4-OH-3,5-diPr—Ph | H | Me | —CH₂— | O | O | CH |
| 7-132 | H | 4-OH-3,5-diiPr—Ph | H | Me | —CH₂— | O | O | CH |
| 7-133 | H | 3,5-ditBu-4-OH—Ph | H | Me | —CH₂— | O | O | CH |
| 7-134 | H | 3,5-ditBu-4-OH—Ph | H | Me | —CH₂— | O | O | N |
| 7-135 | H | 3,5-ditBu-4-OH—Ph | H | Me | —CH₂— | O | S | CH |
| 7-136 | H | 3,5-ditBu-4-OH—Ph | H | Me | —CH₂— | S | S | CH |
| 7-137 | H | 3,5-ditBu-4-OH—Ph | H | Me | —(CH₂)₂— | O | O | CH |
| 7-138 | H | 3,5-ditBu-4-OH—Ph | H | Me | —(CH₂)₂— | O | S | CH |
| 7-139 | H | 3,5-ditBu-4-OH—Ph | H | Me | —(CH₂)₃— | O | S | CH |
| 7-140 | H | 3,5-ditBu-4-OH—Ph | H | Et | —CH₂— | O | O | CH |
| 7-141 | H | 3,5-ditBu-4-OH—Ph | H | Et | —CH₂— | O | S | CH |
| 7-142 | H | 3,5-ditBu-4-OH—Ph | H | tBu | —CH₂— | O | O | CH |
| 7-143 | H | 3,5-ditBu-4-OH—Ph | 5-Cl | Me | —CH₂— | O | S | CH |
| 7-144 | H | 4-OH-2,3,5-triMe—Ph | H | H | —CH₂— | O | S | CH |
| 7-145 | H | 4-OH-2,3,5-triMe—Ph | H | Me | —CH₂— | O | O | CH |
| 7-146 | H | 4-OH-2,3,5-triMe—Ph | H | Me | —CH₂— | O | O | N |
| 7-147 | H | 4-OH-2,3,5-triMe—Ph | H | Me | —CH₂— | O | S | CH |
| 7-148 | H | 4-OH-2,3,5-triMe—Ph | H | Me | —(CH₂)₂— | O | O | CH |
| 7-149 | H | 4-OH-2,3,5-triMe—Ph | H | Me | —(CH₂)₃— | O | O | CH |

TABLE 7-continued

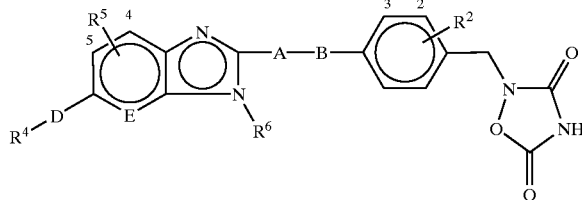

(I-7)

| Cpd. No. | R² | R⁴ | R⁵ | R⁶ | —A— | B | D | E |
|---|---|---|---|---|---|---|---|---|
| 7-150 | H | 4-OH-2,3,5-triMe—Ph | H | Et | —CH₂— | O | O | CH |
| 7-151 | H | 4-OH-2,3,5-triMe—Ph | H | Et | —CH₂— | O | S | CH |
| 7-152 | H | 4-OH-2,3,5-triMe—Ph | H | iPr | —CH₂— | O | O | CH |
| 7-153 | H | 4-OH-2,3,5-triMe—Ph | H | tBu | —CH₂— | O | O | CH |
| 7-154 | H | 4-OH-2,3,5-triMe—Ph | H | Ph | —CH₂— | O | O | CH |
| 7-155 | H | 4-OH-2,3,5-triMe—Ph | H | Bz | —CH₂— | O | O | CH |
| 7-156 | H | 4-OH-2,3,5-triMe—Ph | 5-Cl | Me | —CH₂— | O | O | CH |
| 7-157 | 2-Cl | 4-OH-2,3,5-triMe—Ph | H | Me | —CH₂— | O | O | CH |
| 7-158 | 2-MeO | 4-OH-2,3,5-triMe—Ph | H | Me | —CH₂— | O | O | CH |
| 7-159 | H | 4-OH-2,3,6-triMe—Ph | H | Me | —CH₂— | O | O | CH |
| 7-160 | H | 4-OH-2,3,5,6-tetraMe—Ph | H | Me | —CH₂— | O | O | CH |
| 7-161 | H | 4-OH-3,5-diMeO—Ph | H | Me | —CH₂— | O | O | CH |
| 7-162 | H | 3-NH₂-4-Me—Ph | H | Me | —CH₂— | O | O | CH |
| 7-163 | H | 4-NH₂-2,3-diMe—Ph | H | Me | —CH₂— | O | O | CH |
| 7-164 | H | 4-NH₂-2,6-diMe—Ph | H | Me | —CH₂— | O | O | CH |
| 7-165 | H | 4-NH₂-3,5-diMe—Ph | H | H | —CH₂— | O | O | CH |
| 7-166 | H | 4-NH₂-3,5-diMe—Ph | H | Me | —CH₂— | O | O | CH |
| 7-167 | H | 4-NH₂-3,5-diMe—Ph | H | Me | —CH₂— | O | O | N |
| 7-168 | H | 4-NH₂-3,5-diMe—Ph | H | Me | —CH₂— | O | S | CH |
| 7-169 | H | 4-NH₂-3,5-diMe—Ph | H | Me | —(CH₂)₂— | O | O | CH |
| 7-170 | H | 4-NH₂-3,5-diMe—Ph | H | Et | —CH₂— | O | O | CH |
| 7-171 | H | 4-NH₂-3,5-diMe—Ph | H | Et | —CH₂— | O | S | CH |
| 7-172 | H | 4-NH₂-3,5-diMe—Ph | H | tBu | —CH₂— | O | O | CH |
| 7-173 | H | 4-NH₂-3,5-diMe—Ph | H | Ph | —CH₂— | O | O | CH |
| 7-174 | H | 4-NH₂-3,5-diMe—Ph | H | Bz | —CH₂— | O | O | CH |
| 7-175 | H | 4-NH₂-3,5-diMe—Ph | H | Me | —CH₂— | O | O | CH |
| 7-176 | H | 4-NHMe-3,5-diMe—Ph | H | Me | —CH₂— | O | O | CH |
| 7-177 | H | 4-NHAc-3,5-diMe—Ph | H | Me | —CH₂— | O | O | CH |
| 7-178 | H | 4-NO₂-3,5-diMe—Ph | H | Me | —CH₂— | O | O | CH |
| 7-179 | H | 4-NO₂-3,5-diMe—Ph | H | Me | —CH₂— | O | S | CH |
| 7-180 | H | Pyr(2) | H | Me | —CH₂— | O | O | CH |
| 7-181 | H | Pyr(2) | H | Me | —CH₂— | O | O | N |
| 7-182 | H | Pyr(2) | H | Me | —CH₂— | O | S | CH |
| 7-183 | H | Pyr(2) | H | Me | —(CH₂)₂— | O | O | CH |
| 7-184 | H | Pyr(2) | H | Me | —(CH₂)₃— | O | O | CH |
| 7-185 | H | Pyr(2) | H | Et | —CH₂— | O | O | CH |

TABLE 7-continued

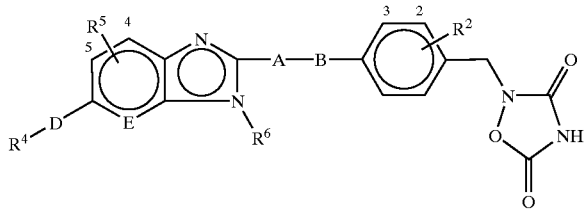

(I-7)

| Cpd. No. | R² | R⁴ | R⁵ | R⁶ | —A— | B | D | E |
|---|---|---|---|---|---|---|---|---|
| 7-186 | H | Pyr(2) | H | Et | —CH₂— | O | S | CH |
| 7-187 | H | Pyr(2) | H | tBu | —CH₂— | O | O | CH |
| 7-188 | H | Pyr(2) | H | Ph | —CH₂— | O | O | CH |
| 7-189 | H | Pyr(2) | 5-Cl | Me | —CH₂— | O | O | CH |
| 7-190 | H | 5-Cl—Pyr(2) | H | Me | —CH₂— | O | O | CH |
| 7-191 | H | 6-Cl—Pyr(2) | H | Me | —CH₂— | O | O | CH |
| 7-192 | H | 6-Me—Pyr(2) | H | Me | —CH₂— | O | O | CH |
| 7-193 | H | 6-MeO—Pyr(2) | H | Me | —CH₂— | O | O | CH |
| 7-194 | H | 3-NH₂—Pyr(2) | H | Me | —CH₂— | O | O | CH |
| 7-195 | H | 5-NH₂—Pyr(2) | H | Me | —CH₂— | O | O | CH |
| 7-196 | H | 3-NO₂—Pyr(2) | H | Me | —CH₂— | O | O | CH |
| 7-197 | H | 5-NO₂—Pyr(2) | H | Me | —CH₂— | O | O | CH |
| 7-198 | H | 5-NH₂-6-Cl—Pyr(2) | H | Me | —CH₂— | O | O | CH |
| 7-199 | 3-MeO | 5-NH₂-6-Cl—Pyr(2) | 5-MeO | Et | —(CH₂)₄— | S | S | CH |
| 7-200 | H | Pyr(3) | H | Me | —CH₂— | O | O | CH |
| 7-201 | H | Pyr(3) | H | Me | —CH₂— | O | O | N |
| 7-202 | H | Pyr(3) | H | Me | —CH₂— | O | S | CH |
| 7-203 | H | Pyr(3) | H | Me | —(CH₂)₂— | O | O | CH |
| 7-204 | H | Pyr(3) | H | Me | —(CH₂)₃— | O | O | CH |
| 7-205 | H | Pyr(3) | H | Et | —CH₂— | O | O | CH |
| 7-206 | H | Pyr(3) | H | Et | —CH₂— | O | S | CH |
| 7-207 | H | Pyr(3) | H | tBu | —CH₂— | O | O | CH |
| 7-208 | H | Pyr(3) | H | Pn | —(CH₂)₃— | O | O | CH |
| 7-209 | H | Pyr(3) | H | Ph | —CH₂— | O | O | CH |
| 7-210 | H | Pyr(3) | H | Ph | —CH₂— | O | S | CH |
| 7-211 | H | Pyr(3) | H | Bz | —CH₂— | O | O | CH |
| 7-212 | 2-Cl | Pyr(3) | H | Me | —CH₂— | O | O | CH |
| 7-213 | H | 5-MeO—Pyr(3) | H | Me | —CH₂— | O | O | CH |
| 7-214 | H | 6-MeO—Pyr(3) | H | Me | —CH₂— | O | O | CH |
| 7-215 | H | 6-MeO—Pyr(3) | H | Me | —CH₂— | O | S | CH |
| 7-216 | H | 6-MeO—Pyr(3) | H | Me | —(CH₂)₃— | O | O | CH |
| 7-217 | H | 6-iPrO—Pyr(3) | H | Me | —CH₂— | O | O | CH |
| 7-218 | H | 6-MeO-5-Me—Pyr(3) | H | Me | —CH₂— | O | O | CH |
| 7-219 | H | 2-NO₂-6-Me—Pyr(3) | H | Me | —CH₂— | O | O | CH |
| 7-220 | H | Pyr(4) | H | Me | —CH₂— | O | O | CH |
| 7-221 | H | Pyr(4) | H | Me | —CH₂— | O | O | N |
| 7-222 | H | Pyr(4) | H | Me | —CH₂— | O | S | CH |
| 7-223 | H | Pyr(4) | H | Me | —CH₂— | S | S | CH |
| 7-224 | H | Pyr(4) | H | Me | —(CH₂)₂— | O | O | CH |
| 7-225 | H | Pyr(4) | H | Et | —CH₂— | O | O | CH |
| 7-226 | H | Pyr(4) | H | Et | —CH₂— | O | S | CH |
| 7-227 | H | Pyr(4) | H | tBu | —CH₂— | O | O | CH |
| 7-228 | H | Pyr(4) | H | Ph | —CH₂— | O | O | CH |
| 7-229 | H | Pyr(4) | H | Bz | —CH₂— | O | S | CH |
| 7-230 | 3-Cl | Pyr(4) | H | Me | —CH₂— | O | O | CH |
| 7-231 | H | 2-Me—Pyr(4) | H | Me | —CH₂— | O | O | CH |
| 7-232 | H | 2,6-diMe—Pyr(4) | H | Me | —CH₂— | O | O | CH |
| 7-233 | H | 2,6-diMe—Pyr(4) | H | Me | —CH₂— | O | S | CH |
| 7-234 | H | 3,6-diMe—Pyr(4) | H | Me | —CH₂— | O | O | CH |
| 7-235 | H | 2-MeO—Pyr(4) | H | Me | —CH₂— | O | O | CH |
| 7-236 | H | 4-Imid(1)-Ph | H | Me | —CH₂— | O | O | CH |
| 7-237 | H | 4-Tz—Ph | H | Me | —CH₂— | O | O | CH |
| 7-238 | H | 4-Ada(1)-Ph | H | Me | —CH₂— | O | O | CH |
| 7-239 | H | 4-CN—Ph | H | Me | —CH₂— | O | O | CH |
| 7-240 | H | 4-Bz-3-OH—Ph | H | Me | —CH₂— | O | O | CH |
| 7-241 | H | pentaF—Ph | H | Me | —CH₂— | O | O | CH |
| 7-242 | H | 4-NHCOPh—Ph | H | Me | —CH₂— | O | O | CH |
| 7-243 | H | 4-NHCO(3-Cl—Ph)—Ph | H | Me | —CH₂— | O | O | CH |
| 7-244 | H | 4-NHCO(2,4-diF—Ph)—Ph | H | Me | —CH₂— | O | O | CH |

TABLE 7-continued

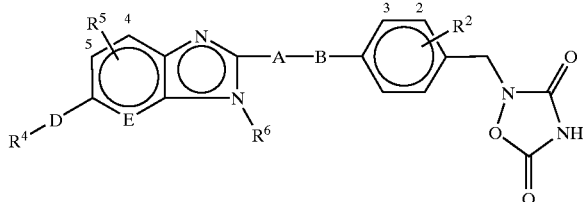

(I-7)

| Cpd. No. | R² | R⁴ | R⁵ | R⁶ | —A— | B | D | E |
|---|---|---|---|---|---|---|---|---|
| 7-245 | H | 4-NHCO(4-OH-3,5-ditBu—Ph)—Ph | H | Me | —CH₂— | O | O | CH |
| 7-246 | H | 4-NHCONp(1)-Ph | H | Me | —CH₂— | O | O | CH |
| 7-247 | H | 4-NHCO(3-Cl—Bz)—Ph | H | Me | —CH₂— | O | O | CH |
| 7-248 | H | 4-NHCOcPn—Ph | H | Me | —CH₂— | O | O | CH |
| 7-249 | H | 4-NHCOcHx—Ph | H | Me | —CH₂— | O | O | CH |
| 7-250 | H | 4-NHCOPyr(3)-Ph | H | Me | —CH₂— | O | O | CH |
| 7-251 | H | 4-NHCOPyr(4)-Ph | H | Me | —CH₂— | O | O | CH |
| 7-252 | H | 4-NHHx—Ph | H | Me | —CH₂— | O | O | CH |
| 7-253 | H | 4-NH(Ac)Hx—Ph | H | Me | —CH₂— | O | O | CH |

TABLE 8

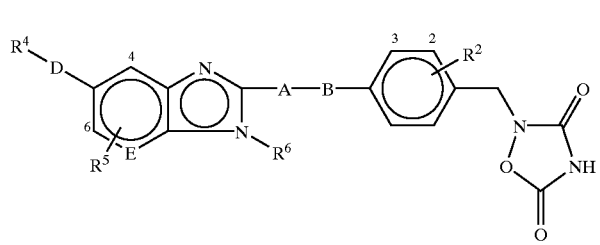

(I-8)

| Cpd. No. | R² | R⁴ | R⁵ | R⁶ | —A— | B | D | E |
|---|---|---|---|---|---|---|---|---|
| 8-1 | H | 4-F—Ph | H | Me | —CH₂— | O | O | CH |
| 8-2 | H | 4-Cl—Ph | H | Me | —CH₂— | O | O | CH |
| 8-3 | H | 2-OH—Ph | H | Me | —CH₂— | O | O | CH |
| 8-4 | H | 2-OH—Ph | H | Me | —CH₂— | O | S | CH |
| 8-5 | H | 3-OH—Ph | H | Me | —CH₂— | O | O | CH |
| 8-6 | H | 3-OH—Ph | H | Me | —CH₂— | O | S | CH |
| 8-7 | H | 4-OH—Ph | H | Me | —CH₂— | O | O | CH |
| 8-8 | H | 4-OH—Ph | H | Me | —CH₂— | O | O | N |
| 8-9 | H | 4-OH—Ph | H | Me | —CH₂— | O | S | CH |
| 8-10 | H | 4-OH—Ph | H | Et | —CH₂— | O | O | CH |
| 8-11 | H | 4-OH—Ph | H | Et | —CH₂— | O | S | CH |
| 8-12 | H | 3-CF₃—Ph | H | Me | —CH₂— | O | O | CH |
| 8-13 | H | 4-iPrO—Ph | H | Me | —CH₂— | O | O | CH |
| 8-14 | H | 4-MeS—Ph | H | Me | —CH₂— | O | O | CH |
| 8-15 | H | 2-NH₂—Ph | H | Me | —CH₂— | O | O | CH |
| 8-16 | H | 3-NH₂—Ph | H | Me | —CH₂— | O | O | CH |
| 8-17 | H | 4-NH₂—Ph | H | Me | —CH₂— | O | O | CH |
| 8-18 | H | 4-NHMe—Ph | H | Me | —CH₂— | O | O | CH |
| 8-19 | H | 4-N(Me)₂—Ph | H | Me | —CH₂— | O | O | CH |
| 8-20 | H | 4-N(Me)₂—Ph | H | Et | —CH₂— | O | O | CH |
| 8-21 | H | 4-Ph—Ph | H | Me | —CH₂— | O | O | CH |
| 8-22 | H | 4-(4-OH-3,5-diMe—Ph)Ph | H | Me | —CH₂— | O | O | CH |
| 8-23 | H | 4-(4-OH-3,5-ditBu—Ph)Ph | H | Me | —CH₂— | O | O | CH |
| 8-24 | H | 4-(4-OH-Bz)Ph | H | Me | —CH₂— | O | O | CH |
| 8-25 | H | 4-PhS—Ph | H | Me | —CH₂— | O | O | CH |
| 8-26 | H | 2-Pyrd(1)-Ph | H | Me | —CH₂— | O | O | CH |
| 8-27 | H | 3-Pyrd(1)-Ph | H | Me | —CH₂— | O | O | CH |
| 8-28 | H | 3-Pyrd(1)-Ph | H | Me | —CH₂— | O | S | CH |
| 8-29 | H | 3-Pyrd(1)-Ph | H | Me | —(CH₂)₂— | O | O | CH |
| 8-30 | H | 3-Pyrd(1)-Ph | H | Et | —CH₂— | O | O | CH |
| 8-31 | H | 4-Pyrd(1)-Ph | H | Me | —CH₂— | O | O | CH |
| 8-32 | H | 4-Pyrd(1)-Ph | H | Me | —CH₂— | O | S | CH |

TABLE 8-continued (I-8)

| Cpd. No. | R² | R⁴ | R⁵ | R⁶ | —A— | B | D | E |
|---|---|---|---|---|---|---|---|---|
| 8-33 | H | 4-Pyrd(1)-Ph | H | Me | —(CH₂)₃— | O | O | CH |
| 8-34 | H | 2-Pip(1)-Ph | H | Me | —CH₂— | O | O | CH |
| 8-35 | H | 3-Pip(1)-Ph | H | Me | —CH₂— | O | O | CH |
| 8-36 | H | 3-Pip(1)-Ph | H | Me | —CH₂— | O | S | CH |
| 8-37 | H | 3-Pip(1)-Ph | H | Et | —(CH₂)₃— | S | O | CH |
| 8-38 | H | 4-Pip(1)-Ph | H | Me | —CH₂— | O | O | CH |
| 8-39 | H | 4-Pip(1)-Ph | H | Me | —CH₂— | O | S | CH |
| 8-40 | H | 4-Pip(1)-Ph | H | Me | —(CH₂)₂— | O | O | CH |
| 8-41 | H | 4-Pip(1)-Ph | H | Me | —(CH₂)₃— | O | O | CH |
| 8-42 | H | 4-Pip(1)-Ph | H | tBu | —CH₂— | O | O | CH |
| 8-43 | H | 4-Pip(1)-Ph | 4-Cl | Me | —CH₂— | O | O | CH |
| 8-44 | 2-MeO | 4-Pip(1)-Ph | H | Me | —CH₂— | O | O | CH |
| 8-45 | H | 2-Mor(4)-Ph | H | Me | —CH₂— | O | O | CH |
| 8-46 | H | 2-Mor(4)-Ph | H | Me | —(CH₂)₃— | O | O | CH |
| 8-47 | H | 3-Mor(4)-Ph | H | Me | —CH₂— | O | O | CH |
| 8-48 | H | 3-Mor(4)-Ph | H | Me | —CH₂— | O | S | CH |
| 8-49 | H | 3-Mor(4)-Ph | H | Me | —(CH₂)₃— | O | O | CH |
| 8-50 | H | 3-Mor(4)-Ph | H | Et | —CH₂— | O | O | CH |
| 8-51 | H | 4-Mor(4)-Ph | H | Me | —CH₂— | O | O | CH |
| 8-52 | H | 4-Mor(4)-Ph | H | Me | —CH₂— | O | S | CH |
| 8-53 | H | 4-TioMor(4)-Ph | H | Me | —CH₂— | O | O | CH |
| 8-54 | H | 4-Pipra(1)-Ph | H | Me | —CH₂— | O | O | CH |
| 8-55 | H | 4-Pipra(1)-Ph | H | Me | —(CH₂)₃— | O | O | CH |
| 8-56 | H | 4-Pipra(1)-Ph | H | Et | —CH₂— | O | O | CH |
| 8-57 | H | 4-NO₂—Ph | H | Me | —CH₂— | O | O | CH |
| 8-58 | H | 2-Cl-4-OH-3,5-diMe—Ph | H | Me | —CH₂— | O | O | CH |
| 8-59 | H | 2-Cl-4-OH-3,5-diMe—Ph | H | Me | —CH₂— | O | O | N |
| 8-60 | H | 2-Cl-4-OH-3,5-diMe—Ph | H | Me | —CH₂— | O | S | CH |
| 8-61 | H | 2-Cl-4-OH-3,5-diMe—Ph | H | Me | —(CH₂)₄— | O | O | CH |
| 8-62 | H | 2-Cl-4-OH-3,5-diMe—Ph | H | Et | —CH₂— | O | O | CH |
| 8-63 | H | 2-Cl-4-OH-3,5-diMe—Ph | H | Et | —CH₂— | O | S | CH |
| 8-64 | H | 2-Cl-4-OH-3,5-diMe—Ph | 6-MeO | Me | —CH₂— | O | O | CH |
| 8-65 | 3-Cl | 2-Cl-4-OH-3,5-diMe—Ph | H | Me | —CH₂— | O | O | CH |
| 8-66 | 2-MeO | 2-Cl-4-OH-3,5-diMe—Ph | H | Me | —CH₂— | O | O | CH |
| 8-67 | H | 4-Cl-3-OH-2,5-diMe—Ph | H | Me | —CH₂— | O | O | CH |
| 8-68 | H | 3-Cl-4-NH₂—Ph | H | Me | —CH₂— | O | O | CH |
| 8-69 | H | 3,5-diCl-4-NH₂—Ph | H | Me | —CH₂— | O | O | CH |
| 8-70 | H | 4-NHMe-3-Cl—Ph | H | Me | —CH₂— | O | O | CH |
| 8-71 | H | 3-Cl-4-Pyrd(1)-Ph | H | Me | —CH₂— | O | O | CH |
| 8-72 | H | 3-OH-4-Pyrd(1)-Ph | H | Me | —CH₂— | O | O | CH |
| 8-73 | H | 3-Cl-6-Me-4-Pyrd(1)-Ph | H | Me | —CH₂— | O | O | CH |
| 8-74 | H | 2-Me-4-Mor(4)-Ph | H | Me | —CH₂— | O | O | CH |
| 8-75 | H | 2-OH-3-Me—Ph | H | Me | —CH₂— | O | O | CH |
| 8-76 | H | 2-OH-4-Me—Ph | H | Me | —CH₂— | O | O | CH |
| 8-77 | H | 2-OH-3,4-diMe—Ph | H | Me | —CH₂— | O | O | CH |
| 8-78 | H | 3-OH-2-Me—Ph | H | Me | —CH₂— | O | O | CH |
| 8-79 | H | 3-OH-4-Me—Ph | H | Me | —CH₂— | O | O | CH |
| 8-80 | H | 3-OH-5-Me—Ph | H | Me | —CH₂— | O | O | CH |

TABLE 8-continued (I-8)

| Cpd. No. | R² | R⁴ | R⁵ | R⁶ | —A— | B | D | E |
|---|---|---|---|---|---|---|---|---|
| 8-81 | H | 3-OH-6-Me—Ph | H | Me | —CH₂— | O | O | CH |
| 8-82 | H | 3-OH-2,4-diMe—Ph | H | Me | —CH₂— | O | O | CH |
| 8-83 | H | 4-OH-2-Me—Ph | H | Me | —CH₂— | O | O | CH |
| 8-84 | H | 4-OH-3-Me—Ph | H | Me | —CH₂— | O | O | CH |
| 8-85 | H | 4-OH-3-Me—Ph | H | Et | —CH₂— | O | O | CH |
| 8-86 | H | 4-OH-3-Me—Ph | 6-Cl | Me | —CH₂— | O | O | CH |
| 8-87 | H | 4-OH-2-tBu—Ph | H | Me | —CH₂— | O | O | CH |
| 8-88 | H | 4-OH-2,3-diMe—Ph | H | Me | —CH₂— | O | O | CH |
| 8-89 | H | 4-OH-2,3-diMe—Ph | H | Me | —CH₂— | O | S | CH |
| 8-90 | H | 4-OH-2,3-diMe—Ph | H | Me | —(CH₂)₃— | S | O | CH |
| 8-91 | H | 4-OH-2,3-diMe—Ph | H | Et | —CH₂— | O | O | CH |
| 8-92 | H | 4-OH-2,5-diMe—Ph | H | Me | —CH₂— | O | O | CH |
| 8-93 | H | 4-OH-3,5-diMe—Ph | H | Me | —CH₂— | O | O | CH |
| 8-94 | H | 4-OH-3,5-diMe—Ph | H | Me | —CH₂— | O | O | N |
| 8-95 | H | 4-OH-3,5-diMe—Ph | H | Me | —CH₂— | O | S | CH |
| 8-96 | H | 4-OH-3,5-diMe—Ph | H | Me | —CH₂— | S | O | CH |
| 8-97 | H | 4-OH-3,5-diMe—Ph | H | Me | —(CH₂)₂— | O | O | CH |
| 8-98 | H | 4-OH-3,5-diMe—Ph | H | Et | —CH₂— | O | O | CH |
| 8-99 | H | 4-OH-3,5-diMe—Ph | H | Et | —CH₂— | O | S | CH |
| 8-100 | H | 4-OH-3,5-diMe—Ph | H | sBu | —CH₂— | O | O | CH |
| 8-101 | H | 4-OH-3,5-diMe—Ph | H | Ph | —CH₂— | O | O | CH |
| 8-102 | H | 3,5-diEt-4-OH—Ph | H | Me | —CH₂— | O | O | CH |
| 8-103 | H | 3-tBu-4-OH-5-Me—Ph | H | Me | —CH₂— | O | O | CH |
| 8-104 | H | 3-tBu-4-OH-5-Me—Ph | H | Me | —CH₂— | O | S | CH |
| 8-105 | H | 4-OH-3,5-diPr—Ph | H | Me | —CH₂— | O | O | CH |
| 8-106 | H | 4-OH-3,5-diiPr—Ph | H | Me | —CH₂— | O | O | CH |
| 8-107 | H | 3,5-ditBu-4-OH—Ph | H | Me | —CH₂— | O | O | CH |
| 8-108 | H | 3,5-ditBu-4-OH—Ph | H | Me | —CH₂— | O | O | N |
| 8-109 | H | 3,5-ditBu-4-OH—Ph | H | Me | —CH₂— | O | S | CH |
| 8-110 | H | 3,5-ditBu-4-OH—Ph | H | Me | —CH₂— | S | S | CH |
| 8-111 | H | 3,5-ditBu-4-OH—Ph | H | Me | —(CH₂)₂— | O | S | CH |
| 8-112 | H | 3,5-ditBu-4-OH—Ph | H | Me | —(CH₂)₃— | O | S | CH |
| 8-113 | H | 3,5-ditBu-4-OH—Ph | H | Et | —CH₂— | O | O | CH |
| 8-114 | H | 3,5-ditBu-4-OH—Ph | H | Et | —CH₂— | O | S | CH |
| 8-115 | H | 3,5-ditBu-4-OH—Ph | 6-Cl | Me | —CH₂— | O | S | CH |

TABLE 8-continued

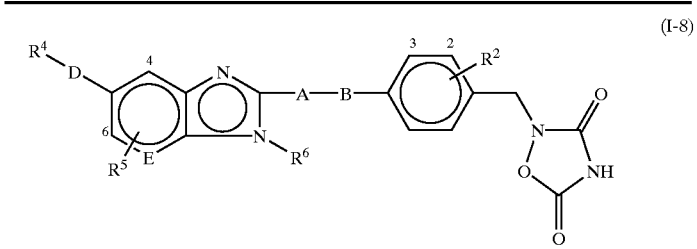

(I-8)

| Cpd. No. | R² | R⁴ | R⁵ | R⁶ | —A— | B | D | E |
|---|---|---|---|---|---|---|---|---|
| 8-116 | H | 4-OH-2,3,5-triMe—Ph | H | H | —CH₂— | O | S | CH |
| 8-117 | H | 4-OH-2,3,5-triMe—Ph | H | Me | —CH₂— | O | O | CH |
| 8-118 | H | 4-OH-2,3,5-triMe—Ph | H | Me | —CH₂— | O | O | N |
| 8-119 | H | 4-OH-2,3,5-triMe—Ph | H | Me | —CH₂— | O | S | CH |
| 8-120 | H | 4-OH-2,3,5-triMe—Ph | H | Me | —(CH₂)₂— | O | O | CH |
| 8-121 | H | 4-OH-2,3,5-triMe—Ph | H | Me | —(CH₂)₃— | O | O | CH |
| 8-122 | H | 4-OH-2,3,5-triMe—Ph | H | Et | —CH₂— | O | O | CH |
| 8-123 | H | 4-OH-2,3,5-triMe—Ph | H | Et | —CH₂— | O | S | CH |
| 8-124 | H | 4-OH-2,3,5-triMe—Ph | H | iPr | —CH₂— | O | O | CH |
| 8-125 | H | 4-OH-2,3,5-triMe—Ph | H | Ph | —CH₂— | O | O | CH |
| 8-126 | H | 4-OH-2,3,5-triMe—Ph | H | Bz | —CH₂— | O | O | CH |
| 8-127 | H | 4-OH-2,3,5-triMe—Ph | 6-Cl | Me | —CH₂— | O | O | CH |
| 8-128 | 2-Cl | 4-OH-2,3,5-triMe—Ph | H | Me | —CH₂— | O | O | CH |
| 8-129 | 2-MeO | 4-OH-2,3,5-triMe—Ph | H | Me | —CH₂— | O | O | CH |
| 8-130 | H | 4-OH-2,3,6-triMe—Ph | H | Me | —CH₂— | O | O | CH |
| 8-131 | H | 4-OH-2,3,5,6-tetraMe—Ph | H | Me | —CH₂— | O | O | CH |
| 8-132 | H | 4-OH-3,5-diMeO—Ph | H | Me | —CH₂— | O | O | CH |
| 8-133 | H | 3-NH₂-4-Me—Ph | H | Me | —CH₂— | O | O | CH |
| 8-134 | H | 4-NH₂-2,3-diMe—Ph | H | Me | —CH₂— | O | O | CH |
| 8-135 | H | 4-NH₂-2,6-diMe—Ph | H | Me | —CH₂— | O | O | CH |
| 8-136 | H | 4-NH₂-3,5-diMe—Ph | H | H | —CH₂— | O | O | CH |
| 8-137 | H | 4-NH₂-3,5-diMe—Ph | H | Me | —CH₂— | O | O | CH |
| 8-138 | H | 4-NH₂-3,5-diMe—Ph | H | Me | —CH₂— | O | O | N |
| 8-139 | H | 4-NH₂-3,5-diMe—Ph | H | Me | —CH₂— | O | S | CH |
| 8-140 | H | 4-NH₂-3,5-diMe—Ph | H | Me | —(CH₂)₂— | O | O | CH |
| 8-141 | H | 4-NH₂-3,5-diMe—Ph | H | Et | —CH₂— | O | O | CH |
| 8-142 | H | 4-NH₂-3,5-diMe—Ph | H | Et | —CH₂— | O | S | CH |
| 8-143 | H | 4-NH₂-3,5-diMe—Ph | H | Ph | —CH₂— | O | O | CH |
| 8-144 | H | 4-NH₂-3,5-diMe—Ph | H | Bz | —CH₂— | O | O | CH |
| 8-145 | H | 4-NHMe-3,5-diMe—Ph | H | Me | —CH₂— | O | O | CH |
| 8-146 | H | 4-NHAc-3,5-diMe—Ph | H | Me | —CH₂— | O | O | CH |
| 8-147 | H | 4-NO₂-3,5-diMe—Ph | H | Me | —CH₂— | O | O | CH |

TABLE 8-continued

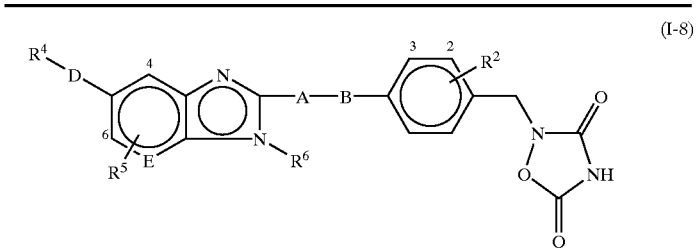

(I-8)

| Cpd. No. | R² | R⁴ | R⁵ | R⁶ | —A— | B | D | E |
|---|---|---|---|---|---|---|---|---|
| 8-148 | H | 4-NO₂-3,5-diMe—Ph | H | Me | —CH₂— | O | S | CH |
| 8-149 | H | Pyr(2) | H | Me | —CH₂— | O | O | CH |
| 8-150 | H | Pyr(2) | H | Me | —CH₂— | O | O | N |
| 8-151 | H | Pyr(2) | H | Me | —CH₂— | O | S | CH |
| 8-152 | H | Pyr(2) | H | Me | —(CH₂)₂— | O | O | CH |
| 8-153 | H | Pyr(2) | H | Me | —(CH₂)₃— | O | O | CH |
| 8-154 | H | Pyr(2) | H | Et | —CH₂— | O | O | CH |
| 8-155 | H | Pyr(2) | H | Et | —CH₂— | O | S | CH |
| 8-156 | H | Pyr(2) | H | Ph | —CH₂— | O | O | CH |
| 8-157 | H | Pyr(2) | 6-Cl | Me | —CH₂— | O | O | CH |
| 8-158 | H | 5-Cl-Pyr(2) | H | Me | —CH₂— | O | O | CH |
| 8-159 | H | 6-Cl-Pyr(2) | H | Me | —CH₂— | O | O | CH |
| 8-160 | H | 6-MeO-Pyr(2) | H | Me | —CH₂— | O | O | CH |
| 8-161 | H | 3-NH₂-Pyr(2) | H | Me | —CH₂— | O | O | CH |
| 8-162 | H | 5-NH₂-Pyr(2) | H | Me | —CH₂— | O | O | CH |
| 8-163 | H | 3-NO₂-Pyr(2) | H | Me | —CH₂— | O | O | CH |
| 8-164 | H | 5-NO₂-Pyr(2) | H | Me | —CH₂— | O | O | CH |
| 8-165 | 3-MeO | 5-NH₂-6-Cl-Pyr(2) | 6-MeO | Et | —(CH₂)₄— | S | S | CH |
| 8-166 | H | Pyr(3) | H | Me | —CH₂— | O | O | CH |
| 8-167 | H | Pyr(3) | H | Me | —CH₂— | O | O | N |
| 8-168 | H | Pyr(3) | H | Me | —CH₂— | O | S | CH |
| 8-169 | H | Pyr(3) | H | Me | —(CH₂)₃— | O | O | CH |
| 8-170 | H | Pyr(3) | H | Et | —CH₂— | O | O | CH |
| 8-171 | H | Pyr(3) | H | Et | —CH₂— | O | S | CH |
| 8-172 | H | Pyr(3) | H | Pn | —(CH₂)₃— | O | O | CH |
| 8-173 | H | Pyr(3) | H | Ph | —CH₂— | O | O | CH |
| 8-174 | H | Pyr(3) | H | Ph | —CH₂— | O | S | CH |
| 8-175 | 2-Cl | Pyr(3) | H | Me | —CH₂— | O | O | CH |
| 8-176 | H | 6-MeO-Pyr(3) | H | Me | —CH₂— | O | O | CH |
| 8-177 | H | 6-MeO-Pyr(3) | H | Me | —CH₂— | O | S | CH |
| 8-178 | H | 6-MeO-Pyr(3) | H | Me | —(CH₂)₃— | O | O | CH |
| 8-179 | H | 6-iPrO-Pyr(3) | H | Me | —CH₂— | O | O | CH |
| 8-180 | H | 6-MeO-5-Me-Pyr(3) | H | Me | —CH₂— | O | O | CH |
| 8-181 | H | 2-NO₂-6-Me-Pyr(3) | H | Me | —CH₂— | O | O | CH |
| 8-182 | H | Pyr(4) | H | Me | —CH₂— | O | O | CH |
| 8-183 | H | Pyr(4) | H | Me | —CH₂— | O | O | N |
| 8-184 | H | Pyr(4) | H | Me | —CH₂— | O | S | CH |
| 8-185 | H | Pyr(4) | H | Me | —CH₂— | S | S | CH |
| 8-186 | H | Pyr(4) | H | Me | —(CH₂)₂— | O | O | CH |
| 8-187 | H | Pyr(4) | H | Et | —CH₂— | O | O | CH |
| 8-188 | H | Pyr(4) | H | Et | —CH₂— | O | S | CH |
| 8-189 | H | Pyr(4) | H | Ph | —CH₂— | O | O | CH |
| 8-190 | H | Pyr(4) | H | Bz | —CH₂— | O | S | CH |
| 8-191 | 3-Cl | Pyr(4) | H | Me | —CH₂— | O | O | CH |
| 8-192 | H | 2-Me-Pyr(4) | H | Me | —CH₂— | O | O | CH |
| 8-193 | H | 2,6-diMe-Pyr(4) | H | Me | —CH₂— | O | O | CH |
| 8-194 | H | 2,6-diMe-Pyr(4) | H | Me | —CH₂— | O | S | CH |
| 8-195 | H | 3,6-diMe-Pyr(4) | H | Me | —CH₂— | O | O | CH |
| 8-196 | H | 2-MeO-Pyr(4) | H | Me | —CH₂— | O | O | CH |
| 8-197 | H | 4-Imid(1)-Ph | H | Me | —CH₂— | O | O | CH |
| 8-198 | H | 4-Tz-Ph | H | Me | —CH₂— | O | O | CH |
| 8-199 | H | 4-Ada(1)-Ph | H | Me | —CH₂— | O | O | CH |
| 8-200 | H | 4-CN—Ph | H | Me | —CH₂— | O | O | CH |
| 8-201 | H | 4-Bz-3-OH—Ph | H | Me | —CH₂— | O | O | CH |
| 8-202 | H | pentaF—Ph | H | Me | —CH₂— | O | O | CH |
| 8-203 | H | 4-NHCOPh—Ph | H | Me | —CH₂— | O | O | CH |
| 8-204 | H | 4-NHCO(3-Cl-Ph)—Ph | H | Me | —CH₂— | O | O | CH |
| 8-205 | H | 4-NHCO(2,4-diF—Ph)—Ph | H | Me | —CH₂— | O | O | CH |

TABLE 8-continued (I-8)

| Cpd. No. | R² | R⁴ | R⁵ | R⁶ | —A— | B | D | E |
|---|---|---|---|---|---|---|---|---|
| 8-206 | H | 4-NHCO(4-OH-3,5-ditBu—Ph)—Ph | H | Me | —CH₂— | O | O | CH |
| 8-207 | H | 4-NHCONp(1)-Ph | H | Me | —CH₂— | O | O | CH |
| 8-208 | H | 4-NHCO(3-Cl-Bz)-Ph | H | Me | —CH₂— | O | O | CH |
| 8-209 | H | 4-NHCOcPn-Ph | H | Me | —CH₂— | O | O | CH |
| 8-210 | H | 4-NHCOcHx-Ph | H | Me | —CH₂— | O | O | CH |
| 8-211 | H | 4-NHCOPyr(3)-Ph | H | Me | —CH₂— | O | O | CH |
| 8-212 | H | 4-NHCOPyr(4)-Ph | H | Me | —CH₂— | O | O | CH |
| 8-213 | H | 4-NHHx-Ph | H | Me | —CH₂— | O | O | CH |
| 8-214 | H | 4-NH(Ac)Hx-Ph | H | Me | —CH₂— | O | O | CH |

TABLE 9

(I-9)

| Cpd. No. | R² | R⁴ | R⁵ | R⁶ | —A— | B | D | E |
|---|---|---|---|---|---|---|---|---|
| 9-1 | H | 4-F—Ph | H | Me | —CH₂— | O | O | CH |
| 9-2 | H | 4-Cl—Ph | H | Me | —CH₂— | O | O | CH |
| 9-3 | H | 2-OH—Ph | H | Me | —CH₂— | O | O | CH |
| 9-4 | H | 2-OH—Ph | H | Me | —CH₂— | O | S | CH |
| 9-5 | H | 2-OH—Ph | H | Et | —CH₂— | O | O | CH |
| 9-6 | H | 2-OH—Ph | H | Et | —CH₂— | O | S | CH |
| 9-7 | H | 3-OH—Ph | H | Me | —CH₂— | O | O | CH |
| 9-8 | H | 3-OH—Ph | H | Me | —CH₂— | O | S | CH |
| 9-9 | H | 3-OH—Ph | H | Et | —CH₂— | O | O | CH |
| 9-10 | H | 3-OH—Ph | H | Et | —CH₂— | O | S | CH |
| 9-11 | H | 4-OH—Ph | H | Me | —CH₂— | O | O | CH |
| 9-12 | H | 4-OH—Ph | H | Me | —CH₂— | O | O | N |
| 9-13 | H | 4-OH—Ph | H | Me | —CH₂— | O | S | CH |
| 9-14 | H | 4-OH—Ph | H | Me | —(CH₂)₂— | O | O | CH |
| 9-15 | H | 4-OH—Ph | H | Et | —CH₂— | O | O | CH |
| 9-16 | H | 4-OH—Ph | H | Et | —CH₂— | O | S | CH |
| 9-17 | H | 4-OH—Ph | H | tBu | —CH₂— | O | O | CH |
| 9-18 | H | 3-CF₃—Ph | H | Me | —CH₂— | O | O | CH |
| 9-19 | H | 4-iPrO—Ph | H | Me | —CH₂— | O | O | CH |
| 9-20 | H | 4-MeS—Ph | H | Me | —CH₂— | O | O | CH |
| 9-21 | H | 2-NH₂—Ph | H | Me | —CH₂— | O | O | CH |
| 9-22 | H | 3-NH₂—Ph | H | Me | —CH₂— | O | O | CH |
| 9-23 | H | 4-NH₂—Ph | H | Me | —CH₂— | O | O | CH |
| 9-24 | H | 4-NHMe—Ph | H | Me | —CH₂— | O | O | CH |
| 9-25 | H | 4-N(Me)₂—Ph | H | Me | —CH₂— | O | O | CH |
| 9-26 | H | 4-N(Me)₂—Ph | H | Et | —CH₂— | O | O | CH |
| 9-27 | H | 4-Ph—Ph | H | Me | —CH₂— | O | O | CH |
| 9-28 | H | 4-(4-OH-3,5-diMe—Ph)Ph | H | Me | —CH₂— | O | O | CH |
| 9-29 | H | 4-(4-OH-3,5-ditBu—Ph)Ph | H | Me | —CH₂— | O | O | CH |
| 9-30 | H | 4-(4-OH-Bz)Ph | H | Me | —CH₂— | O | O | CH |
| 9-31 | H | 4-PhS—Ph | H | Me | —CH₂— | O | O | CH |
| 9-32 | H | 2-Pyrd(1)-Ph | H | Me | —CH₂— | O | O | CH |
| 9-33 | H | 2-Pyrd(1)-Ph | H | Me | —CH₂— | O | S | CH |
| 9-34 | H | 3-Pyrd(1)-Ph | H | Me | —CH₂— | O | O | CH |
| 9-35 | H | 3-Pyrd(1)-Ph | H | Me | —CH₂— | O | S | CH |

TABLE 9-continued

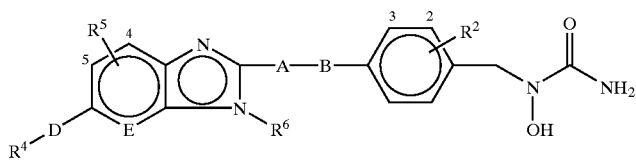

(I-9)

| Cpd. No. | R² | R⁴ | R⁵ | R⁶ | —A— | B | D | E |
|---|---|---|---|---|---|---|---|---|
| 9-36 | H | 3-Pyrd(1)-Ph | H | Me | —(CH₂)₂— | O | O | CH |
| 9-37 | H | 3-Pyrd(1)-Ph | H | Et | —CH₂— | O | O | CH |
| 9-38 | H | 4-Pyrd(1)-Ph | H | Me | —CH₂— | O | O | CH |
| 9-39 | H | 4-Pyrd(1)-Ph | H | Me | —CH₂— | O | O | N |
| 9-40 | H | 4-Pyrd(1)-Ph | H | Me | —CH₂— | O | S | CH |
| 9-41 | H | 4-Pyrd(1)-Ph | H | Me | —(CH₂)₃— | O | O | CH |
| 9-42 | H | 4-Pyrd(1)-Ph | H | Et | —CH₂— | O | O | CH |
| 9-43 | H | 4-Pyrd(1)-Ph | H | Et | —CH₂— | O | S | CH |
| 9-44 | H | 2-Pip(1)-Ph | H | Me | —CH₂— | O | O | CH |
| 9-45 | H | 2-Pip(1)-Ph | H | Me | —CH₂— | O | S | CH |
| 9-46 | H | 3-Pip(1)-Ph | H | Me | —CH₂— | O | O | CH |
| 9-47 | H | 3-Pip(1)-Ph | H | Me | —CH₂— | O | S | CH |
| 9-48 | H | 3-Pip(1)-Ph | H | Et | —(CH₂)₃— | S | O | CH |
| 9-49 | H | 4-Pip(1)-Ph | H | Me | —CH₂— | O | O | CH |
| 9-50 | H | 4-Pip(1)-Ph | H | Me | —CH₂— | O | O | N |
| 9-51 | H | 4-Pip(1)-Ph | H | Me | —CH₂— | O | S | CH |
| 9-52 | H | 4-Pip(1)-Ph | H | Me | —(CH₂)₂— | O | O | CH |
| 9-53 | H | 4-Pip(1)-Ph | H | Me | —(CH₂)₃— | O | O | CH |
| 9-54 | H | 4-Pip(1)-Ph | H | Et | —CH₂— | O | O | CH |
| 9-55 | H | 4-Pip(1)-Ph | H | Et | —CH₂— | O | S | CH |
| 9-56 | H | 4-Pip(1)-Ph | H | tBu | —CH₂— | O | O | CH |
| 9-57 | H | 4-Pip(1)-Ph | 4-Cl | Me | —CH₂— | O | O | CH |
| 9-58 | 2-MeO | 4-Pip(1)-Ph | H | Me | —CH₂— | O | O | CH |
| 9-59 | H | 2-Mor(4)-Ph | H | Me | —CH₂— | O | O | CH |
| 9-60 | H | 2-Mor(4)-Ph | H | Me | —CH₂— | O | S | CH |
| 9-61 | H | 2-Mor(4)-Ph | H | Me | —(CH₂)₃— | O | O | CH |
| 9-62 | H | 3-Mor(4)-Ph | H | Me | —CH₂— | O | O | CH |
| 9-63 | H | 3-Mor(4)-Ph | H | Me | —CH₂— | O | S | CH |
| 9-64 | H | 3-Mor(4)-Ph | H | Me | —(CH₂)₃— | O | O | CH |
| 9-65 | H | 3-Mor(4)-Ph | H | Et | —CH₂— | O | O | CH |
| 9-66 | H | 4-Mor(4)-Ph | H | Me | —CH₂— | O | O | CH |
| 9-67 | H | 4-Mor(4)-Ph | H | Me | —CH₂— | O | O | N |
| 9-68 | H | 4-Mor(4)-Ph | H | Me | —CH₂— | O | S | CH |
| 9-69 | H | 4-Mor(4)-Ph | H | Et | —CH₂— | O | O | CH |
| 9-70 | H | 4-Mor(4)-Ph | H | Et | —CH₂— | O | S | CH |
| 9-71 | H | 4-TioMor(4)-Ph | H | Me | —CH₂— | O | O | CH |
| 9-72 | H | 4-Pipra(1)-Ph | H | Me | —CH₂— | O | O | CH |
| 9-73 | H | 4-Pipra(1)-Ph | H | Me | —CH₂— | O | S | CH |
| 9-74 | H | 4-Pipra(1)-Ph | H | Me | —(CH₂)₃— | O | O | CH |
| 9-75 | H | 4-Pipra(1)-Ph | H | Et | —CH₂— | O | O | CH |
| 9-76 | H | 4-NO₂—Ph | H | Me | —CH₂— | O | O | CH |
| 9-77 | H | 3-Cl-4-OH—Ph | H | Me | —CH₂— | O | O | CH |
| 9-78 | H | 2-Cl-4-OH-3,5-diMe—Ph | H | Me | —CH₂— | O | O | CH |
| 9-79 | H | 2-Cl-4-OH-3,5-diMe—Ph | H | Me | —CH₂— | O | O | N |
| 9-80 | H | 2-Cl-4-OH-3,5-diMe—Ph | H | Me | —CH₂— | O | S | CH |
| 9-81 | H | 2-Cl-4-OH-3,5-diMe—Ph | H | Me | —(CH₂)₂— | O | O | CH |
| 9-82 | H | 2-Cl-4-OH-3,5-diMe—Ph | H | Me | —(CH₂)₄— | O | O | CH |
| 9-83 | H | 2-Cl-4-OH-3,5-diMe—Ph | H | Et | —CH₂— | O | O | CH |
| 9-84 | H | 2-Cl-4-OH-3,5-diMe—Ph | H | Et | —CH₂— | O | S | CH |
| 9-85 | H | 2-Cl-4-OH-3,5-diMe—Ph | H | tBu | —CH₂— | O | O | CH |
| 9-86 | H | 2-Cl-4-OH-3,5-diMe—Ph | 5-MeO | Me | —CH₂— | O | O | CH |
| 9-87 | 3-Cl | 2-Cl-4-OH-3,5-diMe—Ph | H | Me | —CH₂— | O | O | CH |
| 9-88 | 2-MeO | 2-Cl-4-OH-3,5-diMe—Ph | H | Me | —CH₂— | O | O | CH |
| 9-89 | H | 3-Cl-5-OH-2,6-diMe—Ph | H | Me | —CH₂— | O | O | CH |

TABLE 9-continued

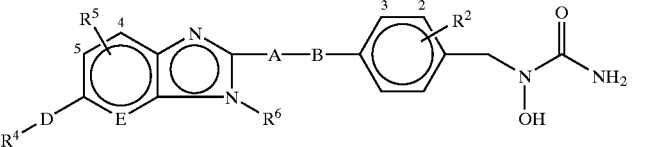

(I-9)

| Cpd. No. | R² | R⁴ | R⁵ | R⁶ | —A— | B | D | E |
|---|---|---|---|---|---|---|---|---|
| 9-90 | H | 4-Cl-3-OH-2,5-diMe—Ph | H | Me | —CH₂— | O | O | CH |
| 9-91 | H | 3-Cl-4-NH₂—Ph | H | Me | —CH₂— | O | O | CH |
| 9-92 | H | 3,5-diCl-4-NH₂—Ph | H | Me | —CH₂— | O | O | CH |
| 9-93 | H | 4-NHMe-3-Cl—Ph | H | Me | —CH₂— | O | O | CH |
| 9-94 | H | 3-Cl-4-Pyrd(1)-Ph | H | Me | —CH₂— | O | O | CH |
| 9-95 | H | 3-OH-4-Pyrd(1)-Ph | H | Me | —CH₂— | O | O | CH |
| 9-96 | H | 3-Cl-6-Me-4-Pyrd(1)-Ph | H | Me | —CH₂— | O | O | CH |
| 9-97 | H | 2-Me-4-Mor(4)-Ph | H | Me | —CH₂— | O | O | CH |
| 9-98 | H | 2-OH-3-Me—Ph | H | Me | —CH₂— | O | O | CH |
| 9-99 | H | 2-OH-4-Me—Ph | H | Me | —CH₂— | O | O | CH |
| 9-100 | H | 2-OH-3,4-diMe—Ph | H | Me | —CH₂— | O | O | CH |
| 9-101 | H | 3-OH-2-Me—Ph | H | Me | —CH₂— | O | O | CH |
| 9-102 | H | 3-OH-4-Me—Ph | H | Me | —CH₂— | O | O | CH |
| 9-103 | H | 3-OH-5-Me—Ph | H | Me | —CH₂— | O | O | CH |
| 9-104 | H | 3-OH-6-Me—Ph | H | Me | —CH₂— | O | O | CH |
| 9-105 | H | 3-OH-2,4-diMe—Ph | H | Me | —CH₂— | O | O | CH |
| 9-106 | H | 4-OH-2-Me—Ph | H | Me | —CH₂— | O | O | CH |
| 9-107 | H | 4-OH-3-Me—Ph | H | Me | —CH₂— | O | O | CH |
| 9-108 | H | 4-OH-3-Me—Ph | H | Me | —CH₂— | O | S | CH |
| 9-109 | H | 4-OH-3-Me—Ph | H | Et | —CH₂— | O | O | CH |
| 9-110 | H | 4-OH-3-Me—Ph | 5-Cl | Me | —CH₂— | O | O | CH |
| 9-111 | H | 4-OH-2-tBu—Ph | H | Me | —CH₂— | O | O | CH |
| 9-112 | H | 4-OH-3-tBu—Ph | H | Me | —CH₂— | O | O | CH |
| 9-113 | H | 4-OH-2,3-diMe—Ph | H | Me | —CH₂— | O | O | CH |
| 9-114 | H | 4-OH-2,3-diMe—Ph | H | Me | —CH₂— | O | S | CH |
| 9-115 | H | 4-OH-2,3-diMe—Ph | H | Me | —(CH₂)₃— | S | O | CH |
| 9-116 | H | 4-OH-2,3-diMe—Ph | H | Et | —CH₂— | O | O | CH |
| 9-117 | H | 4-OH-2,5-diMe—Ph | H | Me | —CH₂— | O | O | CH |
| 9-118 | H | 4-OH-3,5-diMe—Ph | H | Me | —CH₂— | O | O | CH |
| 9-119 | H | 4-OH-3,5-diMe—Ph | H | Me | —CH₂— | O | O | N |
| 9-120 | H | 4-OH-3,5-diMe—Ph | H | Me | —CH₂— | O | S | CH |
| 9-121 | H | 4-OH-3,5-diMe—Ph | H | Me | —CH₂— | S | O | CH |
| 9-122 | H | 4-OH-3,5-diMe—Ph | H | Me | —(CH₂)₂— | O | O | CH |
| 9-123 | H | 4-OH-3,5-diMe—Ph | H | Et | —CH₂— | O | O | CH |
| 9-124 | H | 4-OH-3,5-diMe—Ph | H | Et | —CH₂— | O | S | CH |
| 9-125 | H | 4-OH-3,5-diMe—Ph | H | sBu | —CH₂— | O | O | CH |
| 9-126 | H | 4-OH-3,5-diMe—Ph | H | tBu | —CH₂— | O | O | CH |
| 9-127 | H | 4-OH-3,5-diMe—Ph | H | Ph | —CH₂— | O | O | CH |
| 9-128 | H | 3,5-diEt-4-OH—Ph | H | Me | —CH₂— | O | O | CH |
| 9-129 | H | 3-tBu-4-OH-5-Me—Ph | H | Me | —CH₂— | O | O | CH |
| 9-130 | H | 3-tBu-4-OH-5-Me—Ph | H | Me | —CH₂— | O | S | CH |

TABLE 9-continued

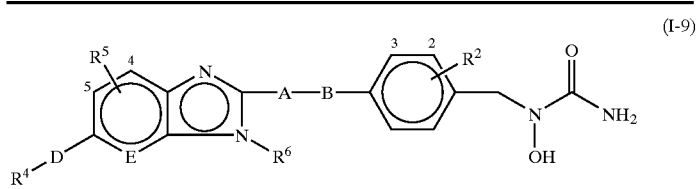

(I-9)

| Cpd. No. | R² | R⁴ | R⁵ | R⁶ | —A— | B | D | E |
|---|---|---|---|---|---|---|---|---|
| 9-131 | H | 4-OH-3,5-diPr—Ph | H | Me | —CH₂— | O | O | CH |
| 9-132 | H | 4-OH-3,5-diiPr—Ph | H | Me | —CH₂— | O | O | CH |
| 9-133 | H | 3,5-ditBu-4-OH—Ph | H | Me | —CH₂— | O | O | CH |
| 9-134 | H | 3,5-ditBu-4-OH—Ph | H | Me | —CH₂— | O | O | N |
| 9-135 | H | 3,5-ditBu-4-OH—Ph | H | Me | —CH₂— | O | S | CH |
| 9-136 | H | 3,5-ditBu-4-OH—Ph | H | Me | —CH₂— | S | S | CH |
| 9-137 | H | 3,5-ditBu-4-OH—Ph | H | Me | —(CH₂)₂— | O | O | CH |
| 9-138 | H | 3,5-ditBu-4-OH—Ph | H | Me | —(CH₂)₂— | O | S | CH |
| 9-139 | H | 3,5-ditBu-4-OH—Ph | H | Me | —(CH₂)₃— | O | S | CH |
| 9-140 | H | 3,5-ditBu-4-OH—Ph | H | Et | —CH₂— | O | O | CH |
| 9-141 | H | 3,5-ditBu-4-OH—Ph | H | Et | —CH₂— | O | S | CH |
| 9-142 | H | 3,5-ditBu-4-OH—Ph | H | tBu | —CH₂— | O | O | CH |
| 9-143 | H | 3,5-ditBu-4-OH—Ph | 5-Cl | Me | —CH₂— | O | S | CH |
| 9-144 | H | 4-OH-2,3,5-triMe—Ph | H | H | —CH₂— | O | S | CH |
| 9-145 | H | 4-OH-2,3,5-triMe—Ph | H | Me | —CH₂— | O | O | CH |
| 9-146 | H | 4-OH-2,3,5-triMe—Ph | H | Me | —CH₂— | O | O | N |
| 9-147 | H | 4-OH-2,3,5-triMe—Ph | H | Me | —CH₂— | O | S | CH |
| 9-148 | H | 4-OH-2,3,5-triMe—Ph | H | Me | —(CH₂)₂— | O | O | CH |
| 9-149 | H | 4-OH-2,3,5-triMe—Ph | H | Me | —(CH₂)₃— | O | O | CH |
| 9-150 | H | 4-OH-2,3,5-triMe—Ph | H | Et | —CH₂— | O | O | CH |
| 9-151 | H | 4-OH-2,3,5-triMe—Ph | H | Et | —CH₂— | O | S | CH |
| 9-152 | H | 4-OH-2,3,5-triMe—Ph | H | iPr | —CH₂— | O | O | CH |
| 9-153 | H | 4-OH-2,3,5-triMe—Ph | H | tBu | —CH₂— | O | O | CH |
| 9-154 | H | 4-OH-2,3,5-triMe—Ph | H | Ph | —CH₂— | O | O | CH |
| 9-155 | H | 4-OH-2,3,5-triMe—Ph | H | Bz | —CH₂— | O | O | CH |
| 9-156 | H | 4-OH-2,3,5-triMe—Ph | 5-Cl | Me | —CH₂— | O | O | CH |
| 9-157 | 2-Cl | 4-OH-2,3,5-triMe—Ph | H | Me | —CH₂— | O | O | CH |
| 9-158 | 2-MeO | 4-OH-2,3,5-triMe—Ph | H | Me | —CH₂— | O | O | CH |
| 9-159 | H | 4-OH-2,3,6-triMe—Ph | H | Me | —CH₂— | O | O | CH |
| 9-160 | H | 4-OH-2,3,5,6-tetraMe—Ph | H | Me | —CH₂— | O | O | CH |
| 9-161 | H | 4-OH-3,5-diMeO—Ph | H | Me | —CH₂— | O | O | CH |
| 9-162 | H | 3-NH₂-4-Me—Ph | H | Me | —CH₂— | O | O | CH |
| 9-163 | H | 4-NH₂-2,3-diMe—Ph | H | Me | —CH₂— | O | O | CH |
| 9-164 | H | 4-NH₂-2,6-diMe—Ph | H | Me | —CH₂— | O | O | CH |

TABLE 9-continued

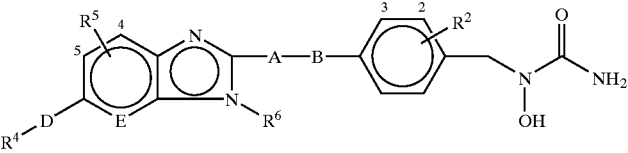

(I-9)

| Cpd. No. | R² | R⁴ | R⁵ | R⁶ | —A— | B | D | E |
|---|---|---|---|---|---|---|---|---|
| 9-165 | H | 4-NH₂-3,5-diMe—Ph | H | H | —CH₂— | O | O | CH |
| 9-166 | H | 4-NH₂-3,5-diMe—Ph | H | Me | —CH₂— | O | O | CH |
| 9-167 | H | 4-NH₂-3,5-diMe—Ph | H | Me | —CH₂— | O | O | N |
| 9-168 | H | 4-NH₂-3,5-diMe—Ph | H | Me | —CH₂— | O | S | CH |
| 9-169 | H | 4-NH₂-3,5-diMe—Ph | H | Me | —(CH₂)₂— | O | O | CH |
| 9-170 | H | 4-NH₂-3,5-diMe—Ph | H | Et | —CH₂— | O | O | CH |
| 9-171 | H | 4-NH₂-3,5-diMe—Ph | H | Et | —CH₂— | O | S | CH |
| 9-172 | H | 4-NH₂-3,5-diMe—Ph | H | tBu | —CH₂— | O | O | CH |
| 9-173 | H | 4-NH₂-3,5-diMe—Ph | H | Ph | —CH₂— | O | O | CH |
| 9-174 | H | 4-NH₂-3,5-diMe—Ph | H | Bz | —CH₂— | O | O | CH |
| 9-175 | H | 4-NH₂-3,5-diEt—Ph | H | Me | —CH₂— | O | O | CH |
| 9-176 | H | 4-NHMe-3,5-diMe—Ph | H | Me | —CH₂— | O | O | CH |
| 9-177 | H | 4-NHAc-3,5-diMe—Ph | H | Me | —CH₂— | O | O | CH |
| 9-178 | H | 4-NO₂-3,5-diMe—Ph | H | Me | —CH₂— | O | O | CH |
| 9-179 | H | 4-NO₂-3,5-diMe—Ph | H | Me | —CH₂— | O | S | CH |
| 9-180 | H | Pyr(2) | H | Me | —CH₂— | O | O | CH |
| 9-181 | H | Pyr(2) | H | Me | —CH₂— | O | O | N |
| 9-182 | H | Pyr(2) | H | Me | —CH₂— | O | S | CH |
| 9-183 | H | Pyr(2) | H | Me | —(CH₂)₂— | O | O | CH |
| 9-184 | H | Pyr(2) | H | Me | —(CH₂)₃— | O | O | CH |
| 9-185 | H | Pyr(2) | H | Et | —CH₂— | O | O | CH |
| 9-186 | H | Pyr(2) | H | Et | —CH₂— | O | S | CH |
| 9-187 | H | Pyr(2) | H | tBu | —CH₂— | O | O | CH |
| 9-188 | H | Pyr(2) | H | Ph | —CH₂— | O | O | CH |
| 9-189 | H | Pyr(2) | 5-Cl | Me | —CH₂— | O | O | CH |
| 9-190 | H | 5-Cl-Pyr(2) | H | Me | —CH₂— | O | O | CH |
| 9-191 | H | 6-Cl-Pyr(2) | H | Me | —CH₂— | O | O | CH |
| 9-192 | H | 6-Me-Pyr(2) | H | Me | —CH₂— | O | O | CH |
| 9-193 | H | 6-MeO-Pyr(2) | H | Me | —CH₂— | O | O | CH |
| 9-194 | H | 3-NH₂-Pyr(2) | H | Me | —CH₂— | O | O | CH |
| 9-195 | H | 5-NH₂-Pyr(2) | H | Me | —CH₂— | O | O | CH |
| 9-196 | H | 3-NO₂-Pyr(2) | H | Me | —CH₂— | O | O | CH |
| 9-197 | H | 5-NO₂-Pyr(2) | H | Me | —CH₂— | O | O | CH |
| 9-198 | H | 5-NH₂-6-Cl-Pyr(2) | H | Me | —CH₂— | O | O | CH |
| 9-199 | 3-MeO | 5-NH₂-6-Cl-Pyr(2) | 5-MeO | Et | —(CH₂)₄— | S | S | CH |
| 9-200 | H | Pyr(3) | H | Me | —CH₂— | O | O | CH |
| 9-201 | H | Pyr(3) | H | Me | —CH₂— | O | O | N |
| 9-202 | H | Pyr(3) | H | Me | —CH₂— | O | S | CH |
| 9-203 | H | Pyr(3) | H | Me | —(CH₂)₂— | O | O | CH |
| 9-204 | H | Pyr(3) | H | Me | —(CH₂)₃— | O | O | CH |
| 9-205 | H | Pyr(3) | H | Et | —CH₂— | O | O | CH |
| 9-206 | H | Pyr(3) | H | Et | —CH₂— | O | S | CH |
| 9-207 | H | Pyr(3) | H | tBu | —CH₂— | O | O | CH |
| 9-208 | H | Pyr(3) | H | Pn | —(CH₂)₃— | O | O | CH |
| 9-209 | H | Pyr(3) | H | Ph | —CH₂— | O | O | CH |
| 9-210 | H | Pyr(3) | H | Ph | —CH₂— | O | S | CH |
| 9-211 | H | Pyr(3) | H | Bz | —CH₂— | O | O | CH |
| 9-212 | 2-Cl | Pyr(3) | H | Me | —CH₂— | O | O | CH |
| 9-213 | H | 5-MeO-Pyr(3) | H | Me | —CH₂— | O | O | CH |
| 9-214 | H | 6-MeO-Pyr(3) | H | Me | —CH₂— | O | O | CH |

TABLE 9-continued

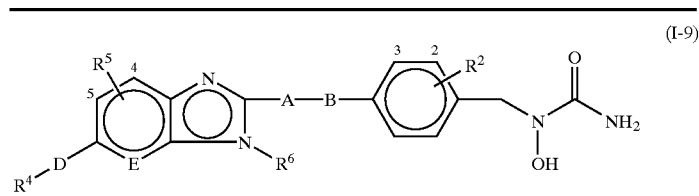

(I-9)

| Cpd. No. | $R^2$ | $R^4$ | $R^5$ | $R^6$ | —A— | B | D | E |
|---|---|---|---|---|---|---|---|---|
| 9-215 | H | 6-MeO-Pyr(3) | H | Me | —CH$_2$— | O | S | CH |
| 9-216 | H | 6-MeO-Pyr(3) | H | Me | —(CH$_2$)$_3$— | O | O | CH |
| 9-217 | H | 6-iPrO-Pyr(3) | H | Me | —CH$_2$— | O | O | CH |
| 9-218 | H | 6-MeO-5-Me-Pyr(3) | H | Me | —CH$_2$— | O | O | CH |
| 9-219 | H | 2-NO$_2$-6-Me-Pyr(3) | H | Me | —CH$_2$— | O | O | CH |
| 9-220 | H | Pyr(4) | H | Me | —CH$_2$— | O | O | CH |
| 9-221 | H | Pyr(4) | H | Me | —CH$_2$— | O | O | N |
| 9-222 | H | Pyr(4) | H | Me | —CH$_2$— | O | S | CH |
| 9-223 | H | Pyr(4) | H | Me | —CH$_2$— | S | S | CH |
| 9-224 | H | Pyr(4) | H | Me | —(CH$_2$)$_2$— | O | O | CH |
| 9-225 | H | Pyr(4) | H | Et | —CH$_2$— | O | O | CH |
| 9-226 | H | Pyr(4) | H | Et | —CH$_2$— | O | S | CH |
| 9-227 | H | Pyr(4) | H | tBu | —CH$_2$— | O | O | CH |
| 9-228 | H | Pyr(4) | H | Ph | —CH$_2$— | O | O | CH |
| 9-229 | H | Pyr(4) | H | Bz | —CH$_2$— | O | S | CH |
| 9-230 | 3-Cl | Pyr(4) | H | Me | —CH$_2$— | O | O | CH |
| 9-231 | H | 2-Me-Pyr(4) | H | Me | —CH$_2$— | O | O | CH |
| 9-232 | H | 2,6-diMe-Pyr(4) | H | Me | —CH$_2$— | O | O | CH |
| 9-233 | H | 2,6-diMe-Pyr(4) | H | Me | —CH$_2$— | O | S | CH |
| 9-234 | H | 3,6-diMe-Pyr(4) | H | Me | —CH$_2$— | O | O | CH |
| 9-235 | H | 2-MeO-Pyr(4) | H | Me | —CH$_2$— | O | O | CH |
| 9-236 | H | 4-Imid(1)-Ph | H | Me | —CH$_2$— | O | O | CH |
| 9-237 | H | 4-Tz-Ph | H | Me | —CH$_2$— | O | O | CH |
| 9-238 | H | 4-Ada(1)-Ph | H | Me | —CH$_2$— | O | O | CH |
| 9-239 | H | 4-CN—Ph | H | Me | —CH$_2$— | O | O | CH |
| 9-240 | H | 4-Bz-3-OH—Ph | H | Me | —CH$_2$— | O | O | CH |
| 9-241 | H | pentaF—Ph | H | Me | —CH$_2$— | O | O | CH |
| 9-242 | H | 4-NHCOPh—Ph | H | Me | —CH$_2$— | O | O | CH |
| 9-243 | H | 4-NHCO(3-Cl-Ph)—Ph | H | Me | —CH$_2$— | O | O | CH |
| 9-244 | H | 4-NHCO(2,4-diF-Ph)—Ph | H | Me | —CH$_2$— | O | O | CH |
| 9-245 | H | 4-NHCO(4-OH-3,5-ditBu—Ph)—Ph | H | Me | —CH$_2$— | O | O | CH |
| 9-246 | H | 4-NHCONp(1)-Ph | H | Me | —CH$_2$— | O | O | CH |
| 9-247 | H | 4-NHCO(3-Cl-Bz)-Ph | H | Me | —CH$_2$— | O | O | CH |
| 9-248 | H | 4-NHCOcPn-Ph | H | Me | —CH$_2$— | O | O | CH |
| 9-249 | H | 4-NHCOcHx-Ph | H | Me | —CH$_2$— | O | O | CH |
| 9-250 | H | 4-NHCOPyr(3)-Ph | H | Me | —CH$_2$— | O | O | CH |
| 9-251 | H | 4-NHCOPyr(4)-Ph | H | Me | —CH$_2$— | O | O | CH |
| 9-252 | H | 4-NHHx-Ph | H | Me | —CH$_2$— | O | O | CH |
| 9-253 | H | 4-NH(Ac)Hx-Ph | H | Me | —CH$_2$— | O | O | CH |

TABLE 10

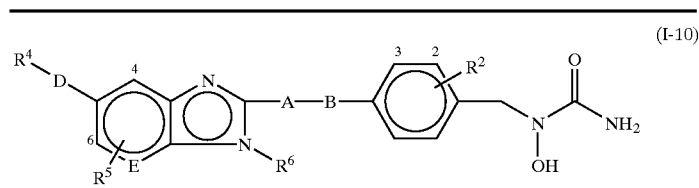

(I-10)

| Cpd. No. | $R^2$ | $R^4$ | $R^5$ | $R^6$ | —A— | B | D | E |
|---|---|---|---|---|---|---|---|---|
| 10-1 | H | 4-F—Ph | H | Me | —CH$_2$— | O | O | CH |
| 10-2 | H | 4-Cl—Ph | H | Me | —CH$_2$— | O | O | CH |
| 10-3 | H | 2-OH—Ph | H | Me | —CH$_2$— | O | O | CH |
| 10-4 | H | 2-OH—Ph | H | Me | —CH$_2$— | O | S | CH |

TABLE 10-continued

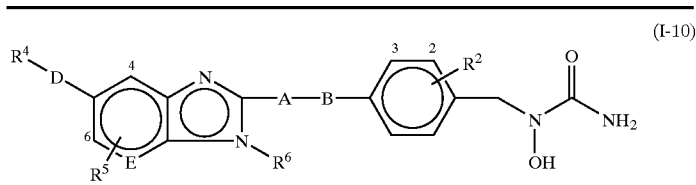

(I-10)

| Cpd. No. | R² | R⁴ | R⁵ | R⁶ | —A— | B | D | E |
|---|---|---|---|---|---|---|---|---|
| 10-5 | H | 3-OH—Ph | H | Me | —CH₂— | O | O | CH |
| 10-6 | H | 3-OH—Ph | H | Me | —CH₂— | O | S | CH |
| 10-7 | H | 4-OH—Ph | H | Me | —CH₂— | O | O | CH |
| 10-8 | H | 4-OH—Ph | H | Me | —CH₂— | O | O | N |
| 10-9 | H | 4-OH—Ph | H | Me | —CH₂— | O | S | CH |
| 10-10 | H | 4-OH—Ph | H | Et | —CH₂— | O | O | CH |
| 10-11 | H | 4-OH—Ph | H | Et | —CH₂— | O | S | CH |
| 10-12 | H | 3-CF₃—Ph | H | Me | —CH₂— | O | O | CH |
| 10-13 | H | 4-iPrO—Ph | H | Me | —CH₂— | O | O | CH |
| 10-14 | H | 4-MeS—Ph | H | Me | —CH₂— | O | O | CH |
| 10-15 | H | 2-NH₂—Ph | H | Me | —CH₂— | O | O | CH |
| 10-16 | H | 3-NH₂—Ph | H | Me | —CH₂— | O | O | CH |
| 10-17 | H | 4-NH₂—Ph | H | Me | —CH₂— | O | O | CH |
| 10-18 | H | 4-NHMe—Ph | H | Me | —CH₂— | O | O | CH |
| 10-19 | H | 4-N(Me)₂—Ph | H | Me | —CH₂— | O | O | CH |
| 10-20 | H | 4-N(Me)₂—Ph | H | Et | —CH₂— | O | O | CH |
| 10-21 | H | 4-Ph—Ph | H | Me | —CH₂— | O | O | CH |
| 10-22 | H | 4-(4-OH-3,5-diMe—Ph)Ph | H | Me | —CH₂— | O | O | CH |
| 10-23 | H | 4-(4-OH-3,5-ditBu—Ph)Ph | H | Me | —CH₂— | O | O | CH |
| 10-24 | H | 4-(4-OH-Bz)Ph | H | Me | —CH₂— | O | O | CH |
| 10-25 | H | 4-PhS—Ph | H | Me | —CH₂— | O | O | CH |
| 10-26 | H | 2-Pyrd(1)-Ph | H | Me | —CH₂— | O | O | CH |
| 10-27 | H | 3-Pyrd(1)-Ph | H | Me | —CH₂— | O | O | CH |
| 10-28 | H | 3-Pyrd(1)-Ph | H | Me | —CH₂— | O | S | CH |
| 10-29 | H | 3-Pyrd(1)-Ph | H | Me | —(CH₂)₂— | O | O | CH |
| 10-30 | H | 3-Pyrd(1)-Ph | H | Et | —CH₂— | O | O | CH |
| 10-31 | H | 4-Pyrd(1)-Ph | H | Me | —CH₂— | O | O | CH |
| 10-32 | H | 4-Pyrd(1)-Ph | H | Me | —CH₂— | O | S | CH |
| 10-33 | H | 4-Pyrd(1)-Ph | H | Me | —(CH₂)₃— | O | O | CH |
| 10-34 | H | 2-Pip(1)-Ph | H | Me | —CH₂— | O | O | CH |
| 10-35 | H | 3-Pip(1)-Ph | H | Me | —CH₂— | O | O | CH |
| 10-36 | H | 3-Pip(1)-Ph | H | Me | —CH₂— | O | S | CH |
| 10-37 | H | 3-Pip(1)-Ph | H | Et | —(CH₂)₃— | S | O | CH |
| 10-38 | H | 4-Pip(1)-Ph | H | Me | —CH₂— | O | O | CH |
| 10-39 | H | 4-Pip(1)-Ph | H | Me | —CH₂— | O | S | CH |
| 10-40 | H | 4-Pip(1)-Ph | H | Me | —(CH₂)₂— | O | O | CH |
| 10-41 | H | 4-Pip(1)-Ph | H | Me | —(CH₂)₃— | O | O | CH |
| 10-42 | H | 4-Pip(1)-Ph | H | tBu | —CH₂— | O | O | CH |
| 10-43 | H | 4-Pip(1)-Ph | 4-Cl | Me | —CH₂— | O | O | CH |
| 10-44 | 2-MeO | 4-Pip(1)-Ph | H | Me | —CH₂— | O | O | CH |
| 10-45 | H | 2-Mor(4)-Ph | H | Me | —CH₂— | O | O | CH |
| 10-46 | H | 2-Mor(4)-Ph | H | Me | —(CH₂)₃— | O | O | CH |
| 10-47 | H | 3-Mor(4)-Ph | H | Me | —CH₂— | O | O | CH |
| 10-48 | H | 3-Mor(4)-Ph | H | Me | —CH₂— | O | S | CH |
| 10-49 | H | 3-Mor(4)-Ph | H | Me | —(CH₂)₃— | O | O | CH |
| 10-50 | H | 3-Mor(4)-Ph | H | Et | —CH₂— | O | O | CH |
| 10-51 | H | 4-Mor(4)-Ph | H | Me | —CH₂— | O | O | CH |
| 10-52 | H | 4-Mor(4)-Ph | H | Me | —CH₂— | O | S | CH |
| 10-53 | H | 4-TioMor(4)-Ph | H | Me | —CH₂— | O | O | CH |
| 10-54 | H | 4-Pipra(1)-Ph | H | Me | —CH₂— | O | O | CH |
| 10-55 | H | 4-Pipra(1)-Ph | H | Me | —(CH₂)₃— | O | O | CH |
| 10-56 | H | 4-Pipra(1)-Ph | H | Et | —CH₂— | O | O | CH |
| 10-57 | H | 4-NO₂—Ph | H | Me | —CH₂— | O | O | CH |
| 10-58 | H | 2-Cl-4-OH-3,5-diMe—Ph | H | Me | —CH₂— | O | O | CH |
| 10-59 | H | 2-Cl-4-OH-3,5-diMe—Ph | H | Me | —CH₂— | O | O | N |
| 10-60 | H | 2-Cl-4-OH-3,5-diMe—Ph | H | Me | —CH₂— | O | S | CH |
| 10-61 | H | 2-Cl-4-OH-3,5-diMe—Ph | H | Me | —(CH₂)₄— | O | O | CH |
| 10-62 | H | 2-Cl-4-OH-3,5-diMe—Ph | H | Et | —CH₂— | O | O | CH |
| 10-63 | H | 2-Cl-4-OH-3,5-diMe—Ph | H | Et | —CH₂— | O | S | CH |

TABLE 10-continued

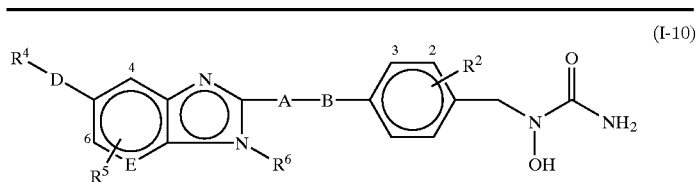
(I-10)

| Cpd. No. | R² | R⁴ | R⁵ | R⁶ | —A— | B | D | E |
|---|---|---|---|---|---|---|---|---|
| 10-64 | H | 2-Cl-4-OH-3,5-diMe—Ph | 6-MeO | Me | —CH₂— | O | O | CH |
| 10-65 | 3-Cl | 2-Cl-4-OH-3,5-diMe—Ph | H | Me | —CH₂— | O | O | CH |
| 10-66 | 2-MeO | 2-Cl-4-OH-3,5-diMe—Ph | H | Me | —CH₂— | O | O | CH |
| 10-67 | H | 4-Cl-3-OH-2,5-diMe—Ph | H | M | —CH₂— | O | O | CH |
| 10-68 | H | 3-Cl-4-NH₂—Ph | H | Me | —CH₂— | O | O | CH |
| 10-69 | H | 3,5-diCl-4-NH₂—Ph | H | Me | —CH₂— | O | O | CH |
| 10-70 | H | 4-NHMe-3-Cl—Ph | H | Me | —CH₂— | O | O | CH |
| 10-71 | H | 3-Cl-4-Pyrd(1)-Ph | H | Me | —CH₂— | O | O | CH |
| 10-72 | H | 3-OH-4-Pyrd(1)-Ph | H | Me | —CH₂— | O | O | CH |
| 10-73 | H | 3-Cl-6-Me-4-Pyrd(1)-Ph | H | Me | —CH₂— | O | O | CH |
| 10-74 | H | 2-Me-4-Mor(4)-Ph | H | Me | —CH₂— | O | O | CH |
| 10-75 | H | 2-OH-3-Me—Ph | H | Me | —CH₂— | O | O | CH |
| 10-76 | H | 2-OH-4-Me—Ph | H | Me | —CH₂— | O | O | CH |
| 10-77 | H | 2-OH-3,4-diMe—Ph | H | Me | —CH₂— | O | O | CH |
| 10-78 | H | 3-OH-2-Me—Ph | H | Me | —CH₂— | O | O | CH |
| 10-79 | H | 3-OH-4-Me—Ph | H | Me | —CH₂— | O | O | CH |
| 10-80 | H | 3-OH-5-Me—Ph | H | Me | —CH₂— | O | O | CH |
| 10-81 | H | 3-OH-6-Me—Ph | H | Me | —CH₂— | O | O | CH |
| 10-82 | H | 3-OH-2,4-diMe—Ph | H | Me | —CH₂— | O | O | CH |
| 10-83 | H | 4-OH-2-Me—Ph | H | Me | —CH₂— | O | O | CH |
| 10-84 | H | 4-OH-3-Me—Ph | H | Me | —CH₂— | O | O | CH |
| 10-85 | H | 4-OH-3-Me—Ph | H | Et | —CH₂— | O | O | CH |
| 10-86 | H | 4-OH-3-Me—Ph | 6-Cl | Me | —CH₂— | O | O | CH |
| 10-87 | H | 4-OH-2-tBu—Ph | H | Me | —CH₂— | O | O | CH |
| 10-88 | H | 4-OH-2,3-diMe—Ph | H | Me | —CH₂— | O | O | CH |
| 10-89 | H | 4-OH-2,3-diMe—Ph | H | Me | —CH₂— | O | S | CH |
| 10-90 | H | 4-OH-2,3-diMe—Ph | H | Me | —(CH₂)₃— | S | O | CH |
| 10-91 | H | 4-OH-2,3-diMe—Ph | H | Et | —CH₂— | O | O | CH |
| 10-92 | H | 4-OH-2,5-diMe—Ph | H | Me | —CH₂— | O | O | CH |
| 10-93 | H | 4-OH-3,5-diMe—Ph | H | Me | —CH₂— | O | O | CH |
| 10-94 | H | 4-OH-3,5-diMe—Ph | H | Me | —CH₂— | O | O | N |
| 10-95 | H | 4-OH-3,5-diMe—Ph | H | Me | —CH₂— | O | S | CH |
| 10-96 | H | 4-OH-3,5-diMe—Ph | H | Me | —CH₂— | S | O | CH |
| 10-97 | H | 4-OH-3,5-diMe—Ph | H | Me | —(CH₂)₂— | O | O | CH |
| 10-98 | H | 4-OH-3,5-diMe—Ph | H | Et | —CH₂— | O | O | CH |
| 10-99 | H | 4-OH-3,5-diMe—Ph | H | Et | —CH₂— | O | S | CH |
| 10-100 | H | 4-OH-3,5-diMe—Ph | H | sBu | —CH₂— | O | O | CH |
| 10-101 | H | 4-OH-3,5-diMe—Ph | H | Ph | —CH₂— | O | O | CH |
| 10-102 | H | 3,5-diEt-4-OH—Ph | H | Me | —CH₂— | O | O | CH |
| 10-103 | H | 3-tBu-4-OH-5-Me—Ph | H | Me | —CH₂— | O | O | CH |

TABLE 10-continued

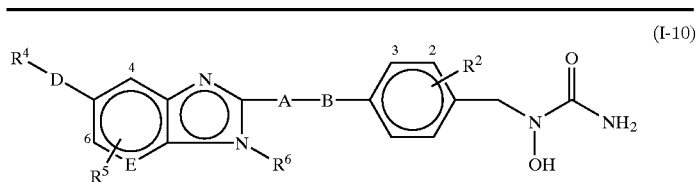

(I-10)

| Cpd. No. | R² | R⁴ | R⁵ | R⁶ | —A— | B | D | E |
|---|---|---|---|---|---|---|---|---|
| 10-104 | H | 3-tBu-4-OH-5-Me—Ph | H | Me | —CH₂— | O | S | CH |
| 10-105 | H | 4-OH-3,5-diPr—Ph | H | Me | —CH₂— | O | O | CH |
| 10-106 | H | 4-OH-3,5-diiPr—Ph | H | Me | —CH₂— | O | O | CH |
| 10-107 | H | 3,5-ditBu-4-OH—Ph | H | Me | —CH₂— | O | O | CH |
| 10-108 | H | 3,5-ditBu-4-OH—Ph | H | Me | —CH₂— | O | O | N |
| 10-109 | H | 3,5-ditBu-4-OH—Ph | H | Me | —CH₂— | O | S | CH |
| 10-110 | H | 3,5-ditBu-4-OH—Ph | H | Me | —CH₂— | S | S | CH |
| 10-111 | H | 3,5-ditBu-4-OH—Ph | H | Me | —(CH₂)₂— | O | S | CH |
| 10-112 | H | 3,5-ditBu-4-OH—Ph | H | Me | —(CH₂)₃— | O | S | CH |
| 10-113 | H | 3,5-ditBu-4-OH—Ph | H | Et | —CH₂— | O | O | CH |
| 10-114 | H | 3,5-ditBu-4-OH—Ph | H | Et | —CH₂— | O | S | CH |
| 10-115 | H | 3,5-ditBu-4-OH—Ph | 6-Cl | Me | —CH₂— | O | S | CH |
| 10-116 | H | 4-OH-2,3,5-triMe—Ph | H | H | —CH₂— | O | S | CH |
| 10-117 | H | 4-OH-2,3,5-triMe—Ph | H | Me | —CH₂— | O | O | CH |
| 10-118 | H | 4-OH-2,3,5-triMe—Ph | H | Me | —CH₂— | O | O | N |
| 10-119 | H | 4-OH-2,3,5-triMe—Ph | H | Me | —CH₂— | O | S | CH |
| 10-120 | H | 4-OH-2,3,5-triMe—Ph | H | Me | —(CH₂)₂— | O | O | CH |
| 10-121 | H | 4-OH-2,3,5-triMe—Ph | H | Me | —(CH₂)₃— | O | O | CH |
| 10-122 | H | 4-OH-2,3,5-triMe—Ph | H | Et | —CH₂— | O | O | CH |
| 10-123 | H | 4-OH-2,3,5-triMe—Ph | H | Et | —CH₂— | O | S | CH |
| 10-124 | H | 4-OH-2,3,5-triMe—Ph | H | iPr | —CH₂— | O | O | CH |
| 10-125 | H | 4-OH-2,3,5-triMe—Ph | H | Ph | —CH₂— | O | O | CH |
| 10-126 | H | 4-OH-2,3,5-triMe—Ph | H | Bz | —CH₂— | O | O | CH |
| 10-127 | H | 4-OH-2,3,5-triMe—Ph | 6-Cl | Me | —CH₂— | O | O | CH |
| 10-128 | 2-Cl | 4-OH-2,3,5-triMe—Ph | H | Me | —CH₂— | O | O | CH |
| 10-129 | 2-MeO | 4-OH-2,3,5-triMe—Ph | H | Me | —CH₂— | O | O | CH |
| 10-130 | H | 4-OH-2,3,6-triMe—Ph | H | Me | —CH₂— | O | O | CH |
| 10-131 | H | 4-OH-2,3,5,6-tetraMe—Ph | H | Me | —CH₂— | O | O | CH |
| 10-132 | H | 4-OH-3,5-diMeO—Ph | H | Me | —CH₂— | O | O | CH |
| 10-133 | H | 3-NH₂-4-Me—Ph | H | Me | —CH₂— | O | O | CH |
| 10-134 | H | 4-NH₂-2,3-diMe—Ph | H | Me | —CH₂— | O | O | CH |
| 10-135 | H | 4-NH₂-2,6-diMe—Ph | H | Me | —CH₂— | O | O | CH |
| 10-136 | H | 4-NH₂-3,5-diMe—Ph | H | H | —CH₂— | O | O | CH |
| 10-137 | H | 4-NH₂-3,5-diMe—Ph | H | Me | —CH₂— | O | O | CH |

TABLE 10-continued

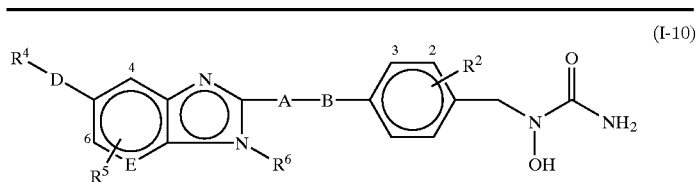

(I-10)

| Cpd. No. | R² | R⁴ | R⁵ | R⁶ | —A— | B | D | E |
|---|---|---|---|---|---|---|---|---|
| 10-138 | H | 4-NH₂-3,5-diMe—Ph | H | Me | —CH₂— | O | O | N |
| 10-139 | H | 4-NH₂-3,5-diMe—Ph | H | Me | —CH₂— | O | S | CH |
| 10-140 | H | 4-NH₂-3, 5-diMe—Ph | H | Me | —(CH₂)₂— | O | O | CH |
| 10-141 | H | 4-NH₂-3,5-diMe—Ph | H | Et | —CH₂— | O | O | CH |
| 10-142 | H | 4-NH₂-3,5-diMe—Ph | H | Et | —CH₂— | O | S | CH |
| 10-143 | H | 4-NH₂-3,5-diMe—Ph | H | Ph | —CH₂— | O | O | CH |
| 10-144 | H | 4-NH₂-3,5-diMe—Ph | H | Bz | —CH₂— | O | O | CH |
| 10-145 | H | 4-NHMe-3,5-diMe—Ph | H | Me | —CH₂— | O | O | CH |
| 10-146 | H | 4-NHAc-3,5-diMe—Ph | H | Me | —CH₂— | O | O | CH |
| 10-147 | H | 4-NO₂-3,5-diMe—Ph | H | Me | —CH₂— | O | O | CH |
| 10-148 | H | 4-NO₂-3,5-diMe—Ph | H | Me | —CH₂— | O | S | CH |
| 10-149 | H | Pyr(2) | H | Me | —CH₂— | O | O | CH |
| 10-150 | H | Pyr(2) | H | Me | —CH₂— | O | O | N |
| 10-151 | H | Pyr(2) | H | Me | —CH₂— | O | S | CH |
| 10-152 | H | Pyr(2) | H | Me | —(CH₂)₂— | O | O | CH |
| 10-153 | H | Pyr(2) | H | Me | —(CH₂)₃— | O | O | CH |
| 10-154 | H | Pyr(2) | H | Et | —CH₂— | O | O | CH |
| 10-155 | H | Pyr(2) | H | Et | —CH₂— | O | S | CH |
| 10-156 | H | Pyr(2) | H | Ph | —CH₂— | O | O | CH |
| 10-157 | H | Pyr(2) | 6-Cl | Me | —CH₂— | O | O | CH |
| 10-158 | H | 5-Cl-Pyr(2) | H | Me | —CH₂— | O | O | CH |
| 10-159 | H | 6-Cl-Pyr(2) | H | Me | —CH₂— | O | O | CH |
| 10-160 | H | 6-MeO-Pyr(2) | H | Me | —CH₂— | O | O | CH |
| 10-161 | H | 3-NH₂-Pyr(2) | H | Me | —CH₂— | O | O | CH |
| 10-162 | H | 5-NH₂-Pyr(2) | H | Me | —CH₂— | O | O | CH |
| 10-163 | H | 3-NO₂-Pyr(2) | H | Me | —CH₂— | O | O | CH |
| 10-164 | H | 5-NO₂-Pyr(2) | H | Me | —CH₂— | O | O | CH |
| 10-165 | 3-MeO | 5-NH₂-6-Cl-Pyr(2) | 6-MeO | Et | —(CH₂)₄— | S | S | CH |
| 10-166 | H | Pyr(3) | H | Me | —CH₂— | O | O | CH |
| 10-167 | H | Pyr(3) | H | Me | —CH₂— | O | O | N |
| 10-168 | H | Pyr(3) | H | Me | —CH₂— | O | S | CH |
| 10-169 | H | Pyr(3) | H | Me | —(CH₂)₃— | O | O | CH |
| 10-170 | H | Pyr(3) | H | Et | —CH₂— | O | O | CH |
| 10-171 | H | Pyr(3) | H | Et | —CH₂— | O | S | CH |
| 10-172 | H | Pyr(3) | H | Pn | —(CH₂)₃— | O | O | CH |
| 10-173 | H | Pyr(3) | H | Ph | —CH₂— | O | O | CH |
| 10-174 | H | Pyr(3) | H | Ph | —CH₂— | O | S | CH |
| 10-175 | 2-Cl | Pyr(3) | H | Me | —CH₂— | O | O | CH |
| 10-176 | H | 6-MeO-Pyr(3) | H | Me | —CH₂— | O | O | CH |
| 10-177 | H | 6-MeO-Pyr(3) | H | Me | —CH₂— | O | S | CH |
| 10-178 | H | 6-MeO-Pyr(3) | H | Me | —(CH₂)₃— | O | O | CH |
| 10-179 | H | 6-iPrO-Pyr(3) | H | Me | —CH₂— | O | O | CH |
| 10-180 | H | 6-MeO-5-Me-Pyr(3) | H | Me | —CH₂— | O | O | CH |
| 10-181 | H | 2-NO₂-6-Me-Pyr(3) | H | Me | —CH₂— | O | O | CH |
| 10-182 | H | Pyr(4) | H | Me | —CH₂— | O | O | CH |
| 10-183 | H | Pyr(4) | H | Me | —CH₂— | O | O | N |
| 10-184 | H | Pyr(4) | H | Me | —CH₂— | O | S | CH |
| 10-185 | H | Pyr(4) | H | Me | —CH₂— | S | S | CH |
| 10-186 | H | Pyr(4) | H | Me | —(CH₂)₂— | O | O | CH |
| 10-187 | H | Pyr(4) | H | Et | —CH₂— | O | O | CH |
| 10-188 | H | Pyr(4) | H | Et | —CH₂— | O | S | CH |
| 10-189 | H | Pyr(4) | H | Ph | —CH₂— | O | O | CH |
| 10-190 | H | Pyr(4) | H | Bz | —CH₂— | O | S | CH |
| 10-191 | 3-Cl | Pyr(4) | H | Me | —CH₂— | O | O | CH |

TABLE 10-continued (I-10)

[Structure: benzimidazole with R4-D, position 4=N, position 6, R5-E, R6-N, linked via A-B to phenyl with R2 at position 2-3, then CH2-N(OH)-C(=O)-NH2]

| Cpd. No. | R² | R⁴ | R⁵ | R⁶ | —A— | B | D | E |
|---|---|---|---|---|---|---|---|---|
| 10-192 | H | 2-Me-Pyr(4) | H | Me | —CH₂— | O | O | CH |
| 10-193 | H | 2,6-diMe-Pyr(4) | H | Me | —CH₂— | O | O | CH |
| 10-194 | H | 2,6-diMe-Pyr(4) | H | Me | —CH₂— | O | S | CH |
| 10-195 | H | 3,6-diMe-Pyr(4) | H | Me | —CH₂— | O | O | CH |
| 10-196 | H | 2-MeO-Pyr(4) | H | Me | —CH₂— | O | O | CH |
| 10-197 | H | 4-Imid(1)-Ph | H | Me | —CH₂— | O | O | CH |
| 10-198 | H | 4-Tz-Ph | H | Me | —CH₂— | O | O | CH |
| 10-199 | H | 4-Ada(1)-Ph | H | Me | —CH₂— | O | O | CH |
| 10-200 | H | 4-CN—Ph | H | Me | —CH₂— | O | O | CH |
| 10-201 | H | 4-Bz-3-OH—Ph | H | Me | —CH₂— | O | O | CH |
| 10-202 | H | pentaF—Ph | H | Me | —CH₂— | O | O | CH |
| 10-203 | H | 4-NHCOPh—Ph | H | Me | —CH₂— | O | O | CH |
| 10-204 | H | 4-NHCO(3-Cl-Ph)—Ph | H | Me | —CH₂— | O | O | CH |
| 10-205 | H | 4-NHCO(2,4-diF—Ph)—Ph | H | Me | —CH₂— | O | O | CH |
| 10-206 | H | 4-NHCO(4-OH-3,5-ditBu—Ph)—Ph | H | Me | —CH₂— | O | O | CH |
| 10-207 | H | 4-NHCONp(1)-Ph | H | Me | —CH₂— | O | O | CH |
| 10-208 | H | 4-NHCO(3-Cl-Bz) | H | Me | —CH₂— | O | O | CH |
| 10-209 | H | 4-NHCOcPn-Ph | H | Me | —CH₂— | O | O | CH |
| 10-210 | H | 4-NHCOcHx-Ph | H | Me | —CH₂— | O | O | CH |
| 10-211 | H | 4-NHCOPyr(3)-Ph | H | Me | —CH₂— | O | O | CH |
| 10-212 | H | 4-NHCOPyr(4)-Ph | H | Me | —CH₂— | O | O | CH |
| 10-213 | H | 4-NHHx-Ph | H | Me | —CH₂— | O | O | CH |
| 10-214 | H | 4-NH(Ac)Hx-Ph | H | Me | —CH₂— | O | O | CH |

Preferred examples of the compounds in the above Tables 1–10 include:
Compound Nos.

1-2, 1-3, 1-6, 1-7, 1-8, 1-10, 1-11,
1-13, 1-18, 1-25, 1-41, 1-42, 1-43, 1-48,
1-51, 1-60, 1-68, 1-69, 1-70, 1-71, 1-72,
1-77, 1-80, 1-86, 1-89, 1-90, 1-94, 1-97,
1-104, 1-127, 1-128, 1-129, 1-130, 1-131, 1-132,
1-133, 1-134, 1-135, 1-136, 1-137, 1-141, 1-142,
1-143, 1-144, 1-148, 1-149, 1-150, 1-153, 1-154,
1-155, 1-156, 1-157, 1-159, 1-160, 1-161, 1-162,
1-163, 1-164, 1-165, 1-168, 1-169, 1-170, 1-171,
1-172, 1-175, 1-181, 1-182, 1-184, 1-185, 1-186,
1-191, 1-193, 1-195, 1-199, 1-200, 1-201, 1-206,
1-208, 1-213, 1-214, 1-215, 1-216, 1-221, 1-223,
1-230, 1-236, 1-241, 1-242, 1-243, 1-244, 1-245,
1-246, 1-248, 1-249, 1-250, 1-251, 1-253, 1-256,
1-257, 1-258, 1-259, 1-260, 1-264, 1-267, 1-269,
1-282, 1-284, 1-285, 1-286, 1-287, 1-288, 1-289,
1-290, 1-292, 1-293, 1-294, 1-295, 1-296, 1-297,
1-298, 1-299, 1-300, 1-302, 1-303, 1-304, 1-305,
1-307, 1-309, 1-312, 1-325, 1-329, 1-330, 1-331,
1-332, 1-333, 1-335, 1-339, 1-342, 1-344, 1-351,
1-354, 1-357, 1-358, 1-359, 1-362, 1-363, 1-366,
1-367, 1-368, 1-369, 1-370, 1-371, 1-375, 1-378,
1-408, 1-421, 1-429, 1-430, 1-433, 1-438, 1-439,
1-440, 1-441, 1-442, 1-447, 1-458, 1-463, 1-465,
1-468, 1-469, 1-470, 1-476, 1-481, 1-482, 1-483,
1-486, 1-487, 1-488, 1-489, 1-497, 1-499, 1-501,
1-502, 1-503, 1-504, 1-506, 1-507, 1-508, 1-513,
1-514, 1-515, 1-519, 1-520, 1-521, 1-522, 1-523,
1-528, 1-538, 1-540, 1-541, 1-543, 1-544, 1-560,
1-561, 1-565, 1-566, 1-567, 1-569, 1-572, 1-574,
1-575, 1-577, 1-578, 1-579, 1-590, 1-592, 1-593,
1-594, 1-595, 1-597, 1-598, 1-599, 1-600, 1-601,
1-602, 1-603, 1-607, 1-608, 1-609, 1-610, 1-613,
1-624, 1-627, 1-631, 1-633, 1-634, 1-635, 1-636,
1-637, 1-638, 1-639, 1-640, 1-641, 1-642, 1-643,
1-644, 1-645, 1-646, 1-647, 1-650, 1-651, 1-652,
1-653, 1-660, 1-661, 1-666, 1-668, 1-669, 1-670,
1-671, 1-690, 1-692, 1-693, 1-696, 1-697, 1-698,
1-705, 1-706, 1-707, 1-708, 1-710, 1-711, 1-713,
1-715, 1-722, 1-723, 1-724, 1-727, 1-728, 1-729,
1-738, 1-739, 1-740, 1-741, 1-742, 1-743, 1-747,
1-748, 1-749, 1-757, 1-758, 1-759, 1-764, 1-765,
1-767, 1-773, 1-777, 1-779, 1-786, 1-796, 1-800,
1-808, 1-809, 1-812, 1-814, 1-820, 1-821, 1-822,
1-823, 1-824, 1-829, 1-830, 1-831, 1-832, 1-839,
1-840, 1-841, 1-846, 1-859, 1-877, 1-878, 1-879,
1-881, 1-883, 1-888, 1-895, 1-897, 1-907, 1-909,
1-910, 1-911, 1-912, 1-913, 1-916, 1-917, 1-920,
1-922, 1-925, 1-926, 1-927, 1-930, 1-932, 1-937,
1-938, 1-939, 1-940, 1-941, 1-946, 1-948, 1-954,
1-956, 1-957, 1-958, 1-979, 1-984, 1-988, 1-989,
1-994, 1-998, 1-1001, 1-1006, 1-1010, 1-1018, 1-1019,
1-1020, 1-1021, 1-1026, 1-1028, 1-1030, 1-1110, 1-1111,
1-1112, 1-1115, 1-1126, 1-1127, 1-1128, 1-1154, 1-1182,
1-1183, 1-1184, 1-1185, 1-1210, 1-1211, 1-1212, 1-1213,
1-1230, 1-1234, 1-1235, 1-1236, 1-1237, 1-1242, 1-1248,
1-1249, 1-1256, 1-1263, 1-1264, 1-1265, 1-1269, 1-1270,
1-1271, 1-1277, 1-1285, 1-1286, 1-1287, 1-1292, 1-1293,
1-1294, 1-1298, 1-1299, 1-1305, 1-1306, 1-1307, 1-1311,
1-1312, 1-1313, 1-1318, 1-1319, 1-1320, 1-1327, 2-18,
2-19, 2-20, 2-21, 2-22, 2-55, 2-56, 2-57,
2-58, 2-59, 2-60, 2-76, 2-77, 2-78, 2-81,
2-83, 2-86, 2-87, 2-88, 2-94, 2-95, 2-96,
2-99, 2-105, 2-115, 2-116, 2-117, 2-119, 2-121,
2-122, 2-123, 2-127, 2-134, 2-135, 2-153, 2-154,

-continued

| | | | | | | |
|---|---|---|---|---|---|---|
| 2-155, | 2-173, | 2-185, | 2-186, | 2-187, | 2-205, | 2-206, |
| 2-218, | 2-219, | 2-229, | 2-230, | 2-231, | 2-232, | 2-233, |
| 2-234, | 2-262, | 2-263, | 2-264, | 2-265, | 2-266, | 2-267, |
| 2-270, | 2-286, | 2-292, | 2-296, | 2-297, | 2-298, | 2-299, |
| 2-300, | 2-325, | 2-326, | 2-334, | 2-335, | 2-339, | 2-340, |
| 2-341, | 2-342, | 2-378, | 2-379, | 2-380, | 2-381, | 2-384, |
| 2-385, | 2-406, | 2-430, | 2-431, | 2-432, | 2-433, | 2-513, |
| 2-534, | 2-541, | 2-545, | 2-547, | 2-548, | 2-549, | 2-552, |
| 2-553, | 3-1, | 3-2, | 3-3, | 3-4, | 3-6, | 3-10, |
| 3-19, | 3-20, | 3-21, | 3-22, | 3-53, | 3-54, | 3-55, |
| 3-56, | 3-57, | 3-58, | 3-59, | 3-60, | 3-69, | 3-76, |
| 3-78, | 3-81, | 3-83, | 3-86, | 3-87, | 3-88, | 3-94, |
| 3-95, | 3-96, | 3-105, | 3-106, | 3-107, | 3-115, | 3-116, |
| 3-117, | 3-119, | 3-120, | 3-127, | 3-134, | 3-136, | 3-137, |
| 3-142, | 3-148, | 3-149, | 3-153, | 3-154, | 3-155, | 3-156, |
| 3-184, | 3-188, | 3-189, | 3-205, | 3-206, | 3-218, | 3-219, |
| 3-229, | 3-230, | 3-231, | 3-232, | 3-234, | 3-239, | 3-241, |
| 3-248, | 3-250, | 3-263, | 3-264, | 3-265, | 3-266, | 3-267, |
| 3-272, | 3-275, | 3-276, | 3-296, | 3-297, | 3-298, | 3-299, |
| 3-306, | 3-326, | 3-334, | 3-335, | 3-338, | 3-339, | 3-340, |
| 3-341, | 3-342, | 3-344, | 3-349, | 3-351, | 3-378, | 3-379, |
| 3-380, | 3-381, | 3-383, | 3-385, | 3-388, | 3-406, | 3-408, |
| 3-430, | 3-431, | 3-432, | 3-433, | 3-521, | 3-522, | 3-530, |
| 3-531, | 3-532, | 3-534, | 3-540, | 3-541, | 3-542, | 3-545, |
| 3-547, | 3-552, | 3-553, | 4-11, | 4-13, | 4-24, | 4-25, |
| 4-32, | 4-38, | 4-44, | 4-49, | 4-59, | 4-60, | 4-62, |
| 4-63, | 4-66, | 4-87, | 4-90, | 4-105, | 4-118, | 4-120, |
| 4-121, | 4-131, | 4-132, | 4-133, | 4-134, | 4-135, | 4-145, |
| 4-146, | 4-147, | 4-159, | 4-166, | 4-167, | 4-168, | 4-180, |
| 4-181, | 4-182, | 4-200, | 4-201, | 4-202, | 4-238, | 4-239, |
| 4-243, | 4-245, | 4-247, | 4-252, | 5-11, | 5-13, | 5-24, |
| 5-25, | 5-32, | 5-33, | 5-35, | 5-39, | 5-44, | 5-45, |
| 5-49, | 5-50, | 5-51, | 5-59, | 5-60, | 5-62, | 5-63, |
| 5-65, | 5-66, | 5-71, | 5-77, | 5-78, | 5-79, | 5-80, |
| 5-105, | 5-112, | 5-118, | 5-119, | 5-120, | 5-122, | 5-131, |
| 5-132, | 5-133, | 5-134, | 5-135, | 5-137, | 5-145, | 5-146, |
| 5-147, | 5-148, | 5-159, | 5-163, | 5-166, | 5-167, | 5-168, |
| 5-170, | 5-171, | 5-180, | 5-181, | 5-182, | 5-183, | 5-192, |
| 5-200, | 5-201, | 5-202, | 5-236, | 5-238, | 5-242, | 5-245, |
| 5-247, | 5-252, | 5-253, | 6-7, | 6-8, | 6-9, | 6-26, |
| 6-45, | 6-47, | 6-48, | 6-58, | 6-59, | 6-60, | 6-67, |
| 6-82, | 6-93, | 6-107, | 6-108, | 6-109, | 6-116, | 6-117, |
| 6-134, | 6-149, | 6-166, | 6-199, | 6-200, | 6-208, | 7-1, |
| 7-2, | 7-3, | 7-4, | 7-11, | 7-13, | 7-24, | 7-25, |
| 7-32, | 7-38, | 7-44, | 7-49, | 7-59, | 7-60, | 7-62, |
| 7-63, | 7-66, | 7-87, | 7-90, | 7-105, | 7-118, | 7-120, |
| 7-121, | 7-131, | 7-132, | 7-133, | 7-134, | 7-135, | 7-145, |
| 7-146, | 7-147, | 7-159, | 7-166, | 7-167, | 7-168, | 7-180, |
| 7-181, | 7-182, | 7-200, | 7-201, | 7-202, | 7-236, | 7-238, |
| 7-239, | 7-241, | 7-242, | 7-243, | 7-244, | 7-245, | 7-247, |
| 7-248, | 7-249, | 7-250, | 7-251, | 7-252, | 7-253, | 8-7, |
| 8-9, | 8-19, | 8-26, | 8-31, | 8-34, | 8-38, | 8-45, |
| 8-47, | 8-48, | 8-51, | 8-58, | 8-67, | 8-82, | 8-93, |
| 8-95, | 8-96, | 8-105, | 8-106, | 8-107, | 8-108, | 8-109, |
| 8-117, | 8-118, | 8-119, | 8-130, | 8-137, | 8-138, | 8-139, |
| 8-149, | 8-150, | 8-151, | 8-166, | 8-167, | 8-168, | 8-199, |
| 8-206, | 8-213, | 9-11, | 9-13, | 9-24, | 9-32, | 9-33, |
| 9-35, | 9-39, | 9-44, | 9-45, | 9-49, | 9-50, | 9-51, |
| 9-59, | 9-60, | 9-62, | 9-63, | 9-65, | 9-66, | 9-71, |
| 9-77, | 9-78, | 9-79, | 9-80, | 9-105, | 9-118, | 9-119, |
| 9-120, | 9-122, | 9-131, | 9-132, | 9-133, | 9-134, | 9-135, |
| 9-137, | 9-145, | 9-146, | 9-147, | 9-148, | 9-159, | 9-163, |
| 9-166, | 9-167, | 9-168, | 9-170, | 9-171, | 9-180, | 9-181, |
| 9-182, | 9-183, | 9-192, | 9-200, | 9-201, | 9-202, | 9-236, |
| 9-238, | 9-239, | 9-242, | 9-245, | 9-247, | 9-250, | 9-252, |
| 10-7, | 10-8, | 10-9, | 10-26, | 10-45, | 10-47, | 10-48, |
| 10-58, | 10-59, | 10-60, | 10-67, | 10-82, | 10-93, | 10-107, |
| 10-108, | 10-109, | 10-116, | 10-117, | 10-133, | 10-149, | 10-166, |
| 10-197, | 10-200, | 10-203, | 10-211 and | 10-213, | | |

More preferred examples include:
Compound Nos.

| | | | | | | |
|---|---|---|---|---|---|---|
| 1-69, | 1-70, | 1-72, | 1-131, | 1-132, | 1-136, | 1-137, |
| 1-142, | 1-149, | 1-150, | 1-153, | 1-154, | 1-155, | 1-157, |
| 1-160, | 1-161, | 1-164, | 1-168, | 1-169, | 1-171, | 1-172, |
| 1-184, | 1-185, | 1-193, | 1-199, | 1-200, | 1-201, | 1-214, |
| 1-215, | 1-216, | 1-221, | 1-241, | 1-242, | 1-243, | 1-246, |
| 1-257, | 1-258, | 1-259, | 1-284, | 1-285, | 1-286, | 1-290, |

-continued

| | | | | | | |
|---|---|---|---|---|---|---|
| 1-292, | 1-302, | 1-329, | 1-330, | 1-357, | 1-368, | 1-369, |
| 1-370, | 1-371, | 1-375, | 1-378, | 1-408, | 1-476, | 1-481, |
| 1-486, | 1-501, | 1-502, | 1-503, | 1-506, | 1-513, | 1-514, |
| 1-515, | 1-520, | 1-521, | 1-522, | 1-523, | 1-560, | 1-577, |
| 1-593, | 1-594, | 1-595, | 1-603, | 1-607, | 1-609, | 1-633, |
| 1-634, | 1-640, | 1-650, | 1-651, | 1-652, | 1-653, | 1-660, |
| 1-708, | 1-727, | 1-729, | 1-739, | 1-740, | 1-741, | 1-742, |
| 1-747, | 1-757, | 1-759, | 1-808, | 1-821, | 1-822, | 1-823, |
| 1-824, | 1-831, | 1-877, | 1-878, | 1-879, | 1-938, | 1-939, |
| 1-940, | 1-1126, | 1-1182, | 1-1210, | 1-1211, | 1-1212, | 1-1234, |
| 1-1235, | 1-1236, | 1-1237, | 1-1242, | 1-1248, | 1-1263, | 1-1269, |
| 1-1270, | 1-1271, | 1-1277, | 1-1285, | 1-1292, | 1-1298, | 1-1305, |
| 1-1306, | 1-1307, | 1-1311, | 1-1312, | 1-1313, | 1-1318, | 2-19, |
| 2-76, | 2-115, | 2-121, | 2-153, | 2-185, | 2-205, | 2-229, |
| 2-233, | 2-264, | 2-266, | 2-267, | 2-296, | 2-298, | 2-339, |
| 2-378, | 2-545, | 2-547, | 3-94, | 3-115, | 3-153, | 3-229, |
| 3-231, | 3-263, | 3-266, | 3-267, | 3-298, | 3-339, | 3-340, |
| 3-341, | 3-342, | 3-430, | 3-432, | 3-530, | 5-11, | 5-44, |
| 5-78, | 5-118, | 5-133, | 5-135, | 5-145, | 5-146, | 5-147, |
| 5-166, | 5-180, | 5-236, | 5-245, | 9-11, | 9-44, | 9-78, |
| 9-118, | 9-133, | 9-135, | 9-145, | 9-147, | 9-180, | 9-238, and |
| 9-239. | | | | | | |

Most preferred examples of the compound include:

Compound No. 1-70: 5-{4-[6-(4-hydroxyphenoxy)-1-methyl-1H-benzimidazol-2-ylmethoxy]benzyl}thiazolidine-2,4-dione, Compound No. 1-131: 5-{4-[1-methyl-6-(4-trifluoromethylphenoxy)-1H-benzimidazol-2-ylmethoxy]benzyl}thiazolidine-2,4-dione, Compound No. 1-132: 5-{4-[1-methyl-6-(4-methoxyphenoxy)-1H-benzimidazol-2-ylmethoxy]benzyl}thiazolidine-2,4-dione, Compound No. 1-136: 5-{4-[1-methyl-6-(4-methylthiophenoxy)-1H-benzimidazol-2-ylmethoxy]benzyl}thiazolidine-2,4-dione, Compound No. 1-142: 5-{4-[6-(4-aminophenoxy)-1-methyl-1H-benzimidazol-2-ylmethoxy]benzyl}thiazolidine-2,4-dione, Compound No. 1-153: 5-{4-[6-(3-dimethylaminophenoxy)-1-methyl-1H-benzimidazol-2-ylmethoxy]benzyl}thiazolidine-2,4-dione, Compound No. 1-164: 5-{4-[6-(4-acetylaminophenoxy)-1-methyl-1H-benzimidazol-2-ylmethoxy]benzyl}thiazolidine-2,4-dione, Compound No. 1-169: 5-{4-[1-methyl-6-(4-phenylphenoxy)-1H-benzimidazol-2-ylmethoxy]benzyl}thiazolidine-2,4-dione, Compound No. 1-171: 5-{4-[6-(4'-hydroxybiphenyl-4-yloxy)-1-methyl-1H-benzimidazol-2-ylmethoxy]benzyl}thiazolidine-2,4-dione, Compound No. 1-184: 5-{4-[6-(4-benzylphenoxy)-1-methyl-1H-benzimidazol-2-ylmethoxy]benzyl}thiazolidine-2,4-dione, Compound No. 1-199: 5-{4-(6-[2-(pyrrolidin-1-yl)phenoxy]-1-methyl-1H-benzimidazol-2-ylmethoxy)benzyl}thiazolidine-2,4-dione, Compound No. 1-241: 5-{4-(6-[2-(piperidin-1-yl)phenoxy]-1-methyl-1H-benzimidazol-2-ylmethoxy)benzyl}thiazolidine-2,4-dione, Compound No. 1-284: 5-{4-(6-[2-(morpholin-4-yl)phenoxy]-1-methyl-1H-benzimidazol-2-ylmethoxy)benzyl}thiazolidine-2,4-dione, Compound No. 1-292: 5-{4-(1-methyl-6-[3-(morpholin-4-yl)phenoxy]-1H-benzimidazol-2-ylmethoxy)benzyl}thiazolidine-2,4-dione, Compound No. 1-368: 5-{4-[6-(2-chloro-4-hydroxy-3,5-dimethylphenoxy)-1-methyl-1H-benzimidazol-2-ylmethoxy]benzyl}thiazolidine-2,4-dione, Compound No. 1-481: 5-{4-[6-(4-hydroxy-2-methylphenoxy)-1-methyl-1H-benzimidazol-2-ylmethoxy]benzyl}thiazolidine-2,4-dione, Compound No. 1-486: 5-{4-[6-(4-hydroxy-3-methylphenoxy)-1-methyl-1H-benzimidazol-2-ylmethoxy]benzyl}thiazolidine-2,4-dione, Compound No. 1-513: 5-{4-[6-(4-hydroxy-2,5-dimethylphenoxy)-1-methyl-1H-benzimidazol-2-ylmethoxy]benzyl}thiazolidine-2,4-dione, Compound No. 1-520: 5-{4-[6-(4-hydroxy-3,5-dimethylphenoxy)-1-methyl-1H-benzimidazol-2-ylmethoxy]benzyl}thiazolidine-2,4-dione, Compound No. 1-593: 5-{4-[6-(3,5-di-t-butyl-4-hydroxyphenoxy)-1-methyl-1H-benzimidazol-2-ylmethoxy]benzyl}thiazolidine-2,4-dione, Compound No. 1-595: 5-{4-[6-(3,5-di-t-butyl-4-hydroxyphenylthio)-1-methyl-1H-benzimidazol-2-ylmethoxy]benzyl}thiazolidine-2,4-dione, Compound No. 1-650: 5-{4-[6-(4-hydroxy-2,3,5-trimethylphenoxy)-1-methyl-1H-benzimidazol-2-ylmethoxy]benzyl}thiazolidine-2,4-dione, Compound No. 1-651: 5-{4-[5-(4-hydroxy-2,3,5-trimethylphenoxy)-3-methyl-3H-imidazo[4,5-b]pyridin-2-ylmethoxy]benzyl}thiazolidine-2,4-dione, Compound No. 1-739: 5-{4-[6-(4-amino-3,5-dimethylphenoxy)-1-methyl-1H-benzimidazol-2-ylmethoxy]benzyl}thiazolidine-2,4-dione, Compound No. 1-808: 5-{4-[6-(4-acetylamino-3,5-dimethylphenoxy)-1-methyl-1H-benzimidazol-2-ylmethoxy]benzyl}thiazolidine-2,4-dione, Compound No. 1-821: 5-{4-[6-(pyridin-2-yloxy)-1-methyl-1H-benzimidazol-2-ylmethoxy]benzyl}thiazolidine-2,4-dione, Compound No. 1-823: 5-{4-[1-methyl-6-(pyridin-2-ylthio)-1H-benzimidazol-2-ylmethoxy]benzyl}thiazolidine-2,4-dione, Compound No. 1-938: 5-{4-[1-methyl-6-(pyridin-3-yloxy)-1H-benzimidazol-2-ylmethoxy]benzyl}thiazolidine-2,4-dione, Compound No. 1-1126: 5-{4-(6-[4-(imidazol-1-yl)phenoxy]-1-methyl-1H-benzimidazol-2-ylmethoxy)benzyl}thiazolidine-2,4-dione, Compound No. 1-1182: 5-{4-(6-[4-(1-adamantyl)phenoxy]-1-methyl-1H-benzimidazol-2-ylmethoxy)benzyl}thiazolidine-2,4-dione, Compound No. 1-1210: 5-{4-[6-(4-cyanophenoxy)-1-methyl-1H-benzimidazol-2-ylmethoxy]benzyl}thiazolidine-2,4-dione, Compound No. 1-1234: 5-{4-[6-(2,5-di-t-butyl-4-hydroxyphenoxy)-1-methyl-1H-benzimidazol-2-ylmethoxy]benzyl}thiazolidine-2,4-dione, Compound No. 1-1235: 5-{4-[6-(pentafluorophenoxy)-1-methyl-1H-benzimidazol-2-ylmethoxy]benzyl}thiazolidine-2,4-dione, Compound No. 1-1248: 5-{4-[6-(4-benzoylaminophenoxy)-1-methyl-1H-benzimidazol-2-ylmethoxy]benzyl}thiazolidine-2,4-dione, Compound No. 1-1263: 5-[4-{6-[4-(2,4-difluorobenzoylamino)phenoxy]-1-methyl-1H-benzimidazol-2-ylmethoxy}benzyl]thiazolidine-2,4-dione, Compound No. 1-1292: 5-{4-[6-(4-cyclopentanecarbonylaminophenoxy)-1-methyl-1H-benzimidazol-2-ylmethoxy]benzyl}thiazolidine-2,4-dione, Compound No. 1-1305: 5-{4-[6-(4-nicotinoylaminophenoxy)-1-methyl-1H-benzimidazol-2-ylmethoxy]benzyl}thiazolidine-2,4-dione, and Compound No. 5-135: 5-{4-[6-(3,5-di-t-butyl-4-hydroxyphenylthio)-1-methyl-1H-benzimidazol-2-ylmethoxy]benzylidene}thiazolidine-2,4-dione.

The compound of the present invention represented by the formula (I) can be prepared easily in accordance with any one of the following methods:

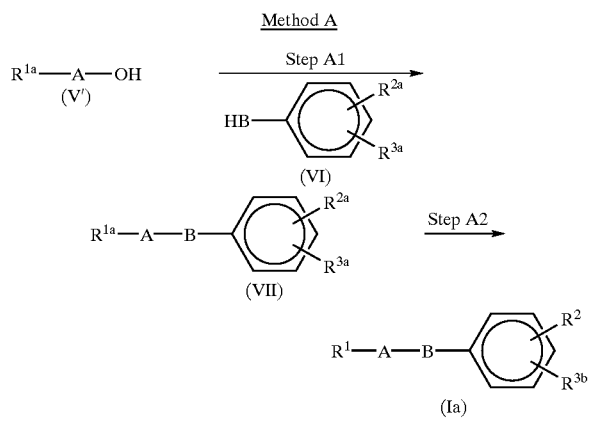

In the above reaction scheme, $R^1$, $R^2$, A and B have the same meanings as described above; $R^{1a}$ represents a similar group to that defined as the group $R^1$ except that any amino and/or hydroxyl group contained in $R^1$ is an amino and/or hydroxyl group which may be protected by an amino- and/or hydroxyl-protecting group; $R^{2a}$ represents a similar group to that as defined as the group $R^2$ except that any amino and/or hydroxyl group contained in $R^2$ is an amino and/or hydroxyl group which may be protected by an amino- and/or hydroxyl-protecting group; $R^{3a}$ represents the following group:

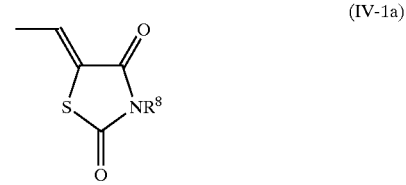

(IV-1a)

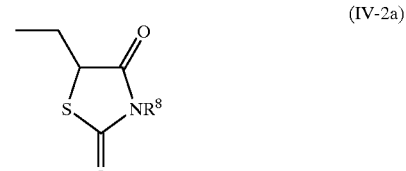

(IV-2a)

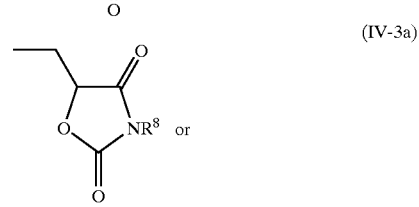

(IV-3a) or

-continued

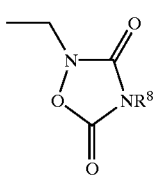
(IV-4a)

(wherein, $R^8$ represents a triphenylmethyl group); and $R^{3b}$ represents the following group:

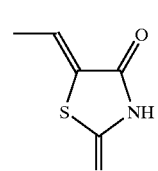
(IV-1)

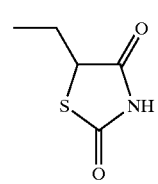
(IV-2)

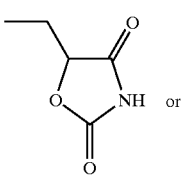
(IV-3) or

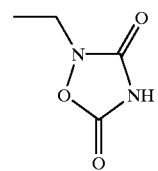
(IV-4)

In the above description, there is no particular limitation on the "protecting group" of the "the amino group which may be protected by an amino-protecting group" in $R^{1a}$ and $R^{2a}$ provided that it is an amino-protecting group used in the field of organic synthetic chemistry. Examples include "aliphatic acyl groups", for example, the above-exemplified $C_{1-7}$ aliphatic acyl groups, halogeno($C_{2-7}$ alkyl)carbonyl groups such as chloroacetyl, dichloroacetyl, trichloroacetyl and trifluoroacetyl groups and $C_{2-7}$ alkylcarbonyl groups substituted with $C_{1-6}$ alkoxy groups such as methoxyacetyl groups; "aromatic acyl groups", for example, the above-exemplified $C_{7-11}$ aromatic acyl groups, halogeno($C_{7-11}$ aromatic acyl) groups such as 2-bromobenzoyl and 4-chlorobenzoyl groups, $C_{7-11}$ aromatic acyl groups substituted with $C_{1-6}$ alkyl groups such as 2,4,6-trimethylbenzoyl and 4-toluoyl, $C_{7-11}$ aromatic acyl groups substituted with $C_{1-6}$ alkoxy groups such as 4-anisoyl, $C_{7-11}$ aromatic acyl groups substituted with nitro groups such as 4-nitrobenzyol groups and 2-nitrobenzyol groups, $C_{7-11}$ aromatic acyl groups substituted with $C_{2-7}$ alkoxycarbonyl groups such as 2-(methoxycarbonyl)-benzoyl groups and $C_{7-11}$ aromatic acyl groups substituted with $C_{6-10}$ aryl groups such as 4-phenylbenzoyl groups; "alkoxycarbonyl groups", for example, the above-exemplified $C_{2-7}$ alkoxycarbonyl groups and $C_{2-7}$ alkoxycarbonyl groups substituted with halogen or tri($C_{1-6}$ alkyl)silyl groups such as 2,2,2-trichloroethoxycarbonyl and 2-trimethylsilylethoxycarbonyl groups; "alkenyloxycarbonyl groups" such as vinyloxycarbonyl groups and allyloxycarbonyl groups; "aralkyloxycarbonyl groups having an aryl ring which may be substituted with 1 or 2 $C_{1-6}$ alkoxy or nitro groups" such as benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups; "silyl groups", for example, tri($C_{1-6}$ alkyl)silyl groups such as trimethylsilyl, triethylsilyl, isopropyldimethylsilyl, t-butyldimethylsilyl, methyldiisopropylsilyl, methyldi-t-butylsilyl and triisopropylsilyl groups and silyl groups substituted with three substituents selected from aryl and $C_{1-6}$ alkyl groups such as diphenylmethylsilyl, diphenylbutylsilyl, diphenylisopropylsilyl and phenyldiisopropylsilyl groups; "aralkyl groups", for example, $C_{1-6}$ alkyl groups substituted with 1 to 3 aryl groups such as benzyl, phenethyl, 3-pheylpropyl, α-naphthylmethyl, β-naphthylmethyl, diphenylmethyl, triphenylmethyl, α-naphthyldiphenylmethyl and 9-anthrylmethyl groups and $C_{1-6}$ alkyl groups substituted with 1 to 3 aryl groups having an aryl ring substituted with $C_{1-6}$ alkyl, $C_{1-6}$ alkoxy or nitro groups, halogen atoms or cyano groups such as 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl, 4-cyanobenzyldiphenylmethyl, bis(2-nitrophenyl)methyl and piperonyl groups; and "substituted methylene groups each of which forms a Schiff base" such as N,N-dimethylaminomethylene, benzylidene, 4-methoxybenzylidene, 4-nitrobenzylidene, salicylidene, 5-chlorosalicylidene, diphenylmethylene and (5-chloro-2-hydroxyphenyl)phenylmethylene groups, of which the $C_{1-7}$ aliphatic acyl groups, $C_{7-11}$ aromatic acyl groups and $C_{2-7}$ alkoxycarbonyl groups are preferred and the $C_{2-7}$ alkoxycarbonyl groups are more preferred and the t-butoxycarbonyl group is most preferred.

In the above description, there is no particular limitation on the "protecting group" of the "hydroxyl group which may be protected by a hydroxyl-protecting group" in $R^{1a}$ and $R^{2a}$ provided that it is a hydroxyl-protecting group used in the field of organic synthetic chemistry. Examples include "aliphatic acyl groups", for example, the above-exemplified $C_{1-7}$ aliphatic acyl groups, $C_{2-7}$ alkylcarbonyl groups substituted with carboxy groups such as succinoyl, glutaroyl and adipoyl groups, halogeno($C_{2-7}$ alkyl)carbonyl groups such as chloroacetyl, dichloroacetyl, trichloroacetyl and trifluoroacetyl groups and $C_{2-7}$ alkylcarbonyl groups substituted with $C_{1-6}$ alkoxy groups such as methoxyacetyl groups; "aromatic acyl groups", for example, the above-exemplified $C_{7-11}$ acyl groups, halogeno($C_{7-11}$ aromatic acyl) groups such as 2-bromobenzoyl and 4-chlorobenzyol groups, $C_{7-11}$ aromatic acyl groups substituted with $C_{1-6}$ alkyl groups such as 2,4,6-trimethylbenzoyl and 4-toluoyl groups, $C_{7-11}$ aromatic acyl groups substituted with $C_{1-6}$ alkoxy groups such as 4 -anisoyl groups, $C_{7-11}$ aromatic acyl groups substituted with carboxy groups such as 2-carboxybenzoyl, 3-carboxybenzoyl and 4-carboxybenzoyl groups, $C_{7-11}$ aromatic acyl groups substituted with nitro groups such as 4-nitrobenzoyl and 2-nitrobenzoyl groups, $C_{7-11}$ aromatic acyl groups substituted with $C_{2-7}$ alkoxycarbonyl groups such as 2-(methoxycarbonyl)benzoyl groups and $C_{7-11}$ aromatic acyl groups substituted with $C_{6-10}$ aryl groups such as 4-phenylbenzoyl groups; "tetrahydropyranyl or tetrahydrothiopyranyl groups" such as tetrahydropyran-2-yl, 3-bromotetrahydropyran-2-yl, 4-methoxytetrahydropyran-4-yl, tetrahydrothiopyran-2-yl and 4-methoxytetrahydrothiopyran-4-yl groups; "tetrahydrofuranyl or tetrahydrothiofuranyl groups" such as tetrahydrofuran-2-yl and tetrahydrothiofuran-2-yl groups; "silyl groups", for example, tri($C_{1-6}$ alkyl)silyl groups such as trimethylsilyl, triethylsilyl, isopropyldimethylsilyl, t-butyldimethylsilyl, methyldiisopropylsilyl, methyldi-t-butylsilyl and triisopropylsilyl groups and silyl groups substituted with 3 substituents selected from aryl and $C_{1-6}$ alkyl groups such as diphenylmethylsilyl, diphenylbutylsilyl, diphenylisopropylsilyl and phenyldiisopropylsilyl groups; "alkoxymethyl groups", for example, ($C_{1-6}$ alkoxy)methyl groups such as methoxymethyl, 1,1-dimethyl-1-methoxymethyl, ethoxymethyl, propoxymethyl, isopropoxymethyl, butoxymethyl and t-butoxymethyl groups, ($C_{1-6}$ alkoxy)methyl groups substituted with $C_{1-6}$ alkoxy groups such as 2-methoxyethoxymethyl groups and halogeno($C_{1-6}$ alkoxy)methyl groups such as 2,2,2-trichloroethoxymethyl and bis(2-chloroethoxy)methyl groups; "substituted ethyl groups", for example, ($C_{1-6}$ alkoxy)ethyl groups such as 1-ethoxyethyl and 1-(isopropoxy)ethyl groups and halogenated ethyl groups such as 2,2,2-trichloroethyl groups; "aralkyl groups", for example, $C_{1-6}$ alkyl groups substituted with 1 to 3 aryl groups such as benzyl, α-naphthylmethyl, β-naphthylmethyl, diphenylmethyl, triphenylmethyl, α-naphthyldiphenylmethyl and 9-anthrylmethyl groups and $C_{1-6}$ alkyl groups substituted with 1 to 3 aryl groups having an aryl ring substituted with $C_{1-6}$ alkyl or $C_{1-6}$ alkoxy groups, halogen atoms or cyano groups such as 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl, 4-cyanobenzyldiphenylmethyl and piperonyl groups; "alkoxycarbonyl groups" such as the above-exemplified $C_{2-7}$ alkoxycarbonyl groups and $C_{2-7}$ alkoxycarbonyl groups substituted with halogen atoms or tri($C_{1-6}$ alkyl)silyl groups such as 2,2,2-trichloroethoxycarbonyl and 2-trimethylsilylethoxycarbonyl groups; "alkenyloxycarbonyl groups" such as vinyloxycarbonyl and allyloxycarbonyl groups; and "aralkyloxycarbonyl groups" having an aryl ring which may be substituted with 1 to 2 $C_{1-6}$ alkoxy or nitro groups such as benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups, of which the $C_{1-7}$ aliphatic acyl, $C_{7-11}$ aromatic acyl, $C_{2-7}$ alkoxycarbonyl and ($C_{1-6}$ alkoxy)methyl groups are preferred, the $C_{7-11}$ aromatic acyl and ($C_{1-6}$ alkoxy)methyl groups are more preferred and the benzoyl and methoxymethyl groups are most preferred.

Method A is a process for the preparation of Compound (Ia), which is Compound (I) wherein $R^3$ is selected from a group of the formula (IV-1) to (IV-4).

Step A1 is a step for preparing the compound of formula (VII) by reacting a compound of the formula (V') with a compound of formula (VI) in an inert solvent in the presence of a phosphine (preferably, tributylphosphine or triphenylphosphine) and an azodicarboxylic acid compound (preferably, diethyl azodicarboxylate or 1,1'-(azodicarbonyl) dipiperidine).

There is no particular limitation on the nature of the inert solvent to be used in the above reaction provided that it has no adverse effect on the present reaction. Examples include aliphatic hydrocarbons such as hexane, heptane, ligroin and petroleum ether; aromatic hydrocarbons such as benzene, toluene and xylene; halogenated hydrocarbons such as chloroform, dichloromethane, 1,2-dichloroethane and carbon tetrachloride; ethers such as diethyl ether, diisopropyl ether, tetrahydrofuran, dioxane, dimethoxyethane and diethylene glycol dimethyl ether; amides such as formamide, dimethylformamide, dimethylacetamide and hexamethylphosphoric triamide; and mixtures of the above-exemplified solvents, of which the aliphatic hydrocarbons, aromatic hydrocarbons, halogenated hydrocarbons, ethers and mixtures of these solvents are preferred (more preferred are the aromatic hydrocarbons and ethers and particularly preferred are toluene and tetrahydrofuran).

The reaction temperature depends on the natures of the raw materials and solvent and the like, however, it usually ranges from −20° C. to 150° C. (preferably from 0° C. to 60° C.).

The reaction time depends on the natures of the raw materials and solvent, the reaction temperature and the like, however, it usually ranges from 30 minutes to 5 days (preferably from 5 hours to 72 hours).

After the completion of the reaction, the resulting compound (VII) of the present reaction is obtained from the reaction mixture by a known method. For example, it can be obtained by removing the insoluble matter from the reaction mixture by filtration; adding to the filtrate an organic solvent, which is not miscible with water such as ethyl acetate, separating the organic layer containing the desired compound, washing with water or the like and drying over anhydrous magnesium sulfate, anhydrous sodium sulfate, anhydrous sodium bicarbonate or the like; and then distilling off the solvent. The product so obtained can be isolated and purified, if necessary, by any suitable combination of conventional methods, for example, recrystallization, reprecipitation or chromatography.

Step A2 is a step for preparing a compound of formula (Ia) by reacting Compound (VII) with an acid in the presence or absence (preferably, in the presence) of an inert solvent, thereby removing the triphenylmethyl group of $R^8$, and then removing the amino- and/or hydroxyl-protecting group in $R^{1a}$ and $R^{2a}$ if necessary.

There is no particular limitation on the nature of the acid to be employed for the former stage of the reaction, provided that it is used in ordinary reactions as an acid catalyst. Examples include inorganic acids such as hydrochloric acid, hydrobromic acid, sulfuric acid, perchloric acid and phosphoric acid; Brønsted acids, for example, organic acids such as acetic acid, formic acid, oxalic acid, methanesulfonic acid, p-toluenesulfonic acid, camphorsulfonic acid, trifluoroacetic acid and trifluoromethanesulfonic acid; Lewis acids such as zinc chloride, tin tetrachloride, boron trichloride, boron trifluoride and boron tribromide; and acidic ion exchange resins, of which inorganic and organic acids (particularly, hydrochloric acid, acetic acid and trifluoroacetic acid) are preferred.

There is no particular limitation on the nature of the inert solvent to be used in the former stage of the reaction provided that it has no adverse effect on the present reaction. Examples include aliphatic hydrocarbons such as hexane, heptane, ligroin and petroleum ether; aromatic hydrocarbons such as benzene, toluene and xylene; halogenated hydrocarbons such as chloroform, dichloromethane, 1,2-dichloroethane and carbon tetrachloride; esters such as methyl acetate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; alcohols such as methanol, ethanol, n-propanol, isopropanol, n-butanol, isobutanol, t-butanol, isoamyl alcohol, diethylene glycol, glycerin, octanol, cyclohexanol and methyl cellosolve; amides such as formamide, dimethylformamide, dimethylacetamide and hexamethylphosphoric triamide; water; and mixtures of the above-exemplified solvents, of which ethers, alcohols and water (particularly, dioxane, tetrahydrofuran, ethanol and water) are preferred.

The reaction temperature depends on the natures of the raw material, acid and solvent, and the like, however, it usually ranges from −20° C. to the boiling point (preferably from 0° C. to 100° C.).

The reaction time depends on the natures of the raw material, acid and solvent, the reaction temperature and the like, however, it usually ranges from 15 minutes to 48 hours (preferably from 30 minutes to 20 hours).

In this step, the target compound (Ia) can also be prepared by subjecting Compound (VII) to catalytic reduction in an inert solvent under atmospheric pressure or under pressure (preferably under pressure), thereby removing the triphenylmethyl group of $R^8$, and then removing the protecting group of the amino group and/or hydroxyl group in $R^{1a}$ and $R^{2a}$ as needed.

There is no particular limitation on the nature of the catalyst to be used in the above catalytic reduction, provided that it is used in ordinary catalytic reductions. Examples include palladium-carbon, Raney nickel, rhodium-aluminum oxide, triphenylphosphine-rhodium oxide, palladium-barium sulfate, palladium black, platinum oxide and platinum black, of which palladium-carbon is preferred.

There is no particular limitation on the nature of the inert solvent to be used in the above catalytic reduction provided that it has no adverse effect on the present reaction. Examples include aliphatic hydrocarbons such as hexane, heptane, ligroin and petroleum ether; aromatic hydrocarbons such as benzene, toluene and xylene; halogenated hydrocarbons such as chloroform, dichloromethane, 1,2-dichloroethane and carbon tetrachloride; ethers such as diethyl ether, diisopropyl ether, tetrahydrofuran, dioxane, dimethoxyethane and diethylene glycol dimethyl ether; alcohols such as methanol, ethanol, n-propanol, isopropanol, n-butanol, isobutanol, t-butanol, isoamyl alcohol, diethylene glycol, glycerin, octanol, cyclohexanol and methyl cellosolve; amides such as formamide, dimethylformamide, dimethylacetamide and hexamethylphosphoric triamide; water; organic acids such as acetic acid and trifluoroacetic acid; and mixtures of the above-exemplified solvents, of which ethers, alcohols and organic acids (particularly, alcohols) are preferred.

The reaction temperature depends on the natures of the raw material, catalyst and solvent to be used and the like, however, it usually ranges from 0° C. to 100° C. (preferably from 10° C. to 50° C.).

The reaction time depends on the natures of the raw material, catalyst and solvent to be used, the reaction temperature and the like, however, it usually ranges from 30 minutes to 48 hours (preferably from 1 hour to 24 hours).

The removal of the protecting group of the amino group or hydroxyl group depends on its nature, however, it is generally carried out as described below in accordance with a method known in the field of Organic synthetic chemistry, for example, T. W. Green (Protective Groups in Organic Synthesis), John Wiley & Sons or J. F. W. McOmis, (Protective Groups in Organic Chemistry), Plenum Press.

When the amino-protecting group is a silyl group, it can be removed by treating with a fluorine-anion-forming compound such as tetrabutylammonium fluoride, hydrofluoric acid, hydrofluoric acid-pyridine or potassium fluoride.

There is no particular limitation on the nature of the solvent to be employed for the above reaction, provided that it has no adverse effect on the reaction. Preferred examples include ethers such as diethyl ether, diisopropyl ether, tetrahydrofuran, dioxane, dimethoxyethane and diethylene glycol dimethyl ether.

Although no particular limitation is imposed on the reaction temperature and reaction time, the reaction is ordinarily carried out at a temperature of from 0 to 50° C. for 10 to 18 hours.

When the amino-protecting group is an aliphatic acyl group, aromatic acyl group, alkoxycarbonyl group or substituted methylene group forming a Schiff base, it can be removed by treating with an acid or base in the presence of an aqueous solvent.

There is no particular limitation on the nature of the acid used in the above reaction, provided that it is ordinarily used as an acid and has no adverse effect on the reaction. Examples include inorganic acids such as hydrobromic acid, hydrochloric acid, sulfuric acid, perchloric acid, phosphoric acid and nitric acid, of which hydrochloric acid is preferred.

There is no particular limitation imposed on the nature of the base to be employed in the above reaction provided that it has no adverse effects on the other part of the compound. Preferred examples include alkali metal carbonates such as lithium carbonate, sodium carbonate and potassium carbonate; alkali metal hydroxides such as lithium hydroxide, sodium hydroxide and potassium hydroxide; metal alkoxides such as lithium methoxide, sodium methoxide, sodium ethoxide or potassium-t-butoxide; and ammonia such as aqueous ammonia and concentrated ammonia-methanol.

There is no particular limitation on the nature of the solvent to be used in the above reaction provided that it can be used in ordinary hydrolysis. Examples include alcohols such as methanol, ethanol, n-propanol, isopropanol, n-butanol, isobutanol, t-butanol, isoamyl alcohol, diethylene glycol, glycerin, octanol, cyclohexanol and methyl cellosolve; ethers such as diethyl ether, diisopropyl ether, tetrahydrofuran, dioxane, dimethoxyethane and diethylene glycol dimethyl ether; water; and mixtures of water and the above-exemplified organic solvents, of which the ethers (particularly dioxane) are preferred.

There is no particular limitation on the reaction temperature and reaction time, and they depend on the natures of the starting substance, solvent and acid or base to be employed. The reaction is usually carried out at a temperature of from 0 to 150° C. for 1 to 10 hours in order to suppress side reactions.

When the amino-protecting group is an aralkyl or aralkyloxycarbonyl group, it is preferably removed by contact with a reducing agent (preferably catalytic reduction in the presence of a catalyst at room temperature) in an inert solvent or by using an oxidizing agent.

There is no particular limitation on the nature of the solvent to be used for the removal by catalytic reduction provided that it has no adverse effect on the present reaction. Examples include aliphatic hydrocarbons such as hexane, heptane, ligroin and petroleum ether; aromatic hydrocarbons such as toluene, benzene and xylene; esters such as methyl acetate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; alcohols such as methanol, ethanol, n-propanol, isopropanol, n-butanol, isobutanol, t-butanol, isoamyl alcohol, diethylene glycol, glycerin, octanol, cyclohexanol and methyl cellosolve; organic acids such as acetic acid; water; and mixed solvents of water and the above-exemplified solvents, of which alcohols, ethers, organic acids and water (particularly, alcohols and organic acids) are preferred.

There is no particular limitation on the nature of the catalyst to be used provided that it is usually employed for catalytic reductions. Preferred examples include palladium-carbon, Raney nickel, platinum oxide, platinum black, rhodium-aluminum oxide, triphenylphosphine-rhodium chloride and palladium-barium sulfate.

Although no particular limitation is imposed on the pressure, the reaction is usually carried out at a pressure of from 1 to 10 atm.

Although the reaction temperature and reaction time depend on the natures of the raw material, catalyst and solvent, and the like, the reaction is usually carried at a temperature of from 0 to 100° C. for 5 minutes to 24 hours.

There is no particular limitation on the nature of the solvent used for the removal by oxidation provided that it has no adverse effect on the present reaction. Water containing organic solvents are preferably employed.

Examples of such an organic solvent include halogenated hydrocarbons such as chloroform, dichloromethane, 1,2-dichloroethane and carbon tetrachloride; nitriles such as acetonitrile; ethers such as diethyl ether, diisopropyl ether, tetrahydrofuran, dioxane, dimethoxyethane and diethylene glycol dimethyl ether; ketones such as acetone; amides such as formamide, dimethylformamide, dimethylacetamide and hexamethylphosphoric triamide; sulfoxides such as dimethylsulfoxide; and sulfolane, of which the halogenated hydrocarbons, ethers and sulfoxides (particularly, the halogenated hydrocarbons and sulfoxides) are preferred.

There is no particular limitation on the oxidizing agent to be used provided that it is ordinarily used in oxidations. Preferred examples include potassium persulfate, sodium persulfate, cerium ammonium nitrate (CAN) and 2,3-dichloro-5,6-dicyano-p-benzoquinone (DDQ). Although the reaction temperature and reaction time depend on the natures of the raw material, catalyst and solvent, and the like, the reaction is usually carried out at a temperature of from 0 to 150° C. for 10 minutes to 24 hours.

When the amino-protecting group is an alkenyloxycarbonyl group, it can be usually removed by treating with a base under similar conditions to those employed when the amino-protecting group is the above-described aliphatic acyl group, aromatic acyl group, alkoxycarbonyl group or substituted methylene group forming a Schiff base.

Incidentally, when the protecting group is an allyloxycarbonyl group, it can be removed conveniently with less side reactions by using, in particular, palladium and triphenylphosphine or nickel tetracarbonyl.

When a silyl group is used as the hydroxyl-protecting group, it can usually be removed by treating with a fluorine-anion-forming compound such as tetrabutyl ammonium fluoride, hydrofluoric acid, hydrofluoric acid-pyridine or potassium fluoride; or by treating with an inorganic acid such as hydrochloric acid, hydrobromic acid, sulfuric acid, perchloric acid or phosphoric acid or an organic acid such as acetic acid, formic acid, oxalic acid, methanesulfonic acid, p-toluenesulfonic acid, camphorsulfonic acid, trifluoroacetic acid or trifluoromethanesulfonic acid.

Incidentally, when the removal of the silyl group is carried out using a fluoride ion, the reaction happens to be accelerated by the addition of an organic acid such as formic acid, acetic acid or propionic acid.

There is no particular limitation on the nature of the inert solvent to be used in the above reaction provided that it has no adverse effect on the present reaction. Preferred examples include ethers such as diethyl ether, diisopropyl ether, tetrahydrofuran, dioxane, dimethoxyethane and diethylene glycol dimethyl ether; nitriles such as acetonitrile and isobutyronitrile; organic acids such as acetic acid; water; and mixtures of the above-exemplified solvents.

Although the reaction temperature and reaction time depend on the natures of the raw material, catalyst and solvent, and the like, the reaction is usually carried at a temperature of from 0 to 100° C. (preferably from 10 to 50° C.) for 1 hour to 24 hours.

When the hydroxyl-protecting group is an aralkyl or aralkyloxycarbonyl group, it is usually preferred to remove the protecting group by contact with a reducing agent (preferably, catalytic reduction at room temperature in the presence of a catalyst) or by using an oxidizing agent, in an inert solvent.

There is no particular limitation on the nature of the solvent to be used in the above reaction provided that it has no adverse effect on the present reaction. Examples include aliphatic hydrocarbons such as hexane, heptane, ligroin and petroleum ether; aromatic hydrocarbons such as toluene, benzene and xylene; esters such as ethyl acetate and propyl acetate; ethers such as diethyl ether, diisopropyl ether, tetrahydrofuran, dioxane, dimethoxyethane and diethylene glycol dimethyl ether; alcohols such as methanol, ethanol, n-propanol, isopropanol, n-butanol, isobutanol, t-butanol, isoamyl alcohol, diethylene glycol, glycerin, octanol, cyclohexanol and methyl cellosolve; amides such as formamide, dimethylformamide, dimethylacetamide and hexamethylphosphoric triamide; fatty acids such as formic acid and acetic acid; water; and mixtures of the above-exemplified solvents, of which alcohols (particularly, methanol) are preferred.

There is no particular limitation on the nature of the catalyst to be used provided that it is usually employed for catalytic reduction. Examples include palladium-carbon, palladium black, Raney nickel, platinum oxide, platinum black, rhodium-aluminum oxide, triphenylphosphine-rhodium chloride and palladium-barium sulfate, of which the palladium-carbon is preferred.

Although no particular limitation is imposed on the pressure, the reaction is usually carried out under a pressure from 1 to 10 atm.

Although the reaction temperature and reaction time depend on the natures of the raw materials, catalyst and solvent, and the like, the reaction is usually carried out at a temperature of from 0 to 100° C. (preferably from 20 to 70° C.) for 5 minutes to 48 hours (preferably from 1 to 24 hours).

There is no particular limitation on the nature of the solvent to be used for the removal by oxidation provided that it has no adverse effect on the present reaction. Water-containing organic solvents are preferred as the solvent.

Specific examples of such an organic solvent include ketones such as acetone; halogenated hydrocarbons such as methylene chloride, chloroform and carbon tetrachloride; nitriles such as acetonitrile; ethers such as diethyl ether, tetrahydrofuran and dioxane; amides such as dimethylformamide, dimethylacetamide and hexamethylphosphoric triamide; and sulfoxides such as dimethylsulfoxide.

There is no particular limitation on the oxidizing agent to be used, provided that it is ordinarily used in oxidation. Preferred examples include potassium persulfate, sodium persulfate, cerium ammonium nitrate (CAN) and 2,3-dichloro-5,6-dicyano-p-benzoquinone (DDQ).

Although the reaction temperature and reaction time depend on the natures of the raw materials, catalyst and solvent, and the like, the reaction is usually carried at a temperature of from 0 to 150° C. for 10 minutes to 24 hours.

The protecting group can also be removed by treating with an alkali metal such as metal lithium or metal sodium in liquid ammonia or an alcohol such as methanol, ethanol, n-propanol, isopropanol, n-butanol, isobutanol, t-butanol, isoamyl alcohol, diethylene glycol, glycerin, octanol, cyclohexanol or methyl cellosolve at −78 to 0° C.

The protecting group can also be removed by using an alkylsilyl halide such as aluminum chloride-sodium iodide or trimethylsilyl iodide in a solvent.

There is no particular limitation on the nature of the solvent to be used provided that it has no adverse effect on the present reaction. Preferred examples include halogenated hydrocarbons such as methylene chloride, chloroform and carbon tetrachloride; nitriles such as acetonitrile; and mixtures of the above-exemplified solvents.

Although the reaction temperature and reaction time depend on the natures of the raw materials and solvent, and the like, the reaction is usually carried out at a temperature of from 0 to 50° C. for 5 minutes to 72 hours.

Incidentally, when the reaction substrate has a sulfur atom, aluminum chloride-sodium iodide is preferably used.

When the hydroxyl-protecting group is an aliphatic acyl, aromatic acyl or alkoxycarbonyl group, it can be removed by treating with a base in a solvent.

There is no particular limitation on the base to be used in the above reaction provided that it has no adverse effect on the remainder of the compound. Preferred examples include alkali metal carbonates such as lithium carbonate, sodium carbonate and potassium carbonate; alkali metal bicarbonates such as lithium bicarbonate, sodium bicarbonate and potassium bicarbonate; alkali metal hydroxides such as lithium hydroxide, sodium hydroxide and potassium hydroxide; metal alkoxides such as lithium methoxide, sodium methoxide, sodium ethoxide and potassium-t-butoxide; and ammonia such as aqueous ammonia and concentrated ammonia-methanol, of which the alkali metal hydroxides, metal alkoxides and ammonia (particularly, the alkali metal hydroxides and metal alkoxides) are preferred.

There is no particular limitation on the nature of the solvent to be used in the above reaction provided that it can be used in ordinary hydrolysis. Examples include ethers such as diethyl ether, diisopropyl ether, tetrahydrofuran, dioxane, dimethoxyethane and diethylene glycol dimethyl ether; alcohols such as methanol, ethanol, n-propanol, isopropanol, n-butanol, isobutanol, t-butanol, isoamyl alcohol, diethylene glycol, glycerin, octanol, cyclohexanol and methyl cellosolve; water; and mixtures of the above-exemplified organic solvents.

There is no particular limitation on the reaction temperature and reaction time, they depend on the natures of the raw materials, base and solvent, and the like. The reaction is usually carried out at a temperature of from −20 to 150° C. for 1 to 10 hours in order to suppress side reactions.

When the hydroxyl-protecting group is an alkoxymethyl, tetrahydropyranyl, tetrahydrothiopyranyl, tetrahydrofuranyl, tetrahydrothiofuranyl or substituted ethyl group, it is usually removed by treating with an acid in a solvent.

There is no particular limitation on the acid to be used in the above reaction, provided that it is usually employed as a Brønsted acid or Lewis acid. Preferred examples include Brønsted acids, for example, hydrogen chloride, inorganic acids such as hydrochloric acid, sulfuric acid and nitric acid, and organic acids such as acetic acid, trifluoroacetic acid, methanesulfonic acid and p-toluenesulfonic acid, and Lewis acids such as boron trifluoride. A strong acidic cation exchange resin such as Dowex 50W can also be employed.

There is no particular limitation on the nature of the solvent to be used for the above reaction, provided that it has no adverse effect on the present reaction. Examples include aliphatic hydrocarbons such as hexane, heptane, ligroin and petroleum ether; aromatic hydrocarbons such as benzene, toluene and xylene; hydrogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; alcohols such as methanol, ethanol, n-propanol, isopropanol, n-butanol, isobutanol, t-butanol, isoamyl alcohol, diethylene glycol, glycerin, octanol, cyclohexanol and methyl cellosolve; ketones such as acetone, methyl ethyl ketone, methyl isobutyl ketone, isophorone and cyclohexane; water; and mixed solvents of the above-exemplified solvents, of which the ethers (particularly tetrahydrofuran) and the alcohols (particularly methanol) are preferred.

Although the reaction temperature and reaction time depend on the raw materials, acid and solvent, and the like, the reaction is usually carried out at a temperature of from −10 to 200° C. (preferably 0 to 150° C.) for 5 minutes to 48 hours (preferably 30 minutes to 10 hours).

When the hydroxyl-protecting group is an alkenyloxycarbonyl group, it can be removed by treating with a base under similar conditions to those employed when the hydroxyl-protecting group is the above-described aliphatic acyl, aromatic acyl or alkoxycarbonyl group.

Incidentally, when the protecting group is an allyloxycarbonyl group, it can be removed more easily with less side reactions by using, in particular, palladium and triphenylphosphine or bis(methyldiphenylphosphine) (1,5-cyclooctadien)iridium (I).hexafluorophosphate.

By the above-described reaction wherein Compound (VII) and an acid are brought into contact or the catalytic reduction of Compound (VII), the amino-protecting group and/or hydroxyl-protecting group happen to be removed at the same time.

The amino-protecting group and/or hydroxyl-protecting group can be removed successively in the desired order.

After the completion of the reaction, the resulting compound (Ia) of the present invention can be obtained from the reaction mixture by a known method. For example, it can be obtained by neutralizing the reaction mixture if necessary; removing the insoluble matter by filtration; adding to the filtrate an organic solvent which is not miscible with water such as ethyl acetate; separating the organic layer containing the desired compound and washing with water or the like; drying over anhydrous magnesium sulfate, anhydrous sodium sulfate, anhydrous sodium bicarbonate or the like; and then distilling off the solvent. The resulting product can be isolated and purified, if necessary, by any suitable combination of conventional methods, for example, recrystallization, reprecipitation or chromatography.

Method B

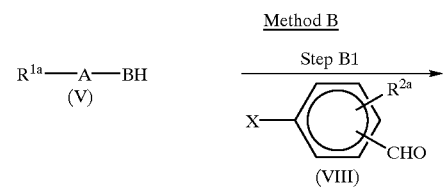

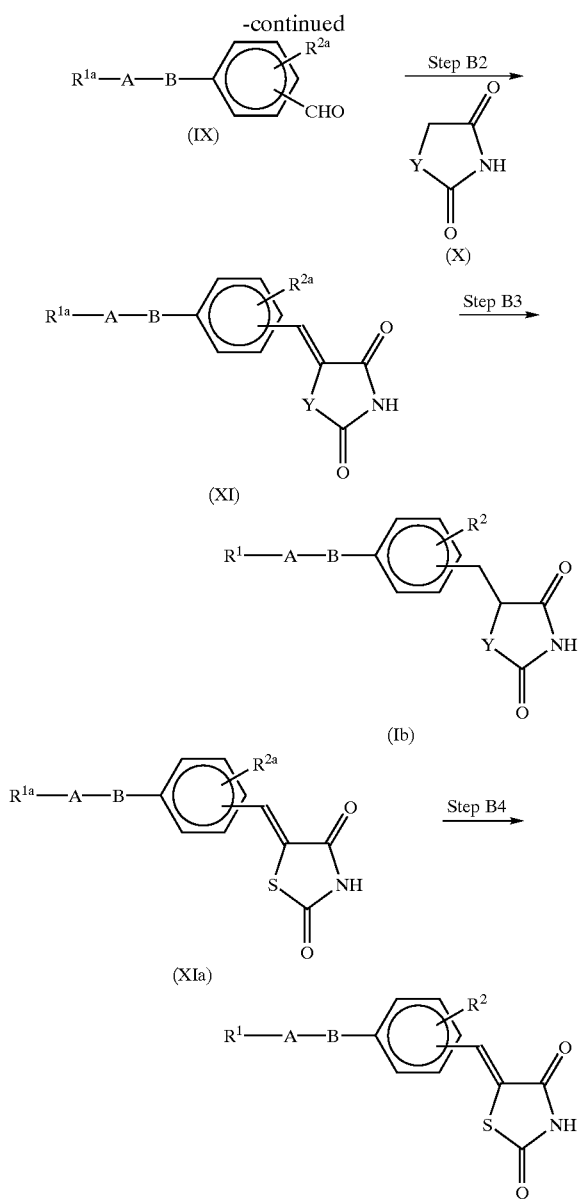

In the above reaction scheme, $R^1$, $R^{1a}$, $R^2$, $R^{2a}$, A and B have the same meanings as described above, X represents the above-described halogen atom and Y represents an oxygen or sulfur atom.

Method B is a process for the preparation of Compound (Ib) which is Compound (I) wherein $R^3$ is the formula (IV-2) or (IV-3) or Compound (Ic) which is Compound (I) wherein $R^3$ is the formula (IV-1).

Step B1 is a step for preparing a compound of formula (IX) by reacting Compound (V) with a base in the presence or absence (preferably, in the presence) of an inert solvent and then reacting the resulting compound with a compound of formula (VIII).

Examples of the base to be used for the above reaction include alkali metal carbonates such as lithium carbonate, sodium carbonate and potassium carbonate; alkali metal bicarbonates such as lithium bicarbonate, sodium bicarbonate and potassium bicarbonate; alkali metal hydrides such as lithium hydride, sodium hydride and potassium hydride; alkali metal hydroxides such as lithium hydroxide, sodium hydroxide and potassium hydroxide; alkali metal alkoxides such as lithium methoxide, sodium methoxide, sodium ethoxide and potassium-t-butoxide; and organic amines such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4.3.0]nona-5-ene, 1,4-diazabicyclo[2.2.2]octane (DABCO), 1,8-diazabicyclo[5.4.0]-7-undecene (DBU), of which the alkali metal hydrides (particularly, the sodium hydride) are preferred.

There is no particular limitation on the nature of the inert solvent to be used in the above reaction provided that it has no adverse effect on the present reaction. Examples include aliphatic hydrocarbons such as hexane, heptane, ligroin and petroleum ether; aromatic hydrocarbons such as benzene, toluene and xylene; ethers such as diethyl ether, diisopropyl ether, tetrahydrofuran, dioxane, dimethoxyethane and diethylene glycol dimethyl ether; amides such as dimethylformamide, dimethylacetamide and hexamethylphosphoric triamide; and mixtures of the above-exemplified solvents, of which the amides (particularly, dimethylformamide) are preferred.

The temperature upon reaction of Compound (V) with the base depends on the natures of the raw materials, base and solvent, and the like, however, it usually ranges from −50 to 200° C. (preferably from 0 to 120° C.).

The time upon reaction of Compound (V) with the base depends on the natures of the raw materials, base and solvent, the reaction temperature and the like, however, it usually ranges from 15 minutes to 24 hours (preferably from 1 hour to 10 hours).

The temperature upon reaction of Compound (V) with Compound (VIII) usually ranges from −20 to 200° C. (preferably from 0 to 150° C.).

The time upon reaction of Compound (V) with Compound (VIII) usually ranges from 30 minutes to 48 hours (preferably from 1 hour to 24 hours).

After the completion of the reaction, the resulting compound (IX) of the present reaction can be obtained from the reaction mixture by a known method. For example, it can be obtained by neutralizing the reaction mixture if necessary; removing the insoluble matter by filtration, adding to the filtrate an organic solvent which is not miscible with water such as ethyl acetate and separating the organic layer containing the desired compound; washing with water or the like; drying over anhydrous magnesium sulfate, anhydrous sodium sulfate, anhydrous sodium bicarbonate or the like; and then distilling off the solvent. The product so obtained can be isolated and purified, if necessary, by any suitable combination of conventional methods for example, recrystallization, reprecipitation or chromatography.

Step B2 is a step for preparing a compound of formula (XI) and it is carried out by reacting Compound (IX) with a compound of formula (X) in an inert solvent in the presence or absence (preferably in the presence) of a catalyst such as sodium acetate, piperidinium acetate or piperidinium benzoate.

There is no particular limitation on the nature of the inert solvent to be used in the above reaction provided that it has no adverse effect on the present reaction. Examples include aliphatic hydrocarbons such as hexane, heptane, ligroin and petroleum ether; aromatic hydrocarbons such as benzene, toluene and xylene; halogenated hydrocarbons such as chloroform, dichloromethane, 1,2-dichloroethane and carbon tetrachloride; esters such as methyl acetate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; alcohols such as methanol, ethanol, n-propanol, isopropanol, n-butanol, isobutanol, t-butanol, isoamyl alcohol, diethylene glycol, glycerin, octanol, cyclohexanol and methyl cellosolve; nitriles such as acetonitrile and isobutyronitrile; amides such as formamide, dimethylformamide, dimethylacetamide and hexamethylphosphoric triamide; and mixtures of the above-exemplified solvents, of which the amides (particularly, dimethylformamide) are preferred.

The reaction temperature depends on the natures of the raw materials, base, solvent and the like, however, it usually ranges from 0 to 200° C. (preferably from 10° C. to 150° C.).

The reaction time depends on the natures of the raw materials, catalyst, solvent, the reaction temperature and the like, however, it usually ranges from 1 hour to 50 hours (preferably from 2 hours to 24 hours).

After the completion of the reaction, the resulting compound (XI) of the present reaction is obtained from the reaction mixture by a known method. For example, it can be obtained by neutralizing the reaction mixture if necessary; removing the insoluble matter from the reaction mixture by filtration and adding to the filtrate an organic solvent, which is not miscible with water, such as ethyl acetate; separating the organic layer containing the desired compound, washing with water or the like and drying over anhydrous magnesium sulfate, anhydrous sodium sulfate, anhydrous sodium bicarbonate or the like; and then distilling off the solvent. The resulting product can be isolated and purified, if necessary, by any suitable combination of conventional methods, for example, recrystallization, reprecipitation and chromatography.

Step B3 is a step for preparing a compound of formula (Ib) by subjecting Compound (XI) to catalytic reduction in an inert solvent and then removing the amino-protecting group and/or hydroxyl-protecting group in $R^{1a}$ and $R^{2a}$ if necessary. The catalytic reduction and the removal, if desired, of the amino- and/or hydroxyl-protecting group are carried out in similar manners to those described in Step A2 of Method A.

Alternatively, this step can be carried out by reacting Compound (XI) with a metal hydride and then removing the amino- and/or hydroxyl-protecting group in $R^{1a}$ and $R^{2a}$ if necessary. The reaction between Compound (XI) and the metal hydride can be conducted in a similar method to that disclosed in WO93/1309A.

Step B4 is a step for preparing a compound of formula (Ic) by removing the amino- and/or hydroxyl-protecting group in $R^{1a}$ and $R^{2}$l of Compound (XIa) which is Compound (XI) having a sulfur atom as Y. This step is carried out in a similar manner to that described in Step A2 of Method A for the removal of the amino- and/or hydroxyl-protecting group.

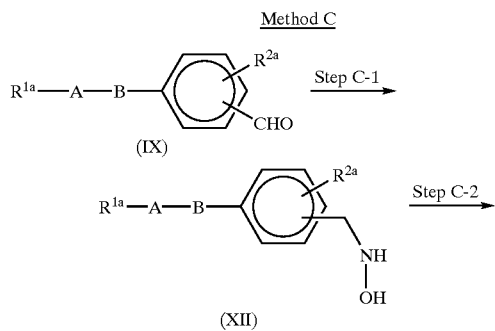

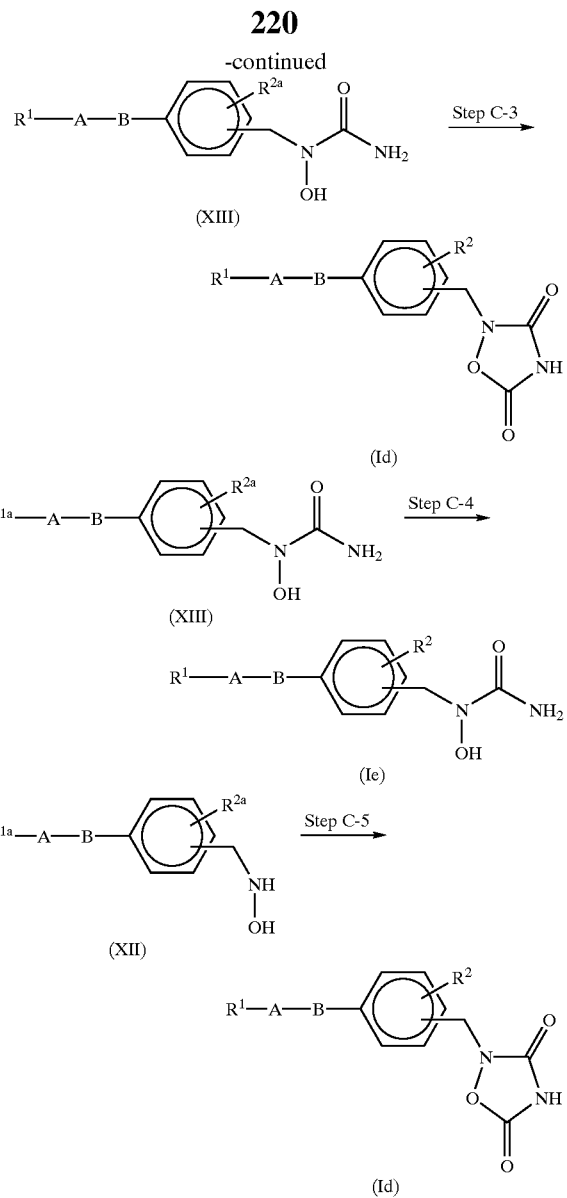

In the above reaction scheme, $R^1$, $R^{1a}$, $R^2$, $R^{2a}$, A and B have the same meanings as described above.

Method C is a process for preparing Compound (Id) which is Compound (I) wherein $R^3$ is of the formula (IV-4) or Compound (Ie) which is Compound (I) wherein $R^3$ is of the formula (IV-5).

Step C1 is a step for preparing the compound of formula (XII) by reacting Compound (IX) with hydroxylamine (hydrochloride) in an inert solvent and then contacting the reaction mixture with a reducing agent.

There is no particular limitation on the nature of the inert solvent to be used upon reaction of Compound (IX) with hydroxylamine (hydrochloride) provided that it has no adverse effect on the present reaction. Examples include aliphatic hydrocarbons such as hexane, heptane, ligroin and petroleum ether; aromatic hydrocarbons such as benzene, toluene and xylene; halogenated hydrocarbons such as chloroform, dichloromethane, 1,2-dichloroethane and carbon tetrachloride; esters such as methyl acetate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; alcohols such as methanol, ethanol, n-propanol, isopropanol, n-butanol, isobutanol, t-butanol, isoamyl alcohol, diethylene glycol, glycerin, octanol, cyclohexanol and methyl cellosolve; nitriles such as acetonitrile and isobutyronitrile; amides such as formamide, dimethylformamide, dimethylacetamide and hexamethylphosphoric triamide; water; and mixtures of the above-exemplified solvents, of which the mixed solvents with an alcohol (particularly, methanol or ethanol) are preferred.

The temperature upon reaction of Compound (IX) with hydroxylamine (hydrochloride) depends on the natures of the raw materials, catalyst, solvent and the like, however, it usually ranges from −20 to 200° C. (preferably from 10 to 120° C.).

The time upon reaction of Compound (IX) with hydroxylamine (hydrochloride) depends on the natures of the raw materials, catalysts, solvent, the reaction temperature and the like, however, it usually ranges from 1 hour to 50 hours (preferably from 2 hours to 24 hours).

Examples of the reducing agent to be used in the latter stage of the reaction include alkali metal borohydrides such as sodium borohydride, lithium borohydride and sodium cyanoborohydride and aluminum hydrides such as diisobutylaluminum hydride, lithium aluminum hydride and lithium triethoxide aluminum hydride, of which the alkali metal borohydrides (particularly, sodium borohydride) are preferred.

There is no particular limitation on the solvent to be used upon the contact with the reducing agent in the latter stage of the reaction, provided that it has no adverse effect on the present reaction. Solvents similar to those used upon the reaction between Compound (IX) and hydroxylamine (hydrochloride) are preferably employed.

The reaction temperature upon contact with the reducing agent in the latter stage of the reaction depends on the natures of the raw material, reducing agent, solvent, and the like, however, it usually ranges from −50 to 200° C. (preferably from 0° C. to 1 20° C.).

The reaction time upon contact with the reducing agent in the latter stage of the reaction depends on the natures of the raw material, reducing agent, solvent, the reaction temperature and the like, however, it usually ranges from 15 minutes to 24 hours (preferably from 1 hour to 12 hours).

After the completion of the reaction, the resulting compound (XII) of the present reaction is obtained from the reaction mixture by a known method. For example, it can be obtained by neutralizing the reaction mixture if necessary; removing the insoluble matter, from the reaction mixture by filtration and adding to the filtrate an organic solvent, which is not miscible with water, such as ethyl acetate; separating the organic layer containing the desired compound, washing with water or the like and drying over anhydrous magnesium sulfate, anhydrous sodium sulfate, anhydrous sodium bicarbonate or the like; and then distilling off the solvent. The resulting product can be isolated and purified, if necessary, by any suitable combination of conventional methods, for example, recrystallization, reprecipitation and chromatography.

Step C2 is a step for preparing a compound of formula (XIII) by reacting Compound (XII) with trimethylsilyl isocyanate in an inert solvent.

There is no particular limitation on the nature of the solvent to be used for the above reaction, provided that it has no adverse effect on the present reaction. Examples include aliphatic hydrocarbons such as hexane, heptane, ligroin and petroleum ether; aromatic hydrocarbons such as benzene, toluene and xylene; halogenated hydrocarbons such as chloroform, dichloromethane, 1,2-dichloroethane and carbon tetrachloride; ethers such as diethyl ether, diisopropyl ether, tetrahydrofuran, dioxane, dimethoxyethane and diethylene glycol dimethyl ether; amides such as formamide, dimethylformamide, dimethylacetamide and hexamethylphosphoric triamide; and mixtures of the above-exemplified solvents, of which the aromatic hydrocarbons, ethers and amides (particularly, diethyl ether, tetrahydrofuran and dimethylformamide) are preferred.

The reaction temperature depends on the natures of the raw materials, solvent and the like, however, it usually ranges from −50 to 200° C. (preferably from 0° C. to 120° C.).

The reaction time depends on the natures of the raw materials, solvent, the reaction temperature and the like, however, it usually ranges from 15 minutes to 48 hours (preferably from 1 hour to 24 hours).

After the completion of the reaction, the resulting compound (XIII) of the present reaction is obtained from the reaction mixture by a known method. For example, it can be obtained by neutralizing the reaction mixture if necessary; removing the insoluble matter from the reaction mixture by filtration and adding to the filtrate an organic solvent, which is not miscible with water, such as ethyl acetate; separating the organic layer containing the target compound, washing with water or the like and drying over anhydrous magnesium sulfate, anhydrous sodium sulfate, anhydrous sodium bicarbonate or the like; and then distilling off the solvent. The resulting product can be isolated and purified, if necessary, by any suitable combination of conventional methods, for example, recrystallization, reprecipitation and chromatography.

Step C3 is a step for preparing a compound of formula (Id) by reacting Compound (XIII) with a carbonylating agent in an inert solvent and then removing the amino- and/or hydroxyl-protecting group in $R^{1a}$ and $R^{2a}$ if necessary.

There is no particular limitation on the nature of the carbonylating agent to be used in the above reaction provided that it is ordinarily employed for carbonylation. Examples include phosgene, diphosgene, triphosgene and 1,1'-carbonyldiimidazole.

There is no particular limitation on the nature of the solvent to be used upon the reaction of Compound (XIII) with the carbonylating agent, provided that it has no adverse effect on the present reaction. Examples include aliphatic hydrocarbons such as hexane, heptane, ligroin and petroleum ether; aromatic hydrocarbons such as benzene, toluene and xylene; halogenated hydrocarbons such as chloroform, dichloromethane, 1,2-dichloroethane and carbon tetrachloride; esters such as methyl acetate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; nitriles such as acetonitrile and isobutyronitrile; amides such as formamide, dimethylformamide, dimethylacetamide and hexamethylphosphoric triamide; and mixtures of the above-exemplified solvents, of which the aromatic hydrocarbons, halogenated hydrocarbons, ethers and amides (particularly tetrahydrofuran, dioxane and dimethylformamide) are preferred.

The temperature upon reaction of Compound (XIII) with the carbonylating agent depends on the natures of the raw materials, solvent and the like, however, it usually ranges from −50 to 200° C. (preferably from 0 to 120° C.).

The time upon reaction of Compound (XIII) with the carbonylating agent depends on the natures of the raw materials, solvent, the reaction temperature and the like, however, it usually ranges from 15 minutes to 50 hours (preferably from 1 hour to 24 hours).

The removal of the amino- and/or hydroxyl-protecting group in $R^{1a}$ and $R^{2a}$ is carried out if necessary in a similar manner to that described in Step A2 for the removal of the amino- and/or hydroxyl-protecting group.

After the completion of the reaction, the resulting compound (Id) of the present reaction is obtained from the reaction mixture by a known method. For example, it can be obtained by neutralizing the reaction mixture if necessary; removing the insoluble matter from the reaction mixture by filtration and adding to the filtrate an organic solvent, which is not miscible with water, such as ethyl acetate to the residue; separating the organic layer containing the desired compound, washing with water or the like and drying over anhydrous magnesium sulfate, anhydrous sodium sulfate, anhydrous sodium bicarbonate or the like; and then distilling off the solvent. The product so obtained can be isolated and purified, if necessary, by any suitable combination of conventional methods, for example, recrystallization, reprecipitation and chromatography.

Step C4 is a step for preparing a compound of formula (Ie) by removing the amino- and/or hydroxyl-protecting group in $R^1$ and $R^2$ of Compound (XIII) in an inert solvent. This step is conducted in a similar manner to that described in Step A2 of Method A for the removal of the amino- and/or hydroxyl-protecting groups.

Step C5 is another step for preparing a compound of formula (Id) by reacting Compound (XII) with N-(chlorocarbonyl)isocyanate in the presence or absence (preferably in the presence) of an inert solvent and then removing the amino- and/or hydroxyl-protecting group in $R^{1a}$ and $R^{2a}$ if desired.

There is no particular limitation on the nature of the solvent to be used upon the reaction of Compound (XII) with N-(chlorocarbonyl)isocyanate, provided that it has no adverse effect on the present reaction. Examples include aliphatic hydrocarbons such as hexane, heptane, ligroin and petroleum ether; aromatic hydrocarbons such as benzene, toluene and xylene; halogenated hydrocarbons such as chloroform, dichloromethane, 1,2-dichloroethane and carbon tetrachloride; esters such as methyl acetate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; nitriles such as acetonitrile and isobutyronitrile; amides such as formamide, dimethylformamide, dimethylacetamide and hexamethylphosphoric triamide; and mixtures of the above-exemplified solvents, of which the aromatic hydrocarbons, halogenated hydrocarbons, ethers and amides (particularly, tetrahydrofuran, dioxane and dimethylformamide) are preferred.

The reaction temperature depends on the natures of the raw materials, solvent and the like, however, it usually ranges from –50 to 100° C. (preferably from –20 to 50° C.).

The reaction time depends on the natures of the raw materials, solvent, the reaction temperature and the like, however, it usually ranges from 15 minutes to 50 hours (preferably from 1 hour to 24 hours).

The removal of the amino- and/or hydroxyl-protecting group in $R^{1a}$ and $R^{2a}$ is carried out, if desired, in a similar manner to that described in Step A2 of Method A for the removal of the amino- and/or hydroxyl-protecting group.

After the completion of the reaction, the resulting compound (Id) of the present reaction is obtained from the reaction mixture by a known method. For example, it can be obtained by neutralizing the reaction mixture if necessary; removing the insoluble matter from the reaction mixture by filtration and adding to the filtrate an organic solvent, which is not miscible with water, such as ethyl acetate to the residue; separating the organic layer containing the target compound, washing with water or the like and drying over anhydrous magnesium sulfate, anhydrous sodium sulfate, anhydrous sodium bicarbonate or the like; and then distilling off the solvent. The product so obtained can be isolated and purified, if necessary, by any suitable combination of conventional methods, for example, recrystallization, reprecipitation and chromatography.

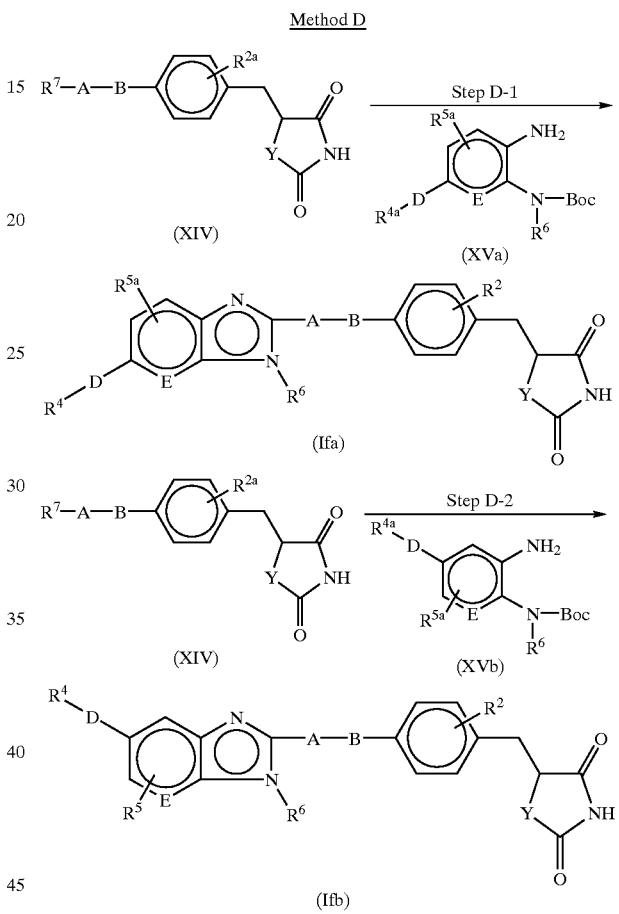

In the above reaction scheme, $R^2$, $R^{2a}$, $R^4$, $R^5$, $R^6$, A, B, D, E and Y have the same meanings as described above; $R^{4a}$ represents a similar group to that in the definition of the group of $R^4$ except that the amino and/or hydroxyl group included in the definition of $R^4$ means an amino and/or hydroxyl group which may be protected by an amino- and/or hydroxyl-protecting group; $R^{5a}$ represents a similar group to that in the definition of the group of $R^5$ except that the amino and/or hydroxyl group included in the definition of $R^5$ means an amino and/or hydroxyl group which may be protected by an amino- and/or hydroxyl-protecting group; $R^7$ represents a formyl, carboxy or $C_{2-7}$ alkoxycarbonyl group and Boc means a t-butoxycarbonyl group.

Method D is a process for preparing Compound (Ifa) which is Compound (I) wherein $R^1$ is a group of formula (II) and $R^3$ is a group of formula (IV-2) or (IV-3) or Compound (Ifb) which is Compound (I) wherein $R^1$ is a group of formula (III) and $R^3$ is a group of formula (IV-2) or (IV-3).

Step D1 is a step for preparing the compound of formula (Ifa) and it is effected by reacting a compound of formula (XIV) with a compound of formula (XVa) and then removing the amino- and/or hydroxyl-protecting group in $R^{2a}$, $R^{4a}$ and $R^{5a}$ if necessary.

When $R^7$ in Compound (XIV) represents a formyl group, Compound (XIV) is reacted with Compound (XVa) in an inert solvent and then the t-butoxycarbonyl group which is an amino-protecting group is removed from the reaction mixture by using an acid for effecting ring closure, followed by reaction with an oxidizing agent.

Alternatively, this step can be carried out by reacting Compound (XIV) with Compound (XVa), isolating and purifying the intermediate obtained by removing the t-butoxycarbonyl group, which is an amino-protecting group, by using an acid from the reaction mixture to effect ring closure, and then bringing an oxidizing agent into contact with the resulting intermediate.

There is no particular limitation on the nature of the solvent to be used upon the reaction of Compound (XIV) with Compound (XVa), provided that it has no adverse effect on the present reaction. Examples include aliphatic hydrocarbons such as hexane, heptane, ligroin and petroleum ether; ethers such as diethyl ether, diisopropyl ether, tetrahydrofuran, dioxane, dimethoxyethane and diethylene glycol dimethyl ether; alcohols such as methanol, ethanol, n-propanol, isopropanol, n-butanol, isobutanol, t-butanol, isoamyl alcohol, diethylene glycol, glycerin, octanol, cyclohexanol and methyl cellosolve; amides such as formamide, dimethylformamide, dimethylacetamide and hexamethylphosphoric triamide; acids such as acetic acid and propionic acid; sulfoxides such as dimethylsulfoxide; sulfolane; and mixtures of the above-exemplified solvents, of which the ethers (particularly, tetrahydrofuran) are preferred.

The temperature upon the reaction of Compound (XIV) with Compound (XVa) depends on the natures of the raw materials, base, solvent and the like, however, it usually ranges from 0 to 200° C. (preferably from 10 to 120° C.).

The reaction time upon the reaction of Compound (XIV) with Compound (XVa) depends on the natures of the raw materials, base, solvent, the reaction temperature and the like, however, it usually ranges from one hour to 50 hours (preferably from 5 hours to 24 hours).

The removal of the t-butoxycarbonyl group, which is an amino-protecting group, by using an acid is carried out in a similar manner to that described in Step A2 for the removal of the alkoxycarboxyl group which is an amino-protecting group.

There is no particular limitation on the nature of the oxidizing agent to be used for the above reaction provided that it is ordinarily used in oxidizing reactions. Examples include inorganic metal oxidizing agents, for example, manganese oxides such as potassium permanganate and manganese dioxide; ruthenium oxides such as ruthenium tetroxide; selenium compounds such as selenium dioxide; iron compounds such as ferric chloride; osmium compounds such as osmium tetroxide, potassium osmate dihydrate ($K_2OsO_4 \cdot 2H_2O$); silver compounds such as silver oxide; mercury compounds such as mercury acetate; lead oxide compounds such as lead oxide and lead tetraacetate; chromic acid compounds such as potassium chromate, chromic acid-sulfuric acid complex and chromic acid-pyridine complex; and cerium compounds such as cerium ammonium nitrate (CAN); inorganic oxidizing agents, for example, such as halogen molecules such as chlorine molecules, bromine molecules and iodine molecules; periodic acid compounds such as sodium periodate; ozone; hydrogen peroxide; nitrous acid compounds such as nitrous acid; chlorous acid compounds such as potassium chlorite and sodium chlorite; and persulfuric acid compounds such as potassium persulfate and sodium persulfate; and organic oxidizing agents, for example, reagents used for DMSO oxidation (complexes between dimethylsulfoxide and dicyclohexylcarbodiimide, oxalyl chloride, acetic anhydride or phosphorus pentaoxide or a complex between pyridine and sulfuric anhydride); combination of a peroxide such as t-butylhydroperoxide and a vanadium or molybdenum complex; stable cations such as triphenylmethyl cations; combination of a succinic imide such as N-bromosuccinic imide and an alkali; oxiranes such as dimethyldioxirane; hypochlorous acid compounds such as t-butyl hypochlorite; azodicarboxylic acid compounds such as azodicarboxylate ester; peracids such as m-chloroperbenzoic acid and perphthalic acid; disulfides such as dimethyl disulfide, diphenyl disulfide and dipyridyl disulfide and triphenyl phosphine; nitrous acid esters such as methyl nitrite; tetrahalogenated carbons such as methane tetrabromide; and quinone compounds such as 2,3-dichloro-5,6-dicyano-p-benzoquinone (DDQ), of which halogen molecules (particularly, iodine molecules) are preferred.

There is no particular limitation on the nature of the solvent to be employed upon contacting with the oxidizing agent, provided that it has no adverse effect on the present reaction. Solvents used upon the reaction of Compound (XIV) with Compound (XVa) are preferably employed.

The reaction temperature and reaction time upon contacting with the oxidizing agent are similar to those employed upon the reaction of Compound (XIV) with Compound (XVa).

When $R^7$ in Compound (XIV) represents a carboxyl group, the compound of formula (XIV) or reactive derivative thereof (an acid halide, active ester or mixed acid anhydride) is reacted with a compound of formula (XVa) or an acid addition salt thereof (e.g. the salt of a mineral acid such as a hydrochloride, nitrate or sulfate) and then the t-butoxycarbonyl group which is an amino-protecting group is removed using an acid, followed by ring closure.

In this step, alternatively, it is possible to isolate and purify the amide compound which is to be an intermediate, remove the t-butoxycarbonyl group, which is an amino-protecting group, from the resulting amide compound in a similar manner to that described in the above step, and then effect ring closure.

The acid halide method is carried out by reacting Compound (XIV) with a halogenating agent (e.g. thionyl chloride, thionyl bromide, oxalyl chloride, oxalyl dichloride, phosphorus oxychloride, phosphorus trichloride or phosphorus pentachloride) to prepare its acid halide and then reacting the resulting acid halide with Compound (XVa) or an acid addition salt thereof in an inert solvent in the presence or absence (preferably in the presence) of a base.

Examples of the base to be used for the above reaction include alkali metal carbonates such as lithium carbonate, sodium carbonate and potassium carbonate; alkali metal bicarbonates such as lithium bicarbonate, sodium bicarbonate and potassium bicarbonate; alkali metal hydrides such as lithium hydride, sodium hydride and potassium hydride; alkali metal hydroxides such as lithium hydroxide, sodium hydroxide and potassium hydroxide; alkali metal alkoxides such as lithium methoxide, sodium methoxide, sodium ethoxide and potassium-t-butoxide; and organic amines such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4.3.0]nona-5-ene, 1,4-diazabicyclo[2.2.2] octane (DABCO), 1,8-diazabicyclo[5.4.0]-7-undecene (DBU), of which the organic amines (particularly, triethylamine) are preferred.

There is no particular limitation on the nature of the solvent to be used in the above reaction provided that it has no adverse effect on the present reaction. Examples include aliphatic hydrocarbons such as hexane, heptane, ligroin and petroleum ether; aromatic hydrocarbons such as benzene, toluene and xylene; hydrogenated hydrocarbons such as dichloromethane, chloroform, 1,2-dichloroethane and carbon tetrachloride; ethers such as diethyl ether, diisopropyl ether, tetrahydrofuran, dioxane, dimethoxyethane and diethylene glycol dimethyl ether; amides such as formamide, dimethylformamide, dimethylacetamide and hexamethylphosphoric triamide; sulfoxides such as dimethyl sulfoxide; and sulfolane, of which the halogenated hydrocarbons, ethers and amides are preferred (dichloromethane, chloroform, tetrahydrofuran and dimethylformamide are particularly preferred).

The reaction temperature depends on the natures of the raw materials, reagents and the like, however, it usually ranges from −20 to 150° C. in each of the reaction of the halogenating agent with Compound (XIV) and the reaction of the acid halide with Compound (XVa) or an acid addition salt thereof. Preferably, the reaction of the halogenating agent and Compound (XIV) is carried out at a temperature of from −10 to 100° C., while that of the acid halide with Compound (XVa) or an acid addition salt thereof is carried out at a temperature of from −20 to 100° C.

The reaction time depends on the natures of the raw materials, reagents, the reaction temperature and the like, however, the reaction time ranges from 30 minutes to 80 hours (preferably from 1 hour to 48 hours) in each of the reaction of the halogenating agent with Compound (XIV) and that of the acid halide with Compound (XVa) or an acid addition salt thereof.

The active ester method is performed by reacting Compound (XIV) with an active esterifying agent in an inert solvent to prepare its active ester and then reacting the ester with Compound (XVa) or an acid addition salt thereof in an inert solvent in the presence or absence (preferably in the presence) of a base.

Examples of the active esterifying agent to be used in the above reaction include N-hydroxy compounds such as N-hydroxysuccinimide, 1-hydroxy-benzotriazole and N-hydroxy-5-norbornene-2,3-dicarboximide; disulfide compounds such as dipyridyl disulfide; carbodiimides such as dicyclohexylcarbodiimide; carbonyldiimidazole; and triphenylphosphine.

There is no particular limitation on the nature of the solvent to be used for the above reaction provided that it has no adverse effect on the present reaction. Examples include aliphatic hydrocarbons such as hexane, heptane, ligroin and petroleum ether; aromatic hydrocarbons such as benzene, toluene and xylene; halogenated hydrocarbons such as dichloromethane, 1,2-dichloroethane and carbon tetrachloride; ethers such as diethyl ether, diisopropyl ether, tetrahydrofuran, dioxane, dimethoxyethane and diethylene glycol dimethyl ether; ketones such as acetone; amides such as formamide, dimethylformamide, dimethylacetamide and hexamethylphosphoric triamide; sulfoxides such as dimethylsulfoxide; and sulfolane, of which the ethers and amides (particularly, dioxane, tetrahydrofuran and dimethylformamide) are preferred.

The bases to be used in the above reaction are similar to those used in the above-described acid halide method.

The reaction temperature depends on the natures of the raw material and reagents and the like, however, the reaction of forming an active ester is usually carried out at a temperature of from −70 to 150° C. (preferably from −10 to 100° C.), while the subsequent reaction between the active ester and Compound (XVa) or an acid addition salt thereof is carried out at a temperature of from −20 to 100° C. (preferably from 0 to 50° C.).

The reaction time depends on the natures of the raw material, reagents, the reaction temperature and the like, however, it usually ranges from 30 minutes to 80 hours (preferably from 1 hour to 48 hours) in each of the reaction to prepare an active ester and the reaction of an active ester with Compound (XVa) or an acid addition salt thereof.

The mixed acid anhydride method is carried out by reacting Compound (XIV) and a mixed-acid-anhydride forming agent in an inert solvent in the presence or absence (preferably in the presence) of a base to prepare the corresponding mixed acid anhydride and then reacting the resulting mixed acid anhydride and Compound (XVa) or an acid addition salt thereof in an inert solvent.

Examples of the base to be used for the above reaction include alkali metal carbonates such as lithium carbonate, sodium carbonate and potassium carbonate; alkali metal bicarbonates such as lithium bicarbonate, sodium bicarbonate and potassium bicarbonate; alkali metal hydrides such as lithium hydride, sodium hydride and potassium hydride; alkali metal hydroxides such as lithium hydroxide, sodium hydroxide and potassium hydroxide; alkali metal alkoxides such as lithium methoxide, sodium methoxide, sodium ethoxide or potassium-t-butoxide; and organic amines such as triethylamine, tributylamine, diisopropyl ethylamine, N-methylmorpholine, pyridine, 4-(N,N-dimethylamino) pyridine, N,N-dimethylaniline, N,N-diethylaniline, 1,5-diazabicyclo[4.3.0]nona-5-ene, 1,4-diazabicyclo[2.2.2]octane (DABCO), 1,8-diazabicyclo[5.4.0]-7-undecene (DBU), of which the organic amines (particularly, triethylamine) are preferred.

Examples of the mixed-acid-anhydride forming agent to be used in the above reaction include $C_{1-4}$ alkyl halocarbonates such as ethyl chlorocarbonate and isobutyl chlorocarbonate; ($C_{1-5}$ alkanoyl) halides such as pivaloyl chloride; and di($C_{1-4}$ alkyl) or di($C_{6-4}$ aryl) cyanophosphates such as diethyl cyanophosphonate and diphenyl cyanophosphonate, of which the di($C_{1-4}$ alkyl) or di($C_{6-14}$ aryl) cyanophosphates (particularly, diethyl cyanophosphonate) are preferred.

There is no particular limitation on the nature of the solvent to be used upon the preparation of the mixed acid anhydride provided that it has no adverse effect on the reaction and can dissolve therein the starting substance to some extent. Examples include aliphatic hydrocarbons such as hexane, heptane, ligroin and petroleum ether; aromatic hydrocarbons such as benzene, toluene and xylene; halogenated hydrocarbons such as dichloromethane, 1,2-dichloroethane and carbon tetrachloride; ethers such as diethyl ether, diisopropyl ether, tetrahydrofuran, dioxane, dimethoxyethane and diethylene glycol dimethyl ether; ketones such as acetone; amides such as formamide, dimethylformamide, dimethylacetamide and hexamethylphosphoric triamide; sulfoxides such as dimethyl sulfoxide; and sulfolane, of which the ethers and amides (particularly, tetrahydrofuran and dimethylformamide) are preferred.

The temperature of reaction for preparing the mixed acid anhydride depends on the natures of the raw materials, reagents and the like, however, it usually ranges from −50 to 100° C. (preferably from 0 to 60° C.).

The time of reaction for preparing the mixed acid anhydride depends on the natures of the raw materials, reagents, reaction temperature and the like, however, it usually ranges from 30 minutes to 72 hours (preferably from 1 hour to 24 hours).

The mixed acid anhydride is reacted with Compound (XVa) or an acid addition salt thereof in an inert solvent in the presence or absence (preferably in the presence) of a base, and the base and inert solvent to be used for this reaction are similar to those employed in the reaction for the preparation of the above-described mixed acid anhydride.

The temperature of reaction of the mixed acid anhydride with Compound (XVa) or an acid addition salt thereof depends on the natures of the raw materials, reagents and the like, however, it usually ranges from −30 to 100° C. (preferably from 0 to 80° C.).

The time of reaction of the mixed acid anhydride with Compound (XVa) or an acid addition salt thereof depends on the natures of the raw materials, reagents, reaction temperature and the like, however, it usually ranges from 5 minutes to 24 hours (preferably from 30 minutes to 16 hours).

When a di($C_{1-4}$ alkyl)cyanophosphoric acid or di($C_{6-4}$ aryl)cyanophosphoric acid is employed in this reaction, Compound (XIV) can be reacted with Compound (XVa) directly in the presence of a base.

The removal of the t-butoxycarbonyl group, which is an amino-protecting group, by using an acid is carried out in a similar manner to that described in step A2 of Method A for the removal of the protecting group from the alkoxycarbonyl-protected amino group by using an acid.

The ring-closure subsequent to the removal of the t-butoxycarbonyl group, which is an amino-protecting group, by using an acid can be carried out in a similar manner to that described in step A2 of Method A for the removal of the protecting group from the alkoxycarboxy-protected amino group by using an acid.

When Compound (XIV) contains a $C_{2-7}$ alkoxycarbonyl group as $R^7$, Compound (XIV) is reacted with Compound (XVa) in the presence or absence (preferably in the absence) of an inert solvent and in the presence or absence of a base, the t-butoxycarbonyl group which is an amino-protecting group is removed using an acid, followed by ring closure.

In this step, alternatively, it is possible to isolate and purify the amide compound which is to be the intermediate, remove the t-butoxycarbonyl group, which is an amino-protecting group, from the resulting amide compound in a similar manner to described in the above reaction, and then effect ring closure.

Examples of the base to be used for the above reaction of Compound (XIV) with Compound (XVa) include alkali metal carbonates such as lithium carbonate, sodium carbonate and potassium carbonate; alkali metal bicarbonates such as lithium bicarbonate, sodium bicarbonate and potassium bicarbonate; alkali metal hydrides such as lithium hydride, sodium hydride and potassium hydride; alkali metal hydroxides such as lithium hydroxide, sodium hydroxide and potassium hydroxide; alkali metal alkoxides such as lithium methoxide, sodium methoxide, sodium ethoxide and potassium-t-butoxide; and organic amines such as triethylamine, tributylamine, diisopropyl ethylamine, N-methylmorpholine, pyridine, 4-(N,N-dimethylamino) pyridine, N,N-dimethylaniline, N,N-diethylaniline, 1,5-diazabicyclo[4.3.0]nona-5-ene, 1,4-diazabicyclo[2.2.2] octane (DABCO), 1,8-diazabicyclo[5.4.0]-7-undecene (DBU), of which the organic amines (particularly, triethylamine) are preferred.

There is no particular limitation on the nature of the solvent to be used upon the reaction of Compound (XIV) with Compound (XVa) provided that it has no adverse effect on the present reaction. Examples include aliphatic hydrocarbons such as hexane, heptane, ligroin and petroleum ether; aromatic hydrocarbons such as benzene, toluene and xylene; ethers such as diethyl ether, diisopropyl ether, tetrahydrofuran, dioxane, dimethoxyethane and diethylene glycol dimethyl ether; alcohols such as methanol, ethanol, n-propanol, isopropanol, n-butanol, isobutanol, t-butanol, isoamyl alcohol, diethylene glycol, glycerin, octanol, cyclohexanol and methyl cellosolve; amides such as formamide, dimethylformamide, dimethylacetamide and hexamethylphosphoric triamide; and mixtures of the above-exemplified solvents, of which the ethers and amides (particularly, tetrahydrofuran, dioxane and dimethylformamide) are preferred.

The reaction temperature depends on the natures of the raw materials, base, solvent and the like, however, it usually ranges from 0 to 200° C. (preferably, from 50 to 150° C.).

The reaction time depends on the natures of the raw materials, base, solvent, the reaction temperature and the like, however, it usually ranges from 1 hour to 50 hours (preferably from 5 hours to 24 hours).

The ring-closure subsequent to the removal of the t-butoxycarbonyl group, which is an amino-protecting group, by using an acid can be carried out in a similar manner to that described in step A2 of Method A for the removal of the protecting group from the alkoxycarboxy-protected amino group by using an acid.

The removal, if necessary, of the amino- and/or hydroxyl-protecting group in $R^{2a}$, $R^{4a}$ and $R^{5a}$ is carried out in a similar manner to that described in Step A2 of Method A for the removal the amino- and/or hydroxyl-protecting group.

After the completion of the reaction, the resulting compound (Ifa) of the present reaction is obtained from the reaction mixture by a known method. For example, it can be obtained by neutralizing the reaction mixture if necessary; removing the insoluble matter from the reaction mixture by filtration and adding to the filtrate an organic solvent, which is not miscible with water such as ethyl acetate to the residue; separating the organic layer containing the target compound, washing with water or the like and drying over anhydrous magnesium sulfate, anhydrous sodium sulfate, anhydrous sodium bicarbonate or the like; and then distilling off the solvent. The resulting compound can be isolated and purified, if necessary, by any suitable combination of conventional methods, for example, recrystallization, reprecipitation and chomatography.

Step D2 is a step for preparing the compound of formula (Ifb) and it is effected in a similar manner to that described in step D1 of Method D, more specifically, by reacting the compound of the formula (XIV) with the compound of the formula (XVb) and then removing the amino- and/or hydroxyl-protecting group in $R^{2a}$, $R^{4a}$ and $R^{5a}$ if necessary. This step is carried out in a similar manner to that described in Step D1.

If $R^4$ of Compound (Ia), (Ib), (Ic), (Id), (Ie), (Ifa) and (Ifb) obtained by the above-described Method A, Method B, Method C and Method D is a phenyl or pyridyl group substituted with an amino group, it is possible to carry out alkylation, arylation, aralkylation or acylation of the amino group if necessary. Such a reaction is known or can be effected in a known method or method analogous thereto [The Chemistry of the Amino Group, chapter 6, 1968, John Wiley & Sons, The Chemistry of the Amino Group, chapter 2, 1970, John Wiley & Sons, etc.]

The raw materials (V), (VI), (VIII), (X), (XIV), (XVa) and (XVb) are each known or are prepared easily by a known method or a method analogous thereto.

The raw materials (V), (XIV), (XVa) and (XVb) can also be prepared, for example, by the following methods.

Method E

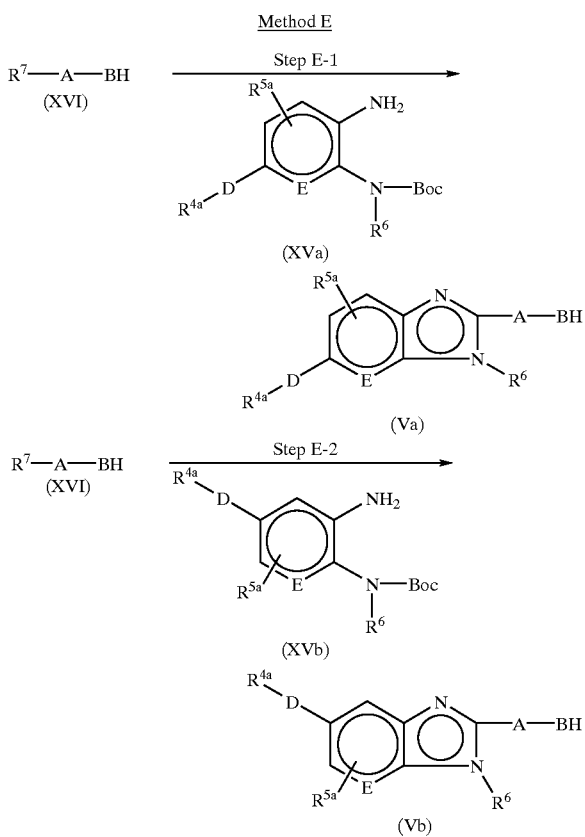

In the above reaction scheme, $R^{4a}$, $R^{5a}$, $R^6$, $R^7$, A, B, D, E and Boc have the same meanings as described above.

Method E is a process for preparing Compounds (Va) and (Vb).

Step E1 is a step for preparing Compound (Va) by reacting a compound of formula (XVI) with Compound (XVa) and then removing the t-butoxycarbonyl group, which is an amino-protecting group, by using an acid, followed by ring closure. This step is conducted in a similar manner to that described in Step D1 of Method D wherein Compound (XIV) is reacted with Compound (XVa) and the t-butoxycarbonyl group, which is an amino-protecting group, is removed by using an acid, followed by ring closure.

In particular, when, in Compound (XVa), E represents a nitrogen atom, the ring closure is preferably carried out using Compound (XVI) in a large excess amount in the absence of a solvent.

Step E2 is a step for preparing Compound (Vb) by reacting the compound of the formula (XVI) with Compound (XVb) and then removing the t-butoxycarbonyl group, which is an amino-protecting group, by using an acid. This step is carried out in a similar manner to that described in Step D1 of Method D, wherein Compound (IXV) having a carboxyl group as $R^7$ is reacted with Compound (XVa) and then the t-butoxycarbonyl group, which is an amino-protecting group, is removed by using an acid.

The ring closure is also conducted in a similar manner to that described in Step D1 of Method D. When, in Compound (XVa), E represents a nitrogen atom, however, the ring closure is preferably carried out using a large excess amount of Compound (XVI) in the absence of a solvent.

After the completion of the reaction, the resulting compound (Va) or (Vb) of the present reaction is obtained from the reaction mixture by a known method. For example, it can be obtained by neutralizing the reaction mixture if necessary; removing the insoluble matter from the reaction mixture by filtration and adding to the filtrate an organic solvent, which is not miscible with water, such as ethyl acetate; separating the organic layer containing the desired compound, washing with water or the like and drying over anhydrous magnesium sulfate, anhydrous sodium sulfate, anhydrous sodium bicarbonate or the like; and then distilling off the solvent. The resulting product can be isolated and purified, if necessary, by any suitable combination of conventional methods, for example, recrystallization, reprecipitation and chromatography.

Method F

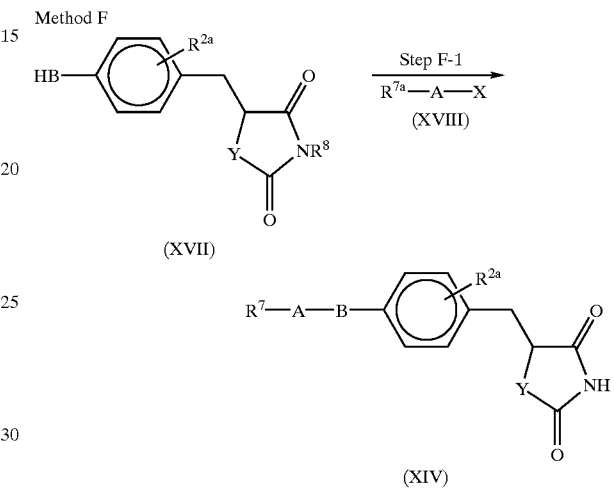

In the above reaction scheme, $R^{2a}$, $R^7$, $R^8$, A, B, X and Y have the same meanings as described above and $R^{7a}$ represents a similar group to that in the definition of $R^7$ except that the formyl or carboxyl group included in the definition of $R^7$ means a formyl or carboxyl group which may be protected by a protecting group.

In the above description, there is no particular limitation on the "protecting group" of the "formyl group which may be protected by a protecting group" provided that it is a formyl-protecting group used in the field of organic synthetic chemistry. Examples include a methyl group substituted with the above-exemplified $C_{1-6}$ alkoxy groups, such as dimethoxymethyl, diethoxymethyl, dipropoxymethyl and dibutoxymethyl, and 1,3-dioxan-2-yl, 1,3-dioxolan-2-yl, 1,3-dithian-2-yl and 1,3-dithiolan-2-yl groups, of which dimethoxymethyl, diethoxymethyl, 1,3-dioxolan-2-yl and 1,3-dithian-2-yl groups are preferred.

In the above description, there is no particular limitation on the "protecting group" of the "carboxyl group which may be protected by a protecting group" provided that it is a carboxyl-protecting group used in the field of organic synthetic chemistry. Examples include $C_{1-6}$ alkyl groups such as methyl, ethyl, propyl, isopropyl, butyl, s-butyl and t-butyl; and $C_{1-6}$ alkyl groups substituted with 1 to 3 $C_{6-10}$ aryl groups which may be substituted with a $C_{1-6}$ alkyl group, $C_{1-6}$ alkoxy group, nitro group, halogen atom or cyano group, such as benzyl, phenethyl, 3-phenylpropyl, 1-naphthylmethyl, diphenylmethyl, triphenylmethyl, 4-methylbenzyl, 4-methoxybenzyl, 4-nitrobenzyl, 4-fluorobenzyl and 4-cyanobenzyl groups, of which the $C_{1-6}$ alkyl groups and benzyl group are preferred.

Method F is a process for preparing Compound (XIV).

Step F1 is a step for preparing Compound (XIV) by reacting the compound of formula (XVII) with a compound of formula (XVIII) in an inert solvent in the presence of a base and then removing the protecting group if the formyl or carboxyl group of $R^{7a}$ is a protected formyl or carboxyl group.

The base employed upon reacting the compound of formula (XVII) with the compound of the formula (XVIII) is similar to that used in the above-described Step B1 of Method B and is preferably an alkali metal hydride (particularly, sodium hydride).

The solvent employed upon reacting the compound of formula (XVII) with the compound of formula (XVIII) is similar to that used in the above-described Step B1 of Method B and is preferably an amide or a mixed solvent of an amide and another solvent (particularly, dimethylformamide).

The reaction temperature upon reacting the compound of formula (XVII) with the compound of formula (XVIII) depends on the natures of the raw materials, base, solvent and the like, however, it usually ranges from −50 to 200° C. (preferably from 0 to 120° C.).

The reaction time upon reacting the compound of formula (XVII) with the compound of formula (XVIII) depends on the natures of the raw materials, base, solvent, the reaction temperature and the like, however, it usually ranges from 30 minutes to 24 hours (preferably from 1 hour to 10 hours).

The removal, if desired, of the protecting group of the formyl group or carboxyl group depends on its nature, however, it is generally carried out by a method known in the field of organic synthetic chemistry, for example, T. W. Green (Protective Groups in Organic Synthesis), John Wiley & Sons or J. F. W. McOmie, (Protective Groups in Organic Chemistry), Plenum Press.

Compound (XIV) wherein $R^7$ is a carboxyl group or Compound (XVIII) wherein $R^{7a}$ is a carboxyl group can be easily prepared by a known method from a compound wherein $R^7$ or $R^{7a}$ represents a formyl or protected formyl group.

After the completion of the reaction, the resulting compound (XIV) of the present reaction is obtained from the reaction mixture by a known method. For example, it can be obtained by neutralizing the reaction mixture if necessary; removing the insoluble matter from the reaction mixture by filtration and adding to the filtrate an organic solvent, which is not miscible with water, such as ethyl acetate; separating the organic layer containing the desired compound, washing with water or the like and drying over anhydrous magnesium sulfate, anhydrous sodium sulfate, anhydrous sodium bicarbonate or the like; and then distilling off the solvent. The resulting product can be isolated and purified, if necessary, by any suitable combination of conventional methods, for example, recrystallization, reprecipitation and chromatography.

Method G

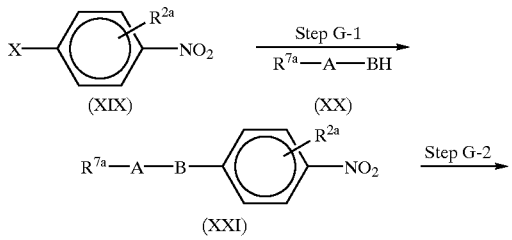

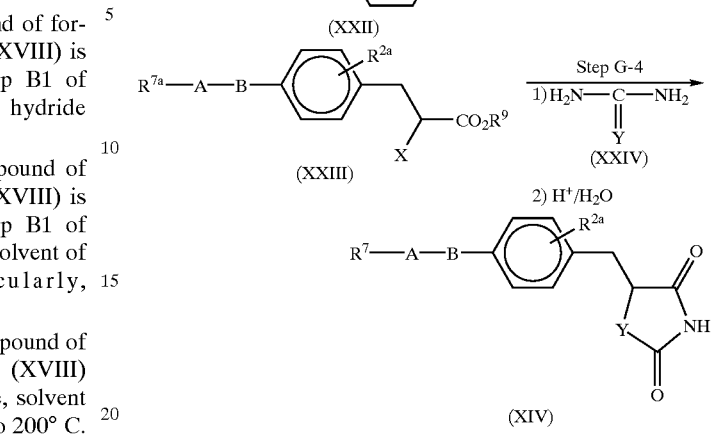

In the above reaction scheme, $R^{2a}$, $R^7$, $R^{7a}$, A, B, X and Y have the same meanings as described above and $R^9$ represents a carboxyl-protecting group (which has the same meaning as described above).

Method G is also a preparation process of Compound (XIV), and is different from Method F.

Step G1 is a step for preparing a compound of formula (XXI) by reacting a compound of formula (XIX) with a compound of formula (XX) in an inert solvent in the presence of a base. This step is carried out in a similar manner to that described in Step F1 of Method F.

Step G2 is a step for preparing a compound of formula (XXII) by reduction of Compound (XXI). This reaction is carried out by catalytic reduction or the zinc-acetic acid method, tin-alcohol method or tin-hydrochloric acid method which is usually employed for the reduction of a nitro group.

Step G3 is a step for preparing a compound of formula (XXIII) and it is achieved by subjecting Compound (XXII) to a Meerwein arylation in a similar method to that described in Japanese Patent Application Kokai No. Sho 55-22657 (U.S. Pat. No. 4,258,193) or S. Oae et al., "Bull. Chem. Soc. Jpn., 53, 1065(1980)".

Step G4 is a step for preparing Compound (XIV) by reacting Compound (XXIII) with a compound of formula (XXIV) and then subjecting the reaction mixture to hydrolysis, and if desired, removing the formyl- or carboxyl-protecting group as defined in the group of $R^{7a}$.

The reaction of Compound (XXIII) with Compound (XXIV) and hydrolysis subsequent thereto are carried out in a similar method to that described in Japanese Patent Application Kokai No. Sho 55-22657 (U.S. Pat. No. 4,258,193).

The removal of the formyl- or carboxyl-protecting group which is defined in the group of $R^{7a}$ is carried out in a similar method to that described in the removal of the formyl- or carboxyl-protecting group in Method F.

After the completion of the reaction, the resulting compound (XIV) of the present reaction is obtained from the reaction mixture by a known method. For example, it can be obtained by neutralizing the reaction mixture if necessary; removing the insoluble matter from the reaction mixture by filtration and adding to the filtrate an organic solvent, which is not miscible with water, such as ethyl acetate; separating the organic layer containing the desired compound, washing with water or the like and drying over anhydrous magnesium sulfate, anhydrous sodium sulfate, anhydrous sodium bicarbonate or the like; and then distilling off the solvent. The compound so obtained can be isolated and purified, if necessary, by any suitable combination of conventional methods, for example, recrystallization, reprecipitation and chromatography.

Method H

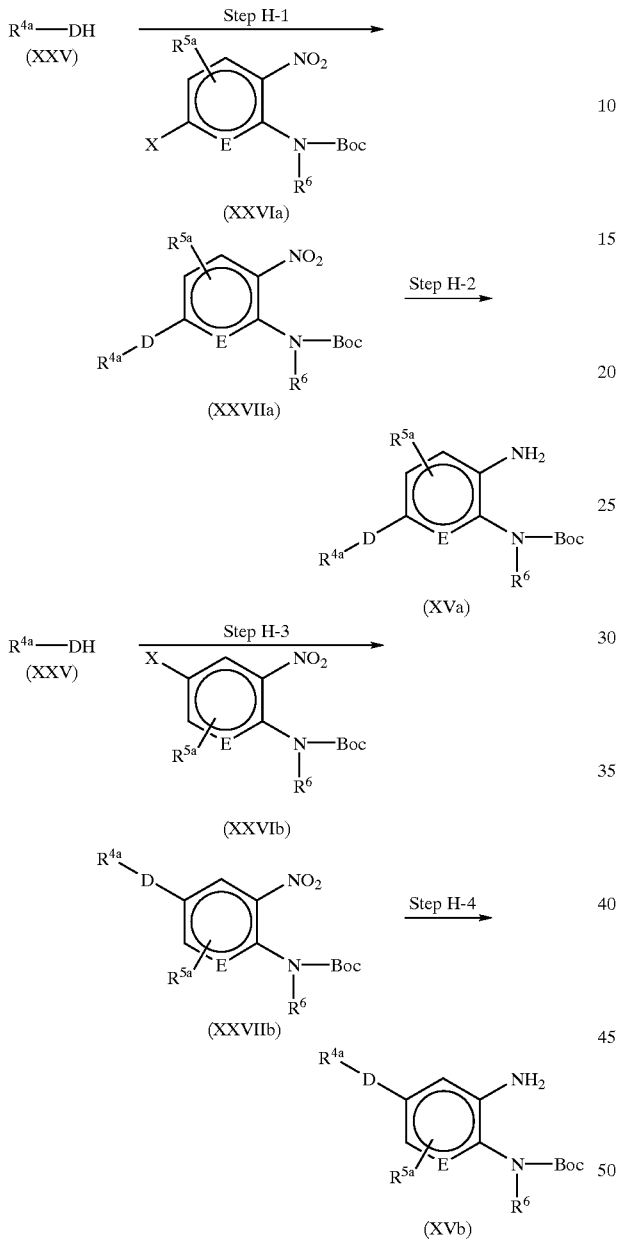

In the above reaction scheme, $R^{4a}$, $R^{5a}$, $R^6$, D, E, X and Boc have the same meanings as described above.

Method H is a process for preparing Compounds (XVa) and (XVb).

Step H1 is a step for preparing a compound of formula (XXVIIa) by reacting a compound of formula (XXV) with a compound of formula (XXVIa) in the presence of a base. This step is carried out in a similar manner to that described in Step F1 of Method F.

Step H2 is a step for preparing Compound (XVa) by reduction of Compound (XXVIIa). This step is carried out in a similar manner to that described in Step G2 of Method G.

Step H3 is a step for preparing Compound (XXVIIb) by reacting a compound of formula (XXV) with a compound of formula (XXVIb) in an inert solvent in the presence of a base. This step is carried out in a similar manner to that described in Step F1 of Method F.

Step H4 is a step for preparing Compound (XVb) by reduction of Compound (XXVIIb). This step is carried out in a similar manner to that described in Step G2.

After the completion of the reaction, the resulting compounds (XVa) and (XVb) of the present reaction are obtained from the reaction mixture by a known method. For example, each of them can be obtained by neutralizing the reaction mixture if necessary; removing the insoluble matter from the reaction mixture by filtration and adding to the filtrate an organic solvent, which is not miscible with water, such as ethyl acetate to the residue; separating the organic layer containing the desired compound, washing with water or the like and drying over anhydrous magnesium sulfate, anhydrous sodium sulfate, anhydrous sodium bicarbonate or the like; and then distilling off the solvent. The resulting compound can be isolated and purified, if necessary, by any suitable combination of conventional methods, for example, recrystallization, reprecipitation and chromatography.

Method I

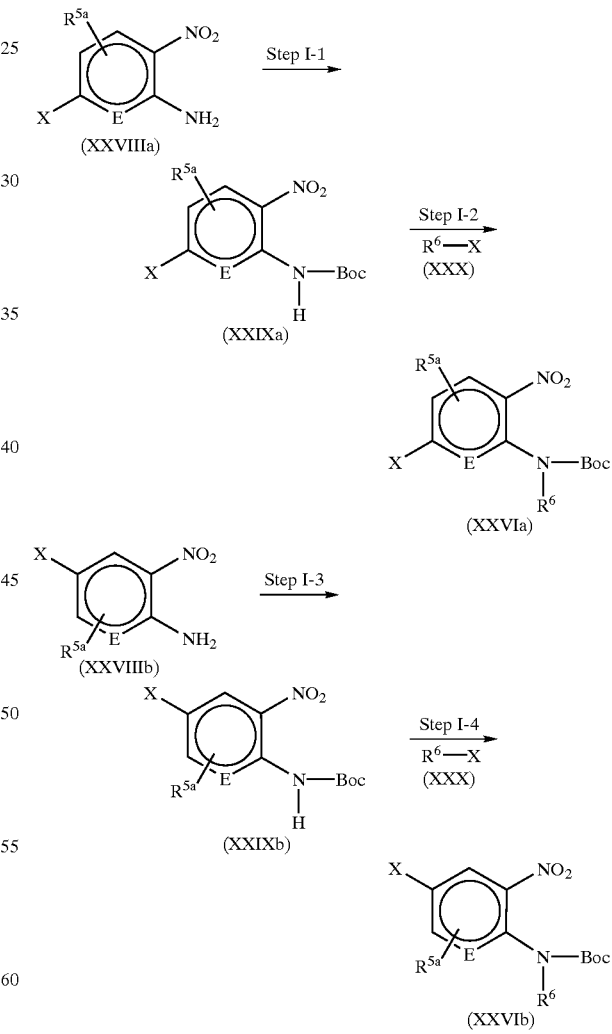

In the above reaction scheme, $R^{5a}$, $R^6$, E, X and Boc have the same meanings as described above.

Method I is a process for preparing Compounds (XXVIa) and (XXVIb).

Step I1 is a step for preparing a compound of formula (XXIXa) by protecting the amino group of a compound of formula (XXVIIa) with a t-butoxycarbonyl group in a similar method to that ordinarily known in the field of organic synthetic chemistry, for example, T. W. Green (Protective Groups in Organic Synthesis), John Wiley & Sons or J. F. W. Mcomie, (Protective Groups in Organic Chemistry), Plenum Press.

Step I2 is a step for preparing Compound (XXVIa) by reacting Compound (XXIXa) with a compound of formula (XXX) in an inert solvent in the presence of a base.

The base used in the above reaction is similar to that used in the above-described Step B1 of Method B and alkali metal hydrides (particularly sodium hydride) are preferred.

The solvent used in the above reaction is similar to that used in Step B1 of Method B and ethers and amides (particularly, tetrahydrofuran, dioxane and dimethylformamide) are preferred.

The reaction temperature depends on the natures of the raw materials, base, solvent and the like, however, it usually ranges from −50 to 200° C. (preferably from 0 to 120° C.).

The reaction time depends on the natures of the raw materials, base, solvent, the reaction temperature and the like, however, it usually ranges from 30 minutes to 24 hours (preferably from 1 hour to 10 hours).

Step I3 is a step for preparing a compound of formula (XXIXb) by protecting the amino group of the compound of the formula (XXVIIIb) with a t-butoxycarbonyl group. This step is carried out in a similar manner to that described in Step I1.

Step I4 is a step for preparing Compound (XXVIb) by reacting Compound (XXIXb) with a compound of formula (XXX) in an inert solvent in the presence of a base. This step is carried out in a similar manner to that described in the above-described Step I2 of Method I.

After the completion of the reaction, the resulting compound (XXVIa) or (XXVIb) of the present reaction is obtained from the reaction mixture by a known method. For example, it can be obtained by neutralizing the reaction mixture if necessary; removing the insoluble matter from the reaction mixture by filtration and adding to the filtrate an organic solvent, which is not miscible with water, such as ethyl acetate; separating the organic layer containing the desired compound, washing with water or the like and drying over anhydrous magnesium sulfate, anhydrous sodium sulfate, anhydrous sodium bicarbonate or the like; and then distilling off the solvent. The resulting product can be isolated and purified, if necessary, by any suitable combination of conventional methods, for example, recrystallization, reprecipitation and chromatography.

Method J

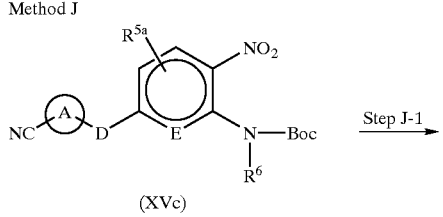

(XVc)

Step J-1

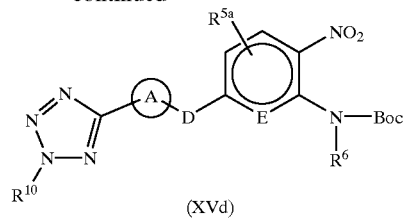

(XVd)

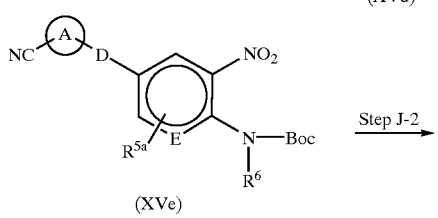

(XVe)

Step J-2

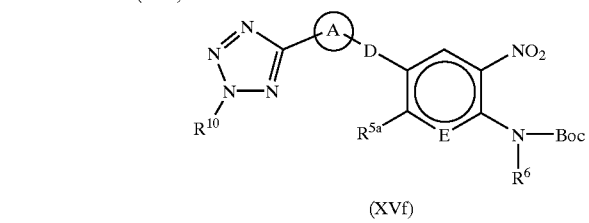

(XVf)

In the above reaction scheme, $R^{5a}$, $R^6$, D, E and Boc have the same meanings as described above, $R^{10}$ represents a hydrogen atom or a triphenylmethyl group and the group of the following formula:

represents a phenyl group which may be substituted with 1 to 4 substituents selected from Substituents α or a pyridyl group which may be substituted with 1 to 3 substituents selected from Substituents α.

Method J is a process for preparing Compound (XVd) or (XVf) having as $R^{4a}$ a phenyl or pyridyl group substituted with a tetrazolyl group which may be protected, and is different from Method H.

Step J1 is a step for preparing Compound (XVd) by reacting Compound (XVc), which is Compound (XVa) having as $R^4$ a cyano-substituted phenyl or pyridyl group, with an azide compound in an inert solvent and then, if desired, protecting the tetrazolyl group of the resulting compound.

There is no particular limitation on the nature of the inert solvent to be used upon the above reaction provided that it has no adverse effect on the present reaction. Examples include aliphatic hydrocarbons such as hexane, heptane, ligroin and petroleum ether; aromatic hydrocarbons such as benzene, toluene and xylene; halogenated hydrocarbons such as chloroform, dichloromethane, 1,2-dichloroethane and carbon tetrachloride; nitriles such as acetonitrile; ethers such as diethyl ether, diisopropyl ether, tetrahydrofuran, dioxane, dimethoxyethane and diethylene glycol dimethyl ether; ketones such as acetone; amides such as formamide, dimethylformamide, dimethylacetamide and hexamethylphosphoryl triamide; and sulfoxides such as dimethylsulfoxide, of which the aromatic hydrocarbons (particularly, toluene) are preferred.

Examples of the azide compound to be used in the above reaction include diarylphosphoryl azide derivatives such as diphenylphosphoryl azide; trialkylsilylazides such as trimethylsilylazide and triethylsilylazide; alkali metal salts of azide such as sodium azide and potassium azide; and trialkyltin azides such as tri-n-butyltin azide, of which the trialkyltin azides (particularly the tri-n-butyltin azide) are preferred.

In the above reaction, the azide compound may be used either singly or in combination with, for example, a trialkylsilyl triflate such as trimethylsilyl triflate or triethylsilyl triflate or a Lewis acid such as trifluoroborane etherate, aluminum chloride or zinc chloride.

Although the reaction temperature depends on the natures of the raw material, azide to be employed and solvent, and the like, it usually ranges from −10 to 200° C. (preferably from 50 to 150° C.).

The reaction time depends on the natures of the raw material, azide to be employed and solvent, the reaction temperature and the like, however, it usually ranges from 15 minutes to 48 hours (preferably from 30 minutes to 30 hours).

The reaction to protect the tetrazolyl group is carried out if necessary by reacting the compound obtained by the above reaction with a halogenated triphenylmethane in an inert solvent in the presence of a base.

The base used in the above reaction is similar to that used in Step B1 of Method B and organic amines (particularly triethylamine) are preferred.

The solvent used in the above reaction is similar to that used upon reaction of Compound (XVc) with an azide compound and a mixture of an ether and an amide (particularly, a mixture of tetrahydrofuran and dimethylformamide) is preferred.

The reaction temperature depends on the natures of the raw materials, base, solvent and the like, however, it usually ranges from −10 to 150° C. (preferably from 0 to 60° C.).

The reaction time depends on the natures of the raw materials, base and solvent, the reaction temperature and the like, however, it usually ranges from 15 minutes to 48 hours (preferably from 30 minutes to 30 hours).

Step J2 is a step for preparing the compound of the formula (XVf) by reacting Compound (XVe), which is Compound (XVb) having as $R^{4a}$ a cyano-substituted phenyl or pyridyl group, with an azide compound and if necessary, protecting the tetrazolyl group of the resulting compound. This step is carried out in a similar manner to that described in Step J1 of Method J.

After the completion of the reaction, the resulting compound (XVd) or (XVf) of the present reaction is obtained from the reaction mixture by a known method. For example, it can be obtained by neutralizing the reaction mixture as desired; removing the insoluble matter, if any, from the reaction mixture by filtration and adding to the filtrate an organic solvent, which is not miscible with water, such as ethyl acetate; separating the organic layer containing the desired compound from the resulting mixture, washing the organic layer with water or the like and drying it over anhydrous magnesium sulfate, anhydrous sodium sulfate, anhydrous sodium bicarbonate or the like; and then distilling off the solvent. The resulting product can be isolated and purified, if necessary, by using in combination the methods ordinarily employed for the separation and purification of an organic compound such as recrystallization, reprecipitation, and chromatography using an appropriate eluant.

The raw materials (XVI), (XVII), (XVIII), (XIX), (XX), (XXIV), (XXV), (XXVIIIa), (XXVIIIb) and (XXX) are known or easily prepared by a known method or a method analogous thereto [e.g. Japanese Patent Application Kokai Hei 9-188669 (EP543662A) and the like].

(Advantages of the Invention)

The compound of formula (I) or a pharmacologically acceptable salt thereof according to the present invention has excellent insulin-resistance improving action, blood sugar lowering action, anti-inflammatory action, immunomodulatory action, aldose reductase inhibitory action, 5-lipoxygenase inhibitory action, lipid peroxide production inhibitory action, PPAR activating action, anti-osteoporosis action, leukotriene antagonism, fat-cell-formation promoting action, cancer-cell proliferation inhibitory action and calcium antagonism and is therefore useful as a preventive agent and/or remedy for diabetes, hyperlipidemia, obesity, glucose tolerance insufficiency, hypertension, fatty liver, diabetic complications (e.g. retinopathy, nephropathy, neurosis, cataracts or coronary disease and the like), arteriosclerosis, pregnancy diabetes, polycystic ovary syndrome, cardiovascular diseases (e.g. ischemic heart disease and the like), cell injury (e.g. brain injury induced by stroke and the like) induced by atherosclerosis or ischemic heart disease, gout, inflammatory diseases (such as arthrosteitis, pain, pyrexia, rheumatoid arthritis, inflammatory enteritis, acne, sunburn, psoriasis, eczema, allergosis, asthma, GI ulcer, cachexia, autoimmune diseases and pancreatitis), cancer, osteoporosis or cataracts.

In addition, the compound of formula (I) or a pharmacologically acceptable salt thereof according to the present invention is useful as a pharmaceutical composition (particularly, as a preventive agent and/or remedy for diabetes or diabetic complications) obtained by using it in combination with at least one of α-glucosidase inhibitors, aldose reductase inhibitors, biguanide preparations, statin base compounds, squalene synthesis inhibitors, fibrate base compounds, LDL catabolism promoters and angiotensin-converting enzyme inhibitors.

[Industrial Applicability]

When the compound of formula (I) or a pharmacologically acceptable salt or prodrug thereof is used according to the present invention, it can be administered as it is or, if necessary, after being mixed with a pharmacologically acceptable excipient, diluent or the like, orally as tablets, capsules, granules, powders or syrups or parenterally as injections or suppositories.

The above pharmaceutical formulations can be prepared in a known manner by using additives. Examples of the additives include an excipient (e.g. organic excipients, for example, sugar derivatives such as lactose, sucrose, dextrose, mannitol and sorbitol; starch derivatives such as corn starch, potato starch, α-starch and dextrin; and cellulose derivatives such as crystalline cellulose, gum arabic, dextran, and pullulan; and inorganic excipients, for example, silicate derivatives such as soft silicic anhydride, synthetic aluminum silicate, calcium silicate and magnesium aluminate metasilicate; phosphate derivatives such as calcium hydrogenphosphate; carbonate derivatives such as calcium carbonate; and sulfates such as calcium sulfate), a lubricant (e.g. stearic acid, metal salts of stearic acid such as calcium stearate and magnesium stearate; talc; colloidal silica; wax such as bee gum or spermaceti; boric acid; adipic acid; sulfates such as sodium sulfate; glycol; fumaric acid; sodium benzoate; DL leucine; fatty acid sodium salts; lauryl sulfates such as sodium lauryl sulfate or magnesium lauryl sulfate; silicic acids such as silicic anhydride or silicic hydrate; and the above-exemplified starch derivatives), a binder (e.g. hydroxypropylcellulose, hydroxypropyl methylcellulose, polyvinyl pyrrolidine, Macrogol and compounds similar to those described in the above excipient), a disintegrator (e.g. cellulose derivatives such as low degree substituted hydroxypropyl cellulose, carboxymethyl cellulose, carboxymethyl cellulose calcium and internally crosslinked carboxymethyl cellulose sodium, and chemically-modified starch-cellulose such as carboxymethyl starch, carboxymethyl starch sodium and crosslinked polyvinyl pyrrolidone), a stabilizer (e.g. a paraoxybenzoate such as methyl paraben and propyl paraben; an alcohol such as chlorobutanol, benzyl alcohol or phenylethyl alcohol; benzalkonium chloride; phenol and phenol derivatives such as cresol; thimerosal; dehydroacetic acid; and sorbic acid), a corrigent (e.g. an ordinarily-employed sweetener, acidifier or flavor), and diluent; all of the foregoing are included within the term "pharmaceutical carrier".

The dose of a drug of the invention will vary depending upon the condition and age of the patient (i.e., a warm-blooded animal and particularly a human), administration method and the like. Orally, it is administered in an amount of 0.001 mg/kg of body weight (preferable 0.01 mg/kg weight) in a single dose as a lower limit and 500 mg/kg of body weight (preferably 50 mg/kg weight) in a single dose as an upper limit, while intravenously, it is administered in an amount of 0.005 mg/kg weight (preferably, 0.05 mg/kg weight) in a single dose as a lower limit and 50 mg/kg weight (preferably, 5 mg/kg weight) in a single dose as an upper limit. It is desirable to be administered in one to several portions per day depending upon the conditions of the patient.

The present invention will hereinafter be described more specifically by examples, Reference Examples and pharmacological test examples. It should, however, be borne in mind that the present invention is not limited to or by these examples.

EXAMPLE 1

5-{4-[5-(4-Hydroxy-2,3,5-trimethylphenoxy)-3-methyl-3H-imidazo[4,5-b]pyridin-2-ylmethoxy]benzyl}thiazolidine-2,4-dione and the hydrochloride thereof (Exemplified Compound No. 1-651)

(1-1) 5-{4-[5-(4-Acetoxy-2,3,5-trimethylphenoxy)-3-methyl-3H-imidazo[4,5-b]pyridin-2-ylmethoxy]benzyl}-3-triphenylmethylthiazolidine-2,4-dione To a mixture of 16.4 g of 5-(4-acetoxy-2,3,5-trimethylphenoxy)-2-hydroxyrmethyl-3-methyl-3H-imidazo[4,5-b]pyridine, 32.5 g of 5-(4-hydroxybenzyl)-3-triphenylmethylthiazolidine-2,4-dione, 17.5 g of azodicarbonyldipiperidine and 400 ml of toluene, 50 ml of a toluene solution of 17.2 ml of tributyl phosphine were added dropwise at room temperature, followed by ultrasonic irradiation for one hour and stirring at room temperature for 3 hours. The reaction mixture was allowed to stand overnight at room temperature. The insoluble matter was filtered off from the reaction mixture and the filtrate was concentrated by evaporation. The residue was purified by chromatography through a silica gel column (eluting solvent: n-hexane/ethyl acetate=2/1→1/1) and crystallized from a 2/1 n-hexane/ethyl acetate mixed solvent. The resulting crystals were collected by filtration, whereby 31.7 g of the desired compound were obtained.

Melting point: 190–191° C.

(1-2a) 5-{4-[5-(4-Hydroxy-2,3,5-trimethylphenoxy)-3-methyl-3H-imidazo[4,5-b]pyridin-2-ylmethoxy]benzyl}thiazolidine-2,4-dione A mixture of 27.0 g of 5-{4-[5-(4-acetoxy-2,3,5-trimethylphenoxy)-3-methyl-3H-imidazo[4,5-b]pyridin-2-ylmethoxy]benzyl}-3-triphenylmethylthiazolidine-2,4-dione, 150 ml of 6N hydrochloric acid and 200 ml of acetic acid was stirred at 80° C. for 5 hours and then poured into ice water. Sodium carbonate was added to the resulting mixture for neutralization. To the mixture, ethyl acetate was added and the insoluble matter was filtered off. The residue was washed with ethanol, whereby 10.2 g of the title compound were obtained. In addition, from the filtrate, the organic layer was separated and the water layer was extracted with ethyl acetate. The organic layer and extract were combined, followed by washing with saturated saline and drying over anhydrous sodium sulfate. The solvent was then distilled off under reduced pressure. The residue was purified by chromatography through a silica gel column (eluting solvent: n-hexane/ethyl acetate=1/1→1/2→ethyl acetate), followed by crystallization from ethanol. The crystals were collected by filtration, whereby 6.90 g of the title compound were obtained.

Melting point: 215–217° C.

(1-2b) 5-{4-[5-(4-Hydroxy-2,3,5-trimethylphenoxy)-3-methyl-3H-imidazo[4,5-b]pyridin-2-ylmethoxy]benzyl}thiazolidine-2,4-dione hydrochloride A mixture of 10.2 g of 5-{4-[5-(4-hydroxy-2,3,5-trimethylphenoxy)-3-methyl-3H-imidazo[4,5-b]pyridin-2-ylmethoxy]benzyl}thiazolidine-2,4-dione, 100 ml of ethyl acetate and 100 ml of 4N hydrochloric acid/ethyl acetate was stirred at room temperature for 6 hours. The reaction mixture was allowed to stand overnight at room temperature. From the reaction mixture, crystals were collected by filtration, whereby 10.7 g of the title compound were obtained.

Melting point: 148–150° C.

EXAMPLE 2

5-{4-[6-(4-Hydroxy-2,3,5-trimethylphenoxy)-1-methyl-1H-benzimidazol-2-ylmethoxy]benzyl}thiazolidine-2,4-dione and hydrochloride thereof (Exemplified Compound No. 1-650

(2-1) t-Butyl N-{2-[4-(2,4-dioxothiazolidin-5-ylmethyl)phenoxyacetylamino]-5-(4-methoxymethoxy-2,3,5-trimethylphenoxy)phenyl}-N-methylcarbamate 7.34 g of diethyl cyanophosphonate were added to a mixture of 18.7 g of t-butyl N-[2-amino-5-(4-methoxymethoxy-2,3,5-trimethylphenoxy)phenyl]-N-methylcarbamate, 12.6 g of 4-(2,4-dioxothiazolidin-5-ylmethyl)phenoxyacetic acid, 4.55 g of triethylamine and 300 ml of anhydrous tetrahydrofuran. The resulting mixture was stirred at room temperature for 17 hours. The reaction mixture was concentrated by evaporation. Water was then added to the concentrate. After extraction with ethyl acetate, the extract was dried over anhydrous sodium sulfate. The solvent was distilled off under reduced pressure. The residue was purified by chromatography through a silica gel column (eluting solvent: n-hexane/ethyl acetate=1/1), whereby 23.1 g of the desired compound were obtained.

Silica gel thin-layer chromatography (developing solvent: n-hexane/ethyl acetate=2/3): Rf value=0.41.

(2-2a) 5-{4-[6-(4-Hydroxy-2,3,5-trimethylphenoxy)-1-methyl-1H-benzimidazol-2-ylmethoxy]benzyl}thiazolidine-2,4-dione 0.49 g of t-butyl N-{2-[4-(2,4-dioxothiazolidin-5-ylmethyl)phenoxyacetylamino]-5-(4-methoxymethoxy-2,3,5-trimethylphenoxy)phenyl}-N-methylcarbamate were dissolved in 10 ml of 4N hydrochloric acid/dioxane solution. The resulting solution was allowed to stand at room temperature for 2 days. To the reaction mixture, water and an aqueous solution of sodium bicarbonate were added, followed by extraction with ethyl acetate. The extract was dried over anhydrous sodium sulfate. The solvent was then distilled off under reduced pressure. The residue was purified by chromatography through a silica gel column with ethyl acetate as an eluting solvent, whereby 0.27 g of the title compound were obtained.

Softening point: 137–147° C.

Silica gel thin-layer chromatography (developing solvent: n-hexane/ethyl acetate=1/2): Rf value=0.21.

(2-2b) 5-{4-[6-(4-Hydroxy-2,3,5-trimethylphenoxy)-1-methyl-1H-benzimidazol-2-ylmethoxy]benzyl}thiazolidine-2,4-dione hydrochloride 18.0 g of the crude product of 5-{4-[6-(4-hydroxy-2,3,5-trimethylphenoxy)-1-methyl-1H-benzimidazol-2-ylmethoxy]benzyl}thiazolidine-2,4-dione were isolated and purified by chromatography through a silica gel column with ethyl acetate as an eluting solvent, followed by suspending in 100 ml of a 4N hydrochloric acid/ethyl acetate solution. The resulting suspension was stirred overnight at room temperature. From the reaction mixture, crystals were collected by filtration and washed with ethyl acetate, whereby 14.7 g of the title compound were obtained.

Melting point: 160–165° C.

EXAMPLE 3

5-{4-[6-(4-Hydroxyphenoxy)-1-methyl-1H-benzimidazol-2-ylmethoxy]benzyl}thiazolidine-2,4-dione (Exemplified Compound No. 1-70)

(3-1) t-Butyl N-{2-[4-(2,4-dioxothiazolidin-5-ylmethyl)phenoxyacetylamino]-5-(4-hydroxyphenoxy)phenyl}-N-methylcarbamate Using 0.79 g of t-butyl N-[2-amino-5-(4-hydroxyphenoxy)phenyl]-N-methylcarbamate, 0.84 g of 4-(2,4-dioxothiazolidin-5-ylmethyl)phenoxyacetic acid, 0.49 g of diethyl cyanophosphonate, 0.30 g of triethylamine and 60 ml of anhydrous tetrahydrofuran, reaction and purification were carried out in a similar manner to that described in Example (2-1), whereby 1.49 g of the desired compound were obtained.

Silica gel thin-layer chromatography (developing solvent: n-hexane/ethyl acetate=1/2): Rf value=0.35.

(3-2) 5-{4-[6-(4-Hydroxyphenoxy)-1-methyl-1H-benzimidazol-2-ylmethoxy]benzyl}thiazolidine-2,4-dione Using 1.49 g of t-butyl N-{2-[4-(2,4-dioxothiazolidin-5-ylmethyl)phenoxyacetylamino]-5-(4-hydroxyphenoxy)phenyl}-N-methylcarbamate and 10 ml of a 4N hydrochloric acid/dioxane solution, reaction and purification were carried out in a similar manner to that described in Example (2-2a), whereby 0.26 g of the title compound were obtained.

Melting point: 126–131° C.

Silica gel thin-layer chromatography (developing solvent: n-hexane/ethyl acetate=1/3): Rf value=0.13.

EXAMPLE 4

5-{4-[6-(4-Hydroxy-3,5-dimethylphenoxy)-1-methyl-1H-benzimidazol-2-ylmethoxy]benzyl}thiazolidine-2,4-dione and the hydrochloride thereof (Exemplified Compound No. 1-520)

(4-1) t-Butyl N-{2-[4-(2,4-dioxothiazolidin-5-ylmethyl)phenoxyacetylamino]-5-(4-methoxymethoxy-3,5-dimethylphenoxy)phenyl}-N-methylcarbamate Using 0.96 g of t-butyl N-[2-amino-5-(4-methoxymethoxy-3,5-dimethylphenoxy)phenyl]-N-methylcarbamate, 0.84 g of 4-(2,4-dioxothiazolidin-5-ylmethyl)phenoxyacetic acid, 0.49 g of diethyl cyanophosphonate, 0.30 g of triethylamine and 60 ml of anhydrous tetrahydrofuran, reaction and purification were carried out in a similar manner to that described in Example (2-1), whereby 1.44 g of the desired compound were obtained.

Silica gel thin-layer chromatography (developing solvent: n-hexane/ethyl acetate=1/1): Rf value=0.27.

(4-2a) 5-{4-[6-(4-Hydroxy-3,5-dimethylphenoxy)-1-methyl-1H-benzimidazol-2-ylmethoxy]benzyl}thiazolidine-2,4-dione Using 1.44 g of t-butyl N-{2-[4-(2,4-dioxothiazolidin-5-ylmethyl)phenoxyacetylamino]-5-(4-methoxymethoxy-3,5-dimethylphenoxy)phenyl}-N-methylcarbamate and 10 ml of a 4N hydrochloric acid/dioxane solution, reaction and purification were carried out in a similar manner to that described in Example (2-2a), whereby 0.62 g of the title compound were obtained.

Melting point: 147–157° C.

Silica gel thin-layer chromatography (developing solvent: n-hexane/ethyl acetate=1/2): Rf value=0.21.

(4-2b) 5-{4-[6-(4-Hydroxy-3,5-dimethylphenoxy)-1-methyl-1H-benzimidazol-2-ylmethoxy]benzyl}thiazolidine-2,4-dione hydrochloride Using 3.11 g of 5-{4-[6-(4-hydroxy-3,5-dimethylphenoxy)-1-methyl-1H-benzimidazol-2-ylmethoxy]benzyl}thiazolidine-2,4-dione and 50 ml of a 4N hydrochloric acid/ethyl acetate solution, reaction and purification were carried out in a similar manner to that described in Example (2-2b), whereby 3.18 g of the title compound were obtained.

Melting point: 206–209° C.

EXAMPLE 5

5-{4-[6-(2-Chloro-4-hydroxy-3,5-dimethylphenoxy)-1-methyl-1H-benzimidazol-2-ylmethoxy]benzyl}thiazolidine-2,4-dione and hydrochloride thereof (Exemplified Compound No. 1-368)

(5a) 5-{4-[6-(2-Chloro-4-hydroxy-3,5-dimethylphenoxy)-1-methyl-1H-benzimidazol-2-ylmethoxy]benzyl}thiazolidine-2,4-dione A mixture of 9.19 g of t-butyl N-[5-(2-chloro-4-methoxymethoxy-3,5-dimethylphenoxy)-2-nitrophenyl]-N-methylcarbamate, 2.5 g of 10% palladium on carbon and 400 ml of methanol was stirred vigorously at room temperature for 90 minutes under a hydrogen atmosphere. The catalyst was then filtered off and the solvent of the filtrate was distilled off under reduced pressure. The residue was dissolved in 250 ml of anhydrous tetrahydrofuran. To the resulting solution, 15.8 g of 4-(2,4-dioxothiazolidin-5-ylmethyl)phenoxyacetic acid, 9.18 g of diethyl cyanophosphonate and 5.69 g of triethylamine were added. The resulting mixture was stirred at room temperature for 64 hours. The reaction mixture was concentrated by evaporation. Water was added to the concentrate, followed by extraction with ethyl acetate. The extract was dried over anhydrous sodium sulfate and the solvent was distilled off under reduced pressure. The residue was purified by chromatography through a silica gel column (eluting solvent: n-hexane/ethyl acetate=1/1) and then dissolved in 200 ml of a 2N hydrochloric acid/dioxane solution. The resulting solution was allowed to stand at room temperature for 19 hours. The reaction mixture was concentrated by evaporation. The concentrate was neutralized with an aqueous sodium bicarbonate solution, followed by extraction with a mixed solvent of ethyl acetate and tetrahydrofuran. The extract solution was dried over anhydrous sodium sulfate. The solvent was distilled off under reduced pressure. The residue was purified by chromatography through a silica gel column (eluting solvent: n-hexane/ethyl acetate=1/2) and reversed-phase preparative high-performance liquid chromatography (developing solvent: acetonitrile/water=7/3), whereby 2.56 g of the title compound were obtained.

Melting point: 240–243° C.

Silica gel thin-layer chromatography (developing solvent: n-hexane/ethyl acetate=1/2): Rf value=0.21.

(5b) 5-{4-[6-(2-Chloro-4-hydroxy-3,5-dimethylphenoxy)-1-methyl-1H-benzimidazol-2-ylmethoxy]benzyl}thiazolidine-2,4-dione hydrochloride Using 2.54 g of 5-{4-[6-(2-chloro-4-hydroxy-3,5-dimethylphenoxy)-1-methyl-1H-benzimidazol-2-ylmethoxy]benzyl}thiazolidine-2,4-dione and 50 ml of a 4N hydrochloric acid/ethyl acetate solution, reaction and purification were carried out in a similar manner to that described in Example (2-2b), whereby 2.67 g of the title compound were obtained.

Melting point: 174–176° C.

EXAMPLE 6

5-{4-[6-(Pyridin-2-yloxy)-1-methyl-1H-benzimidazol-2-ylmethoxy]benzyl}thiazolidine-2,4-dione (Exemplified Compound No. 1-821)

(6-1) t-Butyl N-{2-[4-(2,4-dioxothiazolidin-5-ylmethyl)phenoxyacetylamino]-5-(pyridin-2-yloxy)phenyl}-N-methylcarbamate A mixture of 0.34 g of t-butyl N-[2-nitro-5-(pyridin-2-yloxy)phenyl]-N-methylcarbamate, 50 mg of 10% palladium on carbon and 10 ml of methanol was stirred vigorously at room temperature for 90 minutes under a hydrogen atmosphere. From the reaction mixture, the catalyst was filtered off and the solvent was distilled off under reduced pressure. The residue was dissolved in 10 ml of anhydrous tetrahydrofuran. To the resulting solution, 0.34 g of 4-(2,4-dioxothiazolidin-5-ylmethyl)phenoxyacetic acid, 0.20 g of diethyl cyanophosphonate and 0.12 g of triethylamine were added and the resulting mixture was stirred at room temperature for 18 hours. The reaction mixture was concentrated by evaporation. Water was added to the concentrate, followed by extraction with ethyl acetate. The extract was dried over anhydrous sodium sulfate. The solvent was distilled off under reduced pressure. The residue was purified by chromatography through a silica gel column (eluting solvent: n-hexane/ethyl acetate=1/2), whereby 0.37 g of the desired compound were obtained.

Silica gel thin-layer chromatography (developing solvent: n-hexane/ethyl acetate=1/2): Rf value=0.36.

(6-2) 5-{4-[6-(Pyridin-2-yloxy)-1-methyl-1H-benzimidazol-2-ylmethoxy]benzyl}thiazolidine-2,4-dione Using 0.37 g of t-butyl N-{2-[4-(2,4-dioxothiazolidin-5-ylmethyl)phenoxyacetylamino]-5-(pyridin-2-yloxy)phenyl}-N-methylcarbamate and 20 ml of a 4N hydrochloric acid/dioxane solution, reaction and purification were carried out in a similar manner to that described in Example (2-2a), whereby 0.20 g of the title compound were obtained.

Melting point: 200–210° C.

Silica gel thin-layer chromatography (developing solvent: ethyl acetate): Rf value=0.28.

EXAMPLE 7

5-{4-[6-(3,5-Di-t-butyl-4-hydroxyphenylthio)-1-methyl-1H-benzimidazol-2-ylmethoxy]benzyl}thiazolidine-2,4-dione 1/2 hydrochloride and hydrochloride (Exemplified Compound No. 1-595)

(7-1) t-Butyl N-{2-[4-(2,4-dioxothiazolidin-5-ylmethyl)phenoxyacetylamino]-5-(3,5-di-t-butyl-4-hydroxyphenylthio)phenyl}-N-methylcarbamate A mixture of 359 mg of t-butyl N-[2-nitro-5-(3,5-di-t-butyl-4-hydroxyphenylthio)phenyl]-N-methylcarbamate, 360 mg of 10% palladium on carbon and 50 ml of methanol was vigorously stirred at room temperature for 9 hours under a hydrogen atmosphere. From the reaction mixture, the catalyst was filtered off and the solvent was distilled off under reduced pressure. The residue was dissolved in 20 ml of anhydrous tetrahydrofuran. 248 mg of 4-(2,4-dioxothiazolidin-5-ylmethyl)phenoxyacetic acid, 144 mg of diethyl cyanophosphonate and 89 mg of triethylamine were added to the resulting solution. The resulting mixture was allowed to stand at room temperature for 15 hours. The reaction was then concentrated by evaporation. Water was added to the concentrate, followed by extraction with ethyl acetate. The extract was dried over anhydrous sodium sulfate. The solvent was distilled off under reduced pressure. The residue was purified by chromatography on a silica gel column (eluting solvent: n-hexane/ethyl acetate=3/2), whereby 275 mg of the desired compound were obtained.

Silica gel thin-layer chromatography (developing solvent: n-hexane/ethyl acetate=1/1): Rf value=0.44.

(7-2a) 5-{4-[6-(3,5-Di-t-butyl-4-hydroxyphenylthio)-1-methyl-1H-benzimidazol-2-ylmethoxy]benzyl}thiazolidine-2,4-dione 1/2 hydrochloride 259 mg of t-butyl N-{2-[4-(2,4-dioxothiazolidin-5-ylmethyl)phenoxyacetylamino]-5-(3,5-di-t-butyl-4-hydroxyphenylthio)phenyl}-N-methylcarbamate were dissolved in 10 ml of a 4N hydrochloric acid/dioxane solution. The resulting solution was allowed to stand at room temperature for 18 hours. The reaction mixture was evaporated to dryness under reduced pressure. After the addition of ether, the insoluble matter was collected by filtration and washed with ether. The resulting solid substance was purified by reversed-phase thin-layer chromatography (developing solvent: acetonitrile/water=5/1), whereby 115 mg of the title compound were obtained.

Melting point: 120–123° C.

(7-2b) 5-{4-[6-(3,5-Di-t-butyl-4-hydroxyphenylthio)-1-methyl-1H-benzimidazol-2-ylmethoxy]benzyl}thiazolidine-2,4-dione hydrochloride Using 2.29 g of 5-{4-[6-(3,5-di-t-butyl-4-hydroxyphenylthio)-1-methyl-1H-benzimidazol-2-ylmethoxy]benzyl}thiazolidine-2,4-dione and a 4N hydrochloric acid/ethyl acetate solution, reaction and purification were carried out in a similar manner to that described in Example (2-2b), whereby 1.25 g of the title compound were obtained.

Melting point: 144–146° C.

EXAMPLE 8

5-{4-[6-(4-Amino-3,5-dimethylphenoxy)-1-methyl-1H-benzimidazol-2-ylmethoxy]benzyl}thiazolidine-2,4-dione and dihydrochloride thereof (Exemplified Compound No. 1-739)

(8-1) t-Butyl N-{2-[4-(2,4-Dioxothiazolidin-5-ylmethyl)phenoxyacetylamino]-5-(4-t-butoxycarbonylamino-3,5-dimethylphenoxy)phenyl}-N-methylcarbamate Using 1.56 g of t-butyl N-[2-amino-5-(4-t-butoxycarbonylamino-3,5-dimethylphenoxy)phenyl]-N-methylcarbamate, 1.05 g of 4-(2,4-dioxothiazolidin-5-ylmethyl)phenoxyacetic acid, 0.61 g of diethyl cyanophosphonate, 0.38 g of triethylamine and 30 ml of anhydrous tetrahydrofuran, reaction and purification were carried out in a similar manner to that described in Example (2-1), whereby 1.89 g of the desired compound were obtained.

Silica gel thin-layer chromatography (developing solvent: n-hexane/ethyl acetate=3/2): Rf value=0.19.

(8-2a) 5-{4-[6-(4-Amino-3,5-dimethylphenoxy)-1-methyl-1H-benzimidazol-2-ylmethoxy]benzyl}thiazolidine-2,4-dione Using 1.88 g of t-butyl N-{2-[4-(2,4-dioxothiazolidin-5-ylmethyl]phenoxyacetylamino)-5-(4-t-butoxycarbonylamino-3,5-dimethylphenoxy)phenyl}-N-methylcarbamate and 20 ml of a 4N hydrochloric acid/dioxane solution, reaction and purification were carried out in a similar manner to that described in Example (2-2a), whereby 0.26 g of the title compound were obtained.

Melting point: 209–211° C.

Silica gel thin-layer chromatography (developing solvent: n-hexane/ethyl acetate=1/2): Rf value=0.29.

(8-2b) 5-{4-[6-(4-Amino-3,5-dimethylphenoxy)-1-methyl-1H-benzimidazol-2-ylmethoxy]benzyl}thiazolidine-2,4-dione dihydrochloride Using 0.25 g of 5-{4-[6-(4-amino-3,5-dimethylphenoxy)-1-methyl-1H-benzimidazol-2-ylmethoxy]benzyl}thiazolidine-2,4-dione and 50 ml of a 4N hydrochloric acid/ethyl acetate solution, reaction and purification were carried out in a similar manner to Example (2-2b), whereby 0.25 g of the title compound were obtained.

Melting point: 165–175° C.

EXAMPLE 9

5-{4-[6-(4-Acetylamino-3,5-dimethylphenoxy)-1-methyl-1H-benzimidazol-2-ylmethoxy]benzyl}thiazolidine-2,4-dione hydrochloride (Exemplified Compound No. 1-808)

A mixture of 155 mg of 5-{4-[6-(4-amino-3,5-dimethylphenoxy)-1-methyl-1H-benzimidazol-2-ylmethoxy]benzyl}thiazolidine-2,4-dione dihydrochloride, 36 mg of acetic anhydride, 107 mg of pyridine, 7.3 mg of 4-(N,N-dimethylamino)pyridine and 5 ml of anhydrous tetrahydrofuran was heated under reflux for 2 hours. The reaction mixture was concentrated by evaporation. Water was added to the concentrate, followed by extraction with ethyl acetate. The extract was dried over anhydrous sodium sulfate and the solvent was distilled off under reduced pressure. To the residue, 10 ml of 4N hydrochloric acid/ethyl acetate were added, followed by stirring at room temperature for 21 hours. The insoluble product was collected by filtration, followed by washing with ether, whereby 97 mg of the title compound were obtained.

Softening point: 160–165° C.

EXAMPLE 10

5-{4-(1-Methyl-6-[2-(morpholin-4-yl)phenoxy]-1H-benzimidazol-2-ylmethoxy)benzyl}thiazolidine-2,4-dione and the dihydrochloride thereof (Exemplified Compound No. 1-284)

(10-1) t-Butyl N-{2-[4-(2,4-dioxothiazolidin-5-ylmethyl)phenoxyacetylamino]-5-[2-(morpholin-4-yl)phenoxy]phenyl}-N-methylcarbamate Using 1.18 g of t-butyl N-{2-amino-5-[2-(morpholin-4-yl)phenoxy]-phenyl}-N-methylcarbamate, 0.92 g of 4-(2,4-dioxothiazolidin-5-ylmethyl)phenoxyacetic acid, 0.53 g of diethyl cyanophosphonate, 0.33 g of triethylamine and 30 ml of anhydrous tetrahydrofuran, reaction and purification were carried out in a similar manner to Example (2-1), whereby 1.47 g of the desired compound were obtained.

Silica gel thin-layer chromatography (developing solvent: n-hexane/ethyl acetate=1/1): Rf value=0.30.

(10-2a) 5-{4-(1-Methyl-6-[2-(morpholin-4-yl)phenoxy]-1H-benzimidazol-2-ylmethoxy)benzyl}thiazolidine-2,4-dione Using 1.45 g of t-butyl N-{2-[4-(2,4-dioxothiazolidin-5-ylmethyl)phenoxyacetylamino]-5-[2-(morpholin-4-yl)phenoxy]phenyl}-N-methylcarbamate and 20 ml of 4N hydrochloric acid/dioxane, reaction and purification were carried out in a similar manner to Example 2a, whereby 0.94 g of the title compound were obtained.

Silica gel thin-layer chromatography (developing solvent: n-hexane/ethyl acetate=1/2): Rf value=0.33.

(10-2b) 5-{4-(1-Methyl-6-[2-(morpholin-4-yl)phenoxy]-1H-benzimidazol-2-ylmethoxy)benzyl}thiazolidine-2,4-dione dihydrochloride 0.64 g of 5-{4-(1-methyl-6-[2-(morpholin-4-yl)phenoxy]-1H-benzimidazol-2-ylmethoxy)benzyl}thiazolidine-2,4-dione were dissolved in a mixture of 30 ml of concentrated hydrochloric acid and 30 ml of 1,4-dioxane. The resulting solution was stirred at room temperature for 90 minutes. The reaction mixture was evaporated to dryness, followed by the addition of ether. The insoluble product was collected by filtration and washed with ether, whereby 0.71 g of the title compound were obtained.

Softening point: 120–130° C.

EXAMPLE 11

5-{4-(1-Methyl-6-[3-(morpholin-4-yl)phenoxy]-1H-benzimidazol-2-ylmethoxy)benzyl}thiazolidine-2,4-dione dihydrochloride (Exemplified Compound No. 1-292)

(11-1) t-Butyl N-{2-[4-(2,4-dioxothiazolidin-5-ylmethyl)phenoxyacetylamino]-5-[3-(morpholin-4-yl)phenoxy]phenyl}-N-methylcarbamate Using 1.18 g of t-butyl N-{2-amino-5-[3-(morpholin-4-yl)phenoxy]phenyl}-N-methylcarbamate, 0.92 g of 4-(2,4-dioxothiazolidin-5-ylmethyl)phenoxyacetic acid, 0.53 g of diethyl cyanophosphonate, 0.33 g of triethylamine and 30 ml of anhydrous tetrahydrofuran, reaction and purification were carried out in a similar manner to Example (2-1), whereby 1.48 g of the desired compound were obtained.

Silica gel thin-layer chromatography (developing solvent: n-hexane/ethyl acetate=1/1): Rf value=0.26.

(11-2) 5-{4-(1-Methyl-6-[3-(morpholin-4-yl)phenoxy]-1H-benzimidazol-2-ylmethoxy)benzyl}thiazolidine-2,4-dione dihydrochloride A mixture of t-butyl N-{2-[4-(2,4-dioxothiazolidin-5-ylmethyl)phenoxyacetylamino]-5-[3-(morpholin-4-yl)phenoxy]phenyl)-N-methylcarbamate and 20 ml of 4N hydrochloric acid/dioxane was stirred at room temperature for 3 hours. The reaction mixture was evaporated to dryness under reduced pressure, followed by the addition of ether. The insoluble product was collected by filtration and washed with ether, whereby 1.27 g of the title compound were obtained.

Softening point: 150–160° C.

EXAMPLE 12

5-{4-(1-Methyl-6-[2-(piperidin-1-yl)phenoxy]-1H-benzimidazole-2-ylmethoxy)benzyl}thiazolidine-2,4-dione dihydrochloride (Exemplified Compound No. 1-241)

(12-1) t-Butyl N-{2-[4-(2,4-dioxothiazolidin-5-ylmethyl)phenoxyacetylamino]-5-[2-(piperidin-1-yl)phenoxy]phenyl}-N-methylcarbamate In a similar manner to that described in Example (2-1), a reaction was carried out using t-butyl N-{2-amino-5-[2-

(piperidin-1-yl)phenoxy]phenyl}-N-methyl-carbamate (1.19 g), 4-(2,4-dioxothiazolidin-5-ylmethyl)phenoxyacetic acid (0.93 g), diethyl cyanophosphonate (0.54 g), triethylamine (0.33 g) and anhydrous tetrahydrofuran (20 ml) and the reaction mixture was purified to give the desired product (1.80 g).

Thin layer chromatography on a silica gel plate using n-hexane/ethyl acetate=1/1: Rf=0.39

(12-2) 5-{4-(1-Methyl-6-[2-(piperidin-1-yl)phenoxy]-1H-benzimidazole-2-ylmethoxy)benzyl}thiazolidine-2,4-dione dihydrochloride A mixture of t-Butyl N-{2-[4-(2,4-dioxothiazolidine 5-ylmethyl)phenoxyacetylamino]-5-[2-(piperidin-1-yl) phenoxy]phenyl}-N-methylcarbamate (1.80 g) and 4N hydrogen chloride/dioxane (20 ml) was stirred at ambient temperature for 19 hours. The solvent of the reaction mixture was evaporated to dryness. Ethyl acetate was added to the residue and insoluble product was collected by filtration and subjected to reversed-phase high performance liquid chromatography using acetonitrile/water=1/1 as the eluant and then treated with 4N hydrogen chloride/ethyl acetate to give the title compound (0.47 g).

mp 151–154° C.

EXAMPLE 13

5-{4-[1-Methyl-6-(pyridin-2-ylthio)-1H-benzimidazole-2-ylmethoxy]benzyl}thiazolidine-2, 4-dione and dihydrochloride thereof (Exemplified Compound No. 1-823)

(13-1) t-Butyl N-{2-[4-(2,4-dioxothiazolidin-5-ylmethyl) phenoxyacetylamino]-5-(pyridin-2-ylthio)phenyl}-N-methylcarbamate In a similar manner to that described in Example (2-1), a reaction was carried out using t-butyl N-[2-amino-5-(pyridine-2-ylthio)phenyl]-N-methylcarbamate (0.78 g), 4-(2,4-dioxothiazolidin-5-ylmethyl)phenoxyacetic acid (1.06 g), diethyl cyanophosphonate (0.61 g), triethylamine (0.38 g) and anhydrous tetrahydrofuran (20 ml) and the reaction mixture was purified to give the desired product (0.68 g).

Thin layer chromatography on a silica gel plate using n-hexane/ethyl acetate=1/2: Rf=0.51

(13-2a) 5-{4-[1-Methyl-6-(pyridin-2-ylthio)-1H-benzimidazole-2-ylmethoxy]benzyl}thiazolidine-2,4-dione In a similar manner to that described in Example (2-2a), a reaction was carried out using t-butyl N-{2-[4-(2,4-dioxothiazolidin-5-ylmethyl)phenoxyacetylamino]-5-(pyridin-2-ylthio)phenyl}-N-methylcarbamate (0.63 g) and 4N hydrogen chloride/dioxane (20 ml) and the reaction mixture was purified to give the title compound (0.20 g).

Thin layer chromatography on a silica gel plate using ethyl acetate: Rf=0.26

(13-2b) 5-{4-[1-Methyl-6-(pyridin-2-ylthio)-1H-benzimidazole-2-ylmethoxy]benzyl}thiazolidine-2,4-dione dihydrochloride In a similar manner to that described in Example (2-2b), a reaction was carried out using 5-{4-[1-methyl-6-(pyridine-2-ylthio)-1H-benzimidazole-2-ylmethoxy] benzyl}thiazolidine-2,4-dione (0.20 g) and 4N hydrogen chloride/ethyl acetate (50 ml) and the reaction mixture was purified to give the title compound (0.21 g).

mp 139–147° C.

EXAMPLE 14

5-{4-(1-Methyl-6-[2-(pyrrolidin-1-yl)phenoxy]-1H-benzimidazole-2-ylmethoxy)benzyl}thiazolidine-2, 4-dione (Exemplified Compound No. 1-199)

(14-1) t-Butyl N-{2-[4-(2,4-dioxothiazolidin-5-ylmethyl) phenoxyacetylamino]-5-[2-(pyrrolidin-1-yl)phenoxy] phenyl}-N-methylcarbamate In a similar manner to that described in Example (2-1), a reaction was carried out using t-butyl N-{2-amino-5-[2-(pyrrolidin-1-yl)phenoxy]phenyl}-N-methyl-carbamate (0.77 g), 4-(2,4-dioxothiazolidin-5-ylmethyl)phenoxyacetic acid (0.90 g), diethyl cyanophosphonate (0.52 g), triethylamine (0.32 g) and anhydrous tetrahydrofuran (30 ml) and the reaction mixture was purified to give the desired product (1.26 g).

Thin layer chromatography on a silica gel plate using n-hexane/ethyl acetate=1/1: Rf=0.40

(14-2) 5-{4-(1-Methyl-6-[2-(pyrrolidin-1-yl)phenoxy]-1H-benzimidazole-2-ylmethoxy)benzyl}thiazolidine-2,4-dione In a similar manner to that described in Example (2-2a), a reaction was carried out using t-butyl N-{2-[4-(2,4-dioxothiazolidin-5-ylmethyl)phenoxyacetylamino]-5-[2-(pyrrolidin-1-yl)phenoxy]phenyl}-N-methylcarbamate (1.25 g) and 4N hydrogen chloride/dioxane (25 ml) and the reaction mixture was purified to give the title compound (0.94 g).

Thin layer chromatography on a silica gel plate using n-hexane/ethyl acetate=1/2: Rf=0.27

EXAMPLE 15

5-{4-[6-(2-Hydroxyphenoxy)-1-methyl-1H-benzimidazole-2-ylmethoxy]benzyl}thiazolidine-2, 4-dione hydrochloride (Exemplified Compound No. 1-11)

(15-1) t-Butyl N-{2-[4-(2,4-dioxothiazolidin-5-ylmethyl) phenoxyacetylamino]-5-(2-hydroxyphenoxy)phenyl}-N-methylcarbamate In a similar manner to that described in Example (2-1), a reaction was carried out using t-butyl N-[2-amino-5-(2-hydroxyphenoxy)phenyl]-N-methylcarbamate (0.99 g), 4-(2,4-dioxothiazolidin-5-ylmethyl)phenoxyacetic acid (0.93 g), diethyl cyanophosphonate (0.54 g), triethylamine (0.33 g) and anhydrous tetrahydrofuran (20 ml) and the reaction mixture was purified to give the desired product (1.18 g).

Thin layer chromatography on a silica gel plate using n-hexane/ethyl acetate=2/3: Rf=0.47

(15-1) 5-{4-[6-(2-hydroxyphenoxy)-1-methyl-1H-benzimidazole-2-ylmethoxy]benzyl}thiazolidine-2,4-dione hydrochloride In a similar manner to that described in Example (2-2a), a reaction was carried out using t-butyl N-{2-[4-(2,4-dioxothiazolidin-5-ylmethyl)phenoxyacetylamino]-5-(2-hydroxyphenoxy)phenyl}-N-methylcarbamate (1.16 g) and 4N hydrogen chloride/dioxane (20 ml) and the reaction mixture was purified and then in a similar manner to that described in Example (2-2b) the product was reacted with 4N hydrogen chloride/ethyl acetate (20 ml) and purified to give the title compound (0.79 g).

mp 155–165° C.

EXAMPLE 16

5-{4-(6-[4-(1-Adamantyl)phenoxy]-1-methyl-1H-benzimidazole-2-ylmethoxy)benzyl}thiazolidine-2,4-dione hydrochloride (Exemplified Compound No. 1-1182)

(16-1) t-Butyl N-{2-[4-(2,4-dioxothiazolidin-5-ylmethyl)phenoxyacetylamino]-5-[4-(1-adamantyl)phenoxy]phenyl}-N-methylcarbamate In a similar manner to that described in Example (2-1), a reaction was carried out using t-butyl N-{2-amino-5-[4-(1-adamantyl)phenoxy]phenyl}-N-methylcarbamate (1.34 g), 4-(2,4-dioxothiazolidin-5-ylmethyl)phenoxyacetic acid (0.93 g), diethyl cyanophosphonate (0.54 g), triethylamine (0.33 g) and anhydrous tetrahydrofuran (20 ml) and the reaction mixture was purified to give the desired product (1.83 g).

Thin layer chromatography on a silica gel plate using n-hexane/ethyl acetate=1/1: Rf=0.29

(16-2) 5-{4-(6-[4-(1-Adamantyl)phenoxy]-1-methyl-1H-benzimidazole-2-ylmethoxy)benzyl}thiazolidine-2,4-dione hydrochloride A mixture of t-butyl N-{2-[4-(2,4-dioxothiazolidin-5-ylmethyl)phenoxyacetylamino]-5-[4-(1-adamantyl)phenoxy]phenyl}-N-methylcarbamate (1.82 g) and 4N hydrogen chloride/dioxane (20 ml) was stirred at ambient temperature for 29 hours. The solvent of the reaction mixture was evaporated to dryness and to the residue was added ether and the insoluble product was filtered and washed with ether to give the title compound (1.35 g).

mp 160–165° C.

EXAMPLE 17

5-{4-[6-(3-Dimethylaminophenoxy)-1-methyl-1H-benzimidazole-2-ylmethoxy]benzyl)}thiazolidine-2,4-dione (Exemplified Compound No. 1-153)

(17-1) t-Butyl N-{5-(3-dimethylaminophenoxy)-2-[4-(2,4-dioxothiazolidin-5-ylmethyl)phenoxyacetylamino]phenyl}-N-methylcarbamate In a similar manner to that described in Example (2-1), a reaction was carried out using t-butyl N-[2-amino-5-(3-dimethylaminophenoxy)phenyl]-N-methylcarbamate (1.00 g), 4-(2,4-dioxothiazolidin-5-ylmethyl)phenoxyacetic acid (1.57 g), diethyl cyanophosphonate (0.91 g), triethylamine (0.57 g) and anhydrous tetrahydrofuran (40 ml) and the reaction mixture was purified to give the desired product (1.69 g).

Thin layer chromatography on a silica gel plate using n-hexane/ethyl acetate=1/1: Rf=0.26

(17-2) 5-{4-[6-(3-Dimethylaminophenoxy)-1-methyl-1H-benzimidazole-2-ylmethoxy]benzyl}thiazolidine-2,4-dione In a similar manner to that described in Example (2-2a), a reaction was carried out using t-butyl N-{5-(3-dimethylaminophenoxy)-2-[4-(2,4-dioxothiazolidin-5-ylmethyl)phenoxyacetylamino]phenyl}-N-methylcarbamate (1.68 g) and 4N hydrogen chloride/dioxane (30 ml) and the reaction mixture was purified to give the title compound (0.57 g).

mp 180–186° C.

EXAMPLE 18

5-{4-[1-Methyl-6-(pyridin-3-yloxy)-1H-benzimidazole-2-ylmethoxy]benzyl}thiazolidine-2,4-dione dihydrochloride (Exemplified Compound No. 1-938)

(18-1) t-Butyl N-{2-[4-(2,4-dioxothiazolidin-5-ylmethyl)phenoxyacetylamino]-5-(pyridin-3-yloxy)phenyl}-N-methylcarbamate In a similar manner to that described in Example (2-1), a reaction was carried out using t-butyl N-[2-amino-5-(pyridin-3-yloxy)phenyl]-N-methylcarbamate (0.63 g), 4-(2,4-dioxothiazolidin-5-ylmethyl)phenoxyacetic acid (0.62 g), diethyl cyanophsphonate (0.36 g), triethylamine (0.22 g) and anhydrous tetrahydrofuran (15 ml) and the reaction mixture was purified to give the desired product (0.88 g).

Thin layer chromatography on a silica gel plate using n-hexane/ethyl acetate=1/2: Rf=0.38

(18-2) 5-{4-[1-Methyl-6-(pyridin-3-yloxy)-1H-benzimidazole-2-ylmethoxy]benzyl}thiazolidine-2,4-dione dihydrochloride A mixture of t-butyl N-{2-[4-(2,4-dioxothiazolidine-5-ylmethyl)phenoxyacetylamino]-5-(pyridin-3-yloxy)phenyl}-N-methylcarbamate (0.87 g) and 4N hydrogen chloride/dioxane (15 ml) was stirred at ambient temperature for 4.5 hours and allowed to stand for 9 days at ambient temperature. The insoluble product was collected by filtration and washed with ethyl acetate to give the title compound (0.77 g).

mp 146–156° C.

EXAMPLE 19

5-{4-(6-[4-(Imidazole-1-yl)phenoxy]-1-methyl-1H-benzimidazole-2-ylmethoxy)benzyl}thiazolidine-2,4-dione dihydrochloride (Exemplified Compound No. 1-1126)

(19-1) t-Butyl N-{2-[4-(2,4-dioxothiazolidin-5-ylmethyl)phenoxyacetylamino]-5-[4-(imidazole-1-yl)phenoxy]phenyl}-N-methylcarbamate In a similar manner to that described in Example (2-1), a reaction was carried out using t-butyl N-{2-amino-5-[4-(imidazole-1-yl)phenoxy]phenyl}-N-methylcarbamate (1.14 g), 4-(2,4-dioxothiazolidin-5-ylmethyl)phenoxyacetic acid (0.93 g), diethyl cyanophosphonate (0.54 g), triethylamine (0.33 g) and anhydrous tetrahydrofuran (30 ml) and the reaction mixture was purified to give the desired product (1.75 g).

Thin layer chromatography on a silica gel plate using ethyl acetate/methanol=10/1: Rf=0.51

(19-2) 5-{4-(6-[4-(Imidazole-1-yl)phenoxy]-1-methyl-1H-benzimidazole-2-ylmethoxy)benzyl}thiazolidine-2,4-dione dihydrochloride A mixture of t-butyl N-{2-[4-(2,4-dioxothiazolidin-5-ylmethyl)phenoxyacetylamino]-5-[4-(imidazole-1-yl)phenoxy]phenyl}-N-methylcarbamate (1.75 g) and 4N hydrogen chloride/dioxane (20 ml) was stirred at ambient temperature for 19 hours. The solvent of the reaction mixture was evaporated to dryness. To the residue was added ethyl acetate and insoluble product was collected by filtration. The product was purified by reversed-phase high performance liquid chromatography using acetonitrile/ water=7/13 as the eluant and was treated with 4N hydrogen chloride/acetate to give the title compound (0.20 g).

mp 183–186° C.

EXAMPLE 20

5-{4-[1-Methyl-6-(2-phenylphenoxy)-1H-benzimidazole-2-ylmethoxy]benzyl}thiazolidine-2, 4-dione hydrochloride (Exemplified Compound No. 1-1327)

(20-1) t-Butyl N-{2-[4-(2,4-dioxothiazolidin-5-ylmethyl) phenoxyacetylamino]-5-(2-phenylphenoxy)phenyl}-N-methylcarbamate In a similar manner to that described in Example (2-1), a reaction was carried out using t-butyl N-[2-amino-5-(2-phenylphenoxy)phenyl]-N-methylcarbamate (1.60 g), 4-(2, 4-dioxothiazolidin-5-ylmethyl)phenoxyacetic acid (1.26 g), diethyl cyanophosphonate (0.73 g), triethylamine (0.45 g) and anhydrous tetrahydrofuran (20 ml) and the reaction mixture was purified to give the desired product (2.33 g).

Thin layer chromatography on a silica gel plate using n-hexane/ethyl acetate=3/2: Rf=0.25

(20-2) 5-{4-[1-Methyl-6-(2-phenylphenoxy)-1H-benzimidazole-2-ylmethoxy]benzyl}thiazolidine-2,4-dione hydrochloride A mixture of t-butyl N-{2-[4-(2,4-dioxothiazolidin-5-ylmethyl)phenoxyacetylamino]-5-(2-phenylphenoxy) phenyl}-N-methylcarbamate (2.33 g) and 4N hydrogen chloride/dioxane (20 ml) was stirred at ambient temperature for 20 hours. The solvent of the reaction mixture was evaporated to dryness. To the residue was added ethyl acetate and insoluble product was collected by filtration and washed with ethyl acetate to give the title compound (1.87 g).

mp 142–152° C.

EXAMPLE 21

5-{4-[6-(4-Hydroxy-2,3-dimethylphenoxy)-1-methyl-1H-benzimidazole-2-ylmethoxy] benzyl}thiazolidine-2,4-dione hydrochloride (Exemplified Compound No. 1-506)

(21-1)-t-Butyl N-{2-[4-(2,4-dioxothiazolidin-5-ylmethyl) phenoxyacetylamino]-5-(4-hydroxy-2,3-dimethylphenoxy) phenyl}-N-methylcarbamate In a similar manner to that described in Example (2-1), a reaction was carried out using t-butyl N-[2-amino-5-(4-hydroxy-2,3-dimethylphenoxy)phenyl]-N-methyl-carbamate (1.60 g), 4-(2,4-dioxothiazolidin-5-ylmethyl) phenoxyacetic acid (1.38 g), diethyl cyanophosphonate (0.80 g), triethylamine (0.50 g) and anhydrous tetrahydrofuran (20 ml) and the reaction mixture was purified to give the desired product (2.35 g).

Thin layer chromatography on a silica gel plate using n-hexane/ethyl acetate=1/2: Rf=0.54

(21-2) 5-{4-[6-(4-Hydroxy-2,3-dimethylphenoxy)-1-methyl-1H-benzimidazole-2-ylmethoxy] benzyl}thiazolidine-2,4-dione hydrochloride A mixture of t-butyl N-{2-[4-(2,4-dioxothiazolidin-5-ylmethyl)phenoxyacetylamino]-5-(4-hydroxy-2,3-dimethylphenoxy)phenyl}-N-methylcarbamate (2.35 g) and 4N hydrogen chloride/dioxane (20 ml) was stirred at ambient temperature for 44 hours. The solvent of the reaction mixture was evaporated to dryness. To the residue was added ethyl acetate and insoluble product was collected by filtration and washed with ethyl acetate to give the title compound (1.82 g).

mp 168–170° C.

EXAMPLE 22

5-{4-[1-Methyl-6-(4-phenoxyphenoxy)-1H-benzimidazole-2-ylmethoxy]benzyl}thiazolidine-2, 4-dione hydrochloride (Exemplified Compound No. 1-193)

(22-1) t-Butyl N-{2-[4-(2,4-dioxothiazolidin-5-ylmethyl) phenoxyacetylamino]-5-(4-phenoxyphenoxy)phenyl}-N-methylcarbamate In a similar manner to that described in Example (2-1), a reaction was carried out using t-butyl N-[2-amino-5-(4-phenoxyphenoxy)phenyl]-N-methylcarbamate (1.66 g), 4-(2,4-dioxothiazolidin-5-ylmethyl)phenoxyacetic acid (1.26 g), diethyl cyanophosphonate (0.73 g), triethylamine (0.45 g) and anhydrous tetrahydrofuran (20 ml) and the reaction mixture was purified to give the desired product (1.99 g).

Thin layer chromatography on a silica gel plate using n-hexane/ethyl acetate=1/2: Rf=0.62

(22-2) 5-{4-[1-Methyl-6-(4-phenoxyphenoxy)-1H-benzimidazole-2-ylmethoxy]benzyl}thiazolidine-2,4-dione hydrochloride A mixture of t-butyl N-{2-[4-(2,4-dioxothiazolidine-5-ylmethyl)phenoxyacetylamino]-5-(4-phenoxyphenoxy) phenyl}-N-methylcarbamate (1.99 g) and 4N hydrogen chloride/dioxane (20 ml) was stirred at ambient temperature for 22 hours. The solvent of the reaction mixture was evaporated to dryness. To the residue was added ethyl acetate and insoluble product was collected by filtration and washed with ethyl acetate to give the title compound (1.57 g).

mp 190–200° C.

EXAMPLE 23

5-{4-[6-(4-Hydroxyphenylthio)-1-methyl-1H-benzimidazole-2-ylmethoxy]benzyl}thiazolidine-2, 4-dione and the hydrochloride thereof (Exemplified Compound No. 1-72)

(23-2a) 5-{4-[6-(4-Hydroxyphenylthio)-1-methyl-1H-benzimidazole-2-ylmethoxy]benzyl}-thiazolidine-2,4-dione In a similar manner to that described in Example (2-1), a reaction was carried out using t-butyl N-[2-amino-5-(4-hydroxyphenylthio)phenyl]-N-methylcarbamate (2.36 g), 4-(2,4-dioxothiazolidin-5-ylmethyl)phenoxyacetic acid (2.87 g), diethyl cyanophosphonate (1.67 g), triethylamine (1.03 g) and anhydrous tetrahydrofuran (60 ml) and the reaction mixture was purified. Then, in a similar manner to that described in Example (2-2a) a reaction was carried out using the above product and 4N hydrogen chloride/dioxane (20 ml) and the reaction mixture was purified to give the desired compound (0.72 g).

Thin layer chromatography on a silica gel plate using n-hexane/ethyl acetate=1/2: Rf=0.19

(23-2b) 5-{4-[6-(4-Hydroxyphenylthio)-1-methyl-1H-benzimidazole-2-ylmethoxy]benzyl}thiazolidine-2,4-dione hydrochloride In a similar manner to that described in Example (2-2b), a reaction was carried out using 5-{4-[6-(4-hydroxyphenylthio)-1-methyl-1H-benzimidazole-2-ylmethoxy]benzyl}thiazolidine-2,4-dione (0.72 g) and 4N

EXAMPLE 24

5-{4-[1-Methyl-6-(3-phenylphenoxy)-1H-benzimidazole-2-ylmethoxy]benzyl}thiazolidine-2,4-dione hydrochloride (Exemplified Compound No. 1-168)

(24-1) t-Butyl N-{2-[4-(2,4-dioxothiazolidin-5-ylmethyl)phenoxyacetylamino]-5-(3-phenylphenoxy)phenyl}-N-methylcarbamate In a similar manner to that described in Example (2-1), a reaction was carried out using t-butyl N-[2-amino-5-(3-phenylphenoxy)phenyl]-N-methylcarbamate (1.60 g), 4-(2,4-dioxothiazolidin-5-ylmethyl)phenoxyacetic acid (1.26 g), diethyl cyanophosphonate (0.73 g), triethylamine (0.45 g) and anhydrous tetrahydrofuran (20 ml) and the reaction mixture was purified to give the desired product (2.57 g).

Thin layer chromatography on a silica gel plate using n-hexane/ethyl acetate=1/1: Rf=0.32

(24-2) 5-{4-[1-Methyl-6-(3-phenylphenoxy)-1H-benzimidazole-2-ylmethoxy]benzyl}thiazolidine-2,4-dione hydrochloride A mixture of t-butyl N-{2-[4-(2,4-dioxothiazolidin-5-ylmethyl)phenoxyacetylamino]-5-(3-phenylphenoxy)phenyl}-N-methylcarbamate (2.57 g) and 4N hydrogen chloride/dioxane (30 ml) was stirred at room temperature for 63 hours. The solvent of the reaction mixture was evaporated to dryness and to the residue was added ethyl acetate and insoluble product was isolated by filtration and washed with ethyl acetate to give the title compound (2.01 g).

mp 150–160° C.

EXAMPLE 25

5-{4-[6-(3-t-Butyl-4-hydroxyphenoxy)-1-methyl-1H-benzimidazole-2-ylmethoxy]benzyl}thiazolidine-2,4-dione hydrochloride (Exemplified Compound No. 1-501)

(25-1) t-Butyl N-{2-[4-(2,4-dioxothiazolidin-5-ylmethyl)phenoxyacetylamino]-5-(3-t-butyl-4-hydroxyphenoxy)phenyl}-N-methylcarbamate In a similar manner to that described in Example (2-1), a reaction was carried out using t-butyl N-[2-amino-5-(3-t-butyl-4-hydroxyphenoxy)phenyl]-N-methylcarbamate (1.11 g), 4-(2,4-dioxothiazolidin-5-ylmethyl)phenoxyacetic acid (0.89 g), diethyl cyanophosphonate (0.52 g), triethylamine (0.32 g) and anhydrous tetrahydrofuran (20 ml) and the reaction mixture was purified to give the desired product (1.75 g).

Thin layer chromatography on a silica gel plate using n-hexane/ethyl acetate 1/1: Rf=0.26

(25-2) 5-{4-[6-(3-t-Butyl-4-hydroxyphenoxy)-1-methyl-1H-benzimidazole-2-ylmethoxy]benzyl}thiazolidin-2,4-dione hydrochloride A mixture of t-butyl N-{2-[4-(2,4-dioxothiazolidin-5-ylmethyl)phenoxyacetylamino]-5-(3-t-butyl-4-hydroxyphenoxy)phenyl}-N-methylcarbamate (1.75 g) and 4N hydrogen chloride/dioxane (20 ml) was stirred at room temperature for 14 hours. The solvent of the reaction mixture was evaporated to dryness and to the residue was added ethyl acetate and insoluble product was isolated by filtration and washed with ethyl acetate to give the title compound (1.11 g).

mp 160–170° C.

hydrogen chloride/ethyl acetate (40 ml) and the reaction mixture was purified to give the title compound (0.63 g).

mp 204–207° C.

EXAMPLE 26

5-{4-[6-(2-t-Butyl-4-hydroxyphenoxy)-1-methyl-1H-benzimidazole-2-ylmethoxy]benzyl}thiazolidine-2,4-dione hydrochloride (Exemplified Compound No. 1-499)

(26-1) t-Butyl N-{2-[4-(2,4-dioxothiazolidin-5-ylmethyl)phenoxyacetylamino]-5-(2-t-butyl-4-hydroxyphenoxy)phenyl}-N-methylcarbamate In a similar manner to that described in Example (2-1), a reaction was carried out using t-butyl N-[2-amino-5-(2-t-butyl-4-hydroxyphenoxy)phenyl]-N-methyl-carbamate (0.95 g), 4-(2,4-dioxothiazolidin-5-ylmethyl)phenoxyacetic acid (0.76 g), diethyl cyanophosphonate (0.44 g), triethylamine (0.27 g) and anhydrous tetrahydrofuran (20 ml) and the reaction mixture was purified to give the desired product (1.24 g).

Thin layer chromatography on a silica gel plate using n-hexane/ethyl acetate=1/1: Rf=0.19

(26-2) 5-{4-[6-(2-t-Butyl-4-hydroxyphenoxy)-1-methyl-1H-benzimidazole-2-ylmethoxy]benzyl}thiazolidine-2,4-dione hydrochloride A mixture of t-butyl N-{2-[4-(2,4-dioxothiazolidine-5-ylmethyl)phenoxyacetylamino]-5-(2-t-butyl-4-hydroxyphenoxy)phenyl}-N-methylcarbamate (1.24 g) and 4N hydrogen chloride/dioxane (20 ml) was stirred at room temperature for 14 hours. The solvent of the reaction mixture was evaporated to dryness and to the residue was added ethyl acetate and insoluble product was isolated by filtration and washed with ethyl acetate to give the title compound (0.75 g).

mp 167–172° C.

EXAMPLE 27

5-{4-[1-Methyl-6-(4-phenylphenoxy)-1H-benzimidazole-2-ylmethoxy]benzyl}thiazolidine-2,4-dione hydrochloride (Exemplified Compound No. 1-169)

(27-1) t-Butyl N-{2-[4-(2,4-dioxothiazolidin-5-ylmethyl)phenoxyacetylamino]-5-(4-phenylphenoxy)phenyl}-N-methylcarbamate In a similar manner to that described in Example (2-1), a reaction was carried out using t-butyl N-[2-amino-5-(4-phenylphenoxy)phenyl]-N-methylcarbamate (1.60 g), 4-(2,4-dioxothiazolidin-5-ylmethyl)phenoxyacetic acid (1.26 g), diethyl cyanophosphonate (0.73 g), triethylamine (0.45 g) and anhydrous tetrahydrofuran (20 ml) and the reaction mixture was purified to give the desired product (2.39 g).

Thin layer chromatography on a silica gel plate using n-hexane/ethyl acetate=1/1: Rf=0.32

(27-2) 5-{4-[1-Methyl-6-(4-phenylphenoxy)-1H-benzimidazole-2-ylmethoxy]benzyl}thiazolidine-2,4-dione hydrochloride A mixture of t-butyl N-{2-[4-(2,4-dioxothiazolidin-5-ylmethyl)phenoxyacetylamino]-5-(4-phenylphenoxy)phenyl}-N-methylcarbamate (2.39 g) and 4N hydrogen chloride/dioxane (20 ml) was stirred at room temperature for 21 hours. The solvent of the reaction mixture was evaporated to dryness and to the residue was added ethyl acetate and insoluble product was isolated by filtration and washed with ethyl acetate to give the title compound (1.90 g).

mp 170–180° C.

EXAMPLE 28

5-{4-[6-(4-Hydroxy-2,5-dimethylphenoxy)-1-methyl-1H-benzimidazole-2-ylmethoxy]benzyl}thiazolidine-2,4-dione hydrochloride (Exemplified Compound No. 1-513)

(28-1) t-Butyl N-{2-[4-(2,4-dioxothiazolidin-5-ylmethyl)phenoxyacetylamino]-5-(4-hydroxy-2,5-dimethylphenoxy)phenyl}-N-methylcarbamate In a similar manner to that described in Example (2-1), a reaction was carried out using t-butyl N-[2-amino-5-(4-hydroxy-2,5-dimethylphenoxy)phenyl]-N-methylcarbamate (0.54 g), 4-(2,4-dioxothiazolidin-5-ylmethyl)phenoxyacetic acid (0.51 g), diethyl cyanophosphonate (0.29 g), triethylamine (0.18 g) and anhydrous tetrahydrofuran (10 ml) and the reaction mixture was purified to give the desired product (0.71 g).

Thin layer chromatography on a silica gel plate using n-hexane/ethyl acetate=1/2: Rf=0.68

(28-2) 5-{4-[6-(4-Hydroxy-2,5-dimethylphenoxy)-1-methyl-1H-benzimidazole-2-ylmethoxy]benzyl}thiazolidine-2,4-dione hydrochloride A mixture of t-butyl N-{2-[4-(2,4-dioxothiazolidine-5-ylmethyl)phenoxyacetylamino]-5-(4-hydroxy-2,5-dimethylphenoxy)phenyl}-N-methylcarbamate (0.71 g) and 4N hydrogen chloride/dioxane (10 ml) was stirred at room temperature for 17 hours. The solvent of the reaction mixture was evaporated to dryness. To the residue was added ethyl acetate and insoluble product was isolated by filtration and subjected to reversed-phase high performance liquid chromatography using acetonitrile/water=9/11 as the eluant and then treated with 4N hydrogen chloride/ethyl acetate to give the title compound (0.41 g).

mp 170–171° C.

EXAMPLE 29

5-{4-[6-(3,5-Di-t-butyl-4-hydroxyphenoxy)-1-methyl-1H-benzimidazole-2-ylmethoxy]benzyl}thiazolidine-2,4-dione hydrochloride (Exemplified Compound No. 1-593)

(29-1) t-Butyl N-{2-[4-(2,4-dioxothiazolidin-5-ylmethyl)phenoxyacetylamino]-5-(3,5-di-t-butyl-4-hydroxyphenoxy)phenyl}-N-methylcarbamate In a similar manner to that described in Example (2-1), a reaction was carried out using t-butyl N-[2-amino-5-(3,5-di-t-butyl-4-hydroxyphenoxy)phenyl]-N-methylcarbamate (0.55 g), 4-(2,4-dioxothiazolidin-5-ylmethyl)phenoxyacetic acid (0.42 g), diethyl cyanophosphonate (0.24 g), triethylamine (0.15 g) and anhydrous tetrahydrofuran (20 ml) and the reaction mixture was purified to give the desired product (0.72 g).

Thin layer chromatography on a silica gel plate using n-hexane/ethyl acetate 1/2: Rf=0.68

(29-2) 5-{4-[6-(3,5-Di-t-butyl-4-hydroxyphenoxy)-1-methyl-1H-benzimidazole-2-ylmethoxy]benzyl}thiazolidine-2,4-dione hydrochloride A mixture of t-butyl N-{2-[4-(2,4-dioxothiazolidin-5-ylmethyl)phenoxyacetylamino]-5-(3,5-di-t-butyl-4-hydroxyphenoxy)phenyl}-N-methylcarbamate (0.72 g) and 4N hydrogen chloride/dioxane (20 ml) was stirred at room temperature for 17 hours. The solvent of the reaction mixture was evaporated to dryness. To the residue was added ethyl acetate and insoluble product was isolated by filtration and washed with ethyl acetate to give the title compound (0.41 g).

mp 173–178° C.

EXAMPLE 30

5-{4-[6-(4'-Hydroxybiphenyl-4-yloxy)-1-methyl-1H-benzimidazole-2-ylmethoxy]benzyl}thiazolidine-2,4-dione hydrochloride (Exemplified Compound No. 1-171)

(30-1) t-Butyl N-{2-[4-(2,4-dioxothiazolidin-5-ylmethyl)phenoxyacetylamino]-5-(4'-hydroxybiphenyl-4-yloxy)phenyl}-N-methylcarbamate A mixture of t-butyl N-[2-amino-5-(4'-hydroxybiphenyl-1-yloxy)phenyl]-N-methylcarbamate (0.61 g), 4-(2,4-dioxothiazolidin-5-ylmethyl)phenoxyacetic acid (0.51 g), diethyl cyanophsphonate (0.29 g), triethylamine (0.18 g) and anhydrous tetrahydrofuran (10 ml) was stirred at ambient temperature for 2 days. The reaction mixture was concentrated and the residue was partitioned between ethyl acetate and water. The ethyl acetate layer was dried over anhydrous sodium sulfate. The ethyl acetate was distilled off under reduced pressure and the residue was purified by chromatography on a silica gel column using n-hexane/ethyl acetate=1/1 as the eluant to give the desired product.

(30-2) 5-{4-[6-(4'-hydroxybiphenyl-4-yloxy)-1-methyl-1H-benzimidazole-2-ylmethoxy]benzyl}thiazolidine-2,4-dione hydrochloride A solution of t-butyl N-{2-[4-(2,4-dioxothiazolidin-5-ylmethyl)phenoxyacetylamino]-5-(4'-hydroxybiphenyl-4-yloxy)phenyl}-N-methylcarbamate in 4N hydrogen chloride/dioxane (20 ml) was allowed to stand at room temperature for 4 days. The solvent of the reaction mixture was evaporated to dryness. To the residue was added ethyl acetate and insoluble product was isolated by filtration and washed with ethyl acetate to give the title compound (0.23 g).

mp 160–163° C.

EXAMPLE 31

5-{4-[6-(4-Hydroxy-2-methylphenoxy)-1-methyl-1H-benzimidazole-2-ylmethoxy]benzyl}thiazolidine-2,4-dione hydrochloride (Exemplified Compound No. 1-481) and 5-{4-[6-(4-hydroxy-3-methylphenoxy)-1-methyl-1H-benzimidazole-2-ylmethoxy]benzyl}thiazolidine-2,4-dione hydrochloride (Exemplified Compound No. 1-486)

(31-1) t-Butyl N-{2-[4-(2,4-dioxothiazolidin-5-ylmethyl)phenoxyacetylamino]-5-(4-hydroxy-2-methylphenoxy)phenyl}-N-methylcarbamate In a similar manner to that described in Example (2-1), a reaction was carried out using a mixture of t-butyl N-[2-amino-5-(4-hydroxy-2-methylphenoxy)phenyl]-N-methylcarbamate and N-[2-amino-5-(4-hydroxy-3-methylphenoxy)phenyl]-N-methylcarbamate (1.88 g), 4-(2,4-dioxothiazolidin-5-ylmethyl)phenoxyacetic acid (1.69 g), diethyl cyanophosphonate (0.98 g), triethylamine (0.61 g) and anhydrous tetrahydrofuran (20 ml) and the reaction mixture was purified to give a mixture of the desired products (1.57 g).

Thin layer chromatography on a silica gel plate using n-hexane/ethyl acetate=1/2: Rf=0.53

(31-2a) 5-{4-[6-(4-Hydroxy-2-methylphenoxy)-1-methyl-1H-benzimidazole-2-ylmethoxy]benzyl}thiazolidine-2,4-dione hydrochloride and (31-2b) 5-{4-[6-(4-Hydroxy-3-methylphenoxy)-1-methyl-1H-benzimidazole-2-ylmethoxy]benzyl}thiazolidine-2,4-dione hydrochloride A mixture of t-butyl N-{2-[4-(2,4-dioxothiazolidin-5-ylmethyl)phenoxyacetylamino]-5-(4-hydroxy-2- methylphenoxy)phenyl}-N-methylcarbamate and t-butyl-N-{2-[4-(2,4-dioxothiazolidin-5-ylmethyl)phenoxyacetylamino]-5-(4-hydroxy-3-methylphenoxy)phenyl}-N-methylcarbamate (1.57 g) and 4N hydrogen chloride/dioxane (20 ml) was stirred at room temperature for 66 hours. The solvent of the reaction mixture was evaporated to dryness. To the residue was added ethyl acetate and insoluble product (1.24 g) was isolated by filtration and was purified by reversed-phase high performance liquid chromatography using acetonitrile/water containing acetic acid (0.2%) and triethylamine (0.2%)=2/3 and then treated with 4N hydrogen chloride/ethyl acetate to give 5-{4-[6-(4-hydroxy-2-methylphenoxy)-1-methyl-1H-benzimidazole-2-ylmethoxy]benzyl}thiazolidine-2,4-dione hydrochloride (50 mg; mp 165–168° C.) and 5-{4-[6-(4-hydroxy-3-methylphenoxy)-1-methyl-1H-benzimidazole-2-ylmethoxy]benzyl}thiazolidine-2,4-dione hydrochloride (183 mg; mp 165–168° C.).

EXAMPLE 32

5-[4-{6-[4-(3,5-Di-t-butyl-4-hydroxybenzoylamino)phenoxy]-1-methyl-1H-benzimidazole-2-ylmethoxy}benzyl]thiazolidine-2,4-dione (Exemplified Compound No. 1-1269)

1-Ethyl-3-(3'-dimethylaminopropyl)carbodiimide hydrochloride (287 mg) was added to a solution of 5-{4-[6-(4-aminophenoxy)-1-methyl-1H-benzimidazole-2-ylmethoxy]benzyl}thiazolidine-2,4-dione dihydrochloride (400 mg), cyclopentanecarboxylic acid (204 mg) and triethylamine (304 mg) in dimethylformamide (8 ml). The mixture was stirred at ambient temperature for 1 hour and allowed to stand for 2 nights. The reaction mixture was concentrated and the residue was partitioned between ethyl acetate and water. The ethyl acetate layer was washed with saturated aqueous sodium chloride solution and dried over anhydrous sodium sulfate and the ethyl acetate was evaporated. The residue was purified by chromatography on a silica gel column using n-hexane/ethyl acetate=1/2–1/3 as the eluant to afford a residue. The residue was recrystallized from n-hexane/ethyl acetate=1/3 to give the desired compound (176 mg).

mp 159.8–162.0° C.

EXAMPLE 33

5-{4-[6-(4-Benzyl-3-hydroxyphenoxy)-1-methyl-1H-benzimidazole-2-ylmethoxy]benzyl}thiazolidine-2,4-dione hydrochloride (Exemplified Compound No. 1-1230)

(33-1) t-Butyl N-{2-[4-(2,4-dioxothiazolidin-5-ylmethyl)phenoxyacetylamino]-5-(4-benzyl-3-hydroxyphenoxy)phenyl}-N-methylcarbamate and t-butyl N-{2-[4-(2,4-dioxothiazolidin-5-ylmethyl)phenoxyacetylamino]-5-(4-hydroxy-3-methylphenoxy)phenyl}-N-methylcarbamate In a similar manner to that described in Example (2-1), a reaction was carried out using t-butyl N-[2-amino-5-(4-benzyl-3-hydroxyphenoxy)phenyl]-N-methylcarbamate (1.8 g), 4-(2,4-dioxothiazolidin-5-ylmethyl)phenoxyacetic acid (1.16 g), diethyl cyanophosphonate (0.99 g), triethylamine (0.76 g) and anhydrous tetrahydrofuran (30 ml) and the reaction mixture was purified to give the desired products (1.5 g).

Thin layer chromatography on a silica gel plate using n-hexane/ethyl acetate=1/1: Rf=0.32

(33-2) 5-{4-[6-(4-Benzyl-3-hydroxyphenoxy)-1-methyl-1H-benzimidazole-2-ylmethoxy]benzyl}thiazolidine-2,4-dione hydrochloride A mixture of t-butyl N-{2-[4-(2,4-dioxothiazolidin-5-ylmethyl)phenoxyacetylamino]-5-(4-benzyl-3-hydroxyphenoxy)phenyl}-N-methylcarbamate (1.4 g) and 4N hydrogen chloride/dioxane (20 ml) was stirred at ambient temperature for 3 days. On addition of ethyl acetate and n-hexane insoluble product was formed and isolated by filtration to give the title compound (1.5 g)

mp 205–219° C.

EXAMPLE 34

5-{4-[1-Methyl-6-(4-methylthiophenoxy)-1H-benzimidazole-2-ylmethoxy]benzyl}thiazolidine-2,4-dione and the hydrochloride thereof (Exemplified Compound No. 1-136)

(34-1) t-Butyl N-{2-[4-(2,4-dioxothiazolidin-5-ylmethyl)phenoxyacetylamino]-5-(4-methylthiophenoxy)phenyl}-N-methylcarbamate In a similar manner to that described in Example (2-1), a reaction was carried out using t-butyl N-[2-amino-5-(4-methylthiophenoxy)phenyl]-N-methylcarbamate (1.93 g), 4-(2,4-dioxothiazolidin-5-ylmethyl)phenoxyacetic acid (3.01 g), diethyl cyanophosphonate (1.75 g), triethylamine (1.08 g) and anhydrous tetrahydrofuran (80 ml) and the reaction mixture was purified to give the desired product (2.96 g).

Thin layer chromatography on a silica gel plate using n-hexane/ethyl acetate=7/3: Rf=0.11

(34-2a) 5-{4-[1-Methyl-6-(4-methylthiophenoxy)-1H-benzimidazole-2-ylmethoxy]benzyl}thiazolidine-2,4-dione In a similar manner to that described in Example (2-2a), a reaction was carried out using t-butyl N-{2-[4-(2,4-dioxothiazolidin-5-ylmethyl)phenoxyacetylamino]-5-(4-methylthiophenoxy)phenyl}-N-methylcarbamate (2.95 g) and 4N hydrogen chloride/dioxane (60 ml) and the reaction mixture was purified to give the title compound (2.15 g)

mp 199–200° C.

(34-2b) 5-{4-[1-Methyl-6-(4-methylthiophenoxy)-1H-benzimidazole-2-ylmethoxy]benzyl}thiazolidine-2,4-dione hydrochloride In a similar manner to that described in Example (2-2b), a reaction was carried out using 5-{4-[1-methyl-6-(4-methylthiophenoxy)-1H-benzimidazole-2-ylmethoxy]benzyl}thiazolidine-2,4-dione (1.15 g) and 4N hydrogen chloride/ethyl acetate (20 ml) and the reaction mixture was purified to give the title compound (1.06 g)

mp 137–147° C.

EXAMPLE 35

5-{4-[1-Methyl-6-(4-methoxyphenoxy)-1H-benzimidazole-2-ylmethoxy]benzyl}thiazolidine-2,4-dione and hydrochloride thereof (Exemplified Compound No. 1-132)

(35-1) t-Butyl N-{2-[4-(2,4-dioxothiazolidin-5-ylmethyl)phenoxyacetylamino]-5-(4-methoxyphenoxy)phenyl}-N-methylcarbamate In a similar manner to that described in Example (2-1), a reaction was carried out using t-butyl N-[2-amino-5-(4-methoxyphenoxy)phenyl]-N-methylcarbamate (2.0 g), 4-(2,4-dioxothiazolidin-5-ylmethyl)phenoxyacetic acid (2.0 g), diethyl cyanophosphonate (1.3 g), triethylamine (0.81 g) and anhydrous tetrahydrofuran (50 ml) and the reaction mixture was purified to give the desired product (3.3 g).

Thin layer chromatography on a silica gel plate using n-hexane/ethyl acetate=1/1: Rf=0.61

(35-2a) 5-{4-[1-Methyl-6-(4-methoxyphenoxy)-1H-benzimidazole-2-ylmethoxy]benzyl}thiazolidine-2,4-dione A solution of t-butyl N-{2-[4-(2,4-dioxothiazolidin-5-ylmethyl)phenoxyacetylamino]-5-(4-methoxyphenoxy)phenyl}-N-methylcarbamate (3.28 g) in trifluoroacetic acid (50 ml) was stirred at 65° C. for 8 hours and allowed to stand at ambient temperature for 1 night. The reaction mixture was concentrated and to the residue was added water and neutralized with aqueous sodium bicarbonate solution. The mixture was extracted with ethyl acetate. The ethyl acetate layer was washed with saturated aqueous sodium chloride solution and dried over anhydrous sodium sulfate and then evaporated. On addition of ether/ethyl acetate=1/1 to the residue crystals were formed and isolated by filtration to give the title compound (1.91 g).

mp 122–126° C.

(35-2b) 5-{4-[1-Methyl-6-(4-methoxyphenoxy)-1H-benzimidazole-2-ylmethoxy]benzyl}thiazolidine-2,4-dione hydrochloride In a similar manner to that described in Example (2-2b), a reaction was carried out using 5-{4-[1-methyl-6-(4-methoxyphenoxy)-1H-benzimidazole-2-ylmethoxy]benzyl}thiazolidine-2,4-dione (1.8 g) and 4N hydrogen chloride/ethyl acetate (50 ml) and the reaction mixture was purified to give the title compound (1.85 g).

mp 148–151° C.

EXAMPLE 36

5-{4-[1-Methyl-6-(4-trifluoromethylphenoxy)-1H-benzimidazole-2-ylmethoxy]benzyl}thiazolidine-2,4-dione and the hydrochloride thereof (Exemplified Compound No. 1-131)

(36-1) t-Butyl N-{2-[4-(2,4-dioxothiazolidin-5-ylmethyl)phenoxyacetylamino]-5-(4-trifluoromethylphenoxy)phenyl}-N-methylcarbamate In a similar manner to that described in Example (2-1), a reaction was carried out using t-butyl N-[2-amino-5-(4-trifluoromethylphenoxy)phenyl]-N-methylcarbamate (0.68 g), 4-(2,4-dioxothiazolidin-5-ylmethyl)phenoxyacetic acid (0.73 g), diethyl cyanophosphonate (0.49 g), triethylamine (0.30 g) and anhydrous tetrahydrofuran (50 ml) and the reaction mixture was purified to give the desired product (0.97 g).

Thin layer chromatography on a silica gel plate using n-hexane/ethyl acetate=2/1: Rf=0.23

(35-2a) 5-{4-[1-Methyl-6-(4-trifluoromethylphenoxy)-1H-benzimidazole-2-ylmethoxy]benzyl}thiazolidine-2,4-dione A solution of t-butyl N-{2-[4-(2,4-dioxothiazolidin-5-ylmethyl)phenoxyacetylamino]-5-(4-trifluoromethylphenoxy)phenyl}-N-methylcarbamate (0.95 g) in trifluoroacetic acid (20 ml) was stirred at 60° C. for 3 hours and allowed to stand at ambient temperature overnight. The reaction mixture was concentrated and to the residue was added water and neutralized with aqueous sodium bicarbonate solution (5%). The mixture was extracted with ethyl acetate. The ethyl acetate layer was washed with saturated aqueous sodium chloride solution, dried over anhydrous sodium sulfate and then evaporated. The residue was purified by chromatography on a silica gel column using n-hexane/ethyl acetate=1/2 as the eluant to give the title compound (0.60 g).

Thin layer chromatography on a silica gel plate using n-hexane/ethyl acetate=1/1: Rf=0.29

(36-2b) 5-{4-[1-Methyl-6-(4-trifluoromethylphenoxy)-1H-benzimidazole-2-ylmethoxy]benzyl}thiazolidine-2,4-dione hydrochloride In a similar manner to that described in Example (2-2b), a reaction was carried out using 5-{4-[1-methyl-6-(4-trifluoromethylphenoxy)-1H-benzimidazole-2-ylmethoxy]benzyl}thiazolidine-2,4-dione (0.58 g) and 4N hydrogen chloride/ethyl acetate (20 ml) and the reaction mixture was purified to give the title compound (0.55 g).

mp 145–147° C.

EXAMPLE 37

5-{4-[6-(4-Benzylphenoxy)-1-methyl-1H-benzimidazole-2-ylmethoxy]benzyl}thiazolidine-2,4-dione hydrochloride (Exemplified Compound No. 1-184)

(37-1) t-Butyl N-{2-[4-(2,4-dioxothiazolidin-5-ylmethyl)phenoxyacetylamino]-5-(4-benzylphenoxy)phenyl}-N-methylcarbamate In a similar manner to that described in Example (2-1), a reaction was carried out using t-butyl N-[2-amino-5-(4-benzylphenoxy)phenyl]-N-methylcarbamate (0.61 g), 4-(2,4-dioxothiazolidin-5-ylmethyl)phenoxyacetic acid (0.51 g), diethyl cyanophosphonate (0.29 g), triethylamine (0.18 g) and anhydrous tetrahydrofuran (10 ml) and the reaction mixture was purified to give the desired product (0.91 g).

Thin layer chromatography on a silica gel plate using n-hexane/ethyl acetate=1/1: Rf=0.26

(37-2) 5-{4-[6-(4-Benzylphenoxy)-1-methyl-1H-benzimidazole-2-ylmethoxy]benzyl}thiazolidine-2,4-dione hydrochloride A mixture of t-butyl N-{2-[4-(2,4-dioxothiazolidin-5-ylmethyl)phenoxyacetylamino]-5-(4-benzylphenoxy)phenyl}-N-methylcarbamate (0.91 g) and 4N hydrogen chloride/dioxane (10 ml) was allowed to stand at ambient temperature for 3 days. The solvent of the reaction mixture was evaporated to dryness. To the residue was added ethyl acetate and insoluble product was isolated by filtration and washed with ethyl acetate to give the title compound (0.69 g).

mp 170–180° C.

EXAMPLE 38

5-{4-[6-(3-Hydroxyphenoxy)-1-methyl-1H-benzimidazole-2-ylmethoxy]benzyl}thiazolidine-2,4-dione hydrochloride (Exemplified Compound No. 1-41)

(38-1) t-Butyl N-{2-[4-(2,4-dioxothiazolidin-5-ylmethyl)phenoxyacetylamino]-5-(3-hydroxyphenoxy)phenyl}-N-methylcarbamate In a similar manner to that described in Example (2-1), a reaction was carried out using t-butyl N-[2-amino-5-(3-hydroxyphenoxy)phenyl]-N-methylcarbamate (0.95 g), 4-(2,4-dioxothiazolidin-5-ylmethyl)phenoxyacetic acid (0.89 g), diethyl cyanophosphonate (0.52 g), triethylamine (0.32 g) and anhydrous tetrahydrofuran (30 ml) and the reaction mixture was purified to give the desired product (1.18 g).

Thin layer chromatography on a silica gel plate using n-hexane/ethyl acetate=1/1: Rf=0.28

(38-2) 5-{4-[6-(3-Hydroxyphenoxy)-1-methyl-1H-benzimidazole-2-ylmethoxy]benzyl}thiazolidine-2,4-dione hydrochloride A mixture of t-butyl N-{2-[4-(2,4-dioxothiazolidin-5-ylmethyl)phenoxyacetylamino]-5-(3-hydroxyphenoxy)phenyl}-N-methylcarbamate (1.18 g) and 4N hydrogen chloride/dioxane (20 ml) was allowed to stand at ambient temperature for 18 hours. The solvent of the reaction mixture was evaporated to dryness. To the residue was added ethyl acetate and the mixture was irradiated by ultrasonic waves. The insoluble product was isolated by filtration and washed with ethyl acetate to give the title compound (0.86 g).

mp 192–195° C.

EXAMPLE 39

5-[4-{6-[4-(Tetrazol-5-yl)phenoxy]-1-methyl-1H-benzimidazole-2-ylmethoxy}benzyl]thiazolidine-2, 4-dione hydrochloride (Exemplified Compound No. 1-1154)

(39-1) t-Butyl N-{2-[4-(2,4-dioxothiazolidine-5-ylmethyl)phenoxyacetylamino]-5-[4-(tetrazol-5-yl)phenoxy]phenyl}-N-methylcarbamate In a similar manner to that described in Example (2-1), a reaction was carried out using t-butyl N-{2-amino-5-[4-(tetrazol-5-yl)phenoxy]phenyl}-N-methylcarbamate (0.69 g), 4-(2,4-dioxothiazolidin-5-ylmethyl)phenoxyacetic acid (0.37 g), diethyl cyanophosphonate (0.21 g), triethylamine (0.13 g) and anhydrous tetrahydrofuran (30 ml) and the reaction mixture was purified to give the desired product (0.76 g).

Thin layer chromatography on a silica gel plate using n-hexane/ethyl acetate=1/1: Rf=0.49

(39-2) 5-[4-{6-[4-(Tetrazol-5-yl)phenoxy]-1-methyl-1H-benzimidazole-2-ylmethoxy}benzyl]thiazolidine-2,4-dione hydrochloride A mixture of t-butyl N-{2-[4-(2,4-dioxothiazolidine-5-ylmethyl)phenoxyacetylamino]-5-[4-(tetrazol-5-yl)phenoxy]phenyl}-N-methylcarbamate (0.76 g) and 4N hydrogen chloride/dioxane (20 ml) was stirred at ambient temperature for 24 hours. The solvent of the reaction mixture was evaporated. To the residue was added ethyl acetate and insoluble product was isolated by filtration and washed with ethyl acetate to give the title compound (0.44 g).

mp 232–235° C.

EXAMPLE 40

5-{4-[6-(4-Cyanophenoxy)-1-methyl-1H-benzimidazole-2-ylmethoxy]benzyl}thiazolidine-2, 4-dione hydrochloride (Exemplified Compound No. 1-1210)

A mixture of 5-{4-[6-(4-cyanophenoxy)-1-methyl-1H-benzimidazole-2-ylmethoxy]benzyl}-3-triphenylmethylthiazolidine-2,4-dione (0.69 g) and aqueous acetic acid solution (80%, 25 ml) was stirred at 70° C. for 3 hours. The reaction mixture was concentrated and an aqueous solution of sodium bicarbonate (10%, 250 ml) was added to the residue. The mixture was stirred at ambient temperature for several hours. The insoluble product was isolated by filtration and dried in the air to afford 5-{4-[6-(4-cyanophenoxy)-1-methyl-1H-benzimidazole-2-ylmethoxy]benzyl}thiazolidine-2,4-dione. A mixture of the product and 4N hydrogen chloride/dioxane was stirred at ambient temperature for 2 hours. Insoluble product was isolated by filtration and washed with ethyl acetate to give the title compound (0.41 g).

mp 215–218° C.

EXAMPLE 41

5-[4-(6-Pentafluorophenoxy-1-methyl-1H-benzimidazole-2-ylmethoxy)benzyl]thiazolidine-2,4-dione hydrochloride (Exemplified Compound No. 1-1235)

(41-1a) 5-[4-(6-Pentafluorophenoxy-1-methyl-1H-benzimidazole-2-ylmethoxy)benzyl]thiazolidine-2,4-dione A mixture of 2-hydroxymethyl-1-methyl-6-pentafluorophenoxy-1H- benzimidazole (1.17 g), 5-(4-hydroxybenzyl)-3-triphenylmethylthiazolidine-2,4-dione (1.86 g), azodicarbonyldipiperidine (1.01 g), tri-n-butylphosphine (0.81 g) and toluene (50 ml) was stirred at ambient temperature for 16 hours. The reaction mixture was subjected to chromatography on a silica gel column. The fraction eluted with n-hexane/ethyl acetate=3/2 was collected and the solvent was evaporated to afford 5-[4-(6-pentafluorophenoxy-1-methyl-1H-benzimidazole-2-ylmethoxy)benzyl]-3-triphenylmethylthiazolidine-2,4-dione. A mixture of the product and aqueous acetic acid (80%, 100 ml) was stirred at 70° C. for 1 hour. The reaction mixture was concentrated and then neutralized with aqueous sodium bicarbonate solution (10%). The insoluble product was isolated by filtration and washed with water to afford crystals. The crystals were purified by chromatography on a silica gel column using n-hexane/ethyl acetate=1/1 as the eluant to give the title compound (1.29 g).

Thin layer chromatography on a silica gel plate using n-hexane/ethyl acetate=1/1: Rf=0.42

(41-1b) 5-[4-(6-Pentafluorophenoxy-1-methyl-1H-benzimidazole-2-ylmethoxy)benzyl]thiazolidine-2,4-dione hydrochloride In a similar manner to that described in Example (2-2b), a reaction was carried out using 5-[4-(6-pentafluorophenoxy-1-methyl-1H-benzimidazole-2-ylmethoxy]benzyl}thiazolidine-2,4-dione (1.29 g) and 4N hydrogen chloride/ethyl acetate (30 ml) and the reaction mixture was purified to give the title compound (1.13 g).

mp 169–172° C.

EXAMPLE 42

5-{4-[6-(2,5-Di-t-butyl-4-hydroxyphenoxy)-1-methyl-1H-benzimidazole-2-ylmethoxy] benzyl}thiazolidine-2,4-dione and hydrochloride thereof (Exemplified Compound No. 1-1234)

(42-1) t-Butyl N-{2-[4-(2,4-dioxothiazolidin-5-ylmethyl) phenoxyacetylamino]-5-(2,5-di-t-butyl-4-hydroxyphenoxy) phenyl}-N-methylcarbamate In a similar manner to that described in Example (2-1), a reaction was carried out using t-butyl N-[2-amino-5-(2,5-di-t-butyl-4-hydroxyphenoxy)phenyl]-N-methylcarbamate (0.71 g), 4-(2,4-dioxothiazolidin-5-ylmethyl)phenoxyacetic acid (0.68 g), diethyl cyanophosphonate (0.39 g), triethylamine (0.24 g) and anhydrous tetrahydrofuran (30 ml) and the reaction mixture was purified to give the desired product (1.13 g).

Thin layer chromatography on a silica gel plate using n-hexane/ethyl acetate=1/1: Rf=0.41

(42-2a) 5-{4-[6-(2,5-Di-t-butyl-4-hydroxyphenoxy)-1-methyl-1H-benzimidazole-2-ylmethoxy]benzyl}thiazolidine-2,4-dione In a similar manner to that described in Example (2-2a), a reaction was carried out using t-butyl N-{2-[4-(2,4-dioxothiazolidin-5-ylmethyl)phenoxyacetylamino]-5-(2,5-di-t-butyl-4-hydroxyphenoxy)phenyl}-N-methylcarbamate (1.12 g) and 4N hydrogen chloride/dioxane (25 ml) and the reaction mixture was purified to give the title compound (0.73 g).

Thin layer chromatography on a silica gel plate using n-hexane/ethyl acetate=1/1: Rf=0.19

(42-2b) 5-{4-[6-(2,5-Di-t-butyl-4-hydroxyphenoxy)-1-methyl-1H-benzimidazole-2-ylmethoxy]benzyl}thiazolidine-2,4-dione hydrochloride In a similar manner to that described in Example (2-2b), a reaction was carried out using 5-{4-[6-(2,5-di-t-butyl-4-hydroxyphenoxy)-1-methyl-1H-benzimidazole-2-ylmethoxy]benzyl}thiazolidine-2,4-dione (0.73 g) and 4N hydrogen chloride/ethyl acetate (20 ml) and the reaction mixture was purified to give the title compound (0.31 g).

mp 182–195° C.

EXAMPLE 43

5-{4-[6-(3,5-Di-t-butyl-4-hydroxyphenylthio)-1-methyl-1H-benzimidazole-2-ylmethoxy]benzylidene}thiazolidine-2,4-dione (Exemplified Compound No. 5-135)

A mixture of 4-[6-(3,5-di-t-butyl-4-hydroxyphenylthio)-1-methyl-1H-benzimidazole-2-ylmethoxy]benzaldehyde (502 mg), thiazolidine-2,4-dione (234 mg), piperidine (170 mg) and ethanol (60 ml) was heated at reflux for 19 hours. The reaction mixture was evaporated to dryness and to the residue was added water and insoluble product was isolated by filtration and washed with water and diisopropyl ether to give the title compound (517 mg).

mp 247–249° C.

EXAMPLE 44

5-{4-[6-(4-n-Hexylaminophenoxy)-1-methyl-1H-benzimidazole-2-ylmethoxy]benzyl}thiazolidine-2,4-dione (Exemplified Compound No. 1-1242)

A mixture of t-butyl N-[2-amino-5-(4-t-butoxycarbonyl-n-hexylaminophenoxy)phenyl]-N-methylcarbamate (4.10 g), 4-(2,4-dioxothiazolidin-5-ylmethyl)phenoxyacetic acid (2.81 g), diethyl cyanophsphonate (1.63 g), triethylamine (1.01 g) and anhydrous tetrahydrofuran (100 ml) was stirred at ambient temperature for 28 hours. The reaction mixture was concentrated and the residue was partitioned between ethyl acetate and water. The ethyl acetate layer was dried over anhydrous sodium sulfate and concentrated. A mixture of the residue and 4N hydrogen chloride/dioxane (50 ml) was stirred at ambient temperature for 66 hours. Water was added to the reaction mixture and the mixture was neutralized with sodium bicarbonate and extracted with ethyl acetate. The ethyl acetate was dried over anhydrous sodium sulfate and evaporated. The residue was purified by chromatography on a silica gel column using n-hexane/ethyl acetate=2/3 as the eluant to give the title compound (2.89 g).

mp 177–179° C.

EXAMPLE 45

5-{4-(6-[4-(N-Acetyl-N-n-hexylamino)phenoxy]-1-methyl-1H-benzimidazole-2-ylmethoxy)benzyl}thiazolidine-2,4-dione hydrochloride (Exemplified Compound No. 1-1318)

A mixture of 5-{4-[6-(4-n-hexylaminophenoxy)-1-methyl-1H-benzimidazole-2-ylmethoxy]benzyl}thiazolidine-2,4-dione (502 mg), acetic anhydride (112 mg), pyridine (356 mg), 4-(dimethylamino)pyridine (37 mg) and anhydrous tetrahydrofuran (30 ml) was allowed to stand at ambient temperature for 14 hours. The reaction mixture was concentrated and partitioned between ethyl acetate and water. The ethyl acetate layer was dried over anhydrous sodium sulfate and concentrated. The residue was purified by chromatography on a silica gel column using n-hexane/ethyl acetate=1/3 as the eluant and then treated with 4N hydrogen chloride/ethyl acetate (20 ml) to give the title compound (410 mg).

EXAMPLE 46

5-{4-[6-(4-Aminophenoxy)-1-methyl-1H-benzimidazole-2-ylmethoxy]benzyl}thiazolidine-2,4-dione dihydrochloride (Exemplified Compound No. 1-142)

(46-1) t-Butyl N-{5-(4-aminophenoxy)-2-[4-(2,4-dioxothiazolidin-5-ylmethyl)phenoxyacetylamino]phenyl}-N-methylcarbamate In a similar manner to that described in Example (2-1), a reaction was carried out using t-butyl N-[2-amino-5-(4-t-butoxycarbonylaminophenoxy)phenyl]-N-methylcarbamate (500 mg), 4-(2,4-dioxothiazolidin-5-ylmethyl)phenoxyacetic acid (366 mg), diethyl cyanophosphonate (212 mg), triethylamine (132 mg) and anhydrous tetrahydrofuran (10 ml) and the reaction mixture was purified to give the desired compound (395 mg).

Thin layer chromatography on a silica gel plate using n-hexane/ethyl acetate=2/3: Rf=0.51

(46-2) 5-{4-[6-(4-Aminophenoxy)-1-methyl-1H-benzimidazole-2-ylmethoxy]benzyl}thiazolidine-2,4-dione dihydrochloride A mixture of a solution of t-butyl N-{5-(4-aminophenoxy)-2-[4-(2,4-dioxothiazolidin-5-ylmethyl)phenoxyacetylamino]phenyl}-N-methylcarbamate (27.08 g) in 1,4-dioxane (50 ml) and 4N hydrogen chloride/dioxane (150 ml) was stirred at ambient temperature for 2 days. The insoluble product was isolated by filtration and washed with ethyl acetate to give the title compound (14.43 g).

mp 195° C. (dec)

EXAMPLE 47

5-{4-[6-(4-Acetylaminophenoxy)-1-methyl-1H-benzimidazole-2-ylmethoxy]benzyl}thiazolidine-2,4-dione (Exemplified Compound No. 1-164)

A mixture of 5-{4-[6-(4-aminophenoxy)-1-methyl-1H-benzimidazole-2-ylmethoxy]benzyl}thiazolidine-2,4-dione dihydrochloride (400 mg), acetylchloride (71 mg), triethylamine (263 mg) and anhydrous N,N-dimethylformamide (8 ml) was stirred at ambient temperature for 1 hour. The reaction mixture was concentrated and partioned between ethyl acetate and water. The ethyl acetate layer was washed with saturated aqueous sodium chloride solution and dried over anhydrous sodium sulfate and concentrated. The residue was purified by chromatography on a silica gel column using n-hexane/ethyl acetate=1/4→ethyl acetate→ethyl acetate/methanol=1/10 as the eluant to give the title compound (320 mg).

mp 92.2–95.0° C.

EXAMPLE 48

5-{4-[6-(4-Benzoylaminophenoxy)-1-methyl-1H-benzimidazole-2-ylmethoxy]benzyl}thiazolidine-2,4-dione (Exemplified Compound No. 1-1248)

In a similar manner to that described in Example 47, a reaction was carried out using 5-{4-[6-(4-aminophenoxy)-

1-methyl-1H-benzimidazole-2-ylmethoxy]benzyl}thiazolidine-2,4-dione dihydrochloride (400 mg), benzoylchloride (126 mg), triethylamine (263 mg) and anhydrous N,N-dimethylformamide (8 ml) and the reaction mixture was purified to give the title compound (247 mg).

mp 200.2–204.4° C.

EXAMPLE 49

5-[4-{6-[4-(3-Chlorobenzoylamino)phenoxy]-1-methyl-1H-benzimidazole-2-ylmethoxy}benzyl] thiazolidine-2,4-dione (Exemplified Compound No. 1-1256)

In a similar manner to that described in Example 47, a reaction was carried out using 5-{4-[6-(4-aminophenoxy)-1-methyl-1H-benzimidazole-2-ylmethoxy]benzyl}thiazolidine-2,4-dione dihydrochloride (400 mg), 3-chlorobenzoylchloride (123 mg), triethylamine (263 mg) and anhydrous N,N-dimethylformamide (8 ml) and the reaction mixture was purified to give the title compound (232 mg).

mp 237.8–238.8° C.

EXAMPLE 50

5-{4-[6-(4-Isonicotinoylaminophenoxy)-1-methyl-1H-benzimidazole-2-ylmethoxy]benzyl}thiazolidine-2,4-dione (Exemplified Compound No. 1-1311)

In a similar manner to that described in Example 47, a reaction was carried out using 5-{4-[6-(4-aminophenoxy)-1-methyl-1H-benzimidazole-2-ylmethoxy]benzyl}thiazolidine-2,4-dione dihydrochloride (400 mg), isonicotinoylchloride (142 mg), triethylamine (232 mg) and anhydrous N,N-dimethylformamide (8 ml) and the reaction mixture was purified to give the title compound (306 mg).

mp 222° C. (dec)

EXAMPLE 51

5-{4-[6-(4-Nicotinoylaminophenoxy)-1-methyl-1H-benzimidazole-2-ylmethoxy]benzyl}thiazolidine-2,4-dione (Exemplified Compound No. 1-1305)

In a similar manner to that described in Example 47, a reaction was carried out using 5-{4-[6-(4-aminophenoxy)-1-methyl-1H-benzimidazole-2-ylmethoxy]benzyl}thiazolidine-2,4-dione dihydrochloride (400 mg), nicotinoylchloride (195 mg), triethylamine (354 mg) and anhydrous N,N-dimethylformamide (8 ml) and the reaction mixture was purified to give the title compound (297 mg).

mp 213.0–214.7° C.

EXAMPLE 52

5-[4-{6-[4-(2,4-Difluorobenzoylamino)phenoxy]-1-methyl-1H-benzimidazole-2-ylmethoxy}-benzyl] thiazolidine-2,4-dione (Exemplified Compound No. 1-1236)

In a similar manner to that described in Example 47, a reaction was carried out using 5-{4-[6-(4-aminophenoxy)-1-methyl-1H-benzimidazole-2-ylmethoxy]benzyl}thiazolidine-2,4-dione dihydrochloride (400 mg), 2,4-difluorobenzoylchloride (141 mg), triethylamine (232 mg) and anhydrous N,N-dimethylformamide (8 ml) and the reaction mixture was purified to give the title compound (251 mg).

mp 171.5–174.2° C.

EXAMPLE 53

5-[4-{6-[4-(2-Naphthoylamino)phenoxy]-1-methyl-1H-benzimidazole-2-ylmethoxy}benzyl] thiazolidine-2,4-dione (Exemplified Compound No. 1-1277)

In a similar manner to that described in Example 47, a reaction was carried out using 5-{4-[6-(4-aminophenoxy)-1-methyl-1H-benzimidazole-2-ylmethoxy]benzyl}thiazolidine-2,4-dione dihydrochloride (400 mg), 2-naphthoylchloride (153 mg), triethylamine (232 mg) and anhydrous N,N-dimethylformamide (8 ml) and the reaction mixture was purified to give the title compound (337 mg).

mp 220.7–222.7° C.

EXAMPLE 54

5-{4-[6-(4-Cyclohexanoylaminophenoxy)-1-methyl-1H-benzimidazole-2-ylmethoxy] benzyl}thiazolidine-2,4-dione (Exemplified Compound No. 1-1298)

Ethyl chloroformate (87 mg) was added dropwise to a solution of cyclohexanecarboxylic acid (90 mg) and triethylamine (232 mg) in anhydrous N,N-dimethylformamide (8 ml) at ambient temperature. The mixture was stirred at the same temperature for 1.5 hours. To the reaction mixture was added 5-{4-[6-(4-aminophenoxy)-1-methyl-1H-benzimidazole-2-ylmethoxy]benzyl}thiazolidine-2,4-dione dihydrochloride (400 mg) in small portions. The mixture was stirred at 50° C. for 1.5 hours. The reaction mixture was concentrated and partitioned between ethyl acetate and water. The ethyl acetate layer was dried over anhydrous sodium sulfate and concentrated. On addition of ethyl acetate to the residue insoluble product was formed and isolated by filtration and washed with ethyl acetate to give the title compound (262 mg).

mp 181.7–183.7° C.

EXAMPLE 55

5-{4-[6-(4-Cyclopentanoylaminophenoxy)-1-methyl-1H-benzimidazole-2-ylmethoxy] benzyl}thiazolidine-2,4-dione (Exemplified Compound No. 1-1292)

Ethyl chloroformate (87 mg) was added dropwise to a solution of cyclopentanecarboxylic acid (90 mg) and triethylamine (232 mg) in anhydrous N,N-dimethylformamide (8 ml) at ambient temperature. The mixture was stirred at the same temperature for 1.5 hours. To the reaction mixture was added 5-{4-[6-(4-aminophenoxy)-1-methyl-1H-benzimidazole-2-ylmethoxy]benzyl}thiazolidine-2,4-dione dihydrochloride (400 mg) in small portions. The mixture was stirred at ambient temperature for 5 hours and allowed to stand at the same temperature overnight. After concentration of the mixture, water was added to the reaction mixture and the insoluble product was isolated by filtration and washed with water and ethyl acetate to give the title compound (236 mg).

mp 227.3–228.4° C.

Reference Example 1

4-Methoxymethoxy-2,3,5-trimethylphenol 50 g of sodium hydride (55% by weight) were washed with n-hexane, then 2000 ml of anhydrous tetrahydrofuran were added. To the resulting mixture, 500 ml of a solution of 240 g of 2,3,6-trimethyl-4-pivaloyloxyphenol in anhydrous tetrahydrofuran were added dropwise over 90 minutes under ice cooling; the mixture was then stirred at room temperature for two hours. 86 ml of chloromethyl methyl ether were added dropwise to the reaction mixture over 30 minutes under ice cooling and the mixture was stirred at room temperature for one hour. About 50% by volume of tetrahydrofuran was distilled off from the reaction mixture under reduced pressure. The residue was poured into iced water, followed by extraction with ethyl acetate. The extract was washed with saturated saline and dried over anhydrous sodium acetate. The solvent was distilled off under reduced pressure, whereby 294 g of a yellow oil were obtained. To the yellow oil, 1000 ml of methanol were added, followed by the dropwise addition of 500 ml of a solution of 116 g of potassium hydroxide in methanol under ice cooling. The resulting mixture was stirred at room temperature for one hour. The solvent was distilled off under reduced pressure. The residue was poured into iced water and neutralized with a 6N aqueous hydrochloric acid solution, followed by extraction with ethyl acetate. The extract was washed with saturated saline and then dried over anhydrous sodium sulfate. The solvent was distilled off under reduced pressure. The residue was purified by chromatography through a silica gel column (eluting solvent: n-hexane/ethyl acetate=5/1→3/1), whereby 193 g of the title compound were obtained.

Silica gel thin-layer chromatography (developing solvent: n-hexane/ethyl acetate=3/1): Rf value=0.47.

Reference Example 2

6-(4-Methoxymethoxy-2,3,5-trimethylphenoxy)-2-methylamino-3-nitropyridine

To a suspension of 50 g of sodium hydride (55% by weight, washed with n-hexane) in 1000 ml of anhydrous N,N-dimethylformamide, 300 ml of a solution of 193 g of 4-methoxymethoxy-2,3,5-trimethylphenol in anhydrous N,N-dimethylformamide were added dropwise over one hour under ice cooling; the mixture was then stirred at room temperature for 2 hours. To the reaction mixture, 800 ml of a solution of 197 g of 6-chloro-2-methylamino-3-nitropyridine in anhydrous N,N-dimethylformamide were added dropwise over one hour under ice cooling, followed by stirring at room temperature for 2 hours. The solvent was distilled off under reduced pressure. The residue was poured into iced water. To the resulting mixture, ethyl acetate and water were added. The insoluble product was collected by filtration and washed with water and ethanol, whereby 141 g of the title compound were obtained. Separately, the organic layer was separated from the filtrate and the water layer was extracted with ethyl acetate. The organic layer and extract were combined, followed by washing with saturated saline and drying over anhydrous sodium sulfate. The solvent was distilled off under reduced pressure and the residue was washed with ethanol, whereby 126 g of the title compound were obtained.

Melting point: 102–103° C.

Reference Example 3

2-Hydroxymethyl-5-(4-hydroxy-2,3,5-trimethylphenoxy)-3-methyl-3H-imidazo[4,5-b]pyridine A mixture of 288 g of 6-(4-methoxymethoxy-2,3,5-trimethylphenoxy)-2-methylamino-3-nitropyridine, 14 g of 10% palladium on carbon and 1500 ml of methanol was stirred at room temperature for 2 hours under a hydrogen atmosphere. To the reaction mixture, 14 g of 10% palladium on carbon, 500 ml of methanol and 500 ml of tetrahydrofuran were added and the resulting mixture was stirred at 50° C. for 8 hours under a hydrogen atmosphere. The palladium on carbon in the reaction mixture was filtered off and the filtrate was concentrated by evaporation. To the residue, 500 g of glycolic acid were added and the mixture was stirred at 150° C. for 6 hours. To the reaction mixture, 1000 ml of a 4N aqueous hydrochloric acid solution were added and the mixture was stirred at 120° C. for one hour. The reaction mixture was allowed to stand overnight at room temperature. The reaction mixture was poured into iced water, followed by neutralization with an aqueous sodium hydroxide solution and an aqueous sodium carbonate solution. The resulting solid substance was separated by filtration and purified by chromatography through a silica gel column with tetrahydrofuran as an eluting solvent. The resulting solid substance from the eluate was washed with ethanol, whereby 45.5 g of the title compound were obtained.

Melting point: 181–182° C.

Reference Example 4

2-Acetoxymethyl-5-(4-acetoxy-2,3,5-trimethylphenoxy)-3-methyl-3H-imidazo[4,5-b]pyridine To 400 ml of a solution of 38.0 g of 2-hydroxymethyl-5-(4-hydroxy-2,3,5-trimethylphenoxy)-3-methyl-3H-imidazo[4,5-b]pyridine in pyridine, 69 ml of acetic anhydride were added dropwise under ice cooling. After stirring at room temperature for 3 hours, the reaction mixture was allowed to stand overnight at room temperature. The solvent was distilled off under reduced pressure. Water was added to the residue, followed by extraction with ethyl acetate. The extract was washed with saturated saline and dried over anhydrous sodium sulfate. The solvent was distilled off under reduced pressure. The residue was separated and purified by chromatography through a silica gel column (eluting solvent n-hexane/ethyl acetate=1/2), whereby 39.5 g of the title compound were obtained.

Melting point: 128–129° C.

Reference Example 5

5-(4-Acetoxy-2,3,5-trimethylphenoxy)-2-hydroxymethyl-3-methyl-3H-imidazo[4,5-b]pyridine To 500 ml of a solution of 26.0 g of 2-acetoxymethyl-5-(4-acetoxy-2,3,5-trimethylphenoxy)-3-methyl-3H-imidazo[4,5-b]pyridine in methanol, a 1.2 ml solution (28%) of sodium methoxide in methanol was added dropwise at −18° C., followed by stirring at the same temperature for one hour. Water was added to the reaction mixture, followed by extraction with ethyl acetate. The extract was washed with saturated saline and then dried over anhydrous sodium sulfate. The solvent was distilled off under reduced pressure. The residue was crystallized from ethanol. The crystals were collected by filtration, whereby 20.5 g of the title compound were obtained.

Melting point: 179–180° C.

Reference Example 6 t-Butyl N-[5-(4-methoxymethoxy-2,3,5-trimethylphenoxy)-2-nitrophenyl]-N-methylcarbamate 6.11 g of sodium hydride (55% by weight) were suspended in 300 ml of N,N-dimethylformamide, followed by the addition of 27.5 g of 4-methoxymethoxy-2,3,5-trimethylphenol. The resulting mixture was stirred at room temperature for one hour. To the reaction mixture, 40.1 g of t-butyl N-(5-chloro-2-nitrophenyl)-N-methylcarbamate were added in small portions and the mixture was stirred at 120° C. for 2 hours. The reaction mixture was concentrated by evaporation. Water was added to the concentrate, followed by extraction with ethyl acetate. The extract was dried over anhydrous sodium sulfate. The solvent was distilled off under reduced pressure. The residue was purified by chromatography through a silica gel column (eluting solvent: n-hexane/ethyl acetate=5/1), whereby 57.0 g of the title compound were obtained.

Silica gel thin-layer chromatography (developing solvent: n-hexane/ethyl acetate=4/1): Rf value=0.55.

Reference Example 7 t-Butyl N-[2-amino-5-(4-methoxymethoxy-2,3,5-trimethylphenoxy)phenyl]N-methylcarbamate A mixture of 57.0 g of t-butyl N-[5-(4-methoxymethoxy-2,3,5-trimethylphenoxy)-2-nitrophenyl]-N-methylcarbamate, 3 g of 10% palladium on carbon and 500 ml of methanol was vigorously stirred at room temperature for 8 hours under a hydrogen atmosphere. The palladium on carbon in the reaction mixture was filtered off and the filtrate was concentrated by evaporation. The residue was purified by chromatography through a silica gel column (eluting solvent: n-hexane/ethyl acetate=3/1), whereby 52.5 g of the title compound were obtained.

Silica gel thin-layer chromatography (developing solvent: n-hexane/ethyl acetate=3/1): Rf value=0.31.

Reference Example 8

2-Chloro-3,5-dimethylbenzene-1,4-diol

A mixture of 12.08 g of 3,5-dimethyl-4-nitrosophenol, 11.45 g of cuprous oxide, 100 ml of 1,4-dioxane, 10 ml of acetone and 100 ml of 6N hydrochloric acid was heated under reflux for 2 hours. The reaction mixture was poured into iced water, followed by extraction with ether. The extract was dried over anhydrous sodium sulfate and the solvent was then distilled off under reduced pressure. The residue was dissolved in 150 ml of dichloromethane. To the resulting solution, 3.61 g of sodium borohydride were added under ice cooling, followed by the dropwise addition of 50 ml of methanol at an internal temperature not higher than 10° C. The reaction mixture was stirred at room temperature for 90 minutes. The reaction mixture was concentrated by evaporation. The concentrate was poured into iced water. The resulting mixture was acidified with 3N hydrochloric acid. The precipitated product was collected by filtration, washed successively with water and n-hexane, whereby 5.93 g of the title compound were obtained.

Silica gel thin-layer chromatography (developing solvent: n-hexane/ethyl acetate=4/1): Rf value=0.35.

Reference Example 9

3-Chloro-2,6-dimethyl-4-pivaloyloxyphenol

To a mixture of 5.91 g of 2-chloro-3,5-dimethylbenzene-1,4-diol, 8.13 g of pyridine and 30 ml of dichloromethane, 10 ml of a dichloromethane solution containing 4.54 g of pivaloyl chloride were added dropwise under ice cooling, followed by stirring at the same temperature for one hour and at room temperature for 90 minutes. The reaction mixture was concentrated by evaporation. Water was added to the concentrate and the mixture was extracted with ethyl acetate. The extract was dried over anhydrous sodium sulfate and the solvent was distilled off under reduced pressure. The residue was purified by chromatography through a silica gel column (eluting solvent: n-hexane/ethyl acetate=10/1), whereby 8.02 g of the title compound were obtained.

Silica gel thin-layer chromatography (developing solvent: n-hexane/ethyl acetate=4/1): Rf value=0.53.

Reference Example 10

2-Chloro-4-methoxymethoxy-3,5-dimethylphenol

To 20 ml of an anhydrous tetrahydrofuran suspension containing 1.78 g of sodium hydride (55% by weight), 30 ml of a solution of 8.02 g of 3-chloro-2,6-dimethyl-4-pivaloyloxyphenol in anhydrous tetrahydrofuran were added dropwise, followed by stirring at room temperature for 30 minutes. To the reaction mixture, 3.28 g of chloromethyl methyl ether were added and the mixture was stirred at room temperature for 13 hours. The reaction mixture was then concentrated by evaporation. Water was added to the concentrate, followed by extraction with ethyl acetate. The extract was dried over anhydrous sodium sulfate and the solvent was distilled off under reduced pressure. In 30 ml of methanol, 9.30 g of the residue were dissolved. To the resulting solution, 30 ml of a solution of 3.51 g of potassium hydroxide in methanol were added dropwise, followed by stirring at room temperature for 30 minutes. The reaction mixture was concentrated by evaporation. The concentrate was neutralized with 3N hydrochloric acid and sodium bicarbonate, followed by extraction with ethyl acetate. The extract was dried over anhydrous sodium sulfate and the solvent was distilled off under reduced pressure. The residue was separated and purified by chromatography through a silica gel column (eluting solvent: n-hexane/ethyl acetate=10/1), whereby 5.65 g of the title compound were obtained.

Silica gel thin-layer chromatography (developing solvent: n-hexane/ethyl acetate=10/1): Rf value=0.29.

Reference Example 11

2,6-Dimethyl-4-pivaloyloxyphenol

By using 6.90 g of 2,6-dimethylbenzene-1,4-diol, 6.63 g of pivaloyl chloride, 11.85 g of pyridine and 60 ml of dichloromethane, reaction and purification were carried out in a similar manner to that described in Reference Example 9, whereby 6.77 g of the title compound were obtained.

Melting point: 92–94° C.

Reference Example 12

4-Methoxymethoxy-3,5-dimethylphenol

To 50 ml of an anhydrous tetrahydrofuran suspension containing 1.72 g of sodium hydride (55% by weight), 6.75 g of 2,6-dimethyl-4-pivaloyloxyphenol were added in small portions, followed by stirring at room temperature for 30 minutes. To the reaction mixture, 3.18 g of chloromethyl methyl ether were added and the resulting mixture was stirred at the same temperature for 3 hours. Water was added to the reaction mixture, followed by extraction with ethyl acetate. The extract was dried over anhydrous sodium sulfate and the solvent was distilled off under reduced pressure, whereby 8.17 g of 4-methoxymethoxy-3,5-dimethylphenyl pivaloate were obtained as a crude product.

Silica gel thin-layer chromatography (developing solvent: n-hexane/ethyl acetate=10/1): Rf value=0.39.

8.09 g of crude 4-methoxymethoxy-3,5-dimethylphenyl pivaloate were dissolved in 30 ml of methanol. To the resulting solution, 30 ml of a solution of 3.40 g of potassium hydroxide in methanol were added dropwise, followed by stirring at room temperature for 4 hours. The reaction mixture was concentrated by evaporation. Water was added to the residue. The mixture was neutralized with 3N hydrochloric acid and sodium bicarbonate, followed by extraction with ethyl acetate. The extract was dried over anhydrous sodium sulfate. The solvent was distilled off under reduced pressure. The residue was purified by chromatography through a silica gel column (eluting solvent: n-hexane/ethyl acetate=4/1), whereby 5.58 g of the title compound were obtained.

Silica gel thin-layer chromatography (developing solvent: n-hexane/ethyl acetate=10/1): Rf value=0.10.

Reference Example 13 t-Butyl N-[5-(4-benzyloxyphenoxy)-2-nitrophenyl]-N-methylcarbamate

By using 1.60 g of 4-benzyloxyphenol, 2.29 g of t-butyl N-(5-chloro-2-nitrophenyl)-N-methylcarbamate, 0.35 g of sodium hydride (55% by weight) and 20 ml of anhydrous N,N-dimethylformamide, reaction and purification were carried out in a similar manner to that described in Reference Example 6, whereby 3.33 g of the title compound were obtained.

Melting point: 108–110° C.

Silica gel thin-layer chromatography (developing solvent: n-hexane/ethyl acetate=5/1): Rf value=0.36.

Reference Example 14 t-Butyl N-[5-(4-methoxymethoxy-3,5-dimethylphenoxy)-2-nitrophenyl]-N-methylcarbamate By using 1.46 g of 4-methoxymethoxy-3,5-dimethylphenol, 2.29 g of t-butyl N-(5-chloro-2-nitrophenyl)-N-methylcarbamate, 0.35 g of sodium hydride (55% by weight) and 30 ml of anhydrous N,N-dimethylformamide, reaction and purification were carried out in a similar manner to that described in Reference Example 6, whereby 3.14 g of the title compound were obtained.

Silica gel thin-layer chromatography (developing solvent: n-hexane/ethyl acetate=5/1): Rf value 0.29.

Reference Example 15 t-Butyl N-[5-(2-chloro-4-methoxymethoxy-3,5-dimethylphenoxy)-2-nitrophenyl]-N-methylcarbamate By using 5.65 g of 2-chloro-4-methoxymethoxy-3,5-dimethylphenol, 8.88 g of t-butyl N-(5-chloro-2-nitrophenyl)-N-methylcarbamate, 1.35 g of sodium hydride (55% by weight) and 100 ml of anhydrous N,N-dimethylformamide, reaction and purification were carried out in a similar manner to that described in Reference Example 6, whereby 9.19 g of the title compound were obtained.

Silica gel thin-layer chromatography (developing solvent: n-hexane/ethyl acetate=4/1): Rf value=0.47.

Reference Example 16 t-Butyl N-[5-(pyridine-2-yloxy)-2-nitrophenyl]-N-methylcarbamate

By using 0.76 g of 2-hydroxypyridine, 2.29 g of t-butyl N-(5-chloro-2-nitrophenyl)-N-methylcarbamate, 0.35 g of sodium hydride (55% by weight) and 10 ml of anhydrous N,N-dimethylformamide, reaction and purification were carried out in a similar manner to that described in Reference Example 6, whereby 0.36 g of the title compound were obtained.

Silica gel thin-layer chromatography (developing solvent: n-hexane/ethyl acetate=4/1): Rf value=0.32.

Reference Example 17 t-Butyl N-[5-(3,5-di-t-butyl-4-hydroxyphenylthio)-2-nitrophenyl]-N-methylcarbamate By using 476 mg of 3,5-di-t-butyl-4-hydroxybenzenethiol, 573 mg of t-butyl N-(5-chloro-2-nitrophenyl)-N-methylcarbamate, 175 mg of sodium hydride (55% by weight) and 10 ml of anhydrous N,N-dimethylformamide, reaction and purification were carried out in a similar manner to that described in Reference Example 6, whereby 371 mg of the title compound were obtained.

Silica gel thin-layer chromatography (developing solvent: n-hexane/ethyl acetate=4/1): Rf value=0.59.

Reference Example 18 t-Butyl N-[5-(4-amino-3,5-dimethylphenoxy)-2-nitrophenyl]-N-methylcarbamate

By using 1.10 g of 4-amino-3,5-dimethylphenol, 2.29 g of t-butyl N-(5-chloro-2-nitrophenyl)-N-methylcarbamate, 0.35 g of sodium hydride (55% by weight) and 30 ml of anhydrous N,N-dimethylformamide, reaction and purification were carried out in a similar manner to that described in Reference Example 6, whereby 2.27 g of the title compound were obtained.

Silica gel thin-layer chromatography (developing solvent: n-hexane/ethyl acetate=3/1): Rf value=0.24.

Reference Example 19 t-Butyl N-[5-[4-(t-butoxycarbonylamino-3,5-dimethylphenoxy)-2-nitrophenyl]-N-methylcarbamate A mixture of 2.27 g of t-butyl N-[5-(4-amino-3,5-dimethylphenoxy)-2-nitrophenyl]-N-methylcarbamate, 1.28 g of di-t-butyl dicarbonate, 0.59 g of triethylamine and 20 ml of anhydrous tetrahydrofuran was heated under reflux for 6 hours. The reaction mixture was then concentrated by evaporation. Water was added to the concentrate, followed by extraction with ethyl acetate. The extract was dried over anhydrous sodium sulfate and the solvent was distilled off under reduced pressure. The residue was purified by chromatography through a silica gel column (eluting solvent: n-hexane/ethyl acetate=10/1), whereby 1.74 g of the title compound were obtained.

Melting point: 154–156° C.

Reference Example 20 t-Butyl N-[2-amino-5-(4-hydroxyphenoxy)phenyl]-N-methylcarbamate

By using 3.32 g of t-butyl N-[5-(4-benzyloxyphenoxy)-2-nitrophenyl]-N-methylcarbamate, 0.39 g of 10% palladium on carbon, 100 ml of methanol and 100 ml of 1,4-dioxane, reaction and purification were carried out in a similar manner to that described in Reference Example 7, whereby 2.40 g of the title compound were obtained.

Silica gel thin-layer chromatography (developing solvent: n-hexane/ethyl acetate=1/2): Rf value=0.59.

Reference Example 21 t-Butyl N-[2-amino-5-(4-methoxymethoxy-3,5-dimethylphenoxy)phenyl]-N-methylcarbamate By using 3.12 g of t-butyl N-[5-(4-methoxymethoxy-3,5-dimethylphenoxy)-2-nitrophenyl]-N-methylcarbamate, 0.33 g of 10% palladium on carbon and 30 ml of methanol, reaction and purification were carried out in a similar manner to that described in Reference Example 7, whereby 2.72 g of the title compound were obtained.

Silica gel thin-layer chromatography (developing solvent: n-hexane/ethyl acetate=3/1): Rf value=0.14.

Reference Example 22 t-Butyl N-[2-amino-5-(4-t-butoxycarbonylamino-3,5-dimethylphenoxy)phenyl]-N-methylcarbamate A mixture of 1.71 g of N-[5-(4-t-butoxycarbonylamino-3,5-dimethylphenoxy)-2-nitrophenyl]-N-methylcarbamate, 0.2 g of 10% palladium on carbon and 100 ml of methanol was stirred vigorously at room temperature for 11 hours under a hydrogen atmosphere. The catalyst was filtered off from the reaction mixture and the filtrate was concentrated by evaporation, whereby 1.56 g of the title compound were obtained.

Silica gel thin-layer chromatography (developing solvent: n-hexane/ethyl acetate=3/1): Rf value=0.14.

Reference Example 23 t-Butyl N-{5-[2-(morpholin-4-yl)phenoxy]-2-nitrophenyl}-N-methylcarbamate

By using 0.72 g of 2-(4-morpholino)phenol, 1.15 g of t-butyl N-(5-chloro-2-nitrophenyl)-N-methylcarbamate, 0.17 g of sodium hydride (55% by weight) and 10 ml of anhydrous N,N-dimethylformamide, reaction and purification were carried out in a similar manner to that described in Reference Example 6, whereby 1.44 g of the title compound were obtained.

Silica gel thin-layer chromatography (developing solvent: n-hexane/ethyl acetate=4/1): Rf value=0.34.

Reference Example 24 t-Butyl N-{5-[3-(morpholin-4-yl)phenoxy]-2-nitrophenyl}-N-methylcarbamate

By using 2.16 g of 3-(4-morpholino)phenol, 3.37 g of t-butyl N-(5-chloro-2-nitrophenyl)-N-methylcarbamate and 15 ml of anhydrous N,N-dimethylformamide, reaction and purification were carried out in a similar manner to Reference Example 6, whereby 5.0 g of the title compound were obtained.

Silica gel thin-layer chromatography (developing solvent: benzene/ethyl acetate=10/1): Rf value=0.34.

Reference Example 25 t-Butyl N-{2-amino-5-[2-(morpholin-4-yl)phenoxy]phenyl}-N-methylcarbamate

By using 1.44 g of t-butyl N-{5-[2-(morpholin-4-yl)phenoxy]-2-nitrophenyl}-N-methylcarbamate, 0.20 g of 10% palladium on carbon and 50 ml of methanol, reaction and purification were carried out in a similar manner to Reference Example 7, whereby 1.20 g of the title compound was obtained.

Silica gel thin-layer chromatography (developing solvent: n-hexane/ethyl acetate=2/1): Rf value=0.25.

Reference Example 26 t-Butyl N-{2-amino-5-[3-(morpholin-4-yl)phenoxy]phenyl}-N-methylcarbamate

By using 5.0 g of t-butyl N-{5-[3-(morpholin-4-yl)phenoxy]-2-nitrophenyl}-N-methylcarbamate, 0.5 g of 10% palladium on carbon and a mixed solvent of 30 ml of methanol and 70 ml of toluene, reaction and purification were carried out in a similar manner to that described in Reference Example 7, whereby 4.5 g of the title compound were obtained.

Silica gel thin-layer chromatography (developing solvent: benzene/ethyl acetate=4/1): Rf value=0.23.

Reference Example 27 t-Butyl N-[2-amino-5-(2-piperidinophenoxy)phenyl]-N-methylcarbamate

Sodium hydride (55 wt. %, 1.04 g) was added to a solution of 2-piperidinophenol (3.4 g) in N,N-dimethylformamide (35 ml) in an ice bath under a nitrogen atmosphere. The mixture was stirred at ambient temperature for 15 minutes. To the reaction mixture was added t-butyl N-(5-chloro-2-nitrophenyl)-N-methylcarbamate (5.25 g) in small portions. This mixture was stirred at 60° C. for 2 hours. At the end of this time the solvent was evaporated and water added to the residue. The mixture was neutralized with concentrated hydrogen chloride and extracted with ethyl acetate. The ethyl acetate layer was dried over sodium sulfate and concentrated under reduced pressure. The residue was purified by chromatography on a silica gel column using c-hexane/isopropyl ether=5/1 as the eluant to afford t-butyl N-[2-nitro-5-(2-piperidinophenoxy)phenyl]-N-methylcarbamate, of which Rf value was 0.27 in thin layer chromatography on a silica gel plate using c-hexane/isopropyl ether=5/1 as the eluant. A mixture of a solution of this product in toluene/methanol=7/3 (100 ml) and palladium on carbon (10%, 0.63 g) was vigorously stirred at room temperature under a hydrogen atmosphere for 14.5 hours. The catalyst was removed by filtration and the filtrate was concentrated. The residue was washed with cooled methanol and n-hexane to give the title compound (4.2 g).

mp 108–110° C.

Reference Example 28 t-Butyl N-methyl-N-[2-nitro-5-(pyridin-2-ylthio)phenyl]carbamate

In a similar manner to that described in Reference Example 6, a reaction was carried out using 2-mercaptopyridine (0.89 g), t-butyl N-(5-chloro-2-nitrophenyl)-N-methylcarbamate (2.29 g), sodium hydride (55 wt. %, 0.11 g) and anhydrous N,N-dimethylformamide (40 ml) and the reaction mixture was purified to give the title compound (1.13 g).

Thin layer chromatography on a silica gel plate using n-hexane/ethyl acetate 5/1: Rf=0.20

Reference Example 29 t-Butyl N-[2-amino-5-(2-pyrrolidinophenoxy)phenyl]-N-methylcarbamate

In a similar manner to that described in Reference Example 27, a reaction was carried out using 2-pyrrolidinophenol (1.88 g), t-butyl N-(5-chloro-2-nitrophenyl)-N-methylcarbamate (3.34 g), sodium hydride (55 wt. %, 0.52 g) and anhydrous N,N-dimethylformamide (22 ml) and the reaction mixture was purified to afford t-butyl N-[2-nitro-5-(2-pyrrolidinophenoxy)phenyl]-N-methylcarbamate, of which Rf value was 0.25 in thin layer chromatography on a silica gel plate using c-hexane/ethyl acetate=10/1. In a similar manner to that described in Reference Example 27, a reaction was carried out using this product, palladium on carbon (10%, 0.45 g) and toluene/methanol=7/3 (50 ml) and the reaction mixture was purified to give the title compound (3.0 g).

mp 136–138° C.

Reference Example 30 t-Butyl N-[5-(2-benzyloxyphenoxy)-2-nitrophenyl]-N-methylcarbamate

In a similar manner to that described in Reference Example 6, a reaction was carried out using 2-benzyloxyphenol (2.00 g), t-butyl N-(5-chloro-2-nitrophenyl)-N-methylcarbamate (2.87 g), sodium hydride (55 wt. %, 0.44 g) and anhydrous N,N-dimethylformamide (20 ml) and the reaction mixture was purified to give the title compound (4.16 g).

Thin layer chromatography on a silica gel plate using n-hexane/ethyl acetate=3/1 Rf=0.62

Reference Example 31 t-Butyl N-{5-[4-(1-adamantyl)phenoxy]-2-nitrophenyl}-N-methylcarbamate

In a similar manner to that described in Reference Example 6, a reaction was carried out using 4-(1-adamantyl)phenol (2.28 g), t-butyl N-(5-chloro-2-nitrophenyl)-N-methylcarbamate (2.87 g), sodium hydride (55 wt. %, 0.44 g) and anhydrous N,N-dimethylformamide (40 ml) and the reaction mixture was purified to give the title compound (4.30 g).

Thin layer chromatography on a silica gel plate using n-hexane/ethyl acetate=3/1: Rf=0.76

Reference Example 32 t-Butyl N-[5-(3-dimethylaminophenoxy)-2-nitrophenyl]-N-methylcarbamate

In a similar manner to that described in Reference Example 6, a reaction was carried out using 3-dimethylaminophenol (0.82 g), t-butyl N-(5-chloro-2-nitrophenyl)-N-methylcarbamate (1.72 g), sodium hydride (55 wt. %, 0.26 g) and anhydrous N,N-dimethylformamide (50 ml) and the reaction mixture was purified to give the title compound (2.17 g).

Thin layer chromatography on a silica gel plate using n-hexane/ethyl acetate=9/1: Rf=0.21

Reference Example 33 t-Butyl N-[2-amino-5-(pyridin-3-yloxy)phenyl]-N-methylcarbamate

In a similar manner to that described in Reference Example 27, a reaction was carried out using 3-hydroxypyridine (3.1 g), t-butyl N-(5-chloro-2-nitrophenyl)-N-methylcarbamate (9.3 g), sodium hydride (55 wt. %, 1.4 g) and anhydrous N,N-dimethylformamide (25 ml) and the reaction mixture was purified to afford t-butyl N-[2-nitro-5-(2-pyridin-3-yloxy)phenyl]-N-methylcarbamate (9.2 g). In a similar manner to that described in Reference Example 27, a reaction was carried out using this product, palladium on carbon (10%, 1.0 g) and toluene/methanol=7/3 (100 ml) and the reaction mixture was purified to give the title compound (7.5 g).

mp 101–102° C.

Reference Example 34 t-Butyl N-{5-[4-(imidazol-1-yl)phenoxy]-2-nitrophenyl}-N-methylcarbamate

In a similar manner to that described in Reference Example 6, a reaction was carried out using 4-(imidazol-1-yl)phenol (4.1 g), t-butyl N-(5-chloro-2-nitrophenyl)-N-methylcarbamate (7.85 g), sodium hydride (55 wt. %, 1.25 g) and anhydrous N,N-dimethylformamide (45 ml) and the reaction mixture was purified to give the title compound (8.8 g).

mp 182–184° C.

Reference Example 35 t-Butyl N-methyl-N-[2-nitro-5-(2-phenylphenoxy)phenyl]carbamate

In a similar manner to that described in Reference Example 6, a reaction was carried out using 2-phenylphenol (3.5 g), t-butyl N-(5-chloro-2-nitrophenyl)-N-methylcarbamate (5.6 g), sodium hydride (55 wt. %, 1.08 g) and anhydrous N,N-dimethylformamide (35 ml) and the reaction mixture was purified to give the title compound (8.3 g).

Thin layer chromatography on a silica gel plate using toluene/ethyl acetate=10/1: Rf=0.56

Reference Example 36 t-Butyl N-[5-(4-hydroxy-2,3-dimethylphenoxy)-2-nitrophenyl]-N-methylcarbamate

In a similar manner to that described in Reference Example 6, a reaction was carried out using 2,3-dimethylhydroquinone (1.38 g), t-butyl N-(5-chloro-2-nitrophenyl)-N-methylcarbamate (2.87 g), sodium hydride (55 wt. %, 0.87 g) and anhydrous N-N-dimethylformamide (20 ml) and the reaction mixture was purified to give the title compound (1.92 g).

Thin layer chromatography on a silica gel plate using n-hexane/ethyl acetate=3/1: Rf=0.35

Reference Example 37 t-Butyl N-methyl-N-[2-nitro-5-(4-phenoxyphenoxy)phenyl]carbamate

In a similar manner to that described in Reference Example 6, a reaction was carried out using 4-phenoxyphenol (4.0 g), t-butyl N-(5-chloro-2-nitrophenyl)-N-methylcarbamate (5.8 g), sodium hydride (55 wt. %, 1.1 g) and anhydrous N,N-dimethylformamide (35 ml) and the reaction mixture was purified to give the title compound (8.6 g).

Thin layer chromatography on a silica gel plate using toluene/isopropyl ether=20/1: Rf=0.41

Reference Example 38 t-Butyl N-[5-(4-hydroxyphenylthio)-2-nitrophenyl] N-methylcarbamate

In a similar manner to that described in Reference Example 6, a reaction was carried out using 4-hydroxythiophenol (1.26 g), t-butyl N-(5-chloro-2-nitrophenyl)-N-methylcarbamate (2.87 g), sodium hydride (55 wt. %, 0.87 g) and anhydrous N,N-dimethylformamide (20 ml) and the reaction mixture was purified to give the title compound (2.86 g).

Thin layer chromatography on a silica gel plate using n-hexane/ethyl acetate=3/1: Rf=0.27

Reference Example 39 t-Butyl N-methyl-N-[2-nitro-5-(3-phenylphenoxy)phenyl]carbamate

In a similar manner to that described in Reference Example 6, a reaction was carried out using 3-phenylphenol (4.0 g), t-butyl N-(5-chloro-2-nitrophenyl)-N-methylcarbamate (6.5 g), sodium hydride (55 wt. %, 1.13 g) and anhydrous N,N-dimethylformamide (35 ml) and the reaction mixture was purified to give the title compound (8.7 g).

Thin layer chromatography on a silica gel plate using n-hexane/ethyl acetate=10/1: Rf=0.22

Reference Example 40 t-Butyl N-[5-(3-t-butyl-4-hydroxyphenoxy)-2-nitrophenyl]-N-methylcarbamate and t-butyl N-[5-(2-t-butyl-4-hydroxyphenoxy)-2-nitrophenyl]-N-methylcarbamate In a similar manner to that described in Reference Example 6 a reaction was carried out using t-butylhydroquinone (1.66 g), t-butyl N-(5-chloro-2-nitrophenyl)-N-methylcarbamate (2.87 g), sodium hydride (55 wt. %, 0.87 g) and anhydrous N,N-dimethylformamide (20 ml) and the reaction mixture was purified by chromatography on a silica gel column using n-hexane/ethyl acetate=4/1 to give t-butyl N-[5-(3-t-butyl-4-hydroxyphenoxy)-2-nitrophenyl]-N-methylcarbamate (1.35 g), of which Rf value was 0.45 in thin layer chromatography on a silica gel plate using n-hexane/ethyl acetate=3/1 and t-butyl N-[5-(2-t-butyl-4-hydroxyphenoxy)-2-nitrophenyl]-N-methylcarbamate (1.11 g), of which Rf value was 0.35 in thin layer chromatography on a silica gel plate using n-hexane/ethyl acetate=3/1.

Reference Example 41 t-Butyl N-methyl-N-[2-nitro-5-(4-phenylphenoxy)phenyl]carbamate

In a similar manner to that described in Reference Example 6, a reaction was carried out using 4-phenylphenol (4.0 g), t-butyl N-(5-chloro-2-nitrophenyl)-N-methylcarbamate (6.5 g), sodium hydride (55 wt. %, 1.13 g) and anhydrous N,N-dimethylformamide (35 ml) and the reaction mixture was purified to give the title compound (5.5 g).

mp 166–167° C.

Reference Example 42 t-Butyl N-[5-(3,5-di-t-butyl-4-hydroxyphenoxy)-2-nitrophenyl]-N-methylcarbamate

In a similar manner to that described in Reference Example 6, a reaction was carried out using 2,6-di-t-butylhydroquinone (4.44 g), t-butyl N-(5-chloro-2-nitrophenyl)-N-methylcarbamate (8.60 g), sodium hydride (55 wt. %, 2.18 g) and anhydrous N,N-dimethylformamide (50 ml) and the reaction mixture was purified to give the title compound (0.60 g).

Thin layer chromatography on a silica gel plate using n-hexane/ethyl acetate=10/1: Rf=0.22

Reference Example 43 t-Butyl N-[5-(4-hydroxy-2,5-dimethylphenoxy)-2-nitrophenyl]N-methylcarbamate

In a similar manner to that described in Reference Example 6, a reaction was carried out using 2,5-dimethylhydroquinone (1.38 g), t-butyl N-(5-chloro-2-nitrophenyl)-N-methylcarbamate (2.87 g), sodium hydride (55 wt. %, 0.87 g) and anhydrous N,N-dimethylformamide (20 ml) and the reaction mixture was purified to give the title compound (1.72 g).

Thin layer chromatography on a silica gel plate using toluene/ethyl acetate=5/1: Rf=0.58

Reference Example 44 t-Butyl N-[2-amino-5-(4-hydroxy-2-methylphenoxy)phenyl]-N-methylcarbamate and t-Butyl N-[2-amino-5-(4-hydroxy-3-methylphenoxy)phenyl]-N-methylcarbamate To a suspension of sodium hydride (55 wt. %, 0.87 g) in N,N-dimethylformamide (20 ml) was added methylhydroquinone (1.24 g). The mixture was stirred at ambient temperature for 15 minutes. To this mixture was added t-butyl N-(5-chloro-2-nitrophenyl)-N-methylcarbamate (2.87 g)in small portions and stirred at 120° C. for 2 hours. The reaction mixture was concentrated and the residue was partitioned between ethyl acetate and water. The ethyl acetate layer was dried over sodium sulfate and concentrated under reduced pressure. The residue was purified by chromatography on a silica gel column using n-hexane/ethyl acetate=3/1 as the eluant to afford a mixture (2.20 g) of t-butyl N-[5-(4-hydroxy-2-methylphenoxy)-2-nitrophenyl]-N-methylcarbamate and t-butyl N-[5-(4-hydroxy-3-methylphenoxy)-2-nitrophenyl]-N-methylcarbamate. A mixture of a solution of the above product and palladium on carbon (10%, 0.21 g) was vigorously stirred at ambient temperature under hydrogen atmosphere for 2 hours. At the end of this time the catalyst was removed by filtration and the filtrate was concentrated to give the title compound (1.88 g).

Thin layer chromatography on a silica gel plate using n-hexane/ethyl acetate=2/1: Rf=0.16

Reference Example 45 t-Butyl N-[5-(4'-benzyloxybiphenyl-4-yloxy)-2-nitrophenyl]-N-methylcarbamate

In a similar manner to that described in Reference Example 6, a reaction was carried out using 4'-benzyloxybiphenyl-4-ol (11.07 g), t-butyl N-(5-chloro-2-nitrophenyl)-N-methylcarbamate (11.5 g), sodium hydride (55 wt. %, 2.2 g) and anhydrous N,N-dimethylformamide/anhydrous tetrahydrofuran/anhydrous toluene=1/1/1 (360 ml) and the reaction mixture was purified to give the title compound (14.75 g).

mp 123–125° C.

Reference Example 46 t-Butyl N-[5-(4-cyanophenoxy)-2-nitrophenyl]-N-methylcarbamate

In a similar manner to that described in Reference Example 6, a reaction was carried out using 4-cyanophenol (5.1 g), t-butyl N-(5-chloro-2-nitrophenyl)-N-methylcarbamate (11.5 g), sodium hydride (55 wt. %, 1.19 g) and anhydrous N,N-dimethylformamide/anhydrous tetrahydrofuran=5/3 (80 ml) and the reaction mixture was purified to give the title compound (8.45 g).

mp 141–143° C.

Reference Example 47

N-Methyl-N-[2-nitro-5-(pentafluorophenoxy)phenyl] amine

To a suspension of sodium hydride (55 wt. %, 1.66 g) in anhydrous N,N-dimethylformamide (50 ml) was added pentafluorophenol (6.38 g). The mixture was stirred at ambient temperature for several minutes. To this mixture was added t-butyl N-(5-chloro-2-nitrophenyl)-N-methylcarbamate (10 g) in small portions and the mixture was stirred at 150° C. for 15 hours. The reaction mixture was concentrated and the residue was partitioned between ethyl acetate and water. The extract was dried over anhydrous sodium sulfate and concentrated under reduced pressure. The residue was purified by chromatography on a silica gel column using n-hexane/toluene=4/1 as the eluant to give the title compound (2.2 g).

Thin layer chromatography on a silica gel plate using n-hexane/toluene=2/1: Rf=0.14

Reference Example 48 t-Butyl N-[2-amino-5-(pyridine-2-ylthio)phenyl]-N-methylcarbamate

In a similar manner to that described in Reference Example 7, a reaction was carried out using t-butyl N-methyl-N-[2-nitro-5-(pyridine-2-ylthio)phenyl] carbamate (1.08 g), palladium on carbon (10%, 1.00 g) and methanol (20 ml) and the reaction mixture was purified to give the title compound (0.78 g).

Thin layer chromatography on a silica gel plate using n-hexane/ethyl acetate=3/2: Rf=0.33

Reference Example 49 t-Butyl N-[2-amino-5-(2-hydroxyphenoxy)phenyl]-N-methylcarbamate

In a similar manner to that described in Reference Example 7, a reaction was carried out using t-butyl N-[5-(2-benzyloxyphenoxy)-2-nitrophenyl]-N-methylcarbamate (4.14 g), palladium on carbon (10%, 0.41 g) and methanol (60 ml) and the reaction mixture was purified to give the title compound (2.89 g).

Thin layer chromatography on a silica gel plate using n-hexane/ethyl acetate=2/1: Rf=0.26

Reference Example 50 t-Butyl N-{5-[4-(1-adamantyl)phenoxy]-2-aminophenyl}-N-methylcarbamate

In a similar manner to that described in Reference Example 7, a reaction was carried out using t-butyl N-{5-[4-(1-adamantyl)phenoxy]-2-nitrophenyl}-N-methylcarbamate (4.28 g), palladium on carbon (10%, 0.42 g) and methanol (60 ml) and the reaction mixture was purified to give the title compound (4.00 g).

Thin layer chromatography on a silica gel plate using n-hexane/ethyl acetate=2/1: Rf=0.49

Reference Example 51 t-Butyl N-[2-amino-5-(3-dimethylaminophenoxy) phenyl]-N-methylcarbamate

In a similar manner to that described in Reference Example 7, a reaction was carried out using t-butyl N-[5-(3-dimethylaminophenoxy)-2-nitrophenyl]-N-methylcarbamate (2.14 g), palladium on carbon (10%, 2.14 g) and methanol (40 ml) and the reaction mixture was purified to give the title compound (1.63 g).

Thin layer chromatography on a silica gel plate using n-hexane/ethyl acetate=2/1: Rf=0.41

Reference Example 52 t-Butyl N-{2-amino-5-[4-(imidazole-1-yl)phenoxy] phenyl}-N-methylcarbamate

In a similar manner to that described in Reference Example 7, a reaction was carried out using t-butyl N-{5-[4-(imidazole-1-yl)phenoxy]-2-nitrophenyl}-N-methylcarbamate (8.8 g), palladium on carbon (10%, 0.8 g) and N,N-dimethylformamide (160 ml) and the reaction mixture was purified to give the title compound (5.7 g).

mp 115–116° C.

Reference Example 53 t-Butyl N-[2-amino-5-(2-phenylphenoxy)phenyl]-N-methylcarbamate

In a similar manner to that described in Reference Example 7, a reaction was carried out using t-butyl N-methyl-N-[2-nitro-5-(2-phenylphenoxy)phenyl] carbamate (8.3 g), palladium on carbon (10%, 0.66 g) and toluene/methanol=7/3 (100 ml) and the reaction mixture was purified to give the title compound (6.9 g).

Thin layer chromatography on a silica gel plate using benzene/ethyl acetate=4/1: Rf=0.30

Reference Example 54 t-Butyl N-[2-amino-5-(4-hydroxy-2,3-dimethylphenoxy)phenyl]-N-methylcarbamate

In a similar manner to that described in Reference Example 7, a reaction was carried out using t-butyl N-[5-(4-hydroxy-2,3-dimethylphenoxy)-2-nitrophenyl]-N-methylcarbamate (1.90 g), palladium on carbon (10%, 0.20 g) and methanol (20 ml) and the reaction mixture was purified to give the title compound (1.61 g).

Thin layer chromatography on a silica gel plate using n-hexane/ethyl acetate=2/1: Rf=0.13

Reference Example 55 t-Butyl N-[2-amino-5-(4-phenoxyphenoxy)phenyl]-N-methylcarbamate

In a similar manner to that described in Reference Example 7, a reaction was carried out using t-butyl N-[2-nitro-5-(4-phenoxyphenoxy)phenyl]-N-methylcarbamate (8.6 g), palladium on carbon (10%, 0.6 g) and toluene/methanol=16/3 (190 ml) and the reaction mixture was purified to give the title compound (7.2 g).

mp 105–106° C.

Reference Example 56 t-Butyl N-[2-amino-5-(4-hydroxyphenylthio) phenyl]-N-methylcarbamate

In a similar manner to that described in Reference Example 7, a reaction was carried out using t-butyl N-[5-(4-hydroxyphenylthio)-2-nitrophenyl]-N-methylcarbamate (2.84 g), palladium on carbon (10%, 1.52 g) and methanol (50 ml) and the reaction mixture was purified to give the title compound (2.37 g).

mp 62–67° C.

Thin layer chromatography on a silica gel plate using n-hexane/ethyl acetate=1/2: Rf=0.59

Reference Example 57 t-Butyl N-[2-amino-5-(3-phenylphenoxy)phenyl]-N-methylcarbamate

In a similar manner to that described in Reference Example 7, a reaction was carried out using t-butyl N-[2-nitro-5-(3-phenylphenoxy)phenyl]-N-methylcarbamate (8.7 g), palladium on carbon (10%, 0.69 g) and toluene/methanol=7/3 (100 ml) and the reaction mixture was purified to give the title compound (6.06 g).

mp 114–115° C.

Reference Example 58 t-Butyl N-[2-amino-5-(3-t-butyl-4-hydroxyphenoxy)phenyl]-N-methylcarbamate

In a similar manner to that described in Reference Example 7, a reaction was carried out using t-butyl N-[5-(3-t-butyl-4-hydroxyphenoxy)-2-nitrophenyl]-N-ethylcarbamate (1.29 g), palladium on carbon (10%, 0.16 g) and methanol (40 ml) and the reaction mixture was purified to give the title compound (1.11 g).

Thin layer chromatography on a silica gel plate using n-hexane/ethyl acetate=2/1: Rf=0.18

Reference Example 59 t-Butyl N-[2-amino-5-(2-t-butyl-4-hydroxyphenoxy)phenyl]-N-methylcarbamate

In a similar manner to that described in Reference Example 7, a reaction was carried out using t-butyl N-[5-(2-t-butyl-4-hydroxyphenoxy)-2-nitrophenyl]-N-methylcarbamate (1.09 g), palladium on carbon (10%, 0.15 g) and methanol (20 ml) and the reaction mixture was purified to give the title compound (0.95 g).

Thin layer chromatography on a silica gel plate using n-hexane/ethyl acetate=2/1: Rf=0.18

Reference Example 60 t-Butyl N-[2-amino-5-(4-phenylphenoxy)phenyl]-N-methylcarbamate

In a similar manner to that described in Reference Example 7, a reaction was carried out using t-butyl N-[2-nitro-5-(4-phenylphenoxy)phenyl]-N-methylcarbamate (5.32 g), palladium on carbon (10%, 0.68 g) and toluene/ethyl acetate=1/1 (140 ml) and the reaction mixture was purified to give the title compound (4.82 g).

mp 122–123° C.

Reference Example 61 t-Butyl N-[2-amino-5-(4-hydroxy-2,5-dimethylphenoxy)phenyl]-N-methylcarbamate

In a similar manner to that described in Reference Example 7, a reaction was carried out using t-butyl N-[5-(4-hydroxy-2,5-dimethylphenoxy)-2-nitrophenyl]-N-methylcarbamate (1.73 g), palladium on carbon (10%, 0.17 g) and methanol (50 ml) and the reaction mixture was purified to give the title compound (1.44 g).

Thin layer chromatography on a silica gel plate using n-hexane/ethyl acetate=2/1: Rf=0.17

Reference Example 62 t-Butyl N-[2-amino-5-(4'-hydroxybiphenyl-4-yloxy)phenyl]-N-methylcarbamate

In a similar manner to that described in Reference Example 7, a reaction was carried out using t-butyl N-[5-(4'-benzyloxybiphenyl-4-yloxy)-2-nitrophenyl]-N-methylcarbamate (14.75 g), palladium on carbon (10%, 0.86 g) and toluene/ethyl acetate=1/1 (140 ml) and the reaction mixture was purified to give the title compound (10.2 g).

mp 89–91° C.

Reference Example 63 t-Butyl N-[2-amino-5-(4-hydroxy-3,5-di-t-butylphenoxy)phenyl]-N-methylcarbamate

In a similar manner to that described in Reference Example 7, a reaction was carried out using t-butyl N-[5-(4-hydroxy-3,5-di-t-butylphenoxy)-2-nitrophenyl]-N-methylcarbamate (0.58 g), palladium on carbon (10%, 0.12 g) and methanol (20 ml) and the reaction mixture was purified to give the title compound (0.55 g).

Thin layer chromatography on a silica gel plate using n-hexane/ethyl acetate=3/1: Rf=0.29

Reference Example 64

[2-amino-5-(4-cyanophenoxy)phenyl]methylamine

A solution of t-butyl N-[5-(4-cyanophenoxy)-2-nitrophenyl]-N-methylcarbamate (3.29 g) and stannous chloride dihydrate (10.06 g) in t-butanol/ethyl acetate=1/9 (100 ml) was stirred at 60° C. for 1 hour. To the mixture was then added sodium borohydride (0.17 g) and then the mixture was stirred at the same temperature for 2.5 hours. The reaction mixture was concentrated and water was added to the residue. This mixture was neutralized with sodium bicarbonate and ethyl acetate was added to the neutralized solution. The mixture was filtered through Celite to remove insoluble material. The ethyl acetate layer was separated and dried over anhydrous sodium sulfate and concentrated under reduced pressure. The residue was purified by chromatography on a silica gel column using n-hexane/ethyl acetate= 3/2 as the eluant to give the title compound (1.49 g).

mp 80–82° C.

Reference Example 65 t-Butyl N-[5-(4-benzoyl-3-hydroxyphenoxy)-2-nitrophenyl]-N-methylcarbamate

In a similar manner to that described in Reference Example 6, a reaction was carried out using 2,4-dihydroxybenzophenone (4.5 g), t-butyl N-(5-chloro-2-nitrophenyl)-N-methylcarbamate (6.0 g), sodium hydride (55 wt. %, 1.75 g) and anhydrous N,N-dimethylformamide (130 ml) and the reaction mixture was purified to give the title compound (2.2 g).

Thin layer chromatography on a silica gel plate using n-hexane/ethyl acetate=5/1: Rf=0.36

Reference Example 66 t-Butyl N-[2-amino-5-(4-benzyl-3-hydroxyphenoxy)phenyl]-N-methylcarbamate

A mixture of a solution of N-[5-(4-benzoyl-3-hydroxyphenoxy)-2-nitrophenyl]-N-methylcarbamate (2.1 g) in methanol/tetrahydrofuran=5/3 (80 ml) and palladium on carbon (20%, 0.5 g) was stirred at ambient temperature under a hydrogen atmosphere for 4 hours. The reaction mixture was filtered to remove the catalyst and the filtrate was concentrated to give the title compound (1.8 g).

Thin layer chromatography on a silica gel plate using n-hexane/ethyl acetate=2/1 Rf=0.26

Reference Example 67 t-Butyl N-methyl-N-[5-(4-methylthiophenoxy)-2-nitrophenyl]carbamate

In a similar manner to that described in Reference Example 6, a reaction was carried out using 4-methylthiophenol (0.98 g), t-butyl N-(5-chloro-2-nitrophenyl)-N-methylcarbamate (2.00 g), sodium hydride (55 wt. %, 0.31 g) and anhydrous N,N-dimethylformamide (60 ml) and the reaction mixture was purified to give the title compound (2.56 g).

Thin layer chromatography on a silica gel plate using n-hexane/ethyl acetate=9/1: Rf=0.17

Reference Example 68 t-Butyl N-methyl-N-[5-(4-methoxyphenoxy)-2-nitrophenyl]carbamate

In a similar manner to that described in Reference Example 6, a reaction was carried out using 4-methoxyphenol (5.0 g), t-butyl N-(5-chloro-2-nitrophenyl)-N-methylcarbamate (10.9 g), sodium hydride (55 wt. %, 2.2 g) and anhydrous N,N-dimethylformamide (120 ml) and the reaction mixture was purified to give the title compound (12.2 g).

Thin layer chromatography on a silica gel plate using n-hexane/ethyl acetate=8/1: Rf=0.32

Reference Example 69 t-Butyl N-methyl-N-[2-nitro-5-(4-trifluoromethylphenoxy)phenyl]carbamate

In a similar manner to that described in Reference Example 6, a reaction was carried out using 4-trifluoromethylphenol (3.0 g), t-butyl N-(5-chloro-2-nitrophenyl)-N-methylcarbamate (4.3 g), sodium hydride (55 wt. %, 1.1 g) and anhydrous N,N-dimethylformamide (70 ml) and the reaction mixture was purified to give the title compound (1.26 g)
mp 92–93° C.

Reference Example 70 t-Butyl N-methyl-N-[5-(4-benzylphenoxy)-2-nitrophenyl]carbamate

In a similar manner to that described in Reference Example 6, a reaction was carried out using 4-benzylphenol (7 g), t-butyl N-(5-chloro-2-nitrophenyl)-N-methylcarbamate (9.15 g), sodium hydride (55 wt. %, 1.74 g) and anhydrous N,N-dimethylformamide (70 ml) and the reaction mixture was purified to give the title compound (12.2 g).

Thin layer chromatography on a silica gel plate using toluene/diisopropyl ether 20/1: Rf=0.40

Reference Example 71 t-Butyl N-methyl-N-[5-(3-benzyloxyphenoxy)-2-nitrophenyl]carbamate

In a similar manner to that described in Reference Example 6, a reaction was carried out using 3-benzyloxyphenol (5 g), t-butyl N-(5-chloro-2-nitrophenyl)-N-methylcarbamate (6 g), sodium hydride (55 wt. %, 1.1 g) and anhydrous N,N-dimethylformamide (40 ml) and the reaction mixture was purified to give the title compound (7.8 g).

Thin layer chromatography on a silica gel plate using n-hexane/ethyl acetate 5/1: Rf=0.32

Reference Example 72 t-Butyl N-[2-amino-5-(4-methylthiophenoxy)phenyl]-N-methylcarbamate

In a similar manner to that described in Reference Example 7, a reaction was carried out using t-butyl N-methyl-N-[5-(4-methylthiophenoxy)-2-nitrophenyl]carbamate (2.53 g), palladium on carbon (10%, 2.5 g) and methanol (55 ml) and the reaction mixture was purified to give the title compound (1.94 g).

Thin layer chromatography on a silica gel plate using n-hexane/ethyl acetate=4/1: Rf=0.15

Reference Example 73 t-Butyl N-[2-amino-5-(4-methoxyphenoxy)phenyl]-N-methylcarbamate

In a similar manner to that described in Reference Example 7, a reaction was carried out using t-butyl N-[5-(4-methoxyphenoxy)-2-nitrophenyl]-N-methylcarbamate (7.2 g), palladium on carbon (10%, 0.5 g) and methanol (100 ml) and the reaction mixture was purified to give the title compound (6.23 g).

Thin layer chromatography on a silica gel plate using n-hexane/ethyl acetate=5/1 Rf=0.18

Reference Example 74 t-Butyl N-[2-amino-5-(4-trifluoromethylphenoxy)phenyl]-N-methylcarbamate

Sodium bicarbonate (4.2 g) and sodium dithionite (3.5 g) were added to a solution of t-butyl N-methyl-N-[5-(4-trifluoromethylphenoxy)-2-nitrophenyl]carbamate in water/dioxane=1/5 (60 ml). The mixture was heated at reflux for 1 hour. At the end of this time the reaction mixture was partitioned between ethyl acetate and water. The ethyl acetate layer was washed with saturated aqueous sodium chloride solution and dried over anhydrous sodium sulfate and then concentrated under reduced pressure. The residue was purified by chromatography on a silica gel column using n-hexane/ethyl acetate=3/1-2/1 as the eluant to give the title compound (0.7 g).

Thin layer chromatography on a silica gel plate using n-hexane/ethyl acetate=4/1: Rf=0.27

Reference Example 75 t-Butyl N-[2-amino-5-(4-benzylphenoxy)phenyl]-N-methylcarbamate

In a similar manner to that described in Reference Example 7, a reaction was carried out using t-butyl N-[5-(4-benzylphenoxy)-2-nitrophenyl]-N-methylcarbamate (12.2 g), palladium on carbon (10%, 0.91 g) and toluene/ethyl acetate=1/1 (140 ml) and the reaction mixture was purified to give the title compound (10.1 g).
mp 114–115° C.

Reference Example 76 t-Butyl N-[2-amino-5-(3-hydroxyphenoxy)phenyl]-N-methylcarbamate

In a similar manner to that described in Reference Example 7, a reaction was carried out using t-butyl N-[5-

(3-hydroxyphenoxy)-2-nitrophenyl]-N-methylcarbamate (7.8 g), palladium on carbon (10%, 0.9 g) and toluene/ethyl acetate=1/1 (140 ml) and the reaction mixture was purified to give the title compound (6 g).

Thin layer chromatography on a silica gel plate using n-hexane/ethyl acetate=1/1: Rf=0.50

Reference Example 77 t-Butyl N-methyl-N-[2-nitro-5-(4-tetrazol-5-ylphenoxy)phenyl]carbamate

A mixture of t-butyl N-[5-(4-cyanophenoxy)-2-nitrophenyl]-N-methylcarbamate (2.95 g), azidotributyltin (7.97 g) and anhydrous toluene (30 ml) was heated at reflux for 23 hours. The reaction mixture was concentrated and then partitioned between ethyl acetate and water. The ethyl acetate layer was dried over anhydrous sodium sulfate and concentrated under reduced pressure. The residue was purified by reversed-phase liquid chromatography using water/acetonitrile=1/1 as the eluant to give the title compound (3.20 g).

mp 81–84° C.

Reference Example 78 t-Butyl N-methyl-N-{2-nitro-5-[4-(2-triphenylmethyltetrazol-5-yl)phenoxy]phenyl}carbamate A mixture of t-butyl N-methyl-N-[2-nitro-5-(4-tetrazol-5-ylphenoxy)phenyl]carbamate (3.22 g), triphenylmethyl chloride (2.18 g), triethylamine (0.79 g), anyhdrous tetrahydrofuran (30 ml) and anhydrous N,N-dimethylformamide was stirred at ambient temperature for 24 hours. The reaction mixture was concentrated and partitioned between ethyl acetate and water. The ethyl acetate layer was dried over anhydrous sodium sulfate and then concentrated under reduced pressure. The residue was purified by chromatography on a silica gel column using n-hexane/ethyl acetate=5/1 as the eluant to give the title compound (3.15 g).

mp 161–163° C.

Reference Example 79 t-Butyl N-methyl-N-{2-amino-5-[4-(2-triphenylmethyltetrazol-5-yl)phenoxy]phenyl}carbamate In a similar manner to that described in Reference Example 7, a reaction was carried out using t-butyl N-methyl-N-{2-nitro-5-[4-(2-triphenylmethyltetrazol-5-yl)phenoxy]phenyl}carbamate (0.98 g), palladium on carbon (10%, 0.13 g) and ethyl acetate (100 ml) and the reaction mixture was purified to give the title compound (0.70 g).

mp 192–193° C.

Reference Example 80

2-Hydroxymethyl-1-methyl-6-pentafluorophenoxy-1H-benzimidazole

A mixture of N-methyl-N-[2-nitro-5-(pentafluorophenoxy)phenyl]amine (2.10 g), palladium on carbon (10%, 0.23 g) and methanol (300 ml) was stirred under a hydrogen atmosphere at ambient temperature for 4 hours. The catalyst was removed by filtration and the filtrate was concentrated. The residue was purified by chromatography on a silica gel column using n-hexane/ethyl acetate= 3/1 as the eluant to give N-[2-amino-5-(pentafluorophenoxy)phenyl]-N-methylamine (1.48 g), of which Rf was 0.26 in thin layer chromatography on a silica gel plate using n-hexane/ethyl acetate=4/1. A mixture of this product, glycolic acid (0.76 g), 4N hydrochloric acid (25 ml) and dioxane (25 ml) was heated at reflux for 16 hours. The reaction mixture was concentrated and water was added to the residue. The mixture was neutralized with sodium bicarbonate and extracted with ethyl acetate. The ethyl acetate layer was dried over anhydrous sodium sulfate and concentrated. The residue was purified by chromatography on a silica gel column using ethyl acetate/methanol=20/1 as the eluant. The product was crystallized from n-hexane under irradiation of ultrasonic wave. The crystals were collected by filtration and washed with n-hexane to give the title compound (1.17 g).

mp 121–128° C.

Reference Example 81

4-cyanophenoxy-2-hydroxymethyl-1-methyl-1H-benzimidazole

A mixture of N-[2-amino-5-(4-cyanophenoxy)phenyl]-N-methylamine (1.08 g), glycolic acid (0.68 g) 4N hydrochloric acid (20 ml) and 1,4-dioxane (20 ml) was heated at reflux for 9 hours. The reaction mixture was concentrated and water was added to the residue. The mixture was neutralized with sodium bicarbonate and extracted with ethyl acetate. The ethyl acetate layer was dried over anhydrous sodium sulfate and then concentrated. The residue was purified by chromatography on a silica gel column using ethyl acetate/methanol=20/1 as the eluant to give the title compound (0.86 g).

mp 183–185° C.

Reference Example 82

5-{4-[6-(4-cyanophenoxy)-1-methyl-1H-benzimidazole-2-ylmethoxy]benzyl}-3-triphenylmethylthiazolidine-2,4-dione A mixture of 4-cyanophenoxy-2-hydroxymethyl-1-methyl-1H-benzimidazole (279 mg), 5-(4-hydroxybenzyl)-3-triphenylmethylthiazolidine-2,4-dione (558 mg), azodicarbonylpiperidine (378 mg), tri-n-butylphosphine (303 mg) and toluene (20 ml) was stirred at ambient temperature for 15 hours. The reaction mixture was purified by chromatography on a silica gel column using n-hexane/ethyl acetate= 1/1 as the eluant to give the title compound (706 mg).

mp 135–138° C.

Reference Example 83

4-Benzyloxy-2,5-di-t-butylphenyl acetate

Benzyl bromide (5.17 g) and potassium carbonate (4.15 g) were added to a solution of 2,5-di-t-butyl-4-hydroxyphenyl acetate (5.3 g) in acetone (40 ml). The mixture was stirred at ambient temperature for 48 hours. The reaction mixture was partitioned between ethyl acetate and water. The ethyl acetate layer was dried over anhydrous sodium sufate and concentrated. The residue was purified by chromatography on a silica gel column using c-hexane/diisopropyl ether= 10/1 as the eluant to give the title compound (4.9 g).

Thin layer chromatography on a silica gel plate using c-hexane/diisopropyl ether=10/1: Rf=0.35

Reference Example 84

4-Benzyloxy-2,5-di-t-butylphenol

To a solution of potassium hydroxide (1.51 g) in methanol (12 ml) was added 4-benzyloxy-2,5-di-t-butylphenyl acetate (4.9 g). The mixture was allowed to stand at ambient temperature overnight. The reaction mixture was neutralized with dilute hydrochloric acid and then extracted with ethyl acetate. The ethyl acetate solution was dried over anhydrous sodium sulfate and evaporated to dryness to give the title compound (4.3 g).

Thin layer chromatography on a silica gel plate using c-hexane/diisopropyl ether=10/1 :Rf=0.44

Reference Example 85 t-Butyl N-[5-(4-benzyloxy-2,5-di-t-butylphenoxy)-2-nitrophenyl]-N-methylcarbamate In a similar manner to that described in Reference Example 6, a reaction was carried out using 4-benzyloxy-2,5-di-t-butylphenol (4.3 g), t-butyl N-(5-chloro-2-nitrophenyl)-N-methylcarbamate (3.51 g), sodium hydride (55 wt. %, 0.72 g) and anhydrous N,N-dimethylformamide (15 ml) and the reaction mixture was purified to give the title compound (7.1 g).

Thin layer chromatography on a silica gel plate using c-hexane/diisopropyl ether=10/1 Rf=0.20

Reference Example 86 t-Butyl N-[2-amino-5-(2,5-di-t-butyl-4-hydroxyphenoxy)phenyl]N-methylcarbamate

In a similar manner to that described in Reference Example 7, a reaction was carried out using t-butyl N-[5-(4-benzyloxy-2,5-di-t-butylphenoxy)-2-nitrophenyl]-N-methylcarbamate (7.1 g), palladium on carbon (10%, 0.7 g) and toluene/methanol/ethyl acetate=16/16/25 (57 ml) and the reaction mixture was purified to give the title compound (3.56 g).

mp 208–210° C.

Reference Example 87

6-(3,5-di-t-butyl-4-hydroxy)phenylthio-2-hydroxymethyl-1-methyl-1H-benzimidazole To a solution of [2-amino-5-(3,5-di-t-butyl-4-hydroxyphenylthio)phenyl]methylamine (11.68 g), which was obtained through hydrogenation and treatment with acid of t-butyl N-[5-(3,5-di-t-butyl-4-hydroxyphenoxy)-2-nitrophenyl]-N-methylcarbamate, in 4N hydrochloric acid (300 ml) was added glycolic acid (7.43 g). The mixture was heated at reflux for 6 hours. The reaction mixture was poured into a mixture of ice and water and neutralized with sodium bicarbonate and extracted with ethyl acetate. The ethyl acetate solution was dried over anhydrous sodium sulfate and concentrated. The residue was purified by chromatography on a silica gel column using ethyl acetate/methanol=20/1 as the eluant to give the title compound (8.66 g).

mp 195–198° C.

Reference Example 88

4-[6-(3,5-di-t-butyl-4-hydroxyphenylthio)-1-methyl-1H-benzimidazole-2-ylmethoxy]benzaldehyde A mixture of 6-(3,5-di-t-butyl-4-hydroxy)phenylthio-2-hydroxymethyl-1-methyl-1H-benzimidazole (5.33 g), 4-hydroxybenzaldehyde (2.22 g), 1,1'-(azodicarbonyl)dipiperidine (4.59 g), tri-n-butylphosphine (3.68 g) and anhydrous toluene (300 ml) was stirred at ambient temperature for 64 hours. The reaction mixture was concentrated. The residue was purified by chromatography on a silica gel column using n-hexane/ethyl acetate=1/1 as the eluant to give the title compound (3.74 g).

mp 219–221° C.

Reference Example 89 t-Butyl N-[5-(4-t-butoxycarbonylaminophenoxy)-2-nitrophenyl]-N-methylcarbamate

In a similar manner to that described in Reference Example 6, a reaction was carried out using t-butyl (4-hydroxyphenyl)carbamate (15.6 g), t-butyl N-(5-chloro-2-nitrophenyl)-N-methylcarbamate (21 g), sodium hydride (55 wt. %, 3.22 g) and anhydrous N,N-dimethylformamide (130 ml) and the reaction mixture was purified to give the title compound (27.7 g).

Thin layer chromatography on a silica gel plate using toluene/diisopropyl ether=10/1 : Rf=0.33

Reference Example 90 t-Butyl N-[2-amino-5-(4-t-butoxycarbonylaminophenoxy)phenyl]-N-methylcarbamate

In a similar manner to that described in Reference Example 7, a reaction was carried out using t-butyl N-[5-(4-t-butoxycarbonylaminophenoxy)-2-nitrophenyl]-N-methylcarbamate (27.7 g), palladium on carbon (10%, 1.07 g) and tetrahydrofuran/ethyl acetate=9/8 (170 ml) and the reaction mixture was purified to give the title compound (26.2 g).

Thin layer chromatography on a silica gel plate using c-hexane/tetrahydrofuran=2/1: Rf=0.37

Reference Example 91 t-Butyl N-{5-[4-(t-butoxycarbonyl-n-hexylamino)phenoxy]-2-nitrophenyl}-N-methylcarbamate To a suspension of sodium hydride (55 wt. %, 1.26 g) in anhydrous N,N-dimethylformamide (100 ml) was added N-[5-(4-t-butoxycarbonylaminophenoxy)-2-nitrophenyl]-N-methylcarbamate (12.1 g). The mixture was stirred at ambient temperature for several minutes. To the mixture was added hexyl bromide (6.5 g) under ice cooling and the mixture was stirred at the same temperature for 30 minutes and then at room temperature for 1.0 hour. The reaction mixture was concentrated and the residue was partitioned between ethyl acetate and water. The ethyl acetate layer was dried over anhydrous sodium sulfate and concentrated. The residue was purified by chromatography on a silica gel column using toluene/diisopropyl ether=100/7 as the eluant to give the title compound (13.8 g).

Thin layer chromatography on a silica gel plate using toluene/diisopropyl ether=100/7: Rf=0.32

Reference Example 92 t-Butyl N-{2-amino-5-[4-(t-butoxycarbonyl-n-hexylamino)phenoxy]phenyl}-N-methylcarbamate In a similar manner to that described in Reference Example 7, a reaction was carried out using t-butyl N-{5-[4-(t-butoxycarbonyl-n-hexylamino)phenoxy]-2-nitrophenyl}-N-methylcarbamate (13.8 g), palladium on carbon (10%, 1.0 g) and toluene/ethyl acetate=1/1 (140 ml) and the reaction mixture was purified to give the title compound (13.1 g).

Thin layer chromatography on a silica gel plate using toluene/ethyl acetate=3/1: Rf=0.44

Pharmacological Test Example 1

Anti-lipid-peroxide Action

The inhibitory effect of the invention compound against the production of lipid peroxide was conducted using rat hepatic microsome.

To 400 μl of a 1:2 mixture of a buffer [a 0.1M aqueous tris(hydroxymethyl)aminomethane solution adjusted to pH 7.4 by hydrochloric acid] and a 0.15M aqueous potassium chloride solution were added 5 μl of a solution of a predetermined concentration of the test compound in dimethyl sulfoxide, and 100 μl of hepatic microsome prepared from Wister rat (10 week old), followed by stirring at 37° C. for 5 minutes. To initiate the reaction of said mixture, 10 μl of a 1:1 mixed solution of a 0.5 mM aqueous solution of ferrous sulfate 7 hydrate and a 50 mM aqueous cysteine solution was added and the resulting mixture was stirred at 37° C. for 30 minutes. 1 ml of a 10% aqueous solution of trichloroacetic acid was added to the reaction mixture to terminate the reaction. The reaction mixture was centrifuged at 3000 rpm at 5° C. for 10 minutes and the supernatant was separated. To 1.0 ml of the supernatant, 1.0 ml of 50% aqueous acetic acid containing 0.67% of thiobarbituric acid was added and the mixture was boiled at 100° C. for 15 minutes. After the resulting mixture was allowed to stand at room temperature for 15 minutes, the absorbance at the wavelength of 535 nm was measured. From the absorbance of the control measured without the test compound and that of the test compounds of a predetermined concentration, an inhibition rate (%) was determined and the 50% inhibition concentration of the test compound against lipid peroxide was determined. The results are shown in Table 11.

TABLE 11

| Compound No. of Example | IC$_{50}$ (μg/ml) |
| --- | --- |
| 1-2a | 0.97 |
| 2-2a | 0.54 |
| 4-2a | 0.83 |
| 5b | 1.3 |
| 7-2a | 0.65 |
| 8-2b | 3.2 |

From the above results, it has been found that the compounds of the present invention exhibit excellent anti-lipid-peroxide action.

Pharmacological Test Example 2

5-Lipoxygenase Inhibitory Action

Into 5 μl of a solution of the test compound in dimethylsulfoxide, 750 μl of a 1/15M phosphate buffer (pH 7.4) which was prepared by dissolving a wrapper of phosphate buffer powder (Yatron) in 10 ml of water, 40 μl of a 30 mM aqueous calcium chloride solution, 50 μl of a 20 mM aqueous GSH (glutathione, reduced form) solution, 50 μl of a 40 mM aqueous ATP (adenosine-5-triphosphate) solution and 100 μl of guinea pig polymorphonuclear leukocyte enzyme were added, followed by stirring at 25° C. for 5 minutes. To initiate the reaction, 5 μl of arachidic acid (10 mg/ml ethanol) were added to said mixture and the mixture was stirred at 25° C. for 5 minutes. 50 μl of 2N hydrochloric acid were added to the reaction mixture to terminate the reaction. 2.0 ml of ethyl acetate containing an internal standard substance (internal standard substance: 2 μg/ml of isoamyl paraben) were then added to the reaction mixture. The resulting mixture was extracted for 1 minute by a mixer, followed by centrifugal separation at 3000 rpm for 5 minutes. The ethyl acetate layer was separated, evaporated to dryness under reduced pressure and then dissolved in 200 μl of acetonitrile. By high-performance liquid chromatography, the amount of 5-HETE formed was determined. From the determination of 5-HETE of the control without the test compounds and that of the test compounds, an inhibition rate (%) was found and the 50% inhibition concentration of the test compounds against 5-lipoxygenase was determined. The results are shown in Table 12.

TABLE 12

| Example No. | IC$_{50}$ (μg/ml) |
| --- | --- |
| 1-2a | 0.59 |
| 2-2a | 0.10 |
| 4-2a | 0.20 |
| 5b | 0.53 |

From the above results, it has been found that the compounds according to the present invention exhibit excellent 5-lipoxygenase inhibitory action.

Pharmacological Test Example 3

Hypoglycemic Action

The blood sample was collected from the caudal vein of each of KK mice (4–5 month old) which developed diabetes and its blood sugar level was measured. The mice were then classified into groups (4 mice per group) so that they would be equal in the average of the blood sugar levels of the mice. For three days, powdery food (F-1, produced by Funabashi Farm) adjusted to contain the test compound in an amount of 0.01% was administered to mice. The mouse group to which the test compound was administered refers to "the medicine administered group", while that to which the powdery food free of the test compound was administered refers to "the control". After three days, the blood sample was collected from the caudal vein of each of the mice and the glucose concentration in the plasma obtained by centrifugal separation was measured by a glucose analyzer ("Glucoroder", A&T Inc.). The blood-sugar lowering rate was calculated from the following equation:

Blood sugar lowering rate (%)=(average blood sugar level of the control−average blood sugar level of the medicine administered group)×100/the blood sugar level of the control

TABLE 13

| Example No. | Blood sugar lowering rate (%) |
| --- | --- |
| 1-2b | 48.1 |
| 2-2b | 49.2 |
| 3-2 | 60.1 |
| 4-2a | 67.5 |
| 6-2 | 62.6 |
| 7-2a | 71.7 |
| 13-2b | 68.1 |
| 19-2 | 66.8 |
| 34-2b | 71.2 |
| 40 | 66.4 |
| 51 | 63.6 |

From the above results, it has been found that the compounds of the present invention exhibit excellent hypoglycemic action.

What is claimed is:

1. A substituted fused heterocyclic compound represented by the following formula (I):

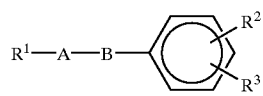
(I)

wherein:

$R^1$ represents a group selected from the following formulae (II) and (III):

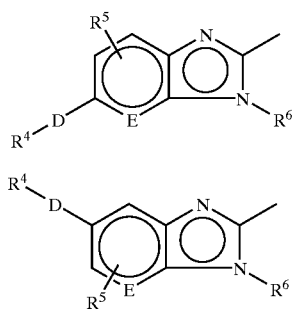
(II)

(III)

in which:

$R^4$ is selected from the group consisting of phenyl groups which are substituted with 1 to 5 substituents selected from Substituents α defined below and pyridyl groups which may be substituted with 1 to 4 substituents selected from Substituents α defined below;

$R^5$ is selected from the group consisting of hydrogen atoms and Substituents α defined below;

$R^6$ is selected from the group consisting of hydrogen atoms, $C_{1-6}$ alkyl groups, $C_{6-10}$ aryl groups which may be substituted with 1 to 3 substituents selected from Substituents β defined below and $C_{7-16}$ aralkyl groups which may be substituted with 1 to 3 substituents selected from Substituents β defined below;

D represents is selected from the group consisting of oxygen and sulfur atoms; and E is selected from the group consisting of CH groups and nitrogen atoms;

$R^2$ is selected from the group consisting of hydrogen atoms and Substituents α defined below;

$R^3$ represents a group selected from the following formulae (IV-1) to (IV-5) or a tautomer thereof in the case of (IV-2), (IV-3) or (IV4):

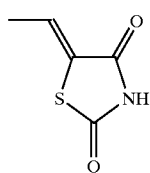
(IV-1)

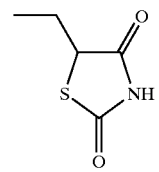
(IV-2)

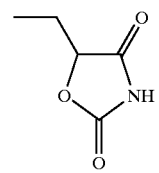
(IV-3)

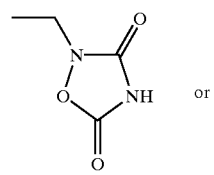
(IV-4) or

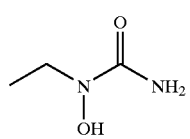
(IV-5)

A represents a $C_{1-6}$ alkylene group;

B is selected from the group consisting of oxygen and sulfur atoms;

Substituents α are selected from the group consisting of halogen atoms, hydroxyl groups, $C_{1-6}$ alkyl groups, halogeno($C_{1-6}$ alkyl) groups, $C_{1-6}$ alkoxy groups, $C_{1-6}$ alkylthio groups, amino groups which may be substituted with substituents selected from Substituents γ defined below, $C_{3-10}$ cycloalkyl, $C_{6-10}$ aryl, $C_{7-16}$ aralkyl, $C_{6-10}$ aryloxy, $C_{7-16}$ aralkyloxy and $C_{6-10}$ arylthio groups each of which may be substituted with 1 to 3 substituents selected from Substituents β defined below, $C_{1-7}$ aliphatic acyloxy groups, 4- to 7-membered saturated nitrogen-containing heterocyclic groups, 5- or 6-membered aromatic nitrogen-containing heterocyclic groups, nitro groups, and cyano groups;

Substituents β are selected from the group consisting of halogen atoms, hydroxyl groups, $C_{1-6}$ alkyl groups, halogeno($C_{1-6}$ alkyl) groups, $C_{1-6}$ alkoxy groups, amino groups which may be substituted with substituents selected from Substituents γ defined below, $C_{6-10}$ aryl groups and nitro groups; and Substituents γ are selected from the group consisting of $C_{1-10}$ alkyl groups, $C_{6-10}$ aryl and $C_{7-16}$ aralkyl groups (each of which may have 1 to 3 substituents selected from the group consisting of halogen atoms and hydroxyl, $C_{1-6}$ alkyl, halogeno($C_{1-6}$ alkyl), $C_{1-6}$ alkoxy and $C_{1-6}$ alkylthio groups) and acyl groups (said acyl group is selected from the group consisting of $C_{1-7}$ aliphatic acyl groups and $C_{7-11}$ aromatic acyl, $C_{8-12}$ aromatic aliphatic acyl, $C_{4-11}$ cycloalkylcarbonyl and 5- or 6-membered aromatic nitrogen-containing heterocyclic carbonyl groups, each of which may have 1 to 3 substituents selected from the group consisting of halogen atoms and hydroxyl, $C_{1-6}$ alkyl, halogeno($C_{1-6}$ alkyl), $C_{1-6}$ alkoxy and $C_{1-6}$ alkylthio groups);

with the proviso that 5-{4-[5-(3,5-di-t-butyl-4-hydroxyphenylthio)-3-methyl-3H-imidazo[4,5-b]pyridin-2-ylmethoxy]benzyl}thiazolidine-2,4-dione is excluded;

or a pharmacologically acceptable salt or prodrug of said compound of the formula (I).

2. A substituted fused heterocyclic compound or a pharmacologically acceptable salt thereof according to claim 1, wherein $R^1$ represents a group of formula (II).

3. A substituted fused heterocyclic compound or a pharmacologically acceptable salt thereof according to claim 1, wherein $R^2$ and $R^5$ are the same or different and each is independently selected from the group consisting of hydrogen atoms, halogen atoms, hydroxyl groups, $C_{1-6}$ alkyl groups, halogeno($C_{1-6}$ alkyl) groups, $C_{1-6}$ alkoxy groups, $C_{1-6}$ alkylthio groups and amino groups which may be substituted with substituents selected from Substituents γ as defined in claim 1.

4. A substituted fused heterocyclic compound or a pharmacologically acceptable salt thereof according to claim 1, wherein $R^2$ and $R^5$ are the same or different and each is independently selected from the group consisting of hydrogen atoms, fluorine atoms, chlorine atoms, hydroxyl groups, methyl groups, ethyl groups, trifluoromethyl groups, methoxy groups, methylthio groups and amino groups.

5. A substituted fused heterocyclic compound or a pharmacologically acceptable salt thereof according to claim 1, wherein $R^2$ and $R^5$ each represent a hydrogen atom.

6. A substituted fused heterocyclic compound or a pharmacologically acceptable salt thereof according to claim 1, wherein $R^3$ represents a group selected from formulae (IV-1) to (IV-3), or a tautomer thereof in the case of (IV-2) and (IV-3).

7. A substituted fused heterocyclic compound or a pharmacologically acceptable salt thereof according to claim 1, wherein $R^3$ represents a group selected from formulae (IV-2) and (IV-3), or a tautomer thereof.

8. A substituted fused heterocyclic compound or a pharmacologically acceptable salt thereof according to claim 1, wherein $R^3$ represents a group of formula (IV-2), or a tautomer thereof.

9. A substituted fused heterocyclic compound or a pharmacologically acceptable salt thereof according to claim 1, wherein $R^4$ represents a pyridyl group which may be substituted with one substituent selected from the group consisting of halogen atoms, hydroxyl groups, $C_{1-6}$ alkyl groups, halogeno($C_{1-6}$ alkyl) groups, $C_{1-6}$ alkoxy groups, $C_{1-6}$ alkylthio groups, amino groups which may be substituted with substituents selected from Substituents γ as defined in claim 1, and nitro groups.

10. A substituted fused heterocyclic compound or a pharmacologically acceptable salt thereof according to claim 1, wherein $R^4$ represents a pyridyl group which may be substituted with one substituent selected from the group consisting of fluorine atoms, chlorine atoms, hydroxyl groups, methyl groups, ethyl groups, t-butyl groups, trifluoromethyl groups, methoxy groups, methylthio groups, amino groups, methylamino groups, dimethylamino groups and nitro groups.

11. A substituted fused heterocyclic compound or a pharmacologically acceptable salt thereof according to claim 1, wherein $R^4$ represents a pyridyl group.

12. A substituted fused heterocyclic compound or a pharmacologically acceptable salt thereof according to claim 1, wherein $R^4$ represents a phenyl group substituted with at least one substituent selected from the group consisting of $C_{3-10}$ cycloalkyl, $C_{6-10}$ aryl and $C_{7-16}$ aralkyl groups, each of which may be substituted with 1 to 3 substituents selected from Substituents β as defined in claim 1, 4- to 7-membered saturated nitrogen-containing heterocyclic groups and 5- or 6-membered aromatic nitrogen-containing heterocyclic groups.

13. A substituted fused heterocyclic compound or a pharmacologically acceptable salt thereof according to claim 1, wherein $R^4$ represents a phenyl group substituted with one substituent selected from the group consisting of $C_{3-10}$ cycloalkyl, $C_{6-10}$ aryl and $C_{7-16}$ aralkyl groups which may be substituted with 1 substituent selected from Substituents β as defined in claim 1, 4- to 7-membered saturated nitrogen-containing heterocyclic groups and 5- or 6-membered aromatic nitrogen-containing heterocyclic groups.

14. A substituted fused heterocyclic compound or a pharmacologically acceptable salt thereof according to claim 1, wherein $R^4$ represents a phenyl group substituted with one substituent selected from the group consisting of $C_{3-10}$ cycloalkyl, $C_{6-10}$ aryl and $C_{7-16}$ aralkyl groups which may be substituted with one substituent selected from the group consisting of halogen atoms, hydroxyl groups, $C_{1-6}$ alkyl groups, halogeno($C_{1-6}$ alkyl) groups, $C_{1-6}$ alkoxy groups and amino groups (wherein said amino groups may be substituted with substituents selected from Substituents γ as defined in claim 1), 4- to 7-membered saturated nitrogen-containing heterocyclic groups and 5- or 6-membered aromatic nitrogen-containing heterocyclic groups.

15. A substituted fused heterocyclic compound or a pharmacologically acceptable salt thereof according to claim 1, wherein $R^4$ represents a phenyl group substituted with one substituent selected from the group consisting of phenyl and benzyl groups which may be substituted with one substituent selected from the group consisting of halogen atoms, hydroxyl groups, $C_{1-6}$ alkyl groups, halogeno($C_{1-6}$ alkyl) groups, $C_{1-6}$ alkoxy groups and amino groups (wherein said amino groups may be substituted with a substituent selected from Substituents γ as defined in claim 1), adamantyl groups, pyrrolidinyl groups, morpholinyl groups, piperidinyl groups, imidazolyl groups, tetrazolyl groups and pyridinyl groups.

16. A substituted fused heterocyclic compound or a pharmacologically acceptable salt thereof according to claim 1, wherein $R^4$ represents a phenyl group substituted with one substituent selected from the group consisting of phenyl and benzyl groups which may be substituted with one substituent selected from the group consisting of fluorine atoms, chlorine atoms, hydroxyl groups, methyl groups, ethyl groups, t-butyl groups, trifluoromethyl groups, methoxy groups, amino groups, methylamino groups and dimethylamino groups, adamantyl groups, pyrrolidinyl groups, morpholinyl groups, piperidinyl groups, imidazolyl groups, tetrazolyl groups and pyridinyl groups.

17. A substituted fused heterocyclic compound or a pharmacologically acceptable salt thereof according to claim 1, wherein $R^4$ represents a substituent selected from the group consisting of 4-biphenylyl, 4-benzylphenyl, 4'-hydroxybiphenylyl, (pyrrolidin-1-yl)phenyl, (morpholin-4-yl)-phenyl, (piperidin-1-yl)phenyl, (pyridin-2-yl)phenyl, (pyridin-3-yl)phenyl and 4-(1-adamantyl)phenyl groups.

18. A substituted fused heterocyclic compound or a pharmacologically acceptable salt thereof according to claim 1, in which $R^4$ is a phenyl group which is substituted with one acylamino group, wherein said amino moiety may be further substituted with a substituent selected from Substituents γ as defined in claim 1, and said phenyl group may be further substituted with 1 to 3 substituents selected from the group consisting of halogen atoms and hydroxyl, $C_{1-6}$ alkyl, halogeno($C_{1-6}$ alkyl), $C_{1-6}$ alkoxy and $C_{1-6}$ alkylthio groups.

19. A substituted fused heterocyclic compound or a pharmacologically acceptable salt thereof according to claim 1, in which $R^4$ is a phenyl group which is substituted with one acylamino group, wherein said amino moiety may be further substituted with a substituent selected from Substituents γ as defined in claim 1, and said phenyl group may be further substituted with 1 to 3 substituents selected from the group consisting of halogen atoms and $C_{1-6}$ alkyl groups.

20. A substituted fused heterocyclic compound or a pharmacologically acceptable salt thereof according to claim 1, in which $R^4$ is a phenyl group which is substituted with one acylamino group, wherein said amino moiety may be further substituted with a substituent selected from the group consisting of $C_{1-10}$ alkyl groups and $C_{7-12}$ aralkyl groups which may have 1 to 3 substituents selected from the group consisting of halogen atoms and hydroxyl, $C_{1-6}$ alkyl, halogeno($C_{1-6}$ alkyl), $C_{1-6}$ alkoxy and $C_{1-6}$ alkylthio groups, and said phenyl group may be further substituted with 1 to 3 $C_{1-6}$ alkyl groups.

21. A substituted fused heterocyclic compound or a pharmacologically acceptable salt thereof according to claim 1, wherein $R^4$ is a phenyl group which is substituted with one substituent selected from the group consisting of $C_{7-11}$ aromatic acylamino, $C_{4-11}$ cycloalkyl-carbonylamino and 5- or 6-membered aromatic nitrogen-containing heterocyclic carbonylamino groups which may have 1 to 3 substituents selected from the group consisting of halogen atoms and hydroxyl, $C_{1-6}$ alkyl, halogeno($C_{1-6}$ alkyl), $C_{1-6}$ alkoxy and $C_{1-6}$ alkylthio groups.

22. A substituted fused heterocyclic compound or a pharmacologically acceptable salt thereof according to claim 1, wherein $R^4$ is a phenyl group substituted with a substituent selected from the group consisting of benzoylamino, 3-chlorobenzoylamino, 2,4-difluorobenzoylamino, 4-hydroxy-3,5-di-t-butylbenzoylamino, naphthoylamino, cyclopentanoylamino, cyclohexanoylamino, nicotinoylamino, isonicotinoylamino, N-acetyl-N-hexylamino and adamantylcarbonylamino groups.

23. A substituted fused heterocyclic compound or a pharmacologically acceptable salt thereof according to claim 1, wherein $R^4$ is a phenyl group which is substituted with one substituent selected from the group consisting of amino groups, amino groups substituted with 1 or 2 substituents (said substituents are the same or different and each is selected from the group consisting of $C_{1-10}$ alkyl groups and $C_{6-10}$ aryl and $C_{7-16}$ aralkyl groups which may have 1 to 3 substituents selected from the group consisting of halogen atoms and hydroxyl, $C_{1-6}$ alkyl, halogeno($C_{1-6}$ alkyl), $C_{1-6}$ alkoxy and $C_{1-6}$ alkylthio groups), nitro groups and cyano groups, and said phenyl group may be further substituted with 1 to 3 substituents selected from the group consisting of halogen atoms and hydroxyl, $C_{1-6}$ alkyl, halogeno($C_{1-6}$ alkyl), $C_{1-6}$ alkoxy and $C_{1-6}$ alkylthio groups.

24. A substituted fused heterocyclic compound or a pharmacologically acceptable salt thereof according to claim 1, wherein $R^4$ is a phenyl group which is substituted with one substituent selected from the group consisting of amino groups, mono- and di-$C_{1-10}$ alkylamino groups, and cyano groups, and said phenyl group may be further substituted with 1 or 2 $C_{1-6}$ alkyl groups.

25. A substituted fused heterocyclic compound or a pharmacologically acceptable salt thereof according to claim 1, wherein $R^4$ is selected from the group consisting of 4-aminophenyl, 4-amino-3,5-dimethylphenyl, 4-amino-3,5-di-t-butylphenyl, 3-dimethylaminophenyl, 4-dimethylaminophenyl and 4-cyanophenyl groups.

26. A substituted fused heterocyclic compound or a pharmacologically acceptable salt thereof according to claim 1, wherein $R^4$ is a phenyl group which is substituted with one substituent selected from the group consisting of $C_{6-10}$ aryloxy, $C_{7-16}$ aralkyloxy and $C_{6-10}$ arylthio groups each of which may be substituted with 1 to 3 substituents selected from Substituents β as defined in claim 1, and said phenyl group may be further substituted with 1 to 3 substituents selected from the group consisting of halogen atoms and hydroxyl, $C_{1-6}$ alkyl, halogeno($C_{1-6}$ alkyl), $C_{1-6}$ alkoxy and $C_{1-6}$ alkylthio groups.

27. A substituted fused heterocyclic compound or a pharmacologically acceptable salt thereof according to claim 1, wherein $R^4$ is a phenyl group which is substituted with a $C_{6-10}$ aryloxy group which may be substituted with 1 to 3 substituents selected from Substituents β as defined in claim 1, and said phenyl group may be further substituted with 1 or 2 $C_{1-6}$ alkyl groups.

28. A substituted fused heterocyclic compound or a pharmacologically acceptable salt thereof according to claim 1, wherein $R^4$ is a phenyl group substituted with one $C_{6-10}$ aryloxy group which may be substituted with one substituent selected from Substituents β as defined in claim 1.

29. A substituted fused heterocyclic compound or a pharmacologically acceptable salt thereof according to claim 1, wherein $R^4$ is a 4-phenoxyphenyl group.

30. A substituted fused heterocyclic compound or a pharmacologically acceptable salt thereof according to claim 1, wherein $R^4$ is a phenyl group substituted with 1 to 5 substituents selected from the group consisting of halogen atoms and hydroxyl, $C_{1-6}$ alkyl, halogeno($C_{1-6}$ alkyl), $C_{1-6}$ alkoxy, $C_{1-6}$ alkylthio and $C_{1-7}$ aliphatic acyloxy groups.

31. A substituted fused heterocyclic compound or a pharmacologically acceptable salt thereof according to claim 1, wherein $R^4$ is a phenyl group which is substituted with one substituent selected from the group consisting of halogen atoms, hydroxyl groups, $C_{1-6}$ alkyl groups, halogeno($C_{1-6}$ alkyl) groups, $C_{1-6}$ alkoxy groups, $C_{1-6}$ alkylthio groups and $C_{1-7}$ aliphatic acyloxy groups, and said phenyl group may be further substituted with 1 to 4 substituents selected from the group consisting of halogen atoms and $C_{1-6}$ alkyl and halogeno($C_{1-6}$ alkyl) groups.

32. A substituted fused heterocyclic compound or a pharmacologically acceptable salt thereof according to claim 1, wherein $R^4$ is a phenyl group substituted with one substituent selected from the group consisting of $C_{1-6}$ alkyl, halogeno($C_{1-6}$ alkyl), $C_{1-6}$ alkoxy and $C_{1-6}$ alkylthio groups or with 1 to 5 halogen atoms.

33. A substituted fused heterocyclic compound or a pharmacologically acceptable salt thereof according to claim 1, wherein $R^4$ is a phenyl group substituted with one substituent selected from the group consisting of halogeno($C_{1-2}$ alkyl), $C_{1-2}$ alkoxy and $C_{1-2}$ alkylthio groups or with 1 to 5 fluorine atoms or chlorine atoms.

34. A substituted fused heterocyclic compound or a pharmacologically acceptable salt thereof as claimed in claim 1, wherein $R^4$ is selected from the group consisting of 4-trifluoromethylphenyl, 4-methylthiophenyl, 4-methoxyphenyl and pentafluorophenyl groups.

35. A substituted fused heterocyclic compound or a pharmacologically acceptable salt thereof according to claim 1, wherein $R^4$ is a phenyl group which is substituted with one substituent selected from the group consisting of hydroxyl and $C_{1-7}$ aliphatic acyloxy groups, and said phenyl group may be further substituted with 1 to 3 substituents selected from the group consisting of halogen atoms and $C_{1-6}$ alkyl groups.

36. A substituted fused heterocyclic compound or a pharmacologically acceptable salt thereof according to claim 1, wherein $R^4$ is a phenyl group which is substituted with one hydroxyl group, and said phenyl group may be further substituted with 1 to 3 substituents selected from the group consisting of halogen atoms and $C_{1-6}$ alkyl groups.

37. A substituted fused heterocyclic compound or a pharmacologically acceptable salt thereof according to claim 1, wherein $R^4$ is a phenyl group which is substituted with one hydroxyl group, and said phenyl group may be further substituted with 1 to 3 substituents selected from the group consisting of fluorine and chlorine atoms and methyl and t-butyl groups.

38. A substituted fused heterocyclic compound or a pharmacologically acceptable salt thereof according to claim 1, wherein $R^4$ is selected from the group consisting of 4-hydroxyphenyl, 4-hydroxy-3,5-dimethylphenyl, 4-hydroxy-3,5-di-t-butylphenyl, 4-hydroxy-2,3,5-trimethylphenyl and 2-chloro-4-hydroxy-3,5-dimethylphenyl groups.

39. A substituted fused heterocyclic compound or a pharmacologically acceptable salt thereof according to claim 1, wherein $R^6$ is selected from the group consisting of hydrogen atoms, $C_{1-6}$ alkyl groups, and phenyl and benzyl groups which may be substituted with 1 to 3 substituents selected from the group consisting of halogen atoms and hydroxyl, $C_{1-6}$ alkyl and halogeno($C_{1-6}$ alkyl) groups.

40. A substituted fused heterocyclic compound or a pharmacologically acceptable salt thereof according to claim 1, wherein $R^6$ is selected from the group consisting of hydrogen atoms, $C_{1-4}$ alkyl groups, and phenyl and benzyl groups which may be substituted with one substituent selected from the group consisting of fluorine atoms, chlorine atoms, hydroxyl groups, methyl groups and ethyl groups.

41. A substituted fused heterocyclic compound or a pharmacologically acceptable salt thereof according to claim 1, wherein $R^6$ is selected from the group consisting of hydrogen atoms and $C_{1-4}$ alkyl groups.

42. A substituted fused heterocyclic compound or a pharmacologically acceptable salt thereof according to claim 1, wherein $R^6$ is a $C_{1-2}$ alkyl group.

43. A substituted fused heterocyclic compound or a pharmacologically acceptable salt thereof according to claim 1, wherein $R^6$ is a methyl group.

44. A substituted fused heterocyclic compound or a pharmacologically acceptable salt thereof according to claim 1, wherein A is a $C_{1-4}$ alkylene group.

45. A substituted fused heterocyclic compound or a pharmacologically acceptable salt thereof according to claim 1, wherein A is a $C_{1-2}$ alkylene group.

46. A substituted fused heterocyclic compound or a pharmacologically acceptable salt thereof according to claim 1, wherein A is a methylene group.

47. A substituted fused heterocyclic compound or a pharmacologically acceptable salt thereof according to claim 1, wherein B is an oxygen atom.

48. A substituted fused heterocyclic compound or a pharmacologically acceptable salt thereof according to claim 1, wherein D is an oxygen atom.

49. A substituted fused heterocyclic compound or a pharmacologically acceptable salt thereof according to claim 1, wherein D is a sulfur atom.

50. A substituted fused heterocyclic compound or a pharmacologically acceptable salt thereof according to claim 1, wherein E is a CH group.

51. A substituted fused heterocyclic compound according to claim 1, which is 5-{4-[6-(4-hydroxy-3,5-dimethylphenoxy)-1-methyl-1H-benzimidazol-2-ylmethoxy]benzyl}thiazolidine-2,4-dione.

52. A substituted fused heterocyclic compound according to claim 1, selected from the following group of compounds and their pharmacologically acceptable salts:

5-{4-[6-(4-hydroxyphenoxy)-1-methyl-1H-benzimidazol-2-ylmethoxy]benzyl}thiazolidine-2,4-dione, 5-{4-[1-methyl-6-(4-trifluoromethylphenoxy)-1H-benzimidazol-2-ylmethoxy]benzyl}thiazolidine-2,4-dione, 5-{4-[1-methyl-6-(4-methoxyphenoxy)-1H-benzimidazol-2-ylmethoxy]benzyl}thiazolidine-2,4-dione, 5-{4-[1-methyl-6-(4-methylthiophenoxy)-1H-benzimidazol-2-ylmethoxy]benzyl}thiazolidine-2,4-dione, 5-{4-[6-(4-aminophenoxy)-1-methyl-1H-benzimidazol-2-ylmethoxy]benzyl}thiazolidine-2,4-dione, 5-{4-[6-(3-dimethylaminophenoxy)-1-methyl-1H-benzimidazol-2-ylmethoxy]benzyl}thiazolidine-2,4-dione, 5-{4-[6-(4-acetylaminophenoxy)-1-methyl-1H-benzimidazol-2-ylmethoxy]benzyl}thiazolidine-2,4-dione, 5-{4-[1-methyl-6-(4-phenylphenoxy)-1H-benzimidazol1-2-ylmethoxy]benzyl}thiazolidine-2,4-dione, 5-{4-[6-(4'-hydroxybiphenyl-4-yloxy)-1-methyl-1H-benzimidazol-2-ylmethoxy]benzyl}thiazolidine-2,4-dione, 5-{4-[6-(4-benzylphenoxy)-1-methyl-1H-benzimidazol-2-ylmethoxy]benzyl}thiazolidine-2,4-dione, 5-{4-(6-[2-(pyrrolidin-1-yl)phenoxy]-1-methyl-1H-benzimidazol-2-ylmethoxy)benzyl}thiazolidine-2,4-dione, 5-{4-(6-[2-(piperidin-1-yl)phenoxy]-1-methyl-1H-benzimidazol-2-ylmethoxy)benzyl}thiazolidine-2,4-dione, 5-{4-(6-[2-(morpholin-4-yl)phenoxy]-1-methyl-1H-benzimidazol-2-ylmethoxy)benzyl}thiazolidine-2,4-dione, 5-{4-(1-methyl-6-[3-(morpholin-4-yl)phenoxy]-1H-benzimidazol-2-ylmethoxy)benzyl}thiazolidine-2,4-dione, 5-{4-[6-(2-chloro-4-hydroxy-3,5-dimethyl-1H-benzimidazol-2-ylmethoxy]benzyl}thiazolidine-2,4-dione, 5-{4-[6-(4-hydroxy-2-methylphenoxy)-1-methyl-1H-benzimidazol-2-ylmethoxy]benzyl}thiazolidine-2,4-dione, 5-{4-[6-(4-hydroxy-3-methylphenoxy)-1-methyl-1H-benzimidazol-2-ylmethoxy]benzyl}thiazolidine-2,4-dione, 5-{4-[6-(4-hydroxy-2,5-dimethylphenoxy)-1-methyl-1H-benzimidazol-2-ylmethoxy]benzyl}thiazolidine-2,4-dione, 5-{4-[6-(4-hydroxy-3,5-dimethylphenoxy)-1-methyl-1H-benzimidazol-2-ylmethoxy]benzyl}thiazolidine-2,4-dione, 5-{4-[6-(3,5-di-t-butyl-4-hydroxyphenoxy)-1-methyl-1H-benzimidazol-2-ylmethoxy]benzyl}thiazolidine-2,4-dione, 5-{4-[6-(3,5-di-t-butyl-4-hydroxyphenylthio)-1-methyl-1H-benzimidazol-2-ylmethoxy]benzyl}thiazolidine-2,4-dione, 5-{4-[6-(4-hydroxy-2,3,5trimethylphenoxy)-1-methyl-1H-benzimidazol-2-ylmethoxy]benzyl}thiazolidine-2,4-dione, 5-{4-[5-(4-hydroxy-2,3,5-trimethylphenoxy)-3-methyl-3H-imidazo[4,5-b]-pyridin-2-ylmethoxy]benzyl}thiazolidine-2,4-dione, 5-{4-[6-(4-amino-3,5-dimethylphenoxy)-1-methyl-1H-benzimidazol-2-ylmethoxy]benzyl}thiazolidine-2,4-dione, 5-{4-[6-(4-acetylamino-3,5-dimethylphenoxy)-1-methyl-1H-benzimidazol-2-ylmethoxy]benzyl}thiazolidine-2,4-dione, 5-{4-[6-(pyridin-2-yloxy)-1-methyl-1H-benzimidazol-2-ylmethoxy]benzyl}thiazolidine-2,4-dione, 5-{4-[1-methyl-6-(pyridin-2-ylthio)-1H-benzimidazol-2-ylmethoxy]benzyl}thiazolidine-2,4-dione, 5-{4-[1-methyl-6-(pyridin-3-yloxy)-1H-benzimidazol-2-ylmethoxy]benzyl}thiazolidine-2,4-dione, 5-{4-(6-[4-(imidazol-1-yl)phenoxy]-1-methyl-1H-benzimidazol-2-ylmethoxy)benzyl}thiazolidine-2,4-dione, 5-{4-(6-[4-(1-adamantyl)phenoxy]-1-methyl-1H-benzimidazol-2-ylmethoxy)benzyl}thiazolidine-2,4-dione, 5-{4-[6-(4-cyanophenoxy)-1-methyl-1H-benzimidazol-2-ylmethoxy]benzyl}thiazolidine-2,4-dione, 5-{4-[6-(2,5-di-t-butyl-4-hydroxyphenoxy)-1-methyl-1H-benzimidazol-2-ylmethoxy]benzyl}thiazolidine-2,4-dione, 5-{4-[6-(pentafluorophenoxy)-1-methyl-1H-benzimidazol-2-ylmethoxy]benzyl}thiazolidine-2,4-dione, 5-{4-[6-(4-benzoylaminophenoxy)-1-methyl-1H-benzimidazol-2-ylmethoxy]benzyl}thiazolidine-2,4-dione, 5-[4-{6-[4-(2,4-difluorobenzoylamino)phenoxy]-1-methyl-1H-benzimidazol-2-ylmethoxy}benzyl]thiazolidine-2,4-dione, 5-{4-[6-(4-cyclopentanecarbonylaminophenoxy)-1-methyl-1H-benzimidazol-2-ylmethoxy]benzyl}thiazolidine-2,4-dione, 5-{4-[6-(4-nicotinoylaminophenoxy)-1-methyl-1H-benzimidazol-2-ylmethoxy]benzyl}thiazolidine-2,4-dione, and 5-{4-[6-(3,5-di-t-butyl-4-hydroxydiphenylthio)-1-methyl-1H-benzimidazol-2-ylmethoxy]benzylidene}thiazolidine-2,4-dione.

53. A pharmaceutical composition comprising an effective amount of a substituted fused heterocyclic compound of the formula (I) or a pharmacologically acceptable salt or prodrug thereof according to claim 1, together with a pharmaceutically acceptable carrier.

54. A pharmaceutical composition comprising an effective amount of a substituted fused heterocyclic compound of the formula (I) or a pharmacologically acceptable salt thereof according to any one of claims 2–52, together with a pharmaceutically acceptable carrier.

55. A pharmaceutical composition according to claim 53, wherein said composition further comprises at least one compound selected from the group consisting of α-glucosidase inhibitors, aldose reductase inhibitors, biguanide preparations, statin base compounds, squalene synthesis inhibitors, fibrate base compounds, LDL catabolism promoters and angiotensin-converting enzyme inhibitors.

56. A method of treating a warm-blooded animal in need thereof to (i) improve insulin resistance, (ii) reduce inflammation, (iii) achieve immunoregulation, (iv) inhibit aldose reductase, (v) inhibit 5-lipoxygenase, (vi) inhibit lipid peroxide production, (vii) activate peroxisome proliferator activated receptor (PPAR), (viii) provide a leukotriene antagonist, (ix) promote fat-cell-formation, (x) inhibit cancer-cell proliferation, or (xi) provide a calcium antagonist comprising administering to said warm-blooded animal an effective amount of a substituted fused heterocyclic compound of the formula (I) or a pharmacologically acceptable salt or prodrug thereof according to claim 1.

57. A method of treating a warm-blooded animal in need thereof to (i) improve insulin resistance, (ii) reduce inflammation, (iii) achieve immunoregulation, (iv) inhibit aldose reductase, (v) inhibit 5-lipoxygenase, (vi) inhibit lipid peroxide production, (vii) activate peroxisome proliferator activated receptor (PPAR), (viii) provide a leukotriene antagonist, (ix) promote fat-cell-formation, (x) inhibit cancer-cell proliferation, or (xi) provide a calcium antagonist comprising administering to said warm-blooded animal an effective amount of a substituted fused heterocyclic compound of the formula (I) or a pharmacologically acceptable salt thereof according to any one of claims 2–52, wherein said warm-blooded animal is a human.

58. A method of treating according to claim 56, wherein said treatment is to inhibit lipid peroxide production.

59. A method of treating according to claim 56, wherein said treatment is to inhibit 5-lipoxygenase.

60. A method of treating according to claim 56, wherein said treatment is to improve insulin resistance.

61. A method of treating according to claim 56, wherein said substituted fused heterocyclic compound or said pharmacologically acceptable salt or prodrug thereof is administered to said warm-blooded animal in combination with at least one compound selected from the group consisting of α-glucosidase inhibitors, aldose reductase inhibitors, biguanide preparations, statin base compounds, squalene synthesis inhibitors, fibrate base compounds, LDL catabolism promoters and angiotensin-converting enzyme inhibitors.

62. A method of prevention or treatment of a disease in a warm-blooded animal selected from the group consisting of diabetes, hyperlipidemia, impaired glucose tolerance, hypertension, diabetic complications, arteriosclerosis, polycystic ovary syndrome, cardiovascular diseases, atherosclerosis, cell injury induced by ischemic heart diseases, gout, inflammatory diseases, cancer and cataracts, comprising administering to said warm-blooded animal an effective amount of a substituted fused heterocyclic compound of the formula (I) according to claim 1.

63. A method of prevention or treatment of a disease in a human selected from the group consisting of diabetes, hyperlipidemia, impaired glucose tolerance, hypertension, diabetic complications, arteriosclerosis, polycystic ovary syndrome, cardiovascular diseases, atherosclerosis, cell injury induced by ischemic heart diseases, gout, inflammatory diseases, cancer and cataracts, comprising administering to said human an effective amount of a substituted fused heterocyclic compound of the formula (I) according to any one of claims 2–52.

64. A method of prevention or treatment according to claim 62, wherein said disease is diabetes mellitus and said warm-blooded animal is a human.

65. A method of prevention or treatment according to claim 62, wherein said disease is pregnancy diabetes and said warm-blooded animal is a human.

66. A method of prevention or treatment according to claim 62, wherein said disease is impaired glucose tolerance and said warm-blooded animal is a human.

67. A method of prevention or treatment according to claim 62, wherein said disease is hyperlipidemia and said warm-blooded animal is a human.

68. A method of prevention or treatment according to claim 62, wherein said substituted fused heterocyclic compound of the formula (I) is administered to a human in combination with at least one compound selected from the group consisting of α-glucosidase inhibitors, aldose reductase inhibitors, biguanide preparations, statin base compounds, squalene synthesis inhibitors, fibrate base compounds, LDL catabolism promoters and angiotensin-converting enzyme inhibitors.

* * * * *